(12) United States Patent
Bordas et al.

(10) Patent No.: US 8,975,417 B2
(45) Date of Patent: Mar. 10, 2015

(54) PYRAZOLOPYRROLIDINE DERIVATIVES AND THEIR USE IN THE TREATMENT OF DISEASE

(71) Applicants: Vincent Bordas, Village-Neuf (FR); Simona Cotesta, Basel (CH); Vito Guagnano, Basel (CH); Heinrich Rueeger, Flueh (CH); Andrea Vaupel, Riehen (CH)

(72) Inventors: Vincent Bordas, Village-Neuf (FR); Simona Cotesta, Basel (CH); Vito Guagnano, Basel (CH); Heinrich Rueeger, Flueh (CH); Andrea Vaupel, Riehen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/282,515

(22) Filed: May 20, 2014

(65) Prior Publication Data

US 2014/0349990 A1   Nov. 27, 2014

(30) Foreign Application Priority Data

May 27, 2013  (EP) .................................... 13169364
Jul. 23, 2013   (EP) .................................... 13177673

(51) Int. Cl.
| | | |
|---|---|---|
| C07D 231/56 | (2006.01) |
| A61K 31/506 | (2006.01) |
| C07D 487/04 | (2006.01) |
| A61K 31/4439 | (2006.01) |
| C07D 471/04 | (2006.01) |
| A61K 31/437 | (2006.01) |
| A61K 31/501 | (2006.01) |
| A61K 31/423 | (2006.01) |
| A61K 31/4192 | (2006.01) |
| A61K 45/06 | (2006.01) |

(52) U.S. Cl.
CPC ............ *A61K 31/506* (2013.01); *C07D 487/04* (2013.01); *A61K 31/4439* (2013.01); *C07D 471/04* (2013.01); *A61K 31/437* (2013.01); *A61K 31/501* (2013.01); *A61K 31/423* (2013.01); *A61K 31/4192* (2013.01); *A61K 45/06* (2013.01)
USPC ...................................................... 548/360.1

(58) Field of Classification Search
USPC ...................................................... 548/360.1
See application file for complete search history.

(56) References Cited

U.S. PATENT DOCUMENTS

| | | | |
|---|---|---|---|
| 6,734,302 B2 | 5/2004 | Kong et al. |
| 7,541,354 B2 | 6/2009 | Fancelli et al. |
| 8,101,644 B2 | 1/2012 | Kai et al. |
| 8,440,693 B2 | 5/2013 | Berghausen et al. |
| 2003/0153580 A1 | 8/2003 | Kong et al. |
| 2006/0069085 A1 | 3/2006 | Zhao et al. |
| 2009/0163545 A1 | 6/2009 | Goldfarb |
| 2010/0210632 A1 | 8/2010 | Kai et al. |
| 2011/0183939 A1 | 7/2011 | Kai et al. |
| 2011/0230457 A1 | 9/2011 | Berghausen et al. |
| 2012/0065210 A1 | 3/2012 | Chu et al. |
| 2013/0281473 A1 | 10/2013 | Berghausen et al. |
| 2013/0317024 A1 | 11/2013 | Cotesta et al. |
| 2014/0011798 A1 | 1/2014 | Furet et al. |
| 2014/0135306 A1 | 5/2014 | Buschmann et al. |

FOREIGN PATENT DOCUMENTS

| | | |
|---|---|---|
| EP | 2 143 713 A1 | 1/2010 |
| WO | 95/19362 A1 | 7/1995 |
| WO | 9519362 A1 | 7/1995 |
| WO | 02/12242 A2 | 2/2002 |
| WO | 03/051359 A1 | 6/2003 |
| WO | 03/095625 A2 | 11/2003 |
| WO | 2005/110996 A1 | 11/2005 |
| WO | 2006/074262 A1 | 7/2006 |
| WO | 2007/068637 A1 | 6/2007 |
| WO | 2007/096334 A1 | 8/2007 |
| WO | 2008/034039 A2 | 3/2008 |
| WO | 2008/120725 A1 | 10/2008 |
| WO | 2010/007116 A2 | 1/2010 |
| WO | 2010/035727 A1 | 4/2010 |
| WO | 2010/141738 A2 | 12/2010 |
| WO | 2011/076786 A1 | 6/2011 |
| WO | 2011/161031 A1 | 12/2011 |
| WO | 2012/046030 A2 | 4/2012 |

(Continued)

OTHER PUBLICATIONS

Andreichikov et al., Chemistry of Oxalyl Derivatives of Methyl Ketones XLIV. Synthesis of 4-Aroyl-1,5-Diphenyltetrahydropyrrole-2,3-Diones and their Reaction with Amines and Hydrazine. Journal of Organic Chemistry 1986;22(8):1572-7.

(Continued)

*Primary Examiner* — Nizal Chandrakumar
(74) *Attorney, Agent, or Firm* — Scott W. Reid

(57) ABSTRACT

The present invention provides a compound of formula (I) or a pharmaceutically acceptable salt thereof;

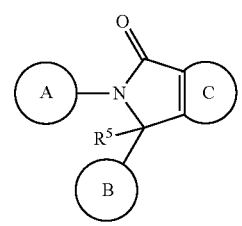

(I)

a method for manufacturing the compounds of the invention, and its therapeutic uses. The present invention further provides a combination of pharmacologically active agents and a pharmaceutical composition.

24 Claims, No Drawings

(56) References Cited

FOREIGN PATENT DOCUMENTS

| WO | 2012/151512 A2 | 11/2012 |
|---|---|---|
| WO | 2012/174487 A2 | 12/2012 |
| WO | 2012/175487 A1 | 12/2012 |
| WO | 2012/175520 A1 | 12/2012 |
| WO | 2013/033268 A2 | 3/2013 |
| WO | 2013/080141 A1 | 6/2013 |
| WO | 2013/111105 A1 | 8/2013 |

OTHER PUBLICATIONS

Chung et al., Fragment-based discovery of bromodomain inhibitors part 1: inhibitor binding modes and implications for lead discovery. J Med Chem. Jan. 26, 2012;55(2):576-86.

Dohrn et al., Berichte der Deutschen Chemischen Gesellschaft [Abteilung] B: Abhandlungen. 1931;64B:2863-5.

Filippakopoulos et al., Benzodiazepines and benzotriazepines as protein interaction inhibitors targeting bromodomains of the BET family. Bioorg Med Chem. Mar. 15, 2012;20(6):1878-86.

Gein et al., 5-Membered 2,3-Dioxoheterocyclic Compounds. Journal of General Chemistry. 1993;63(10):2324-8.

Gein et al., Reactions of 4-Acyl-1-alkoxyaryl-5-aryl-3-hydroxy-2,5-dihydro-1H-pyrrol-2-ones with Nucleophilic Reagents. Russian Journal of Organic Chemistry. 2011;47(1):95-9.

Hackam et al., Translation of research evidence from animals to humans. JAMA. Oct. 11, 2006;296(14):1731-2.

Jordan, Tamoxifen: a most unlikely pioneering medicine. Nat Rev Drug Discov. Mar. 2003;2(3):205-13.

Lee et al., Novel Pyrrolopyrimidine-Based alpha-Helix Mimetics: Cell Permeable Inhibitors of Protein-Protein Interactions. Journal of the American Chemical Society. 2010;133:676-9.

Miyazaki et al., Lead optimization of novel p53-MDM2 interaction inhibitors possessing dihydroimidazothiazole scaffold. Bioorganic and Medicinal Chemistry Letters. 2013;23:728-32.

Richter et al., An Optimised Small-Molecule Stabiliser of the 14-3-3-PMA2 Protein-Protein Interaction. Chem. Eur. J. 2012;18(21):6520-7.

Vanotti et al., Cdc7 Kinase Inhibitors: Pyrrolopyrimidinones as Potential Antitumor Agents. 1. Synthesis and Structure-Activity Relationships. Journal of Medicinal Chemistry. 2008;51:487-501.

Wang et al., Benzimidazole-2-one: A novel anchoring principle for antagonizing p53-Mdm2. Bioorganic & Medicinal Chemistry. 2013;21:3982-95.

Westphal The formation of pyrrolo[3,4-c]pyrazoles. Journal for Practical Chemistry. 1969;311:379-84.

Filippakopoulos et al., Selective inhibition of BET bromodomains. Nature. Dec. 23, 2010;468(7327):1067-73.

Wu et al., The double bromodomain-containing chromatin adaptor Brd4 and transcriptional regulation. J Biol Chem. May 4, 2007;282(18):13141-5.

PYRAZOLOPYRROLIDINE DERIVATIVES AND THEIR USE IN THE TREATMENT OF DISEASE

FIELD OF THE INVENTION

The invention provides pyrazolopyrrolidine derivatives and their use as BET inhibitors, for the treatment of conditions or diseases such as cancer.

BACKGROUND OF THE INVENTION

BET proteins are proteins encoded by either of the genes BRD2, BRD3, BRD4, or BRDT. Each of these proteins bears two N-terminal bromodomains. Bromodomains comprise of a conserved ~110 amino acid segment found in at least 42 diverse proteins that specifically interact with acetylated lysines that occur for example on histone tails (Filippakopoulos and Knapp, FEBS Letters, 586 (2012), 2692-2704). Histones are a constituent part of chromatin and their covalent modifications including lysine acetylation regulate gene transcription. Bromodomains are thus believed to regulate transcription by recruiting proteins to genes that are marked with specific patterns of lysine acetylation.

Several published reports have linked the BET protein family to diseases including cancer, metabolic disease and inflammation. Oncogenic fusions of BRD4 or BRD3 and the Nuclear protein in Testis (NUT) gene caused by chromosomal translocations are underlying an aggressive cancer named NUT midline carcinoma (French et al., J Clin Oncol, 22 (2004), 4135-9; French et al., J Clin Pathol, 63 (2008), 492-6). The BRD3/4 bromodomains are preserved in these fusion proteins, and their inhibition either by knockdown or with the selective BET bromodomain inhibitor JQ1 leads to death and/or differentiation of these cancer cells both in vitro and in animal tumour models (Filippakopoulos et al., Nature, 468 (2010), 1067-73). JQ1 and several other selective BET inhibitors have been shown to bind to BET bromodomains and thereby prevent acetyl-lysine binding, which prevents BET proteins from interacting with chromatin and thereby regulating transcription. BRD4 was also identified from an RNAi screen as a target in acute myeloid leukemia (AML) (Zuber et al., Nature, 478 (2011), 524-8). This finding was validated in vitro and in vivo using the BET inhibitor JQ1 and another selective BET inhibitor named I-BET151 that is chemically unrelated to JQ1 (Dawson et al., Nature, 478 (2011), 529-33). These and other studies showed that BET inhibitors have broad anti-cancer activity in acute leukemias, multiple myeloma and other hematological malignancies. In several cancer models an acute downregulation of the oncogenic transcription factor Myc upon BET inhibition has been observed (Delmore et al., Cell, 146 (2011), 904-17; Mertz et al., Proc Natl Acad Sci USA, 108 (2011), 16669-74). More recent studies suggest that the therapeutic potential of BET inhibitors extends to other cancer indications, for example lung and brain cancer.

Another BET inhibitor named I-BET762 that is closely related to JQ1 in chemical structure and the manner in which it binds to BET bromodomains, was reported to modulate expression of key inflammatory genes and thereby protect against endotoxic shock and bacteria-induced sepsis in mouse models (Nicodeme et al., Nature, 468 (2010), 1119-23). This body of data has been used to support the clinical evaluation of the BET inhibitor RVX-208 in clinical trials in patients suffering from atherosclerosis, coronary artery disease, dyslipidemia, diabetes, and other cardiovascular diseases (McNeill, Curr Opin Investig Drugs, 3 (2010), 357-64 and www.clinicaltrials.gov). Both RVX-208 and I-BET762 have been shown to upregulate Apolipoprotein A-I, which is critically involved in reducing the tissue levels of cholesterol. Finally, BET proteins have been linked to propagation and transcription regulation of several viruses, and therefore it is believed that BET inhibitors could have anti-viral activity (Weidner-Glunde, Frontiers in Bioscience 15 (2010), 537-549).

In summary, inhibitors of BET bromodomains have therapeutic potential in several human diseases.

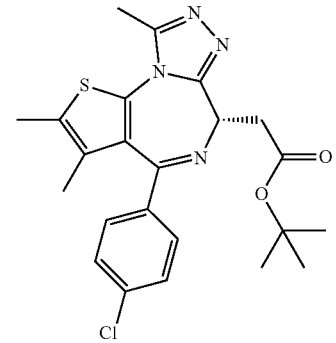

JQ1

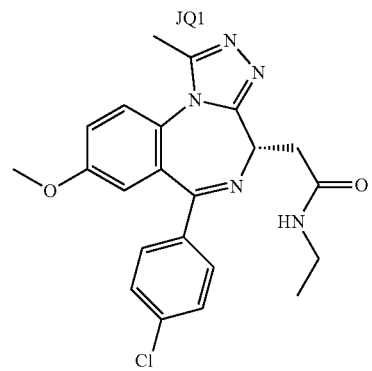

I-BET762

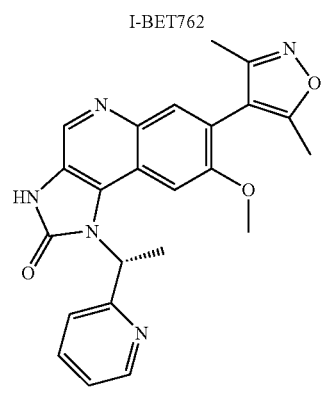

I-BET151

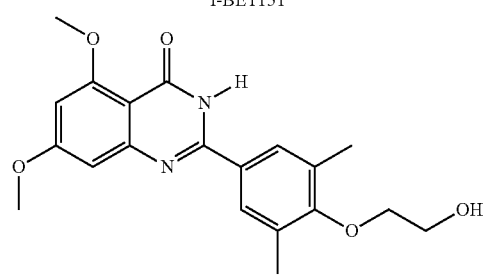

RVX-208

There remains a need for new treatments and therapies for the treatment of cancer. The invention provides compounds as BET inhibitors, pharmaceutically acceptable salts thereof, pharmaceutical compositions thereof and combinations thereof. The invention further provides methods of treating, preventing or ameliorating cancer, comprising administering to a subject in need thereof an effective amount of a BET inhibitor.

Various embodiments of the invention are described herein. Particularly interesting compounds of the invention have good potency in the biological assays described herein. In another aspect they should have a favourable safety profile. In another aspect, they should possess favourable pharmacokinetic properties.

WO2013/08014A1 discloses pyrazolopyrrolidine compounds, capable of inhibiting the interaction between p53, or variants thereof, and MDM2 and/or MDM4.

SUMMARY OF THE INVENTION

According to a first aspect of the invention, there is provided a compound of formula (I) or a pharmaceutically acceptable salt thereof,

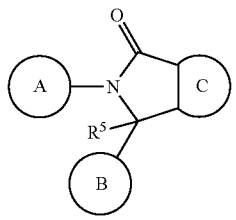
(I)

wherein
ring C is selected from i. 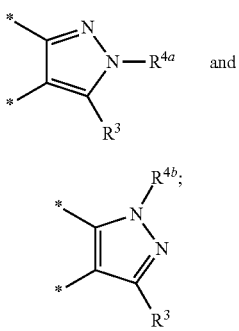

ii.

A is selected from

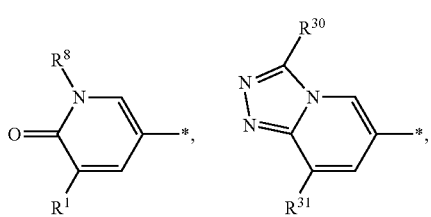

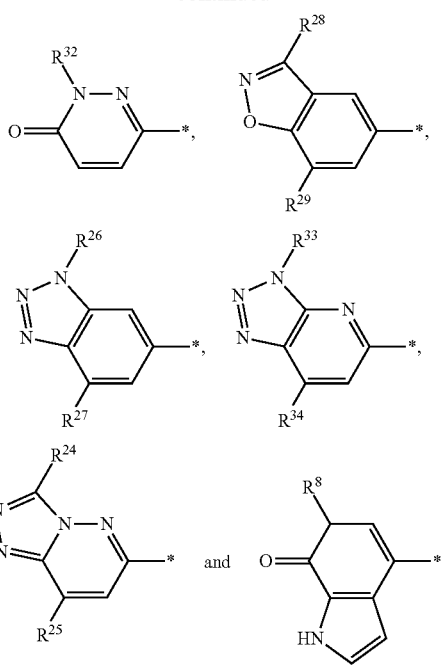

B is selected from

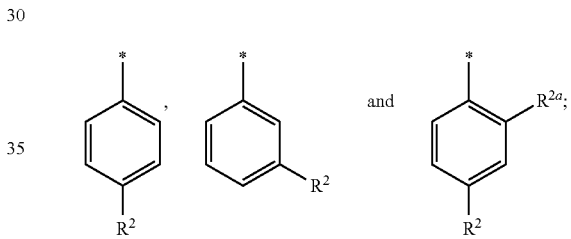

$R^3$ is selected from H, methyl, ethyl, —$CH_2F$, —$CF3$, isopropyl, —OH, ethoxy, methoxy, cyclopropyl, —$CH_2OCH_3$ and —$CH_2OH$;

$R^{4a}$ is selected from H, ($C_1$-$C_4$)alkyl, ($C_3$-$C_6$)cycloalkyl, —$(CH_2)_2$—OH, —$(CH_2)_2$—O—$CH_3$, —C(O)—NH($CH_3$), —C(O)—N($CH_3$)$_2$,

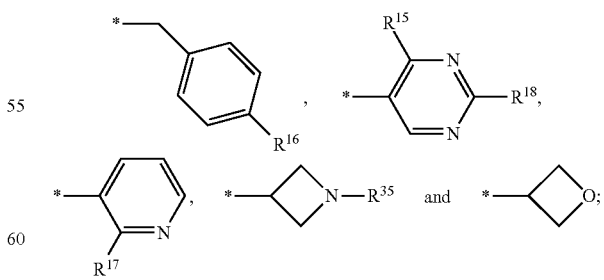

$R^{4b}$ is selected from H, ($C_1$-$C_4$)alkyl, ($C_3$-$C_6$)cycloalkyl, —$(CH_2)_2$—OH, —$(CH_2)_2$—O—$CH_3$, —$(CH_2)_2$—O—$CH_2$—$CF_3$, —$(CH_2)$—CH(OH)—$CF_3$, —C(O)—NH($CH_3$), —C(O)—N($CH_3$)$_2$,

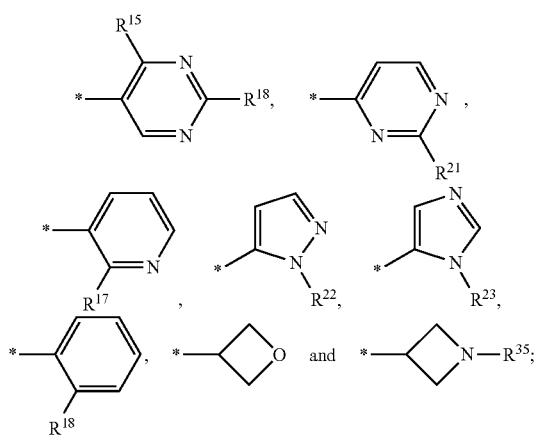

$R^5$ is H;
$R^1$ is selected from H, methyl, chloro and fluoro;
$R^2$ is selected from bromo, chloro, fluoro, —O—CF$_3$ and —CF$_3$;
$R^{2a}$ is fluoro;
$R^8$ is methyl;
$R^{15}$, $R^{16}$, $R^{18}$ and $R^{21}$ are all methoxy;
$R^{17}$ is methyl or methoxy;
$R^{22}$, $R^{23}$, $R^{26}$, $R^{27}$, $R^{28}$, $R^{30}$, $R^{32}$ and $R^{33}$ are all methyl;
$R^{24}$ is methyl or —CHF$_2$;
$R^{25}$ is methyl or —NR$^9$R$^{10}$;
$R^{29}$ is H or methyl;
$R^{31}$ is H, methyl or methoxy;
$R^{34}$ is H or methyl;
$R^9$ is H or methyl;
$R^{10}$ is H, methyl or —C(O)—(C$_1$-C$_3$)alkyl;
$R^{35}$ is H, methyl, —C(O)CH$_3$ or —C(O)OCH$_2$CH$_3$;
and
* indicates the point of attachment to the remainder of the molecule;
with the proviso that
when ring C is i:

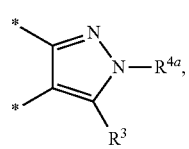

A is:

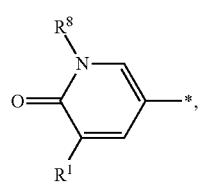

$R^1$ is selected from methyl, chloro and fluoro,

B is:

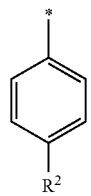

$R^2$ is chloro, fluoro or —CF$_3$,
and the remaining substituents are as defined herein,
then $R^3$ is selected from H, methyl, ethyl, —CH$_2$F, —CF$_3$, —OH, ethoxy, methoxy, —CH$_2$OCH$_3$ and —CH$_2$OH.

In another embodiment, the invention provides a pharmaceutical composition comprising a therapeutically effective amount of a compound according to the definition of formula (I), or a pharmaceutically acceptable salt thereof, or subformulae thereof and one or more pharmaceutically acceptable carriers.

In another embodiment, the invention provides a combination, in particular a pharmaceutical combination, comprising a therapeutically effective amount of the compound according to the definition of formula (I), or a pharmaceutically acceptable salt thereof, or subformulae thereof and one or more therapeutically active agent.

Therefore according to the first aspect of the invention, there is provided a compound of formula (I) or a pharmaceutically acceptable salt thereof, of the following formulae:

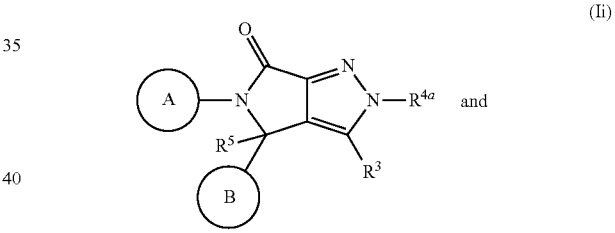

(Ii)

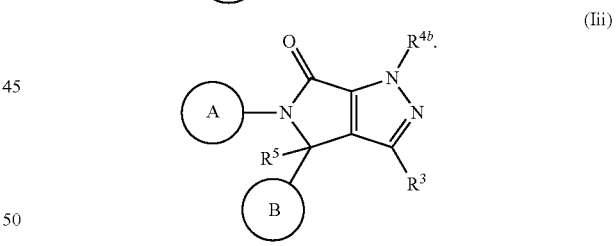

(Iii)

The data disclosed in WO2013/08014A1 show that one enantiomer of the pyrazolopyrrolidine compounds possesses greater p53-MDM2 and p53-MDM4 activity. For examples 139, 140, 141, 142, 143 and 144, the (S)-enantiomer shows significantly greater activity. Surprisingly, for the compounds of the present invention, the optical antipode to the preferred p53-MDM2 inhibitors was found to possess significantly greater activity as BRD4 inhibitors.

For example, (S)-4-(4-chlorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one (example 48) and (R)-4-(4-chlorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one (Example 49) have an IC$_{50}$ of >6.7 μM and 0.017 μM respectively (see table 1, below)

DETAILED DESCRIPTION

Described below are a number of embodiments (E) of the first aspect of the invention, where for convenience E1 is identical thereto.

E1 A compound of formula (I) as defined above, or a pharmaceutically acceptable salt thereof.

E1.1 A compound of formula (I) or a pharmaceutically acceptable salt thereof, according to E1

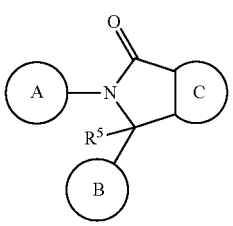
(I)

wherein
ring C is selected from

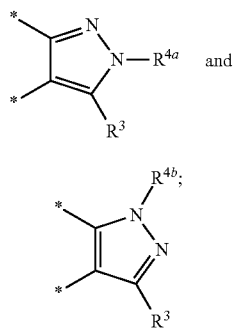

A is selected from

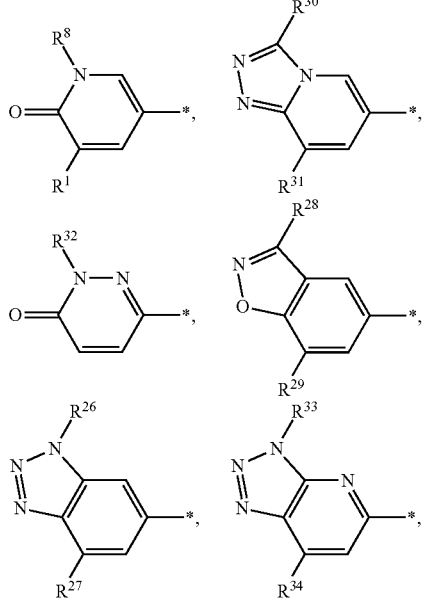

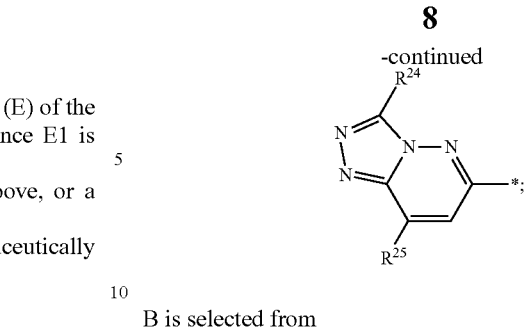

B is selected from

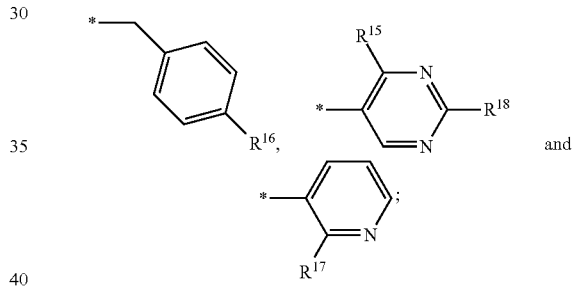

$R^3$ is selected from H, methyl, ethyl, —$CF_3$, isopropyl, —OH, ethoxy, methoxy, cyclopropyl, —$CH_2OCH_3$ and —$CH_2OH$, or $R^3$ is selected from H, methyl, ethyl, —$CF_3$, isopropyl, —OH, ethoxy, methoxy and cyclopropyl;

i. $R^{4a}$ is selected from H, ($C_1$-$C_4$)alkyl, ($C_3$-$C_6$)cycloalkyl, —$(CH_2)_2$—OH, —$(CH_2)_2$—O—$CH_3$, ii.

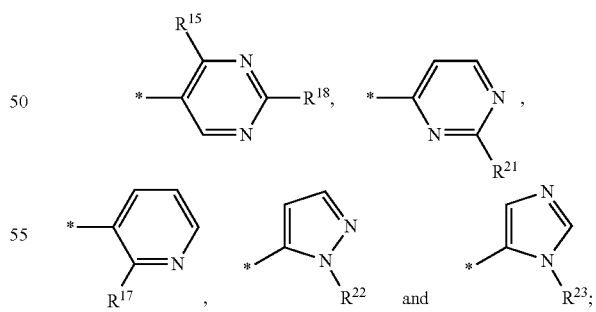

$R^4$ is selected from H, ($C_1$-$C_4$)alkyl, ($C_3$-$C_6$)cycloalkyl, —$(CH_2)_2$—OH, —$(CH_2)_2$—O—$CH_3$, —$(CH_2)_2$—O—$CH_2$—$CF_3$, $R^5$ is H;
$R^1$ is selected from H, methyl, chloro and fluoro;
$R^2$ is selected from chloro, —O—$CF_3$, —$CF_3$;
$R^8$ is methyl;
$R^{15}$, $R^{16}$, $R^{18}$ and $R^{21}$ are all methoxy;
$R^{17}$ is methyl or methoxy;
$R^{22}$, $R^{23}$, $R^{24}$, $R^{26}$, $R^{27}$, $R^{28}$, $R^{39}$, $R^{32}$ and $R^{33}$ are all methyl;
$R^{25}$ is methyl or —$NR^9R^{10}$;

$R^{29}$ is H or methyl;
$R^{31}$ is H, methyl or methoxy;
$R^{34}$ is H or methyl;
$R^{9}$ is H or methyl;
$R^{10}$ is H, methyl or —C(O)—($C_1$-$C_3$)alkyl;
and
* indicates the point of attachment to the remainder of the molecule;
with the proviso that
when ring C is i:

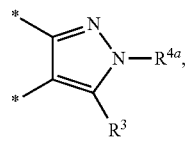

A is:

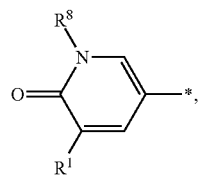

$R^1$ is selected from methyl, chloro and fluoro,
B is:

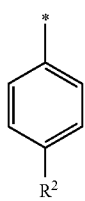

$R^2$ is chloro or —$CF_3$,
and the remaining substituents are as defined herein,
then $R^3$ is selected from H, methyl, ethyl, —$CF_3$, —OH, ethoxy, methoxy, $CH_2OCH_3$ and —$CH_2OH$, or $R^3$ is selected from H, methyl, ethyl, —$CF_3$, —OH, ethoxy and methoxy.

E1.2 A compound of formula (I) or a pharmaceutically acceptable salt thereof, according to E1

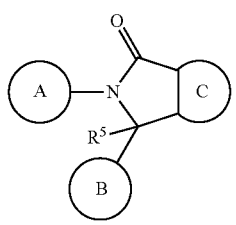 (I)

wherein
ring C is selected from i.

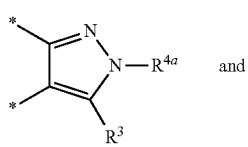 and ii.

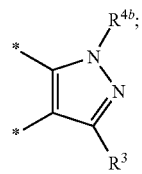

A is selected from

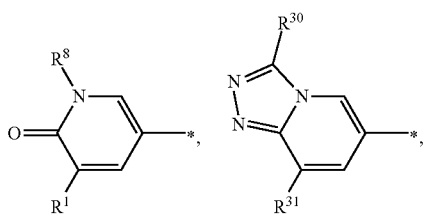

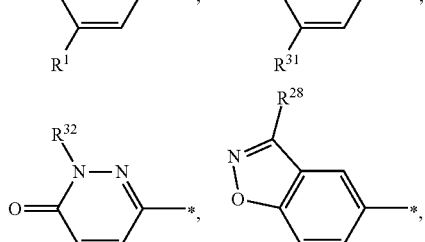

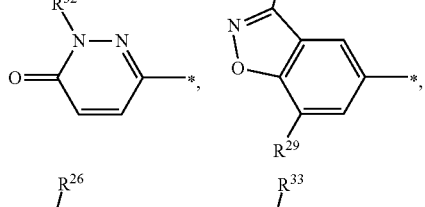

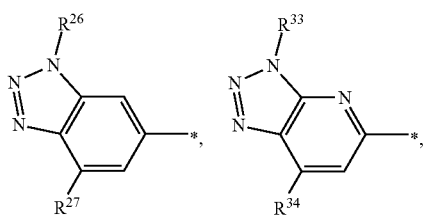

B is selected from

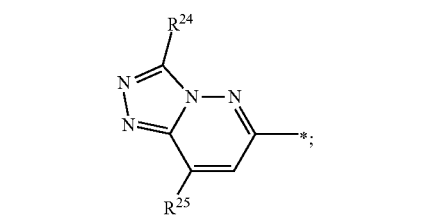

$R^3$ is selected from H, methyl, ethyl, —$CF_3$, isopropyl, —OH, ethoxy, methoxy and cyclopropyl;
$R^{4a}$ is selected from H, ($C_1$-$C_4$)alkyl, ($C_3$-$C_6$)cycloalkyl, —($CH_2$)$_2$—OH, —($CH_2$)$_2$—O—$CH_3$,

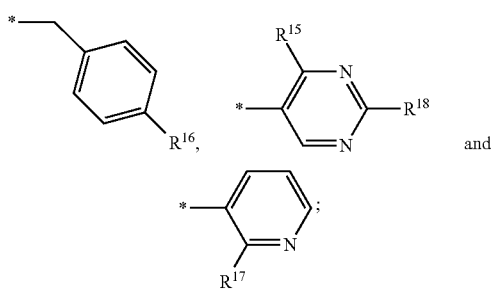

$R^{4b}$ is selected from H, $(C_1\text{-}C_4)$alkyl, $(C_3\text{-}C_6)$cycloalkyl, —$(CH_2)_2$—OH, —$(CH_2)_2$—O—$CH_3$, —$(CH_2)_2$—O—$CH_2$—$CF_3$,

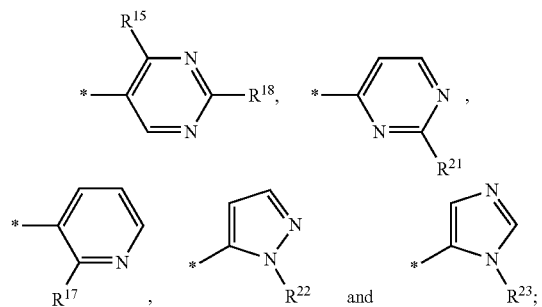

$R^5$ is H;
$R^1$ is selected from H, methyl, chloro and fluoro;
$R^2$ is selected from chloro, —O—$CF_3$, —$CF_3$;
$R^8$ is methyl;
$R^{15}$, $R^{16}$, $R^{18}$ and $R^{21}$ are all methoxy;
$R^{17}$ is methyl or methoxy;
$R^{22}$, $R^{23}$, $R^{24}$, $R^{26}$, $R^{27}$, $R^{28}$, $R^{30}$, $R^{32}$ and $R^{33}$ are all methyl;
$R^{25}$ is methyl or —$NR^9R^{10}$;
$R^{29}$ is H or methyl;
$R^{31}$ is H, methyl or methoxy;
$R^{34}$ is H or methyl;
$R^9$ is H or methyl;
$R^{10}$ is H, methyl or —C(O)—$(C_1\text{-}C_3)$alkyl;
and
* indicates the point of attachment to the remainder of the molecule;
with the proviso that
when ring C is:

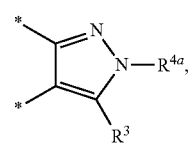

A is:

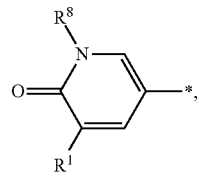

$R^1$ is selected from methyl, chloro and fluoro,
B is:

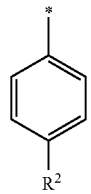

$R^2$ is chloro or —$CF_3$,
and the remaining substituents are as defined herein,
then $R^3$ is selected from H, methyl, ethyl, —$CF_3$, —OH, ethoxy and methoxy.

E2 A compound of formula (I) or a pharmaceutically acceptable salt thereof, according to E1, E1.1 or E1.2, wherein A is selected from

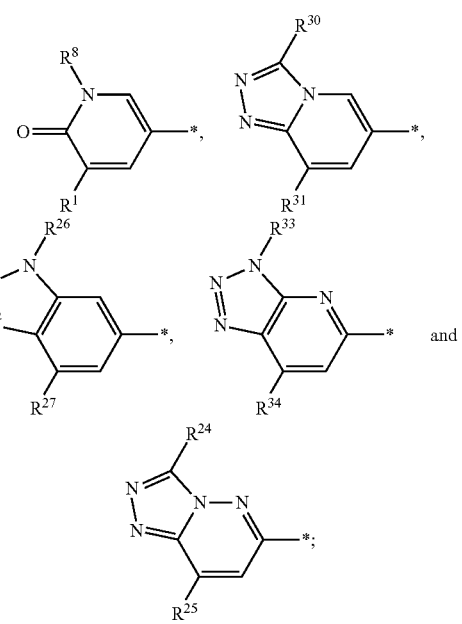

or A is selected from

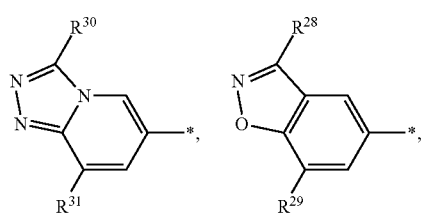

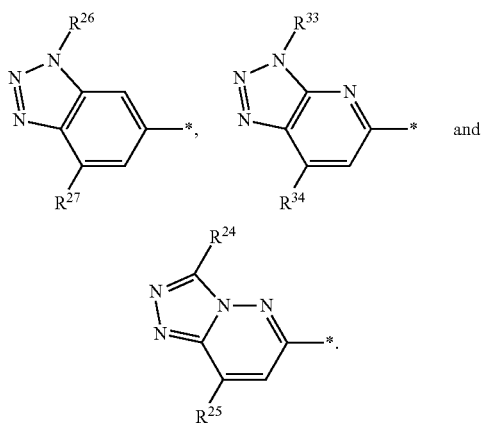

E3 A compound of formula (I) or a pharmaceutically acceptable salt thereof, according to E1 or E1.1 or E1.2, wherein A is

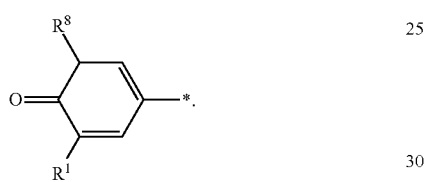

E4 A compound of formula (I) or a pharmaceutically acceptable salt thereof, according to E1 or E1.1 or E1.2, wherein A is

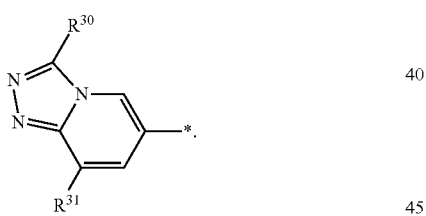

E5 A compound of formula (I) or a pharmaceutically acceptable salt thereof, according to E1 or E1.1 or E1.2, wherein A is

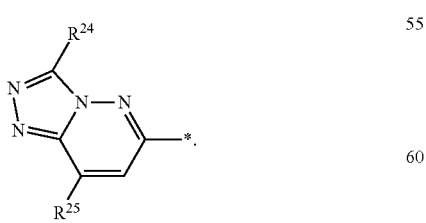

E6 A compound of formula (I) or a pharmaceutically acceptable salt thereof, according to E1 or E1.1 or E1.2, wherein A is selected from

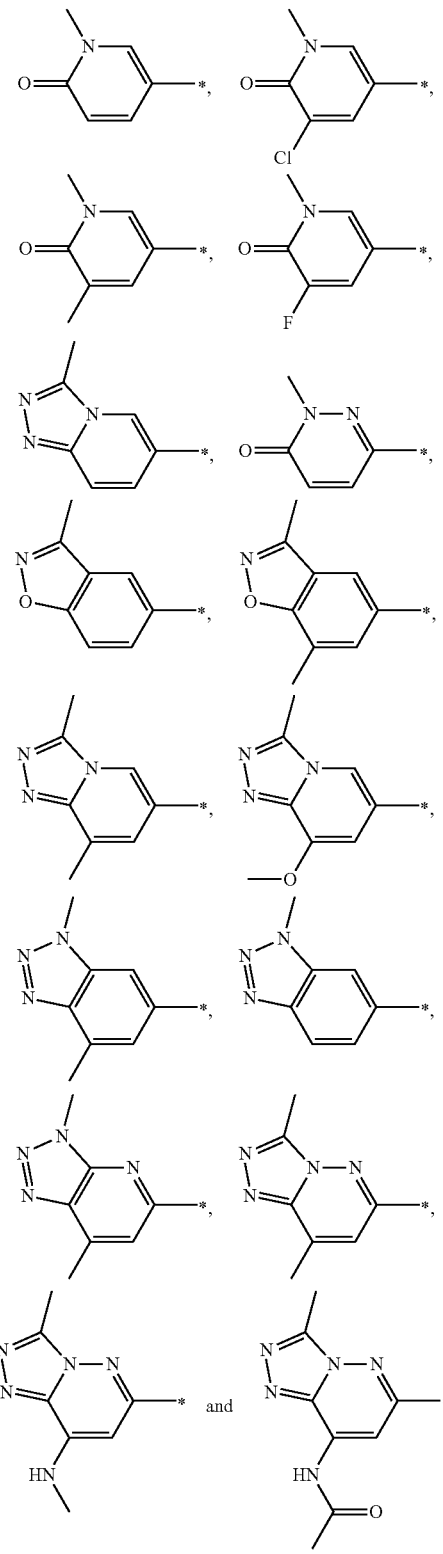

E7 A compound of formula (I) or a pharmaceutically acceptable salt thereof, according to any one of E1, E1.1, E1.2, E2, E3, E4, E5 or E6, wherein B is

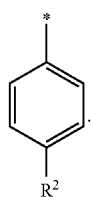

E8 A compound of formula (I) or a pharmaceutically acceptable salt thereof, according to any one of E1, E1.1, E1.2, E2, E3, E4, E5 or E6, wherein B is selected from

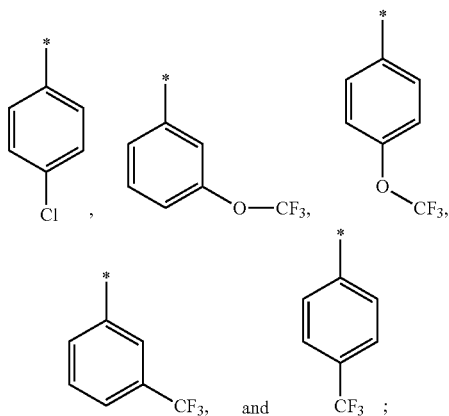

or B is selected from

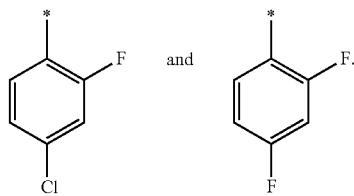 [SMILES: *c1ccc(Cl)cc1F ; "and" ; *c1ccc(F)cc1F]

E9 A compound of formula (I) or a pharmaceutically acceptable salt thereof, according to any one of E1, E1.1, E1.2 and E2 to E8, wherein $R^3$ is selected from H, methyl, ethyl, —$CF_3$, isopropyl, —OH, ethoxy, methoxy and cyclopropyl, or $R^3$ is selected from methyl, ethyl, isopropyl and methoxy, or $R^3$ is selected from H, methyl, ethyl, —$CF_3$, —OH, ethoxy and methoxy.

E10 A compound of formula (I) or a pharmaceutically acceptable salt thereof, according to any one of E1, E1.1, E1.2 and E2 to E9, wherein $R^3$ is methyl.

E11 A compound of formula (I) or a pharmaceutically acceptable salt thereof, according to any one of E1, E1.1, E1.2 and E2 to E10, wherein $R^{4a}$ is selected from methyl, isopropyl, cyclopropyl and

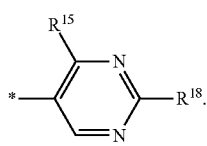

E12 A compound of formula (I) or a pharmaceutically acceptable salt thereof, according to any one of E1, E1.1, E1.2 and E2 to E11, wherein $R^{4a}$ is selected from cyclopropyl and

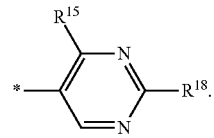

E13 A compound of formula (I) or a pharmaceutically acceptable salt thereof, according to any one of E1, E1.1, E1.2 and E2 to E10, wherein $R^{4a}$ is selected from H, methyl, ethyl, cyclopropyl, isopropyl, —$(CH_2)_2$—OH, —$(CH_2)_2$—O—$CH_3$,

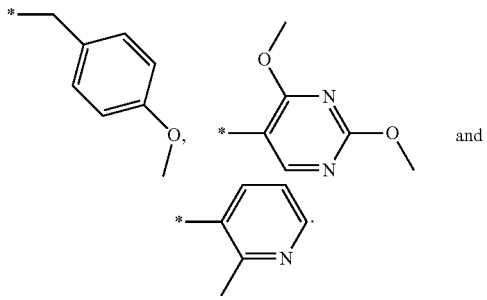

E14 A compound of formula (I) or a pharmaceutically acceptable salt thereof, according to any one of E1, E1.1, E1.2 and E2 to E10, wherein $R^{4b}$ is selected from ethyl, isopropyl, cyclopropyl, —$(CH_2)_2$—OH, —$(CH_2)_2$—O—$CH_3$,

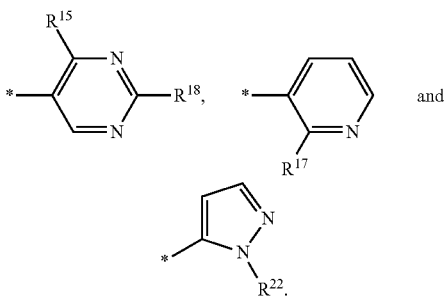

E15 A compound of formula (I) or a pharmaceutically acceptable salt thereof, according to any one of E1, E1.1, E1.2, E2 to E10 and E14, wherein $R^{4b}$ is cyclopropyl.

E16 A compound of formula (I) or a pharmaceutically acceptable salt thereof, according to any one of E1, E1.1, E1.2 and E2 to E10, wherein $R^{4b}$ is selected from H, methyl, ethyl, cyclopropyl, isopropyl, —$(CH_2)_2$—OH, —$(CH_2)_2$—O—$CH_3$, cyclobutyl, —$(CH_2)_2$—O—$CH_2$—$CF_3$,

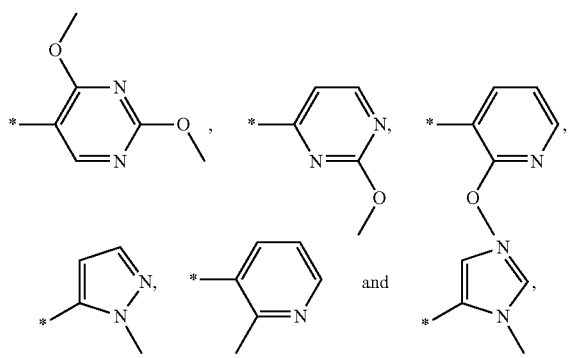

E17 A compound of formula (I) or a pharmaceutically acceptable salt thereof, according to any one of E1, E1.1, E1.2, E2, E3 and E7 to E16, wherein $R^1$ is methyl or chloro.

E18 A compound of formula (I) or a pharmaceutically acceptable salt thereof, according to any one of E1, E1.1, E1.2, E2, E3 and E7 to E17, wherein $R^1$ is methyl.

E19 A compound of formula (I) or a pharmaceutically acceptable salt thereof, according to any one of E1, E1.1, E1.2, E2, E3 and E7 to E18, wherein $R^2$ is chloro.

E20 A compound of formula (I) or a pharmaceutically acceptable salt thereof, according to any one of E1, E1.1, E1.2, E2 to E13 and E17 to E19, wherein ring C is i:

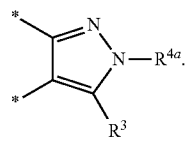

E21 A compound of formula (I) or a pharmaceutically acceptable salt thereof, according to any one of E1, E1.1, E1.2, E2 to DO and E14 to E19, wherein ring C is ii:

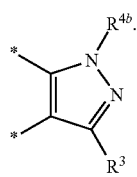

E22 A compound of formula (I) or a pharmaceutically acceptable salt thereof, according to any one of E1, E1.1, E1.2 and E2 to E21, wherein the stereochemistry is as shown in formula (Ia):

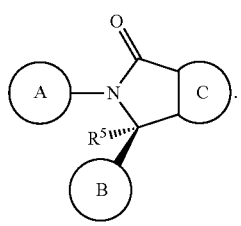

(Ia)

E23 A compound of formula (I) or a pharmaceutically acceptable salt thereof, according to any one of E1, E1.1, E1.2 and E2 to E21, wherein the compound is present as the racemate of the 2 enantiomeric forms (Ia) and (Ib) disclosed herein.

E24 A compound of formula (I) or a pharmaceutically acceptable salt thereof, according to any one of E1, E1.1, E1.2, E2 to E3 and E6 to E23, with the proviso that when ring C is selected from

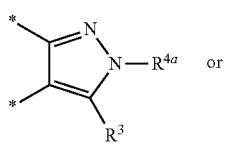  i.

or

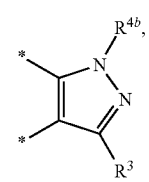  ii.

and A is:

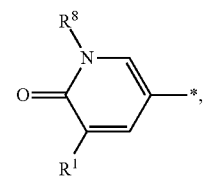

$R^1$ is selected from methyl, chloro and fluoro,

B is:

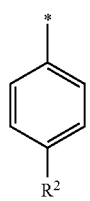

$R^2$ is chloro or —$CF_3$, and the remaining substituents are as defined herein, then $R^3$ is selected from H, methyl, ethyl, —$CF_3$, —OH, ethoxy and methoxy, or $R^3$ is selected from H, methyl, ethyl, —$CF_3$, —OH, ethoxy, methoxy, $CH_2OCH_3$ and $CH_2OH$, or $R^3$ is selected from $R^3$ is selected from H, methyl, ethyl, —$CH_2F$, —CF3, —OH, ethoxy, methoxy, —$CH_2OCH_3$ and —$CH_2OH$;

E25 A compound of formula (I) or a pharmaceutically acceptable salt thereof, according to any one of E1, E1.1, E1.2, E2, E3, E7, E11 to E20, E22 and E23, with the proviso that
when ring C is i:

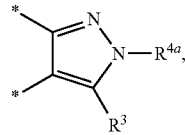

A is:

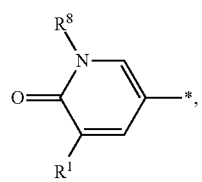

$R^1$ is selected from methyl, chloro and fluoro,
B is:

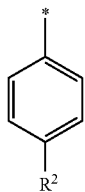

$R^2$ is chloro or —$CF_3$,
and the remaining substituents are as defined herein,
then $R^3$ is selected from H, methyl, ethyl, —$CF_3$, —OH, ethoxy and methoxy.

E26 A compound of formula (I) or a pharmaceutically acceptable salt thereof, according to any one of E1, E1.1, E1.2 and E2 to E10, wherein $R^{4a}$ is selected from H, ($C_1$-$C_4$)alkyl, ($C_3$-$C_6$)cycloalkyl, —($CH_2$)$_2$—OH and —($CH_2$)$_2$—O—$CH_3$;
or $R^{4a}$ is selected from

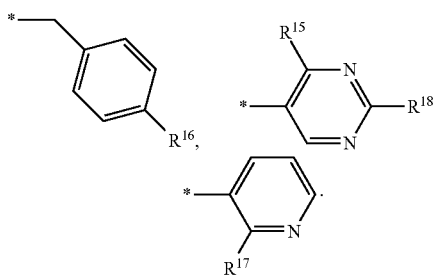

E27 A compound of formula (I) or a pharmaceutically acceptable salt thereof, according to any one of E1, E1.1, E1.2 and E2 to E10, wherein $R^{4b}$ is selected from H, ($C_1$-$C_4$)alkyl, ($C_3$-$C_6$)cycloalkyl, —($CH_2$)$_2$—OH, —($CH_2$)$_2$—O—$CH_3$, and —($CH_2$)$_2$—O—$CH_2$—$CF_3$;

or $R^{4b}$ is selected from

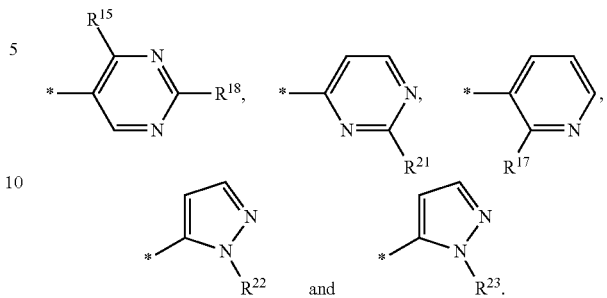

E28 a compound of formula (I) or a pharmaceutically acceptable salt thereof,

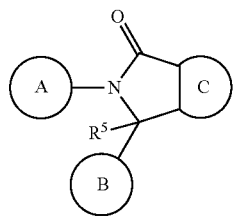

wherein
ring C is selected from

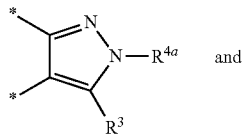

i.

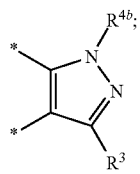

ii.

A is selected from

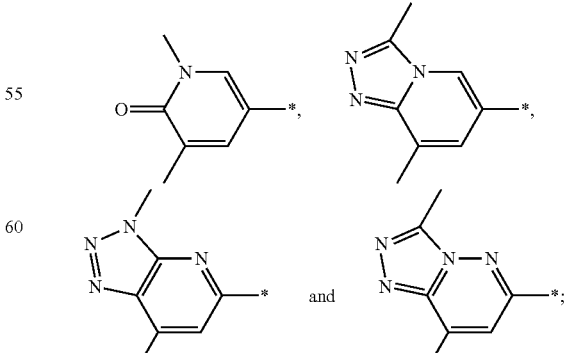

B is selected from

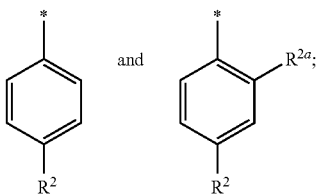

R³ is selected from methyl, ethyl, isopropyl, methoxy, —CH₂OCH₃ and —CH₂OH;
R⁴ᵃ is selected from (C₁-C₄)alkyl preferably methyl or isopropyl; (C₃-C₆)cycloalkyl, preferably cyclopropyl; and

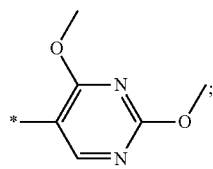

R⁴ᵇ is selected from H; (C₁-C₄)alkyl, preferably ethyl or isopropyl; (C₃-C₆)cycloalkyl, preferably cyclopropyl; —(CH₂)₂—OH; —(CH₂)₂—O—CH₃; —C(O)—N(CH₃)₂;

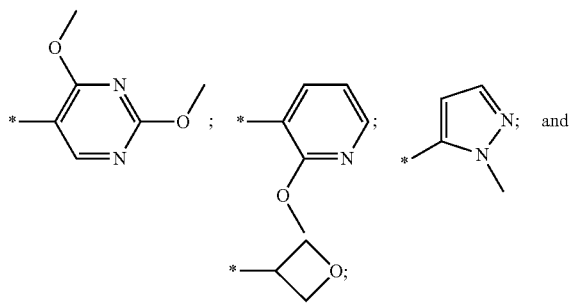

R⁵ is H;
R² is selected from chloro and fluoro;
R²ᵃ is fluoro;
and
* indicates the point of attachment to the remainder of the molecule;
with the proviso that
when ring C is i:

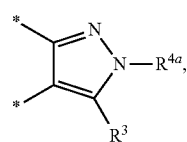

A is:

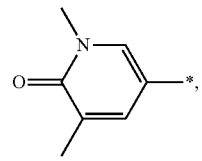

B is:

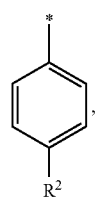

R² is chloro or fluoro,
and the remaining substituents are as defined herein,
then R³ is selected from methyl, ethyl, methoxy, —CH₂OCH₃ and —CH₂OH.

E29 A compound of formula (I) or a pharmaceutically acceptable salt thereof,

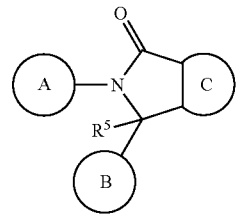
(I)

wherein
ring C is selected from

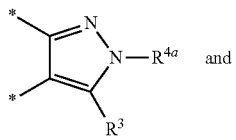
i.

and

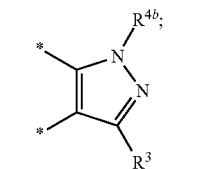
ii.

A is selected from

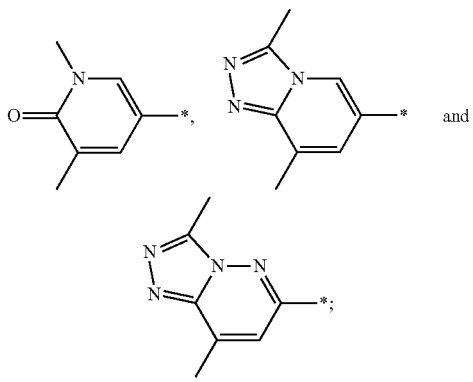

B is

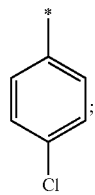

$R^3$ is selected from methyl, ethyl, isopropyl, —CH$_2$OCH$_3$ and —CH$_2$OH;
$R^{4a}$ is selected from (C$_3$-C$_6$)cycloalkyl, preferably cyclopropyl, and

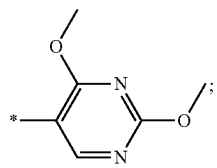 [SMILES: *c1cnc(OC)nc1OC]

$R^{4b}$ is selected from H and (C$_3$-C$_6$)cycloalkyl, preferably $R^{4b}$ is H or cyclopropyl;
$R^5$ is H;
and
* indicates the point of attachment to the remainder of the molecule;
with the proviso that
when ring C is i:

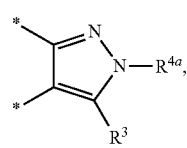

A is:

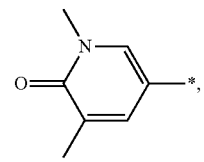

and the remaining substituents are as defined herein, then $R^3$ is selected from methyl, ethyl, —CH$_2$OCH$_3$ and —CH$_2$OH.

E30 A compound of formula (I), or a pharmaceutically acceptable salt thereof, according to any one of E1, E1.1, E1.2, E2, E4, E7, E9, E10, E15 and E21, wherein
A is

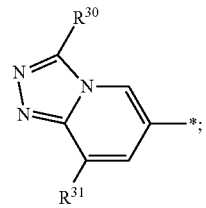

B is

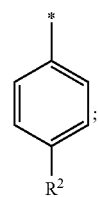

C is ii:

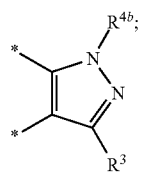

$R^2$ is chloro, —OCF$_3$ or —CF$_3$;
$R^3$ is selected from methyl, ethyl, isopropyl and methoxy, or $R^3$ is methyl;
$R^{4b}$ is cyclopropyl;
$R^{30}$ is methyl; and
$R^{31}$ is H, methyl or methoxy.

E31 A compound of formula (I), or a pharmaceutically acceptable salt thereof, according to any one of E1, E1.1, E1.2, E2, E3, E7, E9, E10, E15 and E21, wherein A is

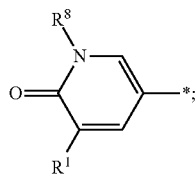

B is

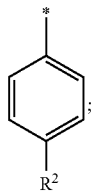

C is ii:

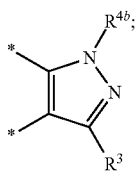

$R^2$ is chloro, —$OCF_3$ or —$CF_3$;
$R^3$ is selected from methyl, ethyl, isopropyl and methoxy, or $R^3$ is methyl;
$R^{4b}$ is cyclopropyl;
$R^1$ is selected from H, methyl, chloro and fluoro; and
$R^8$ is methyl.

E32 A compound of formula (I) or a pharmaceutically acceptable salt thereof, according to E1, selected from:

Example 1: 4-(4-chlorophenyl)-2-(4-methoxybenzyl)-3-methyl-5-(1-methyl-6-oxo-1,6-dihydropyridin-3-yl)-4,5-dihydropyrrolo[3,4-c]pyrazol-6(2H)-one Example 2: 4-(4-chlorophenyl)-3-methyl-5-(1-methyl-6-oxo-1,6-dihydropyridin-3-yl)-4,5-dihydropyrrolo[3,4-c]pyrazol-6(2H)-one Example 3: 4-(4-chlorophenyl)-2,3-dimethyl-5-(1-methyl-6-oxo-1,6-dihydropyridin-3-yl)-4,5-dihydropyrrolo[3,4-c]pyrazol-6(2H)-one Example 4: 4-(4-chlorophenyl)-1,3-dimethyl-5-(1-methyl-6-oxo-1,6-dihydropyridin-3-yl)-4,5-dihydropyrrolo[3,4-c]pyrazol-6(1H)-one Example 5: 5-(5-chloro-1-methyl-6-oxo-1,6-dihydropyridin-3-yl)-4-(4-chlorophenyl)-3-methyl-4,5-dihydropyrrolo[3,4-c]pyrazol-6(2H)-one Example 6: 5-(5-chloro-1-methyl-6-oxo-1,6-dihydropyridin-3-yl)-4-(4-chlorophenyl)-2,3-dimethyl-4,5-dihydropyrrolo[3,4-c]pyrazol-6(2H)-one Example 7: (R)-5-(5-chloro-1-methyl-6-oxo-1,6-dihydropyridin-3-yl)-4-(4-chlorophenyl)-2,3-dimethyl-4,5-dihydropyrrolo[3,4-c]pyrazol-6(2H)-one Example 9: 5-(5-chloro-1-methyl-6-oxo-1,6-dihydropyridin-3-yl)-4-(4-chlorophenyl)-4,5-dihydropyrrolo[3,4-c]pyrazol-6(2H)-one Example 10: 5-(5-chloro-1-methyl-6-oxo-1,6-dihydropyridin-3-yl)-4-(4-chlorophenyl)-2-methyl-4,5-dihydropyrrolo[3,4-c]pyrazol-6(2H)-one Example 11: (R)-5-(5-chloro-1-methyl-6-oxo-1,6-dihydropyridin-3-yl)-4-(4-chlorophenyl)-2-methyl-4,5-dihydropyrrolo[3,4-c]pyrazol-6(2H)-one Example 13: 4-(4-chlorophenyl)-5-(1,5-dimethyl-6-oxo-1,6-dihydropyridin-3-yl)-2-methyl-4,5-dihydropyrrolo[3,4-c]pyrazol-6(2H)-one Example 14: 4-(4-chlorophenyl)-5-(5-fluoro-1-methyl-6-oxo-1,6-dihydropyridin-3-yl)-2-methyl-4,5-dihydropyrrolo[3,4-c]pyrazol-6(2H)-one Example 16: (R)-4-(4-chlorophenyl)-5-(1,5-dimethyl-6-oxo-1,6-dihydropyridin-3-yl)-2-methyl-4,5-dihydropyrrolo[3,4-c]pyrazol-6(2H)-one Example 17: 5-(5-chloro-1-methyl-6-oxo-1,6-dihydropyridin-3-yl)-4-(4-chlorophenyl)-2-cyclopropyl-3-methyl-4,5-dihydropyrrolo[3,4-c]pyrazol-6(2H)-one Example 19: (R)-5-(5-chloro-1-methyl-6-oxo-1,6-dihydropyridin-3-yl)-4-(4-chlorophenyl)-2-cyclopropyl-3-methyl-4,5-dihydropyrrolo[3,4-c]pyrazol-6(2H)-one Example 20: 4-(4-chlorophenyl)-2-cyclopropyl-5-(1,5-dimethyl-6-oxo-1,6-dihydropyridin-3-yl)-3-methyl-4,5-dihydropyrrolo[3,4-c]pyrazol-6(2H)-one Example 21: (R)-4-(4-chlorophenyl)-2-cyclopropyl-5-(1,5-dimethyl-6-oxo-1,6-dihydropyridin-3-yl)-3-methyl-4,5-dihydropyrrolo[3,4-c]pyrazol-6(2H)-one Example 23: 4-(4-chlorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one Example 24: 5-(5-chloro-1-methyl-6-oxo-1,6-dihydropyridin-3-yl)-4-(4-chlorophenyl)-1-cyclopropyl-3-methyl-4,5-dihydropyrrolo[3,4-c]pyrazol-6(1H)-one Example 25: 4-(4-chlorophenyl)-2,3-dimethyl-5-(3-methyl-[1,2,4]triazolo[4,3-a]pyridin-6-yl)-4,5-dihydropyrrolo[3,4-c]pyrazol-6(2H)-one Example 26: 4-(4-chlorophenyl)-5-(1,5-dimethyl-6-oxo-1,6-dihydropyridin-3-yl)-4,5-dihydropyrrolo[3,4-c]pyrazol-6(2H)-one Example 27: 4-(4-chlorophenyl)-5-(1,5-dimethyl-6-oxo-1,6-dihydropyridin-3-yl)-3-methyl-4,5-dihydropyrrolo[3,4-c]pyrazol-6(2H)-one Example 28: 4-(4-chlorophenyl)-5-(1,5-dimethyl-6-oxo-1,6-dihydropyridin-3-yl)-2,3-dimethyl-4,5-dihydropyrrolo[3,4-c]pyrazol-6(2H)-one Example 30: (R)-4-(4-chlorophenyl)-5-(1,5-dimethyl-6-oxo-1,6-dihydropyridin-3-yl)-2,3-dimethyl-4,5-dihydropyrrolo[3,4-c]pyrazol-6(2H)-one Example 31: 4-(4-chlorophenyl)-5-(5-fluoro-1-methyl-6-oxo-1,6-dihydropyridin-3-yl)-2,3-dimethyl-4,5-dihydropyrrolo[3,4-c]pyrazol-6(2H)-one Example 32: 4-(4-chlorophenyl)-2,3-dimethyl-5-(1-methyl-6-oxo-1,6-dihydropyridazin-3-yl)-4,5-dihydropyrrolo[3,4-c]pyrazol-6(2H)-one Example 33: 4-(4-chlorophenyl)-2,3-dimethyl-5-(3-methylbenzo[d]isoxazol-5-yl)-4,5-dihydropyrrolo[3,4-c]pyrazol-6(2H)-one Example 34: 4-(4-chlorophenyl)-1-cyclopropyl-5-(1,5-dimethyl-6-oxo-1,6-dihydropyridin-3-yl)-4,5-dihydropyrrolo[3,4-c]pyrazol-6(1H)-one Example 35: 5-(5-chloro-1-methyl-6-oxo-1,6-dihydropyridin-3-yl)-4-(4-chlorophenyl)-1-cyclopropyl-4,5-dihydropyrrolo[3,4-c]pyrazol-6(1H)-one Example 36: 4-(4-chlorophenyl)-5-(1,5-dimethyl-6-oxo-1,6-dihydropyridin-3-yl)-1-isopropyl-4,5-dihydropyrrolo[3,4-c]pyrazol-6(1H)-one Example 37: 5-(5-chloro-1-methyl-6-oxo-1,6-dihydropyridin-3-yl)-4-(4-chlorophenyl)-2-cyclopropyl-4,5-dihydropyrrolo[3,4-c]pyrazol-6(2H)-one Example 38: 5-(5-chloro-1-methyl-6-oxo-1,6-dihydropyridin-3-yl)-4-(4-chlorophenyl)-1-isopropyl-4,5-dihydropyrrolo[3,4-c]pyrazol-6(1H)-one
Example 39: 4-(4-chlorophenyl)-2-cyclopropyl-5-(1,5-dimethyl-6-oxo-1,6-dihydropyridin-3-yl)-4,5-dihydropyrrolo[3,4-c]pyrazol-6(2H)-one
Example 40: 5-(5-chloro-1-methyl-6-oxo-1,6-dihydropyridin-3-yl)-4-(4-chlorophenyl)-2-cyclopropyl-3-(trifluoromethyl)-4,5-dihydropyrrolo[3,4-c]pyrazol-6(2H)-one
Example 41: 4-(4-chlorophenyl)-5-(1,5-dimethyl-6-oxo-1,6-dihydropyridin-3-yl)-2-isopropyl-4,5-dihydropyrrolo[3,4-c]pyrazol-6(2H)-one
Example 42: 5-(5-chloro-1-methyl-6-oxo-1,6-dihydropyridin-3-yl)-4-(4-chlorophenyl)-2-isopropyl-4,5-dihydropyrrolo[3,4-c]pyrazol-6(2H)-one
Example 43: 4-(4-chlorophenyl)-2-cyclopropyl-5-(1,5-dimethyl-6-oxo-1,6-dihydropyridin-3-yl)-3-(trifluoromethyl)-4,5-dihydropyrrolo[3,4-c]pyrazol-6(2H)-one
Example 44: 5-(5-chloro-1-methyl-6-oxo-1,6-dihydropyridin-3-yl)-4-(4-chlorophenyl)-1-cyclopropyl-3-(trifluoromethyl)-4,5-dihydropyrrolo[3,4-c]pyrazol-6(1H)-one
Example 45: 4-(4-chlorophenyl)-1-cyclopropyl-5-(1,5-dimethyl-6-oxo-1,6-dihydropyridin-3-yl)-3-(trifluoromethyl)-4,5-dihydropyrrolo[3,4-c]pyrazol-6(1H)-one
Example 46: 4-(4-chlorophenyl)-2-(2,4-dimethoxypyrimidin-5-yl)-5-(3,7-dimethylbenzo[d]-isoxazol-5-yl)-3-isopropyl-4,5-dihydropyrrolo[3,4-c]pyrazol-6(2H)-one
Example 47: 5-(5-chloro-1-methyl-6-oxo-1,6-dihydropyridin-3-yl)-4-(4-chlorophenyl)-2-(2,4-dimethoxypyrimidin-5-yl)-3-(trifluoromethyl)-4,5-dihydropyrrolo[3,4-c]pyrazol-6(2H)-one
Example 49: (R)-4-(4-chlorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one
Example 51: (R)-5-(5-chloro-1-methyl-6-oxo-1,6-dihydropyridin-3-yl)-4-(4-chlorophenyl)-1-cyclopropyl-3-methyl-4,5-dihydropyrrolo[3,4-c]pyrazol-6(1H)-one
Example 52: 4-(4-chlorophenyl)-1-(2,4-dimethoxypyrimidin-5-yl)-5-(1,5-dimethyl-6-oxo-1,6-dihydropyridin-3-yl)-3-methyl-4,5-dihydropyrrolo[3,4-c]pyrazol-6(1H)-one
Example 53: 5-(5-chloro-1-methyl-6-oxo-1,6-dihydropyridin-3-yl)-4-(4-chlorophenyl)-1-(2,4-dimethoxypyrimidin-5-yl)-3-methyl-4,5-dihydropyrrolo[3,4-c]pyrazol-6(1H)-one
Example 54: 4-(4-chlorophenyl)-2-(2,4-dimethoxypyrimidin-5-yl)-3-isopropyl-5-(3-methylbenzo-[d]isoxazol-5-yl)-4,5-dihydropyrrolo[3,4-c]pyrazol-6(2H)-one
Example 55: 5-(5-chloro-1-methyl-6-oxo-1,6-dihydropyridin-3-yl)-4-(4-chlorophenyl)-2-(2,4-dimethoxypyrimidin-5-yl)-3-methyl-4,5-dihydropyrrolo[3,4-c]pyrazol-6(2H)-one
Example 56: 4-(4-chlorophenyl)-2-(2,4-dimethoxypyrimidin-5-yl)-5-(1,5-dimethyl-6-oxo-1,6-dihydropyridin-3-yl)-3-methyl-4,5-dihydropyrrolo[3,4-c]pyrazol-6(2H)-one
Example 57: 4-(4-chlorophenyl)-5-(1,5-dimethyl-6-oxo-1,6-dihydropyridin-3-yl)-1,3-dimethyl-4,5-dihydropyrrolo[3,4-c]pyrazol-6(1H)-one
Example 58: 5-(5-chloro-1-methyl-6-oxo-1,6-dihydropyridin-3-yl)-4-(4-chlorophenyl)-1,3-dimethyl-4,5-dihydropyrrolo[3,4-c]pyrazol-6(1H)-one
Example 59: 4-(4-chlorophenyl)-5-(1,5-dimethyl-6-oxo-1,6-dihydropyridin-3-yl)-1-(2-methoxypyrimidin-4-yl)-3-methyl-4,5-dihydropyrrolo[3,4-c]pyrazol-6(1H)-one
Example 60: 4-(4-chlorophenyl)-1-(2,4-dimethoxypyrimidin-5-yl)-5-(1,5-dimethyl-6-oxo-1,6-dihydropyridin-3-yl)-3-ethyl-4,5-dihydropyrrolo[3,4-c]pyrazol-6(1H)-one
Example 62: (R)-4-(4-chlorophenyl)-2-(2,4-dimethoxypyrimidin-5-yl)-5-(3,7-dimethylbenzo[d]-isoxazol-5-yl)-3-isopropyl-4,5-dihydropyrrolo[3,4-c]pyrazol-6(2H)-one
Example 63: 4-(4-chlorophenyl)-5-(1,5-dimethyl-6-oxo-1,6-dihydropyridin-3-yl)-1-isopropyl-3-methyl-4,5-dihydropyrrolo[3,4-c]pyrazol-6(1H)-one
Example 64: 4-(4-chlorophenyl)-5-(1,5-dimethyl-6-oxo-1,6-dihydropyridin-3-yl)-2-isopropyl-3-methyl-4,5-dihydropyrrolo[3,4-c]pyrazol-6(2H)-one
Example 65: 5-(5-chloro-1-methyl-6-oxo-1,6-dihydropyridin-3-yl)-4-(4-chlorophenyl)-2-isopropyl-3-methyl-4,5-dihydropyrrolo[3,4-c]pyrazol-6(2H)-one
Example 66: 5-(5-chloro-1-methyl-6-oxo-1,6-dihydropyridin-3-yl)-4-(4-chlorophenyl)-1-isopropyl-3-methyl-4,5-dihydropyrrolo[3,4-c]pyrazol-6(1H)-one
Example 67: 4-(4-chlorophenyl)-2-(2,4-dimethoxypyrimidin-5-yl)-5-(3,8-dimethyl-[1,2,4]triazolo-[4,3-a]pyridin-6-yl)-3-isopropyl-4,5-dihydropyrrolo[3,4-c]pyrazol-6(2H)-one
Example 68: 4-(4-chlorophenyl)-2-cyclopropyl-5-(1,5-dimethyl-6-oxo-1,6-dihydropyridin-3-yl)-3-ethyl-4,5-dihydropyrrolo[3,4-c]pyrazol-6(2H)-one
Example 69: 4-(4-chlorophenyl)-1-cyclopropyl-5-(1,5-dimethyl-6-oxo-1,6-dihydropyridin-3-yl)-3-ethyl-4,5-dihydropyrrolo[3,4-c]pyrazol-6(1H)-one
Example 70: 4-(4-chlorophenyl)-1-cyclopropyl-5-(3,8-dimethyl-[1,2,4]triazolo[4,3-a]pyridin-6-yl)-3-ethyl-4,5-dihydropyrrolo[3,4-c]pyrazol-6(1H)-one
Example 71: 4-(4-chlorophenyl)-5-(1,5-dimethyl-6-oxo-1,6-dihydropyridin-3-yl)-1-(2-methoxypyridin-3-yl)-3-methyl-4,5-dihydropyrrolo[3,4-c]pyrazol-6(1H)-one
Example 72: 5-(5-chloro-1-methyl-6-oxo-1,6-dihydropyridin-3-yl)-4-(4-chlorophenyl)-1-(2-methoxypyridin-3-yl)-3-methyl-4,5-dihydropyrrolo[3,4-c]pyrazol-6(1H)-one
Example 73: 4-(4-chlorophenyl)-5-(1,5-dimethyl-6-oxo-1,6-dihydropyridin-3-yl)-3-hydroxy-2-methyl-4,5-dihydropyrrolo[3,4-c]pyrazol-6(2H)-one
Example 74: 4-(4-chlorophenyl)-5-(1,5-dimethyl-6-oxo-1,6-dihydropyridin-3-yl)-3-methyl-1-(1-methyl-1H-pyrazol-5-yl)-4,5-dihydropyrrolo[3,4-c]pyrazol-6(1H)-one
Example 76: 4-(4-chlorophenyl)-5-(1,5-dimethyl-6-oxo-1,6-dihydropyridin-3-yl)-3-ethoxy-2-methyl-4,5-dihydropyrrolo[3,4-c]pyrazol-6(2H)-one
Example 77: 4-(4-chlorophenyl)-5-(1,5-dimethyl-6-oxo-1,6-dihydropyridin-3-yl)-3-methoxy-2-methyl-4,5-dihydropyrrolo[3,4-c]pyrazol-6(2H)-one
Example 78: 4-(4-chlorophenyl)-5-(1,5-dimethyl-6-oxo-1,6-dihydropyridin-3-yl)-3-ethyl-1-(2-hydroxyethyl)-4,5-dihydropyrrolo[3,4-c]pyrazol-6(1H)-one
Example 79: 4-(4-chlorophenyl)-5-(3,7-dimethylbenzo[d]isoxazol-5-yl)-3-ethyl-1-(2-hydroxyethyl)-4,5-dihydropyrrolo[3,4-c]pyrazol-6(1H)-one
Example 80: 4-(4-chlorophenyl)-5-(3,7-dimethylbenzo[d]isoxazol-5-yl)-3-ethyl-2-(2-hydroxyethyl)-4,5-dihydropyrrolo[3,4-c]pyrazol-6(2H)-one
Example 81: 4-(4-chlorophenyl)-5-(1,5-dimethyl-6-oxo-1,6-dihydropyridin-3-yl)-3-methyl-2-(2-methylpyridin-3-yl)-4,5-dihydropyrrolo[3,4-c]pyrazol-6(2H)-one
Example 82: 4-(4-chlorophenyl)-5-(1,5-dimethyl-6-oxo-1,6-dihydropyridin-3-yl)-3-methyl-1-(2-methylpyridin-3-yl)-4,5-dihydropyrrolo[3,4-c]pyrazol-6(1H)-one
Example 83: 4-(4-chlorophenyl)-5-(1,5-dimethyl-6-oxo-1,6-dihydropyridin-3-yl)-3-methyl-1-(1-methyl-1H-imidazol-5-yl)-4,5-dihydropyrrolo[3,4-c]pyrazol-6(1H)-one
Example 84: 4-(4-chlorophenyl)-1-cyclopropyl-3-ethyl-5-(8-methoxy-3-methyl-[1,2,4]triazolo[4,3-a]pyridin-6-yl)-4,5-dihydropyrrolo[3,4-c]pyrazol-6(1H)-one
Example 85: 4-(4-chlorophenyl)-1-cyclopropyl-5-(1,4-dimethyl-1H-benzo[d][1,2,3]triazol-6-yl)-3-methyl-4,5-dihydropyrrolo[3,4-c]pyrazol-6(1H)-one Example 86: 4-(4-chlorophenyl)-5-(1,5-dimethyl-6-oxo-1,6-dihydropyridin-3-yl)-3-ethyl-1-(2-methoxyethyl)-4,5-dihydropyrrolo[3,4-c]pyrazol-6(1H)-one
Example 87: 4-(4-chlorophenyl)-5-(3,8-dimethyl-[1,2,4]triazolo[4,3-a]pyridin-6-yl)-3-ethyl-1-(2-methoxyethyl)-4,5-dihydropyrrolo[3,4-c]pyrazol-6(1H)-one
Example 88: 4-(4-chlorophenyl)-5-(3,8-dimethyl-[1,2,4]triazolo[4,3-a]pyridin-6-yl)-3-ethyl-2-(2-methoxyethyl)-4,5-dihydropyrrolo[3,4-c]pyrazol-6(2H)-one
Example 89: 4-(4-chlorophenyl)-5-(1,5-dimethyl-6-oxo-1,6-dihydropyridin-3-yl)-3-ethyl-1-(1-methyl-1H-pyrazol-5-yl)-4,5-dihydropyrrolo[3,4-c]pyrazol-6(1H)-one
Example 90: 4-(4-chlorophenyl)-5-(3,8-dimethyl-[1,2,4]triazolo[4,3-a]pyridin-6-yl)-3-methyl-1-(1-methyl-1H-pyrazol-5-yl)-4,5-dihydropyrrolo[3,4-c]pyrazol-6(1H)-one
Example 91: 1-cyclopropyl-5-(1,5-dimethyl-6-oxo-1,6-dihydropyridin-3-yl)-3-methyl-4-(3-(trifluoromethoxy)phenyl)-4,5-dihydropyrrolo[3,4-c]pyrazol-6(1H)-one
Example 92: 4-(4-chlorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one
Example 93: 4-(4-chlorophenyl)-2-cyclopropyl-5-(3,8-dimethyl-[1,2,4]triazolo[4,3-a]pyridin-6-yl)-3-methyl-4,5-dihydropyrrolo[3,4-c]pyrazol-6(2H)-one
Example 94: 4-(4-chlorophenyl)-1-cyclobutyl-5-(1,5-dimethyl-6-oxo-1,6-dihydropyridin-3-yl)-3-methyl-4,5-dihydropyrrolo[3,4-c]pyrazol-6(1H)-one
Example 95: 1-cyclopropyl-5-(1,5-dimethyl-6-oxo-1,6-dihydropyridin-3-yl)-3-methyl-4-(4-(trifluoromethoxy)phenyl)-4,5-dihydropyrrolo[3,4-c]pyrazol-6(1H)-one
Example 96: 1-cyclopropyl-5-(1,5-dimethyl-6-oxo-1,6-dihydropyridin-3-yl)-3-methyl-4-(3-(trifluoromethyl)phenyl)-4,5-dihydropyrrolo[3,4-c]pyrazol-6(1H)-one
Example 97: 1-cyclopropyl-5-(1,5-dimethyl-6-oxo-1,6-dihydropyridin-3-yl)-3-methyl-4-(4-(trifluoromethyl)phenyl)-4,5-dihydropyrrolo[3,4-c]pyrazol-6(1H)-one
Example 98: 4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one
Example 100: (R)-4-(4-chlorophenyl)-1-(2,4-dimethoxypyrimidin-5-yl)-5-(1,5-dimethyl-6-oxo-1,6-dihydropyridin-3-yl)-3-methyl-4,5-dihydropyrrolo[3,4-c]pyrazol-6(1H)-one
Example 101: 4-(4-chlorophenyl)-5-(3,8-dimethyl-[1,2,4]triazolo[4,3-a]pyridin-6-yl)-1-(2-methoxypyridin-3-yl)-3-methyl-4,5-dihydropyrrolo[3,4-c]pyrazol-6(1H)-one
Example 102: 4-(4-chlorophenyl)-1-cyclopropyl-3-methyl-5-(3-methyl-3H-[1,2,3]triazolo[4,5-b]-pyridin-5-yl)-4,5-dihydropyrrolo[3,4-c]pyrazol-6(1H)-one
Example 104: (R)-4-(4-chlorophenyl)-5-(1,5-dimethyl-6-oxo-1,6-dihydropyridin-3-yl)-1-isopropyl-3-methyl-4,5-dihydropyrrolo[3,4-c]pyrazol-6(1H)-one
Example 105: 4-(4-chlorophenyl)-3-ethyl-5-(8-methoxy-3-methyl-[1,2,4]triazolo[4,3-a]pyridin-6-yl)-1-methyl-4,5-dihydropyrrolo[3,4-c]pyrazol-6(1H)-one
Example 107: (R)-4-(4-chlorophenyl)-1-cyclopropyl-5-(3,8-dimethyl-[1,2,4]triazolo[4,3-a]pyridin-6-yl)-3-ethyl-4,5-dihydropyrrolo[3,4-c]pyrazol-6(1H)-one
Example 108: 4-(4-chlorophenyl)-3-ethyl-5-(8-methoxy-3-methyl-[1,2,4]triazolo[4,3-a]pyridin-6-yl)-1-(2-(2,2,2-trifluoroethoxy)ethyl)-4,5-dihydropyrrolo[3,4-c]pyrazol-6(1H)-one
Example 109: 4-(4-chlorophenyl)-5-(3,7-dimethyl-3H-[1,2,3]triazolo[4,5-b]pyridin-5-yl)-1-(2-methoxypyridin-3-yl)-3-methyl-4,5-dihydropyrrolo[3,4-c]pyrazol-6(1H)-one
Example 110: 4-(4-chlorophenyl)-1-cyclopropyl-5-(3,7-dimethyl-3H-[1,2,3]triazolo[4,5-b]pyridin-5-yl)-3-methyl-4,5-dihydropyrrolo[3,4-c]pyrazol-6(1H)-one
Example 111: 4-(4-chlorophenyl)-5-(3,8-dimethyl-[1,2,4]triazolo[4,3-b]pyridazin-6-yl)-1-(2-methoxypyridin-3-yl)-3-methyl-4,5-dihydropyrrolo[3,4-c]pyrazol-6(1H)-one
Example 113: 4-(4-chlorophenyl)-1-cyclopropyl-3-methyl-5-(3-methyl-8-(methylamino)-[1,2,4]triazolo[4,3-b]pyridazin-6-yl)-4,5-dihydropyrrolo[3,4-c]pyrazol-6(1H)-one
Example 114: 4-(4-chlorophenyl)-5-(3,8-dimethyl-[1,2,4]triazolo[4,3-b]pyridazin-6-yl)-3-methyl-1-(1-methyl-1H-pyrazol-5-yl)-4,5-dihydropyrrolo[3,4-c]pyrazol-6(1H)-one
Example 115: 4-(4-chlorophenyl)-5-(3,8-dimethyl-[1,2,4]triazolo[4,3-a]pyridin-6-yl)-2-ethyl-3-methyl-4,5-dihydropyrrolo[3,4-c]pyrazol-6(2H)-one
Example 116: 4-(4-chlorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one
Example 117: 4-(4-chlorophenyl)-3-cyclopropyl-5-(3,8-dimethyl-[1,2,4]triazolo[4,3-a]pyridin-6-yl)-1-(1-methyl-1H-pyrazol-5-yl)-4,5-dihydropyrrolo[3,4-c]pyrazol-6(1H)-one
Example 119: (R)-4-(4-chlorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one
Example 120: (R)-4-(4-chlorophenyl)-5-(1,5-dimethyl-6-oxo-1,6-dihydropyridin-3-yl)-3-methyl-1-(1-methyl-1H-pyrazol-5-yl)-4,5-dihydropyrrolo[3,4-c]pyrazol-6(1H)-one
Example 122: (R)-4-(4-chlorophenyl)-1-cyclopropyl-5-(3,8-dimethyl-[1,2,4]triazolo[4,3-b]-pyridazin-6-yl)-3-methyl-4,5-dihydropyrrolo[3,4-c]pyrazol-6(1H)-one
Example 125: (R)-4-(4-chlorophenyl)-5-(3,8-dimethyl-[1,2,4]triazolo[4,3-a]pyridin-6-yl)-3-methyl-1-(1-methyl-1H-pyrazol-5-yl)-4,5-dihydropyrrolo[3,4-c]pyrazol-6(1H)-one
Example 126: N-(6-(4-(4-chlorophenyl)-1-cyclopropyl-3-methyl-6-oxopyrrolo[3,4-c]pyrazol-5-(1H,4H,6H)-yl)-3-methyl-[1,2,4]triazolo[4,3-b]pyridazin-8-yl)acetamide
Example 128: (R)-4-(4-chlorophenyl)-5-(1,5-dimethyl-6-oxo-1,6-dihydropyridin-3-yl)-1-(2-methoxypyridin-3-yl)-3-methyl-4,5-dihydropyrrolo[3,4-c]pyrazol-6(1H)-one
Example 129: 4-(4-chlorophenyl)-3-cyclopropyl-5-(3,8-dimethyl-[1,2,4]triazolo[4,3-a]pyridin-6-yl)-1-methyl-4,5-dihydropyrrolo[3,4-c]pyrazol-6(1H)-one
Example 130: 4-(4-chlorophenyl)-1-cyclopropyl-5-(3,8-dimethyl-[1,2,4]triazolo[4,3-a]pyridin-6-yl)-3-(methoxymethyl)-4,5-dihydropyrrolo[3,4-c]pyrazol-6(1H)-one
Example 131: 4-(4-chlorophenyl)-1-cyclopropyl-5-(3,8-dimethyl-[1,2,4]triazolo[4,3-a]pyridin-6-yl)-3-(hydroxymethyl)-4,5-dihydropyrrolo[3,4-c]pyrazol-6(1H)-one
Example 132: 4-(4-chlorophenyl)-1-cyclopropyl-5-(1,5-dimethyl-6-oxo-1,6-dihydropyridin-3-yl)-3-(methoxymethyl)-4,5-dihydropyrrolo[3,4-c]pyrazol-6(1H)-one
Example 133: 4-(4-chlorophenyl)-1-cyclopropyl-5-(1,5-dimethyl-6-oxo-1,6-dihydropyridin-3-yl)-3-(hydroxymethyl)-4,5-dihydropyrrolo[3,4-c]pyrazol-6(1H)-one
Example 134: 4-(4-chlorophenyl)-5-(1,5-dimethyl-6-oxo-1,6-dihydropyridin-3-yl)-3-methyl-2-(oxetan-3-yl)-4,5-dihydropyrrolo[3,4-c]pyrazol-6(2H)-one
Example 135: 4-(4-chlorophenyl)-5-(1,5-dimethyl-6-oxo-1,6-dihydropyridin-3-yl)-3-methyl-1-(oxetan-3-yl)-4,5-dihydropyrrolo[3,4-c]pyrazol-6(1H)-one
Example 136: 4-(4-chlorophenyl)-5-(3,8-dimethyl-[1,2,4]triazolo[4,3-a]pyridin-6-yl)-3-methyl-2-(oxetan-3-yl)-4,5-dihydropyrrolo[3,4-c]pyrazol-6(2H)-one
Example 137: 4-(4-chlorophenyl)-5-(3,8-dimethyl-[1,2,4]triazolo[4,3-a]pyridin-6-yl)-3-methyl-1-(oxetan-3-yl)-4,5-dihydropyrrolo[3,4-c]pyrazol-6(1H)-one
Example 138: 1-(azetidin-3-yl)-4-(4-chlorophenyl)-5-(1,5-dimethyl-6-oxo-1,6-dihydropyridin-3-yl)-3-methyl-4,5-dihydropyrrolo[3,4-c]pyrazol-6(1H)-one Example 139: 4-(4-chlorophenyl)-5-(1,5-dimethyl-6-oxo-1,6-dihydropyridin-3-yl)-3-methyl-2-(1-methylazetidin-3-yl)-4,5-dihydropyrrolo[3,4-c]pyrazol-6(2H)-one
Example 140: 4-(4-chlorophenyl)-5-(1,5-dimethyl-6-oxo-1,6-dihydropyridin-3-yl)-3-methyl-1-(1-methylazetidin-3-yl)-4,5-dihydropyrrolo[3,4-c]pyrazol-6(1H)-one
Example 141: 4-(4-chlorophenyl)-5-(1,5-dimethyl-6-oxo-1,6-dihydropyridin-3-yl)-N,N,3-trimethyl-6-oxo-5,6-dihydropyrrolo[3,4-c]pyrazole-2(4H)-carboxamide
Example 142: 4-(4-chlorophenyl)-5-(1,5-dimethyl-6-oxo-1,6-dihydropyridin-3-yl)-N,N,3-trimethyl-6-oxo-5,6-dihydropyrrolo[3,4-c]pyrazole-1(4H)-carboxamide
Example 143: 4-(4-chlorophenyl)-5-(1,5-dimethyl-6-oxo-1,6-dihydropyridin-3-yl)-N,3-dimethyl-6-oxo-5,6-dihydropyrrolo[3,4-c]pyrazole-1(4H)-carboxamide
Example 144: 4-(4-chlorophenyl)-5-(1,5-dimethyl-6-oxo-1,6-dihydropyridin-3-yl)-N,3-dimethyl-6-oxo-5,6-dihydropyrrolo[3,4-c]pyrazole-2(4H)-carboxamide
Example 145: 4-(4-chlorophenyl)-5-(3,8-dimethyl-[1,2,4]triazolo[4,3-a]pyridin-6-yl)-N,3-dimethyl-6-oxo-5,6-dihydropyrrolo[3,4-c]pyrazole-1(4H)-carboxamide
Example 146: 4-(4-chlorophenyl)-5-(3,8-dimethyl-[1,2,4]triazolo[4,3-a]pyridin-6-yl)-N,3-dimethyl-6-oxo-5,6-dihydropyrrolo[3,4-c]pyrazole-2(4H)-carboxamide
Example 147: 4-(4-chlorophenyl)-5-(1,5-dimethyl-6-oxo-1,6-dihydropyridin-3-yl)-3-ethyl-N,N-dimethyl-6-oxo-5,6-dihydropyrrolo[3,4-c]pyrazole-1(4H)-carboxamide
Example 148: 4-(4-chlorophenyl)-5-(1,5-dimethyl-6-oxo-1,6-dihydropyridin-3-yl)-3-ethyl-N,N-dimethyl-6-oxo-5,6-dihydropyrrolo[3,4-c]pyrazole-2(4H)-carboxamide
Example 149: (R)-4-(4-chlorophenyl)-5-(3,8-dimethyl-[1,2,4]triazolo[4,3-a]pyridin-6-yl)-N,N,3-trimethyl-6-oxo-5,6-dihydropyrrolo[3,4-c]pyrazole-1(4H)-carboxamide
Example 150: (R)-4-(4-chlorophenyl)-5-(3,8-dimethyl-[1,2,4]triazolo[4,3-a]pyridin-6-yl)-N,N,3-trimethyl-6-oxo-5,6-dihydropyrrolo[3,4-c]pyrazole-2(4H)-carboxamide
Example 151: 1-(azetidin-3-yl)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one
Example 152: 2-(azetidin-3-yl)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(2H)-one
Example 153: 1-(1-acetylazetidin-3-yl)-4-(4-chlorophenyl)-5-(1,5-dimethyl-6-oxo-1,6-dihydropyridin-3-yl)-3-methyl-4,5-dihydropyrrolo[3,4-c]pyrazol-6(1H)-one
Example 154: 1-(1-acetylazetidin-3-yl)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one
Example 155: Ethyl 3-(4-(4-chlorophenyl)-5-(1,5-dimethyl-6-oxo-1,6-dihydropyridin-3-yl)-3-methyl-6-oxo-5,6-dihydropyrrolo[3,4-c]pyrazol-1(4H)-yl)azetidine-1-carboxylate
Example 156: Ethyl 3-(4-(4-chlorophenyl)-5-(3,8-dimethyl-[1,2,4]triazolo[4,3-a]pyridin-6-yl)-3-methyl-6-oxo-5,6-dihydropyrrolo[3,4-c]pyrazol-1(4H)-yl)azetidine-1-carboxylate
Example 157: 4-(4-chlorophenyl)-5-(3,8-dimethyl-[1,2,4]triazolo[4,3-a]pyridin-6-yl)-3-methyl-1-(1-methylazetidin-3-yl)-4,5-dihydropyrrolo[3,4-c]pyrazol-6(1H)-one
Example 158: 4-(4-chlorophenyl)-5-(3,8-dimethyl-[1,2,4]triazolo[4,3-a]pyridin-6-yl)-3-methyl-2-(1-methylazetidin-3-yl)-4,5-dihydropyrrolo[3,4-c]pyrazol-6(2H)-one
Example 159: 4-(4-chlorophenyl)-1-cyclopropyl-5-(3,8-dimethyl-[1,2,4]triazolo[4,3-a]pyridin-6-yl)-3-(fluoromethyl)-4,5-dihydropyrrolo[3,4-c]pyrazol-6(1H)-one
Example 160: 4-(4-(4-chlorophenyl)-1-cyclopropyl-3-methyl-6-oxopyrrolo[3,4-c]pyrazol-5(1H,4H,6H)-yl)-6-methyl-1H-pyrrolo[2,3-c]pyridin-7(6H)-one
Example 161: (R)-4-(4-chlorophenyl)-1-cyclopropyl-3-methyl-5-(3-methyl-8-(methylamino)-[1,2,4]triazolo[4,3-b]pyridazin-6-yl)-4,5-dihydropyrrolo[3,4-c]pyrazol-6(1H)-one
Example 162: (R)-4-(4-chlorophenyl)-1-cyclopropyl-5-(1,5-dimethyl-6-oxo-1,6-dihydropyridin-3-yl)-3-(methoxymethyl)-4,5-dihydropyrrolo[3,4-c]pyrazol-6(1H)-one
Example 163: (R)-4-(4-chlorophenyl)-1-cyclopropyl-5-(3,8-dimethyl-[1,2,4]triazolo[4,3-a]pyridin-6-yl)-3-(methoxymethyl)-4,5-dihydropyrrolo[3,4-c]pyrazol-6(1H)-one
Example 164: (R)-4-(4-chlorophenyl)-3-cyclopropyl-5-(3,8-dimethyl-[1,2,4]triazolo[4,3-a]pyridin-6-yl)-1-methyl-4,5-dihydropyrrolo[3,4-c]pyrazol-6(1H)-one
Example 165: (R)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one
Example 166: (R)-4-(4-chlorophenyl)-1-cyclopropyl-5-(3,8-dimethyl-[1,2,4]triazolo[4,3-a]pyridin-6-yl)-3-(hydroxymethyl)-4,5-dihydropyrrolo[3,4-c]pyrazol-6(1H)-one
Example 167: (R)-4-(4-chlorophenyl)-5-(3,8-dimethyl-[1,2,4]triazolo[4,3-a]pyridin-6-yl)-3-methyl-1-((S)-3,3,3-trifluoro-2-hydroxypropyl)-4,5-dihydropyrrolo[3,4-c]pyrazol-6(1H)-one
Example 168: 4-(4-chloro-2-fluorophenyl)-5-(3,8-dimethyl-[1,2,4]triazolo[4,3-a]pyridin-6-yl)-1-isopropyl-3-methyl-4,5-dihydropyrrolo[3,4-c]pyrazol-6(1H)-one
Example 169: 4-(4-chloro-2-fluorophenyl)-5-(3,8-dimethyl-[1,2,4]triazolo[4,3-a]pyridin-6-yl)-2-isopropyl-3-methyl-4,5-dihydropyrrolo[3,4-c]pyrazol-6(2H)-one
Example 170: 4-(4-chloro-2-fluorophenyl)-5-(1,5-dimethyl-6-oxo-1,6-dihydropyridin-3-yl)-1-ethyl-3-methyl-4,5-dihydropyrrolo[3,4-c]pyrazol-6(1H)-one
Example 171: 4-(4-chloro-2-fluorophenyl)-5-(1,5-dimethyl-6-oxo-1,6-dihydropyridin-3-yl)-2-ethyl-3-methyl-4,5-dihydropyrrolo[3,4-c]pyrazol-6(2H)-one
Example 172: 4-(2,4-difluorophenyl)-5-(3,8-dimethyl-[1,2,4]triazolo[4,3-a]pyridin-6-yl)-3-methyl-4,5-dihydropyrrolo[3,4-c]pyrazol-6(2H)-one
Example 173: 4-(2,4-difluorophenyl)-5-(3,8-dimethyl-[1,2,4]triazolo[4,3-a]pyridin-6-yl)-1-(2-methoxypyridin-3-yl)-3-methyl-4,5-dihydropyrrolo[3,4-c]pyrazol-6(1H)-one
Example 174: 4-(2,4-difluorophenyl)-5-(3,8-dimethyl-[1,2,4]triazolo[4,3-a]pyridin-6-yl)-1-isopropyl-3-methyl-4,5-dihydropyrrolo[3,4-c]pyrazol-6(1H)-one
Example 175: 4-(2,4-difluorophenyl)-5-(3,8-dimethyl-[1,2,4]triazolo[4,3-a]pyridin-6-yl)-2-isopropyl-3-methyl-4,5-dihydropyrrolo[3,4-c]pyrazol-6(2H)-one
Example 176: 1-cyclopropyl-4-(2,4-difluorophenyl)-5-(3,8-dimethyl-[1,2,4]triazolo[4,3-a]pyridin-6-yl)-3-methyl-4,5-dihydropyrrolo[3,4-c]pyrazol-6(1H)-one
Example 177: 4-(2,4-difluorophenyl)-5-(3,8-dimethyl-[1,2,4]triazolo[4,3-a]pyridin-6-yl)-1-(2-methoxyphenyl)-3-methyl-4,5-dihydropyrrolo[3,4-c]pyrazol-6(1H)-one
Example 178: 4-(4-chloro-2-fluorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one
Example 179: 4-(4-chloro-2-fluorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one
Example 180: 4-(4-chloro-2-fluorophenyl)-5-(1,5-dimethyl-6-oxo-1,6-dihydropyridin-3-yl)-1-isopropyl-3-methyl-4,5-dihydropyrrolo[3,4-c]pyrazol-6(1H)-one
Example 181: 4-(2,4-difluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one
Example 182: 4-(2,4-difluorophenyl)-5-(3,8-dimethyl-[1,2,4]triazolo[4,3-a]pyridin-6-yl)-2-ethyl-3-methyl-4,5-dihydropyrrolo[3,4-c]pyrazol-6(2H)-one Example 183: 4-(4-chloro-2-fluorophenyl)-5-(3,8-dimethyl-[1,2,4]triazolo[4,3-a]pyridin-6-yl)-3-methyl-4,5-dihydropyrrolo[3,4-c]pyrazol-6(2H)-one
Example 184: 4-(4-chloro-2-fluorophenyl)-5-(3,8-dimethyl-[1,2,4]triazolo[4,3-a]pyridin-6-yl)-1-(2-methoxypyridin-3-yl)-3-methyl-4,5-dihydropyrrolo[3,4-c]pyrazol-6(1H)-one
Example 185: 4-(4-chloro-2-fluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one
Example 186: 4-(4-chloro-2-fluorophenyl)-5-(3,8-dimethyl-[1,2,4]triazolo[4,3-a]pyridin-6-yl)-2-ethyl-3-methyl-4,5-dihydropyrrolo[3,4-c]pyrazol-6(2H)-one
Example 187: 4-(4-chloro-2-fluorophenyl)-5-(3,8-dimethyl-[1,2,4]triazolo[4,3-a]pyridin-6-yl)-1-(2-methoxyphenyl)-3-methyl-4,5-dihydropyrrolo[3,4-c]pyrazol-6(1H)-one
Example 188: (S)-1-cyclopropyl-4-(2,4-difluorophenyl)-5-(3,8-dimethyl-[1,2,4]triazolo[4,3-a]pyridin-6-yl)-3-methyl-4,5-dihydropyrrolo[3,4-c]pyrazol-6(1H)-one
Example 189: (S)-4-(4-chloro-2-fluorophenyl)-5-(3,8-dimethyl-[1,2,4]triazolo[4,3-a]pyridin-6-yl)-1-isopropyl-3-methyl-4,5-dihydropyrrolo[3,4-c]pyrazol-6(1H)-one
Example 190: (S)-4-(4-chloro-2-fluorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one
Example 191: (S)-4-(2,4-difluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one
Example 192: (S)-4-(4-chloro-2-fluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one
Example 193: 4-(2,4-difluorophenyl)-5-(3,8-dimethyl-[1,2,4]triazolo[4,3-a]pyridin-6-yl)-2-(2-methoxypyridin-3-yl)-3-methyl-4,5-dihydropyrrolo[3,4-c]pyrazol-6(2H)-one
Example 194: 4-(4-chloro-2-fluorophenyl)-5-(3,8-dimethyl-[1,2,4]triazolo[4,3-a]pyridin-6-yl)-2-(2-methoxypyridin-3-yl)-3-methyl-4,5-dihydropyrrolo[3,4-c]pyrazol-6(2H)-one
Example 195: 4-(4-chlorophenyl)-1-cyclopropyl-5-(3-(difluoromethyl)-8-methyl-[1,2,4]triazolo[4,3-b]pyridazin-6-yl)-3-methyl-4,5-dihydropyrrolo[3,4-c]pyrazol-6(1H)-one and
Example 196: 4-(4-chloro-2-fluorophenyl)-5-(1,5-dimethyl-6-oxo-1,6-dihydropyridin-3-yl)-3-methyl-4,5-dihydropyrrolo[3,4-c]pyrazol-6(2H)-one.

E33 A compound of formula (I) or a pharmaceutically acceptable salt thereof, according to E1 or E32, selected from
Example 19: (R)-5-(5-chloro-1-methyl-6-oxo-1,6-dihydropyridin-3-yl)-4-(4-chlorophenyl)-2-cyclopropyl-3-methyl-4,5-dihydropyrrolo[3,4-c]pyrazol-6(2H)-one
Example 21: (R)-4-(4-chlorophenyl)-2-cyclopropyl-5-(1,5-dimethyl-6-oxo-1,6-dihydropyridin-3-yl)-3-methyl-4,5-dihydropyrrolo[3,4-c]pyrazol-6(2H)-one
Example 49: (R)-4-(4-chlorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one
Example 51: (R)-5-(5-chloro-1-methyl-6-oxo-1,6-dihydropyridin-3-yl)-4-(4-chlorophenyl)-1-cyclopropyl-3-methyl-4,5-dihydropyrrolo[3,4-c]pyrazol-6(1H)-one
Example 63: 4-(4-chlorophenyl)-5-(1,5-dimethyl-6-oxo-1,6-dihydropyridin-3-yl)-1-isopropyl-3-methyl-4,5-dihydropyrrolo[3,4-c]pyrazol-6(1H)-one
Example 64: 4-(4-chlorophenyl)-5-(1,5-dimethyl-6-oxo-1,6-dihydropyridin-3-yl)-2-isopropyl-3-methyl-4,5-dihydropyrrolo[3,4-c]pyrazol-6(2H)-one
Example 67: 4-(4-chlorophenyl)-2-(2,4-dimethoxypyrimidin-5-yl)-5-(3,8-dimethyl-[1,2,4]triazolo-[4,3-a]pyridin-6-yl)-3-isopropyl-4,5-dihydropyrrolo[3,4-c]pyrazol-6(2H)-one
Example 69: 4-(4-chlorophenyl)-1-cyclopropyl-5-(1,5-dimethyl-6-oxo-1,6-dihydropyridin-3-yl)-3-ethyl-4,5-dihydropyrrolo[3,4-c]pyrazol-6(1H)-one
Example 77: 4-(4-chlorophenyl)-5-(1,5-dimethyl-6-oxo-1,6-dihydropyridin-3-yl)-3-methoxy-2-methyl-4,5-dihydropyrrolo[3,4-c]pyrazol-6(2H)-one
Example 78: 4-(4-chlorophenyl)-5-(1,5-dimethyl-6-oxo-1,6-dihydropyridin-3-yl)-3-ethyl-1-(2-hydroxyethyl)-4,5-dihydropyrrolo[3,4-c]pyrazol-6(1H)-one
Example 85: 4-(4-chlorophenyl)-1-cyclopropyl-5-(1,4-dimethyl-1H-benzo[d][1,2,3]triazol-6-yl)-3-methyl-4,5-dihydropyrrolo[3,4-c]pyrazol-6(1H)-one
Example 87: 4-(4-chlorophenyl)-5-(3,8-dimethyl-[1,2,4]triazolo[4,3-a]pyridin-6-yl)-3-ethyl-1-(2-methoxyethyl)-4,5-dihydropyrrolo[3,4-c]pyrazol-6(1H)-one
Example 90: 4-(4-chlorophenyl)-5-(3,8-dimethyl-[1,2,4]triazolo[4,3-a]pyridin-6-yl)-3-methyl-1-(1-methyl-1H-pyrazol-5-yl)-4,5-dihydropyrrolo[3,4-c]pyrazol-6(1H)-one
Example 93: 4-(4-chlorophenyl)-2-cyclopropyl-5-(3,8-dimethyl-[1,2,4]triazolo[4,3-a]pyridin-6-yl)-3-methyl-4,5-dihydropyrrolo[3,4-c]pyrazol-6(2H)-one
Example 100: (R)-4-(4-chlorophenyl)-1-(2,4-dimethoxypyrimidin-5-yl)-5-(1,5-dimethyl-6-oxo-1,6-dihydropyridin-3-yl)-3-methyl-4,5-dihydropyrrolo[3,4-c]pyrazol-6(1H)-one
Example 101: 4-(4-chlorophenyl)-5-(3,8-dimethyl-[1,2,4]triazolo[4,3-a]pyridin-6-yl)-1-(2-methoxypyridin-3-yl)-3-methyl-4,5-dihydropyrrolo[3,4-c]pyrazol-6(1H)-one
Example 107: (R)-4-(4-chlorophenyl)-1-cyclopropyl-5-(3,8-dimethyl-[1,2,4]triazolo[4,3-a]pyridin-6-yl)-3-ethyl-4,5-dihydropyrrolo[3,4-c]pyrazol-6(1H)-one
Example 110: 4-(4-chlorophenyl)-1-cyclopropyl-5-(3,7-dimethyl-3H-[1,2,3]triazolo[4,5-b]pyridin-5-yl)-3-methyl-4,5-dihydropyrrolo[3,4-c]pyrazol-6(1H)-one
Example 111: 4-(4-chlorophenyl)-5-(3,8-dimethyl-[1,2,4]triazolo[4,3-b]pyridazin-6-yl)-1-(2-methoxypyridin-3-yl)-3-methyl-4,5-dihydropyrrolo[3,4-c]pyrazol-6(1H)-one
Example 116: 4-(4-chlorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one
Example 119: (R)-4-(4-chlorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one
Example 120: (R)-4-(4-chlorophenyl)-5-(1,5-dimethyl-6-oxo-1,6-dihydropyridin-3-yl)-3-methyl-1-(1-methyl-1H-pyrazol-5-yl)-4,5-dihydropyrrolo[3,4-c]pyrazol-6(1H)-one
Example 122: (R)-4-(4-chlorophenyl)-1-cyclopropyl-5-(3,8-dimethyl-[1,2,4]triazolo[4,3-b]-pyridazin-6-yl)-3-methyl-4,5-dihydropyrrolo[3,4-c]pyrazol-6(1H)-one
Example 133: 4-(4-chlorophenyl)-1-cyclopropyl-5-(1,5-dimethyl-6-oxo-1,6-dihydropyridin-3-yl)-3-(hydroxymethyl)-4,5-dihydropyrrolo[3,4-c]pyrazol-6(1H)-one
Example 137: 4-(4-chlorophenyl)-5-(3,8-dimethyl-[1,2,4]triazolo[4,3-a]pyridin-6-yl)-3-methyl-1-(oxetan-3-yl)-4,5-dihydropyrrolo[3,4-c]pyrazol-6(1H)-one
Example 149: (R)-4-(4-chlorophenyl)-5-(3,8-dimethyl-[1,2,4]triazolo[4,3-a]pyridin-6-yl)-N,N,3-trimethyl-6-oxo-5,6-dihydropyrrolo[3,4-c]pyrazole-1(4H)-carboxamide
Example 162: (R)-4-(4-chlorophenyl)-1-cyclopropyl-5-(1,5-dimethyl-6-oxo-1,6-dihydropyridin-3-yl)-3-(methoxymethyl)-4,5-dihydropyrrolo[3,4-c]pyrazol-6(1H)-one
Example 163: (R)-4-(4-chlorophenyl)-1-cyclopropyl-5-(3,8-dimethyl-[1,2,4]triazolo[4,3-a]pyridin-6-yl)-3-(methoxymethyl)-4,5-dihydropyrrolo[3,4-c]pyrazol-6(1H)-one
Example 165: (R)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one Example 166: (R)-4-(4-chlorophenyl)-1-cyclopropyl-5-(3,8-dimethyl-[1,2,4]triazolo[4,3-a]pyridin-6-yl)-3-(hydroxymethyl)-4,5-dihydropyrrolo[3,4-c]pyrazol-6(1H)-one
Example 174: 4-(2,4-difluorophenyl)-5-(3,8-dimethyl-[1,2,4]triazolo[4,3-a]pyridin-6-yl)-1-isopropyl-3-methyl-4,5-dihydropyrrolo[3,4-c]pyrazol-6(1H)-one
Example 185: 4-(4-chloro-2-fluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one
and
Example 191: (S)-4-(2,4-difluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one.

E34 A compound of formula (I) or a pharmaceutically acceptable salt thereof, according to E1, E32 or E33, selected from
Example 49: (R)-4-(4-chlorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one
Example 67: 4-(4-chlorophenyl)-2-(2,4-dimethoxypyrimidin-5-yl)-5-(3,8-dimethyl-[1,2,4]triazolo-[4,3-a]pyridin-6-yl)-3-isopropyl-4,5-dihydropyrrolo[3,4-c]pyrazol-6(2H)-one
Example 93: 4-(4-chlorophenyl)-2-cyclopropyl-5-(3,8-dimethyl-[1,2,4]triazolo[4,3-a]pyridin-6-yl)-3-methyl-4,5-dihydropyrrolo[3,4-c]pyrazol-6(2H)-one
Example 107: (R)-4-(4-chlorophenyl)-1-cyclopropyl-5-(3,8-dimethyl-[1,2,4]triazolo[4,3-a]pyridin-6-yl)-3-ethyl-4,5-dihydropyrrolo[3,4-c]pyrazol-6(1H)-one
Example 119: (R)-4-(4-chlorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one
Example 122: (R)-4-(4-chlorophenyl)-1-cyclopropyl-5-(3,8-dimethyl-[1,2,4]triazolo[4,3-b]-pyridazin-6-yl)-3-methyl-4,5-dihydropyrrolo[3,4-c]pyrazol-6(1H)-one
Example 133: 4-(4-chlorophenyl)-1-cyclopropyl-5-(1,5-dimethyl-6-oxo-1,6-dihydropyridin-3-yl)-3-(hydroxymethyl)-4,5-dihydropyrrolo[3,4-c]pyrazol-6(1H)-one
Example 163: (R)-4-(4-chlorophenyl)-1-cyclopropyl-5-(3,8-dimethyl-[1,2,4]triazolo[4,3-a]pyridin-6-yl)-3-(methoxymethyl)-4,5-dihydropyrrolo[3,4-c]pyrazol-6(1H)-one
Example 165: (R)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one
and
Example 166: (R)-4-(4-chlorophenyl)-1-cyclopropyl-5-(3,8-dimethyl-[1,2,4]triazolo[4,3-a]pyridin-6-yl)-3-(hydroxymethyl)-4,5-dihydropyrrolo[3,4-c]pyrazol-6(1H)-one.

The present disclosure includes compounds of stereochemistry is as shown in formula (Ib):

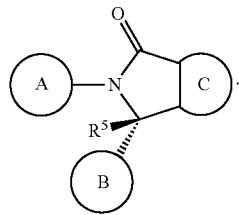

(Ib)

Unless specified otherwise, the term "compounds of the present invention" refers to compounds of formula (I) and subformulae thereof, and salts thereof, as well as all stereoisomers (including diastereoisomers and enantiomers), rotamers, tautomers and isotopically labeled compounds (including deuterium substitutions), as well as inherently formed moieties.

Various embodiments of the invention are described herein. It will be recognized that features specified in each embodiment may be combined with other specified features to provide further embodiments of the present invention.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

In another aspect, the present invention provides compounds of formula I in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}$S, $^{36}$Cl, $^{123}$I, $^{124}$I, $^{125}$I respectively. The invention includes various isotopically labeled compounds as defined herein, for example those into which radioactive isotopes, such as $^{3}$H and $^{14}$C, or those into which non-radioactive isotopes, such as $^{2}$H and $^{13}$C are present. Such isotopically labelled compounds are useful in metabolic studies (with $^{14}$C), reaction kinetic studies (with, for example $^{2}$H or $^{3}$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by BET proteins, or (ii) associated with BET protein activity, or (iii) characterized by activity (normal or abnormal) of BET proteins; or (2) reduce or inhibit the activity of BET proteins; or (3) reduce or inhibit the expression of BET. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of BET proteins; or at least partially reducing or inhibiting the expression of BET proteins.

A "BET protein" is a protein encoded by either of the genes BRD2, BRD3, BRD4, or BRDT". Unless indicated otherwise "BET proteins" or "BET protein" are used herein in the singular and plural forms interchangeably, and the use of either is not limiting. Unless indicated otherwise "BET proteins" includes all, or any combination of, such encoded proteins.

As used herein, the term "($C_3$-$C_6$)cycloalkyl" refers to saturated monocyclic hydrocarbon groups of 3-6 carbon atoms. Exemplary $C_{3-6}$cycloalkyl groups include, but are not limited to, cyclopropyl, cyclobutyl, cyclopentyl and cyclohexyl.

As used herein, the term "($C_1$-$C_4$)alkyl" refers to a fully saturated branched or unbranched hydrocarbon moiety having 1 to 4 carbon atoms. Representative examples of $C_{1-4}$alkyl include methyl, ethyl, n-propyl, iso-propyl, n-butyl, sec-butyl, iso-butyl and tert-butyl.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Compositions:

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The compounds of formula I in free form or in pharmaceutically acceptable salt form, exhibit valuable pharmacological properties, e.g. BET protein modulating properties, e.g. as indicated in tests as provided in the next sections, and are therefore indicated for therapy or for use as research chemicals, e.g. as tool compounds.

Having regard to their activity as BET inhibitors, compounds of the formula (I) in free or pharmaceutically acceptable salt form, are useful in the treatment of conditions which are mediated by the activity of BET proteins, such as cancer, and/or that are responsive (meaning especially in a therapeutically beneficial way) to inhibition of a BET protein, most especially a disease or disorder as mentioned herein below.

Compounds of the invention are believed to be useful in the treatment of diseases or disorders such as cancer. In particular, such cancers include benign or malignant tumours, a soft tissue sarcoma or a sarcoma such as liposarcoma, rhabdomyosarcoma or bone cancer, e.g. osteosarcoma, a carcinoma, such as of the brain, kidney, liver, adrenal gland, bladder, breast, gastric, ovary, colon, rectum, prostate, pancreas, lung (including small cell lung cancer), vagina or thyroid, a glioblastoma, meningioma, glioma, mesothelioma, a neuroendocrine tumor such as neuroblastoma, a multiple myeloma, a gastrointestinal cancer, especially colon carcinoma or colorectal adenoma, a tumor of the head and neck, a melanoma, a prostate hyperplasia, a neoplasia, a neoplasia of epithelial character, a neoplasia originating from blood or bone marrow, a leukemia such as acute myeloid leukemia (AML) or acute lymphoblastic leukemia (ALL) or B-cell chronic lymphocytic leukemia, a lymphoma, such as of B- or T-cell origin, such as diffuse large B cell lymphoma (DLBCL), NUT midline carcinoma or any other neoplasia with chromosomal rearrangements of the BET genes, and metastases in other organs.

In particular, the compounds of the invention may be useful in the treatment of a disease or disorder selected from a neoplasia originating from blood or bone marrow; a leukemia such as acute myeloid leukemia (AML) or acute lymphoblastic leukemia (ALL) or B-cell chronic lymphocytic leukemia; a lymphoma, such as of B- or T-cell origin, such as diffuse large B cell lymphoma (DLBCL); NUT midline carcinoma or any other neoplasia with chromosomal rearrangements of the BET genes; a neuroendocrine tumor such as neuroblastoma; a multiple myeloma; a lung cancer (including small cell lung cancer); and a colon cancer.

Compounds of the invention may also be of use in the treatment of atherosclerosis, coronary artery disease, dyslipidemia, diabetes, and other cardiovascular diseases, and/or as antiviral agents.

Thus, as a further embodiment, the present invention provides the use of a compound of formula (I) or a salt thereof, in therapy. In a further embodiment, the therapy is selected from a disease which may be treated by inhibition of BET proteins. In another embodiment, the disease is a cancer disease selected from the afore-mentioned list.

Thus, as a further embodiment, the present invention provides a compound of formula (I) or a salt thereof, for use in therapy. In a further embodiment, the therapy is selected from a disease which may be treated by inhibition of a BET protein. In another embodiment, the disease is a cancer disease selected from the afore-mentioned list.

In another embodiment, the invention provides a method of treating a disease which is treated by inhibition of a BET protein, comprising administration of a therapeutically acceptable amount of a compound of formula (I) or salt thereof. In a further embodiment, the disease is a cancer disease selected from the afore-mentioned list.

Thus, as a further embodiment, the present invention provides the use of a compound of formula (I) or salt thereof, for the manufacture of a medicament. In a further embodiment, the medicament is for treatment of a disease which may be treated by inhibition of a BET protein. In another embodiment, the disease is a cancer disease selected from the afore-mentioned list.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

Assays

The activity of a compound according to the present invention can be assessed by the following methods.

TR-FRET In-Vitro Binding Assays for BRD2, BRD3, and BRD4:

All assays were performed in 384-well microtiter plates. Each assay plate contained 8-point serial dilutions for 40 test compounds, plus 16 high- and 16 low controls. Liquid handling and incubation steps were done on an Innovadyne Nanodrop Express equipped with a robotic arm (Thermo CatX, Perkin Elmer/Caliper Twister II) and an incubator (Liconic STX40, Thermo Cytomat 2C450). The assay plates were prepared by addition of 50 nl per well of compound solution in 90% DMSO HummingBird nanodispenser (Zinsser Analytic). The assay was started by stepwise addition of 4.5 µL per well of bromo domain protein (50 mM HEPES, pH 7.5, 0.005% Tween20, 0.1% BSA, 50 mM NaCl, 45 nM His-Brd2(60-472) or 45 nM His-Brd3(20-477) or 45 nM His-Brd4(44-477) all proteins produced in-house) and 4.5 µL per well of peptide solution (50 mM HEPES, pH 7.5, 0.005% Tween20, 0.1% BSA, 50 mM NaCl, 60 nM acetyl-histone H4 (AcK 5, 8, 12, 16) (Biosyntan GmbH)). Reactions were incubated at 30° C. for 35 minutes. Subsequently 4.5 µL detection mix (50 mM HEPES, pH 7.5, 0.005% Tween20, 0.1% BSA, 50 mM NaCl, 3 nM Eu-labeled anti-His6 antibody, 21 nM streptavidin-allophycocyanin) were added. After minutes incubation at 30° C., plates were measured in a Perkin Elmer EnVision multilabel reader. Concentrations causing 50% inhibition (IC50 values) were determined from percent inhibition values at different compound concentrations by non-linear regression analysis.

AlphaScreen In-Vitro Binding Assay for CREBBP

In order to assess bromodomain selectivity, we set up a binding assay using the bromodomain encoded by the CREBBP gene. Compounds were tested in the CREBBP assay with a similar protocol, however using AlphaScreen (Amplified Luminescent Proximity Homogeneous Assay, Perkin Elmer) as detection readout instead of TR-FRET. The assay was started by stepwise addition of 4.5 µL per well of bromo domain protein (50 mM HEPES, pH 7.5, 0.005% Tween20, 0.02% BSA, 150 mM NaCl, 324 nM His-CREBBP (1081-1197) (custom production at Viva Biotech Ltd.)) and 4.5 µL per well of peptide solution (50 mM HEPES, pH 7.5, 0.005% Tween20, 0.02% BSA, 150 mM NaCl, 120 nM acetyl-histone H4 (AcK 5, 8, 12) (Biosyntan GmbH)). Reactions were incubated at 30° C. for 35 minutes. Subsequently 4.5 µL per well detection mix (50 mM HEPES, pH 7.5, 0.005% Tween20, 0.02% BSA, 150 mM NaCl, 45 µg/ml Ni-chelate acceptor beads, 45 µg/mL streptavidin-donor beads) (Perkin Elmer)) were added. After 60 minutes incubation at room temperature, plates were measured in a Perkin Elmer EnVision multilabel reader. IC50 values were determined from percent inhibition values at different compound concentrations by non-linear regression analysis.

For further bromodomain selectivity profiling, additional panel assays were performed using analog protocols with minor modifications specific for the individual assay, using either TR-FRET or AlphaScreen for detection.

Preparation of Compound Dilutions

Test compounds were dissolved in DMSO (10 mM) and transferred into 1.4 mL flat bottom or V-shaped Matrix tubes carrying a unique 2D matrix. The stock solutions were stored at +2° C. if not used immediately. For the test procedure the vials were defrosted and identified by a scanner whereby a working sheet was generated that guided the subsequent working steps. Compound dilutions were made in 96 well plates. This format enabled the assay of maximally individual test compounds at 8 concentrations (single points) including 4 reference compounds, if desired (known BET inhibitors from the prior art, for this and other assays of the type disclosed herein). The dilution protocol included the production of "pre-dilution plates", "master plates" and "assay plates".

Pre-Dilution Plates:

Polypropylene 96-well plates were used as pre-dilution plates. A total of 4 pre-dilution plates were prepared including 10 test compounds each on the plate positions A1-A10, one standard compound at A11 and one DMSO control at A12. All dilution steps were done on a HamiltonSTAR robot.

Master Plates:

30 µL of individual compound dilutions including standard compound and controls of the 4 "pre-dilution plates" were transferred into a 384-well "master plate" including the following concentrations 10000, 3003, 1000, 300, 100, 30, 10 and 3 µM, respectively in 90% of DMSO.

Assay Plates:

Identical "assay plates" were then prepared by pipetting 50 nL each of compound dilutions of the "master plates" into 384-well "assay plates" by means of a HummingBird 384-channel dispenser. These plates were used directly for the assay which was performed in a total volume of 13.55 µL. This led to a final compound concentration of 37, 11, 3.7, 1.1, 0.37, 0.11, 0.037 and 0.011 µM and a final DMSO concentration of 0.37% in the assay.

Cell Growth Inhibition Assay

The human leukemia cell lines MV-4-11, THP-1 and K-562 were employed to characterize the effect of BET inhibitors on cellular proliferation and viability. Cells were obtained from the American Type Culture Collection (ATCC) and cultured at 37° C. in a humidified 5% $CO_2$ incubator in the following media: MV-4-11: DMEM high glucose (Animed #1-26F01-I), 10% FCS (Animed #2-01F26-I), 4 mM L-Glutamine (Animed #5-10K50), 1 mM Sodium Pyruvate (Animed # G03625P), 1× Penicillin-Streptomycin (Animed # F12478P); K-562: Iscove's MEM (Animed #1-28F16-I), 10% FCS (Animed #2-01F26-I), 4 mM L-Glutamine (Animed #5-10K50), 1× Penicillin-Streptomycin (Animed # F12478P); THP-1: RPMI-1640 (Animed #1-41F01-I), 10% FCS (Animed #2-01F26-I), 2 mM L-Glutamine (Animed #5-10K50), 10 mM HEPES (Animed #5-31F100), 1 mM Sodium Pyruvate (Animed # G03625P), 1× Penicillin-Streptomycin (Animed # F12478P). The AML lines MV-4-11 and THP-1 are very sensitive to BET inhibitors and show massive cell death upon BET inhibition (Zuber et al., Nature, 478

(2011), 524-8). Compound-mediated suppression of cell proliferation/viability was assessed by quantification of cellular ATP levels using the CellTiter-Glo (CTG) reagent (Promega). Briefly, cells were seeded in 20 μl fresh medium into 384-well plates, followed by addition of 5 μL medium containing compound dilutions at 5-fold their final intended concentration. Dose-response effects were assessed by 3-fold serial dilutions of the test compound, starting at 10 μM. Following incubation of the cells for days at 37° C. and 5% $CO_2$, the effect of inhibitors on cell viability was quantified following addition of 20 μl CTG and luminescence quantification (integration time: 100 ms) as per vendor manual, using a correspondingly equipped Tecan M200 multi-mode platereader (TECAN, Switzerland). For data analysis, the assay background value determined in wells containing medium, but no cells, was subtracted from all data points. To enable differentiation of cytotoxic from cytostatic compounds, the number of viable cells is assessed relative to that observed at the time of compound addition using a separate cell plate (day 0). The effect of a particular test compound concentration on cell proliferation/viability is expressed as percentage of the background- and day 0-corrected luminescence reading obtained for cells treated with vehicle only (DMSO, 0.1% final concentration), which is set as 100%, whereas that luminescence reading for wells containing medium is set as −100%. Compound concentrations leading to half-maximal (IC50) and total growth inhibition (TGI) were determined using standard four parameter curve fitting.

Nut-Foci Formation Assay

HCC2494 NUT midline carcinoma cells (expressing BRD4-NUT-fusion) were obtained from the University of Texas Southwestern and cultured in RPMI-1640 medium containing 10% Foetal Calf Serum at 37° C. in a humidified 5% $CO_2$ incubator.

Compound-mediated inhibition of BRD4 activity was monitored by quantification of the number and intensity of nuclear BRD4-NUT foci using automated immunofluorescence microscopy. Briefly, 5000 cells in 20 μL fresh medium were seeded into Poly-D-Lysine-precoated 384-well plates and incubated overnight at 37° C. and 5% $CO_2$, followed by addition of 5 μl medium containing compound dilutions at 5-fold their final intended concentration. Dose-response effects were assessed by 3-fold serial dilutions of the test compound, starting at 10 μM. Following incubation of the cells for 24 hours at 37° C. and 5% $CO_2$, the cells were fixed by incubation with 3.7% formaldehyde for 10 min, followed by immunofluorescence staining using rabbit anti-NUT (Cell Signaling Technologies, Cat#3625) as primary, and AlexaFluor488-labeled goat anti-rabbit (Invitrogen, Cat#A11008) as secondary antibody (latter complemented with 1 μg/mL Hoechst33342 as DNA dye). Assay plates were imaged using the appropriate filter sets on the Cellomics VTi automated fluorescence microscopy platform (ThermoFisher Scientific) and the population average of the number of NUT-foci per nucleus is quantified using the Cellomics Spot Detection BioApplication image analysis algorithm (ThermoFisher Scientific). The effect of a particular test compound concentration on NUT-foci number and intensity is expressed as percentage of the value obtained for cells treated with vehicle only (DMSO, 0.1% final concentration), which was set as 100. Compound concentrations leading to half-maximal ($IC_{50}$) inhibition of the aforementioned readout parameters were determined using standard four parameter curve fitting.

Using the biochemical and cellular assays as described hereinabove, compounds of the invention exhibit inhibitory efficacy as shown in Table 1 and Table 2.

TABLE 1

Biochemical IC50 values

| Example | IC50 (μM) BRD4 | BRD2 | BRD3 | CREBBP |
|---|---|---|---|---|
| 1 | 0.14 | | | |
| 2 | 0.17 | | | |
| 3 | 0.40 | 0.58 | 0.52 | |
| 4 | 0.23 | | | |
| 5 | 0.36 | 0.73 | 0.37 | 5.6 |
| 6 | 0.19 | 0.35 | 0.18 | 3.5 |
| 7 | 0.072 | 0.10 | 0.067 | |
| 8# | 31 | 36 | 27 | |
| 9 | 0.17 | 0.21 | 0.18 | |
| 10 | 0.15 | 0.15 | 0.13 | |
| 11 | 0.13 | 0.14 | 0.10 | |
| 12# | >37 | >37 | >37 | |
| 13 | 0.13 | 0.18 | 0.15 | |
| 14 | 0.46 | | | |
| 15# | >6.7 | >6.7 | >6.7 | |
| 16 | 0.081 | 0.10 | 0.066 | |
| 17 | 0.14 | 0.18 | 0.097 | 1.3 |
| 18# | 23 | 30 | 27 | |
| 19 | 0.073 | 0.078 | 0.065 | |
| 20 | 0.088 | 0.13 | 0.077 | 1.1 |
| 21 | 0.047 | 0.048 | 0.043 | |
| 22# | >6.7 | >6.7 | >6.7 | |
| 23 | 0.066 | 0.099 | 0.074 | 3.9 |
| 24 | 0.15 | 0.23 | 0.15 | 5.9 |
| 25 | 0.26 | 0.27 | 0.25 | |
| 26 | 0.15 | 0.21 | 0.14 | |
| 27 | 0.095 | 0.31 | 0.18 | 3.8 |
| 28 | 0.14 | 0.32 | 0.16 | 3.3 |
| 29# | 31 | 28 | 25 | |
| 30 | 0.031 | | | |
| 31 | 0.52 | 0.69 | 0.47 | |
| 32 | 0.66 | 1.2 | 0.89 | |
| 33 | 0.7 | 31.2 | 0.92 | >37 |
| 34 | 0.11 | 0.095 | 0.11 | 5.2 |
| 35 | 0.15 | 0.14 | 0.16 | 7.4 |
| 36 | 0.066 | 0.057 | 0.059 | 3.6 |
| 37 | 0.17 | 0.14 | 0.14 | 1.2 |
| 38 | 0.062 | 0.049 | 0.076 | 1.9 |
| 39 | 0.12 | 0.078 | 0.091 | 0.96 |
| 40 | 0.22 | 0.16 | 0.15 | 0.74 |
| 41 | 0.096 | 0.075 | 0.085 | 0.38 |
| 42 | 0.10 | 0.091 | 0.089 | 0.45 |
| 43 | 0.12 | 0.10 | 0.11 | 0.66 |
| 44 | 0.21 | 0.17 | 0.28 | 3.9 |
| 45 | 0.085 | 0.060 | 0.10 | 4.8 |
| 46 | 0.087 | 0.13 | 0.10 | 4.7 |
| 47 | 0.27 | 0.21 | 0.28 | 1.5 |
| 48# | >6.7 | >6.7 | >6.7 | >5.1 |
| 49 | 0.017 | 0.015 | 0.019 | 1.3 |
| 50# | >6.7 | >6.7 | >6.7 | >5.1 |
| 51 | 0.020 | 0.017 | 0.021 | 1.4 |
| 52 | 0.087 | 0.063 | 0.069 | 5.7 |
| 53 | 0.13 | 0.098 | 0.12 | |
| 54 | 0.26 | 0.48 | 0.30 | >37 |
| 55 | 0.15 | 0.098 | 0.079 | 0.6 |
| 56 | 0.095 | 0.069 | 0.061 | 0.56 |
| 57 | 0.12 | 0.27 | 0.13 | 6.8 |
| 58 | 0.41 | 0.56 | 0.29 | 8.2 |
| 59 | 0.39 | 0.61 | 0.48 | 7.3 |
| 60 | 0.14 | 0.16 | 0.12 | 8.8 |
| 61# | >37 | >37 | >37 | >37 |
| 62 | 0.067 | 0.060 | 0.072 | 1.7 |
| 63 | 0.090 | 0.13 | 0.088 | 2.5 |
| 64 | 0.13 | 0.18 | 0.11 | 0.4 |
| 65 | 0.20 | 0.24 | 0.13 | 0.42 |
| 66 | 0.12 | 0.16 | 0.11 | 2.6 |

TABLE 1-continued

Biochemical IC50 values

| Example | BRD4 | BRD2 | BRD3 | CREBBP |
|---|---|---|---|---|
| 67 | 0.024 | 0.043 | 0.028 | 2.8 |
| 68 | 0.044 | 0.037 | 0.040 | 0.95 |
| 69 | 0.027 | 0.026 | 0.028 | 4.1 |
| 70 | 0.024 | 0.031 | 0.029 | 11 |
| 71 | 0.053 | 0.041 | 0.058 | 5.9 |
| 72 | 0.079 | 0.060 | 0.073 | 8.2 |
| 73 | 0.21 | 0.20 | 0.20 | 2 |
| 74 | 0.067 | 0.071 | 0.091 | 6.4 |
| 75 | | | | |
| 76 | 0.12 | 0.10 | 0.10 | 2.9 |
| 77 | 0.13 | 0.12 | 0.12 | 1.9 |
| 78 | 0.063 | 0.079 | 0.057 | 3.1 |
| 79 | 0.078 | 0.11 | 0.086 | 11 |
| 80 | 0.035 | 0.059 | 0.036 | 5 |
| 81 | 0.11 | 0.12 | 0.097 | 0.92 |
| 82 | 0.068 | 0.097 | 0.096 | 6.5 |
| 83 | 0.091 | 0.12 | 0.097 | 6.1 |
| 84 | 0.028 | 0.037 | 0.0615 | >37 |
| 85 | 0.014 | 0.024 | 0.016 | 8.3 |
| 86 | 0.039 | 0.052 | 0.044 | 4.8 |
| 87 | 0.050 | 0.072 | 0.059 | 9.8 |
| 88 | | | | |
| 89 | 0.047 | 0.060 | 0.057 | 2.5 |
| 90 | 0.015 | 0.028 | 0.028 | >37 |
| 91 | | | | |
| 92 | 0.019 | 0.029 | 0.027 | 14.9 |
| 93 | 0.027 | 0.045 | 0.031 | 3.1 |
| 94 | 0.024 | 0.025 | 0.028 | 0.65 |
| 95 | 0.064 | 0.063 | 0.073 | 7.7 |
| 96 | 0.78 | 0.66 | 0.80 | 18 |
| 97 | 0.089 | 0.088 | 0.12 | 3.6 |
| 98 | | | | |
| 99[#] | 7.8 | 6.0 | 7.6 | >37 |
| 100 | 0.025 | 0.028 | 0.027 | 4.2 |
| 101 | 0.034 | 0.043 | 0.036 | 19 |
| 102 | 0.059 | 0.072 | 0.055 | >37 |
| 103[#] | 11 | 5.3 | 6.1 | >37 |
| 104 | 0.013 | 0.014 | 0.015 | 1.2 |
| 105 | 0.068 | 0.13 | 0.15 | >37 |
| 106[#] | 2.2 | 2.9 | 4.4 | >37 |
| 107 | <0.011 | 0.014 | 0.013 | 6.9 |
| 108 | 0.14 | 0.21 | 0.28 | >37 |
| 109 | 0.017 | 0.027 | 0.027 | >37 |
| 110 | 0.012 | 0.018 | 0.014 | >37 |
| 111 | 0.017 | 0.032 | 0.024 | 29.7 |
| 112[#] | >37 | >37 | >37 | >37 |
| 113 | 0.067 | 0.086 | 0.12 | >37 |
| 114 | 0.027 | 0.035 | 0.037 | >37 |
| 115 | 0.043 | 0.048 | 0.046 | 1.2 |
| 116 | 0.032 | 0.036 | 0.032 | 15 |
| 117 | 0.039 | 0.034 | 0.038 | >37 |
| 118[#] | 30 | >37 | >37 | >37 |
| 119 | 0.013 | 0.019 | 0.017 | 8.9 |
| 120 | 0.055 | 0.078 | 0.083 | 4.3 |
| 121[#] | 4.0 | 5.3 | 5.4 | >37 |
| 122 | <0.011 | 0.012 | <0.011 | >37 |
| 123[#] | 14 | 13 | 13 | |
| 124 | 25 | 29 | 37 | >37 |
| 125 | 0.025 | 0.032 | 0.032 | 21 |
| 126 | 1.1 | | >37 | >37 |
| 127[#] | 5.7 | 4.4 | 5.1 | >37 |
| 128 | 0.036 | 0.030 | 0.037 | 3.7 |
| 129 | 0.038 | 0.040 | 0.033 | 25 |
| 130 | 0.042 | 0.053 | 0.053 | 19 |
| 131 | 0.036 | 0.046 | 0.052 | 30 |
| 132 | 0.067 | 0.081 | 0.089 | 4.8 |
| 133 | 0.079 | | 0.080 | |
| 134 | 0.16 | 0.19 | 0.13 | |
| 135 | 0.14 | 0.15 | 0.13 | >37 |
| 136 | 0.11 | 0.14 | 0.13 | 4.3 |
| 137 | 0.080 | 0.092 | 0.10 | >37 |
| 138 | 0.29 | | 0.24 | |
| 139 | 0.19 | 0.16 | 0.12 | |
| 140 | 0.32 | 0.42 | 0.44 | 15 |
| 141 | 0.17 | 0.18 | 0.13 | 1.5 |
| 142 | 0.19 | 0.18 | 0.15 | 4.6 |
| 143 | 0.30 | 0.33 | 0.27 | >37 |
| 144 | 0.15 | 0.16 | 0.14 | |
| 145 | 0.14 | 0.18 | 0.19 | >37 |
| 146 | 0.15 | 0.19 | 0.20 | |
| 147 | 0.13 | 0.14 | 0.12 | |
| 148 | 0.27 | 0.22 | 0.16 | 4.1 |
| 149 | 0.03 | 0.036 | 0.039 | 6.9 |
| 150 | 0.11 | 0.14 | 0.12 | 4.6 |
| 151 | 0.13 | 0.15 | 0.16 | >37 |
| 152 | 0.078 | 0.10 | 0.11 | 3.1 |
| 153 | 0.14 | 0.16 | 0.13 | 12 |
| 154 | 0.091 | 0.12 | 0.12 | >37 |
| 155 | 0.087 | 0.08 | 0.076 | 11 |
| 156 | 0.049 | 0.059 | 0.077 | >37 |
| 157 | 0.077 | 0.077 | 0.20 | >37 |
| 158 | 0.082 | 0.098 | 0.093 | 3.3 |
| 159 | 0.046 | | 0.050 | 6.6 |
| 160 | 0.030 | | 0.052 | 4.4 |
| 161 | 0.021 | 0.033 | 0.024 | |
| 162 | 0.041 | 0.039 | 0.042 | 3.7 |
| 163 | <0.011 | 0.023 | 0.020 | 11 |
| 164 | 0.013 | 0.020 | 0.013 | 5.1 |
| 165 | 0.015 | 0.017 | 0.023 | 4.6 |
| 166 | <0.011 | 0.016 | 0.013 | 14 |
| 167 | 0.040 | 0.042 | 0.045 | 12 |
| 168 | 0.059 | 0.071 | 0.030 | 11 |
| 169 | 0.071 | 0.12 | 0.060 | 2.6 |
| 170 | 0.015 | 0.016 | 0.013 | 0.63 |
| 171 | 0.14 | 0.14 | 0.093 | 1.5 |
| 172 | 0.097 | 0.22 | 0.11 | >37 |
| 173 | 0.058 | 0.079 | 0.087 | >37 |
| 174 | 0.052 | 0.11 | 0.072 | 12 |
| 175 | 0.034 | 0.072 | 0.037 | 13 |
| 176 | 0.10 | 0.12 | 0.090 | >37 |
| 177 | 0.016 | | 0.030 | 11 |
| 178 | 0.066 | 0.068 | 0.062 | 32 |
| 179 | 0.095 | 0.092 | 0.09 | 3.9 |
| 180 | 0.083 | 0.089 | 0.071 | 2.4 |
| 181 | 0.034 | 0.062 | 0.040 | >37 |
| 182 | 0.046 | 0.12 | 0.051 | 27 |
| 183 | 0.082 | | 0.075 | >24 |
| 184 | 0.029 | 0.047 | 0.036 | 24 |
| 185 | <0.037 | 0.071 | 0.036 | 14.2 |
| 186 | 0.069 | 0.14 | 0.061 | 6.1 |
| 187 | 0.027 | | 0.042 | 33 |
| 188 | 0.031 | 0.041 | 0.040 | 19 |
| 189 | 0.029 | 0.040 | 0.033 | 3.8 |
| 190 | 0.022 | 0.028 | 0.025 | 12 |
| 191 | 0.025 | 0.069 | 0.031 | 10 |
| 192 | 0.039 | 0.053 | 0.044 | 7.1 |
| 193 | 0.055 | 0.13 | 0.080 | 16 |
| 194 | 0.045 | 0.090 | 0.065 | 5.2 |
| 195 | <0.011 | 0.020 | 0.016 | >37 |
| 196 | 0.19 | 0.27 | 0.17 | 2.8 |

[#]Denotes reference example

TABLE 2

Cellular IC50 values

| Example | MV-4-11 GI50 (μM) | MV-4-11 TGI (μM) | THP-1 GI50 (μM) | THP-1 TGI (μM) | K-562 GI50 (μM) | K-562 TGI (μM) | HCS Brd4-NUT IC50 (μM) |
|---|---|---|---|---|---|---|---|
| 7 | 0.0711 | 0.107 | 0.103 | 0.191 | 0.632 | >10 | |
| 16 | 0.0758 | 0.116 | 0.101 | 0.207 | 0.624 | >10 | |
| 18# | 3.33 | 4.04 | >10 | >10 | >10 | >10 | |
| 19 | 0.0258 | 0.043 | 0.0746 | 0.125 | 0.242 | >10 | 0.118* |
| 21 | 0.0223 | 0.0378 | 0.0366 | 0.0687 | 0.266 | >10 | |
| 26 | 0.204 | 0.317 | 0.297 | 0.772 | 1.50 | >10 | 0.698* |
| 27 | 0.0559 | 0.158 | 0.12 | 0.363 | 0.463 | >10 | |
| 34 | 0.0828* | 0.140* | 0.162* | 0.321* | 0.601* | >10* | 0.202* |
| 35 | 0.105* | 0.2295* | 0.239* | 0.427* | 0.905* | >10* | |
| 36 | 0.0534* | 0.0927* | 0.103* | 0.191* | 0.430* | >10* | |
| 44 | 0.217 | 0.329 | 0.308 | 0.484 | 0.658 | >10 | 0.164* |
| 45 | 0.251 | 0.373 | 0.357 | 0.698 | 0.994 | >10 | |
| 46 | 0.115 | 0.166 | 0.177 | 0.323 | 0.37 | >10 | |
| 47 | 0.113 | 0.158 | 0.414 | 0.755 | 0.709 | >10 | |
| 49 | 0.0241* | 0.0394* | 0.0290* | 0.0603* | 0.120* | >10* | 0.0341* |
| 51 | 0.0519* | 0.0883* | 0.0725* | 0.126* | 0.318* | >10* | 0.0764* |
| 52 | 0.0974 | 0.156 | 0.198 | 0.345 | 0.424 | >10 | 0.117* |
| 53 | 0.249 | 0.372 | 0.374 | 0.685 | 0.953 | >10 | |
| 54 | 0.458 | 0.661 | 0.637 | 1.43 | 1.53 | >10 | 0.490* |
| 55 | 0.0891 | 0.123 | 0.231 | 0.364 | 0.400 | >10 | 0.0541* |
| 56 | 0.0574 | 0.0981 | 0.0702 | 0.124 | 0.265 | >10 | |
| 57 | 0.0695 | 0.109 | 0.117 | 0.24 | 0.48 | >10 | |
| 58 | 0.0944 | 0.157 | 0.189 | 0.38 | 1.14 | >10 | |
| 59 | 0.22 | 0.325 | 0.317 | 0.598 | 1.25 | >10 | |
| 60 | 0.0869 | 0.154 | 0.166 | 0.302 | 0.456 | >10 | |
| 61# | 0.948 | 1.09 | 2.43 | >10 | >10 | >10 | |
| 62 | 0.0584 | 0.105 | 0.0977 | 0.174 | 0.316 | >10 | |
| 63 | 0.0258 | 0.0509 | 0.0619 | 0.115 | 0.314 | >10 | |
| 64 | 0.0276 | 0.0423 | 0.0648 | 0.113 | 0.292 | >10 | |
| 65 | 0.0675 | 0.109 | 0.121 | 0.217 | 0.554 | >10 | |
| 66 | 0.0677 | 0.106 | 0.126 | 0.248 | 0.908 | >10 | |
| 67 | 0.00855 | 0.0196 | 0.0203 | 0.0385 | 0.0474 | >10 | |
| 68 | 0.0301 | 0.0692 | 0.0477 | 0.117 | 0.157 | >10 | |
| 69 | 0.0274 | 0.0466 | 0.0442 | 0.0983 | 0.135 | >10 | |
| 70 | 0.00902 | 0.0131 | 0.0122 | 0.0305 | 0.0608 | >10 | 0.0114 |
| 71 | 0.0666 | 0.103 | 0.0756 | 0.178 | 0.345 | >10 | |
| 72 | 0.100 | 0.164 | 0.223 | 0.408 | 0.766 | >10 | 0.141 |
| 73 | 3.02 | 4.40 | >10 | >10 | >10 | >10 | >10 |
| 74 | 0.0958 | 0.103 | 0.142 | 0.327 | 0.459 | >10 | 0.0442 |
| 75 | 0.128 | 0.202 | 0.368 | 0.715 | 1.02 | >10 | 0.177 |
| 76 | 0.0532 | 0.107 | 0.140 | 0.300 | 0.339 | >10 | 0.106 |
| 77 | 0.0888 | 0.132 | 0.178 | 0.370 | 0.569 | >10 | 0.0995 |
| 78 | 0.052 | 0.0855 | 0.0854 | 0.223 | 0.392 | >10 | 0.0395 |
| 79 | 0.348 | 0.42 | 0.255 | 0.461 | 0.92 | >10 | 0.15 |
| 80 | 0.356 | 0.472 | 0.354 | 1.03 | 0.868 | >10 | 0.178 |
| 81 | 0.0956 | 0.13 | 0.261 | 0.422 | 0.883 | >10 | 0.0743 |
| 82 | 0.0948 | 0.139 | 0.222 | 0.406 | 0.92 | >10 | 0.0294 |
| 83 | 0.100 | 0.145 | 0.164 | 0.396 | 0.719 | >10 | 0.0968 |
| 84 | 0.0583* | 0.0980* | 0.0869* | 0.1625* | 0.384* | >10* | 0.0920* |
| 86 | 0.0346 | 0.0548 | 0.0638 | 0.123 | 0.229 | >10 | 0.0384 |
| 87 | 0.0164 | 0.0288 | 0.0235 | 0.0598 | 0.128 | >10 | 0.0173 |
| 89 | 0.0465 | 0.0673 | 0.0406 | 0.119 | 0.442 | >10 | 0.0443 |
| 90 | 0.0255 | 0.0436 | 0.051 | 0.115 | 0.276 | >10 | 0.0450 |
| 91 | 0.633 | 0.978 | 0.908 | 1.44 | 2.68 | >10 | 0.736 |
| 92 | 0.0109 | 0.0175 | 0.0192 | 0.0395 | 0.065 | >10 | 0.00701 |
| 93 | 0.0135 | 0.0226 | 0.0264 | 0.0518 | 0.08 | >10 | 0.0179 |
| 94 | 0.0195 | 0.0318 | 0.0344 | 0.0765 | 0.0969 | >10 | 0.0219 |
| 95 | 0.140 | 0.270 | 0.245 | 0.411 | 0.868 | >10 | 0.191 |
| 96 | 0.894 | 1.24 | 1.26 | 2.55 | 5.90 | >10 | 2.01 |
| 97 | 0.0680 | 0.120 | 0.164 | 0.274 | 0.684 | >10 | 0.145 |
| 99# | 2.00 | 4.31 | 2.84 | >10 | >10 | >10 | 8.86 |
| 100 | 0.0405 | 0.0582 | 0.0880 | 0.153 | 0.264 | >10 | 0.0421 |
| 101 | 0.0257 | 0.0447 | 0.0530 | 0.102 | 0.261 | >10 | 0.0661 |
| 102 | 0.0875 | 0.141 | 0.140 | 0.304 | 0.653 | >10 | 0.23 |
| 103# | 3.59 | 6.54 | 7.29 | >10 | >10 | >10 | >10 |
| 104 | 0.00997 | 0.0191 | 0.0262 | 0.0450 | 0.0576 | >10 | 0.0113 |
| 105 | 0.102 | 0.164 | 0.188 | 0.335 | 0.729 | >10 | 0.0986 |
| 106# | 0.649 | 1.48 | 2.11 | 4.68 | 4.06 | >10 | 2.24 |
| 107 | 0.00728 | 0.0113 | 0.00818 | 0.0199 | 0.0379 | >10 | 0.00290 |
| 108 | 0.267 | 0.445 | 0.397 | 0.832 | 1.51 | >10 | 0.635 |
| 109 | 0.0186 | 0.0381 | 0.0398 | 0.0904 | 0.269 | >10 | 0.0438 |
| 110 | 0.00525 | 0.0102 | 0.0106 | 0.0198 | 0.0503 | >10 | 0.00642 |

TABLE 2-continued

Cellular IC50 values

| Example | MV-4-11 GI50 (μM) | MV-4-11 TGI (μM) | THP-1 GI50 (μM) | THP-1 TGI (μM) | K-562 GI50 (μM) | K-562 TGI (μM) | HCS Brd4-NUT IC50 (μM) |
|---|---|---|---|---|---|---|---|
| 111 | 0.0162 | 0.0306 | 0.0220 | 0.0484 | 0.177 | >10 | 0.0343 |
| 112# | 0.758 | 1.21 | 1.28 | 3.17 | 2.81 | >10 | 3.35 |
| 113 | 0.0840 | 0.127 | 0.112 | 0.234 | 0.511 | >10 | 0.151 |
| 114 | 0.0204 | 0.0443 | 0.0304 | 0.0765 | 0.187 | >10 | 0.0232 |
| 115 | 0.0224* | 0.0482* | 0.0348* | 0.0712* | 0.142* | >10* | 0.0397* |
| 116 | 0.0125 | 0.0301 | 0.0188 | 0.0354 | 0.0812 | >10 | 0.0270 |
| 117 | 0.0186 | 0.0391 | 0.0318 | 0.0671 | 0.150 | >10 | 0.0243 |
| 118# | 1.64 | 3.35 | 3.16 | >10 | >10 | >10 | >10 |
| 119 | 0.00615 | 0.0116 | 0.00945 | 0.0226 | 0.0620 | >10 | 0.0125 |
| 120 | 0.0557 | 0.106 | 0.0792 | 0.165 | 0.402 | >10 | 0.0654 |
| 121# | 0.830 | 1.23 | 2.11 | 5.03 | 9.71 | >10 | 6.11 |
| 122 | 0.00341* | 0.00842* | 0.00432* | 0.0107* | 0.0241* | >10* | 0.00730* |
| 123# | 2.87* | 5.81* | 5.88* | >10* | 9.40* | >10* | 8.91* |
| 124# | 0.296* | 0.730* | 0.695* | 1.54 | 2.52* | >10* | 1.73* |
| 125 | 0.0187 | 0.0399 | 0.0258 | 0.0473 | 0.101 | >10 | 0.0323 |
| 126 | 0.404* | 0.682* | 0.576* | 1.15* | 4.15* | >10* | 0.587* |
| 127# | 2.26 | 4.49 | 4.23 | >10 | >10 | >10 | >10 |
| 128 | 0.0345 | 0.0734 | 0.0646 | 0.107 | 0.183 | >10 | 0.0533 |
| 129 | 0.0145* | 0.0290* | 0.0226* | 0.0429* | 0.0989* | >10* | 0.0310* |
| 130 | 0.0161 | 0.0267 | 0.0357 | 0.0813 | 0.195 | >10 | 0.0139 |
| 131 | 0.0245 | 0.0405 | 0.0597 | 0.119 | 0.215 | >10 | 0.0277 |
| 132 | 0.0523 | 0.0995 | 0.107 | 0.233 | 0.427 | >10 | 0.0686 |
| 133 | 0.069 | 0.102 | 0.166 | 0.327 | 0.451 | >10 | 0.0647 |
| 134 | 0.117 | 0.187 | 0.161 | 0.291 | 0.574 | >10 | 0.0922 |
| 135 | 0.0799 | 0.126 | 0.0861 | 0.2 | 0.616 | >10 | 0.0934 |
| 136 | 0.0282 | 0.041 | 0.0802 | 0.186 | 0.335 | >10 | 0.0928 |
| 137 | 0.0231 | 0.0421 | 0.064 | 0.116 | 0.248 | >10 | 0.0577 |
| 138 | 0.251 | 0.353 | 0.904 | 1.51 | 2.06 | >10 | 0.845 |
| 139 | 0.0729 | 0.107 | 0.19 | 0.399 | 0.591 | >10 | 0.366 |
| 140 | 0.106 | 0.154 | 0.392 | 0.925 | 1.37 | >10 | 0.435 |
| 141 | 0.136 | 0.222 | 0.281 | 0.527 | 1.19 | >10 | 0.231 |
| 142 | 0.0793 | 0.121 | 0.239 | 0.448 | 0.712 | >10 | 0.149 |
| 143 | 0.086 | 0.116 | 0.3 | 0.621 | 1.2 | >10 | 0.206 |
| 144 | 0.0598 | 0.107 | 0.214 | 0.361 | 0.432 | >10 | 0.134 |
| 145 | 0.0499 | 0.093 | 0.176 | 0.335 | 0.875 | >10 | 0.108 |
| 146 | 0.0392 | 0.0546 | 0.15 | 0.283 | 0.314 | >10 | 0.091 |
| 147 | 0.067 | 0.1 | 0.157 | 0.365 | 0.792 | >10 | 0.0731 |
| 148 | 0.0817 | 0.114 | 0.157 | 0.372 | 1.13 | >10 | 0.118 |
| 149 | 0.02805* | 0.0505* | 0.06885* | 0.138* | 0.3475* | >10* | 0.0353 |
| 150 | 0.0555* | 0.08635* | 0.1007* | 0.2115* | 0.4055* | >10* | 0.0278 |
| 151 | 0.226 | 0.368 | 0.778 | 1.33 | 2.61 | >10 | 0.554 |
| 152 | 0.4385* | 0.8005* | 2.605* | 3.995* | 4.33* | >10* | 1.35 |
| 153 | 0.115 | 0.161 | 0.229 | 0.515 | 0.925 | >10 | 0.15 |
| 154 | 0.05905* | 0.11155* | 0.243* | 0.5385* | 0.9555* | >10* | 0.208 |
| 155 | 0.0734* | 0.1165* | 0.12045* | 0.305* | 0.6385* | >10* | 0.106 |
| 156 | 0.03565* | 0.05795* | 0.0696* | 0.143* | 0.3745* | >10* | 0.0433 |
| 157 | 0.04995* | 0.08335* | 0.158* | 0.312* | 0.534* | >10* | 0.0997 |
| 158 | 0.0266* | 0.04505* | 0.1425* | 0.298* | 0.4845* | >10* | 0.103 |
| 159 | 0.04* | 0.0812* | 0.03695* | 0.0855* | 0.1165* | >10* | |
| 160 | 0.06615* | 0.1025* | 0.0561* | 0.10655* | 0.4255* | >10* | |
| 161 | 0.0661 | 0.102 | 0.0785 | 0.152 | 0.352 | >10 | 0.0401 |
| 162 | 0.0418* | 0.0903* | 0.0546* | 0.173* | 0.2445* | >10* | |
| 163 | 0.01028* | 0.02195* | 0.0175* | 0.04605* | 0.07975* | >10* | |
| 164 | 0.00769* | 0.01185* | 0.0096* | 0.0173* | 0.0982* | >10* | 0.004915* |
| 165 | 0.0217* | 0.03955* | 0.0383* | 0.0921* | 0.1905* | >10* | |
| 166 | 0.009385* | 0.02625* | 0.01715* | 0.05395* | 0.0946* | >10* | |
| 167 | 0.0276* | 0.0433* | 0.0596* | 0.117* | 0.2945* | >10* | 0.0333 |
| 168 | 0.0241* | 0.04035* | 0.03545* | 0.0949* | 0.10495* | >10* | |
| 169 | 0.0311* | 0.0576* | 0.05045* | 0.121* | 0.2755* | >10* | |
| 170 | 0.00766* | 0.01595* | 0.01345* | 0.03315* | 0.04845* | >10* | |
| 171 | 0.09375* | 0.174* | 0.11835* | 0.2975* | 0.442* | >10* | |
| 172 | 0.1755* | 0.323* | 0.254* | 0.782* | 1.077* | >10* | |
| 173 | 0.0571* | 0.139* | 0.0916* | 0.2825* | 0.3275* | >10* | |
| 174 | 0.0267* | 0.0588* | 0.04375* | 0.105* | 0.1575* | >10* | |
| 175 | 0.04225* | 0.08675* | 0.06625* | 0.1305* | 0.1915* | >10* | |
| 176 | 0.0303* | 0.06315* | 0.0556* | 0.106* | 0.145* | >10* | |
| 177 | 0.06755* | 0.1135* | 0.06445* | 0.153* | 0.331* | >10* | |
| 178 | 0.0282* | 0.0491* | 0.04255* | 0.10705* | 0.137* | >10* | |
| 179 | 0.07735* | 0.1205* | 0.11235* | 0.272* | 0.372* | >10* | |
| 180 | 0.068* | 0.108* | 0.08145* | 0.186* | 0.266* | >10* | |
| 181 | 0.04705* | 0.0886* | 0.0519* | 0.1165* | 0.16* | >10* | |
| 182 | 0.06325* | 0.12* | 0.08755* | 0.2175* | 0.2805* | >10* | |

TABLE 2-continued

| | | | | | K-562 | K-562 | HCS |
| | MV-4-11 | MV-4-11 | THP-1 | THP-1 | GI50 | TGI | Brd4-NUT |
| Example | GI50 (μM) | TGI (μM) | GI50 (μM) | TGI (μM) | (μM) | (μM) | IC50 (μM) |
|---|---|---|---|---|---|---|---|
| 183 | 0.07605* | 0.1255* | 0.135* | 0.3135* | 0.659* | >10* | |
| 184 | 0.0596 | 0.136 | 0.131 | 0.337 | 0.394 | >10 | |
| 185 | 0.0242* | 0.0427* | 0.03675* | 0.0877* | 0.136* | >10* | |
| 186 | 0.04415* | 0.0882* | 0.0615* | 0.145* | 0.2075* | >10* | |
| 187 | 0.1442* | 0.209* | 0.16785* | 0.223* | 0.655* | >10* | |
| 189 | 0.0141* | 0.0269* | 0.011275* | 0.0261* | 0.08855* | >10* | |
| 193 | 0.058* | 0.09855* | 0.06615* | 0.1415* | 0.202* | >10* | |
| 194 | 0.0486 | 0.0936 | 0.0732 | 0.174 | 0.245 | >10 | |
| 195 | 0.02395* | 0.04525* | 0.0303* | 0.08035* | 0.12705* | >10* | |
| 196 | 0.1435* | 0.266* | 0.204* | 0.53* | 0.921* | >10* | |

*Values from n ≥ 2 independent determinations

Combinations

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by a BET protein. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the comtripotassiupound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by a BET protein, wherein the medicament is prepared for administration with another therapeutic agent. The invention also provides the use of another therapeutic agent for treating a disease or condition mediated by a BET protein, wherein the medicament is administered with a compound of formula (I).

The invention also provides a compound of formula (I) for use in a method of treating a disease or condition mediated by a BET protein, wherein the compound of formula (I) is prepared for administration with another therapeutic agent. The invention also provides another therapeutic agent for use in a method of treating a disease or condition mediated by a BET protein, wherein the other therapeutic agent is prepared for administration with a compound of formula (I). The invention also provides a compound of formula (I) for use in a method of treating a disease or condition mediated by a BET protein, wherein the compound of formula (I) is administered with another therapeutic agent. The invention also provides another therapeutic agent for use in a method of treating a disease or condition mediated by a BET protein, wherein the other therapeutic agent is administered with a compound of formula (I).

The invention also provides the use of a compound of formula (I) for treating a disease or condition mediated by a BET protein, wherein the patient has previously (e.g. within 24 hours) been treated with another therapeutic agent. The invention also provides the use of another therapeutic agent for treating a disease or condition mediated by a BET protein, wherein the patient has previously (e.g. within 24 hours) been treated with a compound of formula (I).

In one embodiment, the other therapeutic agent is an anticancer agent.

In a further embodiment, the other therapeutic agent is a modulator of a target in the field of epigenetics, such as an inhibitor of histone deacetylase (HDAC), or an inhibitor of histone methyltransferase (HMT).

Generic Schemes

Typically, the compounds of formula (I) can be prepared according to the Schemes provided infra.

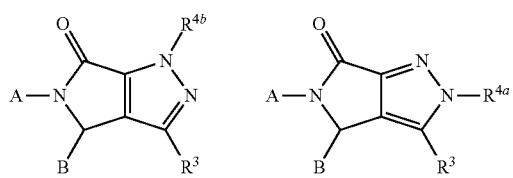

Scheme 1

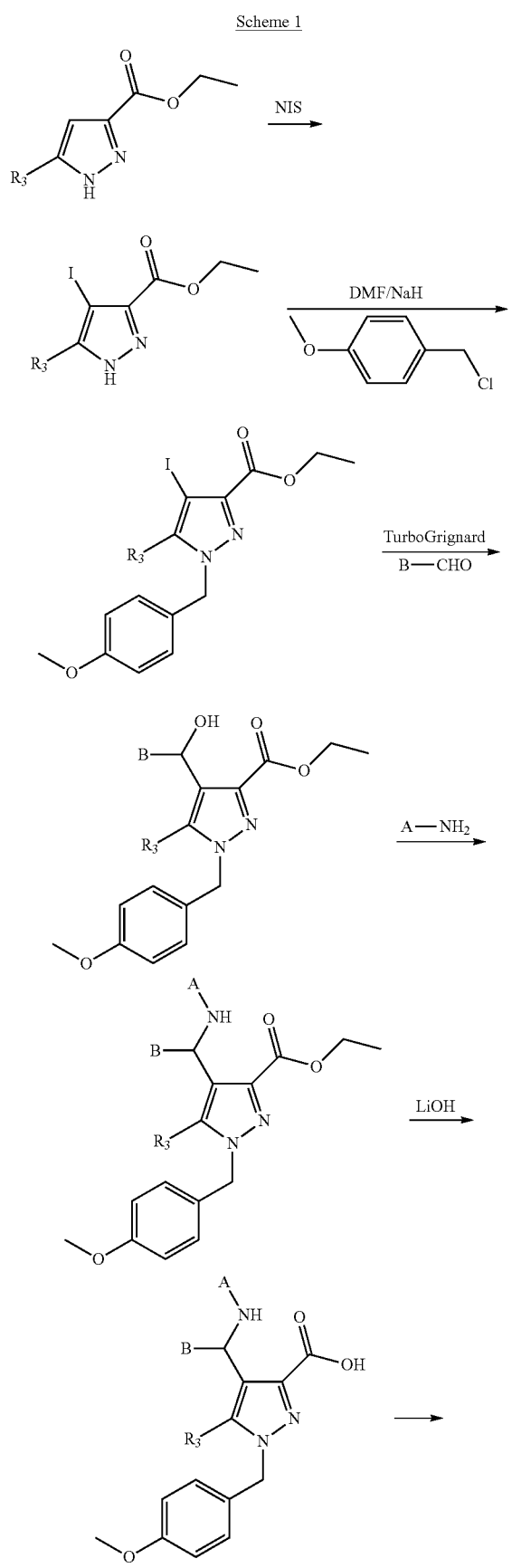
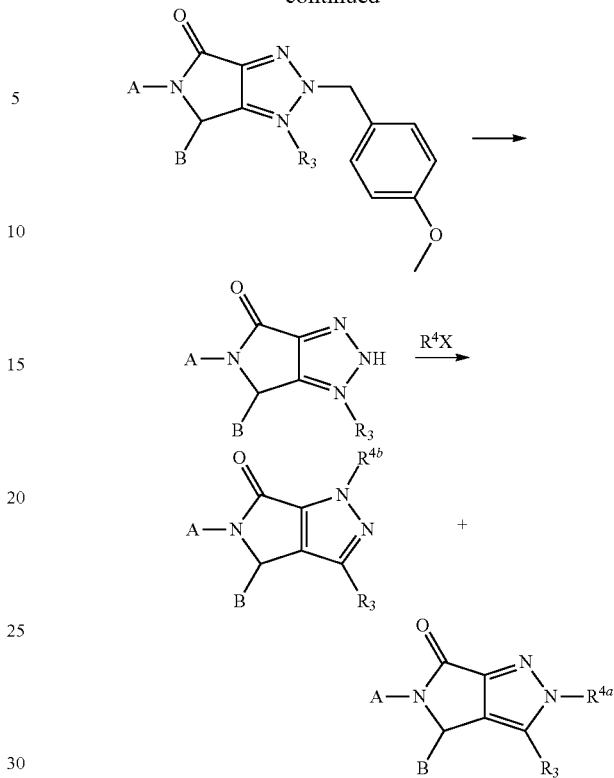

Scheme 1 illustrates one method for preparing compounds of the invention (e.g. Example 1). An ethyl 5-alkyl-1H-pyrazole-3-carboxylate is reacted with N-iodosuccinimide (NIS) to provide a 4-iodo-pyrazole derivative whose pyrazole NH is protected by deprotonation with sodium hydride (NaH) and alkylation with 4-methoxy-benzyl chloride. The resulting iodo derivative can be converted in the corresponding magnesium chloride by reaction with isopropylmagnesium chloride lithium chloride complex solution 1.3 M in THF (TurboGrignard). This freshly made organometallic reagent is reacted with an aldehyde to generate the corresponding secondary alcohol adduct. Conversion of the alcohol into a leaving group, for example mesylate, is accomplished by reaction with methanesulfonic anhydride in the presence of an organic base such as pyridine (together with a catalytic amount of 4-dimethylaminopyridine) or triethylamine. The mesylate can be displaced by reaction with an amine. Cyclization to the lactam can be effected in two steps by initial saponification of the ester group on treatment with a base such as an alkali metal hydroxide (e.g. lithium hydroxide or sodium hydroxide) in a solvent such as wet cycloalkylether or alcohol (e.g. dioxane/water or methanol/water), at room temperature. The freed amino-acid intermediate obtained after neutralization of the reaction mixture with an acid (such as a mineral acid, e.g. hydrochloric acid), extraction and evaporation to dryness is then cyclized intramolecularly by treatment with 1-chloro-N,N,2-trimethylpropenylamine at 0° C.

Deprotection of the pyrazole moiety is achieved by treatment with an organic acid such as trifluoroacetic acid (TFA), at 100° C. under microwave irradiation (e.g. Example 2). Introduction of R4 can be effected by treatment with NaH in DMF followed by alkylation (e.g. Example 3). Specific alkyl (e.g. cyclopropyl) and aryl R4 can also be introduced by coupling reaction with a boronic acid in the presence of either copper(II) acetate and pyridine in dichloroethane (e.g. Example 81) or copper(II) acetate, sodium carbonate and 2,2'-bipyridine in acetonitrile, at 65-70° C. (e.g. Example 85).

Scheme 2

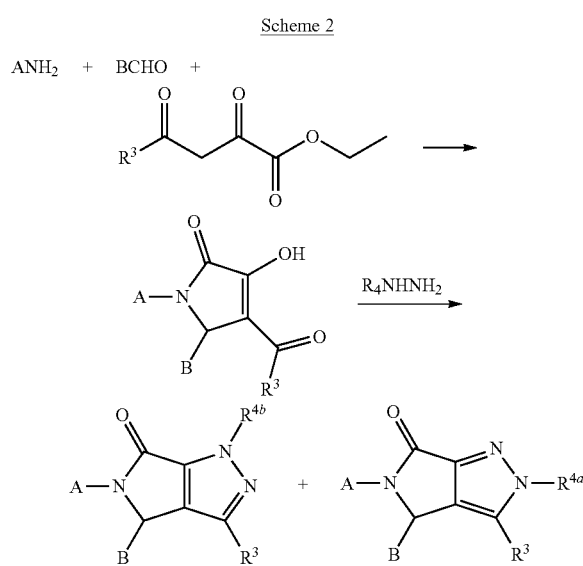

Scheme 2 illustrates an alternative synthetic route for preparing compounds of the invention (e.g. Example 57). Amine, aldehyde and diketoester are reacted in acetic acid at 125° C. For R3=H, (E)-ethyl 4-(dimethylamino)-2-oxobut-3-enoate is used instead of the diketoester (e.g. Example 34). The resulting 3-hydroxy-1H-pyrrol-2(5H)-one intermediate undergoes condensation with the desired hydrazine usually in acetic acid or in a mixture of ethanol and toluene under heating. Modified experimental conditions for the condensation step are described in Examples 60 and 69.

Scheme 3

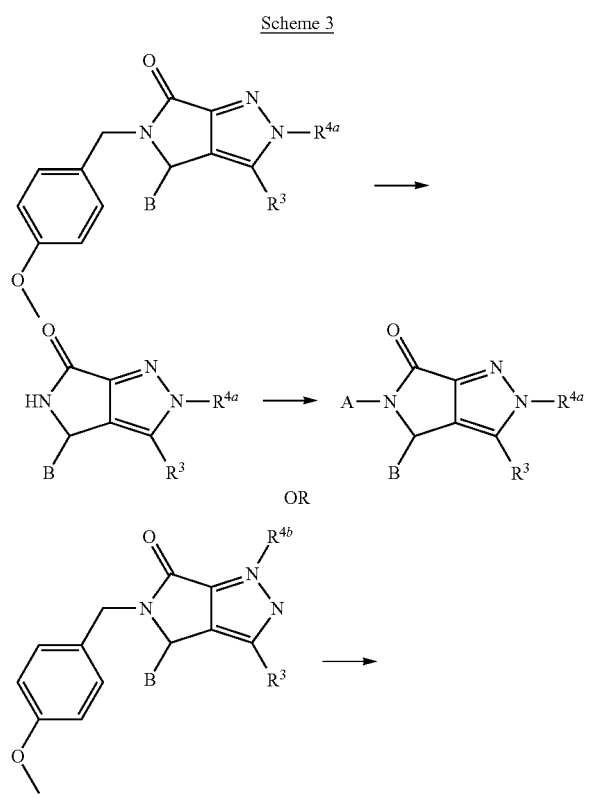

Scheme 3 illustrates an alternative method to introduce A (e.g. Example 25). 5-(4-Methoxybenzyl)-4,5-dihydropyrrolo[3,4-c]pyrazol-6(2H)- or 6(1H)-one intermediates, prepared according to the method described in Scheme 1 (e.g. Step 23.8) or 2 (e.g. Step 71.3), are deprotected by treatment with TFA, at 140° C. under microwave irradiation. The resulting compounds are reacted with the halide A-X in the presence of either 1) tripotassium phosphate, copper(I) iodide, and N,N'-dimethylethylenediamine in dioxane, at a temperature in the range of 100-120° C. (e.g. Examples 23, 24), or 2) $Pd_2(dba)_3$, Xantphos, and $Cs_2CO_3$, in dioxane at 100° C.

Scheme 4

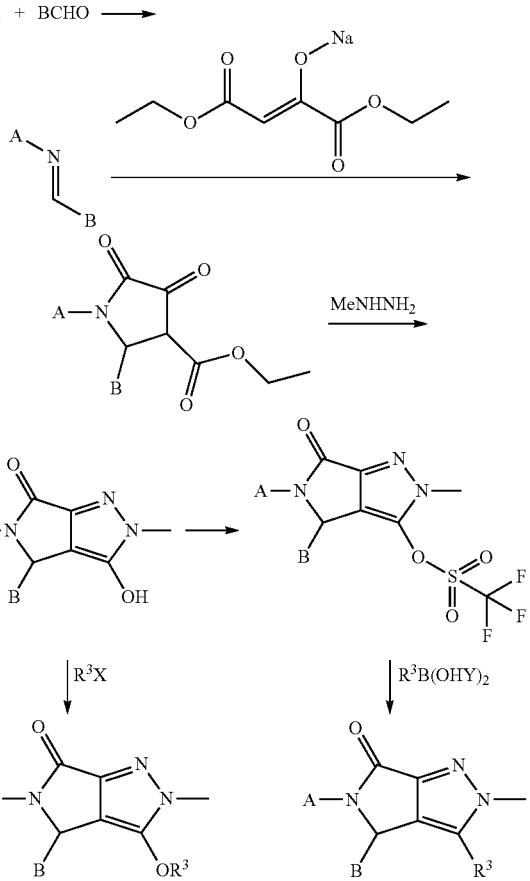

Scheme 4 illustrates one method for preparing compounds of the invention (e.g. Example 73, 76-77). Reaction of the aldehyde BCHO and the amine $ANH_2$ in ethanol at 85° C. produces the corresponding hydrazone which is reacted with the sodium salt of diethyl oxaloacetate in acetic acid at 110° C. The resulting intermediate is treated with methylhydrazine according to a protocol involving: 1) heating the two reactants at 110° C. in a solvent mixture of toluene and ethanol, 2) removal of the solvent by concentration, 3) dilution of the residue in acetic acid and heating of the resulting mixture at 100° C. to convert the intermediate obtained from the first step in a 3-hydroxy-2-methyl-4,5-dihydropyrrolo[3,4-c]pyrazol-6(2H)-one. The hydroxy group can be alkylated by reaction with NaH in DMF, followed by addition of an organic halide (e.g. Examples 76, 77). The hydroxy group can also be converted in the corresponding triflate by treatment with trifluoromethanesulfonic anhydride and triethylamine in dichloromethane. Coupling reaction of the triflate with boronic acids in the presence of a palladium catalyst and a base (e.g. $K_3PO_4$) in dioxane at 110° C. allows for the introduction various $R^3$ groups.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

Synthetic Methods

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

ABBREVIATIONS aq. aqueous
Ar argon
Boc tert-butoxycarbonyl
brine saturated (at rt) sodium chloride solution
br. s broad singlet
CAN ceric ammonium nitrate
$CH_2Cl_2$ dichloromethane
$CH_3CN$ acetonitrile
CPS In 1 L of water: 10 g of $Ce(SO_4)_2 \cdot 4H_2O$, 25 g of phosphomolybdic acid and 60 mL of sulfuric acid 100%
d doublet
DBU 1,8-Diazabicyclo[5.4.0]undec-7-ene
DIEA diisopropyl ethyl amine
DEAD diethyl azodicarboxylate
DMAP 4-dimethylaminopyridine
DMF N,N-dimethylformamide
DMSO dimethylsulfoxide
EDCI 1-[3-(dimethylamino)propyl]-3-ethyl carbodiimide
eq. equivalent
ESI-MS electrospray mass spectrometry
Et ethyl
EtOAc ethyl acetate
EtOH ethanol
h or hr hour(s)
$H_2O$ water
HATU O-(7-azabenzotriazol-1-yl)-N,N,N',N'-tetramethyluronium-hexafluoro phosphate
HCl hydrogen chloride
HOBt 1-hydroxybenzotriazole
HPLC high-performance liquid chromatography
iPrOH propan-2-ol
$K_2CO_3$ potassium carbonate
$K_3PO_4$ potassium phosphate
m multiplet
Me methyl
MeOH methanol
$MgSO_4$ magnesium sulfate
min minute(s)
mL milliliter(s)
MS mass spectrometry
$Ms_2O$ methanesulfonic anhydride
MW microwave
NaH sodium hydride
$NaHCO_3$ sodium bicarbonate
NaOAc sodium acetate
NaOH sodium hydroxide
$Na_2SO_4$ sodium sulfate
$Na_2S_2O_3$ sodium thiosulfate
$NH_4Cl$ ammonium chloride
NMR nuclear magnetic resonance
$Pd(PPh_3)_4$ tetrakis(triphenylphosphine)palladium(0)
Ph phenyl
PPU propyl-pyridyl-urea
$R_f$ ratio of fronts
rt (or RT) room temperature
s singlet
$scCO_2$ supercritical carbon dioxide
SFC supercritical fluid chromatography
t triplet
$t_R$ time of retention
TBAF tetrabutylammonium fluoride
TEA triethylamine
TFA trifluoroacetic acid
THF tetrahydrofuran
TurboGrignard Isopropylmagnesium chloride lithium chloride complex solution 1.3 M in THF
Xantphos 4,5-Bis(diphenylphosphino)-9,9-dimethylxanthene
XthalFluor-E Ethanaminium,N-(difluoro-$\lambda^4$-sulfanylidene)-N-ethyl-, tetrafluoroborate(1-) (1:1)

HPLC Methods:
HPLC 1: Column: Nucleosil 100-3 C18 HD, 4.6×70 mm. Flow: 1 mL/min. Column temperature: 30° C. Gradient: 20% to 100% B in 5 min, 100% B for 1.5 min, 100% to 20% B in 0.5 min; A=0.1% TFA in water, B=0.1% TFA in acetonitrile.

LC-MS Methods:
LC-MS 1:
Column: Waters Acquity HSS T3, 1.8 µm, 2.1×50 mm, oven at 50° C. Flow: 1.2 mL/min. Gradient: 2% to 98% B in 1.40 min, then 98% B for 0.40 min, 98% to 2% B in 0.10 min, 2% B for 0.10 min; A=water+0.05% formic acid+3.75 mM ammonium acetate, B=acetonitrile+0.04% formic acid. Detection UV/VIS (DAD), ESI (+/−). Mass spectrometer range: 100-1600 Da.

LC-MS 2:
Column: Waters Acquity HSS T3, 1.8 µm, 2.1×50 mm, oven at 60° C. Flow: 1.0 mL/min. Gradient: 5% to 98% B in 1.40 min, then 98% B for 0.40 min, 98% to 5% B in 0.10 min, 5% B for 0.10 min; A=water+0.05% formic acid+3.75 mM

Example 1

4-(4-chlorophenyl)-2-(4-methoxybenzyl)-3-methyl-5-(1-methyl-6-oxo-1,6-dihydropyridin-3-yl)-4,5-dihydropyrrolo[3,4-c]pyrazol-6(2H)-one

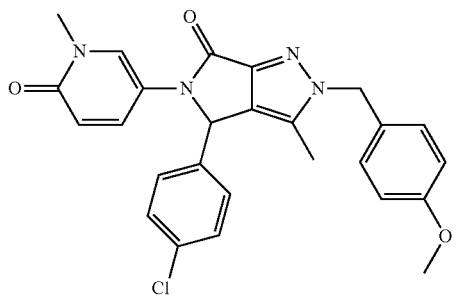 [SMILES: COc1ccc(Cn2nc3c(c2C)C(c2ccc(Cl)cc2)N(c2ccc(=O)n(C)c2)C3=O)cc1]

To a stirred solution of 4-((4-chlorophenyl)(1-methyl-6-oxo-1,6-dihydropyridin-3-ylamino)methyl)-1-(4-methoxybenzyl)-5-methyl-1H-pyrazole-3-carboxylic acid (Step 1.5) (125 mg, 0.254 mmol) in $CH_2Cl_2$ (2 mL) under Ar was added 1-chloro-N,N,2-trimethyl-1-propenylamine (0.047 mL, 0.355 mmol) at 0° C. The reaction mixture was stirred for 1 hr at 0° C., quenched with a saturated aqueous solution of $NaHCO_3$ (75 mL), and extracted with $CH_2Cl_2$. The combined organic layers were washed with a saturated aqueous solution of $NaHCO_3$ (100 mL), dried over $Na_2SO_4$ the solvent was and evaporated off under reduced pressure. The crude residue was purified by silica gel column chromatography ($CH_2Cl_2$/MeOH 0.5-3.5%) to afford the title product (92 mg, 0.194 mmol, 76% yield) as a greenish solid. $t_R$: 4.32 min (HPLC 1); $t_R$: 0.97 min (LC-MS 2); ESI-MS: 475 [M+H]$^+$ (LC-MS 2); $R_f$=0.65 ($CH_2Cl_2$/MeOH 9:1).

Step 1.1: ethyl 4-iodo-5-methyl-1H-pyrazole-3-carboxylate

To a stirred solution of ethyl 3-methylpyrazole-5-carboxylate (3.11 g, 20.17 mmol) in DMF (50 mL) under Ar at 0° C. was added NIS (5.90 g, 26.2 mmol). The reaction mixture was stirred 20 hr at rt and quenched with 500 mL of water. The resulting precipitate was collected to afford the title product (5.61 g, 20.03 mmol, 99% yield) as a white solid. $t_R$: 3.75 min (HPLC 1); $t_R$: 0.78 min (LC-MS 2); ESI-MS: 281 [M+H]$^+$ (LC-MS 2)

Step 1.2: ethyl 4-iodo-1-(4-methoxybenzyl)-5-methyl-1H-pyrazole-3-carboxylate

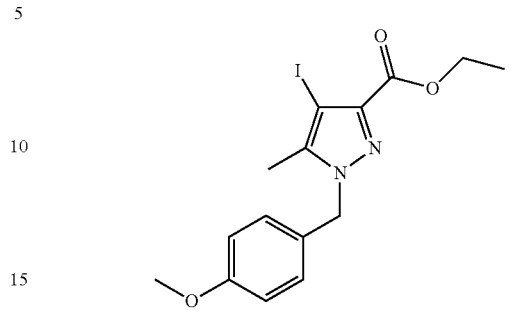

To a stirred solution of ethyl 4-iodo-5-methyl-1H-pyrazole-3-carboxylate (Step 1.1) (7.60 g, 27.1 mmol) in DMF (50 mL) under Ar was added NaH (1.302 g, 32.6 mmol) at 0° C. After 15 min, 4-methoxyphenyl chloride (3.70 mL, 27.1 mmol) was added. The reaction mixture was stirred for 1 hr at rt, quenched with a saturated aqueous solution of $NaHCO_3$ (100 mL) and extracted with EtOAc (100 mL). The combined organic layers were washed with a saturated aqueous solution of $NaHCO_3$ (100 mL), dried over $Na_2SO_4$ and the solvent was evaporated off under reduced pressure. The crude material was purified by silica gel column chromatography (hexane/EtOAc 5-40%) to afford the title product (6.23 g, 15.57 mmol, 57% yield) as a colorless oil. $t_R$: 5.24 min (HPLC 1); $t_R$: 1.12 min (LC-MS 2); ESI-MS: 401 [M+H]$^+$ (LC-MS 2); $R_f$=0.66 (hexane/EtOAc 1:1).

Step 1.3: ethyl 4-((4-chlorophenyl)(hydroxy)methyl)-1-(4-methoxybenzyl)-5-methyl-1H-pyrazole-3-carboxylate

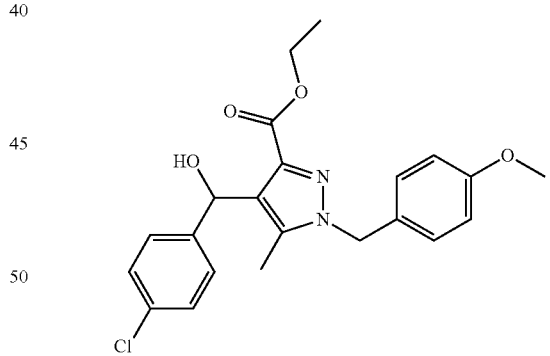

To a stirred solution of ethyl 4-iodo-1-(4-methoxybenzyl)-5-methyl-1H-pyrazole-3-carboxylate (Step 1.2) (6.23 g, 15.57 mmol) in THF (100 mL) under Ar was added Turbo-Grignard (15.57 mL, 20.24 mmol) at −10° C. After 15 min, 4-chlorobenzaldehyde (2.188 g, 15.57 mmol) was added. The reaction mixture was stirred for 30 min at this temperature, quenched with a saturated aqueous solution of $NH_4Cl$ (50 mL), extracted with EtOAc (2×50 mL). The combined organic layers were washed with a saturated aqueous solution of $NH_4Cl$ (75 mL), dried over Na2SO4 and evaporated. The crude material was purified by silica gel column chromatography (hexane/EtOAc 20-50%) to afford the title product (4.50 g, 10.85 mmol, 70% yield) as a colorless oil. $t_R$: 5.34

Step 1.4: ethyl 4-((4-chlorophenyl)(1-methyl-6-oxo-1,6-dihydropyridin-3-ylamino)methyl)-1-(4-methoxybenzyl)-5-methyl-1H-pyrazole-3-carboxylate

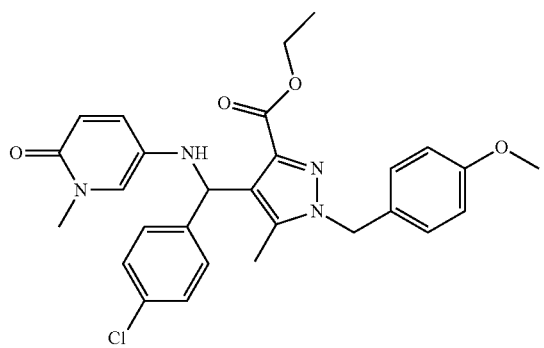 [SMILES: CCOC(=O)c1nn(Cc2ccc(OC)cc2)c(C)c1C(Nc1ccc(=O)n(C)c1)c1ccc(Cl)cc1]

To a stirred solution of Ethyl 4-((4-chlorophenyl)(hydroxy)methyl)-1-(4-methoxybenzyl)-5-methyl-1H-pyrazole-3-carboxylate (Step 1.3) (423 mg, 1.020 mmol) and triethylamine (1.42 mL, 10.20 mmol) in $CH_2Cl_2$ under Ar was added $Ms_2O$ (355 mg, 2.039 mmol) at −10° C. The reaction mixture was stirred for 30 min at this temperature. 5-Amino-1-methyl-2(1H)-pyridinone oxalate salt (218 mg, 1.020 mmol) was added at 30° C. After 1 hr, the reaction mixture was quenched with a saturated aq. NaHCO solution, and extracted with $CH_2Cl_2$. The combined organic layers were washed a saturated aqueous solution of $NaHCO_3$, dried over $Na_2SO_4$ and evaporated. The crude material was purified by silica gel column chromatography ($CH_2Cl_2$/MeOH 1-2%) to afford the title product (147 mg, 0.282 mmol, 28% yield) as a greenish solid. $t_R$: 4.68 min (HPLC 1); $t_R$: 1.06 min (LC-MS 2); ESI-MS: 521 $[M+H]^+$ (LC-MS 2); $R_f$=0.56 ($CH_2Cl_2$/MeOH 9:1).

Step 1.5: 4-((4-chlorophenyl)(1-methyl-6-oxo-1,6-dihydropyridin-3-ylamino)methyl)-1-(4-methoxybenzyl)-5-methyl-1H-pyrazole-3-carboxylic acid

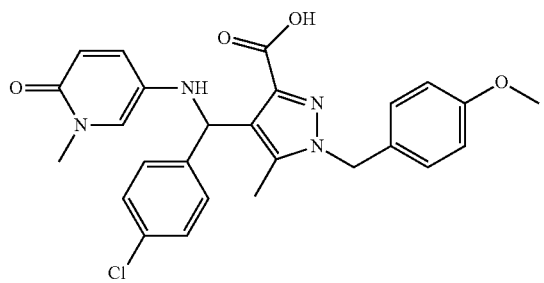 [SMILES: COc1ccc(Cn2nc(C(=O)O)c(C(Nc3ccc(=O)n(C)c3)c3ccc(Cl)cc3)c2C)cc1]

In a 25-mL flask was introduced ethyl 4-((4-chlorophenyl)(1-methyl-6-oxo-1,6-dihydropyridin-3-ylamino)methyl)-1-(4-methoxybenzyl)-5-methyl-1H-pyrazole-3-carboxylate (Step 1.4) (140 mg, 0.269 mmol) and $LiOH \cdot H_2O$ (33.8 mg, 0.806 mmol) in dioxane (2.5 mL) and $H_2O$ (1.0 mL). The reaction mixture was stirred for 3 hr at rt, quenched with 0.5N HCl (50 mL), and extracted with EtOAc. The combined organic layers were washed with 0.5N HCl, dried over $Na_2SO_4$, and evaporated to dryness to afford the title product (128 mg, 0.260 mmol, 97% yield) as a green solid. $t_R$: 3.94 min (HPLC 1); $t_R$: 0.90 min (LC-MS 2); ESI-MS: 493 $[M+H]^+$ (LC-MS 2).

Example 2

4-(4-chlorophenyl)-3-methyl-5-(1-methyl-6-oxo-1,6-dihydropyridin-3-yl)-4,5-dihydropyrrolo[3,4-c]pyrazol-6(2H)-one

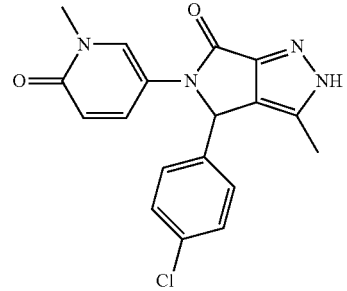 [SMILES: Cc1[nH]nc2c1C(c1ccc(Cl)cc1)N(c1ccc(=O)n(C)c1)C2=O]

In a 2-5 mL MW flask was introduced 4-(4-chlorophenyl)-2-(4-methoxybenzyl)-3-methyl-5-(1-methyl-6-oxo-1,6-dihydropyridin-3-yl)-4,5-dihydropyrrolo[3,4-c]pyrazol-6(2H)-one (Example 1) (85 mg, 0.179 mmol) and TFA (1379 μL, 17.90 mmol). The reaction mixture was stirred for 30 min at 100° C. under MW irradiation, quenched with a saturated aq. $NaHCO_3$ solution, and extracted with $CH_2Cl_2$. The combined organic layers were washed with a saturated aq. solution of $NaHCO_3$, dried over $Na_2SO_4$, and evaporated. The crude material was purified by silica gel column chromatography ($CH_2Cl_2$/MeOH 1-8%) to afford the title compound (32 mg, 0.090 mmol, 50% yield) as a white solid. $t_R$: 3.13 min (HPLC 1); $t_R$: 0.69 min (LC-MS 2); ESI-MS: 355 $[M+H]^+$ (LC-MS 2); $R_f$=0.40 ($CH_2Cl_2$/MeOH 9:1); $^1$H NMR (400 MHz, DMSO-$d_6$) δ ppm 2.03 (s, 3H) 3.34 (s, 3H) 6.09 (s, 1H) 6.30 (d, J=9.4 Hz, 1H) 7.22 (d, J=8.2 Hz, 2H) 7.35 (d, J=8.6 Hz, 2H) 7.44 (dd, J=9.8, 2.74 Hz, 1H) 7.88 (d, J=3.1 Hz, 1H) 13.35 (br. s., 1H).

Example 3

4-(4-chlorophenyl)-2,3-dimethyl-5-(1-methyl-6-oxo-1,6-dihydropyridin-3-yl)-4,5-dihydropyrrolo[3,4-c]pyrazol-6(2H)-one

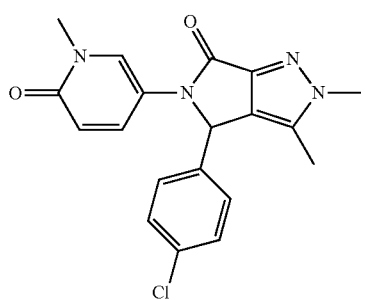 [SMILES: Cc1c2c(nn1C)C(=O)N(c1ccc(=O)n(C)c1)C2c1ccc(Cl)cc1]

To a stirred solution of 4-(4-chlorophenyl)-3-methyl-5-(1-methyl-6-oxo-1,6-dihydropyridin-3-yl)-4,5-dihydropyrrolo[3,4-c]pyrazol-6(2H)-one (Example 2) (25 mg, 0.070 mmol) in DMF (1 mL) under Ar was added NaH (3.38 mg, 0.085 mmol). The reaction mixture was stirred at rt for 30 min and MeI (6.61 μL, 0.106 mmol) was added. After 1 hr at rt, the reaction mixture was quenched with a saturated aq. $NaHCO_3$ solution and extracted with EtOAc. The combined organic layers were washed with a saturated aq. $NaHCO_3$ solution, dried over $Na_2SO_4$, and evaporated. The crude material was purified by preparative HPLC (Gilson gx-281; column: Sunfire C18, 30×100 mm, 5 μm; flow: 30 mL/min; gradient: 5% to 100% B in 20 min; A=0.1% TFA in H₂O, B=CH₃CN; detection: UV) to afford the title product (10 mg, 0.027 mmol, 38% yield). t_R: 3.39 min (HPLC 1); t_R: 0.74 min (LC-MS 2); ESI-MS: 369 [M+H]⁺ (LC-MS 2); ¹H NMR (400 MHz, DMSO-d₆) δ ppm 2.05 (s, 3H) 3.34 (s, 3H) 3.83 (s, 3H) 6.10 (s, 1H) 6.30 (d, J=9.8 Hz, 1H) 7.23 (d, J=8.6 Hz, 2H) 7.35 (d, J=8.6 Hz, 2H) 7.44 (dd, J=9.8, 2.7 Hz, 1H) 7.89 (d, J=2.7 Hz, 1H). In addition to the title compound, a second product was isolated during this purification process and is described in Example 4.

Example 4

4-(4-chlorophenyl)-1,3-dimethyl-5-(1-methyl-6-oxo-1,6-dihydropyridin-3-yl)-4,5-dihydropyrrolo[3,4-c]pyrazol-6(1H)-one

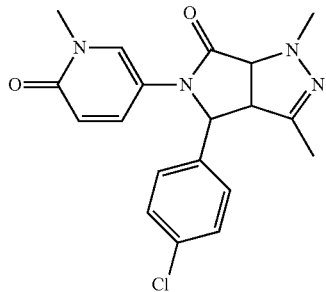 [SMILES: CC1=NN(C)C2C(=O)N(c3ccc(=O)n(C)c3)C(c3ccc(Cl)cc3)C12]

The title product (10 mg, 0.027 mmol, 38% yield) was obtained upon purification of the crude material obtained in Example 3 by preparative HPLC (Gilson gx-281; column: Sunfire C18, 30×100 mm, 5 μm; flow: 30 mL/min; gradient: 5% to 100% B in 20 min; A=0.1% TFA in H₂O, B=CH₃CN; detection: UV) to afford the title product. t_R: 3.55 min (HPLC 1); t_R: 0.79 min (LC-MS 2); ESI-MS: 369 [M+H]⁺ (LC-MS 2); ¹H NMR (400 MHz, DMSO-d₆) δ ppm 1.91 (s, 3H) 3.34 (s, 3H) 3.91 (s, 3H) 6.06 (s, 1H) 6.31 (d, J=9.4 Hz, 1H) 7.25 (d, J=8.2 Hz, 2H) 7.36 (d, J=8.2 Hz, 2H) 7.41 (dd, J=9.5, 2.9 Hz, 1H) 7.86 (d, J=2.7 Hz, 1H).

Example 5

5-(5-chloro-1-methyl-6-oxo-1,6-dihydropyridin-3-yl)-4-(4-chlorophenyl)-3-methyl-4,5-dihydropyrrolo[3,4-c]pyrazol-6(2H)-one

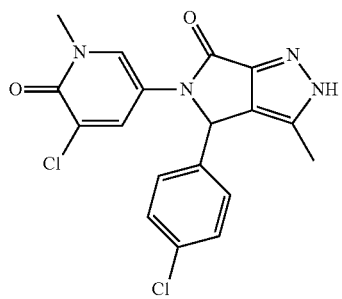

The title compound was prepared in analogy to the procedure described in Example 2 using 5-(5-chloro-1-methyl-6-oxo-1,6-dihydropyridin-3-yl)-4-(4-chlorophenyl)-2-(4-methoxybenzyl)-3-methyl-4,5-dihydropyrrolo[3,4-c]pyrazol-6(2H)-one (Step 5.5). t_R: 3.55 min (HPLC 1); t_R: 0.78 min (LC-MS 2); ESI-MS: 389/391 [M+H]⁺ (LC-MS 2); R_f=0.34 (CH₂Cl₂/MeOH 9:1); ¹H NMR (400 MHz, DMSO-d₆) δ ppm 2.03 (s, 3H) 3.43 (s, 3H) 6.13 (s, 1H) 7.25 (d, J=8.2 Hz, 2H) 7.36 (d, J=8.2 Hz, 2H) 7.90 (d, J=2.4 Hz, 1H) 7.94 (d, J=2.7 Hz, 1H) 13.38 (s, 1H).

Step 5.1:
3-chloro-1-methyl-5-nitropyridin-2(1H)-one

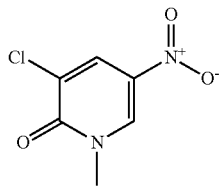

To a stirred suspension of 3-chloro-2-hydroxy-5-nitropyridine (10 g, 57.3 mmol) and K₂CO₃ (15.84 g, 115 mmol) in DMF (100 mL) under Ar was added MeI (5.37 mL, 86 mmol) at 0° C. The reaction mixture was stirred for 1 hr at rt, concentrated, diluted with water, and extracted with EtOAc. The combined organic layers were washed with water, dried over Na₂SO₄, and evaporated to afford the title product (10.38 g, 55.0 mmol, 96% yield) as a yellow solid. t_R: 2.90 min (HPLC 1).

Step 5.2:
5-amino-3-chloro-1-methylpyridin-2(1H)-one

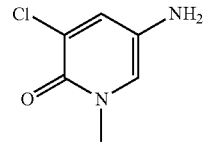

To a stirred solution of 3-chloro-1-methyl-5-nitropyridin-2(1H)-one (Step 5.1) (10.38 g, 55.0 mmol), EtOH (200 mL) and NH₄Cl (79 mL, 550 mmol) was added iron (9.22 g, 165 mmol). The reaction mixture was stirred for 1 hr at 85° C., filtered through a pad of celite, and concentrated. The crude material was purified by silica gel column chromatography (CH₂Cl₂/MeOH 2-10%) to afford the title product (6.77 g, 42.7 mmol, 78% yield) as a black solid. t_R: 0.29 min (LC-MS 1); ESI-MS: 159 [M+H]⁺ (LC-MS 1); R_f=0.28 (CH₂Cl₂/MeOH 9:1).

Step 5.3: Ethyl 4-((5-chloro-1-methyl-6-oxo-1,6-dihydropyridin-3-ylamino)(4-chlorophenyl)methyl)-1-(4-methoxybenzyl)-5-methyl-1H-pyrazole-3-carboxylate

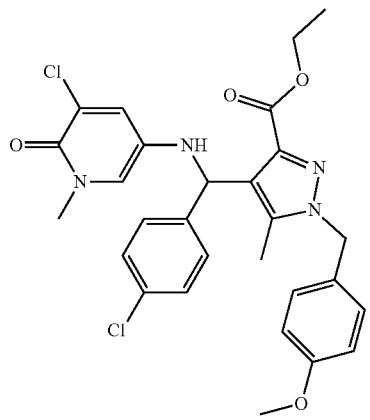 [SMILES: CCOC(=O)c1nn(Cc2ccc(OC)cc2)c(C)c1C(Nc1cc(Cl)c(=O)n(C)c1)c1ccc(Cl)cc1]

The title compound was prepared in an analogous procedure to that described in Step 1.4 using 5-amino-3-chloro-1-methylpyridin-2(1H)-one (Step 5.2). $t_R$: 5.14 min (HPLC 1); $t_R$: 1.14 min (LC-MS 2); ESI-MS: 555/557 [M+H]$^+$ (LC-MS 2); $R_f$=0.37 (CH$_2$Cl$_2$/MeOH 9:1).

Step 5.4: 4-((5-chloro-1-methyl-6-oxo-1,6-dihydropyridin-3-ylamino)(4-chlorophenyl)methyl)-1-(4-methoxybenzyl)-5-methyl-1H-pyrazole-3-carboxylic acid

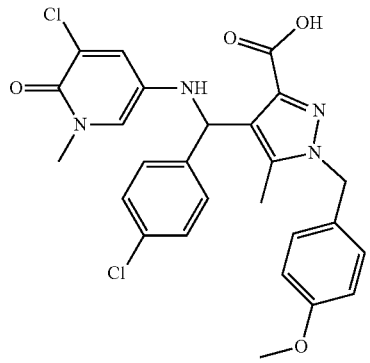 [SMILES: COc1ccc(Cn2nc(C(=O)O)c(C(Nc3cc(Cl)c(=O)n(C)c3)c3ccc(Cl)cc3)c2C)cc1]

The title compound was prepared in analogy to the procedure described in Step 1.5 using ethyl 4-((5-chloro-1-methyl-6-oxo-1,6-dihydropyridin-3-ylamino)(4-chlorophenyl)methyl)-1-(4-methoxy-benzyl)-5-methyl-1H-pyrazole-3-carboxylate (Step 5.3). $t_R$: 4.35 min (HPLC 1); $t_R$: 0.98 min (LC-MS 2); ESI-MS: 527/529 [M+H]$^+$ (LC-MS 2).

Step 5.5: 5-(5-chloro-1-methyl-6-oxo-1,6-dihydropyridin-3-yl)-4-(4-chlorophenyl)-2-(4-methoxy-benzyl)-3-methyl-4,5-dihydropyrrolo[3,4-c]pyrazol-6(2H)-one

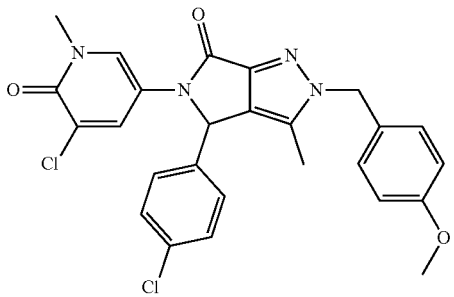 [SMILES: COc1ccc(Cn2nc3c(c2C)C(c2ccc(Cl)cc2)N(c2cc(Cl)c(=O)n(C)c2)C3=O)cc1]

The title compound was prepared in analogy to the procedure described in Example 1 using 4-((5-chloro-1-methyl-6-oxo-1,6-dihydropyridin-3-ylamino)(4-chlorophenyl)methyl)-1-(4-methoxybenzyl)-5-methyl-1H-pyrazole-3-carboxylic acid (Step 5.4). $t_R$: 4.74 min (HPLC 1); $t_R$: 1.04 min (LC-MS 2); ESI-MS: 509/511 [M+H]$^+$ (LC-MS 2); $R_f$=0.64 (CH$_2$Cl$_2$/MeOH 9:1).

Example 6

5-(5-chloro-1-methyl-6-oxo-1,6-dihydropyridin-3-yl)-4-(4-chlorophenyl)-2,3-dimethyl-4,5-dihydropyrrolo[3,4-c]pyrazol-6(2H)-one

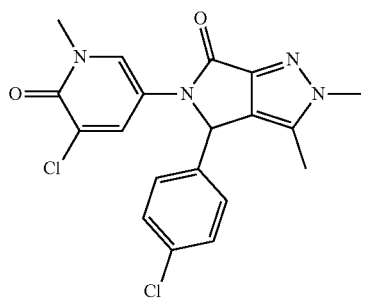 [SMILES: Cc1c2c(nn1C)C(=O)N(c1cc(Cl)c(=O)n(C)c1)C2c1ccc(Cl)cc1]

The title compound was prepared in analogy to the procedure described in Example 3 using 5-(5-chloro-1-methyl-6-oxo-1,6-dihydropyridin-3-yl)-4-(4-chlorophenyl)-3-methyl-4,5-dihydropyrrolo[3,4-c]pyrazol-6(2H)-one (Example 5). After work-up, the crude material was purified by silica gel column chromatography (CH$_2$Cl$_2$/MeOH 0.5-2.5%) to afford the title product. $t_R$: 3.83 min (HPLC 1); $t_R$: 0.84 min (LC-MS 2); ESI-MS: 403/405 [M+H]$^+$ (LC-MS 2); $R_f$=0.43 (CH$_2$Cl$_2$/MeOH 9:1); $^1$H NMR (400 MHz, DMSO-d$_6$) δ ppm 2.05 (s, 3H) 3.43 (s, 3H) 3.83 (s, 3H) 6.14 (s, 1H) 7.24-7.29 (m, 2H) 7.34-7.39 (m, 2H) 7.91 (d, J=2.7 Hz, 1H) 7.95 (d, J=2.7 Hz, 1H).

Example 7

(R)-5-(5-chloro-1-methyl-6-oxo-1,6-dihydropyridin-3-yl)-4-(4-chlorophenyl)-2,3-dimethyl-4,5-dihydro-pyrrolo[3,4-c]pyrazol-6(2H)-one

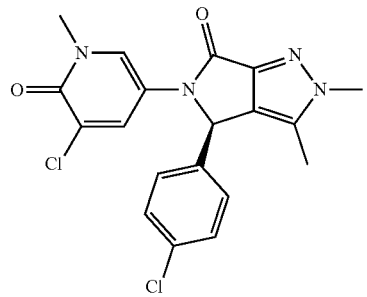 [SMILES: Cc1c2c(nn1C)C(=O)N(c1cc(Cl)c(=O)n(C)c1)[C@@H]2c1ccc(Cl)cc1]

The title compound (40 mg, 0.099 mmol, 33.3% yield) was obtained enantiomerically pure (ee>99%) as a white solid after chiral preparative chromatography (Chiralcel OD-H 30×250 mm; mobile phase: scCO$_2$/EtOH 60:40 (isocratic); flow: 80 mL/min; detection UV: 220 nm) of the racemic mixture of 5-(5-chloro-1-methyl-6-oxo-1,6-dihydropyridin-3-yl)-4-(4-chlorophenyl)-2,3-dimethyl-4,5-dihydropyrrolo[3,4-c]pyrazol-6(2H)-one (Example 6) (120 mg, 0.298 mmol) and trituration of the resulting residue in Et$_2$O. t$_R$: 3.82 min (HPLC 1); t$_R$: 0.86 min (LC-MS 2); ESI-MS: 403/405 [M+H]$^+$ (LC-MS 2).

Reference Example 8

(S)-5-(5-chloro-1-methyl-6-oxo-1,6-dihydropyridin-3-yl)-4-(4-chlorophenyl)-2,3-dimethyl-4,5-dihydro-pyrrolo[3,4-c]pyrazol-6(2H)-one

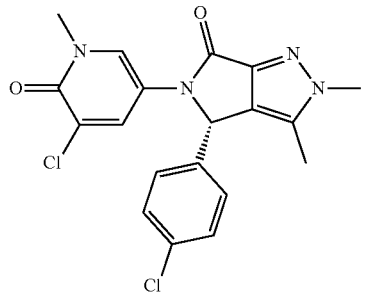

The title compound (43 mg, 0.107 mmol, 36% yield) was obtained enantiomerically pure (ee>99%) as a white solid after chiral preparative chromatography (Chiralcel OD-H 30×250 mm; mobile phase: scCO$_2$/EtOH 60:40 (isocratic); flow: 80 mL/min; detection UV: 220 nm) of the racemic mixture of 5-(5-chloro-1-methyl-6-oxo-1,6-dihydropyridin-3-yl)-4-(4-chlorophenyl)-2,3-dimethyl-4,5-dihydropyrrolo[3,4-c]pyrazol-6(2H)-one (Example 6) (120 mg, 0.298 mmol) and trituration of the resulting residue in Et$_2$O. t$_R$: 3.82 min (HPLC 1); t$_R$: 0.86 min (LC-MS 2); ESI-MS: 403/405 [M+H]$^+$ (LC-MS 2).

Example 9

5-(5-chloro-1-methyl-6-oxo-1,6-dihydropyridin-3-yl)-4-(4-chlorophenyl)-4,5-dihydropyrrolo[3,4-c]pyrazol-6(2H)-one

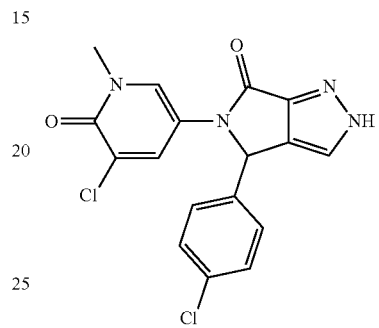

The title compound was prepared in analogy to the procedure described in Example 2 using 5-(5-chloro-1-methyl-6-oxo-1,6-dihydropyridin-3-yl)-4-(4-chlorophenyl)-2-(4-methoxybenzyl)-4,5-dihydropyrrolo[3,4-c]pyrazol-6(2H)-one (Step 9.6). t$_R$: 3.39 min (HPLC 1); t$_R$: 0.74 min (LC-MS 2); ESI-MS: 375/377 [M+H]$^+$ (LC-MS 2); R$_f$=0.30 (CH$_2$Cl$_2$/MeOH 9:1); $^1$H NMR (400 MHz, DMSO-d$_6$) δ ppm 3.44 (s, 3H) 6.19 (s, 1H) 7.24 (d, J=8.6 Hz, 2H) 7.35 (d, J=8.6 Hz, 2H) 7.77-7.85 (m, 1H) 7.89-7.93 (m, 1H) 7.94-7.97 (m, 1H) 13.70 (br. s, 1H).

Step 9.1: ethyl 4-iodo-1H-pyrazole-3-carboxylate

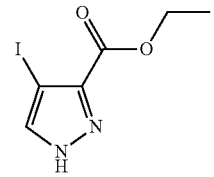

NIS (8.83 g, 39.2 mmol) and TFA (0.825 mL, 10.70 mmol) were added to a stirred solution of ethyl 1H-pyrazole-5-carboxylate (5 g, 35.7 mmol) in CH$_3$CN (120 mL) under Ar. The reaction mixture was stirred for 6 hr at rt, concentrated, diluted with a saturated aqueous solution of NaHCO$_3$, and extracted with EtOAc. The combined organic layers were washed with a saturated aq. NaHCO$_3$ solution, dried over Na$_2$SO$_4$ and evaporated. The crude material was purified by silica gel column chromatography (hexane/EtOAc 10-50%) to afford the title product (8.31 g, 31.2 mmol, 88% yield) as a white solid. t$_R$: 3.47 min (HPLC 1); t$_R$: 0.72 min (LC-MS 2); ESI-MS: 267 [M+H]$^+$ (LC-MS 2); R$_f$=0.55 (hexane/EtOAc 1:1).

Step 9.2: ethyl 4-iodo-1-(4-methoxybenzyl)-1H-pyrazole-3-carboxylate

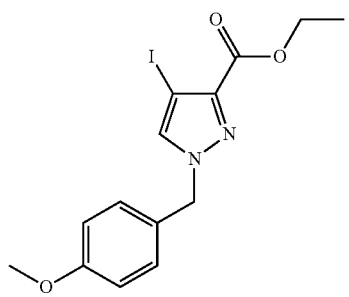 [SMILES: CCOC(=O)c1nn(Cc2ccc(OC)cc2)cc1I]

The title compound was prepared in analogy to the procedure described in Step 1.2 using ethyl 4-iodo-1H-pyrazole-3-carboxylate (Step 9.1). $t_R$: 5.01 min (HPLC 1); $t_R$: 1.08 min (LC-MS 2); ESI-MS: 387 [M+H]$^+$ (LC-MS 2); $R_f$=0.86 (hexane/EtOAc 1:1).

Step 9.3: ethyl 4-((4-chlorophenyl)(hydroxy)methyl)-1-(4-methoxybenzyl)-1H-pyrazole-3-carboxylate

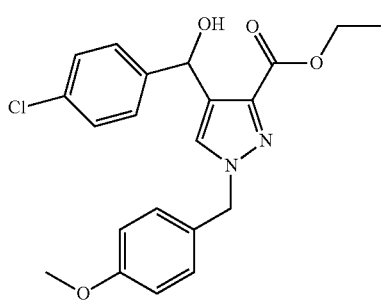 [SMILES: CCOC(=O)c1nn(Cc2ccc(OC)cc2)cc1C(O)c1ccc(Cl)cc1]

The title compound was prepared in analogy to the procedure described in Step 1.3 using ethyl 4-iodo-1-(4-methoxybenzyl)-1H-pyrazole-3-carboxylate (Step 9.2). $t_R$: 5.05 min (HPLC 1); $t_R$; 1.10 min (LC-MS 2); ESI-MS: 401 [M+H]$^+$ (LC-MS 2); $R_f$=0.42 (hexane/EtOAc 1:1).

Step 9.4: ethyl 4-((5-chloro-1-methyl-6-oxo-1,6-dihydropyridin-3-ylamino)(4-chlorophenyl)methyl)-1-(4-methoxybenzyl)-1H-pyrazole-3-carboxylate

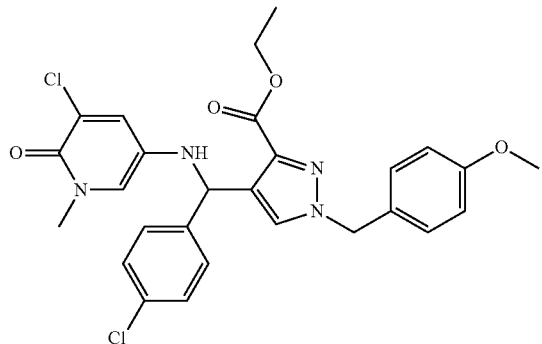 [SMILES: CCOC(=O)c1nn(Cc2ccc(OC)cc2)cc1C(Nc1cc(Cl)c(=O)n(C)c1)c1ccc(Cl)cc1]

The title compound was prepared in analogy to the procedure described in Step 1.4 using ethyl 4-((4-chlorophenyl)(hydroxy)methyl)-1-(4-methoxybenzyl)-1H-pyrazole-3-carboxylate (Step 9.3) and 5-amino-3-chloro-1-methylpyridin-2(1H)-one (Step 5.2). $t_R$: 4.91 min (HPLC 1); $t_R$: 1.08 min (LC-MS 2); ESI-MS: 541/543 [M+H]$^+$ (LC-MS 2); $R_f$=0.32 (CH$_2$Cl$_2$/MeOH 9:1).

Step 9.5: 4-((5-chloro-1-methyl-6-oxo-1,6-dihydropyridin-3-ylamino)(4-chlorophenyl)methyl)-1-(4-methoxybenzyl)-1H-pyrazole-3-carboxylic acid

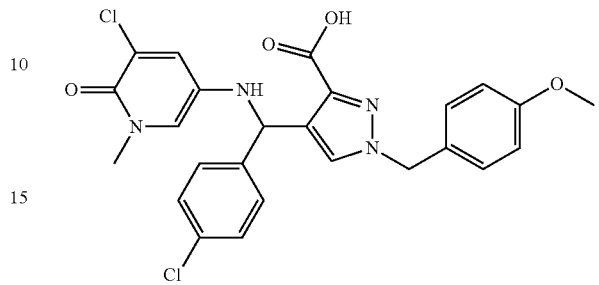

The title compound was prepared in analogy to the procedure described in Step 1.5 using ethyl 4-((5-chloro-1-methyl-6-oxo-1,6-dihydropyridin-3-ylamino)(4-chlorophenyl)methyl)-1-(4-methoxy-benzyl)-1H-pyrazole-3-carboxylate (Step 9.4). $t_R$: 4.19 min (HPLC 1); $t_R$: 0.93 min (LC-MS 2); ESI-MS: 513/515 [M+H]$^+$ (LC-MS 2).

Step 9.6: 5-(5-chloro-1-methyl-6-oxo-1,6-dihydropyridin-3-yl)-4-(4-chlorophenyl)-2-(4-methoxy-benzyl)-4,5-dihydropyrrolo[3,4-c]pyrazol-6(2H)-one

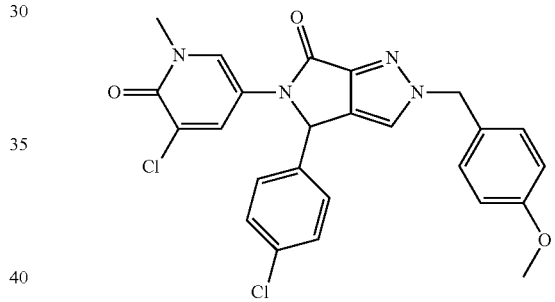

The title compound was prepared in analogy to the procedure described in Example 1 using 4-((5-chloro-1-methyl-6-oxo-1,6-dihydropyridin-3-ylamino)(4-chlorophenyl)methyl)-1-(4-methoxy-benzyl)-1H-pyrazole-3-carboxylic acid (Step 9.5). $t_R$: 4.58 min (HPLC 1); $t_R$: 1.01 min (LC-MS 2); ESI-MS: 495/497 [M+H]$^+$ (LC-MS 2); $R_f$=0.55 (CH$_2$Cl$_2$/MeOH 9:1).

Example 10

5-(5-chloro-1-methyl-6-oxo-1,6-dihydropyridin-3-yl)-4-(4-chlorophenyl)-2-methyl-4,5-dihydropyrrolo[3,4-c]pyrazol-6(2H)-one

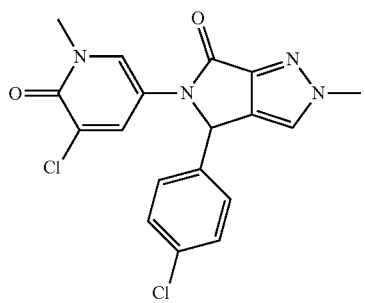 [SMILES: Cn1cc2c(n1)C(=O)N(c1cc(Cl)c(=O)n(C)c1)C2c1ccc(Cl)cc1]

The title compound was prepared in analogy to the procedure described in Example 1 using 4-((5-chloro-1-methyl-6-oxo-1,6-dihydropyridin-3-ylamino)(4-chlorophenyl)methyl)-1-methyl-1H-pyrazole-3-carboxylic acid (Step 10.4). $t_R$: 3.65 min (HPLC 1); $t_R$: 0.82 min (LC-MS 2); ESI-MS: 389/391 [M+H]$^+$ (LC-MS 2); $R_f$=0.56 (CH$_2$Cl$_2$/MeOH 9:1); $^1$H NMR (400 MHz, DMSO-d$_6$) δ ppm 3.45 (s, 3H) 3.98 (s, 3H) 6.21 (s, 1H) 7.26 (d, J=8.4 Hz, 2H) 7.38 (d, J=8.4 Hz, 2H) 7.79 (s, 1H) 7.90-8.04 (m, 2H).

Step 10.1: ethyl 4-iodo-1H-pyrazole-3-carboxylate

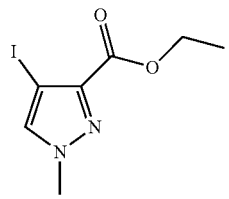

To a stirred solution of ethyl 1-methyl-1H-pyrazole-3-carboxylate (5 g, 32.4 mmol) in CH$_3$CN (200 mL) under Ar was added I$_2$ (4.94 g, 19.46 mmol) and after 5 min CAN (10.67 g, 19.46 mmol). The reaction mixture was stirred for 1 hr at 80° C., concentrated, quenched with a 10% aq. Na$_2$S$_2$O$_3$ solution, and extracted with CH$_2$Cl$_2$. The combined organic layers were washed with brine, dried over Na$_2$SO$_4$ and evaporated. The crude material was purified by silica gel column chromatography (hexane/EtOAc 25-45%) to afford the title product (9.04 g, 32.3 mmol, 100% yield) as a white solid. $t_R$: 3.78 min (HPLC 1); $t_R$: 0.80 min (LC-MS 2); ESI-MS: 281 [M+H]$^+$ (LC-MS 2); $R_f$=0.45 (hexane/EtOAc 1:1).

Step 10.2: ethyl 4-((4-chlorophenyl)(hydroxy)methyl)-1-methyl-1H-pyrazole-3-carboxylate

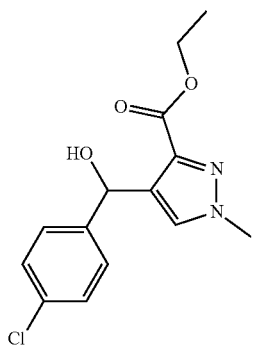 [SMILES: CCOC(=O)c1nn(C)cc1C(O)c1ccc(Cl)cc1]

To a stirred solution of ethyl 4-iodo-1H-pyrazole-3-carboxylate (Step 10.1) (2 g, 7.14 mmol) in THF (40 mL) under Ar was added TurboGrignard (5.77 mL, 7.50 mmol) at −10° C. After 30 min, 4-chlorobenzaldehyde (1.004 g, 7.14 mmol) was added. The reaction mixture was stirred for 60 min at rt, quenched with a saturated aq. NH$_4$Cl solution, and extracted EtOAc. The combined organic layers were washed a saturated aq. NH$_4$Cl solution, dried over Na2SO4 and evaporated. The crude material was purified by silica gel column chromatography (hexane/EtOAc 35-55%) to afford the title product (1.73 g, 5.87 mmol, 82% yield) as a colorless oil. $t_R$: 4.10 min (HPLC 1); $t_R$: 0.89 min (LC-MS 2); ESI-MS: 277/279 [M-18] (LC-MS 2); $R_f$=0.15 (hexane/EtOAc 1:1).

Step 10.3: ethyl 4-((5-chloro-1-methyl-6-oxo-1,6-dihydropyridin-3-ylamino)(4-chlorophenyl)methyl)-1-(4-methoxybenzyl)-1H-pyrazole-3-carboxylate

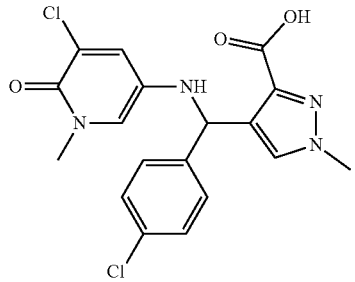 [SMILES: Cn1cc(C(Nc2cc(Cl)c(=O)n(C)c2)c2ccc(Cl)cc2)c(C(=O)O)n1]

To a stirred solution of ethyl 4-((4-chlorophenyl)(hydroxy)methyl)-1-methyl-1H-pyrazole-3-carboxylate (Step 10.2) (346 mg, 1.174 mmol) and triethylamine (0.818 mL, 5.87 mmol) in CH$_2$Cl$_2$ (4 mL) under Ar was added Ms$_2$O (409 mg, 2.348 mmol) at −10° C. The reaction mixture was stirred for 30 min at this temperature. 5-Amino-3-chloro-1-methylpyridin-2(1H)-one (Step 5.2) (186 mg, 1.174 mmol) was added at 30° C. After 20 h at rt, the reaction mixture was quenched with a saturated aq. NaHCO$_3$ solution, and extracted with CH$_2$Cl$_2$. The combined organic layers were washed with a saturated aqueous solution of NaHCO$_3$ (100 mL), dried over Na$_2$SO$_4$ and evaporated. The crude material was purified by silica gel column chromatography (CH$_2$Cl$_2$/MeOH 1-3.5%) to afford the title product (110 mg, 0.253 mmol, 21% yield) as a black solid. $t_R$: 4.15 min (HPLC 1); $t_R$: 0.94 min (LC-MS 2); ESI-MS: 435/437 [M+H]$^+$ (LC-MS 2); $R_f$=0.38 (CH$_2$Cl$_2$/MeOH 9:1).

Step 10.4: 4-((5-chloro-1-methyl-6-oxo-1,6-dihydropyridin-3-ylamino)(4-chlorophenyl)methyl)-1-(4-methoxybenzyl)-1H-pyrazole-3-carboxylic acid The title compound was prepared in analogy to the procedure described in Step 1.5 using ethyl 4-((5-chloro-1-methyl-6-oxo-1,6-dihydropyridin-3-ylamino)(4-chlorophenyl)methyl)-1-(4-methoxybenzyl)-1H-pyrazole-3-carboxylate (Step 10.3). $t_R$: 3.36 min (HPLC 1); $t_R$: 0.77 min (LC-MS 2); ESI-MS: 407/409 [M+H]$^+$ (LC-MS 2).

Example 11

(R)-5-(5-chloro-1-methyl-6-oxo-1,6-dihydropyridin-3-yl)-4-(4-chlorophenyl)-2-methyl-4,5-dihydropyrrolo[3,4-c]pyrazol-6(2H)-one

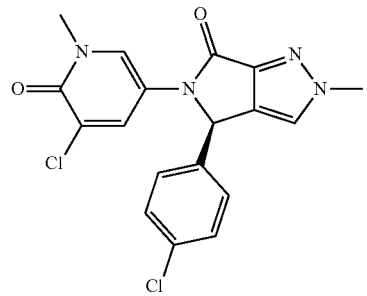 [SMILES: Cn1cc2c(n1)C(=O)N(c1cc(Cl)c(=O)n(C)c1)[C@@H]2c1ccc(Cl)cc1]

The title compound (18.5 mg, 0.048 mmol, 41% yield) was obtained enantiomerically pure (ee>99.5%) after chiral preparative chromatography (Chiralcel OD-H 30×250 mm; mobile phase: scCO$_2$/EtOH70:30 (isocratic); flow: 90 mL/min; detection UV: 215 nm) of the racemic mixture of 5-(5-chloro-1-methyl-6-oxo-1,6-dihydropyridin-3-yl)-4-(4-chlorophenyl)-2-methyl-4,5-dihydropyrrolo[3,4-c]pyrazol-6(2H)-one (Example 10) (45 mg, 0.116 mmol). $t_R$: 3.66 min (HPLC 1); $t_R$: 0.81 min (LC-MS 2); ESI-MS: 389/391 [M+H]$^+$ (LC-MS 2).

Reference Example 12

(S)-5-(5-chloro-1-methyl-6-oxo-1,6-dihydropyridin-3-yl)-4-(4-chlorophenyl)-2-methyl-4,5-dihydropyrrolo[3,4-c]pyrazol-6(2H)-one

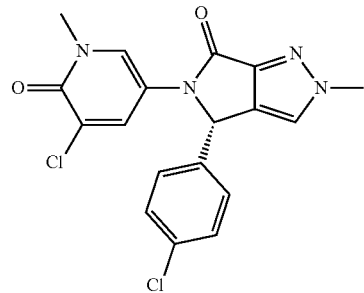 [SMILES: Cn1cc2c(n1)C(=O)N(c1cc(Cl)c(=O)n(C)c1)[C@H]2c1ccc(Cl)cc1]

The title compound (18 mg, 0.046 mmol, 40.0% yield) was obtained enantiomerically pure (ee>99.5%) after chiral preparative chromatography (system: SFC-PicLab-Prep 100; column: Chiralcel OD-H 30×250 mm; mobile phase: scCO$_2$/ethanol 70:30 (isocratic); flow: 90 mL/min; detection UV: 215 nm) of the racemic mixture of 5-(5-chloro-1-methyl-6-oxo-1,6-dihydropyridin-3-yl)-4-(4-chlorophenyl)-2-methyl-4,5-dihydropyrrolo[3,4-c]pyrazol-6(2H)-one (Example 10) (45 mg, 0.116 mmol). $t_R$: 3.69 min (HPLC 1); $t_R$: 0.81 min (LC-MS 2); ESI-MS: 389/391 [M+H]$^+$ (LC-MS 2).

Example 13

4-(4-chlorophenyl)-5-(1,5-dimethyl-6-oxo-1,6-dihydropyridin-3-yl)-2-methyl-4,5-dihydropyrrolo[3,4-c]pyrazol-6(2H)-one

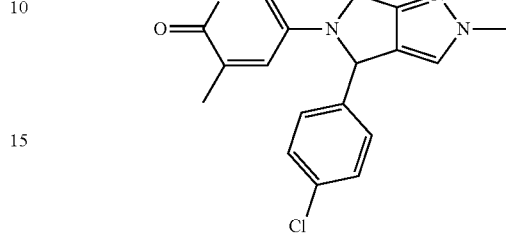

The title compound was prepared in analogy to the procedure described in Example 1 using 4-((4-chlorophenyl)(1,5-dimethyl-6-oxo-1,6-dihydropyridin-3-ylamino)methyl)-1-methyl-1H-pyrazole-3-carboxylic acid (Step 13.2). $t_R$: 3.44 min (HPLC 1); $t_R$: 0.77 min (LC-MS 2); ESI-MS: 369 [M+H]$^+$ (LC-MS 2); R$_f$=0.46 (CH$_2$Cl$_2$/MeOH 9:1); $^1$H NMR (400 MHz, DMSO-d$_6$) δ ppm 1.92 (s, 3H) 3.37 (s, 3H) 3.95 (s, 3H) 6.15 (s, 1H) 7.22 (d, J=8.6 Hz, 2H) 7.38 (d, J=8.6 Hz, 2H) 7.40 (m, 1H) 7.81 (m, 1H) 7.86 (s, 1H).

Step 13.1: ethyl 4-((4-chlorophenyl)(1,5-dimethyl-6-oxo-1,6-dihydropyridin-3-ylamino)methyl)-1-methyl-1H-pyrazole-3-carboxylate

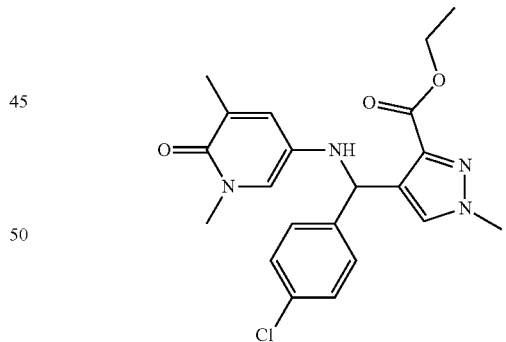

The title compound was prepared in analogy to the procedure described in Step 10.3 using ethyl 4-((4-chlorophenyl)(hydroxy)methyl)-1-methyl-1H-pyrazole-3-carboxylate (Step 10.2) and 5-amino-1,3-dimethylpyridin-2(1H)-one (Step 20.2). After purification by silica gel column chromatography, the resulting residue was further purified by preparative HPLC (Gilson gx-281; column: Sunfire C18, 30×100 mm, 5 μm; flow: 30 mL/min; gradient: 5% to 100% B in 20 min; A=0.1% TFA in H$_2$O, B=CH$_3$CN. detection: UV). $t_R$: 3.91 min (HPLC 1); $t_R$: 0.90 min (LC-MS 2); ESI-MS: 415 [M+H]$^+$ (LC-MS 2); R$_f$=0.46 (CH$_2$Cl$_2$/MeOH 9:1).

Step 13.2: 4-((4-chlorophenyl)(1,5-dimethyl-6-oxo-1,6-dihydropyridin-3-ylamino)methyl)-1-methyl-1H-pyrazole-3-carboxylic acid

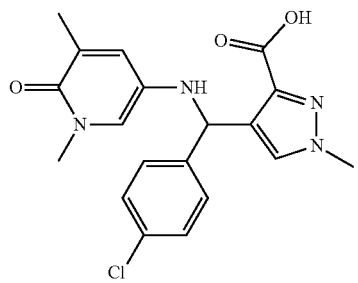 [SMILES: Cc1cc(NC(c2ccc(Cl)cc2)c2cn(C)nc2C(=O)O)cn(C)c1=O]

The title compound was prepared in analogy to the procedure described in Step 1.5 using ethyl 4-((4-chlorophenyl)(1,5-dimethyl-6-oxo-1,6-dihydropyridin-3-ylamino)methyl)-1-methyl-1H-pyrazole-3-carboxylate (Step 13.1). $t_R$: 3.12 min (HPLC 1); $t_R$: 0.71 min (LC-MS 2); ESI-MS: 387 [M+H]$^+$ (LC-MS 2).

Example 14

4-(4-chlorophenyl)-5-(5-fluoro-1-methyl-6-oxo-1,6-dihydropyridin-3-yl)-2-methyl-4,5-dihydropyrrolo[3,4-c]pyrazol-6(2H)-one

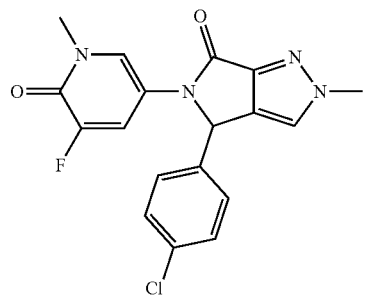 [SMILES: Cn1cc2c(n1)C(=O)N(c1cc(F)c(=O)n(C)c1)C2c1ccc(Cl)cc1]

The title compound was prepared in analogy to the procedure described in Example 1 using 4-((4-chlorophenyl)(5-fluoro-1-methyl-6-oxo-1,6-dihydropyridin-3-ylamino)methyl)-1-methyl-1H-pyrazole-3-carboxylic acid (Step 14.4). Trituration in Et$_2$O was done after purification on silica-gel. $t_R$: 3.46 min (HPLC 1); $t_R$: 0.76 min (LC-MS 2); ESI-MS: 373 [M+H]$^+$ (LC-MS 2); R$_f$=0.44 (CH$_2$Cl$_2$/MeOH 9:1); $^1$H NMR (400 MHz, DMSO-d$_6$) δ ppm 3.46 (s, 3H) 3.98 (s, 3H) 6.21 (s, 1H) 7.26 (d, J=7.3 Hz, 2H) 7.38 (d, J=7.3 Hz, 2H) 7.66 (d, J=11.4 Hz, 1H) 7.76-7.87 (m, 2H).

Step 14.1: 3-fluoro-1-methyl-5-nitropyridin-2(1H)-one

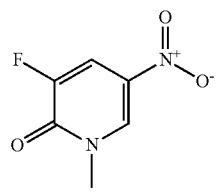

To a stirred suspension of 3-fluoro-2-hydroxy-5-nitropyridine (2.03 g, 12.84 mmol) and K$_2$CO$_3$ (3.55 g, 25.7 mmol) in DMF (20 mL) under Ar was added MeI (1.20 mL, 19.26 mmol). The reaction mixture was stirred for 1 hr at rt, concentrated, diluted with water (100 mL), and extracted with CH$_2$Cl$_2$. (2×150 mL) The combined organic layers were washed with water, dried over Na$_2$SO$_4$ and evaporated to afford the crude title product (2.06 g, 11.97 mmol, 93% yield) as a yellow solid. $t_R$: 2.22 min (HPLC 1); $t_R$: 0.49 min (LC-MS 2); ESI-MS: 173 [M+H]$^+$ (LC-MS 2).

Step 14.2: 5-amino-3-fluoro-1-methylpyridin-2(1H)-one

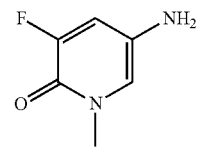

The title compound was prepared in analogy to the procedure described in Step 5.2 using 3-fluoro-1-methyl-5-nitropyridin-2(1H)-one (Step 14.1). $t_R$: 0.22 min (LC-MS 2); ESI-MS: 143 [M+H]$^+$ (LC-MS 2); R$_f$=0.25 (CH$_2$Cl$_2$/MeOH 9:1).

Step 14.3: ethyl 4-((4-chlorophenyl)(5-fluoro-1-methyl-6-oxo-1,6-dihydropyridin-3-ylamino)methyl)-1-methyl-1H-pyrazole-3-carboxylate

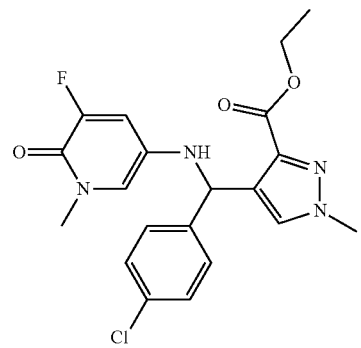

The title compound was prepared in analogy to the procedure described in Step 10.3 using 5-amino-3-fluoro-1-methylpyridin-2(1H)-one (Step 14.2). $t_R$: 3.95 min (HPLC 1); $t_R$: 0.88 min (LC-MS 2); ESI-MS: 419 [M+H]$^+$ (LC-MS 2); R$_f$=0.51 (CH$_2$Cl$_2$/MeOH 9:1).

Step 14.4: 4-((4-chlorophenyl)(5-fluoro-1-methyl-6-oxo-1,6-dihydropyridin-3-ylamino)methyl)-1-methyl-1H-pyrazole-3-carboxylic acid

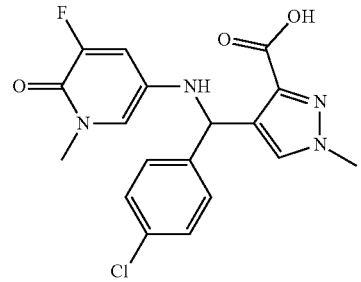 [SMILES: Cn1cc(C(Nc2cc(F)c(=O)n(C)c2)c2ccc(Cl)cc2)c(C(=O)O)n1]

The title compound was prepared in analogy to the procedure described in Step 1.5 using ethyl 4-((4-chlorophenyl)(5-fluoro-1-methyl-6-oxo-1,6-dihydropyridin-3-ylamino)methyl)-1-methyl-1H-pyrazole-3-carboxylate (Step 14.3). $t_R$: 3.22 min (HPLC 1); $t_R$: 0.71 min (LC-MS 2); ESI-MS: 391 [M+H]$^+$ (LC-MS 2).

Reference Example 15

(S)-4-(4-chlorophenyl)-5-(1,5-dimethyl-6-oxo-1,6-dihydropyridin-3-yl)-2-methyl-4,5-dihydropyrrolo[3,4-c]pyrazol-6(2H)-one

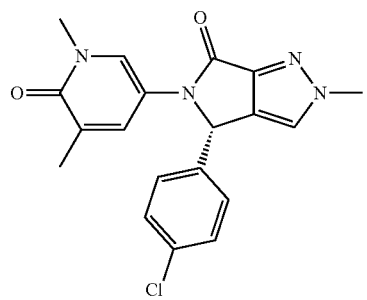

The title compound (80 mg, 0.217 mmol, 58% yield) was obtained as a white solid after a chiral preparative chromatography (system: Thar/Waters SFC-100 MS; column: Novartis OD-I 30×250 mm; mobile phase: scCO$_2$/EtOH 25%-35% in 6 of 8 min; flow: 100 mL/min; detection UV: 250 nm and detection MS: SIR, ESI+) of the racemic mixture of 4-(4-chlorophenyl)-5-(1,5-dimethyl-6-oxo-1,6-dihydropyridin-3-yl)-2-methyl-4,5-dihydropyrrolo[3,4-c]pyrazol-6 (2H)-one (Example 13) (430 mg, 1.166 mmol), followed by a second chiral preparative chromatography (SFC: Thar 100; column DIOL, 25 cm, Ø 3 cm, 5 μm, 60 Å; gradient: 22% B for 1 min, 22-27% B in 6 min, 27-50% B in 1 min, 50% B for 1.5 min, 50%-22% B in 1 min, 22% B for 0.5 min; A: scCO$_2$, B: MeOH; flow: 100 mL/min) of resulting (S)-4-(4-chlorophenyl)-5-(1,5-dimethyl-6-oxo-1,6-dihydropyridin-3-yl)-2-methyl-4,5-dihydropyrrolo[3,4-c]pyrazol-6(2H)-one, and by trituration in Et$_2$O. $t_R$: 0.79 min (HPLC 1); ESI-MS: 369 [M+H]$^+$ (LC-MS 2).

Example 16

(R)-4-(4-chlorophenyl)-5-(1,5-dimethyl-6-oxo-1,6-dihydropyridin-3-yl)-2-methyl-4,5-dihydropyrrolo[3,4-c]pyrazol-6(2H)-one

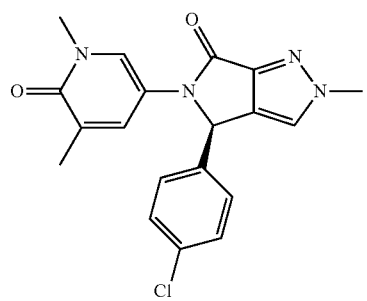 [SMILES: Cc1cc(N2C(=O)c3nn(C)cc3[C@H]2c2ccc(Cl)cc2)cn(C)c1=O]

The title compound (83 mg, 0.225 mmol, 61.5% yield) was obtained as a white solid after a chiral preparative chromatography (system: Thar/Waters SFC-100 MS; column: Novartis OD-I 30×250 mm; mobile phase: scCO$_2$/ethanol 25%-35% in 6 of 8 min; flow: 100 mL/min; detection UV: 250 nm and detection MS: SIR, ESI+) of the racemic mixture of 4-(4-chlorophenyl)-5-(1,5-dimethyl-6-oxo-1,6-dihydropyridin-3-yl)-2-methyl-4,5-dihydro pyrrolo[3,4-c]pyrazol-6 (2H)-one (Example 13) (430 mg, 1.166 mmol), followed by a second chiral preparative chromatography (SFC: Thar 100, column PFP, 25 cm, Ø 3 cm, 5 μm, 120 Å; gradient: 5% B for 1 min, 5-10% B in 6 min, 10-50% B in 1 min, 50% B for 1.5 min, 50%-5% B in min, 5% B for 0.5 min; A: scCO2, B: MeOH; flow 100 mL/min) of resulting (R)-4-(4-chlorophenyl)-5-(1,5-dimethyl-6-oxo-1,6-dihydropyridin-3-yl)-2-methyl-4,5-dihydropyrrolo[3,4-c]pyrazol-6(2H)-one and by trituration in Et$_2$O. $t_R$: 0.79 min (HPLC 1); ESI-MS: 369 [M+H]$^+$ (LC-MS 2).

Example 17

5-(5-chloro-1-methyl-6-oxo-1,6-dihydropyridin-3-yl)-4-(4-chlorophenyl)-2-cyclopropyl-3-methyl-4,5-dihydropyrrolo[3,4-c]pyrazol-6(2H)-one

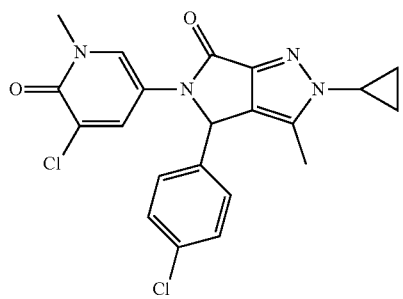 [SMILES: Cc1c2c(nn1C1CC1)C(=O)N(c1cc(Cl)c(=O)n(C)c1)C2c1ccc(Cl)cc1]

The title compound was prepared in analogy to the procedure described in Example 1 using 4-(((5-chloro-1-methyl-6-oxo-1,6-dihydropyridin-3-yl)amino)(4-chlorophenyl)methyl)-1-cyclopropyl-5-methyl-1H-pyrazole-3-carboxylic acid (Step 17.7). $t_R$: 4.28 min (HPLC 1); $t_R$: 0.96 min (LC-MS 2); ESI-MS: 429/431 [M+H]$^+$ (LC-MS 2); R$_f$=0.56 (CH$_2$Cl$_2$/MeOH 9:1); $^1$H NMR (400 MHz, DMSO-d$_6$) δ ppm 0.96-1.19 (m, 4H) 2.14 (s, 3H) 3.43 (s, 3H) 3.57-3.68 (m, 1H) 6.13 (s, 1H) 7.27 (d, J=8.6 Hz, 2H) 7.36 (d, J=8.6 Hz, 2H) 7.89 (d, J=2.3 Hz, 1H) 7.92 (d, J=2.3 Hz, 1H).

Step 17.1: di-tert-butyl 1-cyclopropylhydrazine-1,2-dicarboxylate

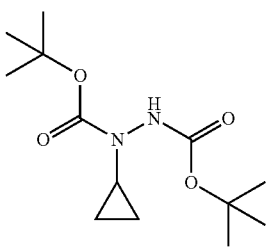 [SMILES: CC(C)(C)OC(=O)NN(C(=O)OC(C)(C)C)C1CC1]

To a stirred solution of cyclopropyl magnesium bromide in THF (104 mL, 52.1 mmol) under Ar was added di-tert-butyl azodicarboxylate (12 g, 52.1 mmol) in THF (50 mL) at −78° C. The reaction mixture was stirred for 30 min at this temperature, quenched with a saturated aq. NH₄Cl solution, and extracted with EtOAc. The combined organic layers were washed with saturated aq. NH₄Cl solution, dried over Na₂SO₄ and evaporated. The crude material was purified by silica gel column chromatography (hexane/EtOAc 2-10%) to afford the title product (11.84 g, 43.5 mmol, 83% yield) as a white solid. R$_f$=0.12 (CPS stain) (hexane/EtOAc 9:1)

Step 17.2: cyclopropylhydrazine

Intermediate 17A

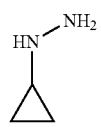

A mixture of di-tert-butyl 1-cyclopropylhydrazine-1,2-dicarboxylate (Step 17.1) (11.84 g, 43.5 mmol) and HCl 4N in dioxane (109 mL, 435 mmol) was stirred for 24 hr at rt. The resulting precipitate was collected by filtration to afford the title product (4.90 g, 43.5 mmol, 100% yield) as a white solid.

Step 17.3: ethyl 1-cyclopropyl-5-methyl-1H-pyrazole-3-carboxylate

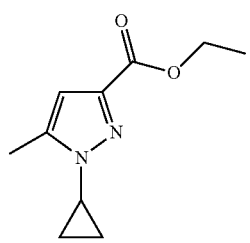

To a stirred solution of cyclopropylhydrazine (Step 17.2) (4.90 g, 45.1 mmol) in toluene (30 mL) and EtOH (30 mL) was added ethyl 2,4-dioxovalerate (6.34 mL, 45.1 mmol). The reaction mixture was stirred for 1 hr at 100° C., quenched with a saturated aq. NaHCO₃ solution, and extracted with EtOAc. The organic layers were combined and washed with a saturated aq. NaHCO₃ solution, dried over Na₂SO₄ and evaporated. The crude material was purified by silica gel column chromatography (hexane/EtOAc 2.5-30%) to afford the title product (3.74 g, 19.26 mmol, 43% yield). t$_R$: 3.84 min (HPLC 1); t$_R$: 0.84 min (LC-MS 2); ESI-MS: 195 [M+H]⁺ (LC-MS 2); R$_f$=0.50 (hexane/EtOAc 1:1).

Step 17.4: ethyl 1-cyclopropyl-4-iodo-5-methyl-1H-pyrazole-3-carboxylate

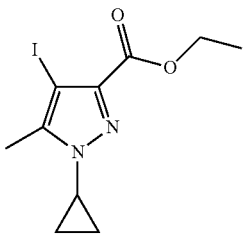

The title compound was prepared in analogy to the procedure described in Step 10.1 using ethyl 1-cyclopropyl-5-methyl-1H-pyrazole-3-carboxylate (Step 17.3). t$_R$: 4.73 min (HPLC 1); t$_R$: 1.03 min (LC-MS 2); ESI-MS: 321 [M+H]⁺ (LC-MS 2); R$_f$=0.69 (hexane/EtOAc 1:1).

Step 17.5: ethyl 4-((4-chlorophenyl)(hydroxy)methyl)-1-cyclopropyl-5-methyl-1H-pyrazole-3-carboxylate

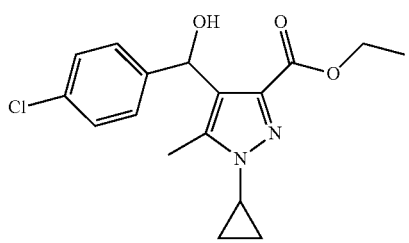 [SMILES: CCOC(=O)c1nn(C2CC2)c(C)c1C(O)c1ccc(Cl)cc1]

The title compound was prepared in analogy to the procedure described in Step 1.3 using ethyl 1-cyclopropyl-4-iodo-5-methyl-1H-pyrazole-3-carboxylate (Step 17.4). t$_R$: 4.94 min (HPLC 1); t$_R$: 1.09 min (LC-MS 2); ESI-MS: 335 [M+H]⁺ (LC-MS 2); R$_f$=0.35 (hexane/EtOAc 1:1).

Step 17.6: ethyl 4-((5-chloro-1-methyl-6-oxo-1,6-dihydropyridin-3-ylamino)(4-chlorophenyl)methyl)-1-cyclopropyl-5-methyl-1H-pyrazole-3-carboxylate

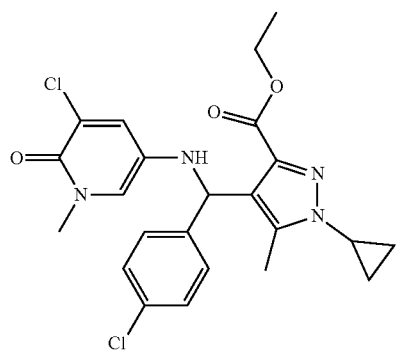 [SMILES: CCOC(=O)c1nn(C2CC2)c(C)c1C(Nc1cc(Cl)c(=O)n(C)c1)c1ccc(Cl)cc1]

The title compound was prepared in analogy to the procedure described in Step 10.3 using ethyl 4-((4-chlorophenyl)(hydroxy)methyl)-1-cyclopropyl-5-methyl-1H-pyrazole-3- carboxylate (Step 17.5) and 5-amino-3-chloro-1-methylpyridin-2(1H)-one (Step 5.2). $t_R$: 4.81 min (HPLC 1); $t_R$: 1.09 min (LC-MS 2); ESI-MS: 475/477 [M+H]$^+$ (LC-MS 2); $R_f$=0.52 (CH$_2$Cl$_2$/MeOH 9:1).

Step 17.7: 4-((5-chloro-1-methyl-6-oxo-1,6-dihydropyridin-3-ylamino)(4-chlorophenyl)methyl)-1-cyclopropyl-5-methyl-1H-pyrazole-3-carboxylic acid

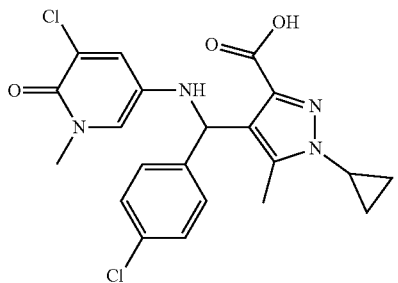 [SMILES: Cc1c(C(Nc2cc(Cl)c(=O)n(C)c2)c2ccc(Cl)cc2)c(C(=O)O)nn1C1CC1]

The title compound was prepared in analogy to the procedure described in Step 1.5 using ethyl 4-((5-chloro-1-methyl-6-oxo-1,6-dihydropyridin-3-ylamino)(4-chlorophenyl)methyl)-1-cyclopropyl-5-methyl-1H-pyrazole-3-carboxylate (Step 17.6). $t_R$: 3.94 min (HPLC 1); $t_R$: 0.89 min (LC-MS 2); ESI-MS: 447/449 [M+H]$^+$ (LC-MS 2).

Reference Example 18

(S)-5-(5-chloro-1-methyl-6-oxo-1,6-dihydropyridin-3-yl)-4-(4-chlorophenyl)-2-cyclopropyl-3-methyl-4,5-dihydropyrrolo[3,4-c]pyrazol-6(2H)-one

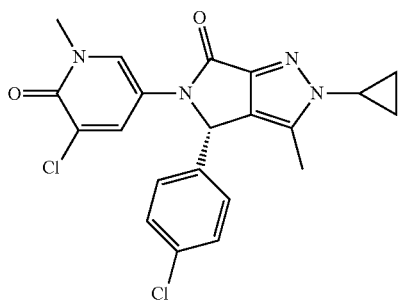 [SMILES: Cc1c2c(nn1C1CC1)C(=O)N(c1cc(Cl)c(=O)n(C)c1)[C@H]2c1ccc(Cl)cc1]

The title compound (54 mg, 0.126 mmol, 43.2% yield) was obtained enantiomerically pure as a white solid (ee>99.5%) after chiral preparative chromatography (System: Gilson PLC 2020; column: Chiralcel OD-H 5 µm, 250×4.6 mm; mobile phase: heptane/EtOH/MeOH 70:20:10; product dissolved in MeOH/EtOH (1:2); flow: 12 mL/min; detection UV: 230 nm) of the racemic mixture of 5-(5-chloro-1-methyl-6-oxo-1,6-dihydropyridin-3-yl)-4-(4-chlorophenyl)-2-cyclopropyl-3-methyl-4,5-dihydropyrrolo[3,4-c]pyrazol-6(2H)-one (Example 17) (125 mg, 0.291 mmol) and trituration in Et$_2$O. $t_R$: 0.97 min (LC-MS 2); ESI-MS: 429/431 [M+H]$^+$ (LC-MS 2).

Example 19

(R)-5-(5-chloro-1-methyl-6-oxo-1,6-dihydropyridin-3-yl)-4-(4-chlorophenyl)-2-cyclopropyl-3-methyl-4,5-dihydropyrrolo[3,4-c]pyrazol-6(2H)-one

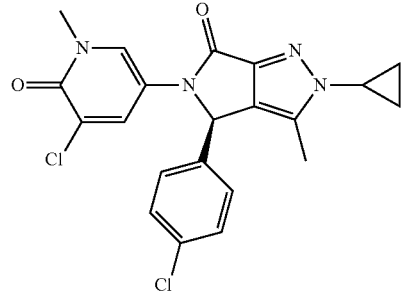 [SMILES: Cc1c2c(nn1C1CC1)C(=O)N(c1cc(Cl)c(=O)n(C)c1)[C@@H]2c1ccc(Cl)cc1]

The title compound (54 mg, 0.126 mmol, 43.2% yield) was obtained enantiomerically pure as a white solid (ee>99.5%) after chiral preparative chromatography (system: Gilson PLC 2020; column: Chiralcel OD-H 5 µm, 250×4.6 mm; mobile phase: heptane/ethanol/MeOH 70:20:10; product dissolved in MeOH/EtOH (1:2); flow: 12 mL/min; detection UV: 230 nm) of the racemic mixture of 5-(5-chloro-1-methyl-6-oxo-1,6-dihydropyridin-3-yl)-4-(4-chlorophenyl)-2-cyclopropyl-3-methyl-4,5-dihydropyrrolo[3,4-c]pyrazol-6(2H)-one (Example 17) (125 mg, 0.291 mmol. $t_R$: 0.97 min (LC-MS 2); ESI-MS: 429/431 [M+H]$^+$ (LC-MS 2).

Example 20

4-(4-chlorophenyl)-2-cyclopropyl-5-(1,5-dimethyl-6-oxo-1,6-dihydropyridin-3-yl)-3-methyl-4,5-dihydropyrrolo[3,4-c]pyrazol-6(2H)-one

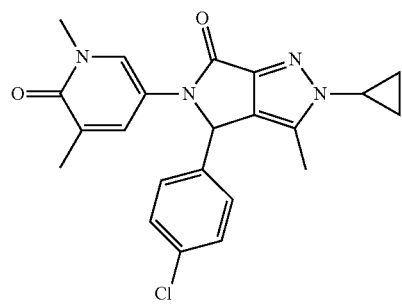

The title compound was prepared in analogy to the procedure described in Example 1 using 4-((4-chlorophenyl)((1,5-dimethyl-6-oxo-1,6-dihydropyridin-3-yl)amino)methyl)-1-cyclopropyl-5-methyl-1H-pyrazole-3-carboxylic acid (Step 20.4). $t_R$: 4.06 min (HPLC 1); $t_R$: 0.92 min (LC-MS 2); ESI-MS: 409.2 [M+H]$^+$ (LC-MS 2); $R_f$=0.39 (CH$_2$Cl$_2$/MeOH 9:1); $^1$H NMR (400 MHz, DMSO-d$_6$) δ ppm 0.94-1.17 (m, 4H) 1.91 (s, 3H) 2.13 (s, 3H) 3.34 (s, 3H) 3.60-3.67 (m, 1H) 6.09 (s, 1H) 7.20-7.26 (m, 2H) 7.32-7.43 (m, 3H) 7.70 (d, J=2.7 Hz, 1H).

Step 20.1: 1,3-dimethyl-5-nitropyridin-2(1H)-one

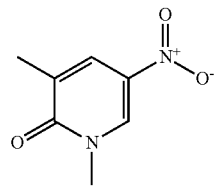

The title compound was prepared in analogy to the procedure described in Step 5.1 using 3-methyl-5-nitropyridin-2-ol. The reaction mixture was filtered and dried, then diluted with water and extracted with EtOAc. The combined organic layers were washed with brine, dried over Na2SO4 and evaporated to afford the title product as a yellow powder. $t_R$: 0.59 min (LC-MS 2); ESI-MS: 169 $[M+H]^+$ (LC-MS 2).

Step 20.2: 5-amino-1,3-dimethylpyridin-2(1H)-one

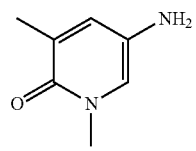

A mixture of 1,3-dimethyl-5-nitropyridin-2(1H)-one (Step 20.1) (16.4 g, 98 mmol), Pd/C 10% (2.0 g), THF (200 mL) and MeOH (200 mL) was stirred for 3 hr at rt under a hydrogen atmosphere (0.1 bar). The reaction mixture was filtered over celite and concentrated. The crude material was purified by chromatography ($CH_2Cl_2$/MeOH/$NH_3$ 98/1/1) to afford the title product (10.3 g, 70.8 mmol, 73% yield) as a green oil. The green oil was triturated in diethyl ether to afford a powder. $t_R$: 0.21 min (LC-MS 2); ESI-MS: 139 $[M+H]^+$ (LC-MS 2); $R_f$=0.35 ($CH_2Cl_2$/MeOH 9:1).

Step 20.3: ethyl 4-((4-chlorophenyl)(1,5-dimethyl-6-oxo-1,6-dihydropyridin-3-ylamino)methyl)-1-cyclopropyl-5-methyl-1H-pyrazole-3-carboxylate

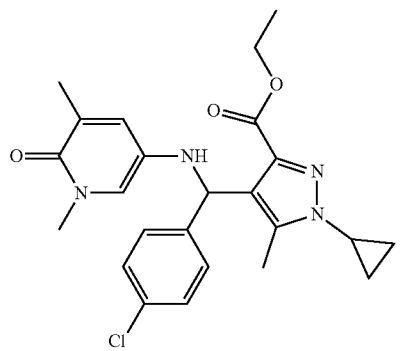 [SMILES: CCOC(=O)c1nn(C2CC2)c(C)c1C(Nc1cc(C)c(=O)n(C)c1)c1ccc(Cl)cc1]

The title compound was prepared in analogy to the procedure described in Step 10.3 using ethyl 4-((4-chlorophenyl)(hydroxy)methyl)-1-cyclopropyl-5-methyl-1H-pyrazole-3-carboxylate (Step 17.5) and 5-amino-1,3-dimethylpyridin-2 (1H)-one (Step 20.2). $t_R$: 4.59 min (HPLC 1); $t_R$: 1.05 min (LC-MS 2); ESI-MS: 455 $[M+H]^+$ (LC-MS 2); $R_f$=0.45 ($CH_2Cl_2$/MeOH 9:1).

Step 20.4: 4-((4-chlorophenyl)(1,5-dimethyl-6-oxo-1,6-dihydropyridin-3-ylamino)methyl)-1-cyclopropyl-5-methyl-1H-pyrazole-3-carboxylic acid

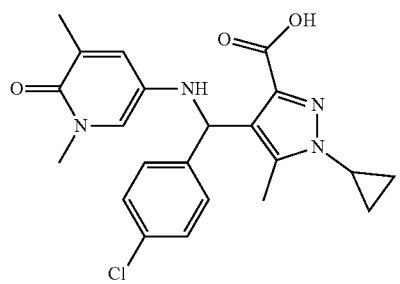 [SMILES: Cc1cc(NC(c2ccc(Cl)cc2)c2c(C(=O)O)nn(C3CC3)c2C)cn(C)c1=O]

The title compound was prepared in analogy to the procedure described in Step 1.5 using ethyl 4-((4-chlorophenyl)(1,5-dimethyl-6-oxo-1,6-dihydropyridin-3-ylamino)methyl)-1-cyclopropyl-5-methyl-1H-pyrazole-3-carboxylate (Step 20.3). $t_R$: 3.64 min (HPLC 1); $t_R$: 0.85 min (LC-MS 2); ESI-MS: 427 $[M+H]^+$ (LC-MS 2).

Example 21

(R)-4-(4-chlorophenyl)-2-cyclopropyl-5-(1,5-dimethyl-6-oxo-1,6-dihydropyridin-3-4-3-methyl-4,5-dihydropyrrolo[3,4-c]pyrazol-6(2H)-one

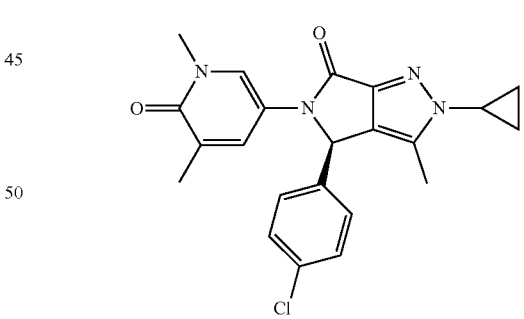

The title compound (37 mg, 0.090 mmol, 30.3% yield) was obtained enantiomerically pure as a white solid (ee>99.5%) after chiral preparative chromatography (system: Gilson PLC 2020; column: Chiralcel OD-H 5 μm, 250×4.6 mm; mobile phase: heptane/ethanol/MeOH 70:20:10; flow: 12 mL/min; detection UV: 230 nm) of the racemic mixture of 4-(4-chlorophenyl)-2-cyclopropyl-5-(1,5-dimethyl-6-oxo-1,6-dihydropyridin-3-yl)-3-methyl-4,5-dihydropyrrolo[3,4-c]pyrazol-6(2H)-one (Example 20) (122 mg, 0.298 mmol) and trituration in $Et_2O$. $t_R$: 0.93 min (LC-MS 2); ESI-MS: 409 $[M+H]^+$ (LC-MS 2).

Reference Example 22

(S)-4-(4-chlorophenyl)-2-cyclopropyl-5-(1,5-dimethyl-6-oxo-1,6-dihydropyridin-3-yl)-3-methyl-4,5-dihydropyrrolo[3,4-c]pyrazol-6(2H)-one

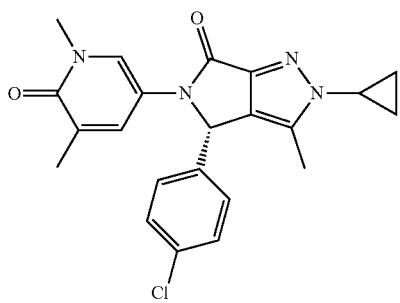 [SMILES: Cc1cc(N2C(=O)c3nn(C4CC4)c(C)c3[C@@H]2c2ccc(Cl)cc2)cn(C)c1=O]

The title compound (22 mg, 0.054 mmol, 18.03% yield) was obtained enantiomerically pure as a white solid (ee>99.5%) after chiral preparative chromatography (Chiralcel OD-H 5 µm, 250×4.6 mm; mobile phase: heptane/ethanol/MeOH 70:20:10; flow: 12 mL/min; detection UV: 230 nm) of the racemic mixture of 4-(4-chlorophenyl)-2-cyclopropyl-5-(1,5-dimethyl-6-oxo-1,6-dihydropyridin-3-yl)-3-methyl-4,5-dihydropyrrolo[3,4-c]pyrazol-6(2H)-one (Example 20) (122 mg, 0.298 mmol), followed by achiral preparative chromatography (SFC: column Reprosil 70 NH2 (250×30 mm, 5 µm)-Dr Maisch; gradient 17-22% in 6 min; flow: 100 mL/min), and trituration in Et$_2$O. $t_R$: 0.93 min (LC-MS 2); ESI-MS: 409 [M+H]$^+$ (LC-MS 2).

Example 23

4-(4-chlorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one

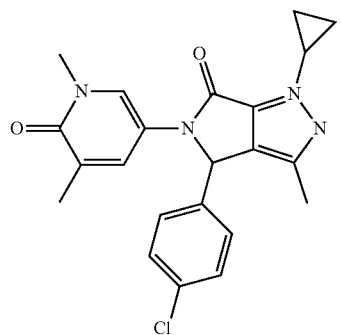

In a 2-mL screw cap vial was introduced 4-(4-chlorophenyl)-1-cyclopropyl-3-methyl-4,5-dihydropyrrolo[3,4-c]pyrazol-6(1H)-one (Step 23.9) (100 mg, 0.348 mmol), 5-iodo-1,3-dimethylpyridin-2(1H)-one (Step 23.2) (104 mg, 0.417 mmol), tripotassium phosphate (148 mg, 0.695 mmol), copper(I) iodide (6.62 mg, 0.035 mmol), N,N'-dimethylethylenediamine (7.48 µL, 0.070 mmol) and dioxane (2 mL). The reaction mixture was stirred for 6 hr at 120° C., concentrated, diluted with water, and extracted with EtOAc. The combined organic layers were washed once with water, dried over Na$_2$SO$_4$ and evaporated. The crude material was purified by silica gel column chromatography (CH$_2$Cl$_2$/MeOH 1-3%) followed by crystallization of the resulting residue in Et$_2$O to provide the title product (85 mg, 0.208 mmol, 69% yield) as a white solid. $t_R$: 4.22 min (HPLC 1); $t_R$: 0.96 min (LC-MS 2); ESI-MS: 409 [M+H]$^+$ (LC-MS 2); R$_f$=0.42 (CH$_2$Cl$_2$/MeOH 9:1); $^1$H NMR (400 MHz, DMSO-d$_6$) δ ppm 0.92-1.15 (m, 2H) 1.18-1.33 (m, 2H) 1.86-2.01 (m, 6H) 3.39 (br. s., 3H) 3.75-3.90 (m, 1H) 6.08 (br. s., 1H) 7.30 (d, J=8.2 Hz, 2H) 7.36-7.47 (m, 3H) 7.75 (br. s., 1H).

Step 23.1: 5-iodo-3-methylpyridin-2-ol

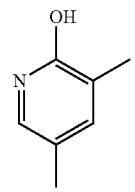

Sodium nitrite (0.708 g, 10.25 mmol) was added to a mixture of 5-iodo-3-methyl-pyridin-2-ylamine (2 g, 8.55 mmol) and H$_2$SO$_4$ (12 mL) at 0° C. The reaction mixture was stirred 15 min at 60° C., allowed to cool down, and poured onto crushed ice. Boric acid (1.057 g, 17.09 mmol) was added and the solution was quickly heated to 100° C. The reaction mixture was cooled down and neutralized with a saturated aq. NH$_4$OH solution. The suspension was filtered to afford the crude title product (1.67 g, 7.11 mmol, 83% yield) as a brown solid. $t_R$: 2.85 min (HPLC 1); $t_R$: 0.62 min (LC-MS 2); ESI-MS: 236 [M+H]$^+$ (LC-MS 2).

Step 23.2: 5-iodo-1,3-dimethylpyridin-2(1H)-one

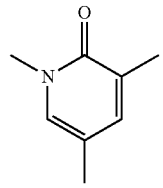

To a stirred suspension of 5-iodo-3-methylpyridin-2-ol (Step 23.1) (1.67 g, 7.11 mmol) and K$_2$CO$_3$ (1.964 g, 14.21 mmol) in DMF (20 mL) was added MeI (0.666 mL, 10.66 mmol) at rt under Ar. The reaction mixture was stirred 1 hr at rt, concentrated, diluted with water, and extracted with EtOAc. The organic layers were combined and washed once with water, dried over Na$_2$SO$_4$ and evaporated. The crude material was purified by silica gel column chromatography (hexane/EtOAc 50-65) to afford the title product (1.40 g, 5.62 mmol, 79% yield) as a brown solid. $t_R$: 3.31 min (HPLC 1); $t_R$: 0.71 min (LC-MS 2); ESI-MS: 250 [M+H]$^+$ (LC-MS 2); R$_f$=0.31 (hexane/EtOAc 1:1).

Step 23.3: ethyl 1-cyclopropyl-3-methyl-1H-pyrazole-5-carboxylate

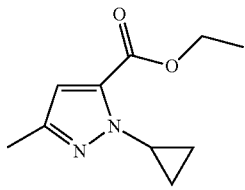

To a stirred solution of cyclopropylhydrazine (Step 17.2) (4.90 g, 45.1 mmol) in toluene (30 mL) and EtOH (30 mL) was added ethyl 2,4-dioxavalerate (6.34 mL, 45.1 mmol). The reaction mixture was stirred for 1 hr at 100° C., quenched with a saturated aq. NaHCO$_3$ solution, and extracted with EtOAc. The combined organic layers were washed with a saturated aq. NaHCO$_3$ solution, dried over Na$_2$SO$_4$ and evaporated. The crude material was purified by silica gel column chromatography (hexane/EtOAc 2.5-30%) to afford the title product (3.01 g, 15.50 mmol, 34% yield). $t_R$: 4.70 min (HPLC 1); $t_R$: 1.01 min (LC-MS 2); ESI-MS: 195 [M+H]$^+$ (LC-MS 2); R$_f$=0.33 (hexane/EtOAc 9:1).

Step 23.4: ethyl 1-cyclopropyl-4-iodo-3-methyl-1H-pyrazole-5-carboxylate

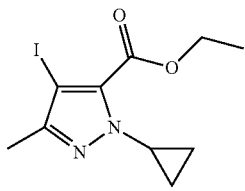

To a stirred solution of ethyl 1-cyclopropyl-5-methyl-1H-pyrazole-3-carboxylate (Step 23.3) (3 g, 15.45 mmol) in CH$_3$CN (80 mL) under Ar was added I$_2$ (2.352 g, 9.27 mmol) and after 5 min CAN (5.08 g, 9.27 mmol). The reaction mixture was stirred for 1 hr at 80° C., concentrated, quenched with a 10% aq. Na$_2$S$_2$O$_3$ solution, and extracted with EtOAC (2×100 mL). The combined organic layers were washed with brine (100 mL), dried over Na$_2$SO$_4$ and evaporated. The crude material was purified by silica gel column chromatography (hexane/EtOAc 2.5-5%) to afford the title product (4.33 g, 13.53 mmol, 80% yield) as a yellow oil. $t_R$: 5.62 min (HPLC 1); $t_R$: 1.20 min (LC-MS 2); ESI-MS: 321 [M+H]$^+$ (LC-MS 2); R$_f$=0.34 (hexane/EtOAc 9:1).

Step 23.5: ethyl 4-((4-chlorophenyl)(hydroxy)methyl)-1-cyclopropyl-3-methyl-1H-pyrazole-5-carboxylate

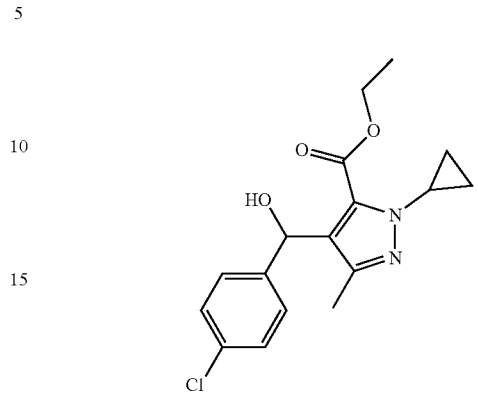

To a stirred solution of ethyl 1-cyclopropyl-4-iodo-5-methyl-1H-pyrazole-3-carboxylate (Step 23.4) (4.33 g, 13.53 mmol)) in THF (100 mL) under Ar was added TurboGrignard (14.88 mmol) at −10° C. After 15 min, 4-chlorobenzaldehyde (1.901 g, 13.53 mmol) was added. The reaction mixture was stirred for 30 min at this temperature, quenched with a saturated aqueous solution of NH$_4$Cl (150 mL), extracted with EtOAc (2×150 mL). The combined organic layers were washed with a saturated aqueous solution of NH$_4$Cl (75 mL), dried (Na$_2$SO$_4$), and evaporated. The crude material was purified by silica gel column chromatography (hexane/EtOAc 5-25%) to afford the title product (2.12 g, 6.33 mmol, 46.8% yield) as a colorless oil. $t_R$: 1.16 min (LC-MS 2); ESI-MS: 335 [M+H]$^+$ (LC-MS 2); R$_f$=0.62 (hexane/EtOAc 1:1).

Step 23.6: ethyl 4-((4-chlorophenyl)((4-methoxybenzyl)amino)methyl)-1-cyclopropyl-3-methyl-1H-pyrazole-5-carboxylate

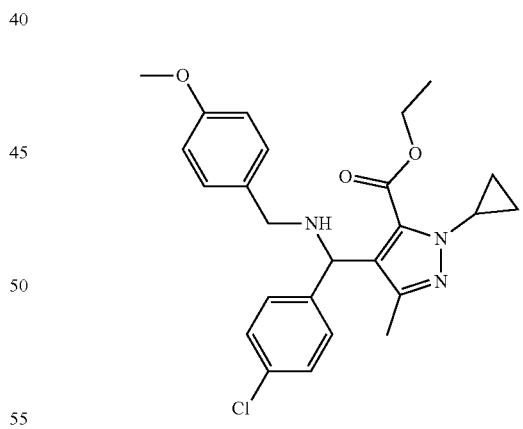

To a stirred solution of ethyl 4-((4-chlorophenyl)(hydroxy)methyl)-1-cyclopropyl-3-methyl-1H-pyrazole-5-carboxylate (Step 23.5) (2.12 g, 6.33 mmol) and triethylamine (4.41 mL, 31.7 mmol) in CH$_2$Cl$_2$ (4 mL) under Ar was added Ms$_2$O (2.206 g, 12.66 mmol) at −10° C. The reaction mixture was stirred for 30 min at this temperature. 4-Methoxybenzylamine (0.827 ml, 6.33 mmol) was added at 30° C. After 15 h at rt, the reaction mixture was quenched with a saturated aqueous solution of NaHCO$_3$ (100 mL), and extracted with CH$_2$Cl$_2$ (2×100 mL). The combined organic layers were washed with a saturated aqueous solution of NaHCO$_3$ (100 mL), dried (Na$_2$SO$_4$) and evaporated. The crude material was purified by silica gel column chromatography (Hex/EtOAc 5-20%) to afford the title product (2.22 g, 4.89 mmol, 77% yield) as a colorless oil. t$_R$: 1.12 min (LC-MS 2); ESI-MS: 454 [M+H]$^+$ (LC-MS 2); R$_f$=0.85 (hexane/EtOAc 1:1).

Step 23.7: 4-((4-chlorophenyl)((4-methoxybenzyl)amino)methyl)-1-cyclopropyl-3-methyl-1H-pyrazole-5-carboxylic acid

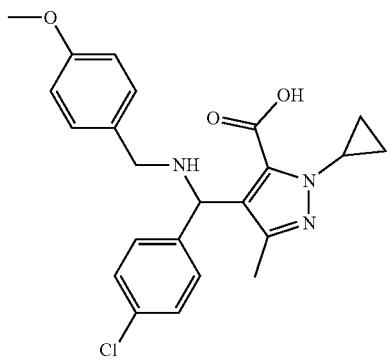 [SMILES: COc1ccc(CNC(c2ccc(Cl)cc2)c2c(C)nn(C3CC3)c2C(=O)O)cc1]

In a 100-mL flask was introduced 4-((4-chlorophenyl)((4-methoxybenzyl)amino)methyl)-1-cyclopropyl-3-methyl-1H-pyrazole-5-carboxylate (Step 23.6) (2.22 g, 4.89 mmol) and LiOH.H$_2$O (0.616 g, 14.67 mmol) in dioxane (15 mL) and H$_2$O (6 mL). The reaction mixture was stirred for hr at rt, quenched with 0.5N HCl (100 mL), and diluted with EtOAc (100 mL). The resulting suspension was filtered to afford the title compound (2.30 g, 4.59 mmol, 94% yield) as a colorless solid. t$_R$: 3.86 min (HPLC 1); t$_R$: 0.87 min (LC-MS 2); ESI-MS: 426 [M+H]$^+$ (LC-MS 2).

Step 23.8: 4-(4-chlorophenyl)-1-cyclopropyl-5-(4-methoxybenzyl)-3-methyl-4,5-dihydropyrrolo[3,4-c]pyrazol-6(1H)-one

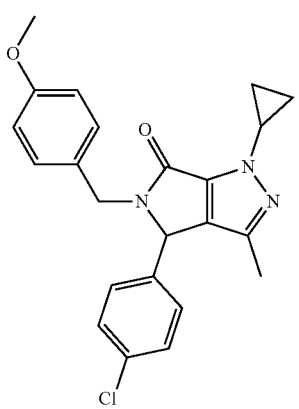 [SMILES: COc1ccc(CN2C(=O)c3c(c(C)nn3C3CC3)C2c2ccc(Cl)cc2)cc1]

To a stirred solution of 4-((4-chlorophenyl)((4-methoxybenzyl)amino)methyl)-1-cyclopropyl-3-methyl-1H-pyrazole-5-carboxylic acid (Step 23.7) (2.30 g, 4.59 mmol) in CH$_2$Cl$_2$ (30 mL) under Ar was added 1-chloro-N,N,2-trimethyl-1-propenylamine (0.846 mL, 6.43 mmol) at 0° C. The reaction mixture was stirred for 1 hr at rt, quenched with a saturated aqueous solution of NaHCO$_3$ (75 mL), and extracted with CH$_2$Cl$_2$ (2×100 mL) The combined organic layers were washed with a saturated aqueous solution of NaHCO$_3$ (100 mL), dried (Na$_2$SO$_4$) and evaporated. The crude material was purified by silica gel column chromatography (Hex/EtOAc 5-30%) to afford the title product (1.82 g, 4.24 mmol, 92% yield) as a yellow oil. t$_R$: 5.76 min (HPLC 1); t$_R$: 1.27 min (LC-MS 2); ESI-MS: 408 [M+H]$^+$ (LC-MS 2); R$_f$=0.66 (hexane/EtOAc 1:1).

Step 23.9: 4(4-chlorophenyl)-1-cyclopropyl-3-methyl-4,5-dihydropyrrolo[3,4-c]pyrazol-6(1H)-one

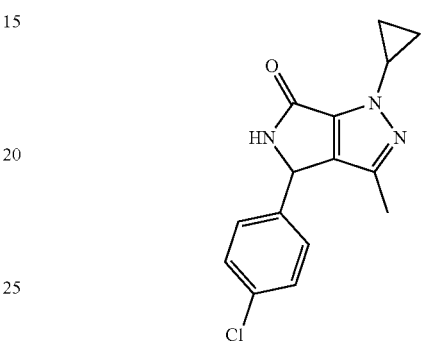

In a 20-mL MW vial was introduced (Step 23.8) (1.82 g, 4.46 mmol) and TFA (10.31 mL, 134 mmol). The reaction mixture was stirred for 2 hr at 100° C. and additional 2 hr at 120° C. MW irradiation. The reaction mixture was quenched with a saturated aq. NaHCO$_3$ solution and extracted with CH$_2$Cl$_2$. The combined organic layers were washed with a saturated aq. NaHCO$_3$ solution, dried over Na$_2$SO$_4$ and evaporated. The crude material was purified by silica gel column chromatography (hexane/EtOAc 20-55%) to afford the title product (713 mg, 2.478 mmol, 55% yield) as a yellow solid. t$_R$: 4.20 min (HPLC 1); t$_R$: 0.93 min (LC-MS 2); ESI-MS: 288 [M+H]$^+$ (LC-MS 2); R$_f$=0.32 (hexane/EtOAc 1:1).

Example 24

5-(5-chloro-1-methyl-6-oxo-1,6-dihydropyridin-3-yl)-4-(4-chlorophenyl)-1-cyclopropyl-3-methyl-4,5-dihydropyrrolo[3,4-c]pyrazol-6(1H)-one

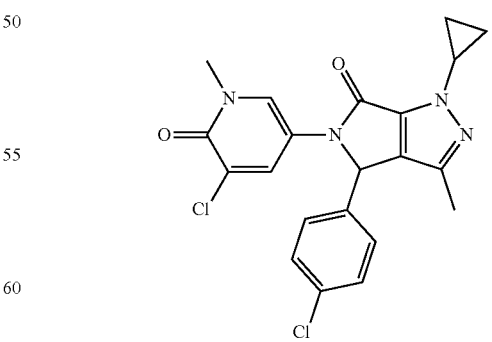

The title compound was prepared in analogy to the procedure described in Example 23 (100° instead of 120° C.) using 3-chloro-5-iodo-1-methylpyridin-2(1H)-one (Step 24.1). After purification by silica gel column chromatography, the resulting residue was triturated in hexane. $t_R$: 4.45 min (HPLC 1); $t_R$: 1.00 min (LC-MS 2); ESI-MS: 429/431 [M+H]$^+$ (LC-MS 2); $R_f$=0.48 (CH$_2$Cl$_2$/MeOH 9:1); $^1$H NMR (400 MHz, DMSO-d$_6$) δ ppm 1.01-1.06 (m, 2H) 1.20-1.25 (m, 2H) 1.91 (s, 3H) 3.45 (s, 3H) 3.76-3.85 (m, 1H) 6.10 (s, 1H) 7.27-7.34 (m, 2H) 7.36-7.43 (m, 2H) 7.90 (d, J=2.7 Hz, 1H) 7.94 (d, J=2.74 Hz, 1H).

Step 24.1: 3-chloro-5-iodo-1-methylpyridin-2(1H)-one

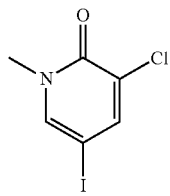

The title compound was prepared in analogy to the procedure described in Step 23.2 using 3-chloro-5-iodo-pyridin-2-ol. $t_R$: 3.30 min (HPLC 1); $t_R$: 0.71 min (LC-MS 2); ESI-MS: 270 [M+H]$^+$ (LC-MS 2); $R_f$=0.79 (CH$_2$Cl$_2$/MeOH 9:1).

Example 25

4-(4-chlorophenyl)-2,3-dimethyl-5-(3-methyl-[1,2,4] triazolo[4,3-a]pyridin-6-yl)-4,5-dihydropyrrolo[3,4-c]pyrazol-6(2H)-one

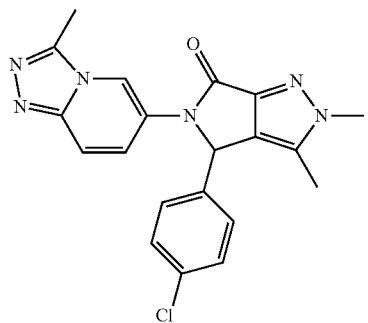 [SMILES: Cc1c2c(nn1C)C(=O)N(c1ccc3nnc(C)n3c1)C2c1ccc(Cl)cc1]

The title compound was prepared in analogy to the procedure described in Example 24 using 4-(4-chlorophenyl)-2,3-dimethyl-4,5-dihydropyrrolo[3,4-c]pyrazol-6(2H)-one (Step 25.6) and 6-bromo-3-methyl[1,2,4]triazolo-[4,3-a]pyridine. After purification by silica gel column chromatography, the resulting residue was purified by SFC (Thar 100; column: PFP, 25 cm, Ø 3 cm, 5 µm, 60 Å; gradient: 10% B for 1 min, 10-15% B in 6 min, 15-50% B in 1 min, 50% B for 1.5 min, 50%-10% B in 1 min, 10% B for 0.5 min; A: scCO$_2$, B: MeOH; flow: 100 mL/min). The residue was triturated in Et$_2$O. $t_R$: 3.26 min (HPLC 1); $t_R$: 0.77 min (LC-MS 2); ESI-MS: 393 [M+H]$^+$ (LC-MS 2); $R_f$=0.37 (CH$_2$Cl$_2$/MeOH 9:1); $^1$H NMR (400 MHz, DMSO-d$_6$) δ ppm 2.11 (s, 3H) 2.64 (s, 3H) 3.88 (s, 3H) 6.49 (s, 1H) 7.35 (s, 4H) 7.47-7.52 (m, 1H) 7.65-7.70 (m, 1H) 8.64 (s, 1H).

Step 25.1: ethyl 4-iodo-1,5-dimethyl-1H-pyrazole-3-carboxylate

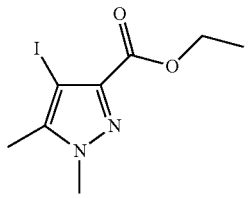

The title compound was prepared in analogy to the procedure described in Step 10.1 (extraction with EtOAc instead of CH$_2$Cl$_2$) using ethyl 1,5-dimethyl-1H-pyrazole-3-carboxylate. $t_R$: 4.06 min (HPLC 1); $t_R$: 0.88 min (LC-MS 2); ESI-MS: 295.0 [M+H]$^+$ (LC-MS 2); $R_f$=0.33 (hexane/EtOAc 1:1).

Step 25.2: ethyl 4-((4-chlorophenyl)(hydroxy)methyl)-1,5-dimethyl-1H-pyrazole-3-carboxylate

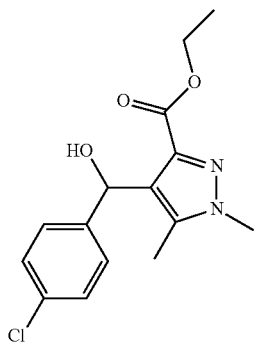 [SMILES: CCOC(=O)c1nn(C)c(C)c1C(O)c1ccc(Cl)cc1]

The title compound was prepared in analogy to the procedure described in Step 1.3 using ethyl 4-iodo-1,5-dimethyl-1H-pyrazole-3-carboxylate (Step 25.1). $t_R$: 4.44 min (HPLC 1); $t_R$: 0.97 min (LC-MS 2); ESI-MS: 291 [M+H-18]$^+$ (LC-MS 2); $R_f$=0.51 (EtOAc).

Step 25.3: ethyl 4-((4-chlorophenyl)((4-methoxybenzyl)amino)methyl)-1,5-dimethyl-1H-pyrazole-3-carboxylate

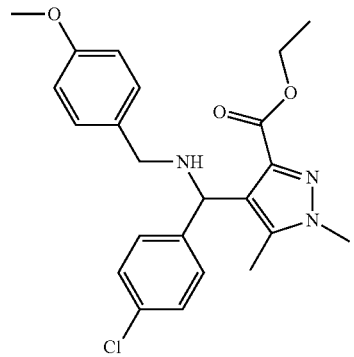

The title compound was prepared in analogy to the procedure described in Step 1.4 using ethyl 4-((4-chlorophenyl)

(hydroxy)methyl)-1,5-dimethyl-1H-pyrazole-3-carboxylate (Step 25.2) and 4-methoxybenzylamine. $t_R$: 3.99 min (HPLC 1); $t_R$: 0.86 min (LC-MS 2); ESI-MS: 428 [M+H]$^+$ (LC-MS 2); $R_f$=0.59 (EtOAc).

Step 25.4: 4-((4-chlorophenyl)((4-methoxybenzyl)amino)methyl)-1,5-dimethyl-1H-pyrazole-3-carboxylic acid

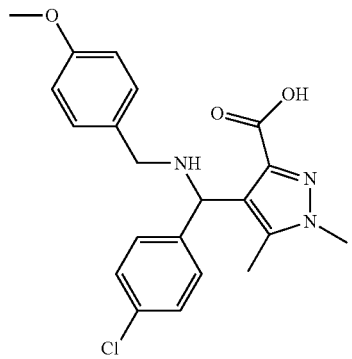

The title compound was prepared in analogy to the procedure described in Step 1.5 using ethyl 4-((4-chlorophenyl)((4-methoxybenzyl)amino)methyl)-1,5-dimethyl-1H-pyrazole-3-carboxylate (Step 25.3). The reaction mixture was quenched with 0.5N HCl, diluted with EtOAc, and cooled down to 0° C. The suspension was filtered to afford crude product as a white solid. $t_R$: 3.38 min (HPLC 1); $t_R$: 0.73 min (LC-MS 2); ESI-MS: 400 [M+H]$^+$ (LC-MS 2).

Step 25.5: 4-(4-chlorophenyl)-5-(4-methoxybenzyl)-2,3-dimethyl-4,5-dihydropyrrolo[3,4-c]pyrazol-6(2H)-one

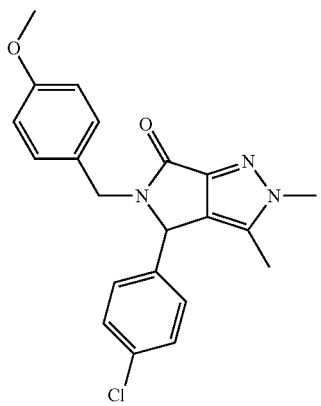 [SMILES: COc1ccc(CN2C(=O)c3nn(C)c(C)c3C2c2ccc(Cl)cc2)cc1]

The title compound was prepared in analogy to the procedure described in Example 1 using 4-((4-chlorophenyl)((4-methoxybenzyl)amino)methyl)-1,5-dimethyl-1H-pyrazole-3-carboxylic acid (Step 25.4). $t_R$: 5.07 min (HPLC 1); $t_R$: 1.11 min (LC-MS 2); ESI-MS: 382.2 [M+H]$^+$ (LC-MS 2); $R_f$=0.46 (EtOAc).

Step 25.6: 4-(4-chlorophenol)-2,3-dimethyl-4,5-dihydropyrrolo[3,4-c]pyrazol-6(2H)-one

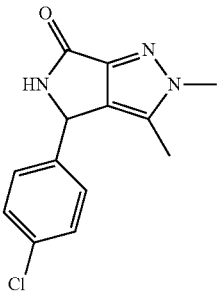 [SMILES: Cc1c2c(nn1C)C(=O)NC2c1ccc(Cl)cc1]

The title compound was prepared in analogy to the procedure described in Example 2 using 4-(4-chlorophenyl)-5-(4-methoxybenzyl)-2,3-dimethyl-4,5-dihydropyrrolo[3,4-c]pyrazol-6(2H)-one (Step 25.5). $t_R$: 3.61 min (HPLC 1); $t_R$: 0.78 min (LC-MS 2); ESI-MS: 262 [M+H]$^+$ (LC-MS 2); $R_f$=0.49 (CH$_2$Cl$_2$/MeOH 9:1).

Example 26

4-(4-chlorophenyl)-5-(1,5-dimethyl-6-oxo-1,6-dihydropyridin-3-yl)-4,5-dihydropyrrolo[3,4-c]pyrazol-6(2H)-one The title compound was prepared in analogy to the procedure described in Example 2 using 4-(4-chlorophenyl)-5-(1,5-dimethyl-6-oxo-1,6-dihydropyridin-3-yl)-2-(4-methoxybenzyl)-4,5-dihydropyrrolo[3,4-c]pyrazol-6(2H)-one (Step 26.3). After purification by silica gel column chromatography, the product was triturated in Et$_2$O. $t_R$: 3.18 min (HPLC 1); $R_f$=0.36 (CH$_2$Cl$_2$/MeOH 9:1); $^1$H NMR (400 MHz, DMSO-d$_6$) δ ppm 1.95 (s, 3H) 3.39 (s, 3H) 6.18 (s, 1H) 7.24 (d, J=8.2 Hz, 2H) 7.38 (d, J=8.6 Hz, 2H) 7.42-7.45 (m, 1H) 7.75 (d, J=2.7 Hz, 1H) 7.83 (s, 1H) 13.69 (s, 1H).

Step 26.1: ethyl 4-((4-chlorophenyl)((1,5-dimethyl-6-oxo-1,6-dihydropyridin-3-yl)amino)methyl)-1-(4-methoxybenzyl)-1H-pyrazole-3-carboxylate

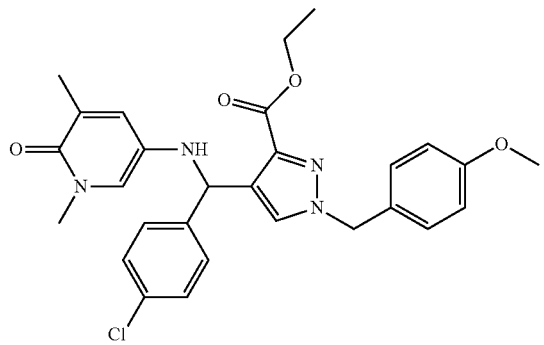 [SMILES: CCOC(=O)c1nn(Cc2ccc(OC)cc2)cc1C(Nc1cc(C)c(=O)n(C)c1)c1ccc(Cl)cc1]

The title compound was prepared in analogy to the procedure described in Step 10.3 using ethyl 4-((4-chlorophenyl)(hydroxy)methyl)-1-(4-methoxybenzyl)-1H-pyrazole-3-carboxylate (Step 9.3) and 5-amino-1,3-dimethylpyridin-2(1H)-one (Step 20.2). $t_R$: 4.72 min (HPLC 1); $t_R$: 1.08 min (LC-MS 2); ESI-MS: 521 [M+H]$^+$ (LC-MS 2); $R_f$=0.16 (EtOAc).

Step 26.2: 4-((4-chlorophenyl)((1,5-dimethyl-6-oxo-1,6-dihydropyridin-3-yl)amino)methyl)-1-(4-methoxybenzyl)-1H-pyrazole-3-carboxylic acid

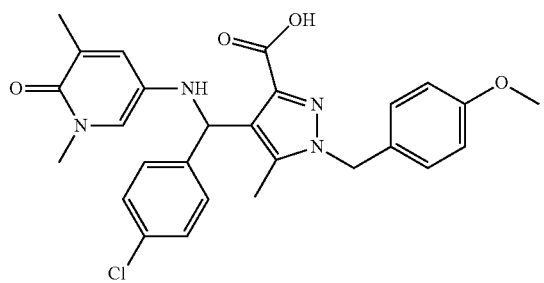

The title compound was prepared in analogy to the procedure described in Step 1.5 using ethyl 4-((4-chlorophenyl)((1,5-dimethyl-6-oxo-1,6-dihydropyridin-3-yl)amino)methyl)-1-(4-methoxy-benzyl)-1H-pyrazole-3-carboxylate (Step 26.1). $t_R$: 3.96 min (HPLC 1); $t_R$: 0.91 min (LC-MS 2); ESI-MS: 493 [M+H]$^+$ (LC-MS 2).

Step 26.3: 4-(4-chlorophenyl)-5-(1,5-dimethyl-6-oxo-1,6-dihydropyridin-3-yl)-2-(4-methoxy-benzyl)-4,5-dihydropyrrolo[3,4-c]pyrazol-6(2H)-one

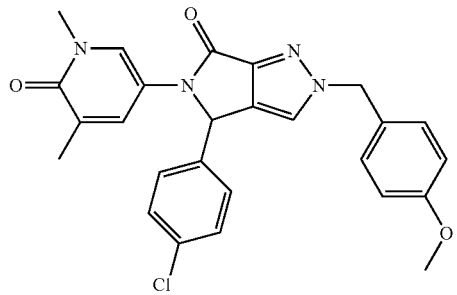 [SMILES: COc1ccc(Cn2cc3c(n2)C(=O)N(c2cc(C)c(=O)n(C)c2)C3c2ccc(Cl)cc2)cc1]

The title compound was prepared in analogy to the procedure described in Example 1 using 4-((4-chlorophenyl)((1,5-dimethyl-6-oxo-1,6-dihydropyridin-3-yl)amino)methyl)-1-(4-methoxy-benzyl)-1H-pyrazole-3-carboxylic acid (Step 26.2). $t_R$: 4.40 min (HPLC 1); $t_R$: 1.00 min (LC-MS 2); ESI-MS: 475 [M+H]$^+$ (LC-MS 2); $R_f$=0.38 (CH$_2$Cl$_2$/MeOH 9:1).

Example 27

4-(4-chlorophenyl)-5-(1,5-dimethyl-6-oxo-1,6-dihydropyridin-3-yl)-3-methyl-4,5-dihydropyrrolo[3,4-c]pyrazol-6(2H)-one

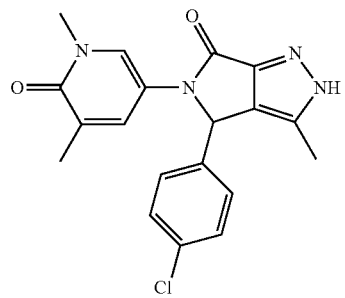 [SMILES: Cc1[nH]nc2c1C(c1ccc(Cl)cc1)N(c1cc(C)c(=O)n(C)c1)C2=O]

The title compound was prepared in analogy to the procedure described in Example 2 using 4-(4-chlorophenyl)-5-(1,5-dimethyl-6-oxo-1,6-dihydropyridin-3-yl)-3-methyl-4,5-dihydropyrrolo[3,4-c]pyrazol-6(2H)-one (Step 27.3). $t_R$: 3.34 min (HPLC 1); $t_R$: 0.76 min (LC-MS 2); ESI-MS: 369 [M+H]$^+$ (LC-MS 2); $R_f$=0.27 (CH$_2$Cl$_2$/MeOH 9:1); $^1$H NMR (400 MHz, DMSO-d$_6$) δ ppm 1.91 (s, 3H) 2.02 (s, 3H) 3.35 (s, 3H) 6.08 (s, 1H) 7.22 (d, J=8.2 Hz, 2H) 7.31-7.42 (m, 3H) 7.71 (d, J=2.7 Hz, 1H) 13.33 (br. s., 1H).

Step 27.1: ethyl 4-((4-chlorophenyl)(1,5-dimethyl-6-oxo-1,6-dihydropyridin-3-ylamino)methyl)-1-(4-methoxybenzyl)-5-methyl-1H-pyrazole-3-carboxylate

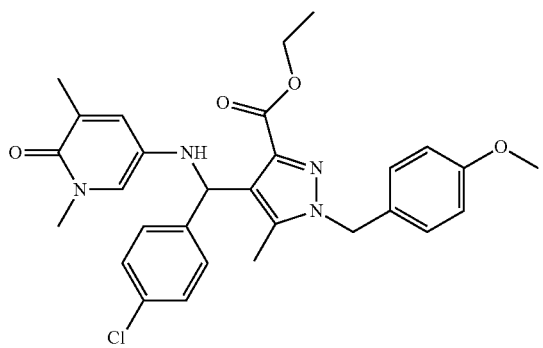 [SMILES: CCOC(=O)c1nn(Cc2ccc(OC)cc2)c(C)c1C(Nc1cc(C)c(=O)n(C)c1)c1ccc(Cl)cc1]

The title compound was prepared in analogy to the procedure described in Step 10.3 using ethyl 4-((4-chlorophenyl)(hydroxy)methyl)-1-(4-methoxybenzyl)-5-methyl-1H-pyrazole-3-carboxylate (Step 1.3) and 5-amino-1,3-dimethylpyridin-2(1H)-one (Step 20.2). $t_R$: 4.94 min (HPLC 1); $t_R$: 1.13 min (LC-MS 2); ESI-MS: 535 [M+H]$^+$ (LC-MS 2); $R_f$=0.45 (CH$_2$Cl$_2$/MeOH 9:1).

Step 27.2: 4-((4-chlorophenyl)(1,5-dimethyl-6-oxo-1,6-dihydropyridin-3-ylamino)methyl)-1-(4-methoxybenzyl)-5-methyl-1H-pyrazole-3-carboxylic acid

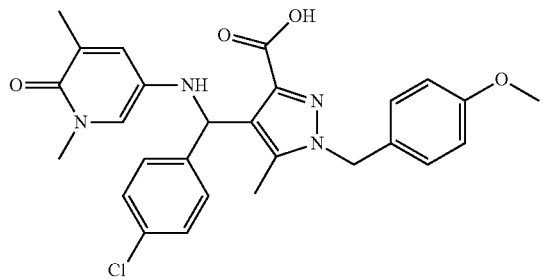 [SMILES: COc1ccc(Cn2nc(C(=O)O)c(C(Nc3cc(C)c(=O)n(C)c3)c3ccc(Cl)cc3)c2C)cc1]

The title compound was prepared in analogy to the procedure described in Step 1.5 using ethyl 4-((4-chlorophenyl)(1,5-dimethyl-6-oxo-1,6-dihydropyridin-3-ylamino)methyl)-1-(4-methoxy-benzyl)-5-methyl-1H-pyrazole-3-carboxylate (Step 27.1). The reaction mixture was quenched with 0.5N HCl and diluted with EtOAc. The suspension was filtered to afford crude product as a white solid. $t_R$: 4.07 min (HPLC 1); $t_R$: 0.96 min (LC-MS 2); ESI-MS: 507 [M+H]$^+$ (LC-MS 2).

Step 27.3: 4-(4-chlorophenyl)-5-(1,5-dimethyl-6-oxo-1,6-dihydropyridin-3-yl)-2-(4-methoxy benzyl)-3-methyl-4,5-dihydropyrrolo[3,4-c]pyrazol-6(2H)-one

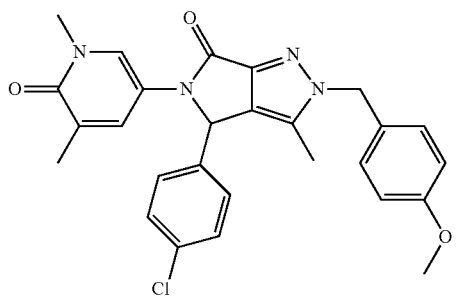

The title compound was prepared in analogy to the procedure described in Example 1 using 4-((4-chlorophenyl)(1,5-dimethyl-6-oxo-1,6-dihydropyridin-3-ylamino)methyl)-1-(4-methoxybenzyl)-5-methyl-1H-pyrazole-3-carboxylic acid (Step 27.2). $t_R$: 4.54 min (HPLC 1); $t_R$: 1.03 min (LC-MS 2); ESI-MS: 489 [M+H]$^+$ (LC-MS 2); $R_f$=0.40 (CH$_2$Cl$_2$/MeOH 9:1).

Example 28

4-(4-chlorophenyl)-5-(1,5-dimethyl-6-oxo-1,6-dihydropyridin-3-yl)-2,3-dimethyl-4,5-dihydropyrrolo[3,4-c]pyrazol-6(2H)-one

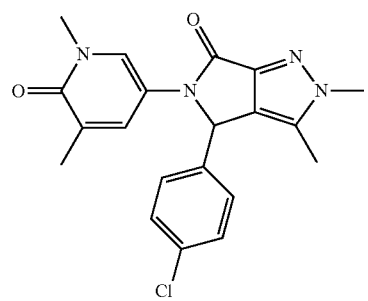 [SMILES: Cc1cc(N2C(=O)c3nn(C)c(C)c3C2c2ccc(Cl)cc2)cn(C)c1=O]

The title compound was prepared in analogy to the procedure described in Example 1 using 4-((4-chlorophenyl)(1,5-dimethyl-6-oxo-1,6-dihydropyridin-3-ylamino)methyl)-1,5-dimethyl-1H-pyrazole-3-carboxylic acid (Step 28.4). $t_R$: 3.62 min (HPLC 1); $t_R$: 0.81 min (LC-MS 2); ESI-MS: 383 [M+H]$^+$ (LC-MS 2); $R_f$=0.55 (CH$_2$Cl$_2$/MeOH 9:1); $^1$H NMR (400 MHz, DMSO-d$_6$) δ ppm 1.92 (s, 3H) 2.05 (s, 3H) 3.35 (s, 3H) 3.83 (s, 3H) 6.10 (s, 1H) 7.24 (d, J=8.6 Hz, 2H) 7.33-7.41 (m, 3H) 7.72 (d, J=2.7 Hz, 1H).

Step 28.1: ethyl 4-iodo-1,5-dimethyl-1H-pyrazole-3-carboxylate

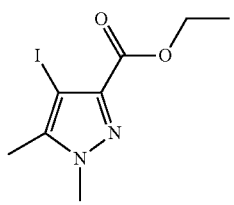

The title compound was prepared in analogy to the procedure described in Step 10.1 using ethyl 1,5-dimethyl-1H-pyrazole-3-carboxylate. $t_R$: 4.07 min (HPLC 1); $t_R$: 0.87 min (LC-MS 2); ESI-MS: 295 [M+H]$^+$ (LC-MS 2); $R_f$=0.33 (hexane/EtOAc 1:1).

Step 28.2: ethyl 4-((4-chlorophenyl)(hydroxy)methyl)-1,5-dimethyl-1H-pyrazole-3-carboxylate Intermediate 28A

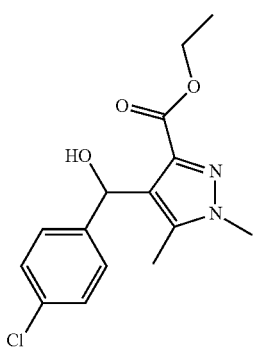 [SMILES: CCOC(=O)c1nn(C)c(C)c1C(O)c1ccc(Cl)cc1]

The title compound was prepared in analogy to the procedure described in Step 1.3 using ethyl 4-iodo-1,5-dimethyl-1H-pyrazole-3-carboxylate (Step 28.1). $t_R$: 4.42 min (HPLC 1); $t_R$: 0.95 min (LC-MS 2); ESI-MS: 291 [M-18+H]$^+$ (LC-MS 2); $R_f$=0.51 (EtOAc).

Step 28.3: ethyl 4-((4-chlorophenyl)(1,5-dimethyl-6-oxo-1,6-dihydropyridin-3-ylamino)methyl)-1,5-dimethyl-1H-pyrazole-3-carboxylate

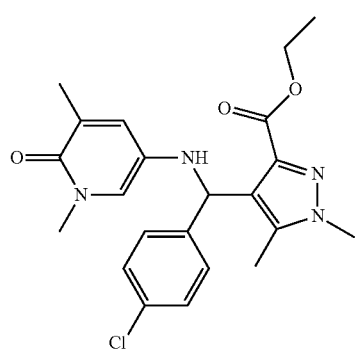 [SMILES: CCOC(=O)c1nn(C)c(C)c1C(Nc1cc(C)c(=O)n(C)c1)c1ccc(Cl)cc1]

The title compound was prepared in analogy to the procedure described in Step 10.3 using ethyl 4-((4-chlorophenyl)(hydroxy)methyl)-1,5-dimethyl-1H-pyrazole-3-carboxylate (Step 28.2) and 5-amino-1,3-dimethylpyridin-2(1H)-one (Step 20.2). $t_R$: 4.17 min (HPLC 1); $t_R$: 0.95 min (LC-MS 2); ESI-MS: 429 [M+H]$^+$ (LC-MS 2); $R_f$=0.47 (CH$_2$Cl$_2$/MeOH 9:1).

Step 28.4: 4-((4-chlorophenyl)(1,5-dimethyl-6-oxo-1,6-dihydropyridin-3-ylamino)methyl)-1,5-dimethyl-1H-pyrazole-3-carboxylic acid

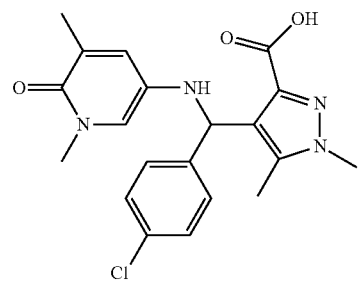 [SMILES: Cc1cc(NC(c2ccc(Cl)cc2)c2c(C(=O)O)nn(C)c2C)cn(C)c1=O]

The title compound was prepared in analogy to the procedure described in Step 1.5 using ethyl 4-((4-chlorophenyl)(1,5-dimethyl-6-oxo-1,6-dihydropyridin-3-ylamino)methyl)-1,5-dimethyl-1H-pyrazole-3-carboxylate (Step 28.3). $t_R$: 3.27 min (HPLC 1); $t_R$: 0.76 min (LC-MS 2); ESI-MS: 401 [M+H]$^+$ (LC-MS 2).

Reference Example 29

(S)-4-(4-chlorophenyl)-5-(1,5-dimethyl-6-oxo-1,6-dihydropyridin-3-yl)-2,3-dimethyl-4,5-dihydropyrrolo[3,4-c]pyrazol-6(2H)-one

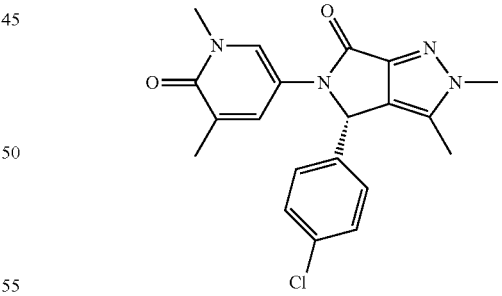

The title compound (23 mg, 0.060 mmol, 34.3% yield) was obtained enantiomerically pure (ee>99.5%) as a white solid after preparative chiral chromatography (Chiralcel OD-H 30×250 mm; mobile phase: scCO$_2$/EtOH 70:30 (isocratic); flow: 80 mL/min; detection UV: 215 nm; cycle time: 12 min) of the racemic mixture of 4-(4-chlorophenyl)-5-(1,5-dimethyl-6-oxo-1,6-dihydropyridin-3-yl)-2,3-dimethyl-4,5-dihydropyrrolo[3,4-c]pyrazol-6(2H)-one (Example 28) (67 mg, 0.175 mmol) and trituration in Et$_2$O. $t_R$: 0.83 min (LC-MS 2); ESI-MS: 383 [M+H]$^+$ (LC-MS 2).

Example 30

(R)-4-(4-chlorophenyl)-5-(1,5-dimethyl-6-oxo-1,6-dihydropyridin-3-yl)-2,3-dimethyl-4,5-dihydropyrrolo[3,4-c]pyrazol-6(2H)-one

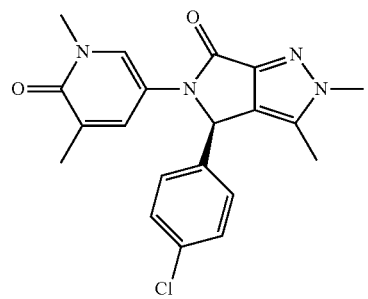 [SMILES: Cc1cc(N2C(=O)c3nn(C)c(C)c3[C@H]2c2ccc(Cl)cc2)cn(C)c1=O]

The title compound (24 mg, 0.063 mmol, 35.8% yield) was obtained enantiomerically pure (ee>99.5%) as a white solid after chiral preparative chromatography (Chiralcel OD-H 30×250 mm; mobile phase: scCO$_2$/EtOH 70:30 (isocratic); flow: 80 mL/min; detection UV: 215 nm; cycle time: 12 min) of the racemic mixture of 4-(4-chlorophenyl)-5-(1,5-dimethyl-6-oxo-1,6-dihydropyridin-3-yl)-2,3-dimethyl-4,5-dihydropyrrolo[3,4-c]pyrazol-6(2H)-one (Example 28) (67 mg, 0.175 mmol) and trituration in Et$_2$O. t$_R$: 0.83 min (LC-MS 2); ESI-MS: 383 [M+H]$^+$ (LC-MS 2).

Example 31

4-(4-chlorophenyl)-5-(5-fluoro-1-methyl-6-oxo-1,6-dihydropyridin-3-yl)-2,3-dimethyl-4,5-dihydropyrrolo[3,4-c]pyrazol-6(2H)-one

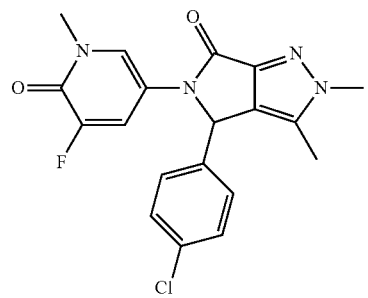

The title compound was prepared in analogy to the procedure described in Example 1 using 4-((4-chlorophenyl)(5-fluoro-1-methyl-6-oxo-1,6-dihydropyridin-3-ylamino)methyl)-1,5-dimethyl-1H-pyrazole-3-carboxylic acid (Step 31.2). t$_R$: 3.64 min (HPLC 1); t$_R$: 0.80 min (LC-MS 2); ESI-MS: 387 [M+H]$^+$ (LC-MS 2); R$_f$=0.51 (CH$_2$Cl$_2$/MeOH 9:1); $^1$H NMR (400 MHz, DMSO-d$_6$) δ ppm 2.06 (s, 3H) 3.43 (s, 3H) 3.83 (s, 3H) 6.13 (s, 1H) 7.23-7.29 (m, 2H) 7.33-7.40 (m, 2H) 7.57-7.67 (m, 1H) 7.79 (br. s, 1H).

Step 31.1: ethyl 4-((4-chlorophenyl)(5-fluoro-1-methyl-6-oxo-1,6-dihydropyridin-3-ylamino)methyl)-1,5-dimethyl-1H-pyrazole-3-carboxylate

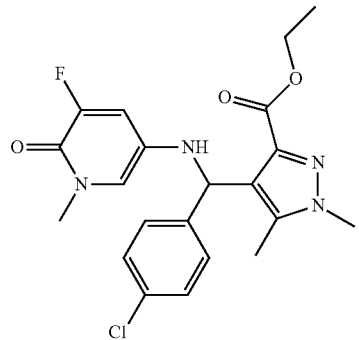 [SMILES: CCOC(=O)c1nn(C)c(C)c1C(Nc1cc(F)c(=O)n(C)c1)c1ccc(Cl)cc1]

The title compound was prepared in analogy to the procedure described in Step 1.4 using ethyl 4-((4-chlorophenyl)(hydroxy)methyl)-1,5-dimethyl-1H-pyrazole-3-carboxylate (Step 28.2) and 5-amino-3-fluoro-1-methylpyridin-2(1H)-one (Step 14.2). t$_R$: 4.17 min (HPLC 1); t$_R$: 0.93 min (LC-MS 2); ESI-MS: 433 [M+H]$^+$ (LC-MS 2); R$_f$=0.77 (CH$_2$Cl$_2$/MeOH 9:1).

Step 31.2: 4-((4-chlorophenyl)(5-fluoro-1-methyl-6-oxo-1,6-dihydropyridin-3-ylamino)methyl)-1,5-dimethyl-1H-pyrazole-3-carboxylic acid

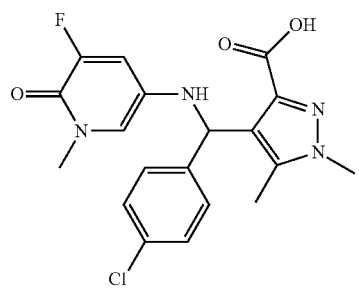 [SMILES: Cc1c(C(Nc2cc(F)c(=O)n(C)c2)c2ccc(Cl)cc2)c(C(=O)O)nn1C]

The title compound was prepared in analogy to the procedure described in Step 1.5 using ethyl 4-((4-chlorophenyl)(5-fluoro-1-methyl-6-oxo-1,6-dihydropyridin-3-ylamino)methyl)-1,5-dimethyl-1H-pyrazole-3-carboxylate (Step 31.1). t$_R$: 3.40 min (HPLC 1); t$_R$: 0.75 min (LC-MS 2); ESI-MS: 405 [M+H]$^+$ (LC-MS 2).

Example 32

4-(4-chlorophenyl)-2,3-dimethyl-5-(1-methyl-6-oxo-1,6-dihydropyridazin-3-yl)-4,5-dihydropyrrolo[3,4-c]pyrazol-6(2H)-one

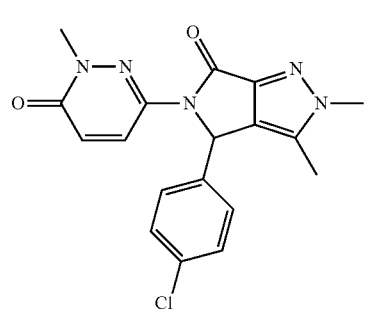

The title compound was prepared in analogy to the procedure described in Example 1 using 4-((4-chlorophenyl)(1-methyl-6-oxo-1,6-dihydropyridazin-3-ylamino)methyl)-1,5-dimethyl-1H-pyrazole-3-carboxylic acid Step 32.3). $t_R$: 3.94 min (HPLC 1); $t_R$: 0.87 min (LC-MS 2); ESI-MS: 370 [M+H]$^+$ (LC-MS 2); R$_f$=0.56 (CH$_2$Cl$_2$/MeOH 9:1); $^1$H NMR (400 MHz, DMSO-d$_6$) δ ppm 2.05 (s, 3H) 3.44 (s, 3H) 3.84 (s, 3H) 6.29 (s, 1H) 6.96 (d, J=9.8 Hz, 1H) 7.29-7.41 (m, 4H) 8.21 (d, J=9.8 Hz, 1H).

Step 32.1: 6-amino-2-methylpyridazin-3(2H)-one

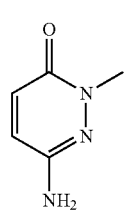

A mixture of 6-aminopyridazin-3-ol (2 g, 18.00 mmol), NaOH (0.720 g, 18.00 mmol) and MeI (1.126 mL, 18.00 mmol) was stirred for 2.5 hr at 85° C. under Ar. The reaction mixture was concentrated. The crude material was purified by silica gel column chromatography (NH$_3$ 1%/CH$_2$Cl$_2$/MeOH 4-7%) to afford the title product (538 mg, 4.30 mmol, 24% yield) as a yellow solid. $t_R$: 0.25 min (LC-MS 2); ESI-MS: 126 [M+H]$^+$ (LC-MS 2); R$_f$=0.36 (CH$_2$Cl$_2$/MeOH 9:1).

Step 32.2: ethyl 4-((4-chlorophenyl)(1-methyl-6-oxo-1,6-dihydropyridazin-3-ylamino)methyl)-1,5-dimethyl-1H-pyrazole-3-carboxylate

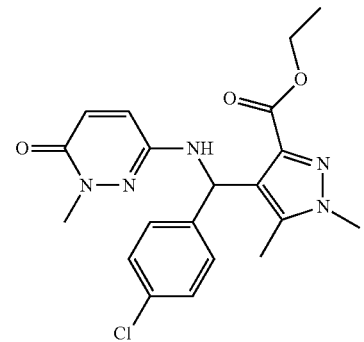 [SMILES: CCOC(=O)c1nn(C)c(C)c1C(Nc1ccc(=O)n(C)n1)c1ccc(Cl)cc1]

The title compound was prepared in analogy with the procedure described in Step 1.4 using ethyl 4-((4-chlorophenyl)(hydroxy)methyl)-1,5-dimethyl-1H-pyrazole-3-carboxylate (Step 28.2) and 6-amino-2-methylpyridazin-3(2H)-one (Step 32.1). $t_R$: 4.25 min (HPLC 1); $t_R$: 0.94 min (LC-MS 2); ESI-MS: 416 [M+H]$^+$ (LC-MS 2); R$_f$=0.43 (CH$_2$Cl$_2$/MeOH 9:1).

Step 32.3: 4-((4-chlorophenyl)(1-methyl-6-oxo-1,6-dihydropyridazin-3-ylamino)methyl)-1,5-dimethyl-1H-pyrazole-3-carboxylic acid

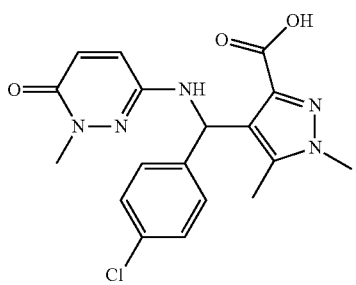 [SMILES: Cc1c(C(Nc2ccc(=O)n(C)n2)c2ccc(Cl)cc2)c(C(=O)O)nn1C]

The title compound was prepared in analogy with the procedure described in Step 1.5 using ethyl 4-((4-chlorophenyl)(1-methyl-6-oxo-1,6-dihydropyridazin-3-ylamino)methyl)-1,5-dimethyl-1H-pyrazole-3-carboxylate (Step 32.2). $t_R$: 3.51 min (HPLC 1); $t_R$: 0.78 min (LC-MS 2); ESI-MS: 388 [M+H]$^+$ (LC-MS 2).

Example 33

4-(4-chlorophenyl)-2,3-dimethyl-5-(3-methylbenzo[d]isoxazol-5-yl)-4,5-dihydropyrrolo[3,4-c]pyrazol-6(2H)-one

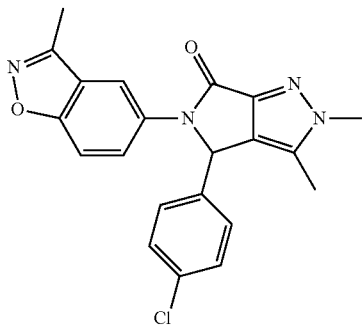 [SMILES: Cc1noc2ccc(N3C(=O)c4nn(C)c(C)c4C3c3ccc(Cl)cc3)cc12]

The title compound was prepared in analogy to the procedure described in Example 1 using 4-((4-chlorophenyl)(3-methylbenzo[d]isoxazol-5-ylamino)methyl)-1,5-dimethyl-1H-pyrazole-3-carboxylic acid (Step 33.5). $t_R$: 4.70 min (HPLC 1); $t_R$: 1.03 min (LC-MS 2); ESI-MS: 393 [M+H]$^+$ (LC-MS 2); $R_f$=0.50 (CH$_2$Cl$_2$/MeOH 9:1); $^1$H NMR (400 MHz, DMSO-d$_6$) δ ppm 2.08 (s, 3H) 2.44-2.57 (m, 3H) 3.85 (s, 3H) 6.52 (s, 1H) 7.29 (s, 4H) 7.63 (d, J=9.0 Hz, 1H) 7.73 (dd, J=9.0, 2.0 Hz, 1H) 8.01 (d, J=1.6 Hz, 1H).

Step 33.1: 2(1-iminoethyl)-4-nitrophenol

A mixture of 2-hydroxy-5-nitroacetophenone (2.96 g, 16.34 mmol) and ammonia in MeOH (11.67 mL, 82 mmol) was stirred for 1 hr at rt. The reaction mixture was concentrated to afford the crude title product (2.94 g, 16.32 mmol, 100% yield) as a yellow solid. $t_R$: 0.53 min (LC-MS 2); ESI-MS: 181 [M+H]$^+$ (LC-MS 2).

Step 33.2: 3-methyl-5-nitrobenzo[d]isoxazole

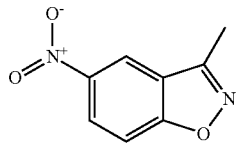

To a stirred suspension of 2-(1-iminoethyl)-4-nitrophenol (Step 33.1) (2.94 g, 16.32 mmol) in THF (40 mL) was added N-chlorosuccinimide (3.27 g, 24.48 mmol) and K$_2$CO$_3$ (4.51 g, 32.6 mmol) under Ar. The reaction mixture was stirred for 3 hr at rt, quenched with brine, and extracted with EtOAc. The combined organic layers were washed with a saturated aq. NaHCO$_3$ solution, dried over Na$_2$SO$_4$ and evaporated. The crude product was purified by silica gel column chromatography (hexane/EtOAc 5-15%) to afford the title product (2.8 g, 15.72 mmol, 96% yield) as a white solid. $t_R$: 4.31 min (HPLC 1); $t_R$: 0.86 min (LC-MS 2); ESI-MS: 179 [M+H]$^+$ (LC-MS 2); $R_f$=0.85 (hexane/EtOAc 1:1).

Step 33.3: 3-methylbenzo[d]isoxazol-5-amine

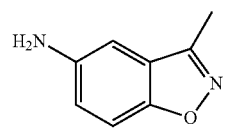

To a stirred solution of 3-methyl-5-nitrobenzo[d]isoxazole (Step 33.2) (1.8 g, 10.10 mmol) in AcOH (40 mL) was added a solution of tin(II) chloride dihydrate (6.84 g, 30.3 mmol) in HCl (15 mL, 494 mmol). The reaction mixture was stirred for 1 hr at 100° C., quenched with a saturated aq. NaHCO$_3$ solution, diluted with water, and extracted with CH$_2$Cl$_2$. The combined organic layers were washed once with a saturated aq. NH$_4$Cl solution, dried over Na$_2$SO$_4$ and evaporated. The crude material was purified by silica gel column chromatography (hexane/EtOAc 20-50) to afford the title product (458 mg, 3.09 mmol, 31% yield) as a pink solid. $t_R$: 0.50 min (LC-MS 2); ESI-MS: 149 [M+H]$^+$ (LC-MS 2); $R_f$=0.45 (hexane/EtOAc 1:1).

Step 33.4: ethyl 4-((4-chlorophenyl)(3-methylbenzo[d]isoxazol-5-ylamino)methyl)-1,5-dimethyl-1H-pyrazole-3-carboxylate

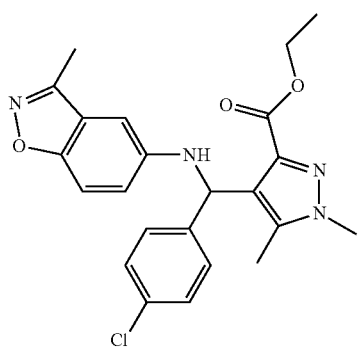 [SMILES: CCOC(=O)c1nn(C)c(C)c1C(Nc1ccc2onc(C)c2c1)c1ccc(Cl)cc1]

The title compound was prepared in analogy to the procedure described in Step 1.4 using ethyl 4-((4-chlorophenyl)(hydroxy)methyl)-1,5-dimethyl-1H-pyrazole-3-carboxylate (Step 28.2) and 3-methylbenzo[d]isoxazol-5-amine (Step 33.3). $t_R$: 5.40 min (HPLC 1); $t_R$: 1.20 min (LC-MS 2); ESI-MS: 439 [M+H]$^+$ (LC-MS 2); $R_f$=0.77 (CH$_2$Cl$_2$/MeOH 9:1).

Step 33.5: 4-((4-chlorophenyl)(3-methylbenzo[d]isoxazol-5-ylamino)methyl)-1,5-dimethyl-1H-pyrazole-3-carboxylic acid

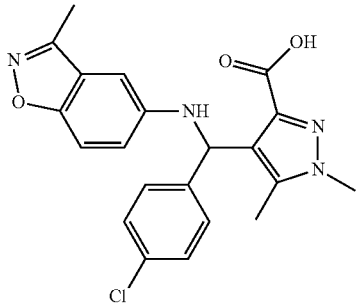 [SMILES: Cc1noc2ccc(NC(c3ccc(Cl)cc3)c3c(C(=O)O)nn(C)c3C)cc12]

The title compound was prepared in analogy to the procedure described in Step 1.5 using ethyl 4-((4-chlorophenyl)(3-methylbenzo[d]isoxazol-5-ylamino)methyl)-1,5-dimethyl-1H-pyrazole-3-carboxylate (Step 33.4). $t_R$: 4.40 min (HPLC 1); $t_R$: 0.99 min (LC-MS 2); ESI-MS: 411 [M+H]$^+$ (LC-MS 2).

Example 34

4-(4-chlorophenyl)-1-cyclopropyl-5-(1,5-dimethyl-6-oxo-1,6-dihydropyridin-3-yl)-4,5-dihydropyrrolo[3,4-c]pyrazol-6(1H)-one

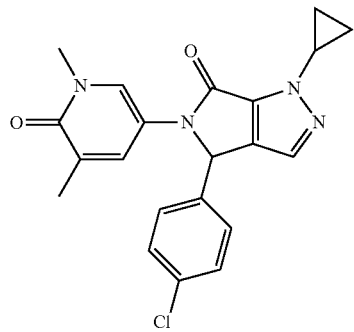 [SMILES: Cc1cc(N2C(=O)c3c(cnn3C3CC3)C2c2ccc(Cl)cc2)cn(C)c1=O]

The title compound was prepared in analogy to the procedure described in Example 1 using 4-((4-chlorophenyl)((1,5-dimethyl-6-oxo-1,6-dihydropyridin-3-yl)amino)methyl)-1-cyclopropyl-1H-pyrazole-5-carboxylic acid (Step 34.5). The crude product was purified by silica gel column chromatography (EtOAc). $t_R$: 4.08 min (HPLC 1); $t_R$: 0.93 min (LC-MS 2); ESI-MS: 395 [M+H]$^+$ (LC-MS 2); $R_f$=0.12 (EtOAc); $^1$H NMR (400 MHz, DMSO-$d_6$) δ ppm 1.03-1.08 (m, 2H) 1.19-1.26 (m, 2H) 1.91 (s, 3H) 3.34 (s, 3H) 3.85-3.93 (m, 1H) 6.07 (s, 1H) 7.20-7.26 (m, 2H) 7.32-7.38 (m, 3H) 7.40 (s, 1H) 7.70 (d, J=2.4 Hz, 1H).

Step 34.1: ethyl 1-cyclopropyl-1H-pyrazole-5-carboxylate

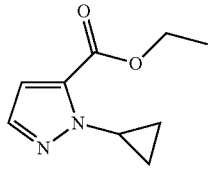

The title compound was prepared in analogy to the procedure described in Step 17.3 using cyclopropylhydrazine (Step 17.2) and ethyl 4-(Dimethylamino)-2-oxobut-3-enoate at 125° C. for 8 hr. The crude product was purified by silica gel column chromatography (hexane/EtOAc 2.5-45%). $t_R$: 4.40 min (HPLC 1); $t_R$: 0.91 min (LC-MS 2); ESI-MS: 181 [M+H]$^+$ (LC-MS 2); $R_f$=0.85 (hexane/EtOAc 1:1).

Step 34.2: ethyl 1-cyclopropyl-4-iodo-1H-pyrazole-5-carboxylate

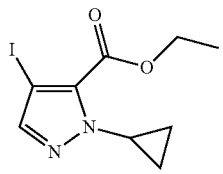

The title compound was prepared in analogy to the procedure described in Step 10.1 using ethyl 1-cyclopropyl-1H-pyrazole-5-carboxylate (Step 34.1). The crude product was purified by silica gel column chromatography (hexane/EtOAc 2-10%). $t_R$: 5.32 min (HPLC 1); $t_R$: 1.12 min (LC-MS 2); ESI-MS: 307 [M+H]$^+$ (LC-MS 2); $R_f$=0.37 (hexane/EtOAc 9:1).

Step 34.3: ethyl 4-((4-chlorophenyl)(hydroxy)methyl)-1-cyclopropyl-1H-pyrazole-5-carboxylate

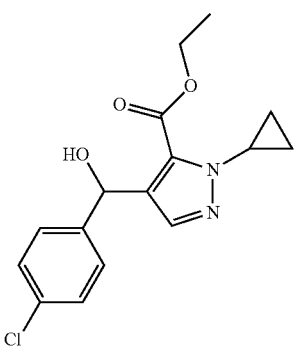 [SMILES: CCOC(=O)c1c(C(O)c2ccc(Cl)cc2)cnn1C1CC1]

The title compound was prepared in analogy to the procedure described in Step 1.3 using ethyl 1-cyclopropyl-4-iodo-1H-pyrazole-5-carboxylate (Step 34.2) at RT for 20 hr. $t_R$: 5.00 min (HPLC 1); $t_R$: 1.11 min (LC-MS 2); ESI-MS: 321 [M+H]$^+$ (LC-MS 2); $R_f$=0.71 (hexane/EtOAc 1:1).

Step 34.4: ethyl 4-((4-chlorophenyl)((1,5-dimethyl-6-oxo-1,6-dihydropyridin-3-yl)amino)methyl)-1-cyclopropyl-1H-pyrazole-5-carboxylate

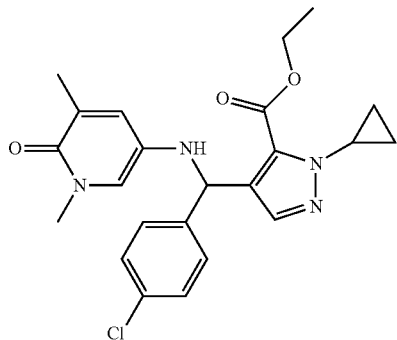

The title compound was prepared in analogy to the procedure described in Step 10.3 using ethyl 4-((4-chlorophenyl)(hydroxy)methyl)-1-cyclopropyl-1H-pyrazole-5-carboxylate (Step 34.3) and 5-amino-1,3-dimethylpyridin-2(1H)-one (Step 20.2). $t_R$: 4.78 min (HPLC 1); $t_R$: 1.10 min (LC-MS 2); ESI-MS: 441 [M+H]$^+$ (LC-MS 2); $R_f$=0.31 (EtOAc).

Step 34.5: 4((4-chlorophenyl)((1,5-dimethyl-6-oxo-1,6-dihydropyridin-3-yl)amino)methyl)-1-cyclopropyl-1H-pyrazole-5-carboxylic acid

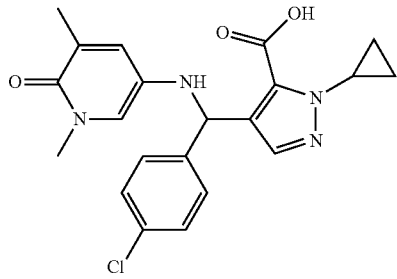 [SMILES: Cc1cc(NC(c2ccc(Cl)cc2)c2cnn(C3CC3)c2C(=O)O)cn(C)c1=O]

The title compound was prepared in analogy to the procedure described in Step 1.5 using ethyl 4-((4-chlorophenyl)((1,5-dimethyl-6-oxo-1,6-dihydropyridin-3-yl)amino)methyl)-1-cyclopropyl-1H-pyrazole-5-carboxylate (Step 34.4). $t_R$: 3.76 min (HPLC 1); $t_R$: 0.83 min (LC-MS 2); ESI-MS: 413 [M+H]$^+$, ESI-MS: 411.1 [M−H]$^-$ (LC-MS 2).

Example 35

5-(5-chloro-1-methyl-6-oxo-1,6-dihydropyridin-3-yl)-4-(4-chlorophenyl)-1-cyclopropyl-4,5-dihydropyrrolo[3,4-c]pyrazol-6(1H)-one

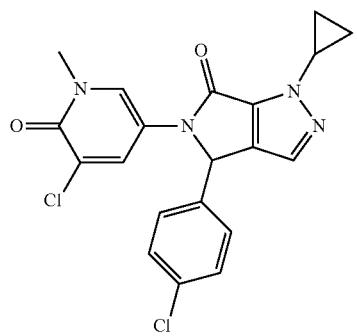 [SMILES: Cn1cc(N2C(=O)c3c(cnn3C3CC3)C2c2ccc(Cl)cc2)cc(Cl)c1=O]

The title compound was prepared in analogy to the procedure described in Example 1 using 4-(((5-chloro-1-methyl-6-oxo-1,6-dihydropyridin-3-yl)amino)(4-chlorophenyl)methyl)-1-cyclopropyl-1H-pyrazole-5-carboxylic acid (Step 35.2). $t_R$: 4.30 min (HPLC 1); $t_R$: 0.98 min (LC-MS 2); ESI-MS: 415/417 [M+H]$^+$ (LC-MS 2); $R_f$=0.33 (EtOAc); $^1$H NMR (400 MHz, DMSO-d$_6$) δ ppm 0.99-1.10 (m, 2H) 1.17-1.30 (m, 2H) 3.42 (s, 3H) 3.83-3.94 (m, 1H) 6.11 (s, 1H) 7.21-7.29 (m, 2H) 7.32-7.38 (m, 2H) 7.41 (s, 1H) 7.88 (d, J=2.4 Hz, 1H) 7.92 (d, J=2.4 Hz, 1H).

Step 35.1: Ethyl 4-(((5-chloro-1-methyl-6-oxo-1,6-dihydropyridin-3-yl)amino)(4-chlorophenyl)-methyl)-1-cyclopropyl-1H-pyrazole-5-carboxylate

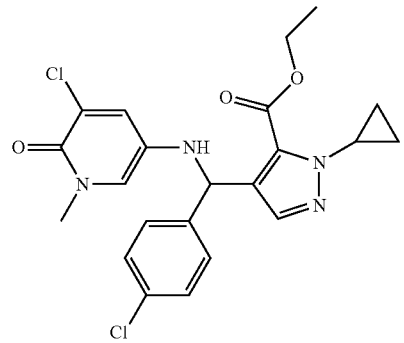 [SMILES: CCOC(=O)c1c(C(Nc2cc(Cl)c(=O)n(C)c2)c2ccc(Cl)cc2)cnn1C1CC1]

The title compound was prepared in analogy to the procedure described in Step 10.3 using ethyl 4-((4-chlorophenyl)(hydroxy)methyl)-1-cyclopropyl-1H-pyrazole-5-carboxylate (Step 34.3) and 5-amino-3-chloro-1-methylpyridin-2(1H)-one (Step 5.2). $t_R$: 5.04 min (HPLC 1); $t_R$: 1.13 min (LC-MS 2); ESI-MS: 461 [M+H]$^+$ (LC-MS 2); $R_f$=0.47 (EtOAc).

Step 35.2: 4-(((5-chloro-1-methyl-6-oxo-1,6-dihydropyridin-3-yl)amino)(4-chlorophenyl)methyl)-1-cyclopropyl-1H-pyrazole-5-carboxylic acid

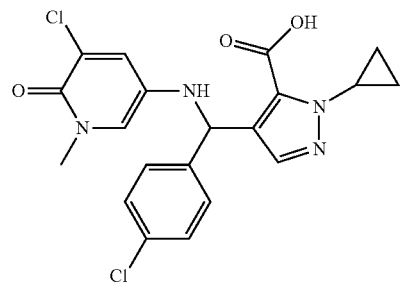 [SMILES: Cn1cc(NC(c2ccc(Cl)cc2)c2cnn(C3CC3)c2C(=O)O)cc(Cl)c1=O]

The title compound was prepared in analogy to the procedure described in Step 1.5 using ethyl 4-(((5-chloro-1-methyl-6-oxo-1,6-dihydropyridin-3-yl)amino)(4-chlorophenyl)methyl)-1-cyclopropyl-1H-pyrazole-5-carboxylate (Step 35.1). $t_R$: 4.04 min (HPLC 1); $t_R$: 0.87 min (LC-MS 2); ESI-MS: 433 [M+H]$^+$, ESI-MS: 431 [M−H]$^-$ (LC-MS 2).

Example 36

4-(4-chlorophenyl)-5-(1,5-dimethyl-6-oxo-1,6-dihydropyridin-3-yl)-1-isopropyl-4,5-dihydropyrrolo[3,4-c]pyrazol-6(1H)-one

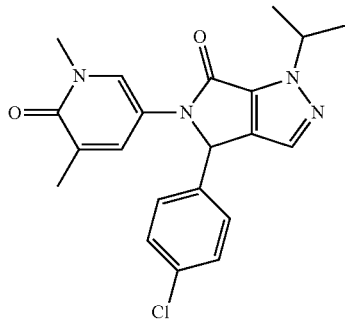 [SMILES: Cc1cc(N2C(=O)c3c(cnn3C(C)C)C2c2ccc(Cl)cc2)cn(C)c1=O]

The title compound was prepared in analogy to the procedure described in Example 1 using 4-((4-chlorophenyl)((1,5-dimethyl-6-oxo-1,6-dihydropyridin-3-yl)amino)methyl)-1-isopropyl-1H-pyrazole-5-carboxylic acid (Step 36.5). $t_R$: 4.31 min (HPLC 1); $t_R$: 0.97 min (LC-MS 2); ESI-MS: 397 [M+H]$^+$ (LC-MS 2); $R_f$=0.22 (EtOAc); $^1$H NMR (400 MHz, DMSO-d$_6$) δ ppm 1.47-1.56 (m, 6H) 1.91 (s, 3H) 3.34 (s, 3H) 4.73-4.87 (m, 1H) 6.09 (s, 1H) 7.18-7.25 (m, 2H) 7.32-7.38 (m, 3H) 7.40 (s, 1H) 7.71 (d, J=2.7 Hz, 1H).

Step 36.1: ethyl 1-isopropyl-1H-pyrazole-5-carboxylate

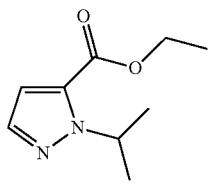

The title compound was prepared in analogy to the procedure described in Step 17.3 using isopropylhydrazine hydrochloride and ethyl 4-(dimethylamino)-2-oxobut-3-enoate at 120° C. for hr. The crude product was purified by silica gel column chromatography (hexane/EtOAc 2.5-40%). $t_R$: 4.74 min (HPLC 1); $t_R$: 1.00 min (LC-MS 2); ESI-MS: 183 [M+H]$^+$ (LC-MS 2); $R_f$=0.95 (hexane/EtOAc 1:1).

Step 36.2: ethyl 4-iodo-1-isopropyl-1H-pyrazole-5-carboxylate

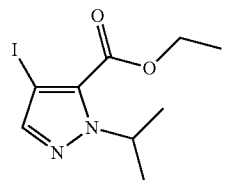

The title compound was prepared in analogy to the procedure described in Step 10.1 using ethyl 1-isopropyl-1H-pyrazole-5-carboxylate (Step 36.1). The crude product was purified by silica gel column chromatography (hexane/EtOAc 2-10%). $t_R$: 5.64 min (HPLC 1); $t_R$: 1.20 min (LC-MS 2); ESI-MS: 309 [M+H]$^+$ (LC-MS 2); $R_f$=0.41 (hexane/EtOAc 9:1).

Step 36.3: ethyl 4-((4-chlorophenyl)(hydroxy)methyl)-1-isopropyl-1H-pyrazole-5-carboxylate

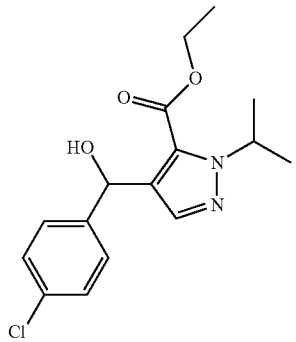 [SMILES: CCOC(=O)c1c(C(O)c2ccc(Cl)cc2)cnn1C(C)C]

The title compound was prepared in analogy to the procedure described in Step 1.3 using ethyl 4-iodo-1-isopropyl-1H-pyrazole-5-carboxylate (Step 36.2) at RT for 20 hr. $t_R$: 5.20 min (HPLC 1); $t_R$: 1.16 min (LC-MS 2); ESI-MS: 323 [M+H]$^+$ (LC-MS 2); $R_f$=0.74 (hexane/EtOAc 1:1).

Step 36.4: ethyl 4-((4-chlorophenyl)((1,5-dimethyl-6-oxo-1,6-dihydropyridin-3-yl)amino)methyl)-1-isopropyl-1H-pyrazole-5-carboxylate

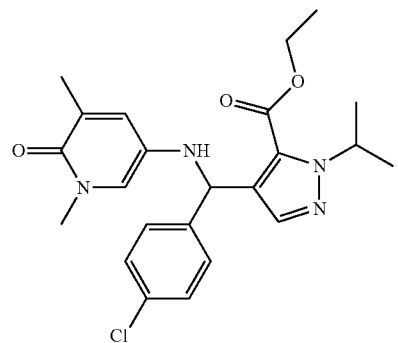 [SMILES: CCOC(=O)c1c(C(Nc2cc(C)c(=O)n(C)c2)c2ccc(Cl)cc2)cnn1C(C)C]

The title compound was prepared in analogy to the procedure described in Step 10.3 using ethyl 4-((4-chlorophenyl)(hydroxy)methyl)-1-isopropyl-1H-pyrazole-5-carboxylate (Step 36.3) and 5-amino-1,3-dimethylpyridin-2(1H)-one (Step 20.2). $t_R$: 4.94 min (HPLC 1); $t_R$: 1.14 min (LC-MS 2); ESI-MS: 443 [M+H]$^+$ (LC-MS 2); $R_f$=0.23 (EtOAc).

Step 36.5: 4((4-chlorophenyl)((1,5-dimethyl-6-oxo-1,6-dihydropyridin-3-yl)amino)methyl)-1-isopropyl-1H-pyrazole-5-carboxylic acid

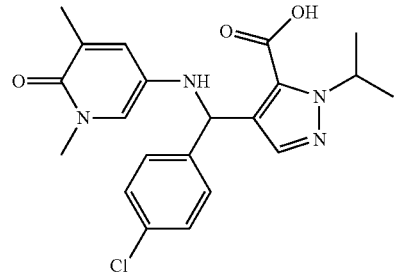 [SMILES: Cc1cc(NC(c2ccc(Cl)cc2)c2cnn(C(C)C)c2C(=O)O)cn(C)c1=O]

The title compound was prepared in analogy to the procedure described in Step 1.5 using ethyl 4-((4-chlorophenyl)((1, 5-dimethyl-6-oxo-1,6-dihydropyridin-3-yl)amino)methyl)-1-isopropyl-1H-pyrazole-5-carboxylate (Step 36.4). $t_R$: 3.86 min (HPLC 1); $t_R$: 0.87 min (LC-MS 2); ESI-MS: 415 [M+H]$^+$, ESI-MS: 413.1 [M–H]$^-$ (LC-MS 2).

Example 37

5-(5-chloro-1-methyl-6-oxo-1,6-dihydropyridin-3-yl)-4-(4-chlorophenyl)-2-cyclopropyl-4,5-dihydropyrrolo[3,4-c]pyrazol-6(2H)-one

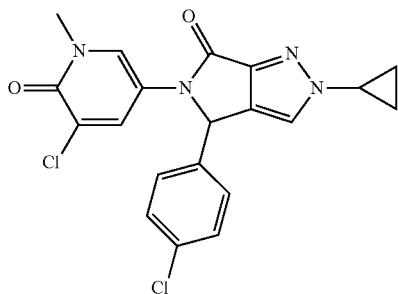 [SMILES: Cn1cc(N2C(=O)c3nn(C4CC4)cc3C2c2ccc(Cl)cc2)cc(Cl)c1=O]

The title compound was prepared in analogy to the procedure described in Example 1 using 4-(((5-chloro-1-methyl-6-oxo-1,6-dihydropyridin-3-yl)amino)(4-chlorophenyl)methyl)-1-cyclopropyl-1H-pyrazole-3-carboxylic acid (Step 37.5). $t_R$: 4.08 min (HPLC 1); $t_R$: 0.92 min (LC-MS 2); ESI-MS: 415 [M+H]$^+$ (LC-MS 2); $R_f$=0.22 (EtOAc); $^1$H NMR (400 MHz, DMSO-d$_6$) δ ppm 0.97-1.05 (m, 2H) 1.09-1.15 (m, 2H) 3.43 (s, 3H) 3.84-3.94 (m, 1H) 6.17 (s, 1H) 7.20-7.26 (m, 2H) 7.33-7.38 (m, 2H) 7.87-7.95 (m, 3H).

Step 37.1: ethyl 1-cyclopropyl-1H-pyrazole-3-carboxylate

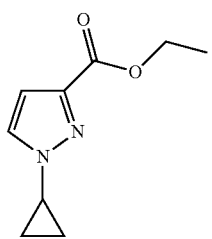

The title compound was prepared in analogy to the procedure described in Step 17.3 using cyclopropylhydrazine (Step 17.2) and ethyl 4-(dimethylamino)-2-oxobut-3-enoate at 125° C. for 8 hr. The crude product was purified by silica gel column chromatography (hexane/EtOAc 2.5-45%). $t_R$: 3.45 min (HPLC 1); $t_R$: 0.74 min (LC-MS 2); ESI-MS: 181 [M+H]$^+$ (LC-MS 2); $R_f$=0.59 (hexane/EtOAc 1:1).

Step 37.2: ethyl 1-cyclopropyl-4-iodo-1H-pyrazole-3-carboxylate

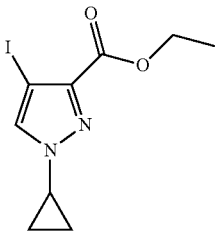

The title compound was prepared in analogy to the procedure described in Step 10.1 using ethyl 1-cyclopropyl-1H-pyrazole-3-carboxylate (Step 37.1). The crude product was purified by silica gel column chromatography (hexane/EtOAc 5-20%). $t_R$: 4.43 min (HPLC 1); $t_R$: 0.95 min (LC-MS 2); ESI-MS: 307 [M+H]$^+$ (LC-MS 2); $R_f$=0.70 (hexane/EtOAc 1:1).

Step 37.3: ethyl 4-((4-chlorophenyl)(hydroxy)methyl)-1-cyclopropyl-1H-pyrazole-3-carboxylate

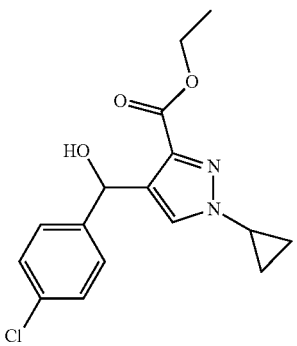 [SMILES: CCOC(=O)c1nn(C2CC2)cc1C(O)c1ccc(Cl)cc1]

The title compound was prepared in analogy to the procedure described in Step 1.3 using ethyl 1-cyclopropyl-4-iodo-1H-pyrazole-3-carboxylate (Step 37.2) at RT for 1 hr. $t_R$: 4.58 min (HPLC 1); $t_R$: 1.02 min (LC-MS 2); ESI-MS: 303 [M-18]$^+$ (LC-MS 2); $R_f$=0.47 (hexane/EtOAc 1:1).

Step 37.4: ethyl 4-(((5-chloro-1-methyl-6-oxo-1,6-dihydropyridin-3-yl)amino)(4-chlorophenyl)methyl)-1-cyclopropyl-1H-pyrazole-3-carboxylate

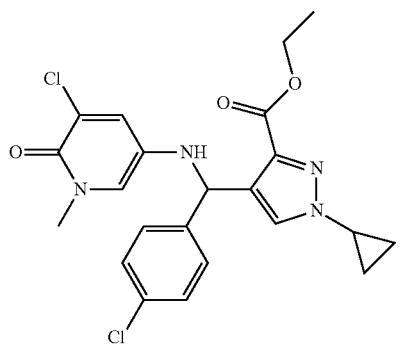 [SMILES: CCOC(=O)c1nn(C2CC2)cc1C(Nc1cc(Cl)c(=O)n(C)c1)c1ccc(Cl)cc1]

The title compound was prepared in analogy to the procedure described in Step 10.3 using ethyl 4-((4-chlorophenyl)(hydroxy)methyl)-1-cyclopropyl-1H-pyrazole-3-carboxylate (Step 37.3) and 5-amino-3-chloro-1-methylpyridin-2(1H)-one (Step 5.2). $t_R$: 4.54 min (HPLC 1); $t_R$: 1.03 min (LC-MS 2); ESI-MS: 461 [M+H]$^+$ (LC-MS 2); $R_f$=0.18 (EtOAc).

Step 37.5: 4-(((5-chloro-1-methyl-6-oxo-1,6-dihydropyridin-3-yl)amino)(4-chlorophenyl)methyl)-1-cyclopropyl-1H-pyrazole-3-carboxylic acid

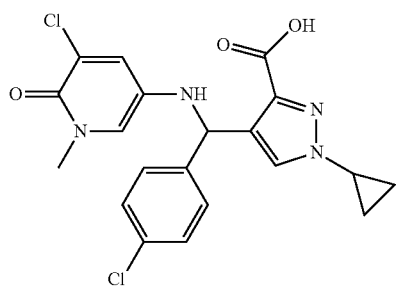 [SMILES: Cn1cc(NC(c2ccc(Cl)cc2)c2cn(C3CC3)nc2C(=O)O)cc(Cl)c1=O]

The title compound was prepared in analogy to the procedure described in Step 1.5 using ethyl 4-(((5-chloro-1-methyl-6-oxo-1,6-dihydropyridin-3-yl)amino)(4-chlorophenyl)methyl)-1-cyclopropyl-1H-pyrazole-3-carboxylate (Step 37.4). $t_R$: 3.73 min (HPLC 1); $t_R$: 0.85 min (LC-MS 2); ESI-MS: 433/435 [M+H]$^+$, ESI-MS: 431/433 [M−H]$^-$ (LC-MS 2).

Example 38

5-(5-chloro-1-methyl-6-oxo-1,6-dihydropyridin-3-yl)-4-(4-chlorophenyl)-1-isopropyl-4,5-dihydropyrrolo[3,4-c]pyrazol-6(1H)-one

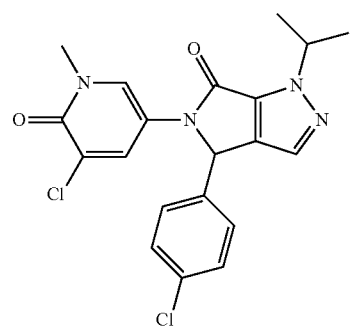 [SMILES: CC(C)n1ncc2c1C(=O)N(c1cc(Cl)c(=O)n(C)c1)C2c1ccc(Cl)cc1]

The title compound was prepared in analogy to the procedure described in Example 1 using 4-(((5-chloro-1-methyl-6-oxo-1,6-dihydropyridin-3-yl)amino)(4-chlorophenyl)methyl)-1-isopropyl-1H-pyrazole-5-carboxylic acid (Step 38.2). $t_R$: 4.55 min (HPLC 1); $t_R$: 1.02 min (LC-MS 2); ESI-MS: 417 [M+H]$^+$ (LC-MS 2); $R_f$=0.41 (EtOAc); $^1$H NMR (400 MHz, DMSO-d$_6$) δ ppm 1.47-1.55 (m, 6H) 3.43 (s, 3H) 4.75-4.86 (m, 1H) 6.13 (s, 1H) 7.21-7.28 (m, 2H) 7.34-7.40 (m, 2H) 7.42 (s, 1H) 7.89 (d, J=2.7 Hz, 1H) 7.94 (d, J=2.7 Hz, 1H).

Step 38.1: ethyl 4-(((5-chloro-1-methyl-6-oxo-1,6-dihydropyridin-3-yl)amino)(4-chlorophenyl)methyl)-1-isopropyl-1H-pyrazole-5-carboxylate

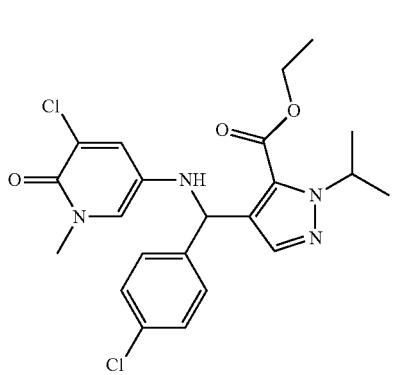 [SMILES: CCOC(=O)c1c(C(Nc2cc(Cl)c(=O)n(C)c2)c2ccc(Cl)cc2)cnn1C(C)C]

The title compound was prepared in analogy to the procedure described in Step 10.3 using ethyl 4-((4-chlorophenyl)(hydroxy)methyl)-1-isopropyl-1H-pyrazole-5-carboxylate (Step 36.3) and 5-amino-3-chloro-1-methylpyridin-2(1H)-one (Step 5.2). $t_R$: 5.17 min (HPLC 1); $t_R$: 1.17 min (LC-MS 2); ESI-MS: 463 [M+H]$^+$ (LC-MS 2); $R_f$=0.53 (EtOAc).

Step 38.2: 4-(((5-chloro-1-methyl-6-oxo-1,6-dihydropyridin-3-yl)amino)(4-chlorophenyl)methyl)-1-isopropyl-1H-pyrazole-5-carboxylic acid

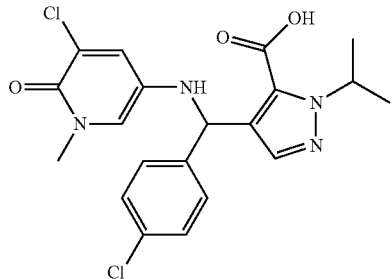 [SMILES: CC(C)n1ncc(C(Nc2cc(Cl)c(=O)n(C)c2)c2ccc(Cl)cc2)c1C(=O)O]

The title compound was prepared in analogy to the procedure described in Step 1.5 using ethyl 4-(((5-chloro-1-methyl-6-oxo-1,6-dihydropyridin-3-yl)amino)(4-chlorophenyl)methyl)-1-isopropyl-1H-pyrazole-5-carboxylate (Step 38.1). $t_R$: 4.17 min (HPLC 1); $t_R$: 0.90 min (LC-MS 2); ESI-MS: 435 [M+H]$^+$, ESI-MS: 433 [M−H]$^-$ (LC-MS 2).

Example 39

4-(4-chlorophenyl)-2-cyclopropyl-5-(1,5-dimethyl-6-oxo-1,6-dihydropyridin-3-yl)-4,5-dihydropyrrolo[3,4-c]pyrazol-6(2H)-one

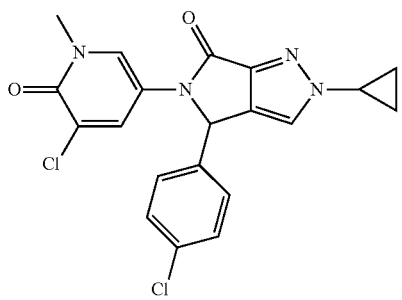 [SMILES: Cn1cc(N2C(=O)c3nn(C4CC4)cc3C2c2ccc(Cl)cc2)cc(Cl)c1=O]

The title compound was prepared in analogy to the procedure described in Example 1 using 4-((4-chlorophenyl)((1,5-dimethyl-6-oxo-1,6-dihydropyridin-3-yl)amino)methyl)-1-cyclopropyl-1H-pyrazole-3-carboxylic acid (Step 39.2). $t_R$: 3.88 min (HPLC 1); $t_R$: 0.88 min (LC-MS 2); ESI-MS: 395 [M+H]$^+$ (LC-MS 2); $R_f$=0.33 (CH$_2$Cl$_2$/MeOH 9:1); $^1$H NMR (400 MHz, DMSO-d$_6$) δ ppm 0.96-1.04 (m, 2H) 1.08-1.14 (m, 2H) 1.90 (s, 3H) 3.34 (s, 3H) 3.83-3.91 (m, 1H) 6.11 (s, 1H) 7.18-7.23 (m, 2H) 7.30-7.38 (m, 3H) 7.68-7.71 (m, 1H) 7.88 (s, 1H).

Step 39.1: ethyl 4-((4-chlorophenyl)((1,5-dimethyl-6-oxo-1,6-dihydropyridin-3-yl)amino)methyl)-1-cyclopropyl-1H-pyrazole-3-carboxylate

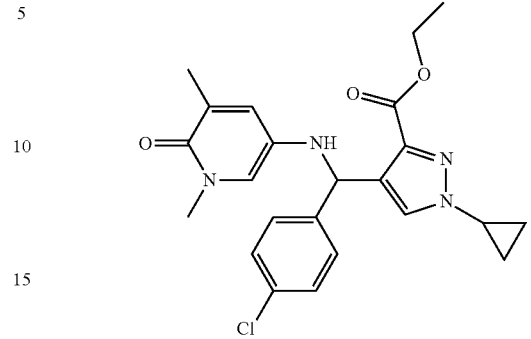

The title compound was prepared in analogy to the procedure described in Step 10.3 using ethyl 4-((4-chlorophenyl)(hydroxy)methyl)-1-cyclopropyl-1H-pyrazole-3-carboxylate (Step 37.3) and 5-amino-1,3-dimethylpyridin-2(1H)-one (Step 20.2). $t_R$: 4.31 min (HPLC 1); $t_R$: 1.00 min (LC-MS 2); ESI-MS: 441 [M+H]$^+$ (LC-MS 2); $R_f$=0.06 (EtOAc).

Step 39.2: 4-((4-chlorophenyl)((1,5-dimethyl-6-oxo-1,6-dihydropyridin-3-yl)amino)methyl)-1-cyclopropyl-1H-pyrazole-3-carboxylic acid

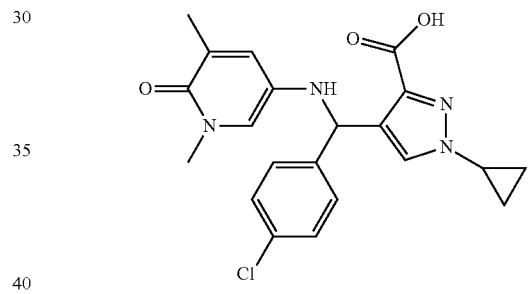

The title compound was prepared in analogy to the procedure described in Step 1.5 using ethyl 4-((4-chlorophenyl)((1,5-dimethyl-6-oxo-1,6-dihydropyridin-3-yl)amino)methyl)-1-cyclopropyl-1H-pyrazole-3-carboxylate (Step 39.1). $t_R$: 3.47 min (HPLC 1); $t_R$: 0.81 min (LC-MS 2); ESI-MS: 413 [M+H]$^+$, ESI-MS: 411 [M−H]$^-$ (LC-MS 2).

Example 40

5-(5-chloro-1-methyl-6-oxo-1,6-dihydropyridin-3-yl)-4-(4-chlorophenyl)-2-cyclopropyl-3-(trifluoromethyl)-4,5-dihydropyrrolo[3,4-c]pyrazol-6(2H)-one

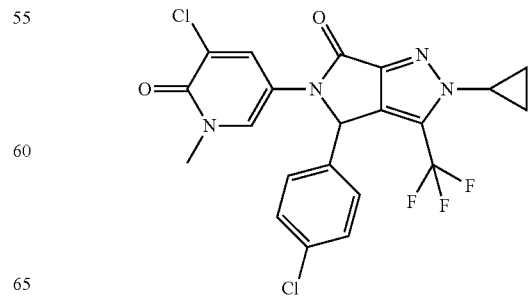

The title compound was prepared in analogy to the procedure described in Example 1 using 4-(((5-chloro-1-methyl-6-oxo-1,6-dihydropyridin-3-yl)amino)(4-chlorophenyl)methyl)-1-cyclopropyl-5-(trifluoromethyl)-1H-pyrazole-3-carboxylic acid (Step 40.4) at RT for 30 min. $t_R$: 1.12 min (LC-MS 2); ESI-MS: 483 [M+H]$^+$ (LC-MS 2); $R_f$=0.69 (CH$_2$Cl$_2$/5% MeOH/1% ammonia); $^1$H NMR (400 MHz, DMSO-d$_6$) δ ppm 1.11-1.22 (m, 2H) 1.22-1.38 (m, 2H) 3.41 (s, 3H) 3.86-4.00 (m, 1H) 6.36 (s, 1H) 7.26 (m, J=8.6 Hz, 2H) 7.36 (m, J=8.6 Hz, 2H) 7.90 (d, J=2.7 Hz, 1H) 7.87 (d, J=2.7 Hz, 1H).

Step 40.1: ethyl 1-cyclopropyl-5-(trifluoromethyl)-1H-pyrazole-3-carboxylate

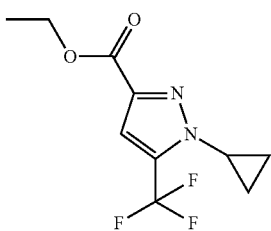 [SMILES: CCOC(=O)c1cc(C(F)(F)F)n(C2CC2)n1]

The title compound was prepared in analogy to the procedure described in Step 17.3 using cyclopropylhydrazine (Step 17.2) and ethyl 5,5,5-trifluoro-2,4-dioxopentanoate at 100° C. for 2 hr. The crude product was purified by silica gel column chromatography (Hexane/EtOAc 9:1). $t_R$: 1.10 min (LC-MS 2); ESI-MS: 249 [M+H]$^+$ (LC-MS 2); $R_f$=0.17 (hexane/EtOAc 9:1).

Step 40.2: ethyl 4-((4-chlorophenyl)(hydroxy)methyl)-1-cyclopropyl-5-(trifluoromethyl)-1H-Pyrazole-3-carboxylate

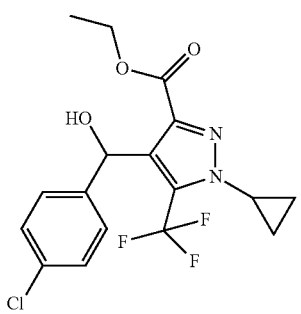 [SMILES: CCOC(=O)c1nn(C2CC2)c(C(F)(F)F)c1C(O)c1ccc(Cl)cc1]

LDA (3.70 mL, 6.66 mmol) was added dropwise to a stirred solution of ethyl 1-cyclopropyl-5-(trifluoromethyl)-1H-pyrazole-3-carboxylate (Step 40.1) (1.18 g, 4.75 mmol) in THF (30 mL). After 15 minutes at −78° C., a solution of 4-chlorobenzaldehyde (668 mg, 4.75 mmol) in THF (5 mL) was slowly added. The reaction was stirred at −78° C. for 15 min, quenched with 1 mL of saturated NH$_4$Cl solution, partitioned between EtOAc and water and both phases separated. The aq. phase was extracted with EtOAc and the combined organic phases were washed with brine, dried over Na$_2$SO$_4$ and concentrated. The crude was purified by silica gel column chromatography (hexane/20% EtOAc) to afford the title product (1.5 g, 3.40 mmol, 71% yield) as a yellow solid. $t_R$: 1.27 min (LC-MS 2); ESI-MS: 389 [M+H]$^+$ (LC-MS 2); $R_f$=0.22 (hexane/EtOAc 8:2).

Step 40.3: ethyl 4-(((5-chloro-1-methyl-6-oxo-1,6-dihydropyridin-3-yl)amino)(4-chlorophenyl)-methyl)-1-cyclopropyl-5-(trifluoromethyl)-1H-pyrazole-3-carboxylate

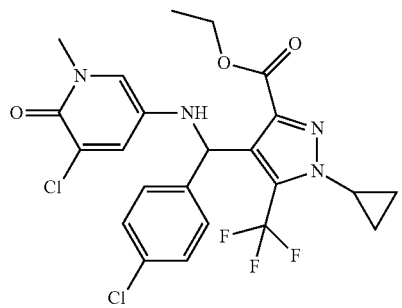 [SMILES: CCOC(=O)c1nn(C2CC2)c(C(F)(F)F)c1C(Nc1cc(Cl)c(=O)n(C)c1)c1ccc(Cl)cc1]

The title compound was prepared in analogy to the procedure described in Step 10.3 using ethyl 4-((4-chlorophenyl)(hydroxy)methyl)-1-cyclopropyl-5-(trifluoromethyl)-1H-pyrazole-3-carboxylate (Step 40.2) and 5-amino-3-chloro-1-methylpyridin-2(1H)-one (Step 5.2) at RT for 3 days. $t_R$: 1.24 min (LC-MS 2); ESI-MS: 529 [M+H]$^+$ (LC-MS 2); $R_f$=0.52 (5% MeOH/CH$_2$Cl$_2$).

Step 40.4: 4-(((5-chloro-1-methyl-6-oxo-1,6-dihydropyridin-3-yl)amino)(4-chlorophenyl)methyl)-1-cyclopropyl-5-(trifluoromethyl)-1H-pyrazole-3-carboxylic acid

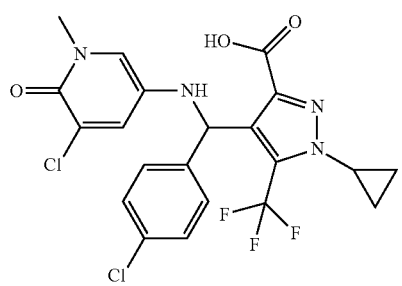

To a solution of ethyl 4-(((5-chloro-1-methyl-6-oxo-1,6-dihydropyridin-3-yl)amino)(4-chlorophenyl)methyl)-1-cyclopropyl-5-(trifluoromethyl)-1H-pyrazole-3-carboxylate (Step 40.3) (350 mg, 0.569 mmol) in THF (3 mL) and MeOH (3 mL) was added 2M NaOH (2.84 mL, 5.69 mmol). The resulting mixture was stirred at RT for 1 hr. Volatiles were evaporated and the resulting aq. phase was adjusted to pH 5 with 2N HCl, extracted twice with EtOAc and the combined organic phases were washed with brine, dried over Na$_2$SO$_4$ and concentrated under reduced pressure. The crude was triturated in EtOAc to afford the title product (222 mg, 0.443 mmol, 78% yield) as an off-white solid. $t_R$: 1.00 min (LC-MS 2); ESI-MS: 501/503 [M+H]$^+$, ESI-MS: 499/501 [M−H]$^−$ (LC-MS 2).

Example 41

4-(4-chlorophenyl)-5-(1,5-dimethyl-6-oxo-1,6-dihydropyridin-3-yl)-2-isopropyl-4,5-dihydropyrrolo[3,4-c]pyrazol-6(2H)-one

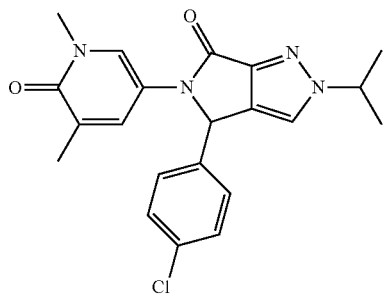 [SMILES: Cc1cc(N2C(=O)c3nn(C(C)C)cc3C2c2ccc(Cl)cc2)cn(C)c1=O]

The title compound was prepared in analogy to the procedure described in Example 1 using 4-((4-chlorophenyl)((1,5-dimethyl-6-oxo-1,6-dihydropyridin-3-yl)amino)methyl)-1-isopropyl-1H-pyrazole-3-carboxylic acid (Step 41.5). $t_R$: 4.05 min (HPLC 1); $t_R$: 0.90 min (LC-MS 2); ESI-MS: 397 [M+H]$^+$ (LC-MS 2); $R_f$=0.60 (CH$_2$Cl$_2$/MeOH 9:1); $^1$H NMR (400 MHz, DMSO-d$_6$) δ ppm 1.38-1.47 (m, 6H) 1.90 (s, 3H) 3.34 (s, 3H) 4.54-4.65 (m, 1H) 6.12 (s, 1H) 7.17-7.24 (m, 2H) 7.30-7.39 (m, 3H) 7.69 (d, J=2.7 Hz, 1H) 7.85 (s, 1H).

Step 41.1: ethyl 1-isopropyl-1H-pyrazole-3-carboxylate

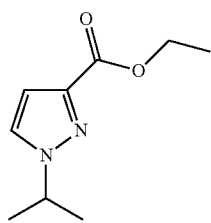

The title compound was prepared in analogy to the procedure described in Step 17.3 using isopropylhydrazine hydrochloride and ethyl 4-(Dimethylamino)-2-oxobut-3-enoate at 120° C. for hr. The crude product was purified by silica gel column chromatography (hexane/EtOAc 2.5-40%). $t_R$: 3.73 min (HPLC 1); $t_R$: 0.80 min (LC-MS 2); ESI-MS: 183 [M+H]$^+$ (LC-MS 2); $R_f$=0.69 (hexane/EtOAc 1:1).

Step 41.2: ethyl 4-iodo-1-isopropyl-1H-pyrazole-3-carboxylate

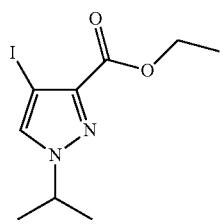

The title compound was prepared in analogy to the procedure described in Step 10.1 using ethyl 1-isopropyl-1H-pyrazole-3-carboxylate (Step 41.1). The crude product was purified by silica gel column chromatography (hexane/EtOAc 5-25%). $t_R$: 4.62 min (HPLC 1); $t_R$: 0.98 min (LC-MS 2); ESI-MS: 309 [M+H]$^+$ (LC-MS 2); $R_f$=0.75 (hexane/EtOAc 1:1).

Step 41.3: ethyl 4-((4-chlorophenyl)(hydroxy)methyl)-1-isopropyl-1H-pyrazole-3-carboxylate

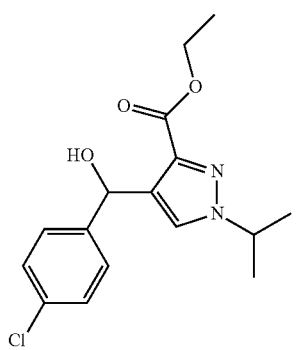 [SMILES: CCOC(=O)c1nn(C(C)C)cc1C(O)c1ccc(Cl)cc1]

The title compound was prepared in analogy to the procedure described in Step 1.3 using ethyl 4-iodo-1-isopropyl-1H-pyrazole-3-carboxylate (Step 41.2) at RT for 1 hr. $t_R$: 4.71 min (HPLC 1); $t_R$: 1.05 min (LC-MS 2); ESI-MS: 305 [M-18]$^+$ (LC-MS 2); $R_f$=0.42 (hexane/EtOAc 1:1).

Step 41.4: ethyl 4-((4-chlorophenyl)((1,5-dimethyl-6-oxo-1,6-dihydropyridin-3-yl)amino)methyl)-1-isopropyl-1H-pyrazole-3-carboxylate

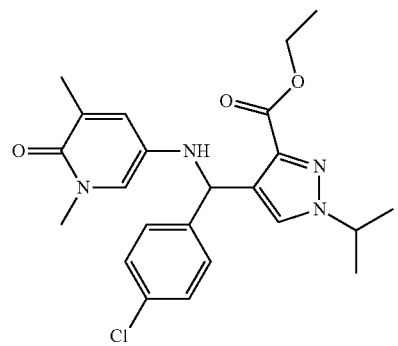 [SMILES: CCOC(=O)c1nn(C(C)C)cc1C(Nc1cc(C)c(=O)n(C)c1)c1ccc(Cl)cc1]

The title compound was prepared in analogy to the procedure described in Step 10.3 using ethyl 4-((4-chlorophenyl)(hydroxy)methyl)-1-isopropyl-1H-pyrazole-3-carboxylate (Step 41.3) and 5-amino-1,3-dimethylpyridin-2(1H)-one (Step 20.2). $t_R$: 4.40 min (HPLC 1); $t_R$: 1.02 min (LC-MS 2); ESI-MS: 443 [M+H]$^+$ (LC-MS 2); $R_f$=0.06 (EtOAc).

Step 41.5: 4-((4-chlorophenyl)((1,5-dimethyl-6-oxo-1,6-dihydropyridin-3-yl)amino)methyl)-1-iso-propyl-1H-pyrazole-3-carboxylic acid

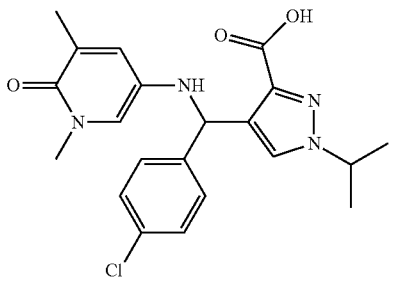 [SMILES: Cc1cc(NC(c2ccc(Cl)cc2)c2cn(C(C)C)nc2C(=O)O)cn(C)c1=O]

The title compound was prepared in analogy to the procedure described in Step 1.5 using ethyl 4-((4-chlorophenyl)((1,5-dimethyl-6-oxo-1,6-dihydropyridin-3-yl)amino)methyl)-1-isopropyl-1H-pyrazole-3-carboxylate (Step 41.4). $t_R$: 3.56 min (HPLC 1); $t_R$: 0.84 min (LC-MS 2); ESI-MS: 415 [M+H]$^+$, ESI-MS: 413 [M−H]$^−$ (LC-MS 2).

Example 42

5-(5-chloro-1-methyl-6-oxo-1,6-dihydropyridin-3-yl)-4-(4-chlorophenyl)-2-isopropyl-4,5-dihydropyrrolo[3,4-c]pyrazol-6(2H)-one

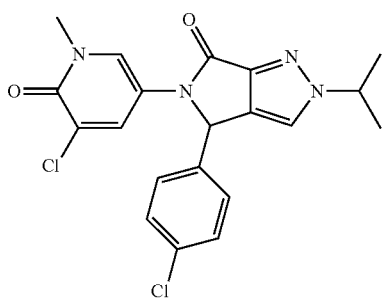 [SMILES: CC(C)n1cc2c(n1)C(=O)N(c1cc(Cl)c(=O)n(C)c1)C2c1ccc(Cl)cc1]

The title compound was prepared in analogy to the procedure described in Example 1 using 4-(((5-chloro-1-methyl-6-oxo-1,6-dihydropyridin-3-yl)amino)(4-chlorophenyl)methyl)-1-isopropyl-1H-pyrazole-3-carboxylic acid (Step 42.2). $t_R$: 4.25 min (HPLC 1); $t_R$: 0.95 min (LC-MS 2); ESI-MS: 417 [m+H]+(LC-MS 2); $R_f$=0.51 (CH$_2$Cl$_2$/MeOH 9:1); $^1$H NMR (400 MHz, DMSO-d$_6$) δ ppm 1.39-1.46 (m, 6H) 3.43 (s, 3H) 4.54-4.67 (m, 1H) 6.16 (s, 1H) 7.20-7.27 (m, 2H) 7.32-7.38 (m, 2H) 7.87 (s, 1H) 7.88-7.90 (m, 1H) 7.91-7.93 (m, 1H).

Step 42.1: Ethyl 4-(((5-chloro-1-methyl-6-oxo-1,6-dihydropyridin-3-yl)amino)(4-chlorophenyl)-methyl)-1-isopropyl-1H-pyrazole-3-carboxylate

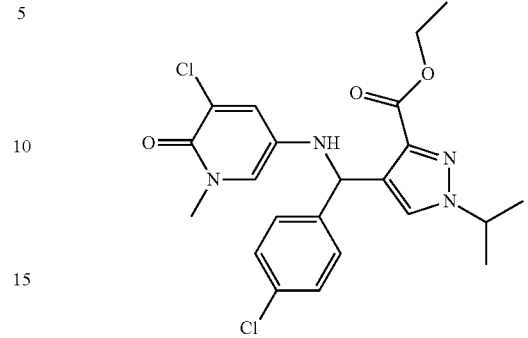

The title compound was prepared in analogy to the procedure described in Step 10.3 using ethyl 4-((4-chlorophenyl)(hydroxy)methyl)-1-isopropyl-1H-pyrazole-3-carboxylate (Step 41.3) and 5-amino-3-chloro-1-methylpyridin-2(1H)-one (Step 5.2). $t_R$: 4.65 min (HPLC 1); $t_R$: 1.07 min (LC-MS 2); ESI-MS: 463 [M+H]$^+$ (LC-MS 2); $R_f$=0.30 (EtOAc).

Step 42.2: 4-(((5-chloro-1-methyl-6-oxo-1,6-dihydropyridin-3-yl)amino)(4-chlorophenyl)methyl)-1-isopropyl-1H-pyrazole-3-carboxylic acid

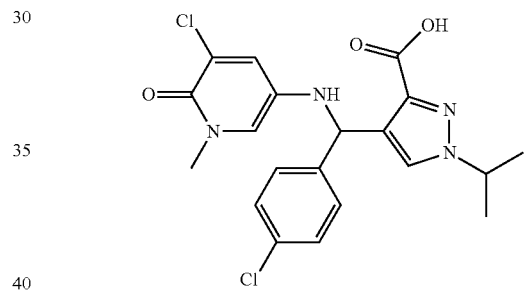

The title compound was prepared in analogy to the procedure described in Step 1.5 using ethyl 4-(((5-chloro-1-methyl-6-oxo-1,6-dihydropyridin-3-yl)amino)(4-chlorophenyl)methyl)-1-isopropyl-1H-pyrazole-3-carboxylate (Step 42.1). $t_R$: 3.84 min (HPLC 1); $t_R$: 0.88 min (LC-MS 2); ESI-MS: 435/437 [M+H]$^+$, ESI-MS: 433/435 [M−H]$^−$ (LC-MS 2).

Example 43

4-(4-chlorophenyl)-2-cyclopropyl-5-(1,5-dimethyl-6-oxo-1,6-dihydropyridin-3-yl)-3-(trifluoromethyl)-4,5-dihydropyrrolo[3,4-c]pyrazol-6(2H)-one

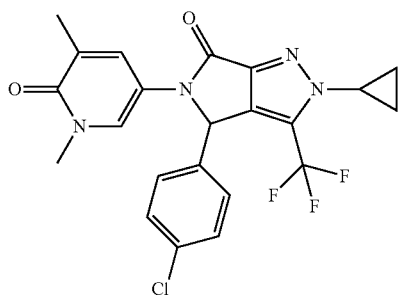 [SMILES: Cc1cc(N2C(=O)c3nn(C4CC4)c(C(F)(F)F)c3C2c2ccc(Cl)cc2)cn(C)c1=O]

The title compound was prepared in analogy to the procedure described in Example 1 using 4-((4-chlorophenyl)((1,5-dimethyl-6-oxo-1,6-dihydropyridin-3-yl)amino)methyl)-1-cyclopropyl-5-(trifluoromethyl)-1H-pyrazole-3-carboxylic acid (Step 43.2) at RT for 30 min. t$_R$: 1.10 min (LC-MS 2); ESI-MS: 463 [M+H]$^+$ (LC-MS 2); R$_f$=0.43 (CH$_2$Cl$_2$/5% MeOH/1% ammonia); $^1$H NMR (400 MHz, DMSO-d$_6$) δ ppm 1.08-1.21 (m, 2H) 1.21-1.37 (m, 2H) 1.89 (s, 3H) 3.33 (s, 3H) 3.87-3.97 (m, 1H) 6.32 (s, 1H) 7.23 (d, J=8.6 Hz, 2H) 7.29-7.39 (m, 3H) 7.68 (d, J=2.7 Hz, 1H).

Step 43.1: ethyl 4-((4-chlorophenyl)((1,5-dimethyl-6-oxo-1,6-dihydropyridin-3-yl)amino)methyl)-1-cyclopropyl-5-(trifluoromethyl)-1H-pyrazole-3-carboxylate

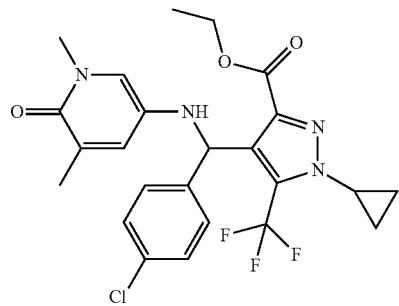 [SMILES: CCOC(=O)c1nn(C2CC2)c(C(F)(F)F)c1C(Nc1cc(C)c(=O)n(C)c1)c1ccc(Cl)cc1]

The title compound was prepared in analogy to the procedure described in Step 10.3 using ethyl 4-((4-chlorophenyl)(hydroxy)methyl)-1-cyclopropyl-5-(trifluoromethyl)-1H-pyrazole-3-carboxylate (Step 40.2) and 5-amino-1,3-dimethylpyridin-2(1H)-one (Step 20.2) at RT for 4 days. t$_R$: 1.22 min (LC-MS 2); ESI-MS: 509 [M+H]$^+$ (LC-MS 2); R$_f$=0.32 (5% MeOH/CH$_2$Cl$_2$).

Step 43.2: 4-((4-chlorophenyl)((1,5-dimethyl-6-oxo-1,6-dihydropyridin-3-yl)amino)methyl)-1-cyclopropyl-5-(trifluoromethyl)-1H-pyrazole-3-carboxylic acid

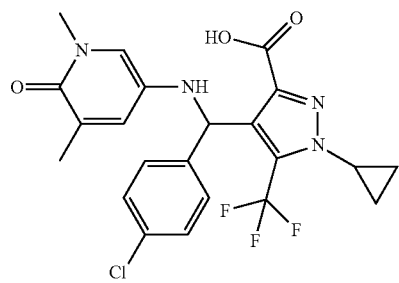 [SMILES: Cc1cc(NC(c2ccc(Cl)cc2)c2c(C(=O)O)nn(C3CC3)c2C(F)(F)F)cn(C)c1=O]

The title compound was prepared in analogy to the procedure described in Step 40.4 using ethyl 4-((4-chlorophenyl)((1,5-dimethyl-6-oxo-1,6-dihydropyridin-3-yl)amino)methyl)-1-cyclopropyl-5-(trifluoromethyl)-1H-pyrazole-3-carboxylate (Step 43.1). t$_R$: 0.97 min (LC-MS 2); ESI-MS: 481 [M+H]$^+$, ESI-MS: 479 [M−H]$^−$ (LC-MS 2).

Example 44

5-(5-chloro-1-methyl-6-oxo-1,6-dihydropyridin-3-yl)-4-(4-chlorophenyl)-1-cyclopropyl-3-(trifluoromethyl)-4,5-dihydropyrrolo[3,4-c]pyrazol-6(1H)-one

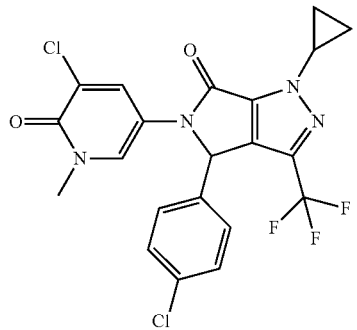 [SMILES: Cn1cc(N2C(=O)c3c(c(C(F)(F)F)nn3C3CC3)C2c2ccc(Cl)cc2)cc(Cl)c1=O]

The title compound was prepared in analogy to the procedure described in Example 1 using 4-(((5-chloro-1-methyl-6-oxo-1,6-dihydropyridin-3-yl)amino)(4-chlorophenyl)methyl)-1-cyclopropyl-3-(trifluoromethyl)-1H-pyrazole-5-carboxylic acid (Step 44.4).; t$_R$: 1.16 min (LC-MS 2); ESI-MS: 483 [M+H]$^+$ (LC-MS 2); R$_f$=0.61 (CH$_2$Cl$_2$/5% MeOH); $^1$H NMR (400 MHz, DMSO-d$_6$) δ ppm 1.08-1.17 (m, 2H) 1.27-1.38 (m, 2H) 3.40 (s, 3H) 3.89-4.09 (m, 1H) 6.27 (s, 1H) 7.25-7.42 (m, 4H) 7.90 (d, J=2.7 Hz, 1H) 7.86 (d, J=2.7 Hz, 1H).

Step 44.1: ethyl 1-cyclopropyl-3-(trifluoromethyl)-1H-pyrazole-5-carboxylate

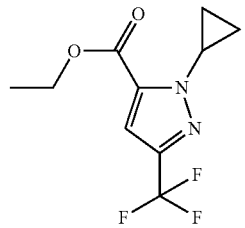 [SMILES: CCOC(=O)c1cc(C(F)(F)F)nn1C1CC1]

The title compound was prepared in analogy to the procedure described in Step 17.3 using cyclopropylhydrazine (Step 17.2) and ethyl 5,5,5-trifluoro-2,4-dioxopentanoate at 100° C. for 2 hr. The crude product was purified by silica gel column chromatography (hexane/EtOAc 9:1). t$_R$: 1.23 min (LC-MS 2); ESI-MS: 249.2 [M+H]$^+$ (LC-MS 2); R$_f$=0.34 (hexane/EtOAc 9:1).

Step 44.2: ethyl 4-((4-chlorophenyl)(hydroxy)methyl)-1-cyclopropyl-3-(trifluoromethyl)-1H-Pyrazole-5-carboxylate

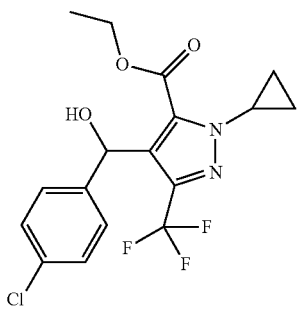 [SMILES: CCOC(=O)c1c(C(O)c2ccc(Cl)cc2)c(C(F)(F)F)nn1C1CC1]

The title compound was prepared in analogy to the procedure described in Step 40.2 using ethyl 1-cyclopropyl-3-(trifluoromethyl)-1H-pyrazole-5-carboxylate (Step 44.1) and 4-chlorobenzaldehyde. $t_R$: 1.29 min (LC-MS 2); ESI-MS: 389 [M+H]$^+$ (LC-MS 2); $R_f$=0.12 (hexane/15% EtOAc).

Step 44.3: ethyl 4-(((5-chloro-1-methyl-6-oxo-1,6-dihydropyridin-3-yl)amino)(4-chlorophenyl)-methyl)-1-cyclopropyl-3-(trifluoromethyl)-1H-pyrazole-5-carboxylate

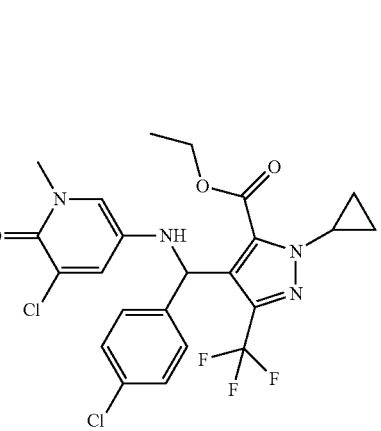

The title compound was prepared in analogy to the procedure described in Step 10.3 using ethyl 4-((4-chlorophenyl)(hydroxy)methyl)-1-cyclopropyl-3-(trifluoromethyl)-1H-pyrazole-5-carboxylate (Step 44.2) and 5-amino-3-chloro-1-methylpyridin-2(1H)-one (Step 5.2) at RT for 60 hr. $t_R$: 1.27 min (LC-MS 2); ESI-MS: 529 [M+H]$^+$ (LC-MS 2); $R_f$=0.34 (EtOAc/CH$_2$Cl$_2$ 1:1).

Step 44.4: 4-(((5-chloro-1-methyl-6-oxo-1,6-dihydropyridin-3-yl)amino)(4-chlorophenyl)methyl)-1-cyclopropyl-3-(trifluoromethyl)-1H-pyrazole-5-carboxylic acid

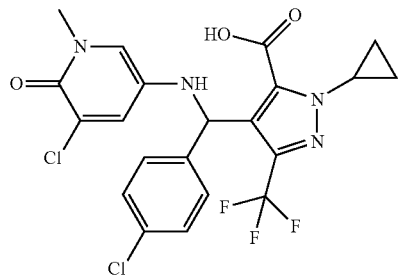

The title compound was prepared in analogy to the procedure described in Step 40.4 using ethyl 4-(((5-chloro-1-methyl-6-oxo-1,6-dihydropyridin-3-yl)amino)(4-chlorophenyl)methyl)-1-cyclopropyl-3-(trifluoromethyl)-1H-pyrazole-5-carboxylate (Step 44.3). $t_R$: 0.92 min (LC-MS 2); ESI-MS: 501/503 [M+H]$^+$, ESI-MS: 499/501 [M−H]$^-$ (LC-MS 2).

Example 45

4-(4-chlorophenyl)-1-cyclopropyl-5-(1,5-dimethyl-6-oxo-1,6-dihydropyridin-3-yl)-3-(trifluoromethyl)-4,5-dihydropyrrolo[3,4-c]pyrazol-6(1H)-one The title compound was prepared in analogy to the procedure described in Example 1 using 4-((4-chlorophenyl)((1,5-dimethyl-6-oxo-1,6-dihydropyridin-3-yl)amino)methyl)-1-cyclopropyl-3-(trifluoromethyl)-1H-pyrazole-5-carboxylic acid (Step 45.2). $t_R$: 1.13 min (LC-MS 2); ESI-MS: 463 [M+H]$^+$ (LC-MS 2); $R_f$=0.61 (CH$_2$Cl$_2$/5% MeOH); $^1$H NMR (400 MHz, DMSO-d$_6$) δ ppm 1.07-1.17 (m, 2H) 1.27-1.40 (m, 2H) 1.89 (s, 3H) 3.32 (s, 3H) 3.95-4.05 (m, 1H) 6.24 (s, 1H) 7.21-7.40 (m, 5H) 7.69 (d, J=2.7 Hz, 1H).

Step 45.1: ethyl 4-((4-chlorophenyl)((1,5-dimethyl-6-oxo-1,6-dihydropyridin-3-yl)amino)methyl)-1-cyclopropyl-3-(trifluoromethyl)-1H-pyrazole-5-carboxylate

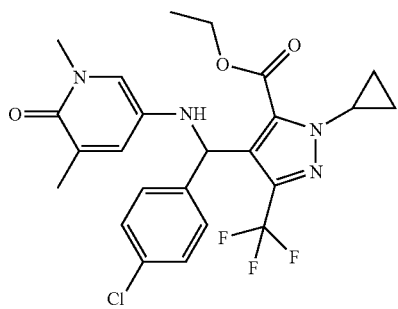 [SMILES: CCOC(=O)c1c(C(Nc2cc(Cl)c(=O)n(C)c2)c2ccc(Cl)cc2)c(C(F)(F)F)nn1C1CC1]

The title compound was prepared in analogy to the procedure described in Step 10.3 using ethyl 4-((4-chlorophenyl)(hydroxy)methyl)-1-cyclopropyl-3-(trifluoromethyl)-1H-pyrazole-5-carboxylate (Step 44.2) and 5-amino-1,3-dimethylpyridin-2(1H)-one (Step 20.2) at RT for 40 hr. $t_R$: 1.29 min (LC-MS 2); ESI-MS: 509 [M+H]$^+$ (LC-MS 2); $R_f$=0.19 (5% MeOH/CH$_2$Cl$_2$).

Step 45.2: 4-((4-chlorophenyl)((1,5-dimethyl-6-oxo-1,6-dihydropyridin-3-yl)amino)methyl)-1-cyclopropyl-3-(trifluoromethyl)-1H-pyrazole-5-carboxylic acid

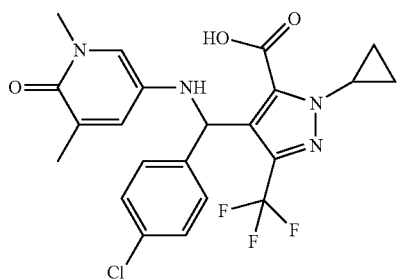 [SMILES: Cc1cc(NC(c2ccc(Cl)cc2)c2c(C(F)(F)F)nn(C3CC3)c2C(=O)O)cn(C)c1=O]

The title compound was prepared in analogy to the procedure described in Step 40.4 using ethyl 4-((4-chlorophenyl)((1,5-dimethyl-6-oxo-1,6-dihydropyridin-3-yl)amino)methyl)-1-cyclopropyl-3-(trifluoromethyl)-1H-pyrazole-5-carboxylate (Step 45.1). $t_R$: 0.91 min (LC-MS 2); ESI-MS: 481/483 [M+H]$^+$, ESI-MS: 479/501 [M−H]$^−$ (LC-MS 2).

Example 46

4-(4-chlorophenyl)-2-(2,4-dimethoxypyrimidin-5-yl)-5-(3,7-dimethylbenzo[d]-isoxazol-5-yl)-3-isopropyl-4,5-dihydropyrrolo[3,4-c]pyrazol-6(2H)-one

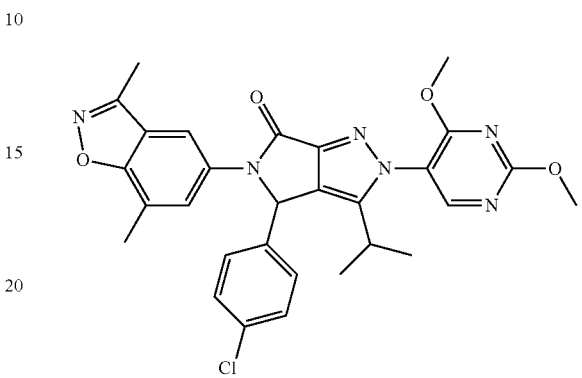

The title compound was prepared in analogy to the procedure described in Example 1 using 4-((4-chlorophenyl)((3,7-dimethylbenzo[d]isoxazol-5-yl)amino)methyl)-1-(2,4-dimethoxypyrimidin-5-yl)-5-isopropyl-1H-pyrazole-3-carboxylic acid (Step 46.13). $t_R$: 1.25 min (LC-MS 2); ESI-MS: 559 [M+H]$^+$ (LC-MS 2); $R_f$=0.50 (EtOAc); $^1$H NMR (400 MHz, DMSO-d$_6$) δ ppm 0.48 (d, J=6.8 Hz, 3H) 1.17 (d, J=6.7 Hz, 3H) 2.45 (s, 3H) 2.52 (s, 3H) 2.61-2.71 (m, 1H) 3.96 (s, 3H) 4.01 (s, 3H) 6.69 (s, 1H) 7.33-7.42 (m, 4H) 7.67 (s, 1H) 7.84 (d, J=1.5 Hz, 1H) 8.64 (s, 1H).

Step 46.1: 1-(2-hydroxy-3-methylphenyl)ethanone

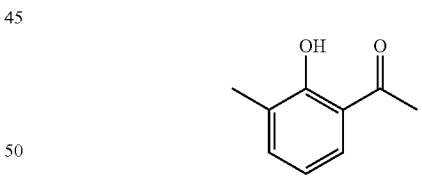

To a colorless solution of 3-methyl-salicylic acid (1 g, 6.57 mmol) in Et$_2$O (50 mL) under argon and cooled down to 0° C. was added dropwise methyllithium 1.6M in Et$_2$O (12.32 mL, 19.72 mmol) over 20 min. The resulting mixture was stirred at this temperature for 30 min then allowed to warm up and stir overnight at RT. The reaction mixture was slowly poured into a stirred mixture of 100 g of ice and HCl 4N (50 mL) and extracted twice with EtOAc. The combined organic layers were washed with 10% NaHCO$_3$ solution and brine, dried over MgSO$_4$, filtered and concentrated under reduced pressure to afford the title product (920 mg, 5.94 mmol, 90% yield) as a pale yellow oil. $t_R$: 0.91 min (LC-MS 2); ESI-MS: 481/483 [M+H]$^+$, ESI-MS: 479/501 [M−H]$^−$ (LC-MS 2); $R_f$=0.55 (hexane/EtOAc 3:1).

Step 46.2: (E)-1-(2-hydroxy-3-methylphenyl)ethanone oxime

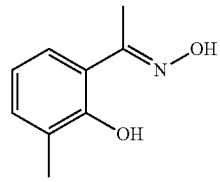

1-(2-hydroxy-3-methylphenyl)ethanone (Step 46.1) (900 mg, 5.87 mmol) was dissolved in MeOH (15 mL) and NaOAc (771 mg, 9.40 mmol) and hydroxylamine hydrochloride (612 mg, 8.81 mmol) were successively added. The resulting mixture was heated up and stirred at 60° C. for 2 hr. The reaction mixture was poured into brine and extracted with EtOAc. The combined organic layers were washed with brine, dried over MgSO$_4$, filtered and concentrated under reduced pressure to afford the title product (964 mg, 5.25 mmol, 89% yield) as a colorless solid. $t_R$: 0.94 min (LC-MS 2); ESI-MS: 166 [M+H]$^+$, ESI-MS: 164 [M−H]$^−$ (LC-MS 2); R$_f$=0.66 (hexane/EtOAc 1:1).

Step 46.3: (E)-1-(2-hydroxy-3-methylphenyl)ethanone O-acetyl oxime

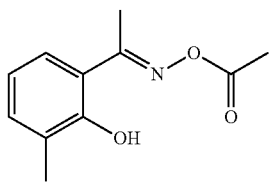

(E)-1-(2-hydroxy-3-methylphenyl)ethanone oxime (Step 46.2) (5.5 g, 30 mmol) was added into Ac$_2$O (48.1 mL, 509 mmol) under argon and the resulting mixture was stirred at RT for 1.5 hr. The reaction was concentrated to 10 mL volume under reduced pressure; the resulting suspension was diluted with cold water and stirred at RT until a fine precipitate occurred. The resulting solid was filtrated off, washed with water and dried to afford the title product (6.03 g, 28.8 mmol, 96% yield) as colorless solid. $t_R$: 1.08 min (LC-MS 2); ESI-MS: 208 [M+H]$^+$; R$_f$=0.60 (hexane/EtOAc 1:1).

Step 46.4: 3,7-dimethylbenzo[d]isoxazole

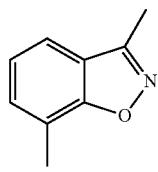

(E)-1-(2-hydroxy-3-methylphenyl)ethanone O-acetyl oxime (Step 46.3) (6.0 g, 29.0 mmol) was dissolved in pyridine (60 mL) and the resulting mixture was heated up and stirred at 130° C. for 40 hr, cooled down to RT and concentrated under reduced pressure. The crude product was purified by silica gel column chromatography (hexane/EtOAc 0-50% EtOAc) to afford the title product (3.62 g, 23.12 mmol, 80% yield) as pale yellow oil. $t_R$: 0.96 min (LC-MS 2); ESI-MS: 148 [M+H]$^+$; R$_f$=0.56 (hexane/EtOAc 3:1).

Step 46.5: 3,7-dimethyl-5-nitrobenzo[d]isoxazole

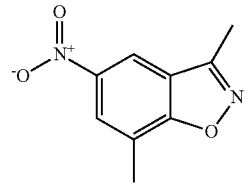

3,7-dimethylbenzo[d]isoxazole (Step 46.4) (2 g, 12.77 mmol) was dissolved in H$_2$SO$_4$ (5 mL), cooled down and stirred at 0° C. HNO$_3$ (0.878 mL, 12.77 mmol) was slowly added and the resulting mixture was stirred at 0° C. for 1 hr. The reaction was diluted with water (60 mL) and extracted three times with CH$_2$Cl$_2$. The combined organic layers were washed with NaHCO$_3$ solution and brine, dried over MgSO$_4$, filtered and concentrated under reduced pressure. The resulting yellow solid was triturated with Et$_2$O, filtrated off, washed with Et$_2$O and dried to afford the title product (1.86 g, 9.29 mmol, 73% yield) as yellow solid. $t_R$: 0.98 min (LC-MS 2); ESI-MS: 193 [M+H]$^+$.

Step 46.6: 3,7-dimethylbenzo[d]isoxazol-5-amine

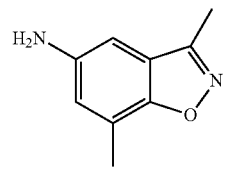

To a suspension of 3,7-dimethyl-5-nitrobenzo[d]isoxazole (Step 46.5) (50 mg, 0.260 mmol) in acetic acid (1.5 mL) was added dropwise a solution of SnCl$_2$.2H$_2$O (176 mg, 0.781 mmol) in HCl conc (0.316 mL, 10.41 mmol) and the resulting mixture was stirred at RT overnight. The reaction was poured into a cold 4N NaOH solution and extracted with EtOAc. The combined organic layers were dried over MgSO$_4$, filtered and concentrated under reduced pressure. The crude product was purified by silica gel column chromatography (hexane/EtOAc 0-55%) to afford the title product (25 mg, 0.153 mmol, 59% yield) as beige solid. $t_R$: 0.57 min (LC-MS 2); ESI-MS: 163 [M+H]$^+$; R$_f$=0.23 (hexane/EtOAc 1:1).

Step 46.7: Di-tert-butyl 1-(2,4-dimethoxypyrimidin-5-yl)hydrazine-1,2-dicarboxylate

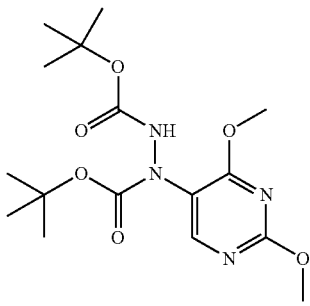 [SMILES: COc1ncc(N(NC(=O)OC(C)(C)C)C(=O)OC(C)(C)C)c(OC)n1]

To a stirred solution of 5-bromo-2,4-dimethoxypyrimidine (400 g, 1.826 mol) in anhydrous THF (3 L) under argon and cooled down to 0° C. was added dropwise TurboGrignard (1.821 L, 2.367 mol). The resulting mixture was stirred at 0° C. until exothermic ceased then, allowed to warm up and stir at RT for 30 min. A solution of di-tert-butyl azodicarboxylate in anhydrous THF (1 L) was added dropwise to the mixture and the reaction was stirred at RT for 1 hr. The reaction was slowly quenched with a saturated aq. NH$_4$Cl solution (2 L), diluted with EtOAc (2 L) and water (2 L) and both phases separated. The aq. phase was extracted with EtOAc (3 L), combined organic layers were washed with brine (3 L), dried over Na$_2$SO$_4$, filtered and concentrated under reduced pressure. The resulting yellow oil was dissolved in Hexane (3 L) and the suspension was stirred at 0° C. for 3 hr, filtrated off and dried to afford a first batch of white crystals. The mother liquor was concentrated under reduced pressure and purified to afford a second batch of white crystals. The two batches were combined to afford the title product (507 g, 1.369 mol, 75% yield) as white crystals. t$_R$: 1.03 min (LC-MS 1); ESI-MS: 371 [M+H]$^+$, ESI-MS: 369 [M–H]$^-$ (LC-MS 1).

Step 46.8: 5-hydrazinyl-2,4-dimethoxypyrimidine

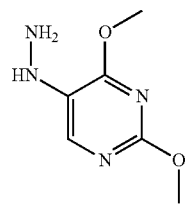

Di-tert-butyl 1-(2,4-dimethoxypyrimidin-5-yl)hydrazine-1,2-dicarboxylate (Step 46.7) (453 g, 1.223 mol) was dissolved in MeOH (2.5 L) and cooled down to 0° C. HCl 4N in gioxane (2.5 L, mol) was added and the resulting mixture was stirred at RT overnight. The reaction was concentrated under reduced pressure, NH$_3$ 4 N (2 L) was added, the resulting mixture was stirred for 1 hr and concentrated under reduced pressure. CH$_2$Cl$_2$ (2 L) was added, the suspension was filtrated off and the filtrate was concentrated under reduced pressure. The crude product was stirred with Et$_2$O (2 L) at 0° C. for 30 min. The resulting suspension was filtrated off and dried to afford the title product (150 g, 864 mmol, 70% yield) as light beige solid. t$_R$: 0.32 min (LC-MS 1); ESI-MS: 171 [M+H]$^+$ (LC-MS 1).

Step 46.9: ethyl 1-(2,4-dimethoxypyrimidin-5-yl)-5-isopropyl-1H-pyrazole-3-carboxylate

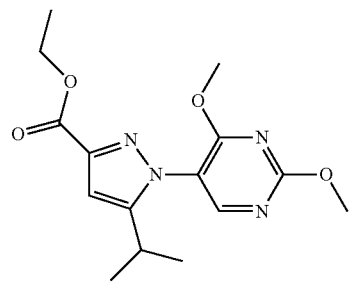 [SMILES: CCOC(=O)c1cc(C(C)C)n(-c2cnc(OC)nc2OC)n1]

5-hydrazinyl-2,4-dimethoxypyrimidine (Step 46.8) (140 g, 823 mmol) was dissolved in toluene (3 L) under nitrogen atmosphere and ethyl-2,4-dioxo-5-methylhexanoate (230 g, 1234 mmol) was added dropwise over 15 min. The reaction mixture was heated up and stirred at 110° C. for 1 hr. The brown solution was quenched with saturated aq. NaHCO$_3$ solution (2 L) and extracted with EtOAc (2×2 L). The combined organic layers were washed with brine (2 L), dried over Na$_2$SO$_4$, filtered and concentrated under reduced pressure. The crude material was stirred in hexane (1 L) at RT and the resulting suspension was filtrated off and dried to afford the title product (193 g, 596 mmol, 72% yield) as white crystals. t$_R$: 1.01 min (LC-MS 1); ESI-MS: 321 [M+H]$^+$ (LC-MS 1).

Step 46.10: ethyl 1-(2,4-dimethoxypyrimidin-5-yl)-4-iodo-5-isopropyl-1H-pyrazole-3-carboxylate

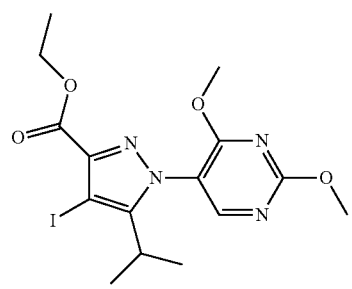 [SMILES: CCOC(=O)c1nn(-c2cnc(OC)nc2OC)c(C(C)C)c1I]

The title compound was prepared in analogy to the procedure described in Step 10.1 using ethyl 1-(2,4-dimethoxypyrimidin-5-yl)-5-isopropyl-1H-pyrazole-3-carboxylate (Step 46.9) at 80° C. for 6 hr. Purification by silica gel column chromatography (heptane/EtOAc 0-100%) afforded the title product as white crystals. t$_R$: 1.14 min (LC-MS 1); ESI-MS: 4477 [M+H]$^+$ (LC-MS 1).

Step 46.11: ethyl 4-((4-chlorophenyl)(hydroxy)methyl)-1-(2,4-dimethoxypyrimidin-5-yl)-5-iso-propyl-1H-pyrazole-3-carboxylate

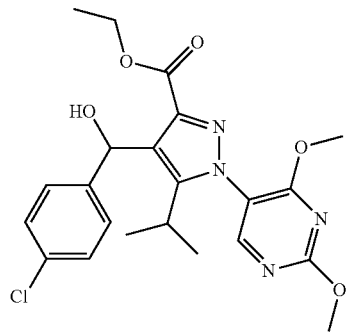 [SMILES: CCOC(=O)c1nn(-c2cnc(OC)nc2OC)c(C(C)C)c1C(O)c1ccc(Cl)cc1]

The title compound was prepared in analogy to the procedure described in Step 1.3 using ethyl 1-(2,4-dimethoxypyrimidin-5-yl)-4-iodo-5-isopropyl-1H-pyrazole-3-carboxylate (Step 46.10) at −20° C. for 1 hr. t$_R$: 1.21 min (LC-MS 2); ESI-MS: 461 [M+H]$^+$ (LC-MS 2); R$_f$=0.40 (hexane/EtOAc 1:1).

Step 46.12: ethyl 4-((4-chlorophenyl)((3,7-dimethylbenzo[d]isoxazol-5-yl)amino)methyl)-1-(2,4-dimethoxypyrimidin-5-yl)-5-isopropyl-1H-pyrazole-3-carboxylate

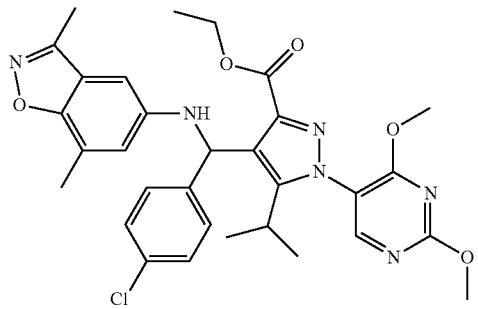 [SMILES: CCOC(=O)c1nn(-c2cnc(OC)nc2OC)c(C(C)C)c1C(Nc1cc(C)c2onc(C)c2c1)c1ccc(Cl)cc1]

To a stirred solution of ethyl 4-((4-chlorophenyl)(hydroxy)methyl)-1-(2,4-dimethoxypyrimidin-5-yl)-5-isopropyl-1H-pyrazole-3-carboxylate (Step 46.11) (500 mg, 1.085 mmol) and triethylamine (0.756 mL, 5.42 mmol) in CH$_2$Cl$_2$ (10 mL) cooled down to 0° C. was added Ms$_2$O (378 mg, 2.170 mmol) and the reaction was stirred for 1 hr at this temperature. 3,7-dimethylbenzo[d]isoxazol-5-amine (Step 46.6) (194 mg, 1.193 mmol) was added and the reaction mixture was allowed to warm up to RT and stir for 1 hr. The reaction was quenched with aq. NaH$_2$PO$_4$ solution and extracted with CH$_2$Cl$_2$. The combined organic layers were dried over MgSO$_4$, filtered and concentrated under reduced pressure. The crude product was purified by silica gel column chromatography (hexane/EtOAc 10-100%) to afford the title product (460 mg, 0.684 mmol, 63% yield) as yellow amorphous solid. t$_R$: 1.38 min (LC-MS 2); ESI-MS: 605 [M+H]$^+$ (LC-MS 2); R$_f$=0.25 (hexane/EtOAc 1:1).

Step 46.13: 4-((4-chlorophenyl)((3,7-dimethylbenzo[d]isoxazol-5-yl)amino)methyl)-1-(2,4-dimethoxypyrimidin-5-yl)-5-isopropyl-1H-pyrazole-3-carboxylic acid

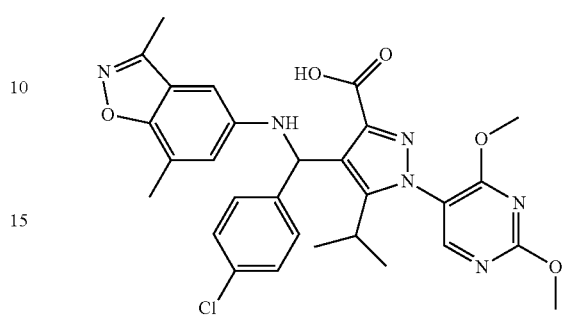

To a stirred solution of ethyl 4-((4-chlorophenyl)((3,7-dimethylbenzo[d]isoxazol-5-yl)amino)-methyl)-1-(2,4-dimethoxypyrimidin-5-yl)-5-isopropyl-1H-pyrazole-3-carboxylate (Step 46.12) (455 mg, 0.677 mmol) in MeOH (10 mL) cooled down to 0° C. was added dropwise 4M NaOH (2.54 mL, 10.15 mmol). The reaction mixture was allowed to warm up and stir at RT for 45 min, acidified with 4N HCl and MeOH was removed under reduced pressure. The aq. layer was extracted with EtOAc, combined organic layers were washed with brine, dried over MgSO$_4$, filtered and concentrated under reduced pressure to afford the title product (450 mg, 0.663 mmol, 98% yield) as a beige amorphous solid. t$_R$: 1.20 min (LC-MS 2); ESI-MS: 577 [M+H]$^+$, ESI-MS: 575 [M−H]$^−$ (LC-MS 2).

Example 47

5-(5-chloro-1-methyl-6-oxo-1,6-dihydropyridin-3-yl)-4-(4-chlorophenyl)-2-(2,4-dimethoxypyrimidin-5-yl)-3-(trifluoromethyl)-4,5-dihydropyrrolo[3,4-c]pyrazol-6(2H)-one

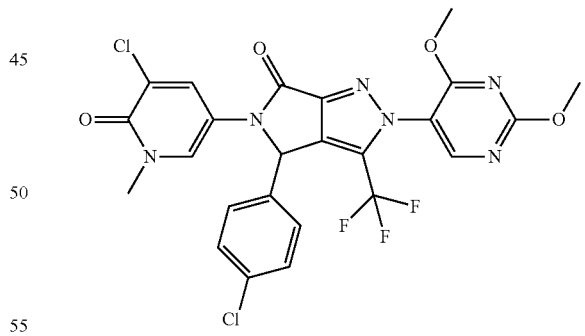

The title compound was prepared in analogy to the procedure described in Example 1 using 4-(((5-chloro-1-methyl-6-oxo-1,6-dihydropyridin-3-yl)amino)(4-chlorophenyl)methyl)-1-(2,4-dimethoxypyrimidin-5-yl)-5-(trifluoromethyl)-1H-pyrazole-3-carboxylic acid (Step 47.4) at RT for 1 hr. The crude product was purified by silica gel chromatography (1% ammonia/5% MeOH/CH$_2$Cl$_2$) and triturated in Et$_2$O. t$_R$: 1.11 min (LC-MS 2); ESI-MS: 581 [M+H]$^+$ (LC-MS 2); R$_f$=0.21 (CH$_2$Cl$_2$/5% MeOH/1% ammonia); $^1$H NMR (400 MHz, DMSO-d$_6$) δ ppm 3.43 (s, 3H) 3.92 (s, 3H) 3.99 (s, 3H) 6.49 (s, 1H) 7.24-7.46 (m, 4H) 7.86-8.01 (m, 2H) 8.74 (s, 1H).

Step 47.1: ethyl 1-(2,4-dimethoxypyrimidin-5-yl)-5-(trifluoromethyl)-1H-pyrazole-3-carboxylate

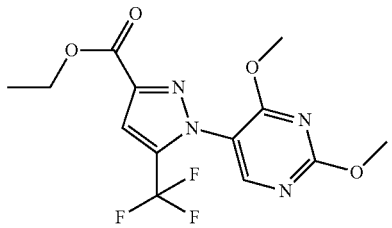 [SMILES: CCOC(=O)c1cc(C(F)(F)F)n(-c2cnc(OC)nc2OC)n1]

The title compound was prepared in analogy to the procedure described in Step 17.3 using 5-hydrazinyl-2,4-dimethoxypyrimidine (Step 46.8) and ethyl 5,5,5-trifluoro-2,4-dioxopentanoate at 100° C. for 2 hr. The crude product was purified by silica gel column chromatography (hexane/30% EtOAc). $t_R$: 1.09 min (LC-MS 2); ESI-MS: 347 [M+H]$^+$ (LC-MS 2); $R_f$=0.31 (hexane/30% EtOAc).

Step 47.2: ethyl 4-((4-chlorophenyl)(hydroxy)methyl)-1-(2,4-dimethoxypyrimidin-5-yl)-5-(trifluoromethyl)-1H-pyrazole-3-carboxylate

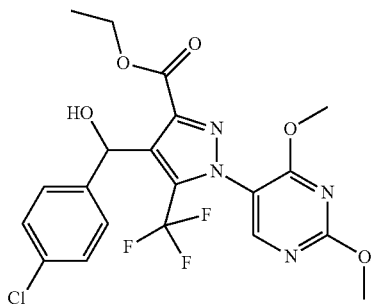 [SMILES: CCOC(=O)c1nn(-c2cnc(OC)nc2OC)c(C(F)(F)F)c1C(O)c1ccc(Cl)cc1]

The title compound was prepared in analogy to the procedure described in Step 40.2 using ethyl 1-(2,4-dimethoxypyrimidin-5-yl)-5-(trifluoromethyl)-1H-pyrazole-3-carboxylate (Step 47.1). The crude product was purified by silica gel column chromatography (hexane/35% EtOAc). $t_R$: 1.24 min (LC-MS 2); ESI-MS: 487 [M+H]$^+$ (LC-MS 2); $R_f$=0.28 (hexane/35% EtOAc).

Step 47.3: ethyl 4-(((5-chloro-1-methyl-6-oxo-1,6-dihydropyridin-3-yl)amino)(4-chlorophenyl)methyl)-1-(2,4-dimethoxypyrimidin-5-yl)-5-(trifluoromethyl)-1H-pyrazole-3-carboxylate

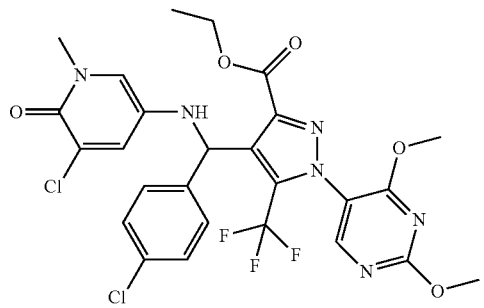 [SMILES: CCOC(=O)c1nn(-c2cnc(OC)nc2OC)c(C(F)(F)F)c1C(Nc1cc(Cl)c(=O)n(C)c1)c1ccc(Cl)cc1]

The title compound was prepared in analogy to the procedure described in Step 40.3 using ethyl 4-((4-chlorophenyl)(hydroxy)methyl)-1-(2,4-dimethoxypyrimidin-5-yl)-5-(trifluoromethyl)-1H-pyrazole-3-carboxylate (Step 47.2) and 5-amino-3-chloro-1-methylpyridin-2(1H)-one (Step 5.2). The crude product was purified by silica gel chromatography (50% EtOAc/CH$_2$Cl$_2$). $t_R$: 1.21 min (LC-MS 2); ESI-MS: 627 [M+H]$^+$ (LC-MS 2); $R_f$=0.20 (50% EtOAc/CH$_2$Cl$_2$).

Step 47.4: 4-(((5-chloro-1-methyl-6-oxo-1,6-dihydropyridin-3-yl)amino)(4-chlorophenyl)methyl)-1-(2,4-dimethoxypyrimidin-5-yl)-5-(trifluoromethyl)-1H-pyrazole-3-carboxylic acid

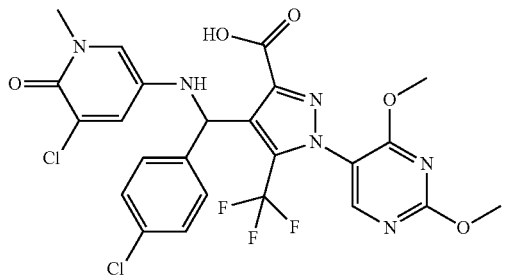 [SMILES: COc1ncc(-n2nc(C(=O)O)c(C(Nc3cc(Cl)c(=O)n(C)c3)c3ccc(Cl)cc3)c2C(F)(F)F)c(OC)n1]

The title compound was prepared in analogy to the procedure described in Step 40.4 using ethyl 4-(((5-chloro-1-methyl-6-oxo-1,6-dihydropyridin-3-yl)amino)(4-chlorophenyl)methyl)-1-(2,4-dimethoxypyrimidin-5-yl)-5-(trifluoromethyl)-1H-pyrazole-3-carboxylate (Step 47.3). $t_R$: 0.97 min (LC-MS 2); ESI-MS: 599 [M+H]$^+$ (LC-MS 2); ESI-MS: 597 [M−H]$^-$ (LC-MS 2).

Reference Example 48

(S)-4-(4-chlorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one

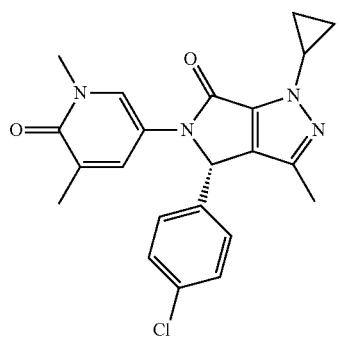 [SMILES: Cc1nn(C2CC2)c2c1[C@H](c1ccc(Cl)cc1)N(c1cc(C)c(=O)n(C)c1)C2=O]

The title compound (26 mg, 0.064 mmol, 38% yield) was obtained enantiomerically pure (ee>99%) after chiral preparative chromatography (Chiralpak AD-H 30×250 mm; mobile phase: scCO$_2$/MeOH 20% isocratic at 4.5-5 min raise to 30% until end; flow: 100 mL/min; detection DAD (250 nm)) of the racemic mixture of 4-(4-chlorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one (Example 23) (67 mg, 0.164 mmol). $t_R$: 0.97 min (LC-MS 2); ESI-MS: 409 [M+H]$^+$ (LC-MS 2).

Example 49

(R)-4-(4-chlorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one

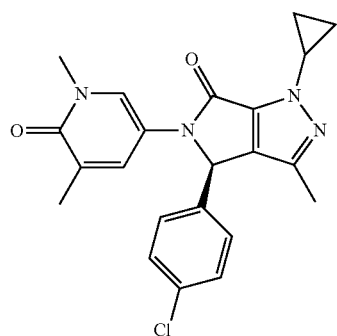 [SMILES: Cc1nn(C2CC2)c2c1[C@@H](c1ccc(Cl)cc1)N(c1cc(C)c(=O)n(C)c1)C2=O]

The title compound (20 mg, 0.049 mmol, 29.9% yield) was obtained enantiomerically pure (ee>99.0%) after chiral preparative chromatography (Chiralpak AD-H 30×250 mm; mobile phase: scCO$_2$/MeOH 20% isocratic at 4.5-5 min raise to 30% until end; flow: 100 mL/min; detection DAD (250 nm)) of the racemic mixture of 4-(4-chlorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one (Example 23) (67 mg, 0.164 mmol). t$_R$: 0.97 min (LC-MS 2); ESI-MS: 409 [M+H]$^+$ (LC-MS 2).

Reference Example 50

(S)-5-(5-chloro-1-methyl-6-oxo-1,6-dihydropyridin-3-yl)-4-(4-chlorophenyl)-1-cyclopropyl-3-methyl-4,5-dihydropyrrolo[3,4-c]pyrazol-6(1H)-one

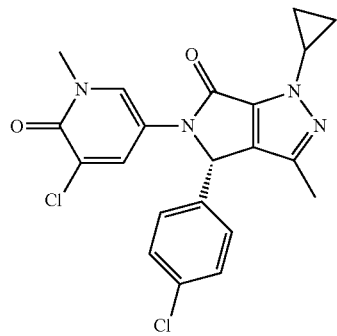 [SMILES: Cc1nn(C2CC2)c2c1[C@H](c1ccc(Cl)cc1)N(c1cc(Cl)c(=O)n(C)c1)C2=O]

The title compound (19 mg, 0.044 mmol, 33.3% yield) was obtained enantiomerically pure (ee>99.0%) after chiral preparative chromatography (system: Thar/Waters SFC-100 MS; column: Chiralpak AD-H 30×250 mm; mobile phase: scCO$_2$/MeOH 20%-30% in 6 min_total 8 min; flow: 100 mL/min; detection DAD (250 nm)) of the racemic mixture of 5-(5-chloro-1-methyl-6-oxo-1,6-dihydropyridin-3-yl)-4-(4-chlorophenyl)-1-cyclopropyl-3-methyl-4,5-dihydropyrrolo[3,4-c]pyrazol-6(1H)-one (Example 24) (57 mg, 0.133 mmol). t$_R$: 1.01 min (LC-MS 2); ESI-MS: 429 [M+H]$^+$ (LC-MS 2).

Example 51

(R)-5-(5-chloro-1-methyl-6-oxo-1,6-dihydropyridin-3-yl)-4-(4-chlorophenyl)-1-cyclopropyl-3-methyl-4,5-dihydropyrrolo[3,4-c]pyrazol-6(1H)-one

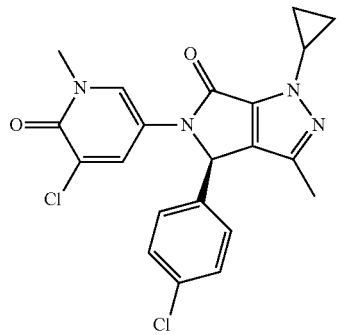 [SMILES: Cc1nn(C2CC2)c2c1[C@@H](c1ccc(Cl)cc1)N(c1cc(Cl)c(=O)n(C)c1)C2=O]

The title compound (17 mg, 0.040 mmol, 30% yield) was obtained enantiomerically pure (ee>99%) after chiral preparative chromatography (Chiralpak AD-H 30×250 mm; mobile phase: scCO$_2$/MeOH 20%-30% in 6 min_total 8 min; flow: 100 mL/min; detection DAD (250 nm)) of the racemic mixture of 5-(5-chloro-1-methyl-6-oxo-1,6-dihydropyridin-3-yl)-4-(4-chlorophenyl)-1-cyclopropyl-3-methyl-4,5-dihydropyrrolo[3,4-c]pyrazol-6(1H)-one (Example 24) (57 mg, 0.133 mmol). t$_R$: 1.01 min (LC-MS 2); ESI-MS: 429 [M+H]$^+$ (LC-MS 2).

Example 52

4-(4-chlorophenyl)-1-(2,4-dimethoxypyrimidin-5-yl)-5-(1,5-dimethyl-6-oxo-1,6-dihydropyridin-3-yl)-3-methyl-4,5-dihydropyrrolo[3,4-c]pyrazol-6(1H)-one

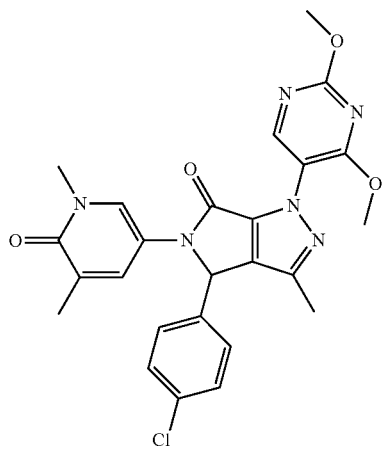 [SMILES: COc1ncc(-n2nc(C)c3c2C(=O)N(c2cc(C)c(=O)n(C)c2)C3c2ccc(Cl)cc2)c(OC)n1]

The title compound was prepared in analogy to the procedure described in Example 1 using 4-((4-chlorophenyl)((1,5-dimethyl-6-oxo-1,6-dihydropyridin-3-yl)amino)methyl)-1-(2,4-dimethoxypyrimidin-5-yl)-3-methyl-1H-pyrazole-5-carboxylic acid (Step 52.4). t$_R$: 4.25 min (HPLC 1); t$_R$: 0.98 min (LC-MS 2); ESI-MS: 507 [M+H]$^+$ (LC-MS 2); R$_f$=0.11 (EtOAc); $^1$H NMR (400 MHz, DMSO-d$_6$) δ ppm 1.89 (s, 3H) 1.99 (s, 3H) 3.33 (s, 3H) 3.93 (s, 3H) 3.96 (s, 3H) 6.17 (s, 1H) 7.27-7.32 (m, 2H) 7.34-7.41 (m, 3H) 7.69-7.71 (m, 1H) 8.56 (s, 1H).

Step 52.1: ethyl 1-(2,4-dimethoxypyrimidin-5-yl)-3-methyl-1H-pyrazole-5-carboxylate

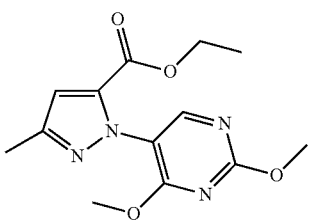

The title compound was prepared in analogy to the procedure described in Step 17.3 using 5-hydrazinyl-2,4-dimethoxypyrimidine (Step 46.8) and ethyl 2,4-dioxavalerate at 110° C. for 1 hr. The crude product was purification by silica gel column chromatography (hexane/EtOAc 10-60%). $t_R$: 4.26 min (HPLC 1); $t_R$: 0.94 min (LC-MS 2); ESI-MS: 293 [M+H]$^+$ (LC-MS 2); $R_f$=0.5 (hexane/EtOAc 1:1).

Step 52.2: ethyl 1-(2,4-dimethoxypyrimidin-5-yl)-4-iodo-3-methyl-1H-pyrazole-5-carboxylate

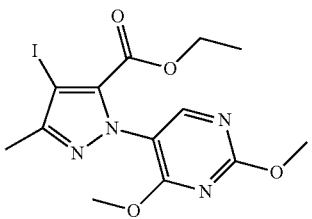

The title compound was prepared in analogy to the procedure described in Step 10.1 using ethyl 1-(2,4-dimethoxypyrimidin-5-yl)-3-methyl-1H-pyrazole-5-carboxylate (Step 52.1). $t_R$: 5.09 min (HPLC 1); $t_R$: 1.12 min (LC-MS 2); ESI-MS: 419 [M+H]$^+$ (LC-MS 2); $R_f$=0.75 (hexane/EtOAc 1:1).

Step 52.3: ethyl 4-((4-chlorophenyl)(hydroxy)methyl)-1-(2,4-dimethoxypyrimidin-5-yl)-3-methyl-1H-pyrazole-5-carboxylate

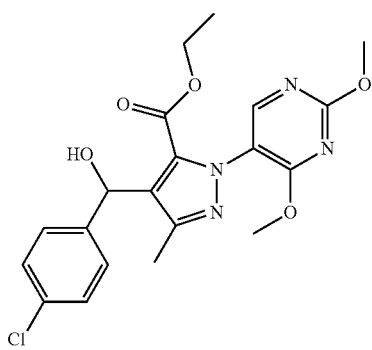 [SMILES: CCOC(=O)c1c(C(O)c2ccc(Cl)cc2)c(C)nn1-c1cnc(OC)nc1OC]

The title compound was prepared in analogy to the procedure described in Step 1.3 using ethyl 1-(2,4-dimethoxypyrimidin-5-yl)-4-iodo-3-methyl-1H-pyrazole-5-carboxylate (Step 52.2) and 4-chlorobenzaldehyde at RT for 30 min. $t_R$: 5.02 min (HPLC 1); $t_R$: 1.11 min (LC-MS 2); ESI-MS: 433 [M+H]$^+$ (LC-MS 2); $R_f$=0.38 (hexane/EtOAc 1:1).

Step 52.4: ethyl 4-((4-chlorophenyl)((1,5-dimethyl-6-oxo-1,6-dihydropyridin-3-yl)amino)methyl)-1-(2,4-dimethoxypyrimidin-5-yl)-3-methyl-1H-pyrazole-5-carboxylate

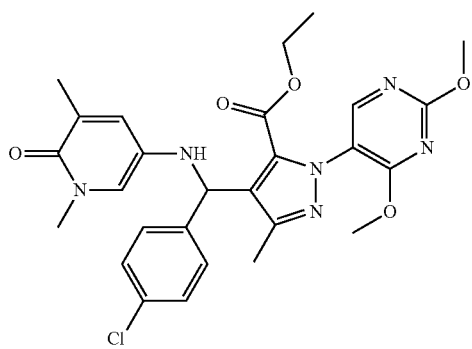 [SMILES: CCOC(=O)c1c(C(Nc2cc(C)c(=O)n(C)c2)c2ccc(Cl)cc2)c(C)nn1-c1cnc(OC)nc1OC]

The title compound was prepared in analogy to the procedure described in Step 10.3 using ethyl 4-((4-chlorophenyl)(hydroxy)methyl)-1-(2,4-dimethoxypyrimidin-5-yl)-3-methyl-1H-pyrazole-5-carboxylate (Step 52.3) and 5-amino-1,3-dimethylpyridin-2(1H)-one (Step 20.2). $t_R$: 4.74 min (HPLC 1); $t_R$: 1.09 min (LC-MS 2); ESI-MS: 553 [M+H]$^+$ (LC-MS 2); $R_f$=0.55 (CH2Cl2/MeOH 9:1).

Step 52.5: 4-((4-chlorophenyl)((1,5-dimethyl-6-oxo-1,6-dihydropyridin-3-yl)amino)methyl)-1-(2,4-dimethoxypyrimidin-5-yl)-3-methyl-1H-pyrazole-5-carboxylic acid

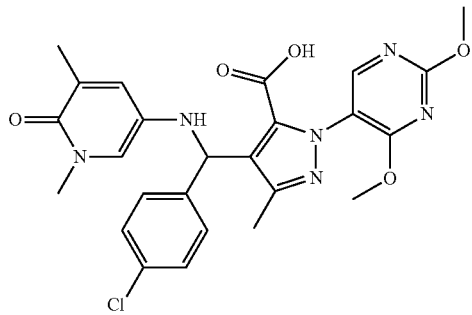 [SMILES: COc1ncc(-n2nc(C)c(C(Nc3cc(C)c(=O)n(C)c3)c3ccc(Cl)cc3)c2C(=O)O)c(OC)n1]

The title compound was prepared in analogy to the procedure described in Step 1.5 using ethyl 4-((4-chlorophenyl)((1,5-dimethyl-6-oxo-1,6-dihydropyridin-3-yl)amino)methyl)-1-(2,4-dimethoxypyrimidin-5-yl)-3-methyl-1H-pyrazole-5-carboxylate (Step 52.4). $t_R$: 3.73 min (HPLC 1); $t_R$: 0.82 min (LC-MS 2); ESI-MS: 525.2 [M+H]$^+$, ESI-MS: 523 [M–H]$^-$ (LC-MS 2).

Example 53

5-(5-chloro-1-methyl-6-oxo-1,6-dihydropyridin-3-yl)-4-(4-chlorophenyl)-1-(2,4-dimethoxypyrimidin-5-yl)-3-methyl-4,5-dihydropyrrolo[3,4-c]pyrazol-6(1H)-one

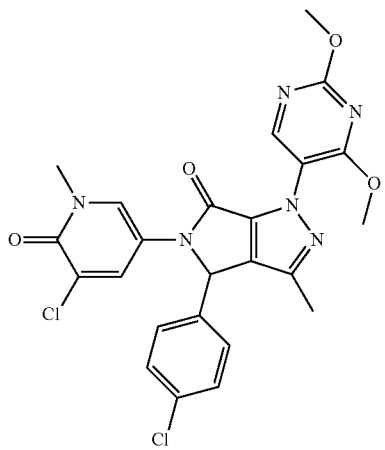 [SMILES: COc1ncc(-n2nc(C)c3c2C(=O)N(c2cc(Cl)c(=O)n(C)c2)C3c2ccc(Cl)cc2)c(OC)n1]

The title compound was prepared in analogy to the procedure described in Example 1 using 4-(((5-chloro-1-methyl-6-oxo-1,6-dihydropyridin-3-yl)amino)(4-chlorophenyl)methyl)-1-(2,4-dimethoxypyrimidin-5-yl)-3-methyl-1H-pyrazole-5-carboxylic acid (Step 52.4). $t_R$: 4.45 min (HPLC 1); $t_R$: 1.02 min (LC-MS 2); ESI-MS: 527/529 [M+H]$^+$ (LC-MS 2); $R_f$=0.41 (CH$_2$Cl$_2$/MeOH 9:1); $^1$H NMR (400 MHz, DMSO-d$_6$) δ ppm 1.99 (s, 3H) 3.41 (s, 3H) 3.93 (s, 3H) 3.96 (s, 3H) 6.21 (s, 1H) 7.30-7.36 (m, 2H) 7.38-7.44 (m, 2H) 7.87 (d, J=2.7 Hz, 1H) 7.92 (d, J=2.7 Hz, 1H) 8.56 (s, 1H).

Step 53.1: ethyl 4-(((5-chloro-1-methyl-6-oxo-1,6-dihydropyridin-3-yl)amino)(4-chlorophenyl)methyl)-1-(2,4-dimethoxypyrimidin-5-yl)-3-methyl-1H-pyrazole-5-carboxylate

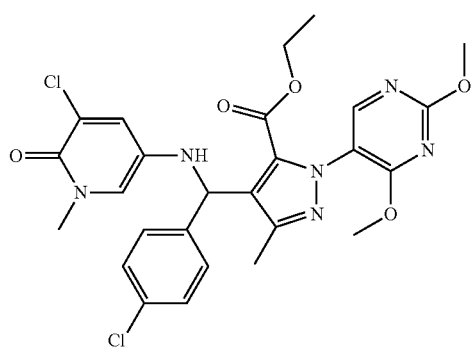 [SMILES: CCOC(=O)c1c(C(Nc2cc(Cl)c(=O)n(C)c2)c2ccc(Cl)cc2)c(C)nn1-c1cnc(OC)nc1OC]

The title compound was prepared in analogy to the procedure described in Step 10.3 using ethyl 4-((4-chlorophenyl)(hydroxy)methyl)-1-(2,4-dimethoxypyrimidin-5-yl)-3-methyl-1H-pyrazole-5-carboxylate (Step 52.3) and 5-amino-3-chloro-1-methylpyridin-2(1H)-one (Step 5.2). $t_R$: 4.89 min (HPLC 1); $t_R$: 1.12 min (LC-MS 2); ESI-MS: 573/575 [M+H]$^+$ (LC-MS 2); $R_f$=0.21 (EtOAc).

Step 53.2: 4-(((5-chloro-1-methyl-6-oxo-1,6-dihydropyridin-3-yl)amino)(4-chlorophenyl)methyl)-1-(2,4-dimethoxypyrimidin-5-yl)-3-methyl-1H-pyrazole-5-carboxylic acid

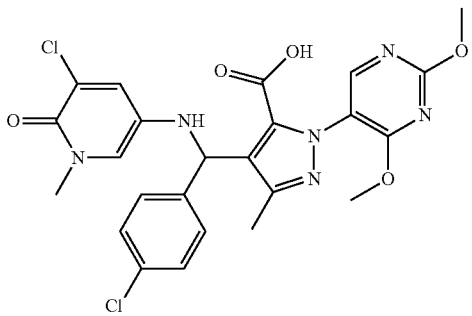 [SMILES: COc1ncc(-n2nc(C)c(C(Nc3cc(Cl)c(=O)n(C)c3)c3ccc(Cl)cc3)c2C(=O)O)c(OC)n1]

The title compound was prepared in analogy to the procedure described in Step 1.5 using ethyl 4-(((5-chloro-1-methyl-6-oxo-1,6-dihydropyridin-3-yl)amino)(4-chlorophenyl)methyl)-1-(2,4-dimethoxypyrimidin-5-yl)-3-methyl-1H-pyrazole-5-carboxylate (Step 53.1). $t_R$: 4.05 min (HPLC 1); $t_R$: 0.85 min (LC-MS 2); ESI-MS: 545/547 [M+H]$^+$, ESI-MS: 543/545 [M−H]$^−$ (LC-MS 2).

Example 54

4-(4-chlorophenyl)-2-(2,4-dimethoxypyrimidin-5-yl)-3-isopropyl-5-(3-methylbenzo-[d]isoxazol-5-yl)-4,5-dihydropyrrolo[3,4-c]pyrazol-6(2H)-one

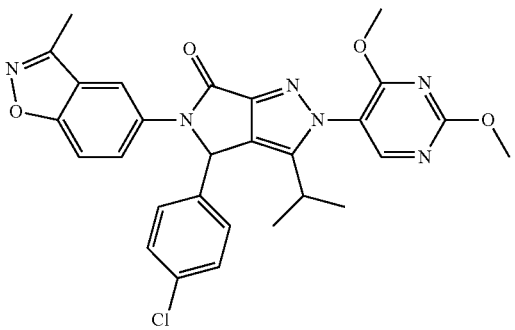 [SMILES: COc1ncc(-n2nc3c(c2C(C)C)C(c2ccc(Cl)cc2)N(c2ccc4onc(C)c4c2)C3=O)c(OC)n1]

The title compound was prepared in analogy to the procedure described in Example 1 using 4-((4-chlorophenyl)((3-methylbenzo[d]isoxazol-5-yl)amino)methyl)-1-(2,4-dimethoxypyrimidin-5-yl)-5-isopropyl-1H-pyrazole-3-carboxylic acid (Step 54.2).; $t_R$: 1.21 min (LC-MS 2); ESI-MS: 545 [M+H]$^+$ (LC-MS 2); $R_f$=0.50 (EtOAc); $^1$H NMR (400 MHz, DMSO-d$_6$) δ ppm 0.48 (d, J=6.8 Hz, 3H) 1.17 (d, J=7.0 Hz, 3H) 2.54 (s, 3H) 2.61-2.71 (m, 1H) 3.96 (s, 3H) 4.01 (s, 3H) 6.71 (s, 1H) 7.31-7.42 (m, 4H) 7.67 (d, J=8.9 Hz, 1H) 7.80 (dd, J=8.9, 2.0 Hz, 1H) 8.04 (d, J=1.8 Hz, 1H).

Step 54.1: ethyl 4-((4-chlorophenyl)((3-methylbenzo[d]isoxazol-5-yl)amino)methyl)-1-(2,4-dimethoxypyrimidin-5-yl)-5-isopropyl-1H-pyrazole-3-carboxylate

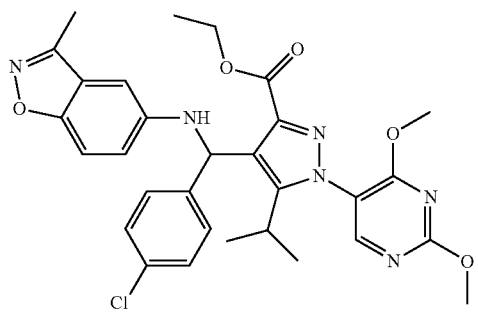 [SMILES: CCOC(=O)c1nn(-c2cnc(OC)nc2OC)c(C(C)C)c1C(Nc1ccc2onc(C)c2c1)c1ccc(Cl)cc1]

The title product was prepared in analogy to the procedure described in Step 46.12 using ethyl 4-((4-chlorophenyl)(hydroxy)methyl)-1-(2,4-dimethoxypyrimidin-5-yl)-5-isopropyl-1H-pyrazole-3-carboxylate (Step 46.11) and 3-methyl-5-nitrobenzo[d]isoxazole (Step 33.3). $t_R$: 1.34 min (LC-MS 2); ESI-MS: 591 [M+H]$^+$ (LC-MS 2); $R_f$=0.25 (hexane/EtOAc 1:1).

Step 54.2: 4-((4-chlorophenyl)((3-methylbenzo[d]isoxazol-5-yl)amino)methyl)-1-(2,4-dimethoxypyrimidin-5-yl)-5-isopropyl-1H-pyrazole-3-carboxylic acid

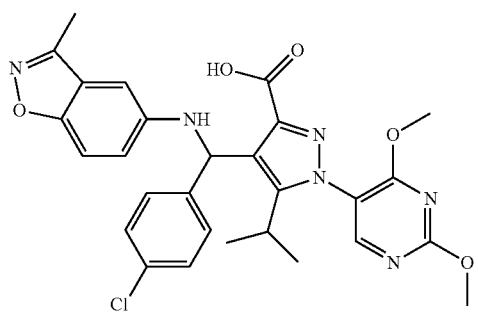 [SMILES: COc1ncc(-n2nc(C(=O)O)c(C(Nc3ccc4onc(C)c4c3)c3ccc(Cl)cc3)c2C(C)C)c(OC)n1]

The title product was prepared in analogy to the procedure described in Step 46.13 using ethyl 4-((4-chlorophenyl)((3-methylbenzo[d]isoxazol-5-yl)amino)methyl)-1-(2,4-dimethoxypyrimidin-5-yl)-5-isopropyl-1H-pyrazole-3-carboxylate (Step 54.1). $t_R$: 1.16 min (LC-MS 2); ESI-MS: 563 [M+H]$^+$; ESI-MS: 561 [M−H]$^−$ (LC-MS 2).

Example 55

5-(5-chloro-1-methyl-6-oxo-1,6-dihydropyridin-3-yl)-4-(4-chlorophenyl)-2-(2,4-dimethoxypyrimidin-5-yl)-3-methyl-4,5-dihydropyrrolo[3,4-c]pyrazol-6(2H)-one

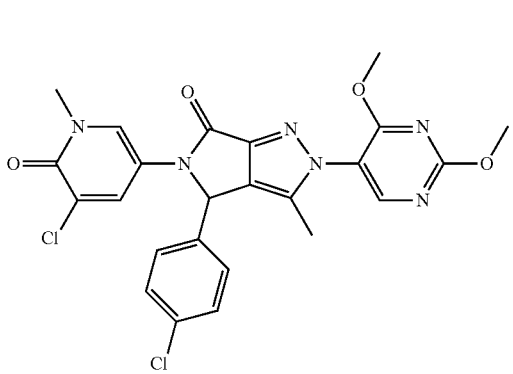 [SMILES: COc1ncc(-n2nc3c(c2C)C(c2ccc(Cl)cc2)N(c2cc(Cl)c(=O)n(C)c2)C3=O)c(OC)n1]

The title compound was prepared in analogy to the procedure described in Example 1 using 4-(((5-chloro-1-methyl-6-oxo-1,6-dihydropyridin-3-yl)amino)(4-chlorophenyl)methyl)-1-(2,4-dimethoxypyrimidin-5-yl)-5-methyl-1H-pyrazole-3-carboxylic acid (Step 55.5). $t_R$: 4.30 min (HPLC 1); $t_R$: 0.98 min (LC-MS 2); ESI-MS: 527/529 [M+H]$^+$ (LC-MS 2); $R_f$=0.37 (CH$_2$Cl$_2$/MeOH 9:1); $^1$H NMR (400 MHz, DMSO-d$_6$) δ ppm 1.91 (s, 3H) 3.44 (s, 3H) 3.92 (s, 3H) 3.96 (s, 3H) 6.24 (s, 1H) 7.29-7.42 (m, 4H) 7.93 (d, J=2.7 Hz, 1H) 7.97 (d, J=2.4 Hz, 1H) 8.53 (s, 1H).

Step 55.1: ethyl 1-(2,4-dimethoxypyrimidin-5-yl)-5-methyl-1H-pyrazole-3-carboxylate

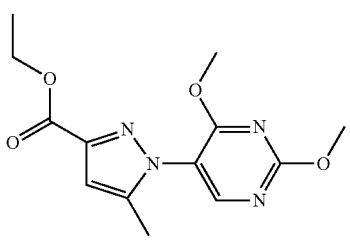 [SMILES: CCOC(=O)c1cc(C)n(-c2cnc(OC)nc2OC)n1]

The title compound was prepared in analogy to the procedure described in Step 17.3 using 5-hydrazinyl-2,4-dimethoxypyrimidine (Step 46.8) and ethyl 2,4-dioxavalerate at 110° C. for 1 hr. Purification by silica gel column chromatography (Hexane/EtOAc 10-60%) afforded the title product. $t_R$: 3.98 min (HPLC 1); $t_R$: 0.88 min (LC-MS 2); ESI-MS: 293 [M+H]$^+$ (LC-MS 2); $R_f$=0.36 (hexane/EtOAc 1:1).

Step 55.2: ethyl 1-(2,4-dimethoxypyrimidin-5-yl)-4-iodo-5-methyl-1H-pyrazole-3-carboxylate

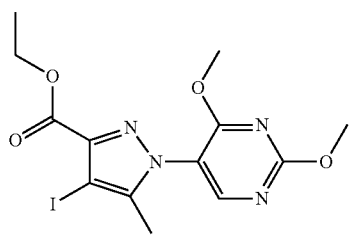 [SMILES: CCOC(=O)c1nn(-c2cnc(OC)nc2OC)c(C)c1I]

The title compound was prepared in analogy to the procedure described in Step 10.1 using ethyl 1-(2,4-dimethoxypyrimidin-5-yl)-3-methyl-1H-pyrazole-5-carboxylate (Step 52.1). $t_R$: 5.09 min (HPLC 1); $t_R$: 1.12 min (LC-MS 2); ESI-MS: 419 [M+H]⁺ (LC-MS 2); $R_f$=0.75 (hexane/EtOAc 1:1).

Step 55.3: ethyl 4-((4-chlorophenyl)(hydroxy)methyl)-1-(2,4-dimethoxypyrimidin-5-yl)-5-methyl-1H-pyrazole-3-carboxylate

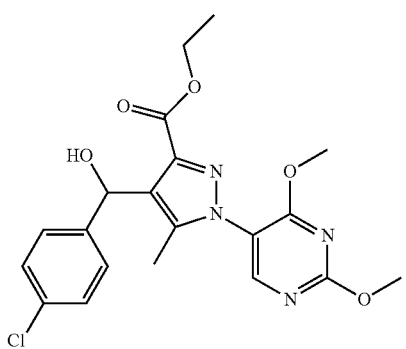 [SMILES: CCOC(=O)c1nn(-c2cnc(OC)nc2OC)c(C)c1C(O)c1ccc(Cl)cc1]

The title compound was prepared in analogy to the procedure described in Step 1.3 using ethyl 1-(2,4-dimethoxypyrimidin-5-yl)-4-iodo-5-methyl-1H-pyrazole-3-carboxylate (Step 55.2) and 4-chlorobenzaldehyde at RT for 30 min. $t_R$: 4.92 min (HPLC 1); $t_R$: 1.09 min (LC-MS 2); ESI-MS: 433 [M+H]⁺ (LC-MS 2); $R_f$=0.24 (Hexane/EtOAc 1:1).

Step 55.4: ethyl 4-(((5-chloro-1-methyl-6-oxo-1,6-dihydropyridin-3-yl)amino)(4-chlorophenyl)-methyl)-1-(2,4-dimethoxypyrimidin-5-yl)-5-methyl-1H-pyrazole-3-carboxylate

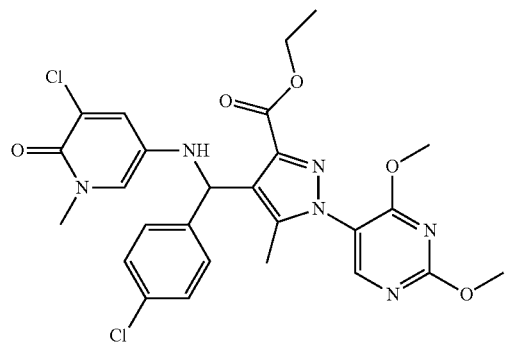

The title compound was prepared in analogy to the procedure described in Step 10.3 using ethyl 4-((4-chlorophenyl)(hydroxy)methyl)-1-(2,4-dimethoxypyrimidin-5-yl)-5-methyl-1H-pyrazole-3-carboxylate (Step 55.3) and 5-amino-3-chloro-1-methylpyridin-2(1H)-one (Step 5.2). $t_R$: 4.76 min (HPLC 1); $t_R$: 1.09 min (LC-MS 2); ESI-MS: 573/575 [M+H]⁺ (LC-MS 2); $R_f$=0.18 (EtOAc).

Step 55.5: 4-(((5-chloro-1-methyl-6-oxo-1,6-dihydropyridin-3-yl)amino)(4-chlorophenyl)methyl)-1-(2,4-dimethoxypyrimidin-5-yl)-5-methyl-1H-pyrazole-3-carboxylic acid

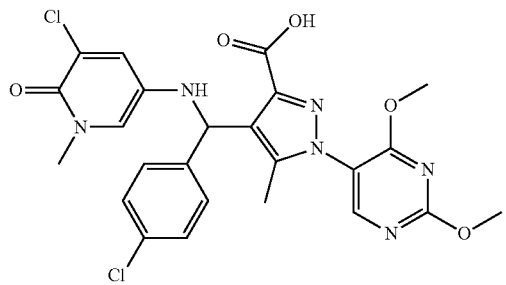 [SMILES: COc1ncc(-n2nc(C(=O)O)c(C(Nc3cc(Cl)c(=O)n(C)c3)c3ccc(Cl)cc3)c2C)c(OC)n1]

The title compound was prepared in analogy to the procedure described in Step 1.5 using ethyl 4-(((5-chloro-1-methyl-6-oxo-1,6-dihydropyridin-3-yl)amino)(4-chlorophenyl)methyl)-1-(2,4-dimethoxypyrimidin-5-yl)-5-methyl-1H-pyrazole-3-carboxylate (Step 55.4). $t_R$: 3.99 min (HPLC 1); $t_R$: 0.85 min (LC-MS 2); ESI-MS: 545/547 [M+H]⁺, ESI-MS: 543/545 [M−H]⁻ (LC-MS 2).

Example 56

4-(4-chlorophenyl)-2-(2,4-dimethoxypyrimidin-5-yl)-5-(1,5-dimethyl-6-oxo-1,6-dihydropyridin-3-yl)-3-methyl-4,5-dihydropyrrolo[3,4-c]pyrazol-6(2H)-one

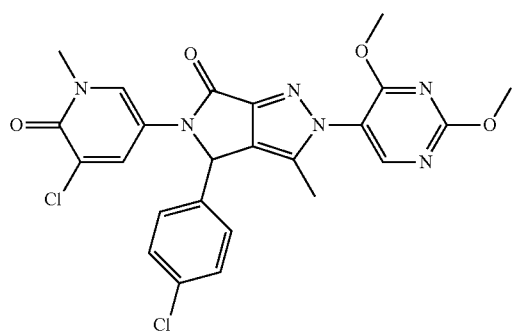 [SMILES: COc1ncc(-n2nc3c(c2C)C(c2ccc(Cl)cc2)N(c2cc(Cl)c(=O)n(C)c2)C3=O)c(OC)n1]

The title compound was prepared in analogy to the procedure described in Example 1 using 4-((4-chlorophenyl)((1,5-dimethyl-6-oxo-1,6-dihydropyridin-3-yl)amino)methyl)-1-(2,4-dimethoxypyrimidin-5-yl)-5-methyl-1H-pyrazole-3-carboxylic acid (Step 56.2). $t_R$: 4.10 min (HPLC 1); $t_R$: 0.94 min (LC-MS 2); ESI-MS: 507 [M+H]⁺ (LC-MS 2); $R_f$=0.44 (CH₂Cl₂/MeOH 9:1); ¹H NMR (400 MHz, DMSO-d₆) δ ppm 1.88-1.95 (m, 6H) 3.35 (s, 3H) 3.92 (s, 3H) 3.96 (s, 3H) 6.21 (s, 1H) 7.26-7.33 (m, 2H) 7.35-7.44 (m, 3H) 7.75 (d, J=2.7 Hz, 1H) 8.53 (d, J=0.8 Hz, 1H).

151

Step 56.1: ethyl 4-((4-chlorophenyl)((1,5-dimethyl-6-oxo-1,6-dihydropyridin-3-yl)amino)methyl)-1-(2,4-dimethoxypyrimidin-5-yl)-5-methyl-1H-pyrazole-3-carboxylate

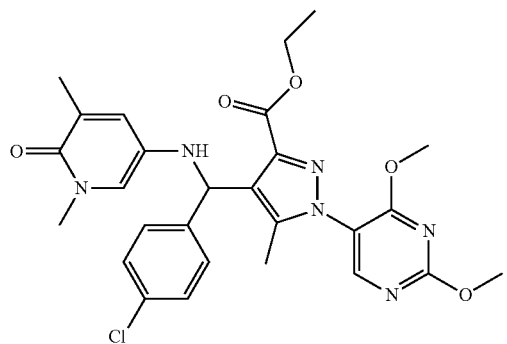 [SMILES: CCOC(=O)c1nn(-c2cnc(OC)nc2OC)c(C)c1C(Nc1cc(C)c(=O)n(C)c1)c1ccc(Cl)cc1]

The title compound was prepared in analogy to the procedure described in Step 10.3 using ethyl 4-((4-chlorophenyl)(hydroxy)methyl)-1-(2,4-dimethoxypyrimidin-5-yl)-5-methyl-1H-pyrazole-3-carboxylate (Step 55.3) and 5-amino-1,3-dimethylpyridin-2(1H)-one (Step 20.2). $t_R$: 4.59 min (HPLC 1); $t_R$: 1.06 min (LC-MS 2); ESI-MS: 553 [M+H]$^+$ (LC-MS 2); $R_f$=0.40 (CH$_2$Cl$_2$/MeOH 9:1).

Step 56.2: 4-((4-chlorophenyl)((1,5-dimethyl-6-oxo-1,6-dihydropyridin-3-yl)amino)methyl)-1-(2,4-dimethoxypyrimidin-5-yl)-5-methyl-1H-pyrazole-3-carboxylic acid

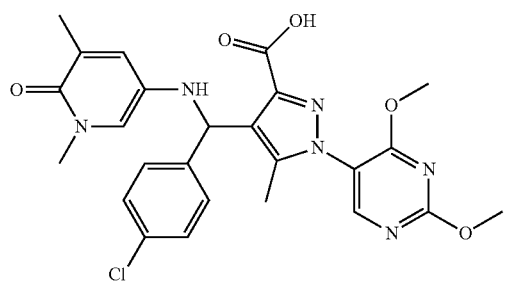 [SMILES: COc1ncc(-n2nc(C(=O)O)c(C(Nc3cc(C)c(=O)n(C)c3)c3ccc(Cl)cc3)c2C)c(OC)n1]

The title compound was prepared in analogy to the procedure described in Step 1.5 using ethyl 4-((4-chlorophenyl)((1,5-dimethyl-6-oxo-1,6-dihydropyridin-3-yl)amino)methyl)-1-(2,4-dimethoxypyrimidin-5-yl)-5-methyl-1H-pyrazole-3-carboxylate (Step 56.1). $t_R$: 3.75 min (HPLC 1); $t_R$: 0.87 min (LC-MS 2); ESI-MS: 525 [M+H]$^+$, ESI-MS: 523 [M−H]$^-$ (LC-MS 2).

152

Example 57

4-(4-chlorophenyl)-5-(1,5-dimethyl-6-oxo-1,6-dihydropyridin-3-yl)-1,3-dimethyl-4,5-dihydropyrrolo[3,4-c]pyrazol-6(1H)-one

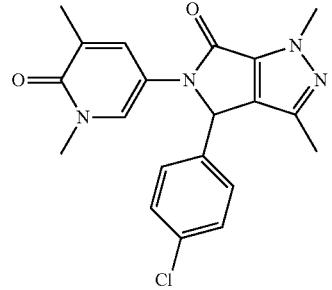 [SMILES: Cc1nn(C)c2c1C(c1ccc(Cl)cc1)N(c1cc(C)c(=O)n(C)c1)C2=O]

To a stirred solution of 5-(3-acetyl-2-(4-chlorophenyl)-4-hydroxy-5-oxo-2,5-dihydro-1H-pyrrol-1-yl)-1,3-dimethylpyridin-2(1H)-one (Step 57.1) (500 mg, 1.341 mmol) in toluene (5 mL) and EtOH (5 mL) was added methyl hydrazine (0.353 mL, 6.71 mmol) and the reaction mixture was heated up and stirred at 110° C. for 18 hr. The reaction was concentrated under reduced pressure. The resulting mixture was diluted with AcOH (10 ml), heated up and stirred at 100° C. for 1 hr, concentrated under reduced pressure and quenched with a saturated aqueous NaHCO$_3$ solution. The aqueous layer was extracted with CH$_2$Cl$_2$. The combined organic layers were dried over Na$_2$SO$_4$ and evaporated under reduced pressure. The crude product was purified by silica gel column chromatography eluting with EtOAc. Trituration in Et$_2$O afforded the title product (191 mg, 0.499 mmol, 37% yield) as white solid. $t_R$: 3.83 min (HPLC 1); $t_R$: 0.91 min (LC-MS 2); ESI-MS: 383 [M+H]$^+$ (LC-MS 2); $R_f$=0.09 (EtOAc); $^1$H NMR (400 MHz, DMSO-d$_6$) δ ppm 1.83-1.97 (m, 6H) 3.33 (s, 3H) 3.89 (s, 3H) 6.04 (s, 1H) 7.24 (d, J=8.2 Hz, 2H) 7.30-7.37 (m, 3H) 7.69 (d, J=2.7, Hz, 1H).

Step 57.1: 5-(3-acetyl-2-(4-chlorophenyl)-4-hydroxy-5-oxo-2,5-dihydro-1H-pyrrol-1-yl)-1,3-dimethylpyridin-2(1H)-one

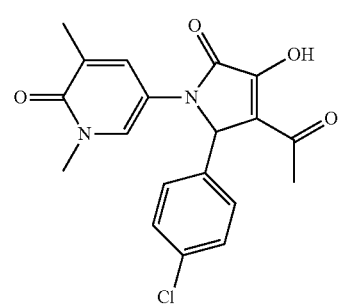 [SMILES: CC(=O)C1=C(O)C(=O)N(c2cc(C)c(=O)n(C)c2)C1c1ccc(Cl)cc1]

A round-bottomed flask was charged 5-amino-1,3-dimethylpyridin-2(1H)-one (Step 20.2) (3 g, 21.71 mmol), 4-chlorobenzaldehyde (2.348 g, 16.70 mmol) and ethyl 2,4-dioxovalerate (3.17 g, 20.04 mmol) in AcOH (50 mL) and the reaction mixture was heated up and stirred at 125° C. for 1 hr. The reaction mixture was concentrated under reduced pressure, quenched with a saturated aq. NaHCO$_3$ solution, extracted with EtOAc. The organic layer was discarded and the aq. phase was adjusted to pH 1-2, extracted EtOAc. The combined organic layers were dried over Na$_2$SO$_4$ and concentrated under reduced pressure to afford the title product (3.82 g, 8.71 mmol, 52% yield) as a black solid. $t_R$: 3.54 min (HPLC 1); $t_R$: 0.75 min (LC-MS 2); ESI-MS: 373 [M+H]$^+$ (LC-MS 2).

Example 58

5-(5-chloro-1-methyl-6-oxo-1,6-dihydropyridin-3-yl)-4-(4-chlorophenyl)-1,3-dimethyl-4,5-dihydropyrrolo[3,4-c]pyrazol-6(1H)-one

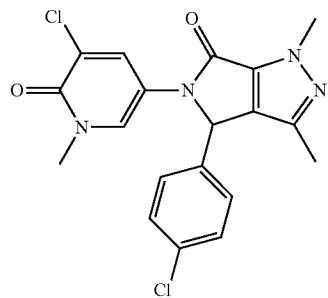 [SMILES: Cc1nn(C)c2c1C(c1ccc(Cl)cc1)N(c1cc(Cl)c(=O)n(C)c1)C2=O]

To a stirred solution of 5-(3-acetyl-2-(4-chlorophenyl)-4-hydroxy-5-oxo-2,5-dihydro-1H-pyrrol-1-yl)-3-chloro-1-methylpyridin-2(1H)-one (Step 57.1) (300 mg, 0.763 mmol) in AcOH (5 mL) was added methyl hydrazine (0.201 mL, 3.81 mmol) and the reaction mixture was stirred for 18 hr at 100° C. The reaction mixture was concentrated under reduced pressure, quenched with a saturated aq. NaHCO$_3$ solution and extracted with CH$_2$Cl$_2$. The combined organic layers were dried over Na$_2$SO$_4$ and evaporated under reduced pressure. The crude product was purified by silica gel column chromatography eluting with EtOAc. Trituration in Et$_2$O/CH$_2$Cl$_2$ (9:1) afforded the title product (60 mg, 0.149 mmol, 20% yield) as white solid. $t_R$: 4.05 min (HPLC 1); $t_R$: 0.95 min (LC-MS 2); ESI-MS: 403/405 [M+H]$^+$ (LC-MS 2); $R_f$=0.24 (EtOAc); $^1$H NMR (400 MHz, DMSO-d$_6$) δ ppm 1.89 (s, 3H) 3.41 (s, 3H) 3.89 (s, 3H) 6.07 (s, 1H) 7.26 (d, J=8.2 Hz, 2H) 7.35 (d, J=8.2 Hz, 2H) 7.86 (d, J=2.0 Hz, 1H) 7.90 (d, J=2.3 Hz, 1H).

Step 58.1: 5-(3-acetyl-2-(4-chlorophenyl)-4-hydroxy-5-oxo-2,5-dihydro-1H-pyrrol-1-yl)-3-chloro-1-methylpyridin-2(1H)-one

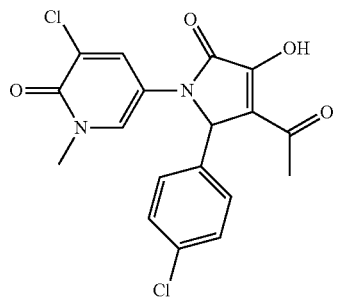 [SMILES: CC(=O)C1=C(O)C(=O)N(c2cc(Cl)c(=O)n(C)c2)C1c1ccc(Cl)cc1]

The title compound was prepared in analogy to the procedure described in Step 57.1 using 5-amino-3-chloro-1-methylpyridin-2(1H)-one (Step 5.2), 4-chlorobenzaldehyde and ethyl 2,4-dioxovalerate at 120° C. for 1 hr. $t_R$: 3.73 min (HPLC 1); $t_R$: 0.74 min (LC-MS 2); ESI-MS: 393/395 [M+H]$^+$ (LC-MS 2).

Example 59

4-(4-chlorophenyl)-5-(1,5-dimethyl-6-oxo-1,6-dihydropyridin-3-yl)-1-(2-methoxypyrimidin-4-yl)-3-methyl-4,5-dihydropyrrolo[3,4-c]pyrazol-6(1H)-one

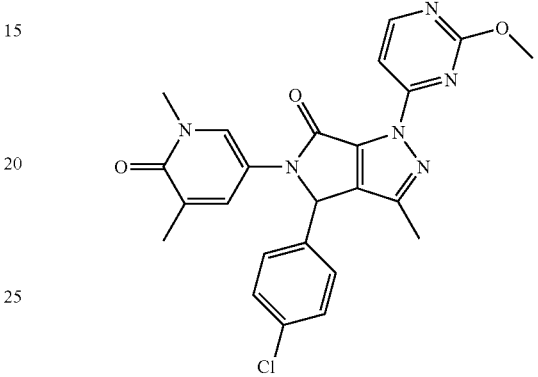

The title compound was prepared in analogy to the procedure described in Example 1 using 4-((4-chlorophenyl)((1,5-dimethyl-6-oxo-1,6-dihydropyridin-3-yl)amino)methyl)-1-(2-methoxypyrimidin-4-yl)-3-methyl-1H-pyrazole-5-carboxylic acid (Step 59.2). Purification by preparative achiral SFC (Silica, gradient 20%-25% in 6 min_total 11 min). $t_R$: 4.24 min (HPLC 1); $t_R$: 1.01 min (LC-MS 2); ESI-MS: 477 [M+H]$^+$ (LC-MS 2); $R_f$=0.44 (CH$_2$Cl$_2$/MeOH 9:1); $^1$H NMR (400 MHz, DMSO-d$_6$) δ ppm 1.91 (s, 3H) 2.02 (s, 3H) 3.36 (s, 3H) 4.04 (s, 3H) 6.18 (s, 1H) 7.29-7.42 (m, 5H) 7.69-7.76 (m, 2H) 8.64-8.70 (m, 1H).

Step 59.1: 4-hydrazinyl-2-methoxypyrimidine

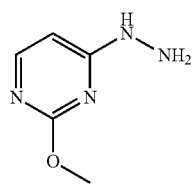

To a stirred solution of 4-chloro-2-methoxypyrimidine (5.7 g, 39.4 mmol) in EtOH (100 mL) under Ar was added hydrazine hydrate (3.83 mL, 79 mmol) and the reaction mixture was heated up and stirred at 85° C. for 1 hr. Volatiles were removed under reduced pressure and the resulting crude material was purified by silica gel column chromatography (CH$_2$Cl$_2$/MeOH/1-5%/NH$_3$ 1%) to afford the title product (4.40 g, 31.4 mmol, 80% yield) as white solid. ESI-MS: 141 [M+H]$^+$ (LC-MS 2); $R_f$=0.47 (CH$_2$Cl$_2$/MeOH 9:1).

Step 59.2: ethyl 1-(2-methoxypyrimidin-4-yl)-3-methyl-1H-pyrazole-5-carboxylate

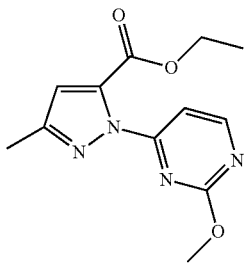 [SMILES: CCOC(=O)c1cc(C)nn1-c1ccnc(OC)n1]

The title product was prepared in analogy to the procedure described in Example 57 using 4-hydrazinyl-2-methoxypyrimidine (Step 59.1). $t_R$: 4.28 min (HPLC 1); $t_R$: 0.93 min (LC-MS 2); ESI-MS: 263 [M+H]$^+$ (LC-MS 2); $R_f$=0.58 (hexane/EtOAc 1:1).

Step 59.3: ethyl 4-iodo-1-(2-methoxypyrimidin-4-yl)-3-methyl-1H-pyrazole-5-carboxylate

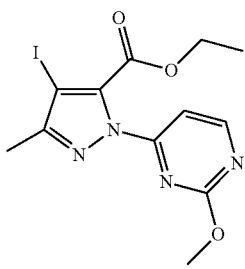 [SMILES: CCOC(=O)c1c(I)c(C)nn1-c1ccnc(OC)n1]

The title compound was prepared in analogy to the procedure described in Step 10.1 using ethyl 1-(2-methoxypyrimidin-4-yl)-3-methyl-1H-pyrazole-5-carboxylate (Step 59.2) at 85° C. for 1 hr. $t_R$: 5.27 min (HPLC 1); $t_R$: 1.18 min (LC-MS 2); ESI-MS: 389 [M+H]$^+$ (LC-MS 2); $R_f$=0.81 (hexane/EtOAc 1:1).

Step 59.4: ethyl 4-((4-chlorophenyl)(hydroxy)methyl)-1-(2-methoxypyrimidin-4-yl)-3-methyl-1H-Pyrazole-5-carboxylate

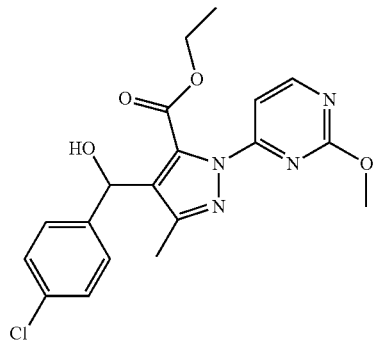 [SMILES: CCOC(=O)c1c(C(O)c2ccc(Cl)cc2)c(C)nn1-c1ccnc(OC)n1]

The title compound was prepared in analogy to the procedure described in Step 1.3 using ethyl 4-iodo-1-(2-methoxypyrimidin-4-yl)-3-methyl-1H-pyrazole-5-carboxylate (Step 59.3) and 4-chlorobenzaldehyde at RT for 60 min. $t_R$: 5.20 min (HPLC 1); $t_R$: 1.18 min (LC-MS 2); ESI-MS: 403 [M+H]$^+$ (LC-MS 2); $R_f$=0.44 (hexane/EtOAc 1:1).

Step 59.5: ethyl 4-((4-chlorophenyl)((1,5-dimethyl-6-oxo-1,6-dihydropyridin-3-yl)amino)methyl)-1-(2-methoxypyrimidin-4-yl)-3-methyl-1H-pyrazole-5-carboxylate

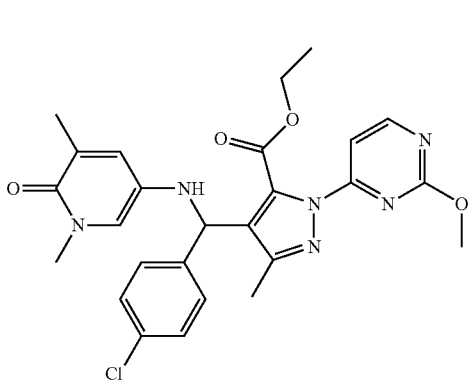 [SMILES: CCOC(=O)c1c(C(Nc2cc(C)c(=O)n(C)c2)c2ccc(Cl)cc2)c(C)nn1-c1ccnc(OC)n1]

The title compound was prepared in analogy to the procedure described in Step 10.3 using ethyl 4-((4-chlorophenyl)(hydroxy)methyl)-1-(2-methoxypyrimidin-4-yl)-3-methyl-1H-pyrazole-5-carboxylate (Step 59.4) and 5-amino-1,3-dimethylpyridin-2(1H)-one (Step 20.2). $t_R$: 4.90 min (HPLC 1); $t_R$: 1.15 min (LC-MS 2); ESI-MS: 523 [M+H]$^+$ (LC-MS 2); $R_f$=0.47 (CH$_2$Cl$_2$/MeOH 9:1).

Step 59.6: 4-((4-chlorophenyl)((1,5-dimethyl-6-oxo-1,6-dihydropyridin-3-yl)amino)methyl)-1-(2-methoxypyrimidin-4-yl)-3-methyl-1H-pyrazole-5-carboxylic acid

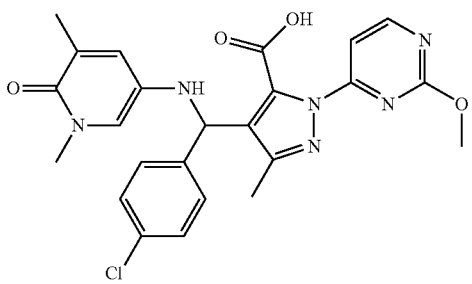 [SMILES: COc1nccc(-n2nc(C)c(C(Nc3cc(C)c(=O)n(C)c3)c3ccc(Cl)cc3)c2C(=O)O)n1]

The title compound was prepared in analogy to the procedure described in Step 1.5 using ethyl 4-((4-chlorophenyl)((1,5-dimethyl-6-oxo-1,6-dihydropyridin-3-yl)amino)methyl)-1-(2-methoxypyrimidin-4-yl)-3-methyl-1H-pyrazole-5-carboxylate (Step 59.5) for 2 hr at RT. $t_R$: 0.92 min (LC-MS 2); ESI-MS: 493 [M+H]$^+$, ESI-MS: 491 [M−H]$^-$ (LC-MS 2).

Example 60

4-(4-chlorophenyl)-1-(2,4-dimethoxypyrimidin-5-yl)-5-(1,5-dimethyl-6-oxo-1,6-dihydropyridin-3-yl)-3-ethyl-4,5-dihydropyrrolo[3,4-c]pyrazol-6(1H)-one

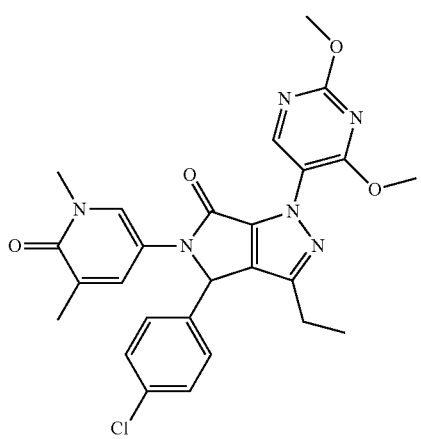 [SMILES: CCc1nn(-c2cnc(OC)nc2OC)c2c1C(c1ccc(Cl)cc1)N(c1cc(C)c(=O)n(C)c1)C2=O]

To a solution of 5-hydrazinyl-2,4-dimethoxypyrimidine hydrochloride (Step 46.8) (413 mg, 2 mmol) in MeOH (5 mL) were added NaOAc (123 mg, 1.5 mmol), sulfamic acid (99 mg, 1 mmol) and 5-(4-chlorophenyl)-1-(1,5-dimethyl-6-oxo-1,6-dihydropyridin-3-yl)-4-propionylpyrrolidine-2,3-dione (Step 60.1) (204 mg, 0.5 mmol) and the reaction mixture was stirred for 2.5 hr at 100° C. in the MW. The reaction mixture was added to a saturated aq. NaHCO$_3$ solution and the aq. layer was extracted with EtOAc. Combined extracts were washed with brine, dried over MgSO$_4$, filtered and concentrated under reduced pressure. The crude material was purified by silica gel column chromatography (hexane/EtOAc/MeOH 80:20:2 to 0:10:1) followed by preparative HPLC to afford, after crystallization from THF/Et$_2$O, the title product (68 mg, 0.124 mmol, 25% yield) as a solid. t$_R$: 1.03 min (LC-MS 2); ESI-MS: 521 [M+H]$^+$ (LC-MS 2); R$_f$=0.36 (EtOAc/MeOH 9:1); $^1$H NMR (400 MHz, DMSO-d$_6$) δ ppm 0.95 (t, J=7.8 Hz, 3H) 1.92 (s, 3H) 2.36 (m, 1H) 2.44 (m, 1H) 3.33 (s, 3H) 3.96 (s, 3H) 3.99 (s, 3H) 6.24 (m, 1H) 7.34 (m, 2H) 7.37-7.45 (m, 3H) 7.72 (s, 1H) 8.59 (s, 1H).

Step 60.1: 5-(4-chlorophenyl)-1-(1,5-dimethyl-6-oxo-1,6-dihydropyridin-3-yl)-4-propionylpyrrolidine-2,3-dione

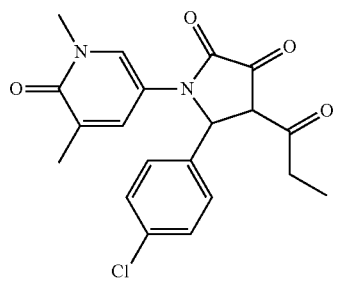 [SMILES: CCC(=O)C1C(=O)C(=O)N(c2cc(C)c(=O)n(C)c2)C1c1ccc(Cl)cc1]

The title compound was prepared in analogy to the procedure described in Step 57.1 using 5-amino-1,3-dimethylpyridin-2(1H)-one (Step 20.2), 4-chlorobenzaldehyde and ethyl 2,4-dioxohexanoate under reflux for 7 hr. The crude product was purified by silica gel chromatography (hexane/CH$_2$Cl$_2$/MeOH 40:60:10 to 0:60:10). t$_R$: 0.82 min (LC-MS 2); ESI-MS: 387 [M+H]$^+$ (LC-MS 2).

Reference Example 61

(S)-4-(4-chlorophenyl)-2-(2,4-dimethoxypyrimidin-5-yl)-5-(3,7-dimethylbenzo[d]isoxazol-5-yl)-3-isopropyl-4,5-dihydropyrrolo[3,4-c]pyrazol-6(2H)-one

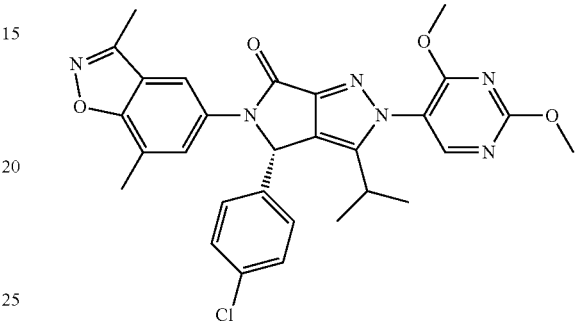

The title compound (153 mg, 0.271 mmol, 47% yield) was obtained enantiomerically pure (ee>99.5%) after chiral preparative chromatography (Chiralcel OD-H, 250×30 mm I.D; mobile phase: scCO$_2$/EtOH 40% isocratic in 5 min; flow: 45 mL/min; detection 220 nm) of the racemic mixture of 4-(4-chlorophenyl)-2-(2,4-dimethoxypyrimidin-5-yl)-5-(3,7-dimethylbenzo[d]isoxazol-5-yl)-3-isopropyl-4,5-dihydropyrrolo[3,4-c]pyrazol-6(2H)-one (Example 46) (320 mg, 0.572 mmol). t$_R$: 1.25 min (LC-MS 2); ESI-MS: 559 [M+H]$^+$ (LC-MS 2).

Example 62

(R)-4-(4-chlorophenyl)-2-(2,4-dimethoxypyrimidin-5-yl)-5-(3,7-dimethylbenzo[d]-isoxazol-5-yl)-3-isopropyl-4,5-dihydropyrrolo[3,4-c]pyrazol-6(2H)-one

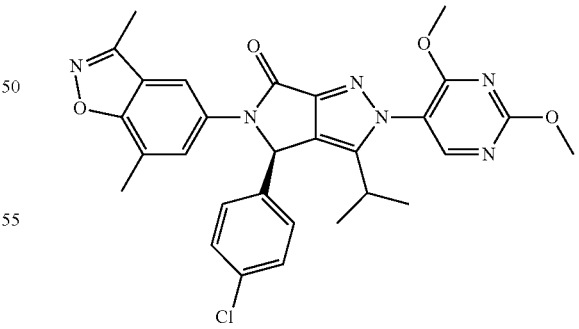

The title compound (159 mg, 0.282 mmol, 49% yield) was obtained enantiomerically pure (ee 99.6%) after chiral preparative chromatography (Chiralcel OD-H, 250×30 mm I.D; mobile phase: scCO$_2$/EtOH 40% isocratic in 5 min; flow: 45 mL/min; detection 220 nm) of the racemic mixture of 4-(4-chlorophenyl)-2-(2,4-dimethoxypyrimidin-5-yl)-5-(3,7-dimethylbenzo[d]isoxazol-5-yl)-3-isopropyl-4,5-dihydropyrrolo[3,4-c]pyrazol-6(2H)-one (Example 46) (320 mg, 0.572 mmol). $t_R$: 1.25 min (LC-MS 2); ESI-MS: 559 [M+H]$^+$ (LC-MS 2).

Example 63

4-(4-chlorophenyl)-5-(1,5-dimethyl-6-oxo-1,6-dihydropyridin-3-yl)-1-isopropyl-3-methyl-4,5-dihydropyrrolo[3,4-c]pyrazol-6(1H)-one

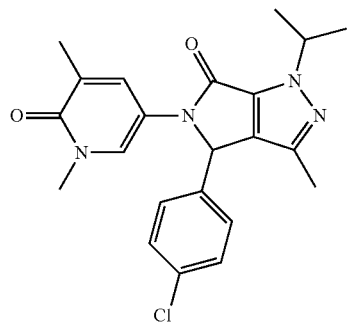 [SMILES: Cc1nn(C(C)C)c2c1C(c1ccc(Cl)cc1)N(c1cc(C)c(=O)n(C)c1)C2=O]

The title compound was prepared in analogy to the procedure described in Example 58 using 5-(3-acetyl-2-(4-chlorophenyl)-4-hydroxy-5-oxo-2,5-dihydro-1H-pyrrol-1-yl)-3-chloro-1-methyl-pyridin-2(1H)-one (Step 57.1) and isopropylhydrazine hydrochloride. The crude material was purified by preparative achiral SFC (column 4-Ethyl-pyridine, gradient 6-11% in 6 min_total 11 min). $t_R$: 4.45 min (HPLC 1); $t_R$: 1.02 min (LC-MS 2); ESI-MS: 411 [M+H]$^+$ (LC-MS 2); $R_f$=0.30 (EtOAc); $^1$H NMR (400 MHz, DMSO-d$_6$) δ ppm 1.43-1.54 (m, 6H) 1.93 (s, 6H) 3.36 (s, 3H) 4.66-4.80 (m, 1H) 6.07 (s, 1H) 7.25 (d, J=8.2 Hz, 2H) 7.34-7.42 (m, 3H) 7.73 (d, J=2.7 Hz, 1H).

Example 64

4-(4-chlorophenyl)-5-(1,5-dimethyl-6-oxo-1,6-dihydropyridin-3-yl)-2-isopropyl-3-methyl-4,5-dihydropyrrolo[3,4-c]pyrazol-6(2H)-one

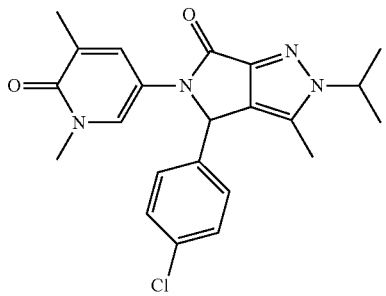 [SMILES: Cc1cc(N2C(=O)c3nn(C(C)C)c(C)c3C2c2ccc(Cl)cc2)cn(C)c1=O]

The title compound was prepared in analogy to the procedure described in Example 58 using 5-(3-acetyl-2-(4-chlorophenyl)-4-hydroxy-5-oxo-2,5-dihydro-1H-pyrrol-1-yl)-3-chloro-1-methyl-pyridin-2(1H)-one (Step 57.1) and isopropylhydrazine hydrochloride. The crude material was purified by preparative achiral SFC (column NH$_2$, gradient 16-21% in 6 min_total 11 min). $t_R$: 4.22 min (HPLC 1); $t_R$: 0.96 min (LC-MS 2); ESI-MS: 411 [M+H]$^+$ (LC-MS 2); $R_f$=0.12 (EtOAc); $^1$H NMR (400 MHz, DMSO-d$_6$) δ ppm 1.35-1.45 (m, 6H) 1.92 (s, 3H) 2.08 (s, 3H) 3.36 (s, 3H) 4.52-4.62 (m, 1H) 6.09 (s, 1H) 7.25 (d, J=8.6 Hz, 2H) 7.33-7.41 (m, 3H) 7.70 (d, J=2.0 Hz, 1H).

Example 65

5-(5-chloro-1-methyl-6-oxo-1,6-dihydropyridin-3-yl)-4-(4-chlorophenyl)-2-isopropyl-3-methyl-4,5-dihydropyrrolo[3,4-c]pyrazol-6(2H)-one

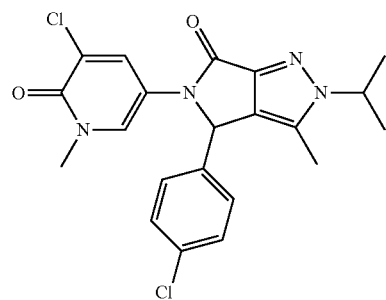 [SMILES: Cc1c2c(nn1C(C)C)C(=O)N(c1cc(Cl)c(=O)n(C)c1)C2c1ccc(Cl)cc1]

The title compound was prepared in analogy to the procedure described in Example 58 using 5-(3-acetyl-2-(4-chlorophenyl)-4-hydroxy-5-oxo-2,5-dihydro-1H-pyrrol-1-yl)-3-chloro-1-methyl-pyridin-2(1H)-one (Step 58.1) and isopropylhydrazine hydrochloride. The crude material was purified by preparative achiral SFC (column 4-Ethyl-pyridine, gradient 17-22% in 6 min_total 11 min). $t_R$: 4.45 min (HPLC 1); $t_R$: 1.01 min (LC-MS 2); ESI-MS: 431 [M+H]$^+$ (LC-MS 2); $R_f$=0.31 (EtOAc); $^1$H NMR (400 MHz, DMSO-d$_6$) δ ppm 1.34-1.42 (m, 6H) 2.07 (s, 3H) 3.43 (s, 3H) 4.52-4.62 (m, 1H) 6.12 (s, 1H) 7.23-7.30 (m, 2H) 7.34-7.40 (m, 2H) 7.87-7.90 (m, 1H) 7.90-7.93 (m, 1H).

Example 66

5-(5-chloro-1-methyl-6-oxo-1,6-dihydropyridin-3-yl)-4-(4-chlorophenyl)-1-isopropyl-3-methyl-4,5-dihydropyrrolo[3,4-c]pyrazol-6(1H)-one

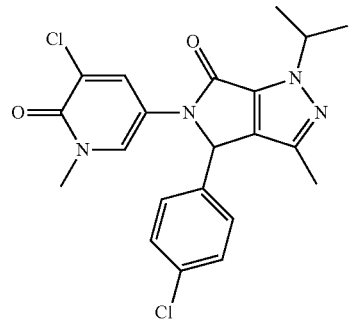 [SMILES: Cc1nn(C(C)C)c2c1C(c1ccc(Cl)cc1)N(c1cc(Cl)c(=O)n(C)c1)C2=O]

The title compound was prepared in analogy to the procedure described in Example 58 using 5-(3-acetyl-2-(4-chlorophenyl)-4-hydroxy-5-oxo-2,5-dihydro-1H-pyrrol-1-yl)-3-chloro-1-methyl-pyridin-2(1H)-one (Step 58.1) and isopropylhydrazine hydrochloride. $t_R$: 4.69 min (HPLC 1); $t_R$: 1.09 min (LC-MS 2); ESI-MS: 431/433 [M+H]$^+$ (LC-MS 2); $R_f$=0.55 (EtOAc); $^1$H NMR (400 MHz, DMSO-d$_6$) δ ppm 1.45-1.57 (m, 6H) 1.93 (s, 3H) 3.44 (s, 3H) 4.67-4.79 (m, 1H) 6.11 (s, 1H) 7.28 (d, J=8.2 Hz, 2H) 7.40 (d, J=8.2 Hz, 2H) 7.91 (d, J=2.0 Hz, 1H) 7.95 (d, J=2.4 Hz, 1H).

Example 67

4-(4-chlorophenyl)-2-(2,4-dimethoxypyrimidin-5-yl)-5-(3,8-dimethyl-[1,2,4]triazolo-[4,3-a]pyridin-6-yl)-3-isopropyl-4,5-dihydropyrrolo[3,4-c]pyrazol-6(2H)-one

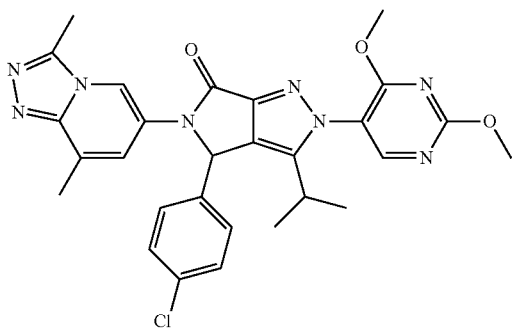 [SMILES: COc1ncc(-n2nc3c(c2C(C)C)C(c2ccc(Cl)cc2)N(c2cc(C)c4nnc(C)n4c2)C3=O)c(OC)n1]

The title compound was prepared in analogy to the procedure described in Example 1 using 4-((4-chlorophenyl)((3,8-dimethyl-[1,2,4]triazolo[4,3-a]pyridin-6-yl)amino)methyl)-1-(2,4-dimethoxypyrimidin-5-yl)-5-isopropyl-1H-pyrazole-3-carboxylic acid (Step 67.6) in a mixture CH$_2$Cl$_2$/DMF 20:1 for 30 min at RT. Purification by preparative achiral SFC (diethyl-amino, gradient 11-16% in 6 min_total 11 min). t$_R$: 1.01 min (LC-MS 2); ESI-MS: 559 [M+H]$^+$ (LC-MS 2); R$_f$=0.40 (CH$_2$Cl$_2$/MeOH 10:1); $^1$H NMR (400 MHz, DMSO-d$_6$) δ ppm 0.49 (d, J=6.8 Hz, 3H) 1.16 (d, J=6.8 Hz, 3H) 2.46 (s, 3H) 2.66 (m, 4H) 3.96 (s, 3H) 4.01 (s, 3H) 6.65 (s, 1H) 7.22-7.68 (m, 5H) 8.49 (s, 1H) 8.64 (s, 1H).

Step 67.1: 2-hydrazinyl-3-methyl-5-nitropyridine

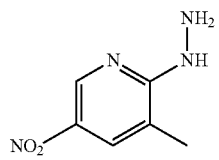

To a solution of 2-chloro-3-methyl-5-nitropyridine (35 g, 200 mmol) in EtOH (400 mL) was added hydrazine hydrate (30.0 g, 600 mmol) and the resulting reaction mixture was stirred at 60° C. for 1 hr. The reaction mixture was cooled down with an ice bath, the resulting precipitate was filtrated off, washed with cold H$_2$O and Et$_2$O and dried at 50° C. under reduced pressure to afford the title product (25.40 g, 113 mmol, 98%) as a yellow solid. t$_R$: 0.43 min (LC-MS 2); ESI-MS: 169 [M+H]$^+$; ESI-MS: 167 [M−H]$^−$ (LC-MS 2).

Step 67.2: N'-(3-methyl-5-nitropyridin-2-yl)acetohydrazide

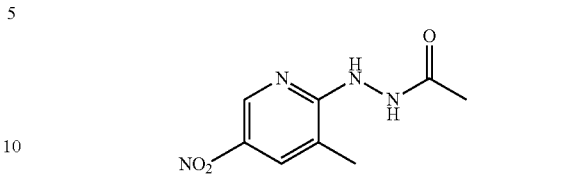

To a suspension 2-hydrazinyl-3-methyl-5-nitropyridine (Step 67.1) (33.2 g, 198 mmol) in dioxane (175 mL) was added Ac$_2$O (20.5 mL, 217 mmol) and the reaction was stirred at RT for min. The reaction mixture was poured onto ice-water and stirred for 1 hr at 0° C. The precipitate was collected by filtration, washed with H$_2$O and Et$_2$O, and dried under reduced pressure at 50° C. to afford the title product (41.5 g, 198 mmol, 99.5% yield) as light beige solid. t$_R$: 0.45 min (LC-MS 2); ESI-MS: 211 [M+H]$^+$; ESI-MS: 209 [M−H]$^−$ (LC-MS 2).

Step 67.3: 3,8-dimethyl-6-nitro-[1,2,4]triazolo[4,3-a]pyridine

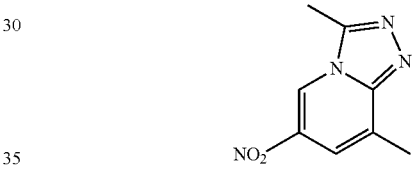

To a suspension of N'-(3-methyl-5-nitropyridin-2-yl)acetohydrazide (Step 67.2) (41.5 g, 198 mmol) in dioxane (180 mL) was added AcOH (35 mL) and the reaction mixture was stirred for 3 hr at 100° C. The reaction mixture was cooled RT and the crystallization was facilitated by the addition of Et$_2$O (700 mL) over a period of 3 hr. After stirring the suspension for 3 hr at 0° C., the crystals were collected, washed with Et$_2$O and dried to afford the title product (23.4 g, 119 mmol, 60% yield) as a light yellow solid. t$_R$: 0.51 min (LC-MS 2); ESI-MS: 193 [M+H]$^+$ (LC-MS 2); TLC (EtOAc/MeOH 9:1) R$_f$=0.35; $^1$H NMR (400 MHz, DMSO-d$_6$) δ ppm 2.60 (s, 3H) 2.80 (s, 3H) 7.87 (d, J=1.9 Hz, 1H) 9.45 (d, J=1.8 Hz, 1H).

Step 67.4: 3,8-dimethyl-[1,2,4]triazolo[4,3-a]pyridin-6-amine

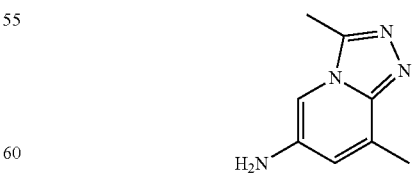

A suspension of 3,8-dimethyl-6-nitro-[1,2,4]triazolo[4,3-a]pyridine (Step 67.3) (14.1 g, 71.9 mmol) and 10% Pd/C (2.75 g, 25.9 mmol) in MeOH (300 mL) was shaken for 5 h under 4 bar hydrogen atmosphere at RT. Further 10% Pd/C was added and the reaction mixture was shaken another 1 hh under hydrogen atmosphere. The mixture was filtered through Celite. The pad of Celite was washed with MeOH and the resulting filtrate was concentrated under reduced pressure. The crude product was purified by silica gel column chromatography (hexane/(CH$_2$Cl$_2$-MeOH 19:1) 50-100% (CH$_2$Cl$_2$-MeOH 19:1)) to afford the title product as yellow solid. t$_R$: 0.29 min (LC-MS 2); ESI-MS: 163 [M+H]$^+$ (LC-MS 2); TLC (CH$_2$Cl$_2$-MeOH 9:1) R$_f$=0.26; $^1$H NMR (400 MHz, DMSO-d$_6$) δ ppm 2.43 (s, 3H) 2.54 (s, 3H) 5.05 (br. s, 2H) 6.75 (br. s, 1H) 7.18 (br. s, 1H).

Step 67.5: ethyl 4-((4-chlorophenyl)((3,8-dimethyl-[1,2,4]triazolo[4,3-a]pyridin-6-yl)amino)-methyl)-1-(2,4-dimethoxypyrimidin-5-yl)-5-isopropyl-1H-pyrazole-3-carboxylate

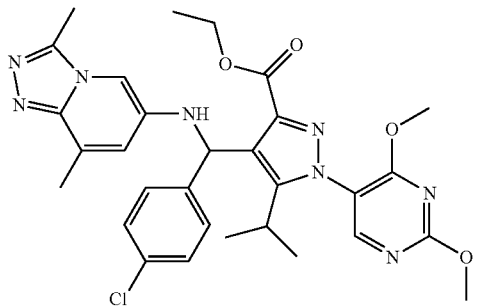 [SMILES: CCOC(=O)c1nn(-c2cnc(OC)nc2OC)c(C(C)C)c1C(Nc1cc(C)c2nnc(C)n2c1)c1ccc(Cl)cc1]

The title compound was prepared in analogy to the procedure described in Step 10.3 using ethyl 4-((4-chlorophenyl)(hydroxy)methyl)-1-(2,4-dimethoxypyrimidin-5-yl)-5-isopropyl-1H-pyrazole-3-carboxylate (Step 46.11) and 3,8-dimethyl-[1,2,4]triazolo[4,3-a]pyridin-6-amine (Step 67.4) overnight at RT. t$_R$: 1.02 min (LC-MS 2); ESI-MS: 605 [M+H]$^+$ (LC-MS 2).

Step 67.6: 4-((4-chlorophenyl)((3,8-dimethyl-[1,2,4]triazolo[4,3-a]pyridin-6-yl)amino)methyl)-1-(2,4-dimethoxypyrimidin-5-yl)-5-isopropyl-1H-pyrazole-3-carboxylic acid

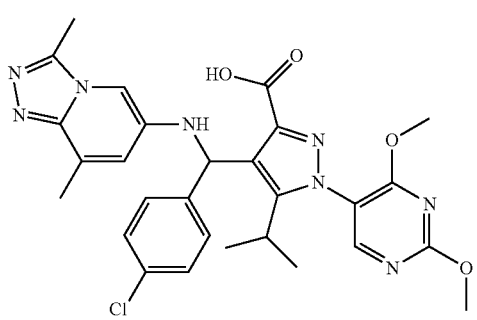 [SMILES: COc1ncc(-n2nc(C(=O)O)c(C(Nc3cc(C)c4nnc(C)n4c3)c3ccc(Cl)cc3)c2C(C)C)c(OC)n1]

The title product was prepared in analogy to the procedure described in Step 46.13 using ethyl 4-((4-chlorophenyl)((3,8-dimethyl-[1,2,4]triazolo[4,3-a]pyridin-6-yl)amino)methyl)-1-(2,4-dimethoxypyrimidin-5-yl)-5-isopropyl-1H-pyrazole-3-carboxylate (Step 67.6). t$_R$: 0.93 min (LC-MS 2); ESI-MS: 577 [M+H]$^+$; ESI-MS: 575 [M−H]$^−$ (LC-MS 2).

Example 68

4-(4-chlorophenyl)-2-cyclopropyl-5-(1,5-dimethyl-6-oxo-1,6-dihydropyridin-3-yl)-3-ethyl-4,5-dihydropyrrolo[3,4-c]pyrazol-6(2H)-one

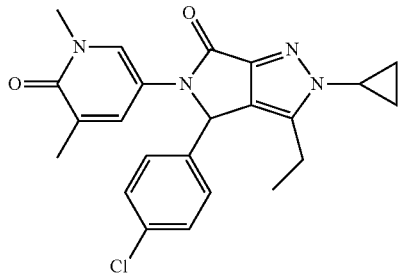 [SMILES: CCc1c2c(nn1C1CC1)C(=O)N(c1cc(C)c(=O)n(C)c1)C2c1ccc(Cl)cc1]

To a solution of 5-(4-chlorophenyl)-1-(1,5-dimethyl-6-oxo-1,6-dihydropyridin-3-yl)-4-propionylpyrrolidine-2,3-dione (Step 60.1) (300 mg, 0.698 mmol) in EtOH (1.5 mL) was added cyclopropylhydrazine hydrochloride (99 mg, 0.907 mmol) and triethylamine (0.126 mL, 0.907 mmol) and the reaction mixture was heated for 0.5 hr at 70° C. and for 0.5 h at 90° C. Sulfamic acid (102 mg, 1.047 mmol) and AcOH (1.5 mL) were added to the mixture and the reaction was submitted to MW irradiation for 2 h at 120° C. The reaction mixture was concentrated under reduced pressure, the residue was added to a saturated aqueous NaHCO$_3$ solution and extracted with EtOAc. Combined organic layers were washed with brine, dried over MgSO$_4$, filtered and concentrated under reduced pressure. The crude product was purified by silica gel column chromatography eluting with hexane/EtOAc/MeOH (20:80:8 to 10:1). The resulting product was further purified by preparative achiral SFC (column Propyl-pyridyl-urea, gradient 12-17% in 6 min_total 11 min) to afford the title product (16 mg, 0.037 mmol, 5% yield) as yellow solid. t$_R$: 0.98 min (LC-MS 2); ESI-MS: 423 [M+H]$^+$ (LC-MS 2); R$_f$=0.24 (EtOAc/MeOH 9:1); $^1$H NMR (400 MHz, DMSO-d$_6$) δ ppm 0.89 (t, J=7.6 Hz, 3H) 1.03-1.24 (m, 4H) 1.94 (s, 3H) 2.53-2.62 (m, 1H) 2.66-2.81 (m, 1H) 3.37 (s, 3H) 3.66-3.75 (m, 1H) 6.17 (s, 1H) 7.24 (d, J=8.3 Hz, 2H) 7.38 (d, J=8.3 Hz, 3H) 7.71 (d, J=2.6 Hz, 1H).

Example 69

4-(4-chlorophenyl)-1-cyclopropyl-5-(1,5-dimethyl-6-oxo-1,6-dihydropyridin-3-yl)-3-ethyl-4,5-dihydropyrrolo[3,4-c]pyrazol-6(1H)-one

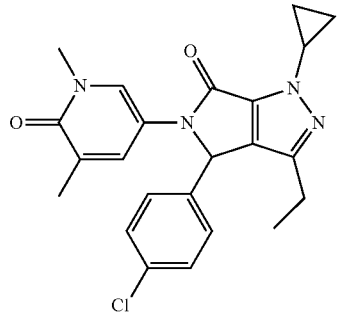 [SMILES: CCc1nn(C2CC2)c2c1C(c1ccc(Cl)cc1)N(c1cc(C)c(=O)n(C)c1)C2=O]

The tile compound was prepared in analogy to the procedure described in Example 68 using 5-(4-chlorophenyl)-1-(1,5-dimethyl-6-oxo-1,6-dihydropyridin-3-yl)-4-propionylpyrrolidine-2,3-dione (Step 60.1) and cyclopropylhydrazine hydrochloride. Further purification by preparative achiral SFC (column Propyl-pyridyl-urea, gradient 7-12% in 6 min_total 11 min) to afford the title product as yellow foam. $t_R$: 1.03 min (LC-MS 2); ESI-MS: 423 [M+H]+ (LC-MS 2); $R_f$=0.43 (EtOAc/MeOH 9:1); $^1$H NMR (400 MHz, DMSO-$d_6$) δ ppm 0.87 (t, J=7.6 Hz, 3H) 1.04 (dd, J=7.2, 1.7 Hz, 2H) 1.19-1.29 (m, 2H) 1.94 (s, 3H) 2.21-2.31 (m, 1H) 2.31-2.41 (m, 1H) 3.37 (s, 3H) 3.82 (dt, J=7.3, 3.6 Hz, 1H) 6.11 (s, 1H) 7.28 (d, J=8.3 Hz, 2H) 7.39 (d, J=8.3 Hz, 3H) 7.73 (d, J=2.5 Hz, 1H).

Example 70

4-(4-chlorophenyl)-1-cyclopropyl-5-(3,8-dimethyl-[1,2,4]triazolo[4,3-a]pyridin-6-yl)-3-ethyl-4,5-dihydropyrrolo[3,4-c]pyrazol-6(1H)-one

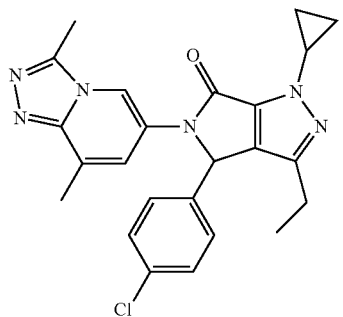 [SMILES: CCc1nn(C2CC2)c2c1C(c1ccc(Cl)cc1)N(c1cc(C)c3nnc(C)n3c1)C2=O]

The title compound was prepared in analogy to the procedure described for Example 68 using 5-(4-chlorophenyl)-1-(3,8-dimethyl-[1,2,4]triazolo[4,3-a]pyridin-6-yl)-4-propionylpyrrolidine-2,3-dione (Step 70.1) and cyclopropylhydrazine hydrochloride. Further purification by preparative achiral SFC (4-ethyl-pyridine, gradient 13-18% in 6 min_total 11 min) to afford the title product as colorless foam. $t_R$: 1.02 min (LC-MS 2); ESI-MS: 447 [M+H]+ (LC-MS 2); $R_f$=0.36 (EtOAc/MeOH 9:1); $^1$H NMR (400 MHz, DMSO-$d_6$) δ ppm 0.91 (t, J=7.6 Hz, 3H) 1.03-1.11 (m, 2H) 1.21-1.32 (m, 2H) 2.29 (dt, J=15.0, 7.6 Hz, 1H) 2.38 (dt, J=15.1, 7.7 Hz, 1H) 2.45 (s, 3H) 2.64 (s, 3H) 3.85 (tt, J=7.4, 3.8 Hz, 1H) 6.48 (s, 1H) 7.28-7.42 (m, 5H) 8.45 (s, 1H).

Step 70.1: 5-(4-chlorophenyl)-1-(3,8-dimethyl-[1,2,4]triazolo[4,3-a]pyridin-6-yl)-4-propionylpyrrolidine-2,3-dione

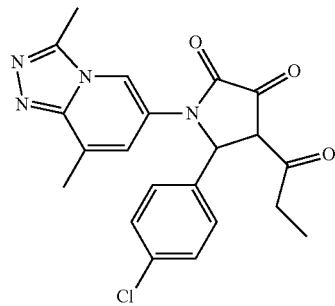 [SMILES: CCC(=O)C1C(=O)C(=O)N(c2cc(C)c3nnc(C)n3c2)C1c1ccc(Cl)cc1]

The title compound was prepared in analogy to the procedure described in Step 60.1 using 3,8-dimethyl-[1,2,4]triazolo[4,3-a]pyridin-6-amine (Step 67.4), 4-chlorobenzaldehyde and ethyl 2,4-dioxohexanoate at 110° C. for 4 hr. $t_R$: 0.79 min (LC-MS 2); ESI-MS: 411 [M+H]+, ESI-MS: 409 [M−H]− (LC-MS 2).

Example 71

4-(4-chlorophenyl)-5-(1,5-dimethyl-6-oxo-1,6-dihydropyridin-3-yl)-1-(2-methoxypyridin-3-yl)-3-methyl-4,5-dihydropyrrolo[3,4-c]pyrazol-6(1H)-one

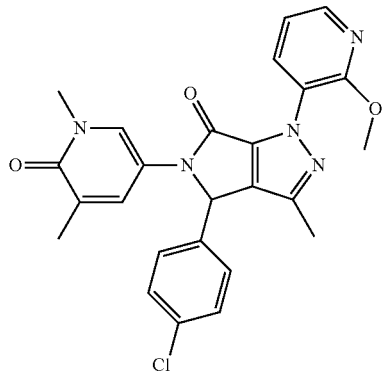 [SMILES: COc1ncccc1-n1nc(C)c2c1C(=O)N(c1cc(C)c(=O)n(C)c1)C2c1ccc(Cl)cc1]

The title compound was prepared in analogy to the procedure described for Example 23 using 4-(4-chlorophenyl)-1-(2-methoxypyridin-3-yl)-3-methyl-4,5-dihydropyrrolo[3,4-c]pyrazol-6(1H)-one (Step 71.4) and 5-iodo-1,3-dimethylpyridin-2(1H)-one (step 23.2) at 100° C. for 16 hr. Further purification by preparative achiral SFC (column Silica, gradient 22-27% in 6 min_total 11 min). $t_R$: 4.34 min (HPLC 1); $t_R$: 1.00 min (LC-MS 2); ESI-MS: 476 [M+H]+ (LC-MS 2); $R_f$=0.51 (CH$_2$Cl$_2$/MeOH 9:1).

Step 71.1: 3-hydrazinyl-2-methoxypyridine

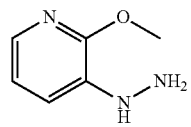

To a stirred solution of 3-amino-2-methoxypyridine (5 g, 40.3 mmol) in 6N HCl (80 mL) was added dropwise a solution of NaNO$_2$ (2.78 g, 40.3 mmol) in water (50 mL) at 0° C. After 30 min at this temperature, a solution of SnCl$_2$.2H$_2$O (22.72 g, 101 mmol) in 6N HCl (80 mL) was added dropwise at 0° C. The reaction mixture was stirred 90 min at 0° C. The reaction mixture was adjusted to pH~10-11 with a solution of KOH 40% in water and extracted with EtOAc. The combined organic layers were washed with water, dried over Na$_2$SO$_4$ and evaporated under reduced pressure to afford the title product (4.97 g, 33.9 mmol, 84% yield) as red oil. $t_R$: 0.31 min (LC-MS 2); ESI-MS: 140 [M+H]+ (LC-MS 2).

Step 71.2: 4-acetyl-5-(4-chlorophenyl)-3-hydroxy-1-(4-methoxybenzyl)-1H-pyrrol-2(5H)-one

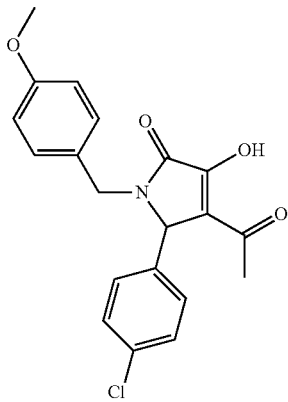 [SMILES: COc1ccc(CN2C(=O)C(O)=C(C(C)=O)C2c2ccc(Cl)cc2)cc1]

The title compound was prepared in analogy to the procedure described in Step 57.1 using 4-methoxybenzylamine, 4-chlorobenzaldehyde and ethyl 2,4-dioxovalerate at 120° C. for 3 hr. The title product precipitated at RT. $t_R$: 4.90 min (HPLC 1); $t_R$: 1.03 min (LC-MS 2); ESI-MS: 372 [M+H]$^+$, ESI-MS: 370 [M–H]$^-$ (LC-MS 2).

Step 71.3: 4-(4-chlorophenyl)-5-(4-methoxybenzyl)-1-(2-methoxypyridin-3-yl)-3-methyl-4,5-dihydropyrrolo[3,4-c]pyrazol-6(1H)-one

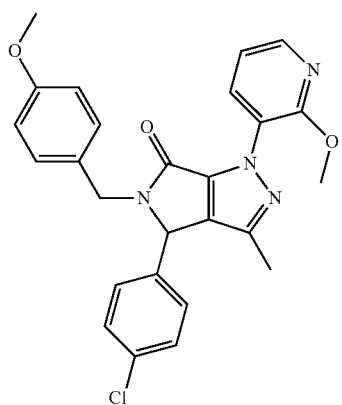 [SMILES: COc1ccc(CN2C(=O)c3c(c(C)nn3-c3cccnc3OC)C2c2ccc(Cl)cc2)cc1]

The title compound was prepared in analogy to the procedure described in Example 57 using 4-acetyl-5-(4-chlorophenyl)-3-hydroxy-1-(4-methoxybenzyl)-1H-pyrrol-2(5H)-one (Step 71.2) and 3-hydrazinyl-2-methoxypyridine (Step 71.1). $t_R$: 5.79 min (HPLC 1); $t_R$: 1.29 min (LC-MS 2); ESI-MS: 475 [M+H]$^+$ (LC-MS 2); $R_f$=0.60 (hexane/EtOAc 1:1).

Step 71.4: 4-(4-chlorophenyl)-1-(2-methoxypyridin-3-yl)-3-methyl-4,5-dihydropyrrolo[3,4-c]-pyrazol-6(1H)-one

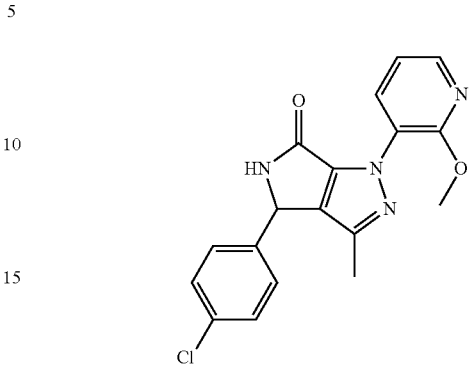

To a stirred solution of 4-(4-chlorophenyl)-5-(4-methoxybenzyl)-1-(2-methoxypyridin-3-yl)-3-methyl-4,5-dihydropyrrolo[3,4-c]pyrazol-6(1H)-one (Step 71.3) (2.8 g, 5.90 mmol) in CH3CN (80 mL) and H$_2$O (20 mL) was added CAN (9.70 g, 17.69 mmol) and the reaction mixture was stirred at RT for 16 hr. The reaction mixture was quenched with brine and extracted with EtOAc. The combined organic layers were washed with brine, dried over Na$_2$SO$_4$ and evaporated under reduced pressure. The crude material was purified by silica gel column chromatography (CH$_2$Cl$_2$/MeOH 1-2.5%). The residue was triturated in CH$_2$Cl$_2$ to afford the title product (1.06 g, 2.93 mmol, 50% yield) as white solid. $t_R$: 4.36 min (HPLC 1); $t_R$: 0.98 min (LC-MS 2); ESI-MS: 355 [M+H]$^+$ (LC-MS 2); $R_f$=0.39 (CH$_2$Cl$_2$/MeOH 9:1).

Example 72

5-(5-chloro-1-methyl-6-oxo-1,6-dihydropyridin-3-yl)-4-(4-chlorophenyl)-1-(2-methoxypyridin-3-yl)-3-methyl-4,5-dihydropyrrolo[3,4-c]pyrazol-6(1H)-one

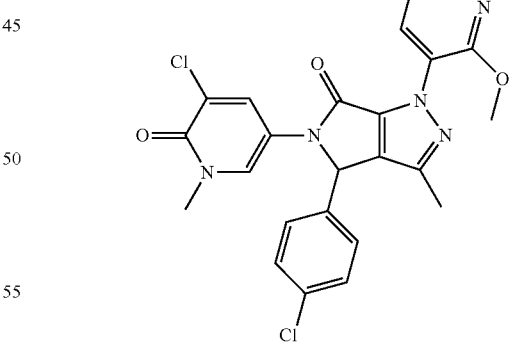

To a stirred solution of 5-(3-acetyl-2-(4-chlorophenyl)-4-hydroxy-5-oxo-2,5-dihydro-1H-pyrrol-1-yl)-3-chloro-1-methylpyridin-2(1H)-one (Step 57.1) (250 mg, 0.636 mmol) and TEA (0.115 ml, 0.827 mmol) in EtOH (2 ml) was added 3-hydrazinyl-2-methoxypyridine (Step 71.1) (115 mg, 0.827 mmol) and the reaction mixture was stirred 1 hr at 90° C. Sulfamic acid (93 mg, 0.954 mmol) and AcOH (2 ml) was added and the reaction mixture was stirred 3 hr at 115° C. The reaction mixture was concentrated under reduced pressure, quenched with a saturated aq. NaHCO₃ solution and extracted with CH₂Cl₂. The combined organic layers were dried over Na₂SO₄ and evaporated under reduced pressure. The crude product was purified by silica gel column chromatography eluting with EtOAC. The residue was further purified by SFC (column Propyl-pyridyl-urea, gradient 13-18% in 6 min_total 11 min) and triturated in hexane/Et₂O (2:1) to afford the title product (13 mg, 0.026 mmol, 4% yield) as white solid. $t_R$: 4.55 min (HPLC 1); $t_R$: 1.04 min (LC-MS 2); ESI-MS: 496 [M+H]⁺ (LC-MS 2); $R_f$=0.41 (EtOAc); ¹H NMR (400 MHz, DMSO-d₆) δ ppm 2.02 (s, 3H) 3.43 (s, 3H) 3.89 (s, 3H) 6.24 (s, 1H) 7.15-7.22 (m, 1H) 7.32-7.37 (m, 2H) 7.40-7.45 (m, 2H) 7.88-7.96 (m, 3H) 8.28-8.33 (m, 1H).

Example 73

4-(4-chlorophenyl)-5-(1,5-dimethyl-6-oxo-1,6-dihydropyridin-3-yl)-3-hydroxy-2-methyl-4,5-dihydropyrrolo[3,4-c]pyrazol-6(2H)-one

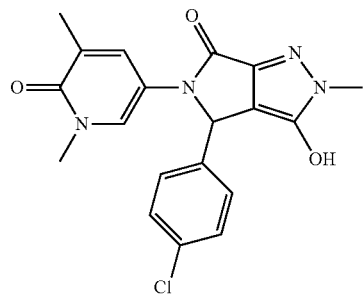 [SMILES: Cc1cc(N2C(=O)c3nn(C)c(O)c3C2c2ccc(Cl)cc2)cn(C)c1=O]

The title compound was prepared in analogy to the procedure described for Example 57 using ethyl 2-(4-chlorophenyl)-1-(1,5-dimethyl-6-oxo-1,6-dihydropyridin-3-yl)-4,5-dioxopyrrolidine-3-carboxylate (Step 73.2) and methyl hydrazine at reflux for 32 hr. $t_R$: 0.68 min (LC-MS 2); ESI-MS: 385 [M+H]⁺, ESI-MS: 383 [M−H]⁻ (LC-MS 2); $R_f$=0.23 (CH₂Cl₂/7.5% MeOH/1% AcOH); ¹H NMR (400 MHz, DMSO-d₆) δ ppm 1.90 (s, 3H) 3.34 (s, 3H) 3.44 (m, 3H) 5.62 (s, 1H) 7.09 (d, J=8.6 Hz, 2H) 7.17-7.34 (m, 3H) 7.60 (d, J=2.7 Hz, 1H).

Step 73.1: (E)-5-((4-chlorobenzylidene)amino)-1,3-dimethylpyridin-2(1H)-one

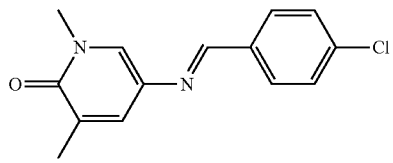 [SMILES: Cc1cc(/N=C/c2ccc(Cl)cc2)cn(C)c1=O]

To a stirred solution of 5-amino-1,3-dimethylpyridin-2 (1H)-one (Step 20.2) (5.2 g, 37.6 mmol) in EtOH (100 mL) were added 4-chlorobenzaldehyde (5.04 g, 35.8 mmol) and AcOH (0.410 mL, 7.17 mmol). The resulting mixture was heated up and stirred at 85° C. for 1 hr. The reaction was concentrated under reduced pressure and the resulting crude mixture was triturated in Et₂O to afford the title product (7.6 g, 29.2 mmol) as beige solid. $t_R$: 0.92 min (LC-MS 2).

Step 73.2: ethyl 2-(4-chlorophenyl)-1-(1,5-dimethyl-6-oxo-1,6-dihydropyridin-3-yl)-4,5-dioxopyrrolidine-3-carboxylate

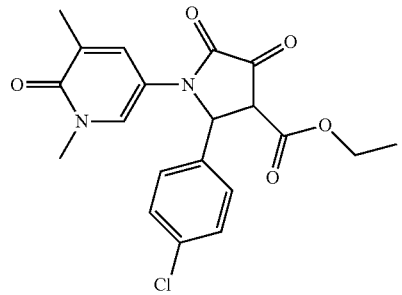 [SMILES: CCOC(=O)C1C(=O)C(=O)N(c2cc(C)c(=O)n(C)c2)C1c1ccc(Cl)cc1]

To a stirred solution of (E)-5-((4-chlorobenzylidene) amino)-1,3-dimethylpyridin-2(1H)-one (Step 73.1) (4 g, 15.34 mmol) in AcOH (40 mL) was added diethyl oxaloacetate sodium salt (6.45 g, 30.7 mmol) and the resulting mixture was heated up and stirred at 110° C. for 1 hr. The reaction was concentrated under reduced pressure, diluted with CH₂Cl₂ and water and both phases separated. The aqueous layer was extracted twice with CH₂Cl₂, combined organic layers were washed with brine, dried over Na₂SO₄, filtered and concentrated under reduced pressure. The crude product was triturated in Et₂O to afford the title product (4.42 g, 8.34 mmol, 54% yield) as beige solid. $t_R$: 0.86 min (LC-MS 2); ESI-MS: 403 [M+H]⁺, ESI-MS: 401 [M−H]⁻ (LC-MS 2).

Example 74

4-(4-chlorophenyl)-5-(1,5-dimethyl-6-oxo-1,6-dihydropyridin-3-yl)-3-methyl-1-(1-methyl-1H-pyrazol-5-yl)-4,5-dihydropyrrolo[3,4-c]pyrazol-6(1H)-one

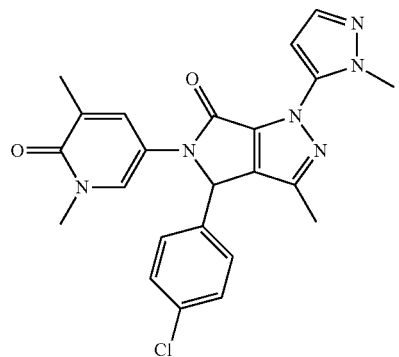 [SMILES: Cc1nn(-c2ccnn2C)c2c1C(c1ccc(Cl)cc1)N(c1cc(C)c(=O)n(C)c1)C2=O]

The title compound was prepared in analogy to the procedure described in Example 58 using 5-(3-acetyl-2-(4-chlorophenyl)-4-hydroxy-5-oxo-2,5-dihydro-1H-pyrrol-1-yl)-3-chloro-1-methyl-pyridin-2(1H)-one (Step 57.1) and 5-hydrazinyl-1-methyl-1H-pyrazole (Step 74.2). The crude material was first purified by silica gel column chromatography (CH₂Cl₂/MeOH 1-4%) followed by preparative achiral SFC (column 4-Ethyl-pyridine, gradient 11-16% in 6 min_total 11 min). $t_R$: 4.09 min (HPLC 1); $t_R$: 0.94 min (LC-MS 2); ESI-MS: 449 [M+H]⁺ (LC-MS 2); $R_f$=0.40 (CH₂Cl₂/MeOH 9:1); ¹H NMR (400 MHz, DMSO-d₆) δ ppm 1.94 (s, 3H) 2.06 (s, 3H) 3.37 (s, 3H) 3.86 (s, 3H) 6.22 (s, 1H) 6.61 (d, J=2.0 Hz, 1H) 7.33-7.47 (m, 5H) 7.57 (d, J=2.0 Hz, 1H) 7.75 (d, J=2.7 Hz, 1H).

Step 74.1: di-tert-butyl 1-(1-methyl-1H-pyrazol-5-yl)hydrazine-1,2-dicarboxylate

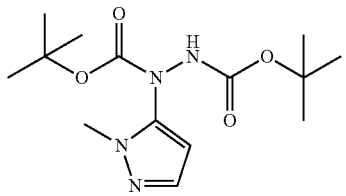 [SMILES: Cn1nccc1N(NC(=O)OC(C)(C)C)C(=O)OC(C)(C)C]

The title compound was prepared in analogy to the procedure described for Step 46.7 using 1-methyl-5-bromopyrazole. The crude product was purified by silica gel column chromatography (hexane/EtOAc 5-30%). $t_R$: 4.46 min (HPLC 1); $t_R$: 1.04 min (LC-MS 2); ESI-MS: 496 [M+H]$^+$ (LC-MS 2); $R_f$=0.51 (Hexane/EtOAc 1:1).

Step 74.2: 5-hydrazinyl-1-methyl-1H-pyrazole

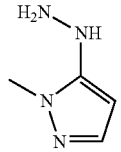

The title compound was prepared in analogy to the procedure described for Step 17.2 using di-tert-butyl 1-(1-methyl-1H-pyrazol-5-yl)hydrazine-1,2-dicarboxylate (Step 74.1). ESI-MS: 113 [M+H]$^+$ (LC-MS 2).

Example 75

Blank

Example 76

4-(4-chlorophenyl)-5-(1,5-dimethyl-6-oxo-1,6-dihydropyridin-3-yl)-3-ethoxy-2-methyl-4,5-dihydropyrrolo[3,4-c]pyrazol-6(2H)-one

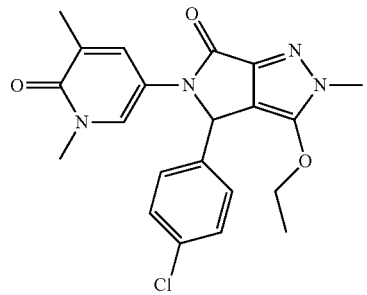 [SMILES: CCOc1c2c(nn1C)C(=O)N(c1cc(C)c(=O)n(C)c1)C2c1ccc(Cl)cc1]

NaH (19.19 mg, 0.48 mmol) was added to a stirred solution of 4-(4-chlorophenyl)-5-(1,5-dimethyl-6-oxo-1,6-dihydropyridin-3-yl)-3-hydroxy-2-methyl-4,5-dihydropyrrolo[3,4-c]pyrazol-6-(2H)-one (Example 73) (142 mg, 0.369 mmol) in DMF (1 mL) at 0° C. and the reaction was stirred at 0° C. for 20 min. Iodoethane (0.036 mL, 0.443 mmol) was added and the resulting mixture was stirred at RT for 20 min. The reaction was diluted with EtOAc and water and both phases separated. The aq. layer was extracted with EtOAc and the combined organic layers were dried over Na$_2$SO$_4$ and concentrated under reduced pressure. The crude material was purified by silica gel column chromatography (1% ammonia/7.5% MeOH/CH$_2$Cl$_2$) to afford, after trituration in Et$_2$O, the title product (77 mg, 0.186 mmol, 50% yield) as white solid. $t_R$: 0.91 min (LC-MS 2); ESI-MS: 413 [M+H]$^+$ (LC-MS 2); $R_f$=0.39 (1% ammonia/7.5% MeOH/CH$_2$Cl$_2$); $^1$H NMR (400 MHz, DMSO-d$_6$) δ ppm 1.09 (t, J=6.8 Hz, 3H) 1.91 (s, 3H) 3.35 (s, 3H) 3.60-3.77 (m, 4H) 3.89-4.03 (m, 1H) 6.20 (s, 1H) 7.25 (d, J=8.6 Hz, 2H) 7.30-7.44 (m, 3H) 7.66 (d, J=2.7 Hz, 1H).

Example 77

4-(4-chlorophenyl)-5-(1,5-dimethyl-6-oxo-1,6-dihydropyridin-3-yl)-3-methoxy-2-methyl-4,5-dihydropyrrolo[3,4-c]pyrazol-6(2H)-one

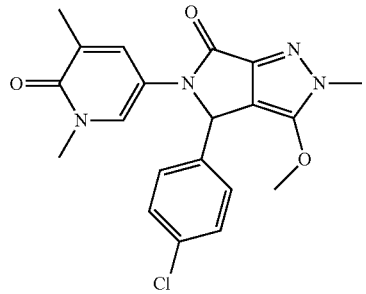 [SMILES: COc1c2c(nn1C)C(=O)N(c1cc(C)c(=O)n(C)c1)C2c1ccc(Cl)cc1]

The title compound was prepared in analogy to the procedure described in Example 76 using 4-(4-chlorophenyl)-5-(1,5-dimethyl-6-oxo-1,6-dihydropyridin-3-yl)-3-hydroxy-2-methyl-4,5-dihydropyrrolo[3,4-c]pyrazol-6(2H)-one (Example 73) and methyl iodide. $t_R$: 0.86 min (LC-MS 2); ESI-MS: 399 [M+H]$^+$ (LC-MS 2); $R_f$=0.33 (1% ammonia/7.5% MeOH/CH$_2$Cl$_2$); $^1$H NMR (400 MHz, DMSO-d$_6$) δ ppm 1.91 (s, 3H) 3.34 (s, 3H) 3.59 (s, 3H) 3.67 (s, 3H) 6.24 (s, 1H) 7.19-7.42 (m, 5H) 7.64 (d, J=2.7 Hz, 1H).

Example 78

4-(4-chlorophenyl)-5-(1,5-dimethyl-6-oxo-1,6-dihydropyridin-3-yl)-3-ethyl-1-(2-hydroxyethyl)-4,5-dihydropyrrolo[3,4-c]pyrazol-6(1H)-one

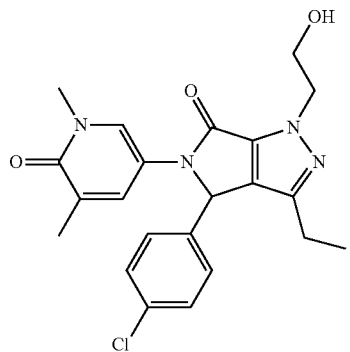 [SMILES: CCc1nn(CCO)c2c1C(c1ccc(Cl)cc1)N(c1cc(C)c(=O)n(C)c1)C2=O]

To a solution of 2-hydrazinylethanol (76 mg, 1.0 mmol) in MeOH (2 mL) was added 5-(4-chlorophenyl)-1-(1,5-dimethyl-6-oxo-1,6-dihydropyridin-3-yl)-4-propionylpyrrolidine-2,3-dione (Step 60.1) (204 mg, 0.5 mmol) and the reaction mixture was heated for 1 hr at 70° C. and for 0.5 hr at 90° C. in the MW. The volume of MeOH was reduced to 1 mL and AcOH (2 mL) and sulfamic acid (97 mg, 1.0 mmol) were added. The reaction mixture was heated for 1 h at 110° C. in the MW. The reaction mixture was concentrated under reduced pressure. The residue was basified with 20% K$_2$CO$_3$ solution and extracted with EtOAc. Combined organic layers were washed with brine, dried over MgSO$_4$, filtered and concentrated under reduced pressure. The crude material was first purified by silica gel column chromatography (hexane/ EtOAc/MeOH 80:20:2 to 0:10:1) then further purified by preparative achiral SFC (column Propyl-pyridyl-urea, gradient 15-20% in 6 min_total 11 min) to afford the title product (97 mg, 0.225 mmol, 45% yield) as colorless foam. t$_R$: 0.84 min (LC-MS 2); ESI-MS: 427 [M+H]$^+$ (LC-MS 2); R$_f$=0.21 (EtOAc/MeOH 9:1); $^1$H NMR (400 MHz, CDCl$_3$) δ ppm 0.91 (t, J=7.6 Hz, 3H) 2.01 (s, 3H) 2.25-2.48 (m, 2H) 3.37 (s, 3H) 3.44 (t, J=6.3 Hz, 1H) 3.95-4.05 (m, 2H) 4.43 (dd, J=5.6, 3.7 Hz, 2H) 5.50 (s, 1H) 6.91-7.03 (m, 4H) 7.25 (d, J=8.3 Hz, 2H).

Example 79

4-(4-chlorophenyl)-5-(3,7-dimethylbenzo[d]isoxazol-5-yl)-3-ethyl-1-(2-hydroxyethyl)-4,5-dihydropyrrolo[3,4-c]pyrazol-6(1H)-one

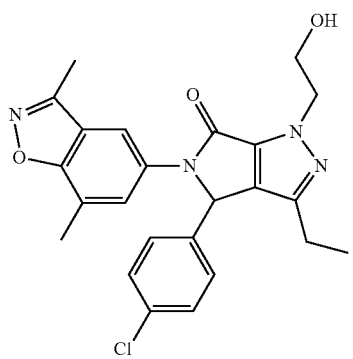 [SMILES: CCc1nn(CCO)c2c1C(c1ccc(Cl)cc1)N(c1cc(C)c3onc(C)c3c1)C2=O]

The title compound was prepared in analogy to the procedure described in Example 78 using 5-(4-chlorophenyl)-1-(3,7-dimethylbenzo[d]isoxazol-5-yl)-4-propionylpyrrolidine-2,3-dione (Step 79.1) and 2-hydrazinylethanol. The crude material was purified by silica gel chromatography (hexane/ EtOAc/MeOH 90:10:1 to 50:50:5 to 0:10:1). t$_R$: 1.10 min (LC-MS 2); ESI-MS: 451 [M+H]$^+$ (LC-MS 2).

Step 79.1: 5-(4-chlorophenyl)-1-(3,7-dimethylbenzo[d]isoxazol-5-yl)-4-propionylpyrrolidine-2,3-dione

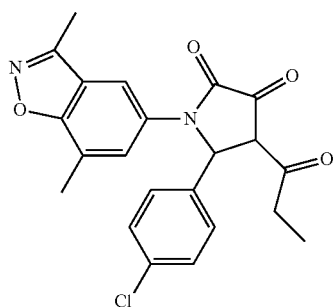 [SMILES: CCC(=O)C1C(=O)C(=O)N(c2cc(C)c3onc(C)c3c2)C1c1ccc(Cl)cc1]

The title compound was prepared in analogy to the procedure described in Step 60.1 using 3,7-dimethylbenzo[d]isoxazol-5-amine (Step 46.6) at 110° C. for 5 hr. The crude material was purified by silica gel chromatography (hexane/ CH$_2$Cl$_2$/MeOH 20:80:8 to 0: 100:10) followed by recrystallization in EtOAc/hexane. t$_R$: 1.08 min (LC-MS 2); ESI-MS: 411 [M+H]$^+$ (LC-MS 2); R$_f$=0.18 (EtOAc).

Example 80

4-(4-chlorophenyl)-5-(3,7-dimethylbenzo[d]isoxazol-5-yl)-3-ethyl-2-(2-hydroxyethyl)-4,5-dihydropyrrolo[3,4-c]pyrazol-6(2H)-one

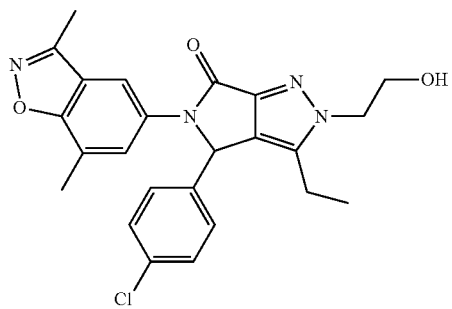 [SMILES: CCc1c2c(nn1CCO)C(=O)N(c1cc(C)c3onc(C)c3c1)C2c1ccc(Cl)cc1]

The title compound was prepared in analogy to the procedure described in Example 79 using 5-(4-chlorophenyl)-1-(3,7-dimethylbenzo[d]isoxazol-5-yl)-4-propionylpyrrolidine-2,3-dione (Step 9.1) and 2-hydrazinylethanol. t$_R$: 1.04 min (LC-MS 2); ESI-MS: 451 [M+H]$^+$ (LC-MS 2).

Example 81

4-(4-chlorophenyl)-5-(1,5-dimethyl-6-oxo-1,6-dihydropyridin-3-yl)-3-methyl-2-(2-methylpyridin-3-yl)-4,5-dihydropyrrolo[3,4-c]pyrazol-6(2H)-one

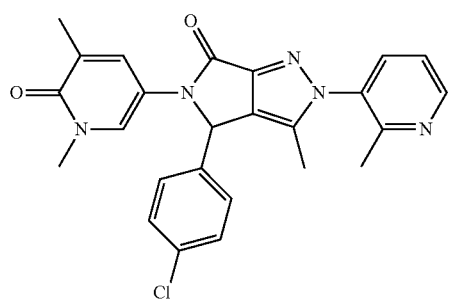 [SMILES: Cc1ncccc1-n1nc2c(c1C)C(c1ccc(Cl)cc1)N(c1cc(C)c(=O)n(C)c1)C2=O]

To a stirred solution of 4-(4-chlorophenyl)-5-(1,5-dimethyl-6-oxo-1,6-dihydropyridin-3-yl)-3-methyl-4,5-dihydropyrrolo[3,4-c]pyrazol-6(1H)-one (Step 81.1) (200 mg, 0.542 mmol) in CAN (4 mL) with molecular sieves (4 g) under Ar were added 2-methylpyridine-3-boronic acid (166 mg, 1.085 mmol), pyridine (0.088 mL, 1.085 mmol) and copper(II) acetate (148 mg, 0.813 mmol) and the reaction mixture was stirred 10 min at 65° C. 2-methylpyridine-3-boronic acid (1.485 g, 10.85 mmol) was added portionwise over a period of 1 hr. The reaction mixture was concentrated under reduced pressure, quenched with a saturated aq. NaHCO$_3$ solution and the aq. layer was extracted with CH$_2$Cl$_2$. The combined organic layers were dried over Na$_2$SO$_4$ and concentrated under reduced pressure. The crude product was purified by silica gel column chromatography (CH$_2$Cl$_2$/MeOH 1.5-5%). followed by preparative achiral SFC (column 4-Ethyl-pyridine, gradient 13-18% in 6 min_ total 11 min) and triturated in Hexane/Et$_2$O (1:1) to afford the title product (11 mg, 0.024 mmol, 4% yield). t$_R$: 3.20 min (HPLC 1); t$_R$: 0.87 min (LC-MS 2); ESI-MS: 460 [M+H]$^+$ (LC-MS 2); R$_f$=0.53 (CH$_2$Cl$_2$/MeOH 9:1); $^1$H NMR (400 MHz, DMSO-d$_6$)$_6$ ppm 1.89 (s, 3H) 1.93 (s, 3H) 2.18 (s, 3H) 3.37 (s, 3H) 6.23 (s, 1H) 7.28-7.49 (m, 6H) 7.77 (d, J=2.7 Hz, 1H) 7.88 (dd, J=7.8, 1.56 Hz, 1H) 8.63 (dd, J=4.9, 1.4 Hz, 1H).

Step 81.1: 4-(4-chlorophenyl)-5-(1,5-dimethyl-6-oxo-1,6-dihydropyridin-3-yl)-3-methyl-4,5-dihydropyrrolo[3,4-c]pyrazol-6(1H)-one

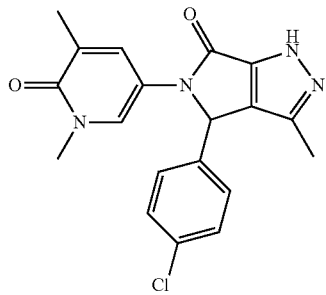 [SMILES: Cc1n[nH]c2c1C(c1ccc(Cl)cc1)N(c1cc(C)c(=O)n(C)c1)C2=O]

The title compound was prepared in analogy to the procedure described in Example 57 using 5-(3-acetyl-2-(4-chlorophenyl)-4-hydroxy-5-oxo-2,5-dihydro-1H-pyrrol-1-yl)-1,3-dimethylpyridin-2(1H)-one (Step 57.1). t$_R$: 3.36 min (HPLC 1).

Example 82

4-(4-chlorophenyl)-5-(1,5-dimethyl-6-oxo-1,6-dihydropyridin-3-yl)-3-methyl-1-(2-methylpyridin-3-yl)-4,5-dihydropyrrolo[3,4-c]pyrazol-6(1H)-one

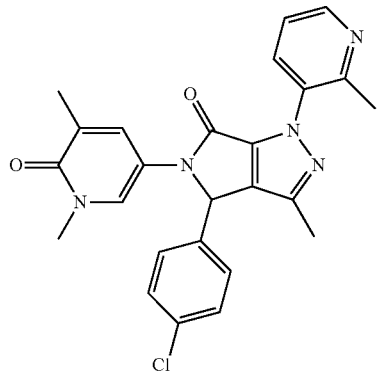 [SMILES: Cc1ncccc1-n1nc(C)c2c1C(=O)N(c1cc(C)c(=O)n(C)c1)C2c1ccc(Cl)cc1]

The title compound was prepared in analogy to the procedure described in Example 81. t$_R$: 3.37 min (HPLC 1); t$_R$: 0.94 min (LC-MS 2); ESI-MS: 460 [M+H]$^+$ (LC-MS 2); R$_f$=0.53 (CH$_2$Cl$_2$/MeOH 9:1); $^1$H NMR (400 MHz, DMSO-d$_6$) δ ppm 1.90 (s, 3H) 2.03 (s, 3H) 2.47 (s, 3H) 3.34 (s, 3H) 6.19 (s, 1H) 7.30-7.46 (m, 6H) 7.71 (d, J=2.3 Hz, 1H) 7.91 (dd, J=7.8, 1.6 Hz, 1H) 8.56 (dd, J=4.7, 1.6 Hz, 1H).

Example 83

4-(4-chlorophenyl)-5-(1,5-dimethyl-6-oxo-1,6-dihydropyridin-3-yl)-3-methyl-1-(1-methyl-1H-imidazol-5-yl)-4,5-dihydropyrrolo[3,4-c]pyrazol-6(1H)-one

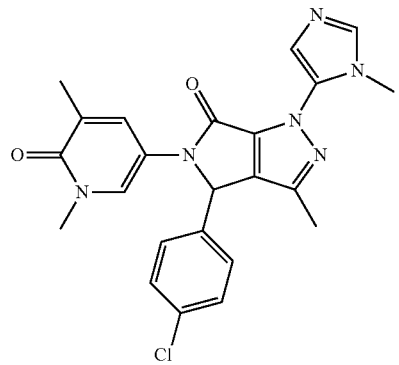 [SMILES: Cc1nn(-c2cncn2C)c2c1C(c1ccc(Cl)cc1)N(c1cc(C)c(=O)n(C)c1)C2=O]

The title compound was prepared in analogy to the procedure described in Example 57 using 5-(3-acetyl-2-(4-chlorophenyl)-4-hydroxy-5-oxo-2,5-dihydro-1H-pyrrol-1-yl)-3-chloro-1-methyl-pyridin-2(1H)-one (Step 57.1) and 5-hydrazinyl-1-methyl-1H-imidazole (Step 83.2). The crude material was first purified by silica gel column chromatography (CH$_2$Cl$_2$/MeOH 2-5%) followed by preparative achiral SFC (column NH$_2$, gradient 22-27% in 6 min_total 11 min) and trituration in Hex/Et$_2$O (1:1). t$_R$: 3.13 min (HPLC 1); t$_R$: 0.80 min (LC-MS 2); ESI-MS: 449 [M+H]$^+$ (LC-MS 2); R$_f$=0.49 (CH$_2$Cl$_2$/MeOH 9:1); $^1$H NMR (400 MHz, DMSO-d$_6$) δ ppm 1.91 (s, 3H) 2.01 (s, 3H) 3.34 (s, 3H) 3.56 (s, 3H) 6.16 (s, 1H) 7.15 (d, J=1.2 Hz, 1H) 7.31-7.43 (m, 5H) 7.69-7.75 (m, 2H).

Step 83.1: di-tert-butyl 1-(1-methyl-1H-imidazol-5-yl)hydrazine-1,2-dicarboxylate

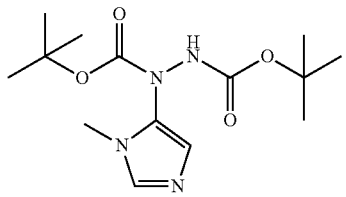 [SMILES: Cn1cncc1N(NC(=O)OC(C)(C)C)C(=O)OC(C)(C)C]

The title compound was prepared in analogy to the procedure described for Step 46.7 using 5-bromo-1-methylimidazole. The crude product was purified by silica gel column chromatography (CH$_2$Cl$_2$/MeOH 1-4%). t$_R$: 3.29 min (HPLC 1); t$_R$: 0.72 min (LC-MS 2); ESI-MS: 313 [M+H]$^+$ (LC-MS 2); R$_f$=0.49 (CH$_2$Cl$_2$/MeOH 9:1).

Step 83.2: 5-hydrazinyl-1-methyl-1H-imidazole

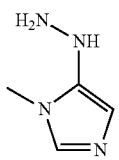

The title compound was prepared in analogy to the procedure described for Step 17.2 using di-tert-butyl 1-(1-methyl-1H-imidazol-5-yl)hydrazine-1,2-dicarboxylate (Step 83.1) at RT for 2 hr. ESI-MS: 113 [M+H]+ (LC-MS 2).

Example 84

4-(4-chlorophenyl)-1-cyclopropyl-3-ethyl-5-(8-methoxy-3-methyl-[1,2,4]triazolo[4,3-a]pyridin-6-yl)-4,5-dihydropyrrolo[3,4-c]pyrazol-6(1H)-one

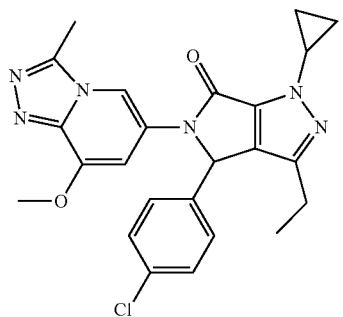 [SMILES: CCc1nn(C2CC2)c2c1C(c1ccc(Cl)cc1)N(c1cc(OC)c3nnc(C)n3c1)C2=O]

The tile compound was prepared in analogy to the procedure described in Example 68 using 5-(4-chlorophenyl)-1-(8-methoxy-3-methyl-[1,2,4]triazolo[4,3-a]pyridin-6-yl)-4-propionylpyrrolidine-2,3-dione (Step 84.5) and cyclopropylhydrazine hydrochloride in MeOH. Further purification by preparative achiral SFC (Propyl-pyridyl-urea, gradient 15-20% in 6 min_total 11 min). $t_R$: 0.98 min (LC-MS 2); ESI-MS: 463 [M+H]+ (LC-MS 2).

Step 84.1: 2-hydrazinyl-3-methoxy-5-nitropyridine

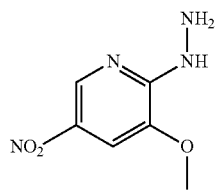

The title compound was prepared in analogy to the procedure described in Step 67.1 using 2-chloro-3-methoxy-5-nitropyridine. $t_R$: 0.46 min (LC-MS 2); ESI-MS: 185.0 [M+H]+ (LC-MS 2); ESI-MS: 183 [M−H]− (LC-MS 2).

Step 84.2: N'-(3-methoxy-5-nitropyridin-2-yl)acetohydrazide

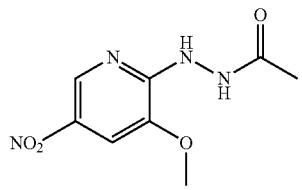 [SMILES: COc1cc([N+](=O)[O-])cnc1NNC(C)=O]

To a suspension of 2-hydrazinyl-3-methoxy-5-nitropyridine (Step 84.1) (20 g, 106 mmol) in dioxane (170 mL) was added at RT Ac₂O (13.1 mL, 138 mmol) and the reaction mixture was stirred for 1 hr at RT. The reaction mixture was poured onto ice-water (700 mL) and stirred for 1 hr at 0° C. The precipitate was collected by filtration, washed with H₂O and Et₂O, and dried under reduced pressure at 50° C. to afford the title product (23.3 g, 101 mmol, 95% yield) as a yellow solid. $t_R$: 0.45 min (LC-MS 2); ESI-MS: 227 [M+H]+ (LC-MS 2); ESI-MS: 225 [M−H]− (LC-MS 2).

Step 84.3: 8-methoxy-3-methyl-6-nitro-[1,2,4]triazolo[4,3-a]pyridine

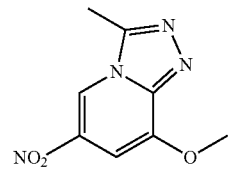

To a suspension of N'-(3-methoxy-5-nitropyridin-2-yl)acetohydrazide (Step 84.2) (23.3 g, 84 mmol) in CH₃CN (200 mL) was added DIEA (11.1 mL, 63.3 mmol) and dropwise POCl₃ (11.8 mL, 127 mmol) and the reaction mixture was stirred for 3.5 hr at 90° C. The cooled mixture was slowly added to water (600 mL), stirred for 30 min before the mixture was neutralized with solid NaHCO₃ to pH 6.5. The product was extracted with CH₂Cl₂/MeOH 6:1. Combined extracts were washed with H₂O, dried over MgSO₄, filtered and concentrated under reduced pressure. The crude material was purified by silica gel column chromatography (hexane/EtOAc/MeOH 50:50:5 to 0:50:5) followed by recrystallization from CH₂Cl₂/EtOAc/Et₂O. $t_R$: 0.49 min (LC-MS 2); ESI-MS: 209 [M+H]+ (LC-MS 2); ¹H NMR (400 MHz, DMSO-d₆) δ ppm 2.79 (s, 3H) 4.10 (s, 3H) 7.29 (d, J=1.7 Hz, 1H) 9.25 (d, J=1.7 Hz, 1H).

Step 84.4: 8-methoxy-3-methyl-[1,2,4]triazolo[4,3-a]pyridin-6-amine

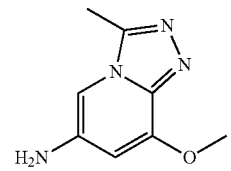

The title compound was prepared in analogy to the procedure described in Step 67.4 using 8-methoxy-3-methyl-6-nitro-[1,2,4]triazolo[4,3-a]pyridine (Step 84.3). The crude product was purified by silica gel column chromatography (CH$_2$Cl$_2$-MeOH 9:1) to afford the title product as yellow solid. TLC (CH$_2$Cl$_2$-MeOH 10:1) R$_f$=0.16; t$_R$: 0.31 min (LC-MS 2); ESI-MS: 179 [M+H]$^+$ (LC-MS 2); $^1$H NMR (400 MHz, DMSO-d$_6$) δ ppm 2.45 (s, 3H) 3.91 (s, 3H) 5.08 (s, 2H) 6.36 (d, J=1.2 Hz, 1H) 6.97 (d, J=1.2 Hz, 1H).

Step 84.5: 5(4-chlorophenyl)-1-(8-methoxy-3-methyl-[1,2,4]triazolo[4,3-a]pyridin-6-yl)-4-propionylpyrrolidine-2,3-dione

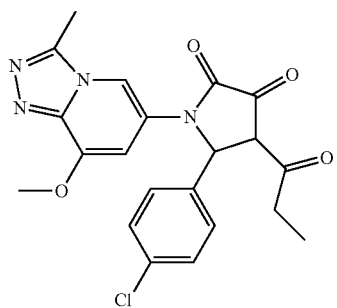 [SMILES: CCC(=O)C1C(=O)C(=O)N(c2cc(OC)c3nnc(C)n3c2)C1c1ccc(Cl)cc1]

The title compound was prepared in analogy to the procedure described in Step 60.1 using 8-methoxy-3-methyl-[1,2,4]triazolo[4,3-a]pyridin-6-amine (Step 84.4) at 110° C. for 2 hr. The reaction mixture was concentrated under reduced pressure; the residue was diluted with 0.5N NaOH and extracted with EtOAc. The combined organic layers were washed with 0.1N NaOH. The combined aqueous layers were acidified with 4N HCl, saturated with NaCl and extracted with EtOAc. The combined organic layers were washed with brine, dried over MgSO$_4$, filtered and concentrated under reduced pressure. t$_R$: 0.77 min (LC-MS 2); ESI-MS: 427 [M+H]$^+$ (LC-MS 2); ESI-MS: 425 [M–H]$^-$ (LC-MS 2).

Example 85

4-(4-chlorophenol)-1-cyclopropyl-5-(1,4-dimethyl-1H-benzo[d][1,2,3]triazol-6-yl)-3-methyl-4,5-dihydropyrrolo[3,4-c]pyrazol-6(1H)-one

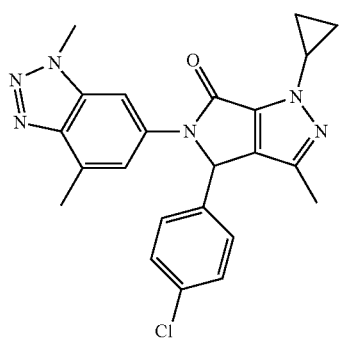 [SMILES: Cc1nn(C2CC2)c2c1C(c1ccc(Cl)cc1)N(c1cc(C)c3nnn(C)c3c1)C2=O]

The title compound was prepared in analogy to the procedure described in Example 23 using 4-(4-chlorophenyl)-1-cyclopropyl-3-methyl-4,5-dihydropyrrolo[3,4-c]pyrazol-6 (1H)-one (Step 85.6) and 6-bromo-1,4-dimethyl-1H-benzo[d][1,2,3]triazole (Step 85.3) at 100° C. for 16 hr. Further purification by preparative achiral SFC (column Propyl-pyridyl-urea, gradient 11-16% in 6 min_total 11 min). t$_R$: 4.95 min (HPLC 1); t$_R$: 1.12 min (LC-MS 2); ESI-MS: 433 [M+H]$^+$ (LC-MS 2); R$_f$=0.84 (CH$_2$Cl$_2$/MeOH 9:1).

Step 85.1: 5-bromo-N,3-dimethyl-2-nitroaniline

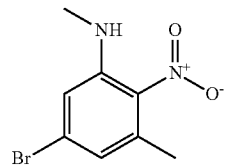

A MW vial was charged with 5-bromo-1-fluoro-3-methyl-2-nitrobenzene (500 mg, 2.137 mmol) and methylamine 2M in THF (5 mL, 10.0 mmol). The MW vial was sealed and the reaction mixture was submitted to MW irradiation for 30 min at 100° C. The reaction was cooled down to RT and concentrated under reduced pressure to afford the title product (520 mg, 2.122 mmol, 99% yield) as yellow solid. t$_R$: 1.19 min (LC-MS 2); ESI-MS: no ionisation (LC-MS 2).

Step 85.2: 5-bromo-N1,3-dimethylbenzene-1,2-diamine

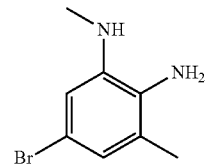

To a solution of 5-bromo-N,3-dimethyl-2-nitroaniline (Step 85.1) (2.7 g, 11.02 mmol) in THF (100 mL) and MeOH (100 mL) was added Raney Nickel (189 mg, 2.203 mmol) and the resulting mixture was stirred under hydrogen atmosphere at RT for 16 hr. The reaction was filtered through a pad of Celite and the resulting filtrate was concentrated under reduced pressure to afford the title product (2.5 g, 10.56 mmol, 96% yield) as off-white solid. t$_R$: 0.94 min (LC-MS 2); ESI-MS: 214 [M+H]$^+$ (LC-MS 2).

Step 85.3: 6-bromo-1,4-dimethyl-1H-benzo[d][1,2,3]triazole

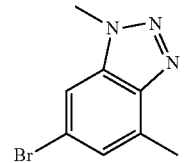

To a solution of 5-bromo-N1,3-dimethylbenzene-1,2-diamine (Step 85.2) (2.5 g, 11.62 mmol) in HCl cc (15 mL, 494 mmol) cooled down to 0° C. was slowly added a solution of NaNO$_2$ (0.962 g, 13.95 mmol) in water (25 mL). The resulting mixture was allowed to warm up and stir at RT for 2 hr. NaOH was added until basic pH, a precipitate occurred. The resulting solid was filtrated off, washed with water and dried under reduced pressure to afford the title product (2.5 g, 9.95 mmol, 86% yield) as beige solid. $t_R$: 0.93 min (LC-MS 2); ESI-MS: 228 [M+H]$^+$ (LC-MS 2).

Step 85.4: 4-(4-chlorophenyl)-5-(4-methoxybenzyl)-3-methyl-4,5-dihydropyrrolo[3,4-c]pyrazol-6(1H)-one

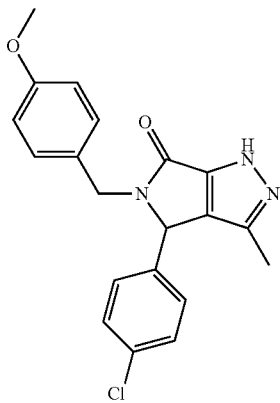 [SMILES: COc1ccc(CN2C(=O)c3[nH]nc(C)c3C2c2ccc(Cl)cc2)cc1]

The title compound was prepared in analogy to the procedure described in Example 57 using 4-acetyl-5-(4-chlorophenyl)-3-hydroxy-1-(4-methoxybenzyl)-1H-pyrrol-2(5H)-one (Step 71.2) and hydrazine hydrate at 100° C. for 16 hr. $t_R$: 4.75 min (HPLC 1); $t_R$: 1.05 min (LC-MS 2); ESI-MS: 368 [M+H]$^+$ (LC-MS 2); ESI-MS: 366 [M−H]$^-$ (LC-MS 2).

Step 85.5: 4-(4-chlorophenyl)-1-cyclopropyl-5-(4-methoxybenzyl)-3-methyl-4,5-dihydropyrrolo-[3,4-c]pyrazol-6(1H)-one

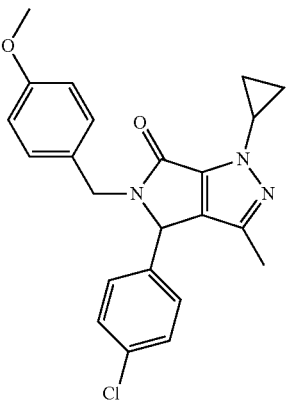 [SMILES: COc1ccc(CN2C(=O)c3c(c(C)nn3C3CC3)C2c2ccc(Cl)cc2)cc1]

To a stirred solution of 4-(4-chlorophenyl)-5-(4-methoxybenzyl)-3-methyl-4,5-dihydropyrrolo[3,4-c]pyrazol-6(1H)-one (Step 85.4) (8.76 g, 23.82 mmol) in 1,2-dichloroethane (100 mL) were added cyclopropylboronic acid (4.09 g, 47.6 mmol), copper (II) acetate (5.19 g, 28.6 mmol), Na$_2$CO$_3$ (5.05 g, 47.6 mmol) and 2,2'-bipyridine (3.72 g, 23.82 mmol) and the resulting mixture was stirred 16 h at 70° C. The reaction mixture was quenched with a saturated aq. NaHCO$_3$ solution and extracted with EtOAc. The combined organic layers were washed with saturated aq. NaHCO$_3$ solution, dried over Na$_2$SO$_4$ and concentrated under reduced pressure. The crude material was purified by silica gel column chromatography (hexane/EtOAc 15-30%) to afford the title product (3.27 g, 7.62 mmol, 32% yield) as yellow solid. $t_R$: 5.77 min (HPLC 1); $t_R$: 1.27 min (LC-MS 2); ESI-MS: 408 [M+H]$^+$ (LC-MS 2); R$_f$=0.65 (hexane/EtOAc 1:1).

Step 85.6: 4-(4-chlorophenyl)-1-cyclopropyl-3-methyl-4,5-dihydropyrrolo[3,4-c]pyrazol-6(1H)-one

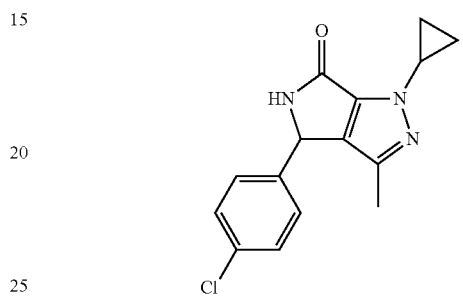

The title compound was prepared in analogy to the procedure described in Step 23.9 using 4-(4-chlorophenyl)-1-cyclopropyl-5-(4-methoxybenzyl)-3-methyl-4,5-dihydropyrrolo[3,4-c]pyrazol-6(1H)-one (Step 85.5) under MW irradiation 140° C. for 2 hr. $t_R$: 4.22 min (HPLC 1); $t_R$: 0.94 min (LC-MS 2); ESI-MS: 288 [M+H]$^+$ (LC-MS 2); R$_f$=0.31 (Hexane/EtOAc 1:1).

Example 86

4-(4-chlorophenyl)-5-(1,5-dimethyl-6-oxo-1,6-dihydropyridin-3-yl)-3-ethyl-1-(2-methoxyethyl)-4,5-dihydropyrrolo[3,4-c]pyrazol-6(1H)-one

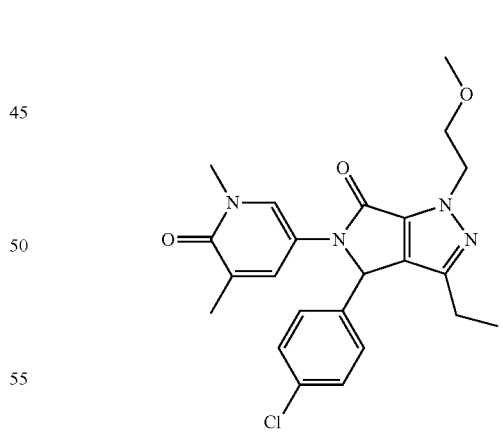

The title compound was prepared in analogy to the procedure described in Example 78 5-(4-chlorophenyl)-1-(1,5-dimethyl-6-oxo-1,6-dihydropyridin-3-yl)-4-propionylpyrrolidine-2,3-dione (Step 60.1), 2-methoxyethyl)hydrazine. The crude material was first purified by silica gel chromatography (hexane/EtOAc/MeOH 80:20:2 to 0:10:1) followed by preparative achiral SFC (4-Ethyl-pyridine, gradient 8-13% in 6 min_total 11 min). $t_R$: 0.95 min (LC-MS 2); ESI-MS: 411 [M+H]$^+$ (LC-MS 2); $^1$H NMR (400 MHz, DMSO-d$_6$) δ ppm 0.93 (t, J=7.6 Hz, 3H) 2.26-2.44 (m, 2H) 2.45 (s, 3H) 2.64 (s, 3H) 3.26 (s, 3H) 3.83 (t, J=5.7 Hz, 2H) 4.35-4.52 (m, 2H) 6.51 (s, 1H) 7.33-7.40 (m, 5H) 8.47 (s, 1H).

Example 87

4-(4-chlorophenyl)-5-(3,8-dimethyl-[1,2,4]triazolo[4,3-a]pyridin-6-yl)-3-ethyl-1-(2-methoxyethyl)-4,5-dihydropyrrolo[3,4-c]pyrazol-6(1H)-one

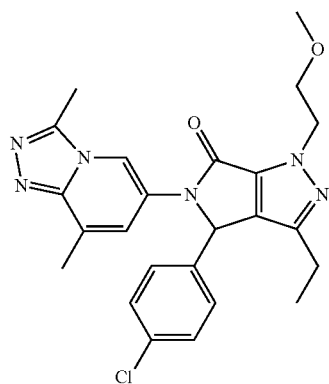 [SMILES: CCc1nn(CCOC)c2c1C(c1ccc(Cl)cc1)N(c1cc(C)c3nnc(C)n3c1)C2=O]

The title compound was prepared in analogy to the procedure described in Example 86 using 5-(4-chlorophenyl)-1-(3,8-dimethyl-[1,2,4]triazolo[4,3-a]pyridin-6-yl)-4-propionylpyrrolidine-2,3-dione (Step 70.1). The crude material was purified by silica gel chromatography (hexane/EtOAc/MeOH 75:25:5 to 5:1). $t_R$: 0.94 min (LC-MS 2); ESI-MS: 465 [M+H]$^+$ (LC-MS 2); $^1$H NMR (400 MHz, DMSO-d$_6$) δ ppm 0.93 (t, J=7.6 Hz, 3H) 2.23-2.44 (m, 2H) 2.45 (s, 3H) 2.64 (s, 3H) 3.26 (s, 3H) 3.83 (t, J=5.7 Hz, 2H) 4.35-4.52 (m, 2H) 6.51 (s, 1H) 7.32-7.40 (m, 5H) 8.47 (s, 1H).

Example 88

4-(4-chlorophenyl)-5-(3,8-dimethyl-[1,2,4]triazolo[4,3-a]pyridin-6-yl)-3-ethyl-2-(2-methoxyethyl)-4,5-dihydropyrrolo[3,4-c]pyrazol-6(2H)-one

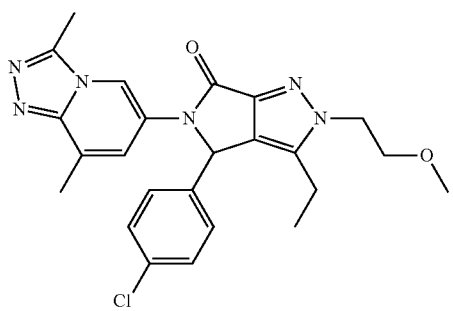 [SMILES: CCc1c2c(nn1CCOC)C(=O)N(c1cc(C)c3nnc(C)n3c1)C2c1ccc(Cl)cc1]

The title compound was prepared in analogy to the procedure described in Example 87 using 5-(4-chlorophenyl)-1-(3,8-dimethyl-[1,2,4]triazolo[4,3-a]pyridin-6-yl)-4-propionylpyrrolidine-2,3-dione (Step 70.1). $t_R$: 0.90 min (LC-MS 2); ESI-MS: 465 [M+H]$^+$ (LC-MS 2).

Example 89

4-(4-chlorophenyl)-5-(1,5-dimethyl-6-oxo-1,6-dihydropyridin-3-yl)-3-ethyl-1-(1-methyl-1H-pyrazol-5-yl)-4,5-dihydropyrrolo[3,4-c]pyrazol-6(1H)-one

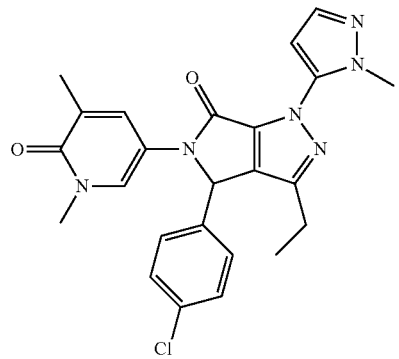 [SMILES: CCc1nn(-c2ccnn2C)c2c1C(c1ccc(Cl)cc1)N(c1cc(C)c(=O)n(C)c1)C2=O]

The title compound was prepared in analogy to the procedure described in Example 57 using 5-(2-(4-chlorophenyl)-4-hydroxy-5-oxo-3-propionyl-2,5-dihydro-1H-pyrrol-1-yl)-1,3-dimethylpyridin-2(1H)-one (Step 89.1) and 5-hydrazinyl-1-methyl-1H-pyrazole (Step 74.2). The crude material was first purified by silica gel column chromatography (1% ammonia/5% MeOH/CH$_2$Cl$_2$) followed by preparative achiral SFC (column 4-Ethyl-pyridine, gradient 10-15% in 6 min_total 11 min) and trituration in Et$_2$O. $t_R$: 1.01 min (LC-MS 2); ESI-MS: 463 [M+H]$^+$ (LC-MS 2); R$_f$=0.42 (1% ammonia/5% MeOH/CH$_2$Cl$_2$); $^1$H NMR (400 MHz, DMSO-d$_6$) δ ppm 0.97 (t, J=7.6 Hz, 3H) 1.94 (s, 3H) 2.35-2.48 (m, 2H) 3.37 (s, 3H) 3.86 (s, 3H) 6.25 (s, 1H) 6.63 (d, J=2.0 Hz, 1H) 7.34-7.48 (m, 5H) 7.58 (d, J=1.9 Hz, 1H) 7.75 (d, J=2.4 Hz, 1H).

Step 89.1: 5-(2-(4-chlorophenyl)-4-hydroxy-5-oxo-3-propionyl-2,5-dihydro-1H-pyrrol-1-yl)-1,3-dimethylpyridin-2(1H)-one

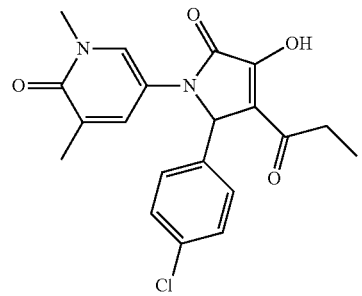 [SMILES: CCC(=O)C1=C(O)C(=O)N(c2cc(C)c(=O)n(C)c2)C1c1ccc(Cl)cc1]

The title compound was prepared in analogy to the procedure described in Step 84.5 using 5-amino-1,3-dimethylpyridin-2(1H)-one (Step 20.2) at 100° C. for 2 hr. $t_R$: 0.83 min (LC-MS 2); ESI-MS: 387 [M+H]$^+$ (LC-MS 2); $^1$H NMR (400 MHz, DMSO-d$_6$) d ppm 0.81-0.97 (m, 3H) 1.92 (s, 3H) 2.59-2.88 (m, 2H) 3.36 (s, 3H) 5.81 (s, 1H) 7.14-7.38 (m, 4H) 7.44 (dd, J=2.8, 1.0 Hz, 1H) 7.81 (d, J=2.6 Hz, 1H) 11.97 (br. s., 1H).

Example 90

4-(4-chlorophenyl)-5-(3,8-dimethyl-[1,2,4]triazolo[4,3-a]pyridin-6-yl)-3-methyl-1-(1-methyl-1H-pyrazol-5-yl)-4,5-dihydropyrrolo[3,4-c]pyrazol-6(1H)-one

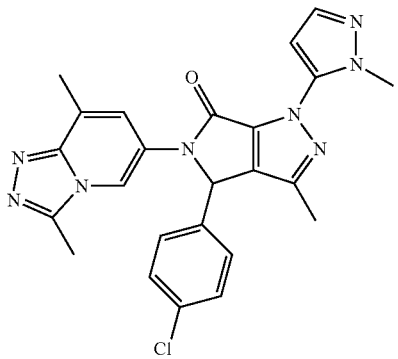

The title compound was prepared in analogy to the procedure described in Example 57 using 4-acetyl-5-(4-chlorophenyl)-1-(3,8-dimethyl-[1,2,4]triazolo[4,3-a]pyridin-6-yl)-3-hydroxy-1H-pyrrol-2(5H)-one (Step 90.1) and 5-hydrazinyl-1-methyl-1H-pyrazole (Step 74.2). The crude material was purified by silica gel column chromatography (1% ammonia/7.5% MeOH/CH$_2$Cl$_2$) and triturated in Et$_2$O. t$_R$: 0.92 min (LC-MS 2); ESI-MS: 473 [M+H]$^+$ (LC-MS 2); R$_f$=0.34 (1% ammonia/7.5% MeOH/CH$_2$Cl$_2$); $^1$H NMR (400 MHz, DMSO-d$_6$) δ ppm 2.06 (s, 3H) 2.43 (s, 3H) 2.60 (s, 3H) 3.85 (s, 3H) 6.55 (s, 1H) 6.58-6.68 (m, 1H) 7.31 (s, 1H) 7.37 (m, J=8.6 Hz, 2H) 7.45 (m, J=8.6 Hz, 2H) 7.56 (d, J=2.4 Hz, 1H) 8.44 (s, 1H).

Step 90.1: 4-acetyl-5-(4-chlorophenyl)-1-(3,8-dimethyl-[1,2,4]triazolo[4,3-a]pyridin-6-yl)-3-hydroxy-1H-pyrrol-2(5H)-one

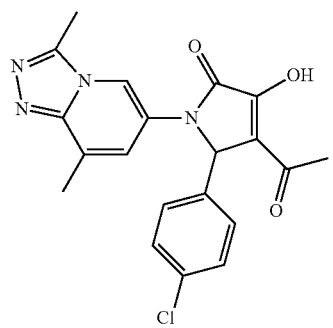 [SMILES: CC(=O)C1=C(O)C(=O)N(c2cc(C)c3nnc(C)n3c2)C1c1ccc(Cl)cc1]

The title compound was prepared in analogy to the procedure described in Step 84.5 using 3,8-dimethyl-[1,2,4]triazolo[4,3-a]pyridin-6-amine (Step 67.4), 4-chlorobenzaldehyde and ethyl 2,4-dioxovalerate. t$_R$: 0.70 min (LC-MS 2); ESI-MS: 397 [M+H]$^+$ (LC-MS 2); $^1$H NMR (400 MHz, DMSO-d$_6$) δ ppm 2.36 (s, 3H) 2.44 (s, 3H) 2.63 (s, 3H) 6.14 (s, 1H) 7.27 (d, J=8.4 Hz, 2H) 7.33-7.40 (m, 3H) 8.53 (s, 1H).

Example 91

1-cyclopropyl-5-(1,5-dimethyl-6-oxo-1,6-dihydropyridin-3-yl)-3-methyl-4-(3-(trifluoromethoxy)phenyl)-4,5-dihydropyrrolo[3,4-c]pyrazol-6(1H)-one

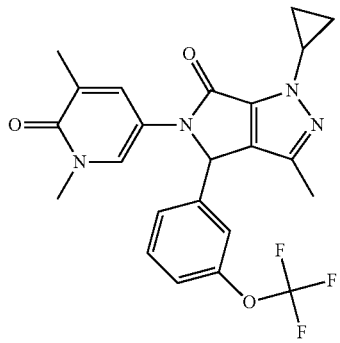 [SMILES: Cc1nn(C2CC2)c2c1C(c1cccc(OC(F)(F)F)c1)N(c1cc(C)c(=O)n(C)c1)C2=O]

To a solution of 4-acetyl-1-(1,5-dimethyl-6-oxo-1,6-dihydropyridin-3-yl)-5-(3-(trifluoromethoxy)-phenyl)pyrrolidine-2,3-dione (Step 91.1) (50 mg, 0.118 mmol) in Dioxane (1 mL) were added cyclopropylhydrazine hydrochloride (Step 17.2) (25.7 mg, 0.237 mmol) and TEA (0.082 mL, 0.592 mmol) and the resulting mixture was heated up and stirred at 120° C. for 2 hr. AcOH was added to acidify the reaction mixture and stirred at 100° C. for 30 min. The reaction was cooled down to RT and concentrated under reduced pressure. The residue was dissolved in EtOAc and washed with a saturated aq. NaHCO$_3$ solution and brine, dried over Na$_2$SO$_4$, filtered and concentrated under reduced pressure. The crude material was purified by silica gel column chromatography (CH$_2$Cl$_2$/(CH$_2$Cl$_2$/MeOH 19:1 NH$_3$) 0-100%) to afford the title product (10 mg, 0.021 mmol, 18.1% yield) as yellow foam. t$_R$: 1.03 min (LC-MS 2); ESI-MS: 459 [M+H]$^+$ (LC-MS 2); $^1$H NMR (400 MHz, DMSO-d$_6$) δ ppm 1.04 (d, J=6.3 Hz, 2H) 1.24 (br. s., 3H) 1.93 (s, 6H) 3.37-3.39 (m, 1H) 3.81 (br. s., 1H) 6.13 (s, 1H) 7.22-7.57 (m, 5H) 7.76 (br. s., 1H).

Step 91.1: 4-acetyl-1-(1,5-dimethyl-6-oxo-1,6-dihydropyridin-3-yl)-5-(3-(trifluoromethoxy)-phenyl)pyrrolidine-2,3-dione

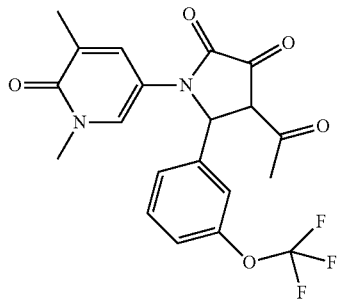 [SMILES: CC(=O)C1C(=O)C(=O)N(c2cc(C)c(=O)n(C)c2)C1c1cccc(OC(F)(F)F)c1]

The title compound was prepared in analogy to the procedure described in Step 57.1 using 5-amino-1,3-dimethylpyridin-2(1H)-one (Step 20.2), 3-trifluoromethoxy-benzaldehyde and ethyl acetopyruvate at 110° C. for 4 hr. t$_R$: 0.79 min (LC-MS 2); ESI-MS: 423 [M+H]$^+$ (LC-MS 2); ESI-MS: 421 [M−H]$^-$ (LC-MS 2).

Example 92

4-(4-chlorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one

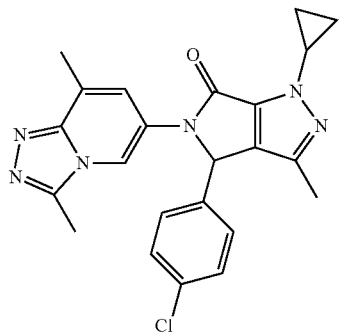 [SMILES: Cc1nn(C2CC2)c2c1C(c1ccc(Cl)cc1)N(c1cc(C)c3nnc(C)n3c1)C2=O]

A mixture of 4-acetyl-5-(4-chlorophenyl)-1-(3,8-dimethyl-[1,2,4]triazolo[4,3-a]pyridin-6-yl)-3-hydroxy-1H-pyrrol-2(5H)-one (Step 92.1) (630 mg, 1.588 mmol) and cyclopropylhydrazine hydrochloride (517 mg, 4.76 mmol) in EtOH (8 mL) and toluene (8 mL) was stirred for 2 hr at reflux. The reaction mixture was concentrated, diluted with $CH_2Cl_2$/saturated aq. $NaHCO_3$ solution, and extracted with $CH_2Cl_2$. The combined organic layers were washed with water and brine, dried over $Na_2SO_4$ and evaporated. The crude material was purified by silica gel column chromatography (1% ammonia/5% MeOH/$CH_2Cl_2$) to afford the title product (412 mg, 0.952 mmol, 59.9% yield) as a yellow foam. $t_R$: 0.95 min (LC-MS 2); ESI-MS: 433 [M+H]+ (LC-MS 2); $R_f$=0.28 (1% ammonia/5% MeOH/$CH_2Cl_2$); $^1$H NMR (400 MHz, DMSO-$d_6$) δ ppm 0.98-1.11 (m, 2H) 1.18-1.29 (m, 2H) 1.92 (s, 3H) 2.43 (s, 3H) 2.61 (s, 3H) 3.75-3.87 (m, 1H) 6.41 (s, 1H) 7.27-7.39 (m, 5H) 8.33-8.48 (m, 1H).

Step 92.1: 4-acetyl-5-(4-chlorophenyl)-1-(3,8-dimethyl-[1,2,4]triazolo[4,3-a]pyridin-6-yl)-3-hydroxy-1H-pyrrol-2(5H)-one A mixture of 3,8-dimethyl-[1,2,4]triazolo[4,3-a]pyridin-6-amine (Step 67.4) (2 g, 12.33 mmol), 4-chlorobenzaldehyde (1.576 g, 11.21 mmol) and ethyl 2,4-dioxopentanoate (1.773 g, 11.21 mmol) in acetic acid (10 mL) was stirred for 2 hr at 100° C. The reaction mixture was concentrated, diluted with $CH_2Cl_2$/1N NaOH and extracted with $CH_2Cl_2$. The combined organic layers were dried over $Na_2SO_4$, evaporated and discarded as they contained no desired product. The aqueous was acidified to pH 3 with 6N HCl and extracted with $CH_2Cl_2$. The combined organic extracts were dried over $Na_2SO_4$ and concentrated to afford the title compound (3.88 g, 8.80 mmol, 79% yield) as a beige foam. $t_R$: 0.70 min (LC-MS 2); ESI-MS: 397 [M+H]+ (LC-MS 2); $^1$H NMR (400 MHz, DMSO-$d_6$) δ ppm 2.36 (s, 3H) 2.44 (s, 3H) 2.63 (s, 3H) 6.14 (s, 1H) 7.27 (d, J=8.44 Hz, 2H) 7.33-7.40 (m, 3H) 8.53 (s, 1H).

Example 93

4-(4-chlorophenyl)-2-cyclopropyl-5-(3,8-dimethyl-[1,2,4]triazolo[4,3-a]pyridin-6-yl)-3-methyl-4,5-dihydropyrrolo[3,4-c]pyrazol-6(2H)-one

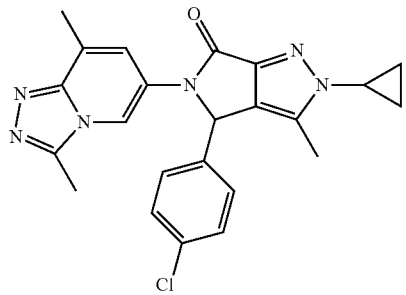 [SMILES: Cc1cc(N2C(=O)c3nn(C4CC4)c(C)c3C2c2ccc(Cl)cc2)cn2c(C)nnc12]

The title compound was prepared in analogy to the procedure described for Example 92 using 4-(4-chlorophenyl)-5-(3,8-dimethyl-[1,2,4]triazolo[4,3-a]pyridin-6-yl)-3-methyl-4,5-dihydropyrrolo-[3,4-c]pyrazol-6(1H)-one (Example 98). $t_R$: 0.92 min (LC-MS 2); ESI-MS: 433 [M+H]+ (LC-MS 2); $R_f$=0.20 (1% ammonia/5% MeOH/$CH_2Cl_2$); $^1$H NMR (400 MHz, DMSO-$d_6$) δ ppm 0.95-1.24 (m, 4H) 2.20 (s, 3H) 2.45 (s, 3H) 2.63 (s, 3H) 3.62-3.79 (m, 1H) 6.49 (s, 1H) 7.36 (s, 5H) 8.46 (s, 1H).

Example 94

4-(4-chlorophenyl)-1-cyclobutyl-5-(1,5-dimethyl-6-oxo-1,6-dihydropyridin-3-yl)-3-methyl-4,5-dihydropyrrolo[3,4-c]pyrazol-6(1H)-one

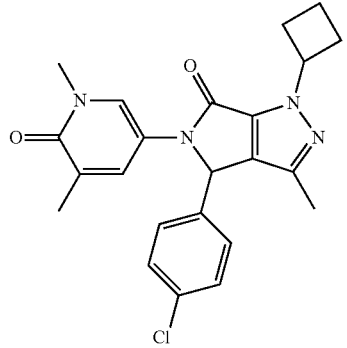 [SMILES: Cc1nn(C2CCC2)c2c1C(c1ccc(Cl)cc1)N(c1cc(C)c(=O)n(C)c1)C2=O]

The title compound was prepared in analogy to the procedure described in Example 23 using 4-(4-chlorophenyl)-1-cyclobutyl-3-methyl-4,5-dihydropyrrolo[3,4-c]pyrazol-6(1H)-one (Step 94.1) and 5-iodo-1,3-dimethylpyridin-2(1H)-one (Step 23.2) 16 hr at 100° C. The crude material was purified by silica gel column chromatography ($CH_2Cl_2$/MeOH 0.5-2%) followed by trituration in hexane/$Et_2O$ (3:1). $t_R$: 4.74 min (HPLC 1); $t_R$: 1.08 min (LC-MS 2); ESI-MS: 423 [M+H]+ (LC-MS 2); $R_f$=0.50 ($CH_2Cl_2$/MeOH 9:1); $^1$H NMR (400 MHz, DMSO-$d_6$) δ ppm 1.70-1.84 (m, 2H) 1.90-1.94 (m, 6H) 2.34-2.45 (m, 2H) 2.57-2.73 (m, 2H) 3.35 (s, 3H) 4.91-5.04 (m, 1H) 6.06 (s, 1H) 7.25 (d, J=8.6 Hz, 2H) 7.33-7.40 (m, 3H) 7.72 (d, J=2.7 Hz, 1H).

189

Step 94.1: 4-(4-chlorophenyl)-1-cyclobutyl-5-(4-methoxybenzyl)-3-methyl-4,5-dihydropyrrolo[3,4-c]pyrazol-6(1H)-one

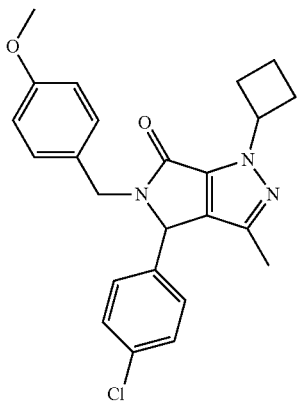 [SMILES: COc1ccc(CN2C(=O)c3c(c(C)nn3C3CCC3)C2c2ccc(Cl)cc2)cc1]

To a stirred solution of 4-(4-chlorophenyl)-5-(4-methoxybenzyl)-3-methyl-4,5-dihydropyrrolo[3,4-c]pyrazol-6(1H)-one (Step 85.4) (1 g, 2.72 mmol), PPh$_3$ (0.792 g, 3.02 mmol) and cyclobutanol (0.321 mL, 4.11 mmol) in THF (25 mL) under Ar was added dropwise DEAD in toluene (1.424 ml, 3.13 mmol) and the reaction mixture was stirred 16 h at RT. PPh$_3$ (0.792 g, 3.02 mmol) and DEAD in toluene (1.424 ml, 3.13 mmol) were further added and the reaction mixture was stirred for 24 hr at RT. The reaction was quenched with a saturated aq. NaHCO$_3$ solution and extracted with CH$_2$Cl$_2$. The combined organic layers were washed with a saturated aq. NaHCO$_3$ solution, dried over Na$_2$SO$_4$ and concentrated under reduced pressure. The crude material was purified by silica gel column chromatography (hexane/EtOAc 10-30%) to afford the title product (899 mg, 2.024 mmol, 75% yield) as white solid. t$_R$: 6.24 min (HPLC 1); t$_R$: 1.37 min (LC-MS 2); ESI-MS: 422 [M+H]$^+$ (LC-MS 2); R$_f$=0.83 (hexane/EtOAc 1:1).

Step 94.2: 4-(4-chlorophenyl)-1-cyclobutyl-3-methyl-4,5-dihydropyrrolo[3,4-c]pyrazol-6(1H)-one

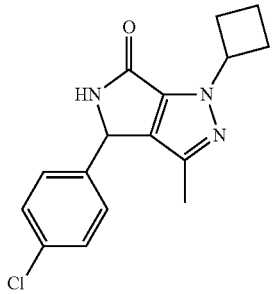 [SMILES: Cc1nn(C2CCC2)c2c1C(c1ccc(Cl)cc1)NC2=O]

The title compound was prepared in analogy to the procedure described in Step 23.9 using 4-(4-chlorophenyl)-1-cy-

190 clobutyl-3-methyl-4,5-dihydropyrrolo[3,4-c]pyrazol-6(1H)-one (Step 94.1) under MW irradiation 140° C. for 2 hr. The crude material was purified by silica gel column chromatography (hexane/EtOAc 15-35%) t$_R$: 4.75 min (HPLC 1); t$_R$: 1.05 min (LC-MS 2); ESI-MS: 302 [M+H]$^+$ (LC-MS 2); R$_f$=0.61 (Hexane/EtOAc 1:1).

Example 95

1-cyclopropyl-5-(1,5-dimethyl-6-oxo-1,6-dihydropyridin-3-yl)-3-methyl-4-(4-(trifluoromethoxy)phenyl)-4,5-dihydropyrrolo[3,4-c]pyrazol-6(1H)-one

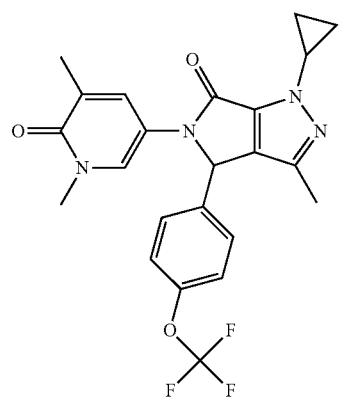 [SMILES: Cc1nn(C2CC2)c2c1C(c1ccc(OC(F)(F)F)cc1)N(c1cc(C)c(=O)n(C)c1)C2=O]

The title compound was prepared in analogy to the procedure described in Example 91 using 4-acetyl-1-(1,5-dimethyl-6-oxo-1,6-dihydropyridin-3-yl)-5-(4-(trifluoromethoxy)phenyl)pyrrolidine-2,3-dione (Step 95.1). t$_R$: 1.03 min (LC-MS 2); ESI-MS: 459 [M+H]$^+$ (LC-MS 2).

Step 95.1: 4-acetyl-1-(1,5-dimethyl-6-oxo-1,6-dihydropyridin-3-yl)-5-(4-(trifluoromethoxy)-phenyl)pyrrolidine-2,3-dione

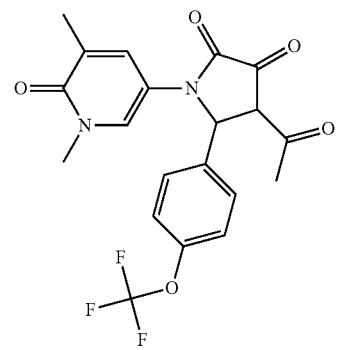 [SMILES: CC(=O)C1C(=O)C(=O)N(c2cc(C)c(=O)n(C)c2)C1c1ccc(OC(F)(F)F)cc1]

The title compound was prepared in analogy to the procedure described in Step 57.1 using 5-amino-1,3-dimethylpyridin-2(1H)-one (Step 20.2), 4-trifluoromethoxy-benzaldehyde and ethyl acetopyruvate. t$_R$: 0.79 min (LC-MS 2); ESI-MS: 423 [M+H]$^+$ (LC-MS 2); ESI-MS: 421 [M−H]$^-$ (LC-MS 2).

Example 96

1-cyclopropyl-5-(1,5-dimethyl-6-oxo-1,6-dihydropyridin-3-yl)-3-methyl-4-(3-(trifluoromethyl)phenyl)-4,5-dihydropyrrolo[3,4-c]pyrazol-6(1H)-one

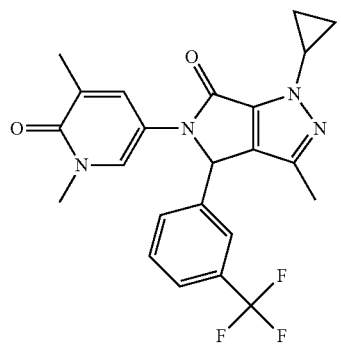 [SMILES: Cc1nn(C2CC2)c2c1C(c1cccc(C(F)(F)F)c1)N(c1cc(C)c(=O)n(C)c1)C2=O]

The title compound was prepared in analogy to the procedure described in Example 91 using 4-acetyl-1-(1,5-dimethyl-6-oxo-1,6-dihydropyridin-3-yl)-5-(3-(trifluoromethyl)phenyl)pyrrolidine-2,3-dione (Step 96.1). $t_R$: 1.00 min (LC-MS 2); ESI-MS: 443 [M+H]$^+$ (LC-MS 2); $^1$H NMR (400 MHz, DMSO-d$_6$) δ ppm 0.96-1.09 (m, 2H) 1.19-1.29 (m, 2H) 1.92 (d, J=10.7 Hz, 9H) 3.82 (dt, J=7.4, 3.6 Hz, 1H) 6.20 (s, 1H) 7.41 (d, J=1.2 Hz, 1H) 7.50-7.60 (m, 2H) 7.64-7.81 (m, 3H).

Step 96.1: 4-acetyl-1-(1,5-dimethyl-6-oxo-1,6-dihydropyridin-3-yl)-5-(3-(trifluoromethyl)phenyl)-pyrrolidine-2,3-dione

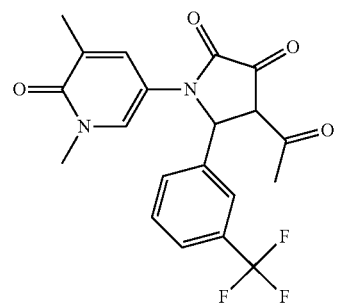 [SMILES: CC(=O)C1C(=O)C(=O)N(c2cc(C)c(=O)n(C)c2)C1c1cccc(C(F)(F)F)c1]

The title compound was prepared in analogy to the procedure described in Step 57.1 using 5-amino-1,3-dimethylpyridin-2(1H)-one (Step 20.2), 3-trifluoromethylbenzaldehyde and ethyl acetopyruvate. $t_R$: 0.76 min (LC-MS 2); ESI-MS: 407 [M+H]$^+$ (LC-MS 2); ESI-MS: 405 [M−H]$^−$ (LC-MS 2).

Example 97

1-cyclopropyl-5-(1,5-dimethyl-6-oxo-1,6-dihydropyridin-3-yl)-3-methyl-4-(4-(trifluoromethyl)phenyl)-4,5-dihydropyrrolo[3,4-c]pyrazol-6(1H)-one

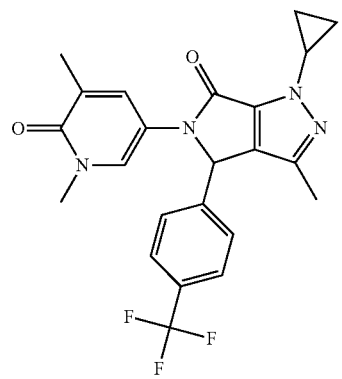 [SMILES: Cc1nn(C2CC2)c2c1C(c1ccc(C(F)(F)F)cc1)N(c1cc(C)c(=O)n(C)c1)C2=O]

The title compound was prepared in analogy to the procedure described in Example 91 using 4-acetyl-1-(1,5-dimethyl-6-oxo-1,6-dihydropyridin-3-yl)-5-(4-(trifluoromethyl)phenyl)pyrrolidine-2,3-dione (Step 97.1) at 120° C. for 4 hr. $t_R$: 1.01 min (LC-MS 2); ESI-MS: 443 [M+H]$^+$ (LC-MS 2); $^1$H NMR (400 MHz, DMSO-d$_6$) δ ppm 1.04 (dd, J=7.4, 2.1 Hz, 2H) 1.17-1.28 (m, 2H) 1.93 (d, J=13.7 Hz, 6H) 3.36 (br. s., 3H) 3.82 (dt, J=7.4, 3.7 Hz, 1H) 6.21 (s, 1H) 7.44 (d, J=1.3 Hz, 1H) 7.51 (d, J=8.1 Hz, 2H) 7.71 (d, J=8.2 Hz, 2H) 7.79 (d, J=2.4 Hz, 1H).

Step 97.1: 4-acetyl-1-(1,5-dimethyl-6-oxo-1,6-dihydropyridin-3-yl)-5-(4-(trifluoromethyl)phenyl)-pyrrolidine-2,3-dione

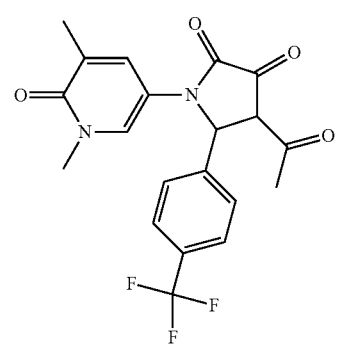 [SMILES: CC(=O)C1C(=O)C(=O)N(c2cc(C)c(=O)n(C)c2)C1c1ccc(C(F)(F)F)cc1]

The title compound was prepared in analogy to the procedure described in Step 57.1 using 5-amino-1,3-dimethylpyridin-2(1H)-one (Step 20.2), 4-trifluormethylbenzaldehyde and ethyl acetopyruvate. $t_R$: 0.76 min (LC-MS 2); ESI-MS: 407 [M+H]$^+$ (LC-MS 2); ESI-MS: 405 [M−H]$^−$ (LC-MS 2).

Example 98

4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one

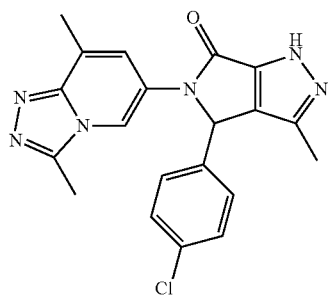 [SMILES: Cc1n[nH]c2c1C(c1ccc(Cl)cc1)N(c1cc(C)c3nnc(C)n3c1)C2=O]

The title compound was prepared in analogy to the procedure described in Example 57 using 4-acetyl-5-(4-chlorophenyl)-1-(3,8-dimethyl-[1,2,4]triazolo[4,3-a]pyridin-6-yl)-3-hydroxy-1H-pyrrol-2(5H)-one (Step 90.1) and hydrazine hydrate. The crude material was purified by silica gel column chromatography (7.5% MeOH/CH$_2$Cl$_2$) and triturated in Et$_2$O. t$_R$: 0.75 min (LC-MS 2); ESI-MS: 393 [M+H]$^+$ (LC-MS 2); R$_f$=0.23 (7.5% MeOH/CH$_2$Cl$_2$); $^1$H NMR (400 MHz, DMSO-d$_6$) δ ppm 2.08 (s, 3H) 2.46 (s, 3H) 2.64 (s, 3H) 6.48 (s, 1H) 7.19-7.46 (m, 5H) 8.47 (s, 1H) 13.49 (br. s., 1H).

Reference Example 99

(S)-4-(4-chlorophenyl)-1-(2,4-dimethoxypyrimidin-5-yl)-5-(1,5-dimethyl-6-oxo-1,6-dihydropyridin-3-yl)-3-methyl-4,5-dihydropyrrolo[3,4-c]pyrazol-6(1H)-one

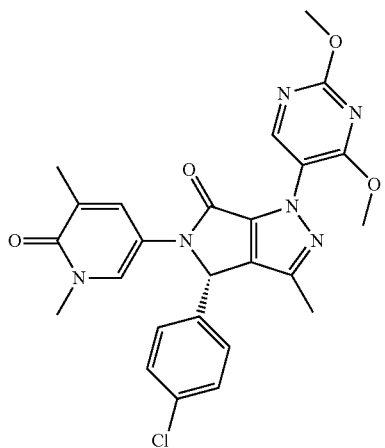 [SMILES: COc1ncc(-n2nc(C)c3c2C(=O)N(c2cc(C)c(=O)n(C)c2)[C@H]3c2ccc(Cl)cc2)c(OC)n1]

The title compound (206 mg, 0.406 mmol, 32.7% yield) was obtained enantiomerically pure (ee>99%) after chiral preparative chromatography (Chiralpak AD-H 30×250 mm; mobile phase: scCO$_2$/MeOH 70:30 isocratic 6.5 min; flow: 100 mL/min; detection 270 nm) of the racemic mixture of 4-(4-chlorophenyl)-1-(2,4-dimethoxypyrimidin-5-yl)-5-(1,5-dimethyl-6-oxo-1,6-dihydropyridin-3-yl)-3-methyl-4,5-dihydropyrrolo[3,4-c]pyrazol-6(1H)-one (Example 52) (630 mg, 1.243 mmol). Second purification by chiral preparative chromatography (Chiralpak AD-H 20×250 mm; mobile phase: EtOH/MeOH 50:50 isocratic in 17 min; flow: 12 mL/min; detection 270 nm). t$_R$: 4.24 min (HPLC 1); t$_R$: 0.99 min (LC-MS 2); ESI-MS: 507 [M+H]$^+$ (LC-MS 2).

Example 100

(R)-4-(4-chlorophenyl)-1-(2,4-dimethoxypyrimidin-5-yl)-5-(1,5-dimethyl-6-oxo-1,6-dihydropyridin-3-yl)-3-methyl-4,5-dihydropyrrolo[3,4-c]pyrazol-6(1H)-one

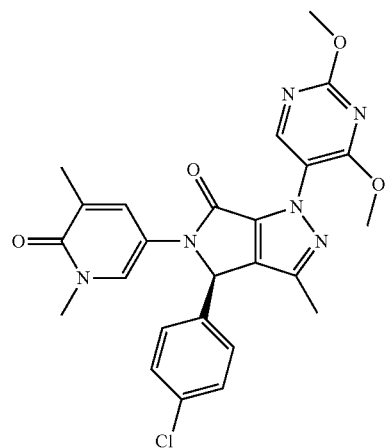 [SMILES: COc1ncc(-n2nc(C)c3c2C(=O)N(c2cc(C)c(=O)n(C)c2)[C@@H]3c2ccc(Cl)cc2)c(OC)n1]

The title compound (199 mg, 0.393 mmol, 31.6% yield) was obtained enantiomerically pure (ee=98.8%) after chiral preparative chromatography (system: Thar/Waters SFC-100 MS; column: Chiralpak AD-H 30×250 mm; mobile phase: scCO$_2$/MeOH 70:30 isocratic in 6.5 min; flow: mL/min; detection 270 nm) of the racemic mixture of 4-(4-chlorophenyl)-1-(2,4-dimethoxypyrimidin-5-yl)-5-(1,5-dimethyl-6-oxo-1,6-dihydropyridin-3-yl)-3-methyl-4,5-dihydropyrrolo[3,4-c]pyrazol-6(1H)-one (Example 52) (630 mg, 1.243 mmol). Second purification by chiral preparative chromatography (Chiralpak AD-H 20×250 mm; mobile phase: EtOH/MeOH 50:50 isocratic in 17 min; flow: 12 mL/min; detection 270 nm). t$_R$: 4.24 min (HPLC 1); t$_R$: 0.99 min (LC-MS 2); ESI-MS: 507 [M+H]$^+$ (LC-MS 2).

Example 101

4-(4-chlorophenyl)-5-(3,8-dimethyl-[1,2,4]triazolo[4,3-a]pyridin-6-yl)-1-(2-methoxypyridin-3-yl)-3-methyl-4,5-dihydropyrrolo[3,4-c]pyrazol-6(1H)-one

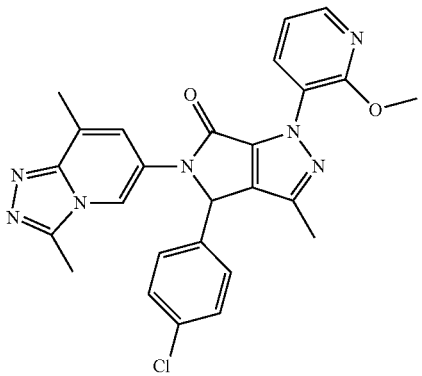 [SMILES: COc1ncccc1-n1nc(C)c2c1C(=O)N(c1cc(C)c3nnc(C)n3c1)C2c1ccc(Cl)cc1]

The title compound was prepared in analogy to the procedure described in Example 57 using 4-acetyl-5-(4-chlorophenyl)-1-(3,8-dimethyl-[1,2,4]triazolo[4,3-a]pyridin-6-yl)-3-hydroxy-1H-pyrrol-2(5H)-one (Step 90.1) and 3-hydrazinyl-2-methoxypyridine (Step 71.1). The crude material was purified by silica gel column chromatography (1% ammonia/5% MeOH/CH$_2$Cl$_2$) followed by preparative achiral SFC (column Propyl-pyridyl-urea, gradient 12-17% in 6 min_total 11 min) and triturated in Et$_2$O. $t_R$: 0.99 min (LC-MS 2); ESI-MS: 500 [M+H]$^+$ (LC-MS 2); R$_f$=0.33 (1% ammonia/5% MeOH/CH$_2$Cl$_2$); $^1$H NMR (400 MHz, DMSO-d$_6$) δ ppm 2.07 (s, 3H) 2.45 (s, 3H) 2.62 (s, 3H) 3.92 (s, 3H) 6.59 (s, 1H) 7.21 (dd, J=7.6, 5.01 Hz, 1H) 7.34 (s, 1H) 7.37-7.48 (m, 4H) 8.00 (dd, J=7.6, 1.71 Hz, 1H) 8.33 (dd, J=4.9, 1.6 Hz, 1H) 8.47 (s, 1H).

Example 102

4-(4-chlorophenyl)-1-cyclopropyl-3-methyl-5-(3-methyl-3H-[1,2,3]triazolo[4,5-b]-pyridin-5-yl)-4,5-dihydropyrrolo[3,4-c]pyrazol-6(1H)-one

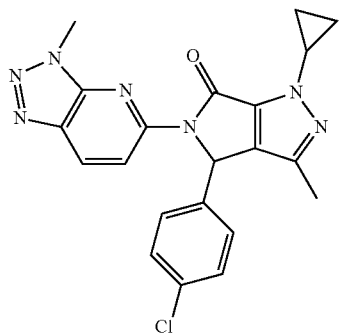 [SMILES: Cc1nn(C2CC2)c2c1C(c1ccc(Cl)cc1)N(c1ccc3nnn(C)c3n1)C2=O]

A flask was charged with 5-chloro-3-methyl-3H-[1,2,3]triazolo[4,5-b]pyridine (Step 102.3) (132 mg, 0.782 mmol), 4-(4-chlorophenyl)-1-cyclopropyl-3-methyl-4,5-dihydropyrrolo[3,4-c]pyrazol-6(1H)-one (Step 85.6) (150 mg, 0.521 mmol) Pd2(dba)3 (47.7 mg, 0.052 mmol), Xantphos (60.3 mg, 0.104 mmol) and Cs$_2$CO$_3$ (340 mg, 1.043 mmol) in dioxane (3 mL) and the resulting mixture was heated up and stirred at 100° C. for 16 hr. The reaction was diluted with EtOAc and water and both phases separated. The aqueous layer was extracted with EtOAc, the combined organic layers were washed with water and brine, dried over Na$_2$SO$_4$ and concentrated under reduced pressure. Palladium was removed using a Varian PL-Thiol MP SPE cartridge and the residue was purified by silica gel column chromatography (50% EtOAc/hexane) to afford, after trituration in Et$_2$O, the title product (153 mg, 0.357 mmol, 68% yield) as white solid. $t_R$: 1.20 min (LC-MS 2); ESI-MS: 420 [M+H]$^+$ (LC-MS 2); R$_f$=0.24 (50% EtOAc/Hexane); $^1$H NMR (400 MHz, DMSO-d$_6$) δ ppm 0.99-1.16 (m, 2H) 1.21-1.35 (m, 2H) 1.95 (d, J=3.6 Hz, 3H) 3.87 (td, J=7.3, 3.6 Hz, 1H) 4.14 (d, J=3.7 Hz, 3H) 6.63 (d, J=3.6 Hz, 1H) 7.26-7.42 (m, 2H) 7.42-7.58 (m, 2H) 8.30-8.48 (m, 1H) 8.54 (dt, J=9.2, 3.2 Hz, 1H).

Step 102.1:
6-chloro-N-methyl-3-nitropyridin-2-amine

Methylamine 2M in THF (67 mL, 134 mmol) was added to a stirred solution of 2,6-dichloro-3-nitropyridine (12, 93 g, 67 mmol) in THF (100 mL) at 0° C. and the resulting mixture was stirred at RT for 16 hr. The reaction was concentrated under reduced pressure; the residue was partitioned between water and EtOAc and both phases separated. The aq. layer was extracted with EtOAc, the combined organic layer were washed with brine, dried over Na$_2$SO$_4$, filtered and concentrated under reduced pressure. The crude material was purified by silica gel column chromatography (25% EtOAc/hexane) to afford the title product (10.54 g, 53.4 mmol, 80% yield) as yellow solid. $t_R$: 0.96 min (LC-MS 2); ESI-MS: 187 [M+H]$^+$ (LC-MS 2); R$_f$=0.72 (25% EtOAc/hexane).

Step 102.2: 6-chloro-N2-methylpyridine-2,3-diamine

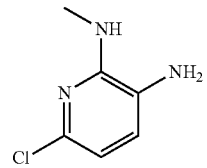

The title compound was prepared in analogy to the procedure described in Step 85.2 using 6-chloro-N-methyl-3-nitropyridin-2-amine (Step 102.1) at RT for 23 hr. The crude material was purified by silica gel column chromatography (25% EtOAc/hexane) to afford a purple solid. $t_R$: 0.64 min (LC-MS 2); ESI-MS: 158 [M+H]$^+$ (LC-MS 2); R$_f$=0.12 (25% EtOAc/Hexane).

Step 102.3: 5-chloro-3-methyl-3H-[1,2,3]triazolo[4,5-b]pyridine

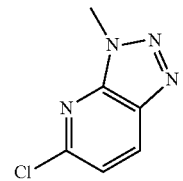

NaNO$_2$ (350 mg, 5.08 mmol) was added to a stirred solution of 6-chloro-N2-methylpyridine-2,3-diamine (Step 102.2) (800 mg, 5.08 mmol) in 2N HCl (8 mL) at 0° C. and the resulting mixture was stirred for 10 min at 0° C. The reaction was basified with 2N NaOH and extracted with CH$_2$Cl$_2$. The combined organic layers were washed with brine, dried over Na$_2$SO$_4$, filtered and concentrated under reduced pressure. The crude material was purified by silica gel column chromatography (50% EtOAc/hexane) to afford the title product (545 mg, 3.23 mmol, 64% yield) as beige solid. $t_R$: 0.69 min (LC-MS 2); ESI-MS: 168/170 [M+H]$^+$ (LC-MS 2); $R_f$=0.46 (50% EtOAc/hexane); $^1$H NMR (400 MHz, DMSO-d$_6$) δ ppm 4.25 (s, 3H) 7.44-7.62 (m, 1H) 8.62 (d, J=8.6 Hz, 1H).

Reference Example 103

(S)-4-(4-chlorophenyl)-5-(1,5-dimethyl-6-oxo-1,6-dihydropyridin-3-yl)-1-isopropyl-3-methyl-4,5-dihydropyrrolo[3,4-c]pyrazol-6(1H)-one

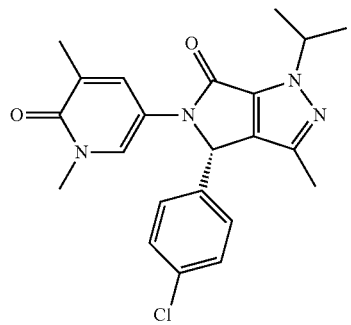

The title compound (163 mg, 0.397 mmol, 36.5% yield) was obtained enantiomerically pure (ee=100%) after chiral preparative chromatography (Chiralpak AD-H 30×250 mm ID; mobile phase: scCO$_2$/MeOH 78:22 isocratic; flow: 60 mL/min; detection 270 nm) of the racemic mixture of 4-(4-chlorophenyl)-5-(1,5-dimethyl-6-oxo-1,6-dihydropyridin-3-yl)-1-isopropyl-3-methyl-4,5-dihydropyrrolo[3,4-c]pyrazol-6(1H)-one (Example 63) (446 mg, 1.085 mmol) and trituration in hexane/Et$_2$O (3:1). $t_R$: 4.45 min (HPLC 1); $t_R$: 0.99 min (LC-MS 2); ESI-MS: 411 [M+H]$^+$ (LC-MS 2).

Example 104

(R)-4-(4-chlorophenyl)-5-(1,5-dimethyl-6-oxo-1,6-dihydropyridin-3-yl)-1-isopropyl-3-methyl-4,5-dihydropyrrolo[3,4-c]pyrazol-6(1H)-one

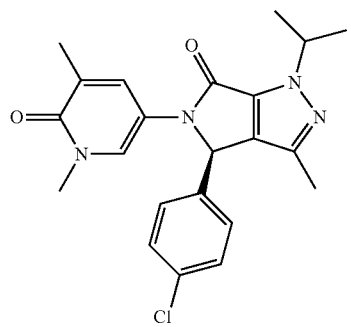 [SMILES: Cc1nn(C(C)C)c2c1[C@@H](c1ccc(Cl)cc1)N(c1cc(C)c(=O)n(C)c1)C2=O]

The title compound (172 mg, 0.419 mmol, 38.6% yield) was obtained enantiomerically pure (ee>99.1%) after chiral preparative chromatography (Chiralpak AD-H 30×250 mm ID; mobile phase: scCO$_2$/MeOH 78:22 isocratic; flow: 60 mL/min; detection 270 nm) of the racemic mixture of 4-(4-chlorophenyl)-5-(1,5-dimethyl-6-oxo-1,6-dihydropyridin-3-yl)-1-isopropyl-3-methyl-4,5-dihydropyrrolo[3,4-c]pyrazol-6(1H)-one (Example 63) (446 mg, 1.085 mmol) and trituration in hexane/Et$_2$O (3:1). $t_R$: 4.45 min (HPLC 1); $t_R$: 0.99 min (LC-MS 2); ESI-MS: 411 [M+H]$^+$ (LC-MS 2).

Example 105

4-(4-chlorophenol)-3-ethyl-5-(8-methoxy-3-methyl-[1,2,4]triazolo[4,3-a]pyridin-6-yl)-1-methyl-4,5-dihydropyrrolo[3,4-c]pyrazol-6(1H)-one

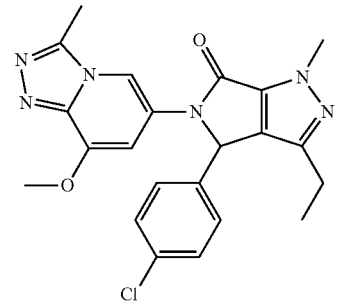 [SMILES: CCc1nn(C)c2c1C(c1ccc(Cl)cc1)N(c1cc(OC)c3nnc(C)n3c1)C2=O]

The tile compound was prepared in analogy to the procedure described in Example 68 using 5-(4-chlorophenyl)-1-(8-methoxy-3-methyl-[1,2,4]triazolo[4,3-a]pyridin-6-yl)-4-propionylpyrrolidine-2,3-dione (Step 84.5) and methyl hydrazine in MeOH. The crude material was first purified by silica gel column chromatography (hexane/EtOAc/MeOH 75:25:5 to 5:1) followed by preparative achiral SFC (Propyl-pyridyl-urea, gradient 13-18% in 6 min_total 11 min). $t_R$: 0.89 min (LC-MS 2); ESI-MS: 437 [M+H]$^+$ (LC-MS 2).

Reference Example 106

(S)-4-(4-chlorophenyl)-1-cyclopropyl-5-(3,8-dimethyl-[1,2,4]triazolo[4,3-a]pyridin-6-yl)-3-ethyl-4,5-dihydropyrrolo[3,4-c]pyrazol-6(1H)-one

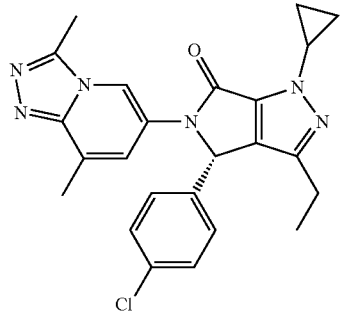 [SMILES: CCc1nn(C2CC2)c2c1[C@H](c1ccc(Cl)cc1)N(c1cc(C)c3nnc(C)n3c1)C2=O]

The title compound (112 mg, 0.246 mmol, 44% yield) was obtained enantiomerically pure (ee=99.2%) after chiral preparative chromatography (Chiralpak AD-H 50×250 mm; mobile phase: scCO$_2$/EtOH/isopropylamine 70:30:0.3 isocratic, after 10 min 50:50, cycle time 20 min; flow: 160 mL/min; detection 265 nm) of the racemic mixture of 4-(4-chlorophenyl)-5-(1,5-dimethyl-6-oxo-1,6-dihydropyridin-3-yl)-1-(2-methoxypyridin-3-yl)-3-methyl-4,5-dihydropyrrolo[3,4-c]pyrazol-6(1H)-one (Example 71) (250 mg, 0.559 mmol). $t_R$: 1.00 min (LC-MS 2); ESI-MS: 447 [M+H]$^+$ (LC-MS 2).

Example 107

(R)-4-(4-chlorophenyl)-1-cyclopropyl-5-(3,8-dimethyl-[1,2,4]triazolo[4,3-a]pyridin-6-yl)-3-ethyl-4,5-dihydropyrrolo[3,4-c]pyrazol-6(1H)-one

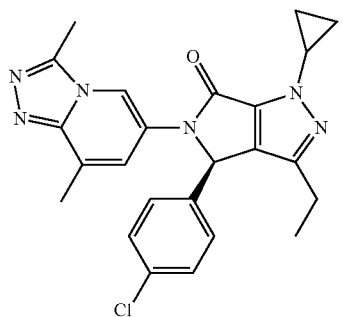 [SMILES: CCc1nn(C2CC2)c2c1[C@@H](c1ccc(Cl)cc1)N(c1cc(C)c3nnc(C)n3c1)C2=O]

The title compound (109 mg, 0.239 mmol, 43% yield) was obtained enantiomerically pure (ee=98.8%) after chiral preparative chromatography (Chiralpak AD-H 50×250 mm; mobile phase: scCO$_2$/EtOH/isopropylamine 70:30:0.3 isocratic, after 10 min 50:50, cycle time 20 min; flow: 160 mL/min; detection 265 nm) of the racemic mixture of 4-(4-chlorophenyl)-5-(1,5-dimethyl-6-oxo-1,6-dihydropyridin-3-yl)-1-(2-methoxypyridin-3-yl)-3-methyl-4,5-dihydropyrrolo[3,4-c]pyrazol-6(1H)-one (Example 71) (250 mg, 0.559 mmol). $t_R$: 1.00 min (LC-MS 2); ESI-MS: 447 [M+H]$^+$ (LC-MS 2); $^1$H NMR (400 MHz, DMSO-d$_6$) δ ppm 0.91 (t, J=7.6 Hz, 3H) 1.00-1.11 (m, 2H) 1.20-1.30 (m, 2H) 2.21-2.43 (m, 2H) 2.45 (s, 3H) 2.64 (s, 3H) 3.85 (m, 1H) 6.48 (s, 1H) 7.26-7.41 (m, 5H) 8.45 (s, 1H).

Example 108

4-(4-chlorophenyl)-3-ethyl-5-(8-methoxy-3-methyl-[1,2,4]triazolo[4,3-a]pyridin-6-yl)-1-(2-(2,2,2-trifluoroethoxy)ethyl)-4,5-dihydropyrrolo[3,4-c]pyrazol-6(1H)-one

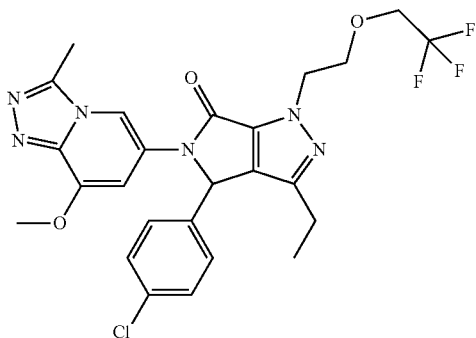 [SMILES: CCc1nn(CCOCC(F)(F)F)c2c1C(c1ccc(Cl)cc1)N(c1cc(OC)c3nnc(C)n3c1)C2=O]

The tile compound was prepared in analogy to the procedure described in Example 68 using 5-(4-chlorophenyl)-1-(8-methoxy-3-methyl-[1,2,4]triazolo[4,3-a]pyridin-6-yl)-4-propionylpyrrolidine-2,3-dione (Step 84.5) and (2-(2,2,2-trifluoroethoxy)ethyl)hydrazine hydrochloride in MeOH and TEA. The crude material was first purified by silica gel chromatography (hexane/EtOAc/MeOH 75:25:5 to 5:1) followed by preparative achiral SFC (Propyl-pyridyl-urea, gradient 13-18% in 6 min_total 11 min). $t_R$: 1.04 min (LC-MS 2); ESI-MS: 549 [M+H]$^+$ (LC-MS 2).

Example 109

4-(4-chlorophenyl)-5-(3,7-dimethyl-3H-[1,2,3]triazolo[4,5-b]pyridin-5-yl)-1-(2-methoxypyridin-3-yl)-3-methyl-4,5-dihydropyrrolo[3,4-c]pyrazol-6(1H)-one

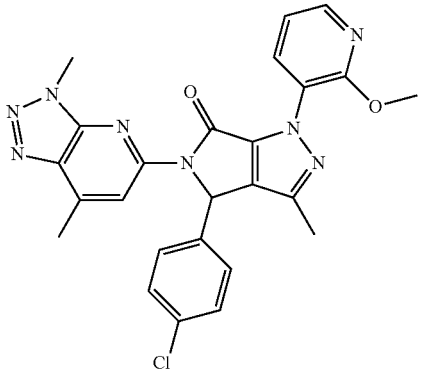 [SMILES: COc1ncccc1-n1nc(C)c2c1C(=O)N(c1cc(C)c3nnn(C)c3n1)C2c1ccc(Cl)cc1]

The title compound was prepared in analogy to the procedure described in Example 102 using 5-chloro-3,7-dimethyl-3H-[1,2,3]triazolo[4,5-b]pyridine (Step 109.4) and 4-(4-chlorophenyl)-1-(2-methoxypyridin-3-yl)-3-methyl-4,5-dihydropyrrolo[3,4-c]pyrazol-6(1H)-one (Step 71.4). The crude material was first purified by silica gel chromatography (40% EtOAc/Hexane) followed by preparative achiral SFC (column 4-Ethyl-pyridine, gradient 6-11% in 6 min_total 11 min). $t_R$: 1.25 min (LC-MS 2); ESI-MS: 501 [M+H]$^+$ (LC-MS 2); $R_f$=0.19 (40% EtOAc/hexane); $^1$H NMR (400 MHz, DMSO-d$_6$) δ ppm 2.04 (s, 3H) 2.66 (s, 3H) 3.92 (s, 3H) 4.10 (s, 3H) 6.74 (s, 1H) 7.14-7.26 (m, 1H) 7.36 (m, J=8.6 Hz, 2H) 7.49 (m, J=8.6 Hz, 2H) 7.96-8.05 (m, 1H) 8.14 (d, J=0.8 Hz, 1H) 8.28-8.38 (m, 1H).

Step 109.1: 2,6-dichloro-4-methyl-3-nitropyridine

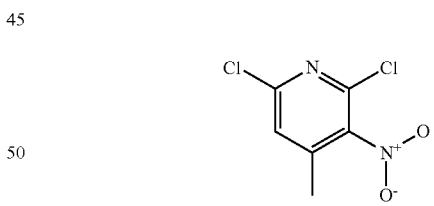

To a suspension of 2,6-dichloro-4-methylpyridine (1 g, 6.17 mmol) in trifluoroacetic acid anhydride (5 mL, 35.4 mmol) cooled down to 0° C. was added dropwise nitric acid (0.579 mL, 12.96 mmol) into it. The resulting solution was stirred at RT for 18 hr. The reaction mixture was added slowly to a chilled solution of sodium metabisulfite (1.183 g, 6.17 mmol) in water (8 mL) and stirred at RT for 2 hr. The reaction mixture was neutralized to pH 7 using 8N NaOH solution and extracted twice with CH$_2$Cl$_2$. The combined organic layers were washed with brine, dried over Na$_2$SO$_4$, filtered and concentrated under reduced pressure to afford the title product (1.187 g, 5.73 mmol, 93% yield) as white solid. $t_R$: 1.07 min (LC-MS 2); ESI-MS: 208 [M+H]$^+$ (LC-MS 2); $^1$H NMR (400 MHz, DMSO-d$_6$) δ ppm 2.39 (s, 3H) 7.90 (s, 1H).

Step 109.2:
6-chloro-N,4-dimethyl-3-nitropyridin-2-amine

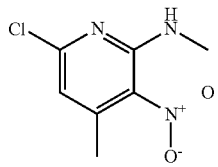

The title compound was prepared in analogy to the procedure described in Step 102.2 using 2,6-dichloro-4-methyl-3-nitropyridine (Step 109.1) at RT for 30 min. $t_R$: 1.08 min (LC-MS 2); ESI-MS: 202 [M+H]$^+$ (LC-MS 2); $R_f$=0.72 (25% EtOAc/hexane); $^1$H NMR (400 MHz, DMSO-$d_6$) δ ppm 2.39 (s, 3H) 2.90 (d, J=4.6 Hz, 3H) 6.73 (s, 1H) 7.95 (d, J=3.9 Hz, 1H).

Step 109.3:
6-chloro-N2,4-dimethylpyridine-2,3-diamine

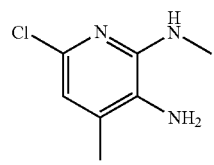

A flask was charged with 6-chloro-N,4-dimethyl-3-nitropyridin-2-amine (Step 109.2) (1 g, 4.96 mmol), Iron (1.385 g, 24.80 mmol) and 7N NH$_4$Cl (21.26 mL, 149 mmol) in EtOH (40 mL) and the resulting mixture was heated up and stirred at 85° C. for 30 min. The reaction was filtered through a pad of Celite and volatils were removed under reduced pressure. The resulting aq. layer was extracted with CH$_2$Cl$_2$, the combined organic layers were washed with brine, dried over Na$_2$SO$_4$ and concentrated under reduced pressure. The crude paterial was purified by silica gel column chromatography (50% EtOAc/hexane) to afford the title product (660 mg, 3.85 mmol, 78% yield) as beige oil. $t_R$: 0.74 min (LC-MS 2); ESI-MS: 172 [M+H]$^+$ (LC-MS 2); $R_f$=0.39 (50% EtOAc/hexane); $^1$H NMR (400 MHz, DMSO-$d_6$) δ ppm 1.98 (s, 3H) 2.77 (d, J=4.7 Hz, 3H) 4.46 (s, 2H) 5.91 (d, J=4.3 Hz, 1H) 6.28 (s, 1H).

Step 109.4: 5-chloro-3,7-dimethyl-3H-[1,2,3]triazolo[4,5-b]pyridine

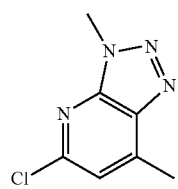

The title compound was prepared in analogy to the procedure described in Step 102.3 using 6-chloro-N2,4-dimethylpyridine-2,3-diamine (Step 109.3). The crude material was purified by silica gel column chromatography (25% EtOAc/hexane) to afford the title product (545 mg, 3.23 mmol, 64% yield) as beige solid. $t_R$: 0.78 min (LC-MS 2); ESI-MS: 183 [M+H]$^+$ (LC-MS 2); $R_f$=0.41 (25% EtOAc/hexane); $^1$H NMR (400 MHz, DMSO-$d_6$) δ ppm 2.75 (s, 3H) 4.25 (s, 3H) 7.39-7.53 (m, 1H).

Example 110

4-(4-chlorophenyl)-1-cyclopropyl-5-(3,7-dimethyl-3H-[1,2,3]triazolo[4,5-b]pyridin-5-yl)-3-methyl-4,5-dihydropyrrolo[3,4-c]pyrazol-6(1H)-one

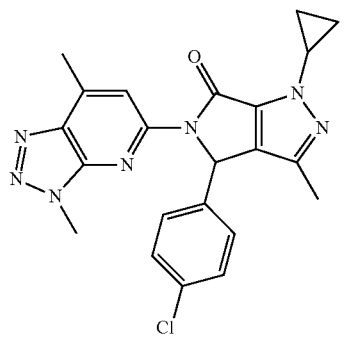 [SMILES: Cc1nn(C2CC2)c2c1C(c1ccc(Cl)cc1)N(c1cc(C)c3nnn(C)c3n1)C2=O]

The title compound was prepared in analogy to the procedure described in Example 102 using 5-chloro-3,7-dimethyl-3H-[1,2,3]triazolo[4,5-b]pyridine (Step 109.4) and 4-(4-chlorophenyl)-1-cyclopropyl-3-methyl-4,5-dihydropyrrolo[3,4-c]pyrazol-6(1H)-one (Step 85.6). The reaction mixture was quenched with a saturated aq. NaHCO$_3$ solution (75 mL) and extracted with EtOAc. The combined organic layers were washed with a saturated aq. NaHCO$_3$ solution, dried over Na$_2$SO$_4$ and concentrated under reduced pressure. The crude material was first purified by silica gel chromatography (hexane/EtOAc 25-45%). $t_R$: 5.69 min (HPLC 1); $t_R$: 1.26 min (LC-MS 2); ESI-MS: 434 [M+H]$^+$ (LC-MS 2); $R_f$=0.58 (EtOAc/hexane 1:1); $^1$H NMR (400 MHz, DMSO-$d_6$) δ ppm 1.02-1.11 (m, 2H) 1.19-1.27 (m, 2H) 1.91 (s, 3H) 2.68 (s, 3H) 3.78-3.87 (m, 1H) 4.08 (s, 3H) 6.58 (s, 1H) 7.31 (d, J=8.6 Hz, 2H) 7.43 (d, J=8.2 Hz, 2H) 8.21 (s, 1H).

Example 111

4-(4-chlorophenyl)-5-(3,8-dimethyl-[1,2,4]triazolo[4,3-b]pyridazin-6-yl)-1-(2-methoxypyridin-3-yl)-3-methyl-4,5-dihydropyrrolo[3,4-c]pyrazol-6(1H)-one

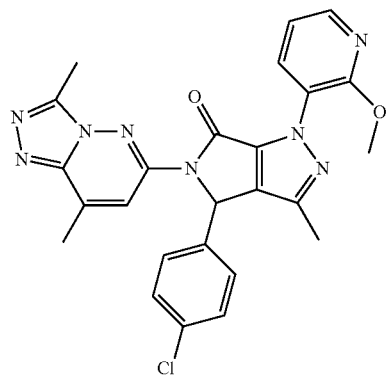 [SMILES: COc1ncccc1-n1nc(C)c2c1C(=O)N(c1cc(C)c3nnc(C)n3n1)C2c1ccc(Cl)cc1]

The title product was prepared in analogy to the procedure described in Example 110 using 4-(4-chlorophenyl)-1-(2- methoxypyridin-3-yl)-3-methyl-4,5-dihydropyrrolo[3,4-c]pyrazol-6(1H)-one (Step 71.4) and 6-chloro-3,8-dimethyl-[1,2,4]triazolo[4,3-b]pyridazine (Step 111.2). The crude material was first purified by silica gel column chromatography (CH$_2$Cl$_2$/MeOH 1-5%), followed by preparative achiral SFC (column Propyl-pyridyl-urea, gradient 9-14% in 6 min_total 11 min). t$_R$: 4.71 min (HPLC 1); t$_R$: 1.10 min (LC-MS 2); ESI-MS: 501 [M+H]$^+$ (LC-MS 2); R$_f$=0.44 (CH$_2$Cl$_2$/MeOH 9:1); $^1$H NMR (400 MHz, DMSO-d$_6$) δ ppm 2.03 (s, 3H) 2.51-2.57 (m, 6H) 3.92 (s, 3H) 6.61 (s, 1H) 7.20 (dd, J=7.8, 5.1 Hz, 1H) 7.37-7.44 (m, 2H) 7.47-7.54 (m, 2H) 7.97-8.06 (m, 2H) 8.32 (d, J=4.3 Hz, 1H).

Step 111.1:
6-chloro-3-hydrazinyl-4-methylpyridazine

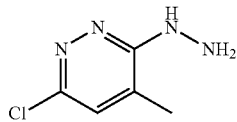

A mixture of 3,6-dichloro-4-methylpyridazine (5 g, 30.7 mmol) in hydrazine hydrate (30.4 mL, 153 mmol) was heated up and stirred at 80° C. for 24 hr. The reaction was cooled down to RT; the resulting solid was filtrated off, washed with water and dried under reduced pressure. Recrystallization in hot EtOH followed by trituration in EtOH and ultra sounds afforded the title product (721 mg, 4.55 mmol, 14.8% yield) as white solid. t$_R$: 0.34 min (LC-MS 2); ESI-MS: 159 [M+H]$^+$ (LC-MS 2).

Step 111.2: 6-chloro-3,8-dimethyl-[1,2,4]triazolo[4,3-b]pyridazine

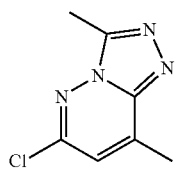

6-chloro-3-hydrazinyl-4-methylpyridazine (Step 111.1) (721 mg, 4.55 mmol) was dissolved in AcOH (15 mL, 262 mmol) and the resulting mixture was heated up and stirred at 115° C. for 1 hr. The reaction was cooled down to RT, diluted with CH$_2$Cl$_2$ and poured into a saturated aq. NaHCO$_3$ solution. The aq. layer was extracted with CH$_2$Cl$_2$. The combined organic layers were dried over Na$_2$SO$_4$, filtered and concentrated under reduced pressure to afford the title product (752 mg, 3.91 mmol, 84% yield) as grey solid. t$_R$: 0.59 min (LC-MS 2); ESI-MS: 183 [M+H]$^+$ (LC-MS 2).

Reference Example 112 tert-butyl (6-(4-(4-chlorophenyl)-1-cyclopropyl-3-methyl-6-oxopyrrolo[3,4-c]pyrazol-5(1H,4H,6H)-yl)-3-methyl-[1,2,4]triazolo[4,3-b]pyridazin-8-yl)(methyl)carbamate

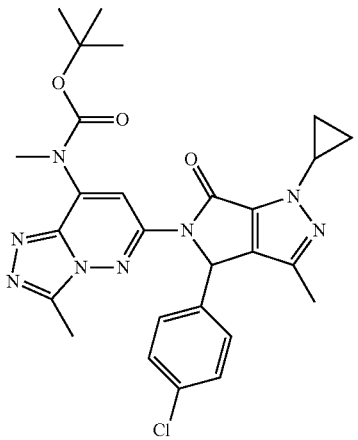 [SMILES: Cc1nn(C2CC2)c2c1C(c1ccc(Cl)cc1)N(c1cc(N(C)C(=O)OC(C)(C)C)c3nnc(C)n3n1)C2=O]

The title compound was prepared in analogy to the procedure described in Example 110 using 4-(4-chlorophenyl)-1-cyclopropyl-3-methyl-4,5-dihydropyrrolo[3,4-c]pyrazol-6(1H)-one (Step 85.6) and tert-butyl (6-chloro-3-methyl-[1,2,4]triazolo[4,3-b]pyridazin-8-yl)(methyl)carbamate (Step 112.5). t$_R$: 5.60 min (HPLC 1); t$_R$: 1.29 min (LC-MS 2); ESI-MS: 549 [M+H]$^+$ (LC-MS 2); R$_f$=0.56 (CH$_2$Cl$_2$/MeOH 9:1); $^1$H NMR (400 MHz, DMSO-d$_6$) δ ppm 1.03-1.09 (m, 2H) 1.19-1.25 (m, 2H) 1.43 (s, 9H) 1.90 (s, 3H) 2.52 (s, 3H) 3.44 (s, 3H) 3.79-3.88 (m, 1H) 6.45 (s, 1H) 7.33-7.38 (m, 2H) 7.43-7.48 (m, 2H) 8.30 (s, 1H).

Step 112.1: 3,6-dichloropyridazin-4-amine

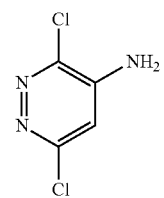

A MW vial was charged with 3,4,6-trichloropyridazine (5 g, 27.3 mmol) and 7N NH$_3$ in MeOH (19.47 mL, 136 mmol). The MW vial was sealed and the resulting mixture was submitted to MW irradiation at 100° C. for 30 min. The reaction was cooled down to RT and concentrated under reduced pressure. The crude product was purified by silica gel column chromatography (hexane/EtOAc 35-60%) to afford the title product (1.49 g, 8.63 mmol, 32% yield) as yellow solid. t$_R$: 1.61 min (HPLC 1); t$_R$: 0.45 min (LC-MS 2); ESI-MS: 163 [M+H]$^+$ (LC-MS 2); R$_f$=0.40 (hexane/EtOAc 1:1).

Step 112.2: 6-chloro-3-hydrazinylpyridazin-4-amine

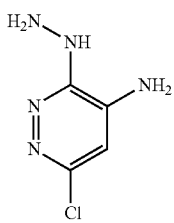

To a stirred suspension of 3,6-dichloropyridazin-4-amine (Step 112.1) (1.49 g, 9.09 mmol) in EtOH (15 mL) was added hydrazine hydrate (11.04 mL, 227 mmol) and the resulting mixture was heated up and stirred at 100° C. for 3 hr. The reaction was cooled down to RT and concentrated under reduced pressure. The crude product was triturated with water (25 mL) to afford the title product (478 mg, 3 mmol, 33% yield) as yellow solid. $t_R$: 0.24 min (LC-MS 2); ESI-MS: 160 [M+H]$^+$ (LC-MS 2); ESI-MS: 158 [M–H]$^-$ (LC-MS 2).

Step 112.3: 6-chloro-3-methyl-[1,2,4]triazolo[4,3-b]pyridazin-8-amine

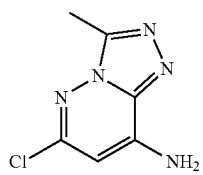

A MW vial was charged with 6-chloro-3-hydrazinylpyridazin-4-amine (Step 112.2) (475 mg, 2.98 mmol) and potassium acetate (467 mg, 4.76 mmol) in AcOH (5 mL). The MW vial was sealed and the resulting mixture was heated up and stirred at 170° C. for 4 hr. The reaction was cooled down to RT and concentrated under reduced pressure. The crude product was purified by silica gel column chromatography (NH$_3$ 1%/CH$_2$Cl$_2$/MeOH 1-3%) to afford the title product (450 mg, 2.451 mmol, 82% yield). $t_R$: 2.32 min (HPLC 1); $t_R$: 0.55 min (LC-MS 2); ESI-MS: 184 [M+H]$^+$ (LC-MS 2); ESI-MS: 182 [M–H]$^-$ (LC-MS 2); R$_f$=0.45 (CH$_2$Cl$_2$/MeOH 9:1).

Step 112.4: tert-butyl (6-chloro-3-methyl-[1,2,4]triazolo[4,3-b]pyridazin-8-yl)carbamate

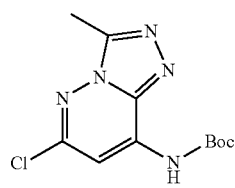 [SMILES: Cc1nnc2c(NC(=O)OC(C)(C)C)cc(Cl)nn12]

To a stirred solution of 6-chloro-3-methyl-[1,2,4]triazolo[4,3-b]pyridazin-8-amine (Step 112.3) (308 mg, 1.678 mmol), TEA (0.935 mL, 6.71 mmol) and DMAP (205 mg, 1.678 mmol) in THF (10 mL) under Ar was added Boc$_2$O (1.168 mL, 5.03 mmol) and the resulting mixture was stirred at RT for 16 hr. The reaction was quenched with brine (50 mL) and extracted with EtOAc. The combined organic layers were washed with brine, dried over Na$_2$SO$_4$, filtered and concentrated under reduced pressure. The crude product was purified by silica gel column chromatography (hexane/EtOAc 40-50%) to afford the title product (307 mg, 1.117 mmol, 66% yield) as white solid. $t_R$: 4.71 min (HPLC 1); $t_R$: 1.04 min (LC-MS 2); ESI-MS: 284 [M+H]$^+$ (LC-MS 2); ESI-MS: 282 [M–H]$^-$ (LC-MS 2); R$_f$=0.35 (hexane/EtOAc 1:1).

Step 112.5: tert-butyl (6-chloro-3-methyl-[1,2,4]triazolo[4,3-b]pyridazin-8-yl)(methyl)carbamate

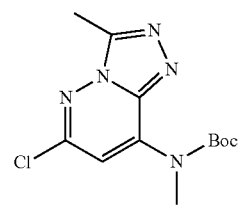 [SMILES: Cc1nnc2c(N(C)C(=O)OC(C)(C)C)cc(Cl)nn12]

To a stirred solution of tert-butyl (6-chloro-3-methyl-[1,2,4]triazolo[4,3-b]pyridazin-8-yl)carbamate (Step 112.4) (202 mg, 0.712 mmol) in DMF (4 mL) under Ar was added NaH (34.2 mg, 0.854 mmol) and the resulting mixture was stirred at RT for 30 min. MeI (0.053 mL, 0.854 mmol) was added to the mixture and stirred for further 30 min. The reaction was quenched with a saturated aq. NaHCO$_3$ solution and extracted with EtOAc. The combined organic layers were washed with a saturated aq. NaHCO$_3$ solution, dried over Na$_2$SO$_4$, filtered and concentrated under reduced pressure. The crude product was purified by silica gel column chromatography (hexane/EtOAc 25-40%) to afford the title product (208 mg, 0.699 mmol, 98% yield) as white solid. $t_R$: 4.45 min (HPLC 1); $t_R$: 1.00 min (LC-MS 2); ESI-MS: 298 [M+H]$^+$ (LC-MS 2); R$_f$=0.45 (hexane/EtOAc 1:1).

Example 113

4-(4-chlorophenyl)-1-cyclopropyl-3-methyl-5-(3-methyl-8-(methylamino)-[1,2,4]triazolo[4,3-b]pyridazin-6-yl)-4,5-dihydropyrrolo[3,4-c]pyrazol-6(1H)-one

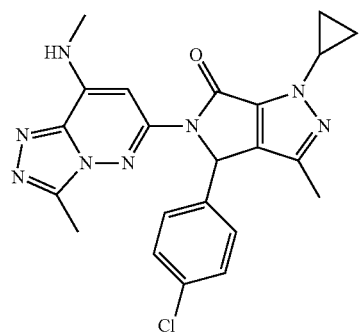 [SMILES: CNc1cc(N2C(=O)c3c(c(C)nn3C3CC3)C2c2ccc(Cl)cc2)nn2c(C)nnc12]

To a stirred solution of tert-butyl (6-(4-(4-chlorophenyl)-1-cyclopropyl-3-methyl-6-oxopyrrolo[3,4-c]pyrazol-5(1H, 4H,6H)-yl)-3-methyl-[1,2,4]triazolo[4,3-b]pyridazin-8-yl)(methyl)carbamate (Example 112) (200 mg, 0.364 mmol) in CH$_2$Cl$_2$ (4 mL) was added TFA (0.561 mL, 7.29 mmol) and the resulting mixture was stirred at RT for 2 hr. The reaction was quenched with a saturated aq. NaHCO$_3$ solution and extracted with CH$_2$Cl$_2$. The combined organic layers were washed with a saturated aq. NaHCO$_3$ solution, dried over Na$_2$SO$_4$ and concentrated under reduced pressure. The crude product was purified by silica gel column chromatography (CH$_2$Cl$_2$/MeOH 1-4%) followed by trituration in Et$_2$O to afford the title product (130 mg, 0.290 mmol, 79% yield). t$_R$: 4.73 min (HPLC 1); t$_R$: 1.09 min (LC-MS 2); ESI-MS: 449 [M+H]$^+$ (LC-MS 2); R$_f$=0.40 (CH$_2$Cl$_2$/MeOH 9:1); $^1$H NMR (400 MHz, DMSO-d$_6$) δ ppm 1.01-1.08 (m, 2H) 1.19-1.26 (m, 2H) 1.90 (s, 3H) 2.45 (s, 3H) 2.85-2.94 (m, 3H) 3.77-3.84 (m, 1H) 6.41 (s, 1H) 7.03 (s, 1H) 7.31-7.36 (m, 2H) 7.37-7.42 (m, 2H) 8.01-8.10 (m, 1H).

Example 114

4-(4-chlorophenyl)-5-(3,8-dimethyl-[1,2,4]triazolo[4,3-b]pyridazin-6-yl)-3-methyl-1-(1-methyl-1H-pyrazol-5-yl)-4,5-dihydropyrrolo[3,4-c]pyrazol-6(1H)-one

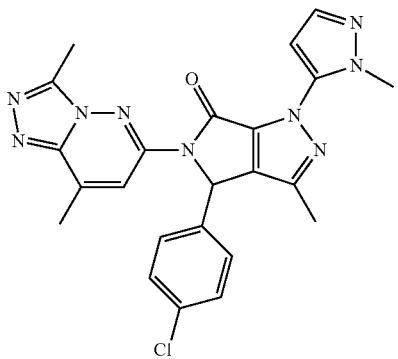 [SMILES: Cc1nn(-c2ccnn2C)c2c1C(c1ccc(Cl)cc1)N(c1cc(C)c3nnc(C)n3n1)C2=O]

The title compound was prepared in analogy to the procedure described in Example 110 using 4-(4-chlorophenyl)-3-methyl-1-(1-methyl-1H-pyrazol-5-yl)-4,5-dihydropyrrolo[3,4-c]pyrazol-6(1H)-one (Step 114.2) and 6-chloro-3,8-dimethyl-[1,2,4]triazolo[4,3-b]pyridazine (Step 111.2). The crude material was first purified by silica gel column chromatography (CH$_2$Cl$_2$/MeOH 1-5%), followed by preparative achiral SFC (column NH$_2$, gradient 9-14% in 6 min_total 11 min) and trituration in Et$_2$O. t$_R$: 4.37 min (HPLC 1); t$_R$: 1.01 min (LC-MS 2); ESI-MS: 474 [M+H]$^+$ (LC-MS 2); ESI-MS: 472 [M-H]$^-$ (LC-MS 2); R$_f$=0.45 (CH$_2$Cl$_2$/MeOH 9:1); $^1$H NMR (400 MHz, DMSO-d$_6$) δ ppm 2.05 (s, 3H) 2.53 (s, 3H) 2.56 (s, 3H) 3.85 (s, 3H) 6.60 (s, 1H) 6.65 (d, J=2.0 Hz, 1H) 7.39 (d, J=8.2 Hz, 2H) 7.54-7.60 (m, 3H) 8.02-8.05 (m, 1H).

Step 114.1: 4-(4-chlorophenyl)-5-(4-methoxybenzyl)-3-methyl-1-(1-methyl-1H-pyrazol-5-yl)-4,5-dihydropyrrolo[3,4-c]pyrazol-6(1H)-one

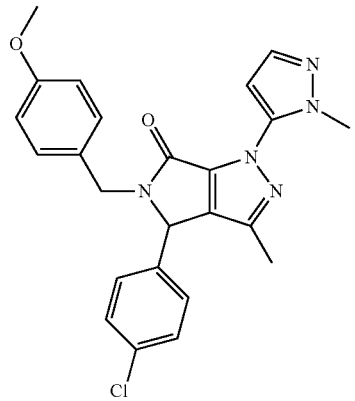 [SMILES: COc1ccc(CN2C(=O)c3c(c(C)nn3-c3ccnn3C)C2c2ccc(Cl)cc2)cc1]

To a stirred solution of 4-acetyl-5-(4-chlorophenyl)-3-hydroxy-1-(4-methoxybenzyl)-1H-pyrrol-2(5H)-one (Step 71.2) (3 g, 8.07 mmol) in EtOH (50 mL) and toluene (50 mL) was added 5-hydrazinyl-1-methyl-1H-pyrazole (Step 74.2) (1.941 g, 10.49 mmol) and the resulting mixture was heated up and stirred at 115° C. for 20 hr. The reaction was quenched with a saturated aq. NaHCO$_3$ solution and extracted with EtOAc. The combined organic layers were dried over Na$_2$SO$_4$ and concentrated under reduced pressure. The crude product was purified by silica gel column chromatography (hexane/EtOAc 40-50%) to afford the title product (3.15 g, 6.89 mmol, 85% yield) as yellow solid. t$_R$: 5.60 min (HPLC 1); t$_R$: 1.24 min (LC-MS 2); ESI-MS: 448 [M+H]$^+$ (LC-MS 2); R$_f$=0.41 (hexane/EtOAc 1:1).

Step 114.2: 4-(4-chlorophenyl)-3-methyl-1-(1-methyl-1H-pyrazol-5-yl)-4,5-dihydropyrrolo[3,4-c]pyrazol-6(1H)-one

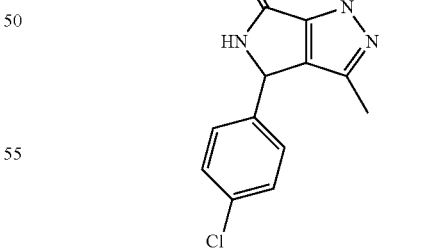

The title compound was prepared in analogy to the procedure described in Step 85.6 using 4-(4-chlorophenyl)-5-(4-methoxybenzyl)-3-methyl-1-(1-methyl-1H-pyrazol-5-yl)-4,5-dihydropyrrolo-[3,4-c]pyrazol-6(1H)-one (Step 114.1). t$_R$: 4.14 min (HPLC 1); t$_R$: 0.92 min (LC-MS 2); ESI-MS: 328 [M+H]$^+$ (LC-MS 2); ESI-MS: 326 [M-H]$^-$ (LC-MS 2); R$_f$=0.61 (EtOAc).

Example 115

4-(4-chlorophenyl)-5-(3,8-dimethyl-[1,2,4]triazolo[4,3-a]pyridin-6-yl)-2-ethyl-3-methyl-4,5-dihydropyrrolo[3,4-c]pyrazol-6(2H)-one

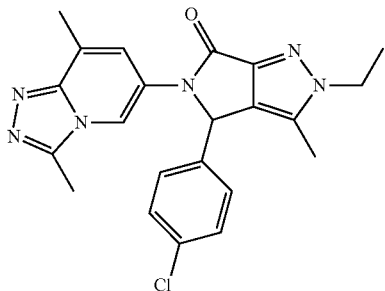 [SMILES: CCn1nc2c(c1C)C(c1ccc(Cl)cc1)N(c1cc(C)c3nnc(C)n3c1)C2=O]

NaH (21.18 mg, 0.529 mmol) was added to a stirred solution of 4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one (Example 98) (160 mg, 0.407 mmol) in DMF (4 mL) at 0° C. and the resulting mixture was stirred at 0° C. for 30 min. Iodoethane (0.039 mL, 0.489 mmol) was added and the reaction mixture was stirred at RT for 30 min. The reaction was quenched with water, diluted with EtOAc and both phases were separated. The aq. layer was extracted with EtOAc. The combined organic layers were washed with brine, dried over Na$_2$SO$_4$ and concentrated under reduced pressure. The crude material was purified by preparative achiral SFC (column NH$_2$, gradient 19-24% in 6 min, total 11 min) to afford, after trituration in Et$_2$O, 31 mg, 0.074 mmol, 18% yield) as white solid. t$_R$: 0.88 min (LC-MS 2); ESI-MS: 421 [M+H]$^+$ (LC-MS 2); $^1$H NMR (400 MHz, DMSO-d$_6$) δ ppm 1.38 (t, J=7.2 Hz, 3H) 2.13 (s, 3H) 2.46 (s, 3H) 2.63 (s, 3H) 4.20 (q, J=7.2 Hz, 2H) 6.49 (s, 1H) 7.33-7.40 (m, 5H) 8.46 (s, 1H).

Example 116

4-(4-chlorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one

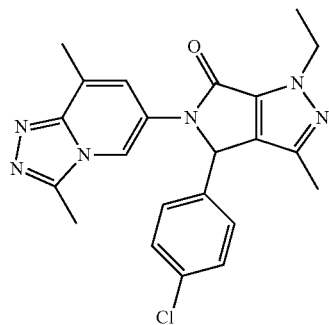 [SMILES: CCn1nc(C)c2c1C(=O)N(c1cc(C)c3nnc(C)n3c1)C2c1ccc(Cl)cc1]

The title compound was prepared in analogy to the procedure described in Example 115 using 4-(4-chlorophenyl)-5-(3,8-dimethyl-[1,2,4]triazolo[4,3-a]pyridin-6-yl)-3-methyl-4,5-dihydropyrrolo-[3,4-c]pyrazol-6(1H)-one (Example 98). t$_R$: 0.93 min (LC-MS 2); ESI-MS: 421 [M+H]$^+$ (LC-MS 2); $^1$H NMR (400 MHz, DMSO-d$_6$) δ ppm 1.45 (t, J=7.2 Hz, 3H) 1.95 (s, 3H) 2.43 (s, 3H) 2.61 (s, 3H) 4.28 (q, J=7.4 Hz, 2H) 6.43 (s, 1H) 7.26-7.41 (m, 5H) 8.44 (s, 1H).

Example 117

4-(4-chlorophenyl)-3-cyclopropyl-5-(3,8-dimethyl-[1,2,4]triazolo[4,3-a]pyridin-6-yl)-1-(1-methyl-1H-pyrazol-5-yl)-4,5-dihydropyrrolo[3,4-c]pyrazol-6(1H)-one

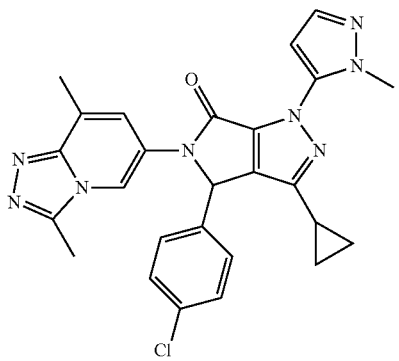 [SMILES: Cc1cc(N2C(=O)c3c(c(C4CC4)nn3-c3ccnn3C)C2c2ccc(Cl)cc2)cn2c(C)nnc12]

The title compound was prepared in analogy to the procedure described in Step 114.1 using 5-(4-chlorophenyl)-4-(cyclopropanecarbonyl)-1-(3,8-dimethyl-[1,2,4]triazolo[4,3-a]pyridin-6-yl)-3-hydroxy-1H-pyrrol-2(5H)-one (Step 117.1) and 5-hydrazinyl-1-methyl-1H-pyrazole (Step 74.2). The crude material was first purified by silica gel column chromatography (1% ammonia/5% MeOH/CH$_2$Cl$_2$) followed by preparative achiral SFC (column Silica, gradient 23-28% in 6 min_total 11 min). A third purification was performed by preparative HPLC (Gilson gx-281. Column: Sunfire C18, 30×100 mm, 5 mm. Flow: 30 mL/min. Gradient: 30% to 60% B in min; A=0.1% TFA in H2O, B=CH$_3$CN. Detection: UV). The fractions were combined, basified with NaHCO$_3$, the CH$_3$CN was removed under reduced pressure and the resulting aqueous layer was extracted with CH$_2$Cl$_2$, the organic layer was washed with brine, dried over Na$_2$SO$_4$ and concentrated under reduced pressure to afford, after trituration in Et$_2$O, a white solid. t$_R$: 0.99 min (LC-MS 2); ESI-MS: 499 [M+H]$^+$ (LC-MS 2); $^1$H NMR (400 MHz, DMSO-d$_6$) δ ppm 0.03-0.14 (m, 1H) 0.67-0.80 (m, 2H) 0.80-0.92 (m, 1H) 1.78-1.85 (m, 1H) 2.42 (s, 3H) 2.61 (s, 3H) 3.85 (s, 3H) 6.55 (s, 1H) 6.63 (d, J=2.0 Hz, 1H) 7.30 (s, 1H) 7.37 (d, J=8.6 Hz, 2H) 7.46 (d, J=8.6 Hz, 2H) 7.56 (d, J=1.6 Hz, 1H) 8.39 (s, 1H).

Step 117.1: 5-(4-chlorophenyl)-4-(cyclopropanecarbonyl)-1-(3,8-dimethyl-[1,2,4]triazolo[4,3-a]pyridin-6-yl)-3-hydroxy-1H-pyrrol-2(5H)-one

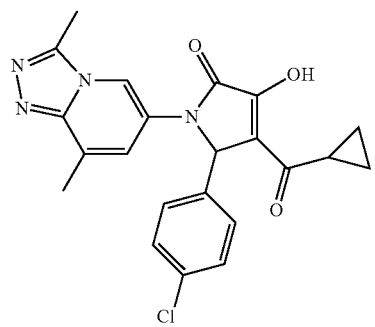 [SMILES: Cc1cc(N2C(=O)C(O)=C(C(=O)C3CC3)C2c2ccc(Cl)cc2)cn2c(C)nnc12]

The title compound was prepared in analogy to the procedure described in Step 84.5 using 3,8-dimethyl-[1,2,4]triazolo[4,3-a]pyridin-6-amine (Step 67.4), 4-chlorobenzaldehyde and ethyl 4-cyclopropyl-2,4-dioxobutanoate. $t_R$: 0.82 min (LC-MS 2); ESI-MS: 483 [M+H]$^+$ (LC-MS 2); $^1$H NMR (400 MHz, DMSO-d$_6$) δ ppm 0.60-0.97 (m, 4H) 2.41 (s, 3H) 2.55-2.68 (m, 3H) 2.85-2.93 (m, 1H) 6.12 (s, 1H) 7.11-7.28 (m, 2H) 7.28-7.41 (m, 3H) 8.50 (s, 1H) —OH missing.

Reference Example 118

(S)-4-(4-chlorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one

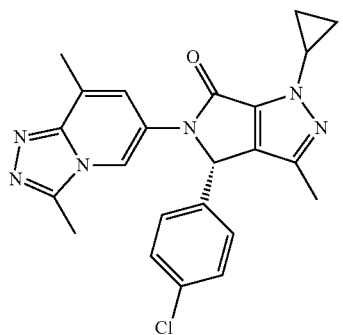 [SMILES: Cc1nn(C2CC2)c2c1[C@H](c1ccc(Cl)cc1)N(c1cc(C)c3nnc(C)n3c1)C2=O]

The title compound (25 mg, 0.058 mmol, 37.9% yield) was obtained enantiomerically pure (ee>99.0%) after chiral preparative chromatography (system: Thar SFC200; column: Chiralpak AD-H 50×250 mm; mobile phase: scCO$_2$/MeOH 50:50 isocratic in 14 min; flow: 100 mL/min; detection 300 nm) of the racemic mixture of 4-(4-chlorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one (Example 92) (66 mg, 0.152 mmol) and trituration in Et$_2$O. $t_R$: 0.95 min (LC-MS 2); ESI-MS: 433 [M+H]$^+$ (LC-MS 2).

Example 119

(R)-4-(4-chlorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one

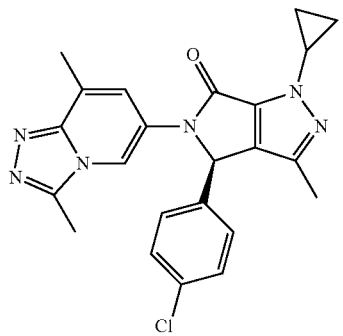 [SMILES: Cc1nn(C2CC2)c2c1[C@@H](c1ccc(Cl)cc1)N(c1cc(C)c3nnc(C)n3c1)C2=O]

The title compound (25 mg, 0.058 mmol, 37.9% yield) was obtained enantiomerically pure (ee>99.0%) after chiral preparative chromatography (system: Thar SFC200; column: Chiralpak AD-H 50×250 mm; mobile phase: scCO$_2$/MeOH 50:50 isocratic in 14 min; flow: 100 mL/min; detection 300 nm) of the racemic mixture of 4-(4-chlorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one (Example 92) (66 mg, 0.152 mmol) and trituration in Et$_2$O. $t_R$: 0.95 min (LC-MS 2); ESI-MS: 433 [M+H]$^+$ (LC-MS 2).

Example 120

(R)-4-(4-chlorophenyl)-5-(1,5-dimethyl-6-oxo-1,6-dihydropyridin-3-yl)-3-methyl-1-(1-methyl-1H-pyrazol-5-yl)-4,5-dihydropyrrolo[3,4-c]pyrazol-6(1H)-one

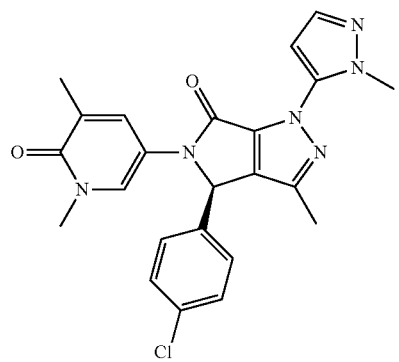 [SMILES: Cc1nn(-c2ccnn2C)c2c1[C@@H](c1ccc(Cl)cc1)N(c1cc(C)c(=O)n(C)c1)C2=O]

The title compound (45 mg, 0.100 mmol, 40% yield) was obtained enantiomerically pure (ee=98.3%) after chiral preparative chromatography (Chiralpak AD-H 50×250 mm; mobile phase: scCO$_2$/MeOH 50:50 isocratic in 12 min; flow: 100 mL/min; detection 300 nm) of the racemic mixture of 4-(4-chlorophenyl)-5-(1,5-dimethyl-6-oxo-1,6-dihydropyridin-3-yl)-3-methyl-1-(1-methyl-1H-pyrazol-5-yl)-4,5-dihydropyrrolo[3,4-c]pyrazol-6(1H)-one (Example 74) (112 mg, 0.249 mmol) and trituration in hexane/Et$_2$O (3:1). $t_R$: 4.09 min (HPLC 1); $t_R$: 0.94 min (LC-MS 2); ESI-MS: 449 [M+H]$^+$ (LC-MS 2).

Reference Example 121

(S)-4-(4-chlorophenyl)-5-(1,5-dimethyl-6-oxo-1,6-dihydropyridin-3-yl)-3-methyl-1-(1-methyl-1H-pyrazol-5-yl)-4,5-dihydropyrrolo[3,4-c]pyrazol-6(1H)-one

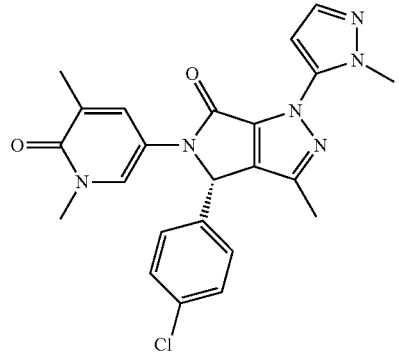 [SMILES: Cc1nn(-c2ccnn2C)c2c1[C@H](c1ccc(Cl)cc1)N(c1cc(C)c(=O)n(C)c1)C2=O]

The title compound (47 mg, 0.105 mmol, 42% yield) was obtained enantiomerically pure (ee>99%) after chiral preparative chromatography (Chiralpak AD-H 50×250 mm; mobile phase: scCO$_2$/MeOH 50:50 isocratic in 12 min; flow: 100 mL/min; detection 300 nm) of the racemic mixture of 4-(4-chlorophenyl)-5-(1,5-dimethyl-6-oxo-1,6-dihydropyridin-3-yl)-3-methyl-1-(1-methyl-1H-pyrazol-5-yl)-4,5-dihydropyrrolo[3,4-c]pyrazol-6(1H)-one (Example 74) (112 mg, 0.249 mmol) and trituration in hexane/Et$_2$O (3:1). t$_R$: 4.09 min (HPLC 1); t$_R$: 0.94 min (LC-MS 2); ESI-MS: 449 [M+H]$^+$ (LC-MS 2).

Example 122

(R)-4-(4-chlorophenyl)-1-cyclopropyl-5-(3,8-dimethyl-[1,2,4]triazolo[4,3-b]-pyridazin-6-yl)-3-methyl-4,5-dihydropyrrolo[3,4-c]pyrazol-6(1H)-one

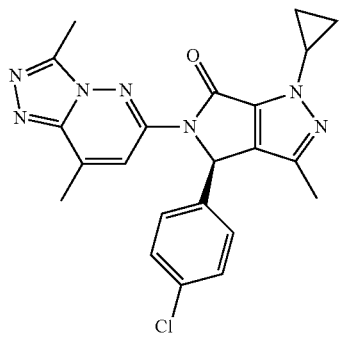 [SMILES: Cc1nn(C2CC2)c2c1[C@@H](c1ccc(Cl)cc1)N(c1cc(C)c3nnc(C)n3n1)C2=O]

The title compound (20 mg, 0.046 mmol, 26% yield) was obtained enantiomerically pure (ee>99%) after chiral preparative chromatography (Chiralpak AD-H 50×250 mm; mobile phase: scCO$_2$/MeOH 50:50 isocratic in 15 min; flow: 100 mL/min; detection 270 nm) of the racemic mixture of 4-(4-chlorophenyl)-1-cyclopropyl-5-(3,8-dimethyl-[1,2,4]triazolo[4,3-b]pyridazin-6-yl)-3-methyl-4,5-dihydropyrrolo[3,4-c]pyrazol-6(1H)-one (Step 122.1) (77 mg, 0.177 mmol). t$_R$: 4.67 min (HPLC 1); t$_R$: 1.08 min (LC-MS 2); ESI-MS: 434 [M+H]$^+$ (LC-MS 2).

Step 122.1: 4-(4-chlorophenyl)-1-cyclopropyl-5-(3,8-dimethyl-[1,2,4]triazolo[4,3-b]pyridazin-6-yl)-3-methyl-4,5-dihydropyrrolo[3,4-c]pyrazol-6(1H)-one

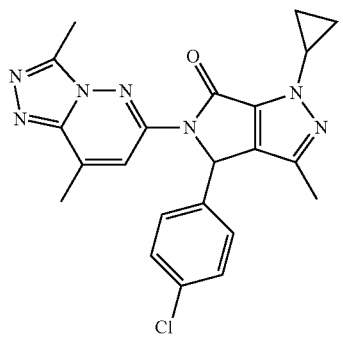

The title compound was prepared in analogy to the procedure described in Example 110 using 4-(4-chlorophenyl)-1-cyclopropyl-3-methyl-4,5-dihydropyrrolo[3,4-c]pyrazol-6(1H)-one (Step 85.6) and 6-chloro-3,8-dimethyl-[1,2,4]triazolo[4,3-b]pyridazine (Step 111.2). The crude material was first purified by silica gel column chromatography (EtOAc/MeOH 0.5-1%), followed by preparative achiral SFC (column 4-Ethyl-pyridine, gradient 9-14% in 6 min_total 11 min). t$_R$; 4.66 min (HPLC 1); t$_R$: 1.08 min (LC-MS 2); ESI-MS: 434 [M+H]$^+$ (LC-MS 2); R$_f$=0.14 (EtOAc); $^1$H NMR (400 MHz, DMSO-d$_6$) δ ppm 1.04-1.08 (m, 2H) 1.21-1.26 (m, 2H) 1.90 (s, 3H) 2.51 (s, 3H) 2.57 (d, J=1.2 Hz, 3H) 3.82 (dt, J=7.4, 3.7 Hz, 1H) 6.45 (s, 1H) 7.32-7.37 (m, 2H) 7.42-7.47 (m, 2H) 8.08-8.14 (m, 1H).

Reference Example 123

(S)-4-(4-chlorophenyl)-1-cyclopropyl-5-(3,8-dimethyl-[1,2,4]triazolo[4,3-b]pyridazin-6-yl)-3-methyl-4,5-dihydropyrrolo[3,4-c]pyrazol-6(1H)-one

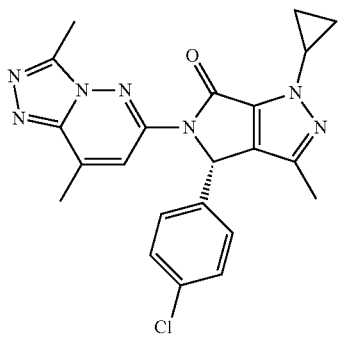 [SMILES: Cc1nn(C2CC2)c2c1C(c1ccc(Cl)cc1)N(c1cc(C)c3nnc(C)n3n1)C2=O]

The title compound (19 mg, 0.044 mmol, 24.7% yield) was obtained enantiomerically pure (ee=98.7%) after chiral preparative chromatography (Chiralpak AD-H 50×250 mm; mobile phase: scCO$_2$/MeOH 50:50 isocratic in 15 min; flow: 100 mL/min; detection 270 nm) of the racemic mixture of 4-(4-chlorophenyl)-1-cyclopropyl-5-(3,8-dimethyl-[1,2,4]triazolo[4,3-b]pyridazin-6-yl)-3-methyl-4,5-dihydropyrrolo[3,4-c]pyrazol-6(1H)-one (Step 122.1) (77 mg, 0.177 mmol). t$_R$: 4.67 min (HPLC 1); t$_R$: 1.08 min (LC-MS 2); ESI-MS: 434 [M+H]$^+$ (LC-MS 2).

Reference Example 124

(S)-4-(4-chlorophenyl)-5-(3,8-dimethyl-[1,2,4]triazolo[4,3-a]pyridin-6-yl)-3-methyl-1-(1-methyl-1H-pyrazol-5-yl)-4,5-dihydropyrrolo[3,4-c]pyrazol-6(1H)-one

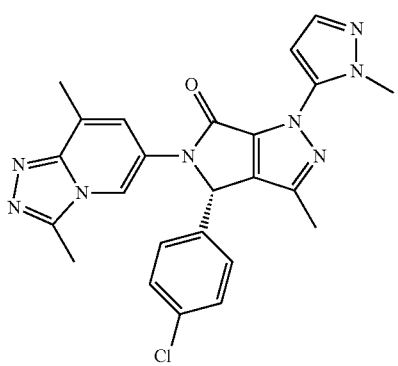 [SMILES: Cc1nn(-c2ccnn2C)c2c1[C@H](c1ccc(Cl)cc1)N(c1cc(C)c3nnc(C)n3c1)C2=O]

The title compound (73 mg, 0.154 mmol, 44.5% yield) was obtained enantiomerically pure (ee>99.0%) after chiral preparative chromatography (System: Gilson PLC 2020 HPLC system; column: Chiralpak AD-H 20×250 mm 5 µm; mobile phase: EtOH/MeOH 60:40 isocratic; flow: 10 mL/min; detection 210 nm) of the racemic mixture of 4-(4-chlorophenyl)-5-(3,8-dimethyl-[1,2,4]triazolo[4,3-a]pyridin-6-yl)-3-methyl-1-(1-methyl-1H-pyrazol-5-yl)-4,5-dihydropyrrolo[3,4-c]pyrazol-6(1H)-one (Example 90) (164 mg, 0.347 mmol). $t_R$: 0.92 min (LC-MS 2); ESI-MS: 473 [M+H]$^+$ (LC-MS 2).

Example 125

(R)-4-(4-chlorophenyl)-5-(3,8-dimethyl-[1,2,4]triazolo[4,3-a]pyridin-6-yl)-3-methyl-1-(1-methyl-1H-pyrazol-5-yl)-4,5-dihydropyrrolo[3,4-c]pyrazol-6(1H)-one

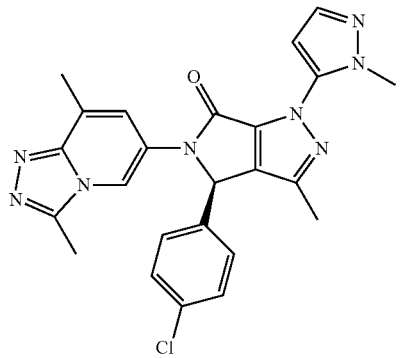 [SMILES: Cc1nn(-c2ccnn2C)c2c1[C@@H](c1ccc(Cl)cc1)N(c1cc(C)c3nnc(C)n3c1)C2=O]

The title compound (77 mg, 0.163 mmol, 47% yield) was obtained enantiomerically pure (ee>99%) after chiral preparative chromatography (Chiralpak AD-H 20×250 mm 5 μm; mobile phase: EtOH/MeOH 60:40 isocratic; flow: 10 mL/min; detection 210 nm) of the racemic mixture of 4-(4-chlorophenyl)-5-(3,8-dimethyl-[1,2,4]triazolo[4,3-a]pyridin-6-yl)-3-methyl-1-(1-methyl-1H-pyrazol-5-yl)-4,5-dihydropyrrolo[3,4-c]pyrazol-6(1H)-one (Example 90) (164 mg, 0.347 mmol). $t_R$: 0.92 min (LC-MS 2); ESI-MS: 473 [M+H]$^+$ (LC-MS 2).

Example 126

N-(6-(4-(4-chlorophenyl)-1-cyclopropyl-3-methyl-6-oxopyrrolo[3,4-c]pyrazol-5-(1H,4H,6H)-yl)-3-methyl-[1,2,4]triazolo[4,3-b]pyridazin-8-yl)acetamide

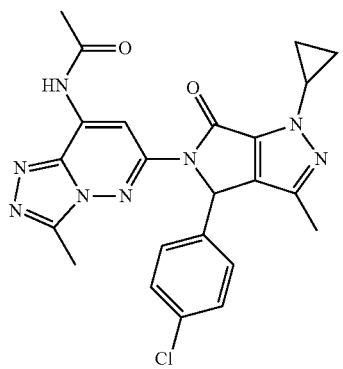 [SMILES: CC(=O)Nc1cc(N2C(=O)c3c(c(C)nn3C3CC3)C2c2ccc(Cl)cc2)nn2c(C)nnc12]

A flask was charged with 5-(8-amino-3-methyl-[1,2,4]triazolo[4,3-b]pyridazin-6-yl)-4-(4-chlorophenyl)-1-cyclopropyl-3-methyl-4,5-dihydropyrrolo[3,4-c]pyrazol-6(1H)-one (Step 126.3) (40 mg, 0.092 mmol) and Ac$_2$O (0.434 mL, 4.60 mmol) in pyridine (2 mL) under Ar and the resulting mixture was heated up and stirred for 20 hr at 115° C. The reaction was quenched with a saturated aq.NaHCO$_3$ solution and extracted with EtOAc. The combined organic layers were washed with a saturated aq. NaHCO$_3$ solution, dried over Na$_2$SO$_4$, filtered and concentrated under reduced pressure. The crude product was purified by silica gel column chromatography (CH$_2$Cl$_2$/MeOH 1-4%) and triturated in Et$_2$O to afford the title product (27 mg, 0.057 mmol, 62% yield) as white solid. $t_R$: 4.73 min (HPLC 1); $t_R$: 1.07 min (LC-MS 2); ESI-MS: 477 [M+H]$^+$ (LC-MS 2); ESI-MS: 475 [M−H]$^-$ (LC-MS 2); R$_f$=0.50 (CH$_2$Cl$_2$/MeOH 9:1); $^1$H NMR (400 MHz, DMSO-d$_6$) δ ppm 1.02-1.11 (m, 2H) 1.17-1.30 (m, 2H) 1.90 (s, 3H) 2.25 (s, 3H) 2.51 (s, 3H) 3.76-3.88 (m, 1H) 6.43 (s, 1H) 7.29-7.37 (m, 2H) 7.38-7.48 (m, 2H) 9.12 (s, 1H) 11.07 (s, 1H).

Step 126.1: tert-butyl (6-chloro-3-methyl-[1,2,4]triazolo[4,3-b]pyridazin-8-yl)(4-methoxybenzyl)-carbamate

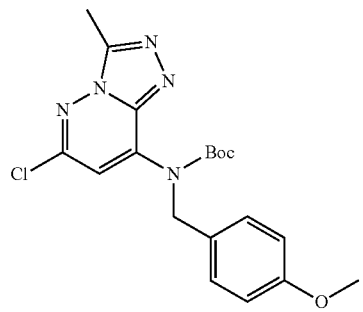 [SMILES: COc1ccc(CN(C(=O)OC(C)(C)C)c2cc(Cl)nn3c(C)nnc23)cc1]

The title compound was prepared in analogy to the procedure described in Step 112.5 using tert-butyl (6-chloro-3-methyl-[1,2,4]triazolo[4,3-b]pyridazin-8-yl)carbamate (Step 112.4) and 4-methoxybenzylchloride at 80° C. for 1 hr. The crude product was purified by silica gel column chromatography (hexane/EtOAc 10-25%). $t_R$: 5.35 min (HPLC 1); $t_R$: 1.19 min (LC-MS 2); ESI-MS: 404 [M+H]$^+$ (LC-MS 2); R$_f$=0.74 (hexane/EtOAc 1:1) Step 126.2: tert-butyl (6-(4-(4-chlorophenyl)-1-cyclopropyl-3-methyl-6-oxopyrrolo[3,4-c]pyrazol-5

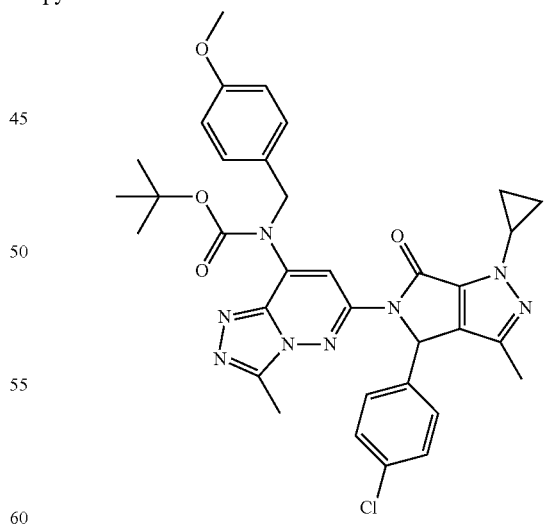

The title compound was prepared in analogy to the procedure described in Example 110 using 4-(4-chlorophenyl)-1-cyclopropyl-3-methyl-4,5-dihydropyrrolo[3,4-c]pyrazol-6(1H)-one (Step 85.6) and tert-butyl (6-chloro-3-methyl-[1,2,4]triazolo[4,3-b]pyridazin-8-yl)(4-methoxybenzyl)-carbamate (Step 126.1). The crude product was purified by silica gel column chromatography (CH$_2$Cl$_2$/MeOH 0.5-2.5%). t$_R$: 6.05 min (HPLC 1); t$_R$: 1.37 min (LC-MS 2); ESI-MS: 655 [M+H]$^+$ (LC-MS 2); ESI-MS: 653 [M−H]$^−$ (LC-MS 2); R$_f$=0.45 (CH$_2$Cl$_2$/MeOH 9:1).

Step 126.3: 5-(8-amino-3-methyl-[1,2,4]triazolo[4,3-b]pyridazin-6-yl)-4-(4-chlorophenyl)-1-cyclopropyl-3-methyl-4,5-dihydropyrrolo[3,4-c]pyrazol-6(1H)-one

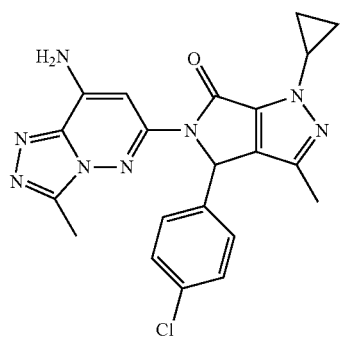 [SMILES: Cc1nn(C2CC2)c2c1C(c1ccc(Cl)cc1)N(c1cc(N)c3nnc(C)n3n1)C2=O]

The title compound was prepared in analogy to the procedure described in Step 23.9 using tert-butyl (6-(4-(4-chlorophenyl)-1-cyclopropyl-3-methyl-6-oxopyrrolo[3,4-c]pyrazol-5(1H,4H,6H)-yl)-3-methyl-[1,2,4]triazolo[4,3-b]pyridazin-8-yl)(4-methoxybenzyl)carbamate (Step 126.2) at RT for min then, 80° C. for 10 min. The crude product was purified by silica gel column chromatography (CH$_2$Cl$_2$/MeOH 1.5-4%). t$_R$: 4.33 min (HPLC 1); t$_R$: 1.01 min (LC-MS 2); ESI-MS: 435 [m+H]+(LC-MS 2); ESI-MS: 433 [M−H]$^−$ (LC-MS 2); R$_f$=0.54 (CH$_2$Cl$_2$/MeOH 9:1); $^1$H NMR (400 MHz, DMSO-d$_6$) δ ppm 1.01-1.07 (m, 2H) 1.20-1.25 (m, 2H) 1.89 (s, 3H) 2.45 (s, 3H) 3.77-3.85 (m, 1H) 6.40 (s, 1H) 7.21 (s, 1H) 7.30-7.41 (m, 4H) 7.49 (br. s., 2H).

Reference Example 127

(S)-4-(4-chlorophenyl)-5-(1,5-dimethyl-6-oxo-1,6-dihydropyridin-3-yl)-1-(2-methoxypyridin-3-yl)-3-methyl-4,5-dihydropyrrolo[3,4-c]pyrazol-6(1H)-one

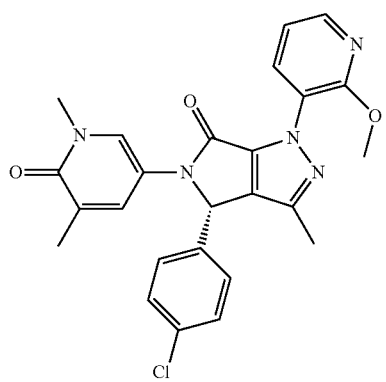 [SMILES: COc1ncccc1-n1nc(C)c2c1C(=O)N(c1cc(C)c(=O)n(C)c1)[C@H]2c1ccc(Cl)cc1]

The title compound (75 mg, 0.158 mmol, 44% yield) was obtained enantiomerically pure (ee>99%) after chiral preparative chromatography (Chiralpak AD-H 50×250 mm; mobile phase: scCO$_2$/MeOH 60:40 isocratic in 12 min; flow: 100 mL/min; detection 290 nm) of the racemic mixture of 4-(4-chlorophenyl)-5-(1,5-dimethyl-6-oxo-1,6-dihydropyridin-3-yl)-1-(2-methoxypyridin-3-yl)-3-methyl-4,5-dihydropyrrolo[3,4-c]pyrazol-6(1H)-one (Example 71) (170 mg, 0.357 mmol) followed by trituration in hexane/Et$_2$O (3:1). t$_R$: 4.33 min (HPLC 1); t$_R$: 1.00 min (LC-MS 2); ESI-MS: 476 [M+H]$^+$ (LC-MS 2).

Example 128

(R)-4-(4-chlorophenyl)-5-(1,5-dimethyl-6-oxo-1,6-dihydropyridin-3-yl)-1-(2-methoxypyridin-3-yl)-3-methyl-4,5-dihydropyrrolo[3,4-c]pyrazol-6(1H)-one

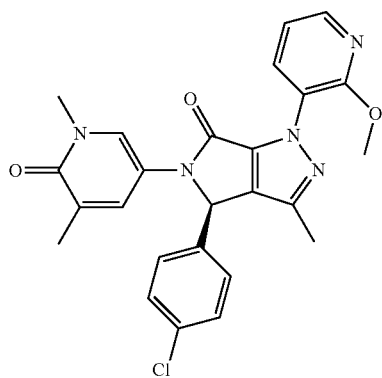 [SMILES: COc1ncccc1-n1nc(C)c2c1C(=O)N(c1cc(C)c(=O)n(C)c1)[C@@H]2c1ccc(Cl)cc1]

The title compound (36 mg, 0.076 mmol, 21.2% yield) was obtained enantiomerically pure (ee>99.0%) after chiral preparative chromatography (Chiralpak AD-H 50×250 mm; mobile phase: scCO$_2$/MeOH 60:40 isocratic in 12 min; flow: 100 mL/min; detection 290 nm) of the racemic mixture of 4-(4-chlorophenyl)-5-(1,5-dimethyl-6-oxo-1,6-dihydropyridin-3-yl)-1-(2-methoxypyridin-3-yl)-3-methyl-4,5-dihydropyrrolo[3,4-c]pyrazol-6(1H)-one (Example 71) (170 mg, 0.357 mmol) followed by trituration in hexane/Et$_2$O (3:1). t$_R$: 4.33 min (HPLC 1); t$_R$: 1.00 min (LC-MS 2); ESI-MS: 476 [M+H]$^+$ (LC-MS 2).

Example 129

4-(4-chlorophenyl)-3-cyclopropyl-5-(3,8-dimethyl-[1,2,4]triazolo[4,3-a]pyridin-6-yl)-1-methyl-4,5-dihydropyrrolo[3,4-c]pyrazol-6(1H)-one

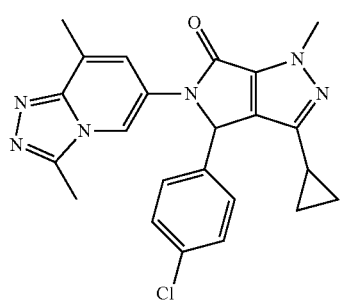 [SMILES: Cc1cc(N2C(=O)c3c(c(C4CC4)nn3C)C2c2ccc(Cl)cc2)cn2c(C)nnc12]

The title compound was prepared in analogy to the procedure described in Step 112.5 using 4-(4-chlorophenyl)-3- cyclopropyl-5-(3,8-dimethyl-[1,2,4]triazolo[4,3-a]pyridin-6-yl)-4,5-dihydropyrrolo[3,4-c]pyrazol-6(1H)-one (Step 129.1) and MeI at RT for 30 min. The crude product was purified by preparative achiral SFC (column NH2, gradient 19-24% in 6 min_total 11 min). $t_R$: 0.95 min (LC-MS 2); ESI-MS: 433.2 [M+H]$^+$ (LC-MS 2); $^1$H NMR (400 MHz, DMSO-d$_6$) δ ppm-0.10-0.07 (m, 1H) 0.50-0.78 (m, 3H) 1.59-1.76 (m, 1H) 1.92 (s, 3H) 3.36 (s, 3H) 3.92 (s, 3H) 6.09 (s, 1H) 7.27 (d, J=8.4 Hz, 2H) 7.32-7.45 (m, 3H) 7.68 (d, J=2.7 Hz, 1H).

Step 129.1: 4-(4-chlorophenyl)-3-cyclopropyl-5-(3,8-dimethyl-[1,2,4]triazolo[4,3-a]pyridin-6-yl)-4,5-dihydropyrrolo[3,4-c]pyrazol-6(1H)-one

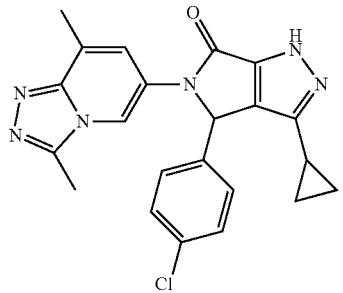 [SMILES: Cc1cc(N2C(=O)c3[nH]nc(C4CC4)c3C2c2ccc(Cl)cc2)cn2c(C)nnc12]

The title compound was prepared in analogy to the procedure described in Example 57 using 5-(4-chlorophenyl)-4-(cyclopropanecarbonyl)-1-(3,8-dimethyl-[1,2,4]triazolo[4,3-a]pyridin-6-yl)-3-hydroxy-1H-pyrrol-2(5H)-one (Step 117.1) and hydrazine hydrate. The crude product was purified by silica gel column chromatography (7.5% MeOH/CH$_2$Cl$_2$). $t_R$: 0.83 min (LC-MS 2); ESI-MS: 419 [M+H]$^+$ (LC-MS 2); $^1$H NMR (400 MHz, DMSO-d$_6$) δ ppm 0.00-0.11 (m, 1H) 0.44-0.65 (m, 1H) 0.65-0.78 (m, 1H) 0.80-0.90 (m, 1H) 1.68-1.88 (m, 1H) 2.42 (s, 3H) 2.61 (s, 3H) 6.44 (s, 1H) 7.16-7.45 (m, 5H) 8.38 (d, J=0.8 Hz, 1H) 13.55 (br. s., 1H).

Example 130

4-(4-chlorophenyl)-1-cyclopropyl-5-(3,8-dimethyl-[1,2,4]triazolo[4,3-a]pyridin-6-yl)-3-(methoxymethyl)-4,5-dihydropyrrolo[3,4-c]pyrazol-6(1H)-one

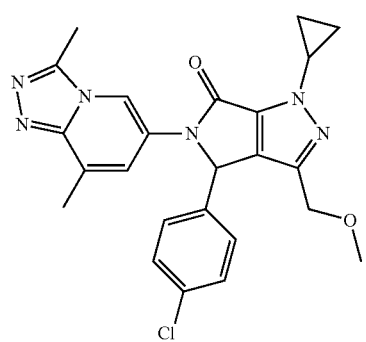 [SMILES: COCc1nn(C2CC2)c2c1C(c1ccc(Cl)cc1)N(c1cc(C)c3nnc(C)n3c1)C2=O]

The title compound was prepared using an analogous procedure to that described in Example 23 using 4-(4-chlorophenyl)-1-cyclopropyl-3-(methoxymethyl)-4,5-dihydropyrrolo[3,4-c]pyrazol-6(1H)-one (Step 130.4) and 6-bromo-3,8-dimethyl-[1,2,4]triazolo[4,3-a]pyridine (Step 130.6). The reaction mixture was stirred for 16 h at 110° C. After purification by silica gel column chromatography (CH$_2$Cl$_2$/MeOH 1-5.5%), the resulting residue was purified by SFC (column: PPU, 25 cm, Ø 3 cm, 5 µm, 100 Å; gradient: 12% B for 1 min, 12-17% B in 6 min, 17-50% B in 1 min, 50% B for 1.5 min, 50%-12% B in 1 min, 12% B for 0.5 min; A: scCO$_2$, B: MeOH; flow: 100 mL/min) to provide the title compound (151 mg) as a colorless solid. $t_R$: 0.94 min (LC-MS 2); ESI-MS: 463.1 [M+H]$^+$ (LC-MS 2); $R_f$=0.37 (CH$_2$Cl$_2$/MeOH 9:1); $^1$H NMR (400 MHz, DMSO-d6) δ ppm 1.03-1.11 (m, 2H) 1.23-1.31 (m, 2H) 2.42 (s, 3H) 2.61 (s, 3H) 3.06 (s, 3H) 3.84-3.92 (m, 1H) 3.99 (d, J=12.12 Hz, 1H) 4.23 (d, J=12.51 Hz, 1H) 6.46 (s, 1H) 7.28-7.35 (m, 4H) 7.37 (br. s, 1H) 8.48 (br. s, 1H).

Step 130.1: ethyl 5-methoxy-2,4-dioxopentanoate

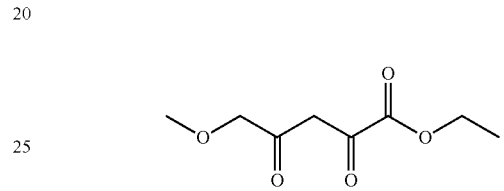

Methoxyacetone (5.22 mL, 56.8 mmol) was added dropwise to a cold (0° C.), stirred solution of sodium ethoxide (21% in EtOH, 20.2 g, 62.4 mmol) and EtOH (50 mL), under an argon atmosphere. The reaction mixture was stirred for 30 min at 0° C. Then, diethyl oxalate (7.71 mL, 56.8 mmol) was added. The reaction mixture was allowed to warm to rt, stirred for 16 h, quenched by addition of 1N HCl (75 mL), and extracted with CH$_2$Cl$_2$. The combined organic layers were dried over Na$_2$SO$_4$ and the solvent was evaporated off under reduced pressure. The crude material was purified by silica gel column chromatography (hexane/EtOAc 5-10%) to afford the title compound (3.21 g) as a yellow oil. $t_R$: 0.70 min (LC-MS 2); ESI-MS: 189.1 [M+H]$^+$ (LC-MS 2); $R_f$=0.25 (hexane/EtOAc 1:1, CPS staining).

Step 130.2: 5-(4-chlorophenyl)-3-hydroxy-4-(2-methoxyacetyl)-1-(4-methoxybenzyl)-1H-pyrrol-2(5H)-one

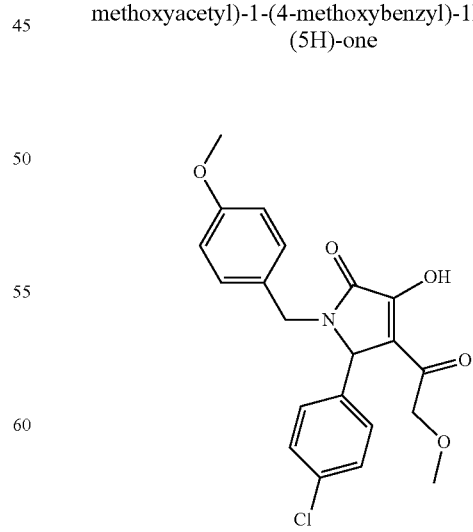

The title compound was prepared using an analogous procedure to that described in Step 57.1 but using equimolar amounts of ethyl 5-methoxy-2,4-dioxopentanoate (Step 130.1), 4-chlorobenzaldehyde, and 4-methoxybenzylamine. The reaction mixture was stirred for 2 h at 120° C. and allowed to cool to rt. The precipitate was collected by filtration to provide the title compound (5.21 g) as a colorless solid. $t_R$: 0.94 min (LC-MS 2); ESI-MS: 402.1 [M+H]$^+$ (LC-MS 2).

Step 130.3: 4-(4-chlorophenyl)-1-cyclopropyl-5-(4-methoxybenzyl)-3-(methoxymethyl)-4,5-dihydropyrrolo[3,4-c]pyrazol-6(1H)-one

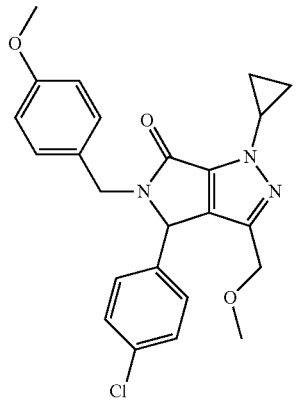 [SMILES: COCc1nn(C2CC2)c2c1C(c1ccc(Cl)cc1)N(Cc1ccc(OC)cc1)C2=O]

Cyclopropylhydrazine (2.71 g) (Step 17.2) was added to a solution of 5-(4-chlorophenyl)-3-hydroxy-4-(2-methoxyacetyl)-1-(4-methoxybenzyl)-1H-pyrrol-2(5H)-one (5 g, 12.4 mmol) (Step 130.2) in a mixture of EtOH and toluene (60 mL, 1:1, v/v). The reaction mixture was stirred 16 h at 115° C., concentrated, quenched with a saturated aq. NaHCO$_3$ solution, and extracted with EtOAc (2×100 mL). The combined organic layers were dried over Na$_2$SO$_4$ and the solvent was evaporated off under reduced pressure. The crude material was purified by silica gel column chromatography (hexane/EtOAc 20-50%) to afford the title compound (2.62 g) as a yellow solid. $t_R$: 1.24 min (LC-MS 2); ESI-MS: 438.1 [M+H]$^+$ (LC-MS 2); R$_f$=0.50 (hexane/EtOAc 1:1).

Step 130.4: 4-(4-chlorophenyl)-1-cyclopropyl-3-(methoxymethyl)-4,5-dihydropyrrolo[3,4-c]pyrazol-6(1H)-one

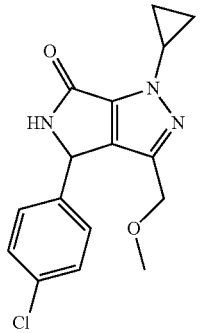 [SMILES: COCc1nn(C2CC2)c2c1C(c1ccc(Cl)cc1)NC2=O]

The title compound was prepared using an analogous procedure to that described in Step 23.9 but using 4-(4-chlorophenyl)-1-cyclopropyl-5-(4-methoxybenzyl)-3-(methoxymethyl)-4,5-dihydropyrrolo[3,4-c]pyrazol-6(1H)-one (Step 130.3) and stirring the reaction mixture for 3 h at 110° C. under MW irradiation. The crude material was purified by silica gel column chromatography (hexane/EtOAc 40-65%) to afford the title compound (933 mg) as a colorless solid. $t_R$: 0.91 min (LC-MS 2); ESI-MS: 318.0 [M+H]$^+$ (LC-MS 2); R$_f$=0.19 (hexane/EtOAc 1:1).

Step 130.5: 5-bromo-2-hydrazinyl-3-methylpyridine

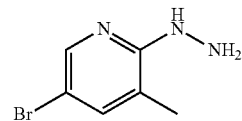

Hydrazine hydrate (119 mL, 2422 mmol) was added to a suspension of 5-bromo-2-chloro-3-methylpyridine (50 g, 242 mmol) in 2-methoxyethanol (250 mL). The resulting solution was stirred 30 h at 120° C. and concentrated. The yellow residue was purified by trituration with H$_2$O to provide the title compound (24 g) as a colorless solid. $t_R$: 0.39 min (LC-MS 2); ESI-MS: 201.9 [M+H]$^+$ (LC-MS 2)

Step 130.6: 6-bromo-3,8-dimethyl-[1,2,4]triazolo[4,3-a]pyridine

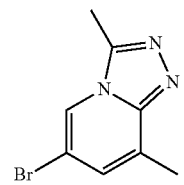

A solution of acetic anhydride (12.22 mL, 129 mmol) in THF (10 mL) was added over a 10 min period to a suspension of 5-bromo-2-hydrazinyl-3-methylpyridine (25 g, 118 mmol) (Step 130.5) in dioxane (125 mL) and acetic acid (25 mL), at rt. The reaction mixture was stirred for 10 min at rt, heated to 100° C., stirred for 7 h at this temperature, and concentrated. The solid residue was purified by trituration with TBME to provide the title compound (25.7 g) as a colorless solid. $t_R$: 0.39 min (LC-MS 2); ESI-MS: 225.9 [M+H]$^+$ (LC-MS 2).

Example 131

4-(4-chlorophenyl)-1-cyclopropyl-5-(3,8-dimethyl-[1,2,4]triazolo[4,3-a]pyridin-6-yl)-3-(hydroxymethyl)-4,5-dihydropyrrolo[3,4-c]pyrazol-6(1H)-one

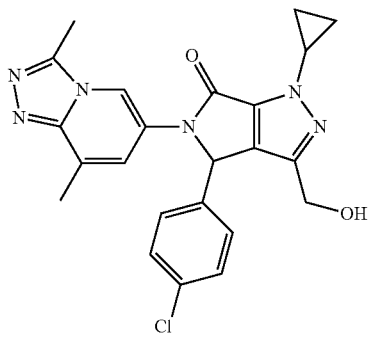 [SMILES: Cc1cc(N2C(=O)c3c(c(CO)nn3C3CC3)C2c2ccc(Cl)cc2)cn2c(C)nnc12]

BBr₃ (1 M in CH₂Cl₂, 0.337 mL, 0.337 mmol) was added to a solution of 4-(4-chlorophenyl)-1-cyclopropyl-5-(3,8-dimethyl-[1,2,4]triazolo[4,3-a]pyridin-6-yl)-3-(methoxymethyl)-4,5-dihydropyrrolo[3,4-c]pyrazol-6(1H)-one (130 mg, 0.281 mmol) (Example 130) in CH₂Cl₂ (5 mL), under an argon atmosphere. The reaction mixture was stirred for 1 h at rt, quenched with brine (100 mL), and extracted with EtOAc (2×100 mL). The combined organic layers were washed with brine (100 mL), dried on Na₂SO₄ and the solvent was evaporated off under reduced pressure. After purification by silica gel column chromatography (CH₂Cl₂/MeOH 2-8%), the resulting residue was triturated in diethyl ether to provide the title compound (28 mg) as a colorless solid. t$_R$: 0.77 min (LC-MS 2); ESI-MS: 449.1 [M+H]⁺ (LC-MS 2); R$_f$=0.29 (CH₂Cl₂/MeOH 9:1); ¹H NMR (400 MHz, DMSO-d6) δ ppm 1.02-1.09 (m, 2H) 1.19-1.28 (m, 2H) 2.42 (s, 3H) 2.61 (s, 3H) 3.80-3.90 (m, 1H) 4.06 (dd, J=12.90, 5.87 Hz, 1H) 4.30 (dd, J=12.90, 4.30 Hz, 1H) 5.10 (dd, J=5.87, 4.30 Hz, 1H) 6.46 (s, 1H) 7.26-7.41 (m, 5H) 8.49 (s, 1H).

Example 132

4-(4-chlorophenyl)-1-cyclopropyl-5-(1,5-dimethyl-6-oxo-1,6-dihydropyridin-3-yl)-3-(methoxymethyl)-4,5-dihydropyrrolo[3,4-c]pyrazol-6(1H)-one

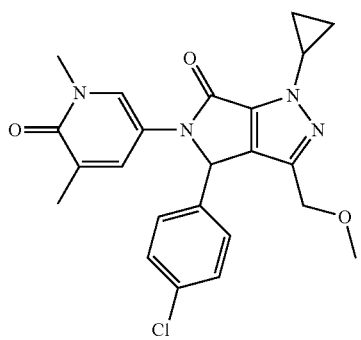 [SMILES: COCc1nn(C2CC2)c2c1C(c1ccc(Cl)cc1)N(c1cc(C)c(=O)n(C)c1)C2=O]

The title compound was prepared using an analogous procedure to that described in Example but using 4-(4-chlorophenyl)-1-cyclopropyl-3-(methoxymethyl)-4,5-dihydropyrrolo[3,4-c]pyrazol-6(1H)-one (Step 130.4) and 5-bromo-1,3-dimethyl-2-pyridone. The crude material was purified by silica gel column chromatography (CH₂Cl₂/MeOH 0.5-3.5%) to provide the title compound (286 mg) as a colorless solid. t$_R$: 0.95 min (LC-MS 2); ESI-MS: 439.1 [M+H]⁺ (LC-MS 2); R$_f$=0.48 (CH₂Cl₂/MeOH 9:1); ¹H NMR (400 MHz, DMSO-d6) δ ppm 1.00-1.07 (m, 2H) 1.20-1.27 (m, 2H) 1.91 (s, 3H) 3.02 (s, 3H) 3.34 (s, 3H) 3.81-3.89 (m, 1H) 3.97 (d, J=12.51 Hz, 1H) 4.20 (d, J=12.51 Hz, 1H) 6.09 (s, 1H) 7.20-7.28 (m, 2H) 7.31-7.37 (m, 2H) 7.40-7.45 (m, 1H) 7.76 (d, J=2.74 Hz, 1H).

Example 133

4-(4-chlorophenyl)-1-cyclopropyl-5-(1,5-dimethyl-6-oxo-1,6-dihydropyridin-3-yl)-3-(hydroxymethyl)-4,5-dihydropyrrolo[3,4-c]pyrazol-6(1H)-one

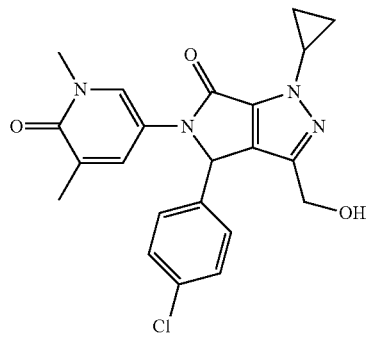 [SMILES: Cc1cc(N2C(=O)c3c(c(CO)nn3C3CC3)C2c2ccc(Cl)cc2)cn(C)c1=O]

The title compound was prepared according to an analogous procedure to that described in Example 131 but performing the addition of BBr₃ at 0° C. and stirring the reaction mixture for 10 min at this temperature before quenching it. The crude material was purified by silica gel column chromatography (CH₂Cl₂/MeOH 0.5-3.5%) to provide the title compound (286 mg) as a colorless solid. t$_R$: 0.78 min (LC-MS 2); ESI-MS: 425.1 [M+H]⁺ (LC-MS 2); R$_f$=0.30 (CH₂Cl₂/MeOH 9:1); ¹H NMR (400 MHz, DMSO-d6) δ ppm 1.00-1.05 (m, 2H) 1.20-1.24 (m, 2H) 1.91 (s, 3H) 3.36 (s, 3H) 3.79-3.86 (m, 1H) 4.04 (dd, J=13.10, 6.06 Hz, 1H) 4.26 (dd, J=12.90, 4.30 Hz, 1H) 5.01 (dd, J=5.87, 4.69 Hz, 1H) 6.07 (s, 1H) 7.21-7.26 (m, 2H) 7.30-7.36 (m, 2H) 7.38-7.42 (m, 1H) 7.74 (d, J=2.74 Hz, 1H).

Example 134

4-(4-chlorophenyl)-5-(1,5-dimethyl-6-oxo-1,6-dihydropyridin-3-yl)-3-methyl-2-(oxetan-3-yl)-4,5-dihydropyrrolo[3,4-c]pyrazol-6(2H)-one

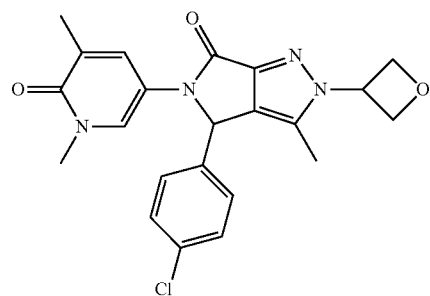 [SMILES: Cc1cc(N2C(=O)c3nn(C4COC4)c(C)c3C2c2ccc(Cl)cc2)cn(C)c1=O]

To a stirred solution of 4-(4-chlorophenyl)-5-(1,5-dimethyl-6-oxo-1,6-dihydropyridin-3-yl)-3-methyl-4,5-dihydropyrrolo[3,4-c]pyrazol-6(1H)-one (Example 27) (100 mg, 0.271 mmol) in DMF (3 mL) was added under Ar NaH (13.01 mg, 0.325 mmol) at 0° C. The reaction mixture was stirred for 30 min at rt. 3-Iodooxetane (0.030 mL, 0.352 mmol) was added. The reaction mixture was stirred for 30 min at rt, quenched with a saturated aqueous solution of sodium bicarbonate (75 mL), and extracted with EtOAc (2×75 mL). The combined organic layers were washed with a saturated aqueous solution of sodium bicarbonate (75 mL), dried on Na$_2$SO$_4$ and evaporated. The residue was purified by silica gel column chromatography (CH$_2$Cl$_2$/MeOH 1-4%), followed by preparative achiral SFC (column: PPU, 250×30 mm, 5 µm, 100 A, Princeton; eluent: MeOH/scCO$_2$; gradient: 1 min 20% MeOH, 20-25% MeOH in 6 min, 25-50% MeOH in 1 min, 1.5 min 50% MeOH; flow: 100 mL/min) to afford 27 mg of 4-(4-chlorophenyl)-5-(1,5-dimethyl-6-oxo-1,6-dihydropyridin-3-yl)-3-methyl-1-(oxetan-3-yl)-4,5-dihydropyrrolo[3,4-c]pyrazol-6(1H)-one (Example 135) and ten fractions containing the impure title compound. These fractions were collected and evaporated to afford after a second SFC purification 16 mg of 4-(4-chlorophenyl)-5-(1,5-dimethyl-6-oxo-1,6-dihydropyridin-3-yl)-3-methyl-2-(oxetan-3-yl)-4,5-dihydropyrrolo[3,4-c]pyrazol-6(2H)-one (title compound). $t_R$: 0.81 min (LC-MS 2); ESI-MS: 425.1 [M+H]$^+$ (LC-MS 2); $R_f$=0.25 (CH$_2$Cl$_2$/MeOH 9:1); $^1$H NMR (400 MHz, DMSO-d6) δ ppm 1.92 (s, 3H) 2.02 (s, 3H) 3.36 (s, 3H) 4.84-5.03 (m, 4H) 5.56-5.69 (m, 1H) 6.12 (s, 1H) 7.14-7.29 (m, 2H) 7.31-7.38 (m, 2H) 7.39-7.42 (m, 1H) 7.73 (d, J=2.74 Hz, 1H).

Example 135

4-(4-chlorophenyl)-5-(1,5-dimethyl-6-oxo-1,6-dihydropyridin-3-yl)-3-methyl-1-(oxetan-3-yl)-4,5-dihydropyrrolo[3,4-c]pyrazol-6(1H)-one

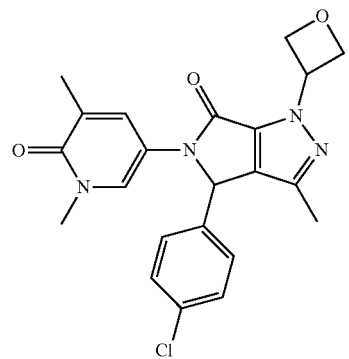 [SMILES: Cc1nn(C2COC2)c2c1C(c1ccc(Cl)cc1)N(c1cc(C)c(=O)n(C)c1)C2=O]

The preparation of the title compound is described in Example 134. $t_R$: 0.87 min (LC-MS 2); ESI-MS: 425.1 [M+H]$^+$ (LC-MS 2); $R_f$=0.42 (CH$_2$Cl$_2$/MeOH 9:1); $^1$H NMR (400 MHz, DMSO-d6) δ ppm 1.91 (s, 3H) 1.97 (s, 3H) 3.35 (s, 3H) 4.88-4.96 (m, 2H) 4.97-5.06 (m, 2H) 5.65-5.73 (m, 1H) 6.09 (s, 1H) 7.23-7.31 (m, 2H) 7.33-7.42 (m, 3H) 7.70 (d, J=2.74 Hz, 1H).

Example 136

4-(4-chlorophenyl)-5-(3,8-dimethyl-[1,2,4]triazolo[4,3-a]pyridin-6-yl)-3-methyl-2-(oxetan-3-yl)-4,5-dihydropyrrolo[3,4-c]pyrazol-6(2H)-one

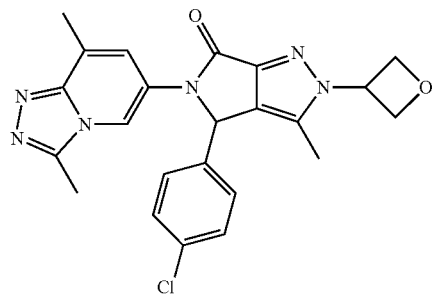 [SMILES: Cc1cc(N2C(=O)c3nn(C4COC4)c(C)c3C2c2ccc(Cl)cc2)cn2c(C)nnc12]

The title compound was prepared using an analogous procedure to that described in Example 134 using 4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one (Example 98) (200 mg, 0.509 mmol) and stirring the reaction mixture for 30 min at 80° C. after addition of 3-iodooxetane. Purification of the crude product afforded 50 mg of a 4-(4-chlorophenyl)-5-(3,8-dimethyl-[1,2,4]triazolo[4,3-a]pyridin-6-yl)-3-methyl-1-(oxetan-3-yl)-4,5-dihydropyrrolo[3,4-c]pyrazol-6(1H)-one (Example 137) and 31 mg of a 4-(4-chlorophenyl)-5-(3,8-dimethyl-[1,2,4]triazolo[4,3-a]pyridin-6-yl)-3-methyl-2-(oxetan-3-yl)-4,5-dihydropyrrolo[3,4-c]pyrazol-6(2H)-one (title compound). $t_R$: 0.79 min (LC-MS 2); ESI-MS: 449.1 [M+H]$^+$ (LC-MS 2); $R_f$=0.40 (CH$_2$Cl$_2$/MeOH 9:1); $^1$H NMR (400 MHz, DMSO-d6) δ ppm 2.05 (s, 3H) 2.43 (s, 3H) 2.61 (s, 3H) 4.85-5.00 (m, 4H) 5.60-5.70 (m, 1H) 6.49 (s, 1H) 7.25-7.38 (m, 5H) 8.45 (s, 1H).

Example 137

4-(4-chlorophenyl)-5-(3,8-dimethyl-[1,2,4]triazolo[4,3-a]pyridin-6-yl)-3-methyl-1-(oxetan-3-yl)-4,5-dihydropyrrolo[3,4-c]pyrazol-6(1H)-one

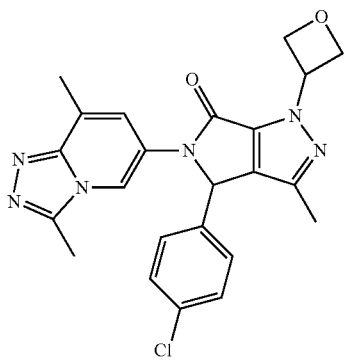 [SMILES: Cc1nn(C2COC2)c2c1C(c1ccc(Cl)cc1)N(c1cc(C)c3nnc(C)n3c1)C2=O]

The preparation of the title compound is described in Example 136. $t_R$: 0.86 min (LC-MS 2); ESI-MS: 449.1 [M+H]$^+$ (LC-MS 2); $R_f$=0.45 (CH$_2$Cl$_2$/MeOH 9:1); $^1$H NMR (400 MHz, DMSO-d6) δ ppm 2.00 (s, 3H) 2.43 (s, 3H) 2.61 (s, 3H) 4.91-4.99 (m, 2H) 5.00-5.08 (m, 2H) 5.68-5.79 (m, 1H) 6.46 (s, 1H) 7.26-7.42 (m, 5H) 8.43 (s, 1H).

Example 138

1-(azetidin-3-yl)-4-(4-chlorophenyl)-5-(1,5-dimethyl-6-oxo-1,6-dihydropyridin-3-yl)-3-methyl-4,5-dihydropyrrolo[3,4-c]pyrazol-6(1H)-one

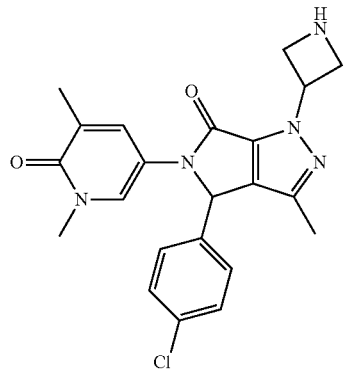 [SMILES: Cc1nn(C2CNC2)c2c1C(c1ccc(Cl)cc1)N(c1cc(C)c(=O)n(C)c1)C2=O]

Step 138.1: a) Tert-butyl 3-(4-(4-chlorophenyl)-5-(1,5-dimethyl-6-oxo-1,6-dihydropyridin-3-yl)-3-methyl-6-oxo-5,6-dihydropyrrolo[3,4-c]pyrazol-1(4H)-yl)azetidine-1-carboxylate and b) tert-butyl 3-(4-(4-chlorophenyl)-5-(1,5-dimethyl-6-oxo-1,6-dihydropyridin-3-yl)-3-methyl-6-oxo-5,6-dihydropyrrolo[3,4-c]pyrazol-2(4H)-yl)azetidine-1-carboxylate The title compound was prepared using an analogous procedure to that described in Example stirring the reaction mixture for 30 min at 80° C. after addition of tert-butyl 3-iodoazetidine-1-carboxylate. The crude material was purified by silica gel column chromatography (CH$_2$Cl$_2$/MeOH 1-4.5%) to afford:

283 mg of tert-butyl 3-(4-(4-chlorophenyl)-5-(1,5-dimethyl-6-oxo-1,6-dihydropyridin-3-yl)-3-methyl-6-oxo-5,6-dihydropyrrolo[3,4-c]pyrazol-1(4H)-yl)azetidine-1-carboxylate. $t_R$: 1.12 min (LC-MS 2); ESI-MS: 524.1 [M+H]$^+$ (LC-MS 2); R$_f$=0.54 (CH$_2$Cl$_2$/MeOH 9:1).

65 mg of and tert-butyl 3-(4-(4-chlorophenyl)-5-(1,5-dimethyl-6-oxo-1,6-dihydropyridin-3-yl)-3-methyl-6-oxo-5,6-dihydropyrrolo[3,4-c]pyrazol-2(4H)-yl)azetidine-1-carboxylate. $t_R$: 1.04 min (LC-MS 2); ESI-MS: 524.3 [M+H]$^+$ (LC-MS 2); R$_f$=0.48 (CH$_2$Cl$_2$/MeOH 9:1).

Step 138.2: 1-(azetidin-3-yl)-4-(4-chlorophenyl)-5-(1,5-dimethyl-6-oxo-1,6-dihydropyridin-3-yl)-3-methyl-4,5-dihydropyrrolo[3,4-c]pyrazol-6(1H)-one To a stirred solution of tert-butyl 3-(4-(4-chlorophenyl)-5-(1,5-dimethyl-6-oxo-1,6-dihydropyridin-3-yl)-3-methyl-6-oxo-5,6-dihydropyrrolo[3,4-c]pyrazol-1(4H)-yl)azetidine-1-carboxylate (Step 138.1a) (280 mg, 0.534 mmol) in CH$_2$Cl$_2$ (4 mL) was added TFA (0.412 mL, 5.34 mmol). The reaction mixture was stirred for 1 h at rt, quenched by addition of a saturated aqueous solution of NaHCO$_3$, and extracted with CH$_2$Cl$_2$. The combined organic layers were dried on Na$_2$SO$_4$ and evaporated. The residue was purified by silica gel column chromatography (NH$_3$ 1%/CH$_2$Cl$_2$/MeOH 1-4%) to afford 200 mg of the title compound as a colorless solid. $t_R$: 0.66 min (LC-MS 2); ESI-MS: 424.1 [M+H]$^+$ (LC-MS 2); R$_f$=0.09 (CH$_2$Cl$_2$/MeOH 9:1); $^1$H NMR (400 MHz, DMSO-d6) δ ppm 1.91 (s, 3H) 1.94 (s, 3H) 3.35 (s, 3H) 3.70-3.78 (m, 2H) 4.06-4.14 (m, 2H) 5.26-5.37 (m, 1H) 6.07 (br. s, 1H) 7.23-7.29 (m, 2H) 7.34-7.40 (m, 3H) 7.71 (d, J=2.74 Hz, 1H).

Example 139

4-(4-chlorophenyl)-5-(1,5-dimethyl-6-oxo-1,6-dihydropyridin-3-yl)-3-methyl-2-(1-methylazetidin-3-yl)-4,5-dihydropyrrolo[3,4-c]pyrazol-6(2H)-one

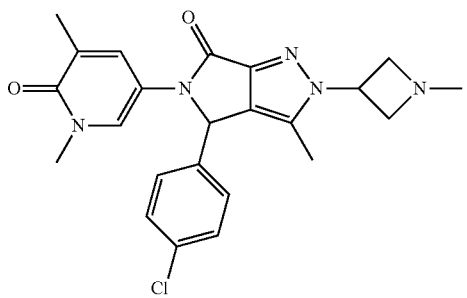 [SMILES: Cc1cc(N2C(=O)c3nn(C4CN(C)C4)c(C)c3C2c2ccc(Cl)cc2)cn(C)c1=O]

Step 139.1: 2-(azetidin-3-yl)-4-(4-chlorophenyl)-5-(1,5-dimethyl-6-oxo-1,6-dihydropyridin-3-yl)-3-methyl-4,5-dihydropyrrolo[3,4-c]pyrazol-6(2H)-one The title compound was prepared using an analogous procedure to that described in Step 138.2 using tert-butyl 3-(4-(4-chlorophenyl)-5-(1,5-dimethyl-6-oxo-1,6-dihydropyridin-3-yl)-3-methyl-6-oxo-5,6-dihydropyrrolo[3,4-c]pyrazol-2(4H)-yl)azetidine-1-carboxylate (Step 138.1 b). $t_R$: 0.61 min (LC-MS 2); ESI-MS: 424.1 [M+H]$^+$ (LC-MS 2); R$_f$=0.05 (CH$_2$Cl$_2$/MeOH 9:1).

Step 139.2: 4-(4-chlorophenyl)-5-(1,5-dimethyl-6-oxo-1,6-dihydropyridin-3-yl)-3-methyl-2-(1-methylazetidin-3-yl)-4,5-dihydropyrrolo[3,4-c]pyrazol-6(2H)-one To a stirred solution of 2-(azetidin-3-yl)-4-(4-chlorophenyl)-5-(1,5-dimethyl-6-oxo-1,6-dihydropyridin-3-yl)-3-methyl-4,5-dihydropyrrolo[3,4-c]pyrazol-6(2H)-one (Step 139.1) (35 mg, 0.083 mmol) in MeOH (1 mL) was added formaldehyde (0.023 mL, 0.248 mmol) under argon. After 30 min at rt, sodium triacetoxyborohydride (87 mg, 0.413 mmol) was added. The reaction mixture was stirred for 1 h at rt, dilute with water (75 mL) and extracted with EtOAc (2×100 mL).

The combined organic extracts were washed with water (100 mL), dried on Na$_2$SO$_4$ and evaporated. The residue was purified by silica gel column chromatography (NH$_3$ 1%/CH$_2$Cl$_2$/MeOH 4-6%) to afford 21 mg of the title compounds as a colorless solid. $t_R$: 0.61 min (LC-MS 2); ESI-MS: 438.2 [M+H]$^+$ (LC-MS 2); R$_f$=0.25 (CH$_2$Cl$_2$/MeOH 9:1); $^1$H NMR (400 MHz, DMSO-d6) δ ppm 1.92 (s, 3H) 2.03 (s, 3H) 2.32 (s, 3H) 3.32-3.38 (m, 4H) 3.41-3.47 (m, 1H) 3.69-3.79 (m, 2H) 4.93-5.02 (m, 1H) 6.10 (s, 1H) 7.24 (d, J=8.60 Hz, 2H) 7.33-7.42 (m, 3H) 7.71 (d, J=2.74 Hz, 1H).

Example 140

4-(4-chlorophenyl)-5-(1,5-dimethyl-6-oxo-1,6-dihydropyridin-3-yl)-3-methyl-1-(1-methylazetidin-3-yl)-4,5-dihydropyrrolo[3,4-c]pyrazol-6(1H)-one

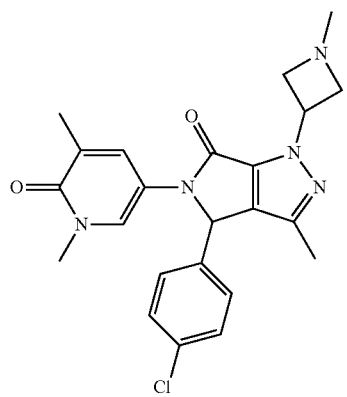 [SMILES: Cc1nn(C2CN(C)C2)c2c1C(c1ccc(Cl)cc1)N(c1cc(C)c(=O)n(C)c1)C2=O]

The title compound was prepared using an analogous procedure to that described in Step 139.2 using 1-(azetidin-3-yl)-4-(4-chlorophenyl)-5-(1,5-dimethyl-6-oxo-1,6-dihydropyridin-3-yl)-3-methyl-4,5-dihydropyrrolo[3,4-c]pyrazol-6(1H)-one (Step 138.2). $t_R$: 0.61 min (LC-MS 2); ESI-MS: 438.1 [M+H]$^+$ (LC-MS 2); R$_f$=0.29 (CH$_2$Cl$_2$/MeOH 9:1); $^1$H NMR (400 MHz, DMSO-d6) δ ppm 1.83-1.96 (m, 6H) 2.33 (s, 3H) 3.35 (s, 3H) 3.45-3.59 (m, 2H) 3.66-3.78 (m, 2H) 4.97-5.10 (m, 1H) 6.07 (s, 1H) 7.26 (d, J=8.60 Hz, 2H) 7.33-7.42 (m, 3H) 7.71 (d, J=2.74 Hz, 1H).

Example 141

4-(4-chlorophenyl)-5-(1,5-dimethyl-6-oxo-1,6-dihydropyridin-3-yl)-N,N,3-trimethyl-6-oxo-5,6-dihydropyrrolo[3,4-c]pyrazole-2(4H)-carboxamide

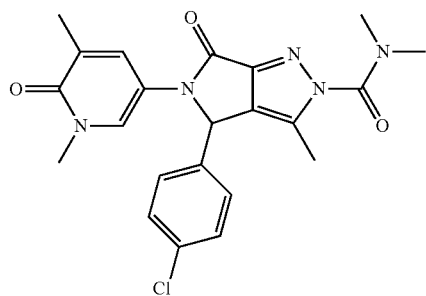 [SMILES: Cc1cc(N2C(=O)c3nn(C(=O)N(C)C)c(C)c3C2c2ccc(Cl)cc2)cn(C)c1=O]

A mixture of 4-(4-chlorophenyl)-5-(1,5-dimethyl-6-oxo-1,6-dihydropyridin-3-yl)-3-methyl-4,5-dihydropyrrolo[3,4-c]pyrazol-6(1H)-one (Example 27) (200 mg, 0.542 mmol) and dimethylcarbamic chloride (0.06 mL, 0.651 mmol) in pyridine (2 mL) for 8 h at 100° C. The reaction mixture was concentrated, diluted in CH$_2$Cl$_2$/water, and extracted twice with CH$_2$Cl$_2$. The combined organic extracts were washed with brine, dried (Na$_2$SO$_4$) and concentrated. The residue was purified by chromatography (1% ammonia/5% MeOH/CH$_2$Cl$_2$), subsequent preparative achiral SFC (column: Reprosil 70 NH2, 250×30 mm, 5 µm, Dr Maisch; eluent: MeOH/scCO$_2$; gradient: 1 min 15% MeOH, 15-20% MeOH in 6 min, 20-50% MeOH in 1 min, 1.5 min 50% MeOH; flow: 100 mL/min) and trituration of the resulting products in diethyl ether to afford 68 mg of 4-(4-chlorophenyl)-5-(1,5-dimethyl-6-oxo-1,6-dihydropyridin-3-yl)-N,N,3-trimethyl-6-oxo-5,6-dihydropyrrolo[3,4-c]pyrazole-1(4H)-carboxamide (Example 142) and 62 mg of the title compound. $t_R$: 0.85 min (LC-MS 2); ESI-MS: 440.1 [M+H]$^+$ (LC-MS 2); $^1$H NMR (400 MHz, DMSO-d6) δ ppm 1.95 (s, 3H) 2.15 (s, 3H) 2.95 (s, 3H) 3.08 (s, 3H) 3.38 (s, 3H) 6.22 (s, 1H) 7.33 (d, J=8.42 Hz, 2H) 7.37-7.48 (m, 3H) 7.79 (d, J=2.64 Hz, 1H).

Example 142

4-(4-chlorophenyl)-5-(1,5-dimethyl-6-oxo-1,6-dihydropyridin-3-yl)-N,N,3-trimethyl-6-oxo-5,6-dihydropyrrolo[3,4-c]pyrazole-1(4H)-carboxamide

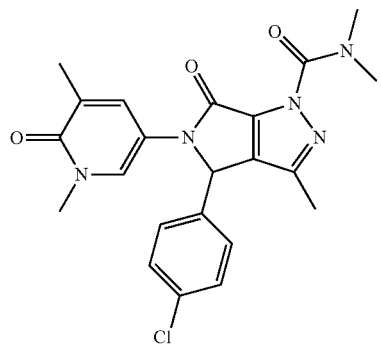 [SMILES: Cc1nn(C(=O)N(C)C)c2c1C(c1ccc(Cl)cc1)N(c1cc(C)c(=O)n(C)c1)C2=O]

The preparation of the title compound is described in Example 141. $t_R$: 0.88 min (LC-MS 2); ESI-MS: 440.1 [M+H]$^+$ (LC-MS 2); $^1$H NMR (400 MHz, DMSO-d6) δ ppm 1.92 (s, 3H) 1.98 (s, 3H) 3.05 (s, 6H) 3.35 (s, 3H) 6.13 (s, 1H) 7.20-7.34 (m, 2H) 7.34-7.48 (m, 3H) 7.73 (d, J=2.74 Hz, 1H).

Example 143

4-(4-chlorophenyl)-5-(1,5-dimethyl-6-oxo-1,6-dihydropyridin-3-yl)-N,3-dimethyl-6-oxo-5,6-dihydropyrrolo[3,4-c]pyrazole-1(4H)-carboxamide

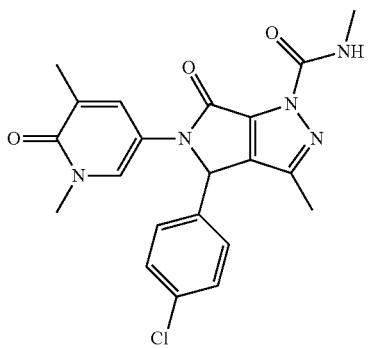 [SMILES: CNC(=O)n1nc(C)c2c1C(=O)N(c1cc(C)c(=O)n(C)c1)C2c1ccc(Cl)cc1]

A mixture of 4-(4-chlorophenyl)-5-(1,5-dimethyl-6-oxo-1,6-dihydropyridin-3-yl)-3-methyl-4,5-dihydropyrrolo[3,4-c]pyrazol-6(1H)-one (Example 27) (150 mg, 0.407 mmol), N-methyl-1H-imidazole-1-carboxamide [Duspara, Petar A.; Islam, Md. Sadequl; Lough, Alan J.; Batey, Robert A. Journal of Organic Chemistry (2012), 77(22), 10362-10368] (50.9 mg, 0.407 mmol) and triethylamine (0.057 mL, 0.407 mmol) in CH$_2$Cl$_2$ (4 mL) was stirred for 16 h at rt. N-methyl-1H-imidazole-1-carboxamide (50 mg) was added. The reaction mixture was stirred for 3 days at rt, diluted with CH$_2$Cl$_2$/water and extracted twice with CH$_2$Cl$_2$. The combined organic extracts were washed with brine, dried (Na$_2$SO$_4$) and concentrated. The residue was purified by chromatography (1% ammonia/5% MeOH/DCM), subsequent preparative achiral SFC (column: Reprosil 70 NH2, 250×30 mm, 5 μm, Dr Maisch; eluent: MeOH/scCO$_2$; gradient: 1 min 21% MeOH, 21-26% MeOH in 6 min, 26-50% MeOH, in 1 min, 1.5 min 50% MeOH; flow: 100 mL/min) and trituration of the resulting products in diethyl ether to afford 57 mg of 4-(4-chlorophenyl)-5-(1,5-dimethyl-6-oxo-1,6-dihydropyridin-3-yl)-N,3-dimethyl-6-oxo-5,6-dihydropyrrolo[3,4-c]pyrazole-2(4H)-carboxamide (Example 144) and 26 mg of the title compound. t$_R$: 0.84 min (LC-MS 2); ESI-MS: 426.1 [M+H]$^+$ (LC-MS 2); R$_f$=0.24 (NH$_3$ 1%/CH$_2$Cl$_2$/MeOH 5%); $^1$H NMR (400 MHz, DMSO-d6) δ ppm 1.92 (s, 3H) 1.98 (s, 3H) 2.83 (d, J=4.30 Hz, 3H) 3.35 (s, 3H) 6.17 (s, 1H) 7.26-7.45 (m, 5H) 7.74 (br. s., 1H) 8.53 (d, J=4.30 Hz, 1H).

Example 144

4-(4-chlorophenyl)-5-(1,5-dimethyl-6-oxo-1,6-dihydropyridin-3-yl)-N,3-dimethyl-6-oxo-5,6-dihydropyrrolo[3,4-c]pyrazole-2(4H)-carboxamide

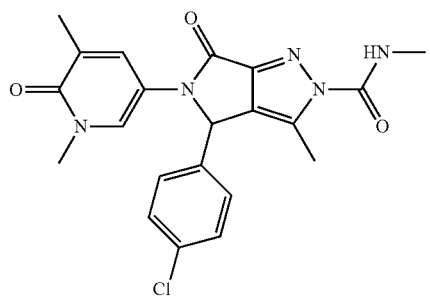 [SMILES: CNC(=O)n1nc2c(c1C)C(c1ccc(Cl)cc1)N(c1cc(C)c(=O)n(C)c1)C2=O]

The preparation of the title compound is described in Example 143. t$_R$: 0.89 min (LC-MS 2); ESI-MS: 426.1 [M+H]$^+$ (LC-MS 2); R$_f$=0.29 (NH$_3$ 1%/CH$_2$Cl$_2$/MeOH 5%); $^1$H NMR (400 MHz, DMSO-d6) δ ppm 1.92 (s, 3H) 2.29 (s, 3H) 2.77 (d, J=4.69 Hz, 3H) 3.35 (s, 3H) 6.22 (s, 1H) 7.24-7.33 (m, 2H) 7.33-7.48 (m, 3H) 7.76 (d, J=2.74 Hz, 1H) 8.73 (d, J=4.69 Hz, 1H).

Example 145

4-(4-chlorophenyl)-5-(3,8-dimethyl-[1,2,4]triazolo[4,3-a]pyridin-6-yl)-N,3-dimethyl-6-oxo-5,6-dihydropyrrolo[3,4-c]pyrazole-1(4H)-carboxamide

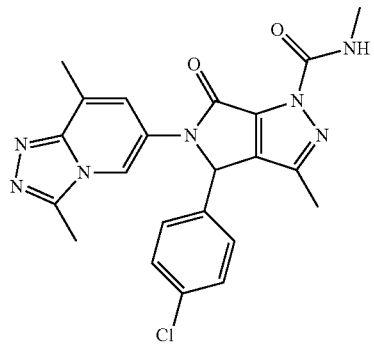 [SMILES: CNC(=O)n1nc(C)c2c1C(=O)N(c1cc(C)c3nnc(C)n3c1)C2c1ccc(Cl)cc1]

The title compound was prepared using an analogous procedure to that described in Example 143 using 4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one (Example 98). Purification of the crude product afforded 65 mg of 4-(4-chlorophenyl)-5-(3,8-dimethyl-[1,2,4]triazolo[4,3-a]pyridin-6-yl)-N,3-dimethyl-6-oxo-5,6-dihydropyrrolo[3,4-c]pyrazole-2(4H)-carboxamide (Example 146) and 26 mg of the title compound. t$_R$: 0.82 min (LC-MS 2); ESI-MS: 450.1 [M+H]$^+$ (LC-MS 2); R$_f$=0.22 (NH$_3$ 1%/CH$_2$Cl$_2$/MeOH 5%); $^1$H NMR (600 MHz, DMSO-d6) δ ppm 2.04 (s, 3H) 2.46 (s, 3H) 2.64 (s, 3H) 2.87 (d, J=4.40 Hz, 3H) 6.55 (s, 1H) 7.23-7.41 (m, 3H) 7.41-7.50 (m, 2H) 8.44-8.60 (m, 2H).

Example 146

4-(4-chlorophenyl)-5-(3,8-dimethyl-[1,2,4]triazolo[4,3-a]pyridin-6-yl)-N,3-dimethyl-6-oxo-5,6-dihydropyrrolo[3,4-c]pyrazole-2(4H)-carboxamide

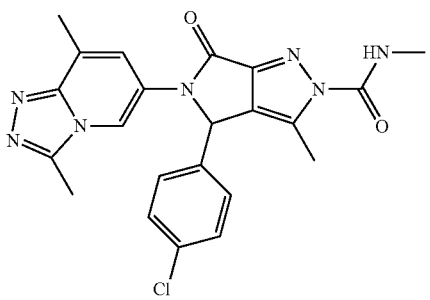 [SMILES: CNC(=O)n1nc2c(c1C)C(c1ccc(Cl)cc1)N(c1cc(C)c3nnc(C)n3c1)C2=O]

The preparation of the title compound is described in Example 145. t$_R$: 0.88 min (LC-MS 2); ESI-MS: 450.1 [M+H]$^+$ (LC-MS 2); R$_f$=0.19 (NH$_3$ 1%/CH$_2$Cl$_2$/MeOH 5%); $^1$H NMR (600 MHz, DMSO-d6) δ ppm 2.32 (s, 3H) 2.44 (s, 3H) 2.62 (s, 3H) 2.79 (d, J=4.69 Hz, 3H) 6.57 (s, 1H) 7.29-7.42 (m, 5H) 8.48 (s, 1H) 8.77 (d, J=4.69 Hz, 1H).

Example 147

4-(4-chlorophenyl)-5-(1,5-dimethyl-6-oxo-1,6-dihydropyridin-3-yl)-3-ethyl-N,N-dimethyl-6-oxo-5,6-dihydropyrrolo[3,4-c]pyrazole-1(4H)-carboxamide

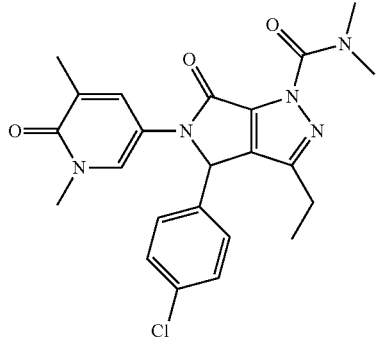 [SMILES: CCc1nn(C(=O)N(C)C)c2c1C(c1ccc(Cl)cc1)N(c1cc(C)c(=O)n(C)c1)C2=O]

Step 147.1: 5-(2-(4-chlorophenyl)-4-hydroxy-5-oxo-3-propionyl-2,5-dihydro-1H-pyrrol-1-yl)-1,3-dimethylpyridin-2(1H)-one A mixture of 5-amino-1,3-dimethylpyridin-2(1H)-one (Step 20.2) (1.77 g, 12.78 mmol), 4-chlorobenzaldehyde (1.63 g, 11.62 mmol) and ethyl 4-cyclopropyl-2,4-dioxobutanoate (2 g, 11.62 mmol) in acetic acid (10 mL) was stirred for 2 h at 100° C. The reaction mixture was concentrated, diluted with CH$_2$Cl$_2$/1 N NaOH, and extracted with CH$_2$Cl$_2$. The combined organic extracts were discarded. The aqueous layer was acidified to pH 3 with 6 N HCl and extracted twice with CH$_2$Cl$_2$. The combined organic extracts were dried (Na$_2$SO$_4$) and concentrated to afford 3.06 g of the title compound as a beige foam. $t_R$: 0.83 min (LC-MS 2); ESI-MS: 387.0 [M+H]$^+$ (LC-MS 2).

Step 147.2: 4-(4-chlorophenyl)-5-(1,5-dimethyl-6-oxo-1,6-dihydropyridin-3-yl)-3-ethyl-4,5-dihydropyrrolo[3,4-c]pyrazol-6(1H)-one A mixture of 5-(2-(4-chlorophenyl)-4-hydroxy-5-oxo-3-propionyl-2,5-dihydro-1H-pyrrol-1-yl)-1,3-dimethylpyridin-2(1H)-one (Step 147.1) (1.5 g, 3.88 mmol), hydrazine monohydrate (0.942 mL, 19.39 mmol), ethanol (8 mL) and toluene (8 mL) was stirred for 18 h at reflux. The reaction mixture was concentrated, diluted with acetic acid (50 mL), stirred for 1 h at reflux, diluted with CH$_2$Cl$_2$/saturated aqueous solution of NaHCO$_3$, and extracted twice with CH$_2$Cl$_2$. The combine organic extracts were washed with water and brine, dried (Na$_2$SO$_4$) and concentrated. The residue was purified by silica gel column chromatography (CH$_2$Cl$_2$/MeOH 7.5%) and subsequent trituration of the resulting product in diethyl ether to afford 961 mg of the title compound as a yellow solid. $t_R$: 0.82 min (LC-MS 2); ESI-MS: 383.1 [M+H]$^+$ (LC-MS 2); R$_f$=0.19 (NH$_3$ 1%/CH$_2$Cl$_2$/MeOH 5%); $^1$H NMR (400 MHz, DMSO-d6) δ ppm 0.90 (t, J=7.64 Hz, 3H) 1.94 (s, 3H) 2.35-2.47 (m, 2H) 3.38 (s, 3H) 6.15 (s, 1H) 7.25 (d, J=8.44 Hz, 2H) 7.31-7.51 (m, 3H) 7.73 (d, J=2.69 Hz, 1H) 13.41 (br. s., 1H).

Step 147.3 4-(4-chlorophenyl)-5-(1,5-dimethyl-6-oxo-1,6-dihydropyridin-3-yl)-3-ethyl-N,N-dimethyl-6-oxo-5,6-dihydropyrrolo[3,4-c]pyrazole-1(4H)-carboxamide The title compound was prepared using an analogous procedure to that described in Example 141 using 4-(4-chlorophenyl)-5-(1,5-dimethyl-6-oxo-1,6-dihydropyridin-3-yl)-3-ethyl-N,N-dimethyl-6-oxo-5,6-dihydropyrrolo[3,4-c]pyrazole-1(4H)-carboxamide (Step 147.2) (100 mg, 0.261 mmol) and stirring the reaction mixture for 4 h at 100° C. Purification of the crude product afforded 22 mg of 4-(4-chlorophenyl)-5-(1,5-dimethyl-6-oxo-1,6-dihydropyridin-3-yl)-3-ethyl-N,N-dimethyl-6-oxo-5,6-dihydropyrrolo[3,4-c]pyrazole-2(4H)-carboxamide (Example 148) and 28 mg of the title compound. $t_R$: 0.95 min (LC-MS 2); ESI-MS: 454.1 [M+H]$^+$ (LC-MS 2); R$_f$=0.44 (NH$_3$ 1%/CH$_2$Cl$_2$/MeOH 5%); $^1$H NMR (400 MHz, DMSO-d6) δ ppm 0.91 (t, J=7.62 Hz, 3H) 1.91 (s, 3H) 2.27-2.41 (m, 2H) 3.05 (s, 6H) 3.35 (s, 3H) 6.18 (s, 1H) 7.29 (d, J=8.60 Hz, 2H) 7.31-7.47 (m, 3H) 7.72 (d, J=2.74 Hz, 1H).

Example 148

4-(4-chlorophenyl)-5-(1,5-dimethyl-6-oxo-1,6-dihydropyridin-3-yl)-3-ethyl-N,N-dimethyl-6-oxo-5,6-dihydropyrrolo[3,4-c]pyrazole-2(4H)-carboxamide

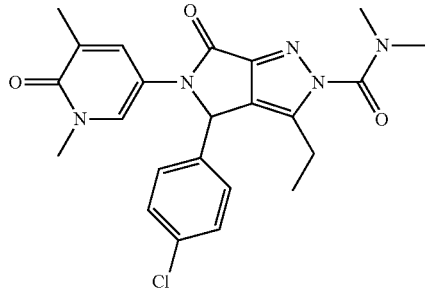 [SMILES: CCc1c2c(nn1C(=O)N(C)C)C(=O)N(c1cc(C)c(=O)n(C)c1)C2c1ccc(Cl)cc1]

The preparation of the title compound is described in Example 147. $t_R$: 0.91 min (LC-MS 2); ESI-MS: 454.1 [M+H]$^+$ (LC-MS 2); R$_f$=0.54 (NH$_3$ 1%/CH$_2$Cl$_2$/MeOH 5%); $^1$H NMR (400 MHz, DMSO-d6) δ ppm 0.83 (t, J=7.62 Hz, 3H) 1.92 (s, 3H) 2.37-2.47 (m, 1H) 2.55-2.72 (m, 1H) 2.89 (s, 3H) 3.07 (s, 3H) 3.35 (s, 3H) 6.23 (s, 1H) 7.23-7.33 (m, 2H) 7.30-7.44 (m, 3H) 7.73 (d, J=2.74 Hz, 1H).

Example 149

(R)-4-(4-chlorophenyl)-5-(3,8-dimethyl-[1,2,4]triazolo[4,3-a]pyridin-6-yl)-N,N,3-trimethyl-6-oxo-5,6-dihydropyrrolo[3,4-c]pyrazole-1(4H)-carboxamide

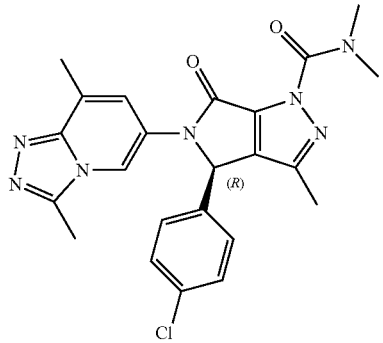

The title compound was prepared using an analogous procedure to that described in Example 141 using 4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one (Example 98) (200 mg, 0.509 mmol) and stirring the reaction mixture for 4 h at 100° C. The crude product was purified by silica gel column chromatography (NH₃ 1%/CH₂Cl₂/MeOH 7.5%) and subsequent chiral chromatography. Chiral preparative chromatography (system: Gilson PLC 2020; column: Chiralpak AD-H 5 μm, 20×250 mm; mobile phase: heptane/iPrOH 20-50%; flow: 11 mL/min; detection UV: 220 nm) afforded 20 mg of (R)-4-(4-chlorophenyl)-5-(3,8-dimethyl-[1,2,4]triazolo[4,3-a]pyridin-6-yl)-N,N,3-trimethyl-6-oxo-5,6-dihydropyrrolo[3,4-c]pyrazole-1(4H)-carboxamide (the title compound), 24 mg of (S)-4-(4-chlorophenyl)-5-(3,8-dimethyl-[1,2,4]triazolo[4,3-a]pyridin-6-yl)-N,N,3-trimethyl-6-oxo-5,6-dihydropyrrolo[3,4-c]pyrazole-1(4H)-carboxamide, 42 mg of (R)-4-(4-chlorophenyl)-5-(3,8-dimethyl-[1,2,4]triazolo[4,3-a]pyridin-6-yl)-N,N,3-trimethyl-6-oxo-5,6-dihydropyrrolo[3,4-c]pyrazole-2(4H)-carboxamide (Example 150) and 39 mg of (S)-4-(4-chlorophenyl)-5-(3,8-dimethyl-[1,2,4]triazolo[4,3-a]pyridin-6-yl)-N,N,3-trimethyl-6-oxo-5,6-dihydropyrrolo[3,4-c]pyrazole-2(4H)-carboxamide (Example 150). The four isomers were obtained enantiomerically pure (>99% ee).

(R)-4-(4-chlorophenyl)-5-(3,8-dimethyl-[1,2,4]triazolo[4,3-a]pyridin-6-yl)-N,N,3-trimethyl-6-oxo-5,6-dihydropyrrolo[3,4-c]pyrazole-1(4H)-carboxamide. t$_R$: 40 min (system: Gilson PLC 2020; column: Chiralpak AD-H 5 μm, 4.6×250 mm; mobile phase: heptane/iPrOH 20-50%; flow: 1 mL/min; detection UV: 220 nm); t$_R$: 0.91 min (LC-MS 2); ESI-MS: 464.1 [M+H]⁺ (LC-MS 2); ¹H NMR (400 MHz, DMSO-d6) δ ppm 2.01 (s, 3H) 2.43 (s, 3H) 2.61 (s, 3H) 3.07 (s, 6H) 6.50 (s, 1H) 7.22-7.46 (m, 5H) 8.45 (s, 1H).

(S)-4-(4-chlorophenyl)-5-(3,8-dimethyl-[1,2,4]triazolo[4,3-a]pyridin-6-yl)-N, N,3-trimethyl-6-oxo-5,6-dihydropyrrolo[3,4-c]pyrazole-1(4H)-carboxamide. t$_R$: 17.9 min (system: Gilson PLC 2020; column: Chiralpak AD-H 5 μm, 4.6× 250 mm; mobile phase: heptane/iPrOH 20-50%; flow: 1 mL/min; detection UV: 220 nm).

Example 150

(R)-4-(4-chlorophenyl)-5-(3,8-dimethyl-[1,2,4]triazolo[4,3-a]pyridin-6-yl)-N,N,3-trimethyl-6-oxo-5,6-dihydropyrrolo[3,4-c]pyrazole-2(4H)-carboxamide

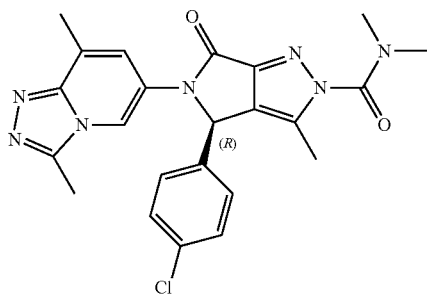

The preparation of the title compound is described in Example 149.

(R)-4-(4-chlorophenyl)-5-(3,8-dimethyl-[1,2,4]triazolo[4,3-a]pyridin-6-yl)-N,N,3-trimethyl-6-oxo-5,6-dihydropyrrolo[3,4-c]pyrazole-2(4H)-carboxamide. t$_R$: 100.7 min (system: Gilson PLC 2020; column: Chiralpak AD-H 5 μm, 4.6× 250 mm; mobile phase: heptane/iPrOH 20-50%; flow: 1 mL/min; detection UV: 220 nm); t$_R$: 0.83 min (LC-MS 2); ESI-MS: 464.1 [M+H]⁺ (LC-MS 2); ¹H NMR (400 MHz, DMSO-d6) δ ppm 2.15 (s, 3H) 2.44 (s, 3H) 2.61 (s, 3H) 2.93 (s, 3H) 3.07 (s, 3H) 6.53 (s, 1H) 7.27-7.45 (m, 5H) 8.48 (s, 1H).

(S)-4-(4-chlorophenyl)-5-(3,8-dimethyl-[1,2,4]triazolo[4,3-a]pyridin-6-yl)-N, N,3-trimethyl-6-oxo-5,6-dihydropyrrolo[3,4-c]pyrazole-2(4H)-carboxamide. t$_R$: 26.8 min (system: Gilson PLC 2020; column: Chiralpak AD-H 5 μm, 4.6× 250 mm; mobile phase: heptane/iPrOH 20-50%; flow: 1 mL/min; detection UV: 220 nm).

Example 151

1-(azetidin-3-yl)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one

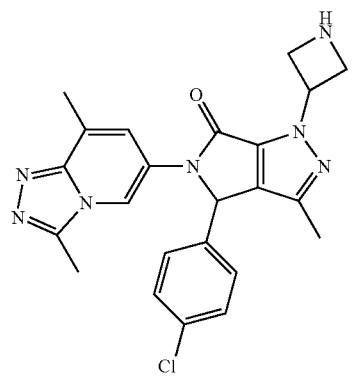 [SMILES: Cc1nn(C2CNC2)c2c1C(c1ccc(Cl)cc1)N(c1cc(C)c3nnc(C)n3c1)C2=O]

Step 151.1: a) Tert-butyl 3-(4-(4-chlorophenyl)-5-(3,8-dimethyl-[1,2,4]triazolo[4,3-a]pyridin-6-yl)-3-methyl-6-oxo-5,6-dihydropyrrolo[3,4-c]pyrazol-1(4H)-yl)azetidine-1-carboxylate and b) tert-butyl 3-(4-(4-chlorophenyl)-5-(3,8-dimethyl-[1,2,4]triazolo[4,3-a]pyridin-6-yl)-3-methyl-6-oxo-5,6-dihydropyrrolo[3,4-c]pyrazol-2(4H)-yl)azetidine-1-carboxylate The title compound was prepared using an analogous procedure to that described in Example 134 using 4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one (Example 98) (750 mg, 1.909 mmol) and stirring the reaction mixture for 30 min at 80° C. after addition of tert-butyl 3-iodoazetidine-1-carboxylate. The crude material was purified by silica gel column chromatography (CH₂Cl₂/MeOH 1-4%) followed by preparative HPLC (Gilson gx-281. Column: Sunfire C18, 30×100 mm, 5 μm. Flow: 30 mL/min. Gradient: 5% to 60% B in 20 min; A=0.1% TFA in H2O, B=CH3CN. Detection: UV) to afford:

641 mg of tert-butyl 3-(4-(4-chlorophenyl)-5-(3,8-dimethyl-[1,2,4]triazolo[4,3-a]pyridin-6-yl)-3-methyl-6-oxo-5,6-dihydropyrrolo[3,4-c]pyrazol-1(4H)-yl)azetidine-1-carboxylate (title compound). t$_R$: 1.09 min (LC-MS 2); ESI-MS: 548.2 [M+H]⁺ (LC-MS 2); R$_f$=0.40 (CH₂Cl₂/MeOH 9:1).

228 mg of tert-butyl 3-(4-(4-chlorophenyl)-5-(3,8-dimethyl-[1,2,4]triazolo[4,3-a]pyridin-6-yl)-3-methyl-6-oxo-5, 6-dihydropyrrolo[3,4-c]pyrazol-2(4H)-yl)azetidine-1-carboxylate. t$_R$: 1.02 min (LC-MS 2); ESI-MS: 548.2 [M+H]⁺ (LC-MS 2); R$_f$=0.38 (CH₂Cl₂/MeOH 9:1).

Step 151.2: 1-(azetidin-3-yl)-4-(4-chlorophenol)-5-(3,8-dimethyl-[1,2,4]triazolo[4,3-a]pyridin-6-yl)-3-methyl-4,5-dihydropyrrolo[3,4-c]pyrazol-6(1H)-one The title compound (405 mg) was prepared using an analogous procedure to that described in Step 138.2 using of tert-butyl 3-(4-(4-chlorophenyl)-5-(3,8-dimethyl-[1,2,4]triazolo[4,3-a]pyridin-6-yl)-3-methyl-6-oxo-5,6-dihydropyrrolo[3,4-c]pyrazol-1(4H)-yl)azetidine-1-carboxylate (Step 151.1a) (640 mg, 1.168 mmol). $t_R$: 0.63 min (LC-MS 2); ESI-MS: 448.1 [M+H]$^+$ (LC-MS 2); $R_f$=0.06 (CH$_2$Cl$_2$/MeOH 9:1); $^1$H NMR (400 MHz, DMSO-d6) δ ppm 1.97 (s, 3H) 2.43 (s, 3H) 2.61 (s, 3H) 3.79 (t, J=8.21 Hz, 2H) 4.08-4.23 (m, 2H) 5.30-5.41 (m, 1H) 6.46 (s, 1H) 7.29-7.40 (m, 5H) 8.45 (s, 1H).

Example 152

2-(azetidin-3-yl)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(2H)-one

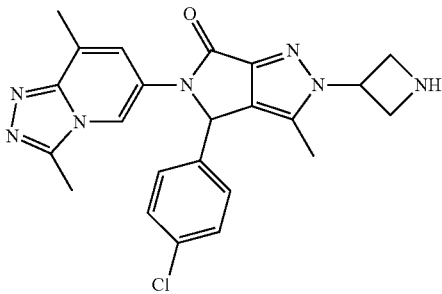 [SMILES: Cc1cc(N2C(=O)c3nn(C4CNC4)c(C)c3C2c2ccc(Cl)cc2)cn2c(C)nnc12]

The title compound (90 mg) was prepared using an analogous procedure to that described in Step 138.2 using tert-butyl 3-(4-(4-chlorophenyl)-5-(3,8-dimethyl-[1,2,4]triazolo[4,3-a]pyridin-6-yl)-3-methyl-6-oxo-5,6-dihydropyrrolo[3,4-c]pyrazol-2(4H)-yl)azetidine-1-carboxylate (Step 151.1b) (220 mg, 0.401 mmol). $t_R$: 0.59 min (LC-MS 2); ESI-MS: 448.1 [M+H]$^+$ (LC-MS 2); $R_f$=0.05 (CH$_2$Cl$_2$/MeOH 9:1); $^1$H NMR (400 MHz, DMSO-d6) δ ppm 2.06 (s, 3H) 2.43 (s, 3H) 2.61 (s, 3H) 3.72-3.85 (m, 2H) 3.99-4.12 (m, 2H) 5.22-5.31 (m, 1H) 6.48 (s, 1H) 7.29-7.37 (m, 5H) 8.44 (d, J=0.78 Hz, 1H).

Example 153

1-(1-acetylazetidin-3-yl)-4-(4-chlorophenyl)-5-(1,5-dimethyl-6-oxo-1,6-dihydropyridin-3-yl)-3-methyl-4,5-dihydropyrrolo[3,4-c]pyrazol-6(1H)-one

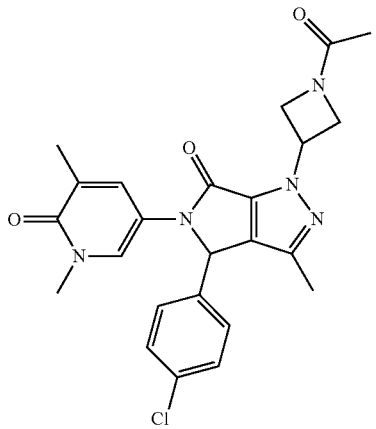 [SMILES: CC(=O)N1CC(n2nc(C)c3c2C(=O)N(c2cc(C)c(=O)n(C)c2)C3c2ccc(Cl)cc2)C1]

To a stirred solution of 1-(azetidin-3-yl)-4-(4-chlorophenyl)-5-(1,5-dimethyl-6-oxo-1,6-dihydropyridin-3-yl)-3-methyl-4,5-dihydropyrrolo[3,4-c]pyrazol-6(1H)-one (Step 138.2) (70 mg, 0.165 mmol) in CH$_2$Cl$_2$ (1 mL) was added triethylamine (0.092 mL, 0.661 mmol) and acetic anhydride (0.031 mL, 0.330 mmol) under argon. The reaction mixture was stirred for 1 h at rt, diluted with water (75 mL), and extracted with EtOAC (2×100 mL). The combined organic extracts were dried (Na$_2$SO$_4$) and concentrated. The residue was purified by silica gel column chromatography (CH$_2$Cl$_2$/MeOH 1-5%) and subsequent trituration of the resulting material in diethyl ether to afford 50 mg of the title compound as a colorless solid. $t_R$: 0.81 min (LC-MS 2); ESI-MS: 466.1 [M+H]$^+$ (LC-MS 2); $R_f$=0.46 (CH$_2$Cl$_2$/MeOH 9:1); $^1$H NMR (400 MHz, DMSO-d6) δ ppm 1.79 (d, J=2.74 Hz, 3H) 1.91 (s, 3H) 1.95 (s, 3H) 3.35 (s, 3H) 4.16-4.25 (m, 1H) 4.28-4.35 (m, 1H) 4.48-4.56 (m, 1H) 4.57-4.64 (m, 1H) 5.32-5.41 (m, 1H) 6.09 (s, 1H) 7.26-7.31 (m, 2H) 7.34-7.41 (m, 3H) 7.70 (d, J=2.35 Hz, 1H).

Example 154

1-(1-acetylazetidin-3-yl)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one

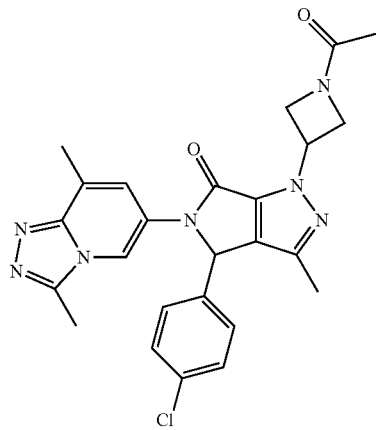 [SMILES: CC(=O)N1CC(n2nc(C)c3c2C(=O)N(c2cc(C)c4nnc(C)n4c2)C3c2ccc(Cl)cc2)C1]

The title compound (79 mg) was prepared using an analogous procedure to that described in Example 153 using 1-(azetidin-3-yl)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one (Step 151.2) (100 mg, 0.223 mmol). $t_R$: 0.79 min (LC-MS 2); ESI-MS: 490.1 [M+H]$^+$ (LC-MS 2); $R_f$=0.51 (CH$_2$Cl$_2$/MeOH 9:1); $^1$H NMR (400 MHz, DMSO-d6) δ ppm 1.81 (d, J=4.30 Hz, 3H) 1.98 (s, 3H) 2.43 (s, 3H) 2.61 (s, 3H) 4.18-4.38 (m, 2H) 4.49-4.67 (m, 2H) 5.36-5.47 (m, 1H) 6.46 (s, 1H) 7.29-7.41 (m, 5H) 8.43 (s, 1H).

Example 155

Ethyl 3-(4-(4-chlorophenyl)-5-(1,5-dimethyl-6-oxo-1,6-dihydropyridin-3-yl)-3-methyl-6-oxo-5,6-dihydropyrrolo[3,4-c]pyrazol-1(4H)-yl)azetidine-1-carboxylate

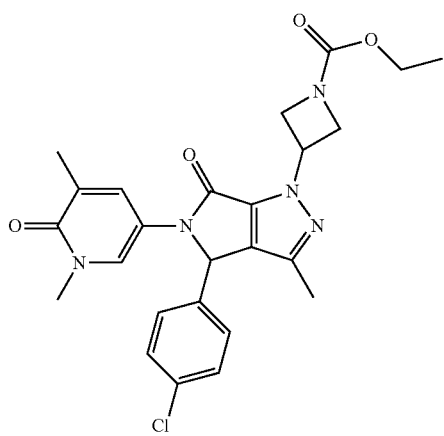 [SMILES: CCOC(=O)N1CC(n2nc(C)c3c2C(=O)N(c2cc(C)c(=O)n(C)c2)C3c2ccc(Cl)cc2)C1]

To a stirred solution of 1-(azetidin-3-yl)-4-(4-chlorophenyl)-5-(1,5-dimethyl-6-oxo-1,6-dihydropyridin-3-yl)-3-methyl-4,5-dihydropyrrolo[3,4-c]pyrazol-6(1H)-one (Step 138.2) (50 mg, 0.118 mmol) in CH$_2$Cl$_2$ (1 mL) was added triethylamine (0.066 mL, 0.472 mmol) and ethyl chloroformate (0.023 mL, 0.236 mmol) under argon. The reaction mixture was stirred for 1 h at rt, diluted with water (75 mL), and extracted with EtOAC (2×100 mL). The combined organic extracts were washed with water (100 mL), dried (Na$_2$SO$_4$) and concentrated. The residue was purified by silica gel column chromatography (CH$_2$Cl$_2$/MeOH 1-3.5%) and trituration of the resulting material in diethyl ether to afford 37 mg of the title compound as a colorless solid. t$_R$: 0.99 min (LC-MS 2); ESI-MS: 496.1 [M+H]$^+$ (LC-MS 2); R$_f$=0.49 (CH$_2$Cl$_2$/MeOH 9:1); $^1$H NMR (400 MHz, DMSO-d6) δ ppm 1.16 (t, J=7.04 Hz, 3H) 1.91 (s, 3H) 1.95 (s, 3H) 3.35 (s, 3H) 4.02 (q, J=7.04 Hz, 2H) 4.22-4.45 (m, 4H) 5.32-5.43 (m, 1H) 6.08 (s, 1H) 7.25-7.31 (m, 2H) 7.34-7.42 (m, 3H) 7.70 (d, J=2.35 Hz, 1H).

Example 156

Ethyl 3-(4-(4-chlorophenyl)-5-(3,8-dimethyl-[1,2,4]triazolo[4,3-a]pyridin-6-yl)-3-methyl-6-oxo-5,6-dihydropyrrolo[3,4-c]pyrazol-1(4H)-yl)azetidine-1-carboxylate

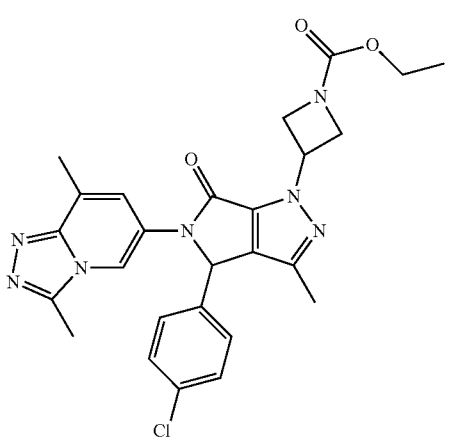 [SMILES: CCOC(=O)N1CC(n2nc(C)c3c2C(=O)N(c2cc(C)c4nnc(C)n4c2)C3c2ccc(Cl)cc2)C1]

The title compound (50 mg) was prepared using an analogous procedure to that described in Example 155 using Hazetidin-3-yl)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one (Step 151.2) (80 mg, 0.179 mmol). t$_R$: 0.96 min (LC-MS 2); ESI-MS: 520.1 [M+H]$^+$ (LC-MS 2); R$_f$=0.60 (CH$_2$Cl$_2$/MeOH 9:1); $^1$H NMR (400 MHz, DMSO-d6) δ ppm 1.17 (t, J=7.04 Hz, 3H) 1.98 (s, 3H) 2.43 (s, 3H) 2.61 (s, 3H) 4.03 (q, J=7.04 Hz, 2H) 4.40 (br. s., 4H) 5.34-5.45 (m, 1H) 6.45 (s, 1H) 7.27-7.44 (m, 5H) 8.43 (s, 1H).

Example 157

4-(4-chlorophenyl)-5-(3,8-dimethyl-[1,2,4]triazolo[4,3-a]pyridin-6-yl)-3-methyl-1-(1-methylazetidin-3-yl)-4,5-dihydropyrrolo[3,4-c]pyrazol-6(1H)-one

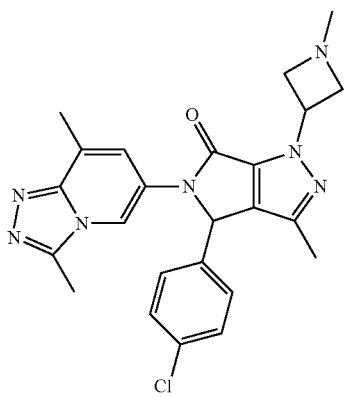 [SMILES: Cc1nn(C2CN(C)C2)c2c1C(c1ccc(Cl)cc1)N(c1cc(C)c3nnc(C)n3c1)C2=O]

The title compound (53 mg) was prepared using an analogous procedure to that described in Step 139.2 using 1-(azetidin-3-yl)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one (Step 151.2) (100 mg, 0.223 mmol) and 3 equivalents of sodium triacetoxyborohydride. The crude product was purified by silica gel column chromatography (NH$_3$ 1%/CH$_2$Cl$_2$/MeOH 2-3%) and trituration of the resulting material in hexane/diethyl ether (1:1). t$_R$: 0.66 min (LC-MS 2); ESI-MS: 462.1 [M+H]$^+$ (LC-MS 2); R$_f$=0.24 (CH$_2$Cl$_2$/MeOH 9:1); $^1$H NMR (400 MHz, DMSO-d6) δ ppm 1.96 (s, 3H) 2.34 (s, 3H) 2.43 (s, 3H) 2.61 (s, 3H) 3.47-3.61 (m, 2H) 3.72-3.81 (m, 2H) 5.02-5.13 (m, 1H) 6.44 (s, 1H) 7.28-7.41 (m, 5H) 8.44 (s, 1H).

Example 158

4-(4-chlorophenyl)-5-(3,8-dimethyl-[1,2,4]triazolo[4,3-a]pyridin-6-yl)-3-methyl-2-(1-methylazetidin-3-yl)-4,5-dihydropyrrolo[3,4-c]pyrazol-6(2H)-one

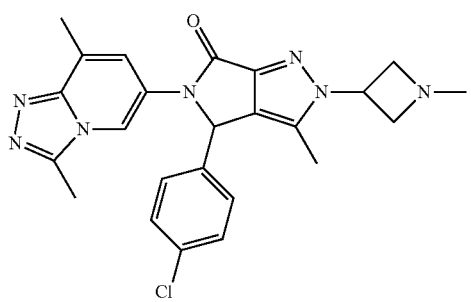 [SMILES: Cc1cc(N2C(=O)c3nn(C4CN(C)C4)c(C)c3C2c2ccc(Cl)cc2)cn2c(C)nnc12]

The title compound (48 mg) was prepared using an analogous procedure to that described in Step 139.2 using 2-(azetidin-3-yl)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(2H)-one (Example 152) (75 mg, 0.167 mmol) and 3 equivalents of sodium triacetoxyborohydride. The crude product was purified by silica gel column chromatography (NH₃ 1%/CH₂Cl₂/MeOH 2-3.5%) followed by trituration of the resulting material in diethyl ether. $t_R$: 0.60 min (LC-MS 2); ESI-MS: 462.1 [M+H]⁺ (LC-MS 2); $R_f$=0.21 (CH₂Cl₂/MeOH 9:1); ¹H NMR (400 MHz, DMSO-d6) δ ppm 2.06 (s, 3H) 2.33 (s, 3H) 2.43 (s, 3H) 2.61 (s, 3H) 3.35-3.41 (m, 1H) 3.42-3.48 (m, 1H) 3.71-3.80 (m, 2H) 4.96-5.06 (m, 1H) 6.46 (s, 1H) 7.28-7.36 (m, 5H) 8.43 (s, 1H).

Example 159

4-(4-chlorophenyl)-1-cyclopropyl-5-(3,8-dimethyl-[1,2,4]triazolo[4,3-a]pyridin-6-yl)-3-(fluoromethyl)-4,5-dihydropyrrolo[3,4-c]pyrazol-6(1H)-one

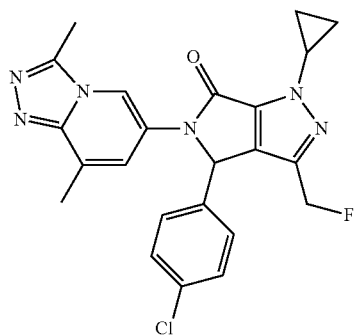 [SMILES: Cc1cc(N2C(=O)c3c(c(CF)nn3C3CC3)C2c2ccc(Cl)cc2)cn2c(C)nnc12]

To a stirred solution of 4-(4-chlorophenyl)-1-cyclopropyl-5-(3,8-dimethyl-[1,2,4]triazolo[4,3-a]pyridin-6-yl)-3-(hydroxymethyl)-4,5-dihydropyrrolo[3,4-c]pyrazol-6(1H)-one (Example 131) (218 mg, 0.486 mmol) in CH₂Cl₂ (4 mL) was added DBU (0.110 mL, 0.728 mmol) and Xthal-Fluor-E (167 mg, 0.728 mmol) at 0° C., under argon. The reaction mixture was stirred for 1 h at 0° C. (internal temperature), for 36 h at rt, quenched by addition of saturated aqueous solution of sodium bicarbonate (75 mL), and extracted with EtOAc (2×100 mL). The combined organic extracts were washed with brine (100 mL), dried (Na₂SO₄) and concentrated. The residue was purified by silica gel chromatography on Combiflash Isco (eluent: MeOH/CH₂Cl₂; gradient: 1 min 1% MeOH, 1-3.4% MeOH in 11.7 min, 1.8 min 3.4% MeOH; flow: 40 mL/min). The resulting material was further purified by preparative achiral SFC (column: CN-Diol, 250×30 mm, 5 µm, 60 A, Princeton; eluent: MeOH/scCO₂; gradient: 1 min 7% MeOH, 7-12% MeOH in 12 min, 12% to 50% MeOH, in 1 min, 1.5 min 50% MeOH; flow: 100 mL/min) to afford 16 mg of the title compound as a colorless solid. $t_R$: 0.95 min (LC-MS 2); ESI-MS: 451.2 [M+H]⁺ (LC-MS 2); $R_f$=0.53 (CH₂Cl₂/MeOH 9:1); ¹H NMR (400 MHz, DMSO-d6) δ ppm 0.06-1.13 (m, 2H) 1.26-1.32 (m, 2H) 2.43 (s, 3H) 2.61 (s, 3H) 3.90-3.97 (m, 1H) 4.93-5.33 (m, 2H) 6.53 (d, J=1.56 Hz, 1H) 7.27-7.39 (m, 5H) 8.46 (d, J=1.17 Hz, 1H).

Example 160

4-(4-(4-chlorophenyl)-1-cyclopropyl-3-methyl-6-oxopyrrolo[3,4-c]pyrazol-5(1H,4H,6H)-yl)-6-methyl-1H-pyrrolo[2,3-c]pyridin-7(6H)-one

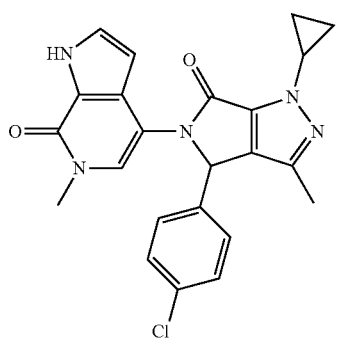 [SMILES: Cc1nn(C2CC2)c2c1C(c1ccc(Cl)cc1)N(c1cn(C)c(=O)c3[nH]ccc13)C2=O]

Step 160.1: 4-bromo-6-methyl-1H-pyrrolo[2,3-c]pyridin-7(6H)-one

4-Bromo-7-methoxy-1H-pyrrolo[2,3-c]pyridine (63 g, 0.27 mol) [Zhang, Zhongxing; Yang, Zhong; Meanwell, Nicholas A.; Kadow, John F.; Wang, Tao Journal of Organic Chemistry (2002), 67(7), 2345-2347] was dissolved in acetonitrile/water (1:1, 1260 mL) and potassium iodide (36.84 g, 0.22 mol) was added. The reaction mixture was stirred for 15 min at room temperature. Trimethylchlorosilane (52.7 mL, 0.41 mol) was added drop wise at room temperature. After completion of addition, the reaction mixture was heated to 70° C. and stirred for 20 h. The completion of the reaction was monitored by TLC using DCM: MeOH (9.3:0.7) as a mobile phase. After completion of the reaction, organic solvent was removed under reduced pressure. The resulting solid was filtered out and washed with water (1000 mL), hexane (1000 mL) and dried in vacuum to afford pure 50 g of the title compound. ¹H NMR (400 MHz, DMSO-d6) δ ppm 3.40 (s, 3H) 6.21 (dd, J=2.6, J=2.0, 1 H) 7.37 (t, J=2.8, 1 H) 11.18 (s, 1H) 12.36 (s, 1H).

Step 160.2: 4-bromo-6-methyl-1-(phenylsulfonyl)-1H-pyrrolo[2,3-c]pyridin-7(6H)-one Sodium hydride (49.3 mg, 1.233 mmol) was added to a stirred solution of 4-bromo-6-methyl-1H-pyrrolo[2,3-c]pyridin-7(6H)-one (Step 160.1) (200 mg, 0.881 mmol) in DMF (4 mL) at 0° C. and the resulting mixture was stirred for 1 h at 0° C. Benzenesulfonyl chloride (0.124 mL, 0.969 mmol) was added. The reaction mixture was stirred for 30 min at 0° C., diluted in EtOAc/water, and extracted twice with EtOAc. The combined organic extracts were washed with water and brine, dried (Na$_2$SO$_4$) and concentrated. The residue was purified by silica gel chromatography on Combiflash Isco (eluent: EtOAc/hexane; gradient: 30-51% EtOAc in 11.1 min; flow: 30 mL/min) to afford 298 mg of the title compound as a colorless solid. t$_R$: 1.00 min (LC-MS 2); ESI-MS: 367.1/369.1 [M+H]$^+$ (LC-MS 2); R$_f$=0.19 (EtOAC/hexane 1:1); $^1$H NMR (400 MHz, DMSO-d6) δ ppm 8.15-7.95 (m, 3H), 7.79 (s, 1H), 7.75-7.68 (m, 1H), 7.65-7.57 (m, 2H), 6.60 (d, J=3.5 Hz, 1H), 3.37 (s, 3H).

Step 160.3: 4-(4-(4-chlorophenyl)-1-cyclopropyl-3-methyl-6-oxopyrrolo[3,4-c]pyrazol-5(1H,4H,6H)-yl)-6-methyl-1-(phenylsulfonyl)-1H-pyrrolo[2,3-c]pyridin-7(6H)-one A mixture of 4-(4-chlorophenyl)-1-cyclopropyl-3-methyl-4,5-dihydropyrrolo[3,4-c]pyrazol-6(1H)-one (Step 23.9) (100 mg, 0.348 mmol), 4-bromo-6-methyl-1-(phenylsulfonyl)-1H-pyrrolo[2,3-c]pyridin-7(6H)-one (Step 160.2) (140 mg, 0.382 mmol), copper(I) iodide (66.2 mg, 0.348 mmol), K$_3$PO$_4$ (148 mg, 0.695 mmol), and N,N'-dimethylethylenediamine (0.056 mL, 0.521 mmol) in dioxane (3 mL) were stirred for 14 h at 100° C. The reaction mixture was diluted in CH$_2$Cl$_2$/water and extracted twice with CH$_2$Cl$_2$. The combined organic extracts were dried (Na$_2$SO$_4$) and concentrated to afford 280 mg (31% purity) of the title compound as a yellow oil. t$_R$: 1.14 min (LC-MS 2); ESI-MS: 574.2.

Step 160.4: 4-(4-(4-chlorophenyl)-1-cyclopropyl-3-methyl-6-oxopyrrolo[3,4-c]pyrazol-5(1H,4H,6H)-yl)-6-methyl-1H-pyrrolo[2,3-c]pyridin-7(6H)-one A mixture of 4-(4-(4-chlorophenyl)-1-cyclopropyl-3-methyl-6-oxopyrrolo[3,4-c]pyrazol-5(1H,4H,6H)-yl)-6-methyl-1-(phenylsulfonyl)-1H-pyrrolo[2,3-c]pyridin-7(6H)-one (Step 160.3) (280 mg, 0.151 mmol) and potassium tert-butoxide (33.9 mg, 0.302 mmol) in dioxane (3 mL) was stirred for 1 h at 80° C., diluted in CH$_2$Cl$_2$/water and extracted twice with CH$_2$Cl$_2$. The combined organic extracts were washed with water and brine, dried (Na$_2$SO$_4$) and concentrated. The residue was purified by silica gel chromatography on Combiflash Isco (eluent: MeOH/DCM; gradient: 0% to 5% MeOH in 15.0 min; flow: 30 mL/min). The resulting product was further purified by preparative achiral SFC (column: silica, 250×30 mm, 5 μm, 60 A, Princeton; eluent: MeOH/scCO$_2$; gradient: 1 min 18% MeOH, 18-23% MeOH in 6 min, 23% to 50% MeOH, in 1 min, 1.5 min 50% MeOH; flow: 100 mL/min) and subsequent trituration in diethyl ether to afford mg of the title compound as a yellow solid. t$_R$: 0.93 min (LC-MS 2); ESI-MS: 434.3 [M+H]$^{+(LC-MS}$ 2); R$_f$=0.37 (CH$_2$Cl$_2$/MeOH 95:5); $^1$H NMR (400 MHz, DMSO-d6) δ ppm 12.05 (s, 1H), 7.39-7.07 (m, 6H), 6.37-6.15 (m, 1H), 6.07 (s, 1H), 3.95-3.66 (m, 1H), 3.41 (s, 3H), 1.91 (s, 3H), 1.39-0.83 (m, 4H).

Example 161

(R)-4-(4-chlorophenyl)-1-cyclopropyl-3-methyl-5-(3-methyl-8-(methylamino)-[1,2,4]triazolo[4,3-b]pyridazin-6-yl)-4,5-dihydropyrrolo[3,4-c]pyrazol-6(1H)-one

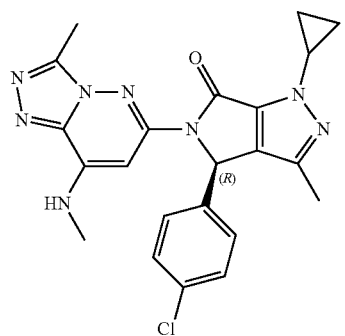

The title compound (38 mg, 34% yield) was obtained enantiomerically pure (>99% ee) after chiral preparative chromatography (system: Gilson PLC 2020; column: Chiralpak ID 5 μm, 20×250 mm; mobile phase: heptane/CH$_2$Cl$_2$/EtOH 70:25:5; flow: 10 mL/min; detection UV: 275 nm) of the racemic mixture of 4-(4-chlorophenyl)-1-cyclopropyl-3-methyl-5-(3-methyl-8-(methylamino)-[1,2,4]triazolo[4,3-b]pyridazin-6-yl)-4,5-dihydropyrrolo[3,4-c]pyrazol-6(1H)-one (Example 113).

(R)-4-(4-chlorophenyl)-1-cyclopropyl-3-methyl-5-(3-methyl-8-(methylamino)-[1,2,4]triazolo[4,3-b]pyridazin-6-yl)-4,5-dihydropyrrolo[3,4-c]pyrazol-6(1H)-one. t$_R$: 12.76 min (system: Agilent HPLC; column: Chiralpak ID 5 μm, 4.6×250 mm; mobile phase: heptane/CH$_2$Cl$_2$/EtOH 70:25:5; flow: 1 mL/min; detection UV: 275 nm).

(S)-4-(4-chlorophenyl)-1-cyclopropyl-3-methyl-5-(3-methyl-8-(methylamino)-[1,2,4]triazolo[4,3-b]pyridazin-6-yl)-4,5-dihydropyrrolo[3,4-c]pyrazol-6(1H)-one. t$_R$: 9.62 min (system: Agilent HPLC; column: Chiralpak ID 5 μm, 4.6×250 mm; mobile phase: heptane/CH$_2$Cl$_2$/EtOH 70:25:5; flow: 1 mL/min; detection UV: 275 nm).

Example 162

(R)-4-(4-chlorophenyl)-1-cyclopropyl-5-(1,5-dimethyl-6-oxo-1,6-dihydropyridin-3-yl)-3-(methoxymethyl)-4,5-dihydropyrrolo[3,4-c]pyrazol-6(1H)-one

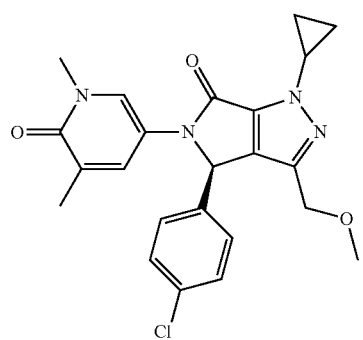 [SMILES: COCc1nn(C2CC2)c2c1[C@@H](c1ccc(Cl)cc1)N(c1cc(C)c(=O)n(C)c1)C2=O]

The title compound (32 mg, 42% yield) was obtained enantiomerically pure (>99% ee) after chiral preparative chromatography (system: Gilson PLC 2020; column: Chiralcel OD-H 5 μm, 20×250 mm; mobile phase: heptane/iPrOH 80:20; flow: 10 mL/min; detection UV: 210 nm) of the racemic mixture of 4-(4-chlorophenyl)-1-cyclopropyl-5-(1,5-dimethyl-6-oxo-1,6-dihydropyridin-3-yl)-3-(methoxymethyl)-4,5-dihydropyrrolo[3,4-c]pyrazol-6(1H)-one (Example 132).

(R)-4-(4-chlorophenyl)-1-cyclopropyl-5-(1,5-dimethyl-6-oxo-1,6-dihydropyridin-3-yl)-3-(methoxymethyl)-4,5-dihydropyrrolo[3,4-c]pyrazol-6(1H)-one. $t_R$: 7.51 min (system: Agilent HPLC; column: Chiralcel OD-H 5 μm, 4.6×250 mm; mobile phase: heptane/iPrOH 60:40; flow: mL/min; detection UV: 210 nm).

(S)-4-(4-chlorophenyl)-1-cyclopropyl-5-(1,5-dimethyl-6-oxo-1,6-dihydropyridin-3-yl)-3-(methoxymethyl)-4,5-dihydropyrrolo[3,4-c]pyrazol-6(1H)-one. $t_R$: 5.34 min (system: Agilent HPLC; column: Chiralcel OD-H 5 μm, 4.6×250 mm; mobile phase: heptane/iPrOH 60:40; flow: 1 mL/min; detection UV: 210 nm).

Example 163

(R)-4-(4-chlorophenol)-1-cyclopropyl-5-(3,8-dimethyl-[1,2,4]triazolo[4,3-a]pyridin-6-yl)-3-(methoxymethyl)-4,5-dihydropyrrolo[3,4-c]pyrazol-6(1H)-one

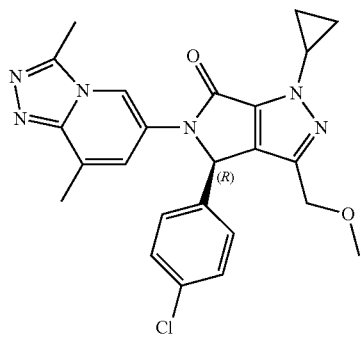

The title compound (134 mg, 39% yield) was obtained enantiomerically pure (>99% ee) after chiral preparative SFC (system: Mg II preparative SFC; column: Chiralpak AD-H, 30×250 mm; mobile phase: scCO$_2$/EtOH 60:40; flow: 50 mL/min; temperature: 38° C.; detection UV: 220 nm) of the racemic mixture of 4-(4-chlorophenyl)-1-cyclopropyl-5-(3,8-dimethyl-[1,2,4]triazolo[4,3-a]pyridin-6-yl)-3-(methoxymethyl)-4,5-dihydropyrrolo[3,4-c]pyrazol-6(1H)-one (Example 129) and subsequent silica gel chromatography on Combiflash Isco (eluent: CH$_2$Cl$_2$/MeOH; gradient: 1.5-10% MeOH in 12.0 min, 3 min 10% MeOH; flow: 18 mL/min).

(R)-4-(4-chlorophenyl)-1-cyclopropyl-5-(3,8-dimethyl-[1,2,4]triazolo[4,3-a]pyridin-6-yl)-3-(methoxymethyl)-4,5-dihydropyrrolo[3,4-c]pyrazol-6(1H)-one. $t_R$: 5.15 min (system: Thar analytical SFC; column: Chiralpak AD-H, 4.6×250 mm; mobile phase: scCO$_2$/EtOH+0.05% DEA 60:40; flow: 2.4 mL/min; temperature: 35° C.; detection UV: 220 nm).

(S)-4-(4-chlorophenyl)-1-cyclopropyl-5-(3,8-dimethyl-[1,2,4]triazolo[4,3-a]pyridin-6-yl)-3-(methoxymethyl)-4,5-dihydropyrrolo[3,4-c]pyrazol-6(1H)-one. $t_R$: 2.87 min (system: Thar analytical SFC; column: Chiralpak AD-H, 4.6×250 mm; mobile phase: scCO$_2$/EtOH+0.05% DEA 60:40; flow: 2.4 mL/min; temperature: 35° C.; detection UV: 220 nm).

Example 164

(R)-4-(4-chlorophenyl)-3-cyclopropyl-5-(3,8-dimethyl-[1,2,4]triazolo[4,3-a]pyridin-6-yl)-1-methyl-4,5-dihydropyrrolo[3,4-c]pyrazol-6(1H)-one

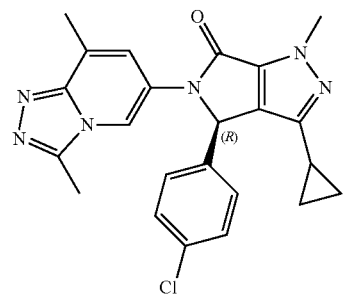

The title compound (26 mg, 34% yield) was obtained enantiomerically pure (>99% ee) after chiral preparative chromatography (system: VWR prep HPLC; column: Chiralpak AD-H 20 μm, 76.5×393 mm; mobile phase: heptane/EtOH 60:40; flow: 80 mL/min; detection UV: 240 nm) of the racemic mixture of 4-(4-chlorophenyl)-3-cyclopropyl-5-(3,8-dimethyl-[1,2,4]triazolo[4,3-a]pyridin-6-yl)-1-methyl-4,5-dihydropyrrolo[3,4-c]pyrazol-6(1H)-one (Example 129) followed by trituration in diethyl ether.

(R)-4-(4-chlorophenyl)-3-cyclopropyl-5-(3,8-dimethyl-[1,2,4]triazolo[4,3-a]pyridin-6-yl)-1-methyl-4,5-dihydropyrrolo[3,4-c]pyrazol-6(1H)-one. $t_R$: 8.80 min (system: Shmadzu HPLC; column: Chiralpak AD-H 5 μm, 4.6×250 mm; mobile phase: heptane/EtOH 50:50; flow: 0.8 mL/min; detection UV: 240 nm).

(S)-4-(4-chlorophenyl)-3-cyclopropyl-5-(3,8-dimethyl-[1,2,4]triazolo[4,3-a]pyridin-6-yl)-1-methyl-4,5-dihydropyrrolo[3,4-c]pyrazol-6(1H)-one. $t_R$: 5.48 min (system: Agilent HPLC; column: Chiralcel OD-H 5 μm, 20×250 mm; mobile phase: heptane/iPrOH 60:40; flow: 1 mL/min; detection UV: 210 nm).

Example 165

(R)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one

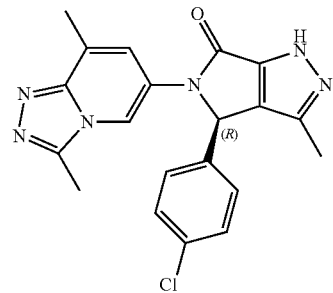

The title compound (133 mg, 44% yield) was obtained enantiomerically pure (>99% ee) after chiral preparative SFC (system: Thar SFC200; column: Chiralpak OD-H, 30×250 mm; mobile phase: scCO$_2$/MeOH 70:30; flow: 120 g/min; detection UV: 265 nm) of the racemic mixture of 4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one (Example 129) and subsequent trituration in diethyl ether.

(R)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one. t$_R$: 6.72 min (system: Thar/Waters SFC Investigator MS (ZQ); column: Chiralpak OD-H, 4.6×250 mm; mobile phase: scCO$_2$/MeOH+1% IPA 5-50%; flow: 4 mL/min; detection UV: DAD (200-350 nm)).

(S)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one. t$_R$: 3.59 min (system: Thar/Waters SFC Investigator MS (ZQ); column: Chiralpak OD-H, 4.6×250 mm; mobile phase: scCO$_2$/MeOH+1% IPA 5-50%; flow: 4 mL/min; detection UV: DAD (200-350 nm)).

Example 166

(R)-4-(4-chlorophenol)-1-cyclopropyl-5-(3,8-dimethyl-[1,2,4]triazolo[4,3-a]pyridin-6-yl)-3-(hydroxymethyl)-4,5-dihydropyrrolo[3,4-c]pyrazol-6(1H)-one

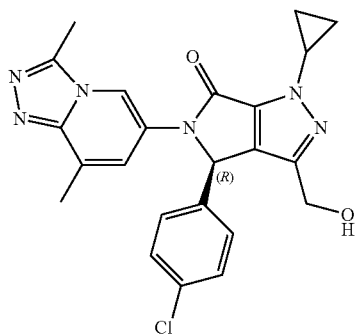

The title compound (48 mg, 37% yield) was obtained enantiomerically pure (>99% ee) after chiral preparative SFC (system: Mg II preparative SFC; column: Chiralpak AS-H, 30×250 mm; mobile phase: scCO$_2$/iPrOH 60:40; flow: 50 mL/min; temperature: 38° C.; detection UV: 220 nm) of the racemic mixture of 4-(4-chlorophenyl)-1-cyclopropyl-5-(3,8-dimethyl-[1,2,4]triazolo[4,3-a]pyridin-6-yl)-3-(hydroxymethyl)-4,5-dihydropyrrolo[3,4-c]pyrazol-6(1H)-one (Example 131) and subsequent trituration in diethyl ether.

(R)-4-(4-chlorophenyl)-1-cyclopropyl-5-(3,8-dimethyl-[1,2,4]triazolo[4,3-a]pyridin-6-yl)-3-(hydroxymethyl)-4,5-dihydropyrrolo[3,4-c]pyrazol-6(1H)-one. t$_R$: 4.33 min (system: Thar analytical SFC; column: Chiralpak AS-H, 4.6×250 mm; mobile phase: scCO$_2$/IPrOH+0.05% DEA 60:40; flow: 2.4 mL/min; temperature: 35° C.; detection UV: 220 nm).

(S)-4-(4-chlorophenyl)-1-cyclopropyl-5-(3,8-dimethyl-[1,2,4]triazolo[4,3-a]pyridin-6-yl)-3-(hydroxymethyl)-4,5-dihydropyrrolo[3,4-c]pyrazol-6(1H)-one. t$_R$: 2.91 min (system: Thar analytical SFC; column: Chiralpak AS-H, 4.6×250 mm; mobile phase: scCO$_2$/iPrOH+0.05% DEA 60:40; flow: 2.4 mL/min; temperature: 35° C.; detection UV: 220 nm).

Example 167

(R)-4-(4-chlorophenyl)-5-(3,8-dimethyl-[1,2,4]triazolo[4,3-a]pyridin-6-yl)-3-methyl-1-((S)-3,3,3-trifluoro-2-hydroxypropyl)-4,5-dihydropyrrolo[3,4-c]pyrazol-6(1H)-one

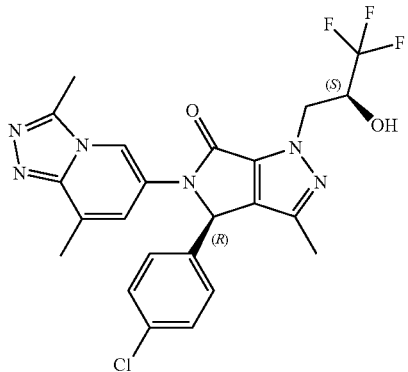

The title compound was prepared in analogy to the procedure described for Example 68 using 5-(4-chlorophenyl)-1-(3,8-dimethyl-[1,2,4]triazolo[4,3-a]pyridin-6-yl)-4-propionylpyrrolidine-2,3-dione (Step 70.1) and (S)-1,1,1-trifluoro-3-hydrazinylpropan-2-ol. The crude mixture of diastereoisomers was separated by preparative achiral SFC (column NH$_2$, isocratic 10% for 18 min_total 22 min) and trituration in Hex/Et$_2$O (1:1) to provide the desired (R,S)-diastereoisomer. t$_R$: 0.92 min (LC-MS 2); ESI-MS: 505 [M+H]$^+$ (LC-MS 2); $^1$H NMR (400 MHz, DMSO-d$_6$) δ ppm 2.00 (s, 3H) 2.46 (s, 3H) 2.64 (s, 3H) 4.40 (dd, J=13.9, 8.9 Hz, 1H) 4.55 (dd, J=13.9, 3.9 Hz, 1H) 4.65 (m, 1H) 6.51 (s, 1H) 6.81 (d, J=6.4 Hz, 1H) 7.20-7.48 (m, 5H) 8.48 (s, 1H) and the (S,S)-diastereoisomer. t$_R$: 0.93 min (LC-MS 2); ESI-MS: 505 [M+H]$^+$ (LC-MS 2); $^1$H NMR (400 MHz, DMSO-d$_6$) δ ppm 1.99 (s, 3H) 2.46 (s, 3H) 2.64 (s, 3H), 4.40 (m, 1H) 4.55 (m, 1H) 4.66 (m, 1H) 6.50 (s, 1H) 6.79 (d, J=6.4 Hz, 1H) 7.32-7.40 (m, 5H) 8.47 (s, 1H).

Example 168

4-(4-chloro-2-fluorophenyl)-5-(3,8-dimethyl-[1,2,4]triazolo[4,3-a]pyridin-6-yl)-1-isopropyl-3-methyl-4,5-dihydropyrrolo[3,4-c]pyrazol-6(1H)-one

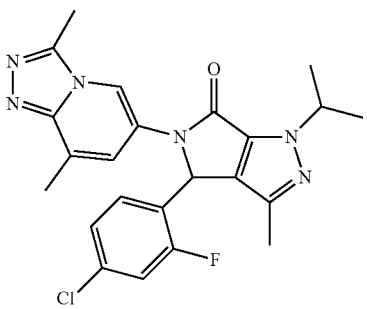 [SMILES: Cc1nn(C(C)C)c2c1C(c1ccc(Cl)cc1F)N(c1cc(C)c3nnc(C)n3c1)C2=O]

Step 168.1: 4-acetyl-5-(4-chloro-2-fluorophenyl)-1-(3,8-dimethyl-[1,2,4]triazolo[4,3-a]pyridin-6-yl)-3-hydroxy-1H-pyrrol-2(5H)-one The title compound was prepared in analogy to the procedure described in Step 57.1 except using 2-fluoro,4-chloro benzaldehyde and 3,8-dimethyl-[1,2,4]triazolo[4,3-a]pyridin-6-amine (Step 67.4) as starting materials. $t_R$: 0.71 min (LC-MS 2); ESI-MS: 415.3 [M+H]$^+$ (LC-MS 2); $^1$H NMR (400 MHz, MeOH-d4) δ ppm 2.46 (s, 3H) 2.57 (s, 3H) 2.75 (s, 3H) 7.01-7.17 (m, 2H) 7.30 (t, J=8.01 Hz, 1H) 7.71 (br. s, 1H) 8.67 (s, 1H).

Step 168.2: 4-(4-chloro-2-fluorophenyl)-5-(3,8-dimethyl-[1,2,4]triazolo[4,3-a]pyridin-6-yl)-1-isopropyl-3-methyl-4,5-dihydropyrrolo[3,4-c]pyrazol-6(1H)-one The title compound was prepared in analogy to the procedure described in Example 57 using 4-acetyl-5-(4-chloro-2-fluorophenyl)-1-(3,8-dimethyl-[1,2,4]triazolo[4,3-a]pyridin-6-yl)-3-hydroxy-1H-pyrrol-2(5H)-one (Step 168.1) as and isopropyl hydrazine as starting materials. Purification of the crude product afforded 16 mg of 4-(4-chloro-2-fluorophenyl)-5-(3,8-dimethyl-[1,2,4]triazolo[4,3-a]pyridin-6-yl)-2-isopropyl-3-methyl-4,5-dihydropyrrolo[3,4-c]pyrazol-6(2H)-one (Example 169) and 185 mg of the title compound $t_R$: 1.04 min (LC-MS 2); ESI-MS: 453.2 [M+H]$^+$, ESI-MS: 451.2 [M−H]$^-$ (LC-MS 2). $^1$H NMR (400 MHz, DMSO-d6) δ ppm 8.49 (s, 1H), 7.49-7.37 (m, 2H), 7.34 (s, 1H), 7.23 (d, J=8.3 Hz, 1H), 6.63 (s, 1H), 4.78 (p, J=6.7 Hz, 1H), 2.64 (s, 3H), 2.47 (s, 3H), 2.02 (s, 3H), 1.53 (t, J=6.2 Hz, 6H).

Example 169

4-(4-chloro-2-fluorophenyl)-5-(3,8-dimethyl-[1,2,4]triazolo[4,3-a]pyridin-6-yl)-2-isopropyl-3-methyl-4,5-dihydropyrrolo[3,4-c]pyrazol-6(2H)-one

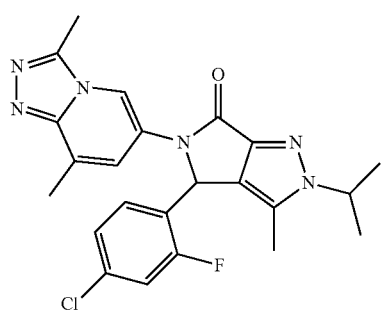 [SMILES: Cc1cc(N2C(=O)c3nn(C(C)C)c(C)c3C2c2ccc(Cl)cc2F)cn2c(C)nnc12]

The preparation of the title compound is described in Example 168. $t_R$: 0.98 min (LC-MS 2); ESI-MS: 452.2 [M+H]$^+$ (LC-MS 2).

Example 170

4-(4-chloro-2-fluorophenyl)-5-(1,5-dimethyl-6-oxo-1,6-dihydropyridin-3-yl)-1-ethyl-3-methyl-4,5-dihydropyrrolo[3,4-c]pyrazol-6(1H)-one

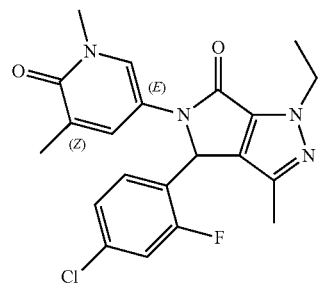 [SMILES: CCn1nc(C)c2c1C(=O)N(c1cc(C)c(=O)n(C)c1)C2c1ccc(Cl)cc1F]

Step 170.1: 5-(3-acetyl-2-(4-chloro-2-fluorophenyl)-4-hydroxy-5-oxo-2,5-dihydro-1H-pyrrol-1-yl)-1,3-dimethylpyridin-2(1H)-one The title compound was prepared in analogy to the procedure described in Step 57.1 except using 2-fluoro,4-chloro benzaldehyde and 5-amino-1,3-dimethylpyridin-2(1H)-one (step 20.2) as starting materials. $t_R$: 0.74 min (LC-MS 2); ESI-MS: 391.2[M+H]$^+$/389.2[M−H] (LC-MS 2).

Step 170.2: 4-(4-chloro-2-fluorophenyl)-5-(1,5-dimethyl-6-oxo-1,6-dihydropyridin-3-yl)-1-ethyl-3-methyl-4,5-dihydropyrrolo[3,4-c]pyrazol-6(1H)-one The title compound was prepared in analogy to the procedure described in Example 57 using 5-(3-acetyl-2-(4-chloro-2-fluorophenyl)-4-hydroxy-5-oxo-2,5-dihydro-1H-pyrrol-1-yl)-1,3-dimethylpyridin-2(1H)-one (Step 170.1) and ethyl hydrazine as starting materials. Purification of the crude product afforded 18 mg of 4-(4-chloro-2-fluorophenyl)-5-(1,5-dimethyl-6-oxo-1,6-dihydropyridin-3-yl)-2-ethyl-3-methyl-4,5-dihydropyrrolo[3,4-c]pyrazol-6(2H)-one (Example 171) and 45 mg of the title compound $t_R$: 0.97 min (LC-MS 2); ESI-MS: 415.2 [M+H] (LC-MS 2).

Example 171

4-(4-chloro-2-fluorophenyl)-5-(1,5-dimethyl-6-oxo-1,6-dihydropyridin-3-yl)-2-ethyl-3-methyl-4,5-dihydropyrrolo[3,4-c]pyrazol-6(2H)-one

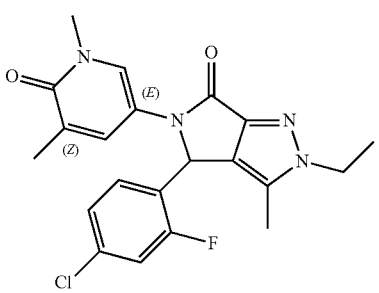 [SMILES: CCn1nc2c(c1C)C(c1ccc(Cl)cc1F)N(c1cc(C)c(=O)n(C)c1)C2=O]

The preparation of the title compound is described in Example 170. $t_R$: 0.92 min (LC-MS 2); ESI-MS: 415.2 [M+H]$^+$ (LC-MS 2).

Example 172

4-(2,4-difluorophenyl)-5-(3,8-dimethyl-[1,2,4]triazolo[4,3-a]pyridin-6-yl)-3-methyl-4,5-dihydropyrrolo[3,4-c]pyrazol-6(2H)-one

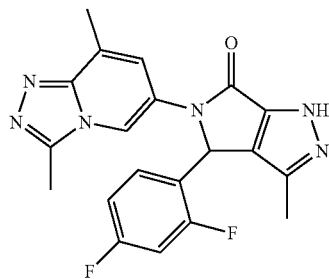 [SMILES: Cc1n[nH]c2c1C(c1ccc(F)cc1F)N(c1cc(C)c3nnc(C)n3c1)C2=O]

Step 172.1: 4-acetyl-5-(2,4-difluorophenyl)-1-(3,8-dimethyl-[1,2,4]triazolo[4,3-a]pyridin-6-yl)-3-hydroxy-1H-pyrrol-2(5H)-one The title compound was prepared in analogy to the procedure described in Step 57.1 except using 2,4-difluoro benzaldehyde and 5-amino-1,3-dimethylpyridin-2-(1H)-one (step 20.2) as starting materials. $t_R$: 0.64 min (LC-MS 2); ESI-MS: 399.2 [M+H]$^+$ (LC-MS 2)/397.2[M−H] (LC-MS 2). $^1$H NMR (400 MHz; MeOH-d4) δ ppm 2.46 (s, 3H) 2.53 (s, 3H) 2.71 (s, 3H) 6.24 (s, 1H) 6.75-6.93 (m, 2H) 7.21-7.39 (m, 1H) 7.48 (s, 1H).

Step 172.2: 4-(2,4-difluorophenyl)-5-(3,8-dimethyl-[1,2,4]triazolo[4,3-a]pyridin-6-yl)-3-methyl-4,5-dihydropyrrolo[3,4-c]pyrazol-6(2H)-one The title compound was prepared in analogy to the procedure described in Step 147.2 using 4-acetyl-5-(2,4-difluorophenyl)-1-(3,8-dimethyl-[1,2,4]triazolo[4,3-a]pyridin-6-yl)-3-hydroxy-1H-pyrrol-2(5H)-one (step 172.1) and hydrazine monohydrate as starting materials. Purification of the crude product by flash chromatography afforded 147 mg of the title compound $t_R$: 0.70 min (LC-MS 2); ESI-MS: 395.3 [M+H]/393.2 [M−H] (LC-MS 2).

Example 173

4-(2,4-difluorophenyl)-5-(3,8-dimethyl-[1,2,4]triazolo[4,3-a]pyridin-6-yl)-1-(2-methoxypyridin-3-yl)-3-methyl-4,5-dihydropyrrolo[3,4-c]pyrazol-6(1H)-one

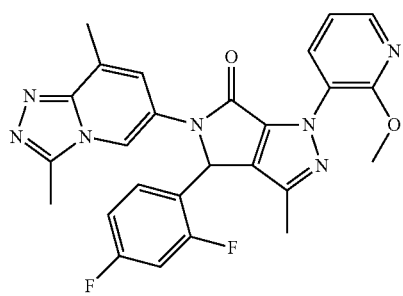 [SMILES: COc1ncccc1-n1nc(C)c2c1C(=O)N(c1cc(C)c3nnc(C)n3c1)C2c1ccc(F)cc1F]

4-(2,4-difluorophenyl)-5-(3,8-dimethyl-[1,2,4]triazolo[4,3-a]pyridin-6-yl)-3-methyl-4,5-dihydropyrrolo[3,4-c]pyrazol-6(2H)-one (Example 172; 80 mg, 0.203 mmol) was dissolved in CH$_2$Cl$_2$ (4.2 mL), 2-methoxy-3-pyridine boronic acid (62 mg, 0.402 mmol), pyridine (21 μL, 0.304 mmol) and Cu(OAc)$_2$ (73 mg, 0.406 mmol) were added and the reaction mixture allowed to stir at rt for 4.5 d. It was diluted with CH$_2$Cl$_2$ and water. The phases were separated and the organic layer was dried (Na$_2$SO$_4$) filtered and concentrated. The resulting residue was purified by SFC (Thar 100; column: PFP, 25 cm, Ø 3 cm, 5 μm, 60 Å; gradient: 18% B for 1 min, 18-23% B in 6 min, 23-50% B in 1 min, 50% B for 1 min, 50%-18% B in 1 min, 10% B for 0.5 min; A: scCO$_2$, B: MeOH; flow: 100 mL/min) afforded 8 mg of 4-(2,4-difluorophenyl)-5-(3,8-dimethyl-[1,2,4]triazolo[4,3-a]pyridin-6-yl)-2-(2-methoxypyridin-3-yl)-3-methyl-4,5-dihydropyrrolo[3,4-c]pyrazol-6(2H)-one (Example 193) and 10 mg of the title compound $t_R$: 0.94 min (LC-MS 2); ESI-MS: 503.2 [M+H]/500.3 [M−H] (LC-MS 2).

Example 174

4-(2,4-difluorophenyl)-5-(3,8-dimethyl-[1,2,4]triazolo[4,3-a]pyridin-6-yl)-1-isopropyl-3-methyl-4,5-dihydropyrrolo[3,4-c]pyrazol-6(1H)-one

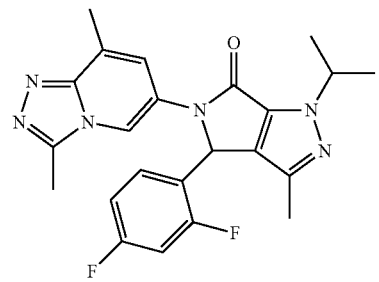 [SMILES: Cc1nn(C(C)C)c2c1C(c1ccc(F)cc1F)N(c1cc(C)c3nnc(C)n3c1)C2=O]

The title compound was prepared in analogy to the procedure described in Example 57 using 4-acetyl-5-(2,4-difluorophenyl)-1-(3,8-dimethyl-[1,2,4]triazolo[4,3-a]pyridin-6-yl)-3-hydroxy-1H-pyrrol-2(5H)-one (Step 172.1) and isopropyl hydrazine as starting materials. Purification of the crude product afforded 12 mg of 4-(2,4-difluorophenyl)-5-(3,8-dimethyl-[1,2,4]triazolo[4,3-a]pyridin-6-yl)-2-isopropyl-3-methyl-4,5-dihydropyrrolo[3,4-c]pyrazol-6(2H)-one (Example 175) and 104 mg of the title compound $t_R$: 0.96 min (LC-MS 2); ESI-MS: 437.3 [M+H] (LC-MS 2).

Example 175

4-(2,4-difluorophenyl)-5-(3,8-dimethyl-[1,2,4]triazolo[4,3-a]pyridin-6-yl)-2-isopropyl-3-methyl-4,5-dihydropyrrolo[3,4-c]pyrazol-6(2H)-one

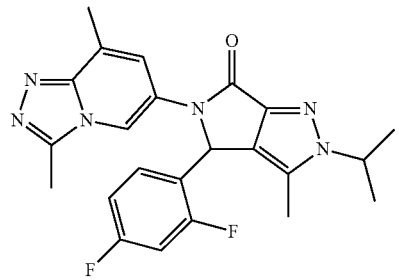 [SMILES: Cc1cc(N2C(=O)c3nn(C(C)C)c(C)c3C2c2ccc(F)cc2F)cn2c(C)nnc12]

The preparation of the title compound is described in Example 174. $t_R$: 0.91 min (LC-MS 2); ESI-MS: 437.3 [M+H]$^+$ (LC-MS 2).

Example 176

1-cyclopropyl-4-(2,4-difluorophenyl)-5-(3,8-dimethyl-[1,2,4]triazolo[4,3-a]pyridin-6-yl)-3-methyl-4,5-dihydropyrrolo[3,4-c]pyrazol-6(1H)-one

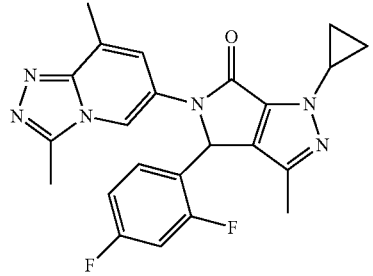 [SMILES: Cc1nn(C2CC2)c2c1C(c1ccc(F)cc1F)N(c1cc(C)c3nnc(C)n3c1)C2=O]

The title compound was prepared in analogy to the procedure described in Step 57.1 using 4-acetyl-5-(2,4-difluorophenyl)-1-(3,8-dimethyl-[1,2,4]triazolo[4,3-a]pyridin-6-yl)-3-hydroxy-1H-pyrrol-2(5H)-one (Step 172.1) and cyclopropyl hydrazine as starting materials. Purification of the crude product afforded 138 mg of the title compound $t_R$: 0.91 min (LC-MS 2); ESI-MS: 435.3 [M+H]/433.3 [M–H] (LC-MS 2). $^1$H NMR (400 MHz, MeOH-d4) δ ppm 8.41 (s, 1H), 7.35 (s, 1H), 7.33-7.18 (m, 1H), 6.96 (dd, J=22.4, 11.5 Hz, 2H), 6.53 (s, 1H), 3.88-3.70 (m, 1H), 2.70 (s, 2H), 2.53 (s, 3H), 2.04 (s, 2H), 1.30 (d, J=15.2 Hz, 4H).

Example 177

4-(2,4-difluorophenyl)-5-(3,8-dimethyl-[1,2,4]triazolo[4,3-a]pyridin-6-yl)-1-(2-methoxyphenyl)-3-methyl-4,5-dihydropyrrolo[3,4-c]pyrazol-6(1H)-one

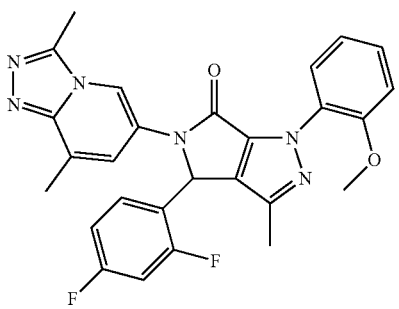 [SMILES: COc1ccccc1-n1nc(C)c2c1C(=O)N(c1cc(C)c3nnc(C)n3c1)C2c1ccc(F)cc1F]

The title compound was prepared in analogy to the procedure described in Example 57 using 4-(2,4-difluorophenyl)-5-(3,8-dimethyl-[1,2,4]triazolo[4,3-a]pyridin-6-yl)-1-(2-methoxyphenyl)-3-methyl-4,5-dihydropyrrolo[3,4-c]pyrazol-6(1H)-one (Step 172.1) and 2-methoxy phenyl hydrazine as starting materials. Purification of the crude product afforded the title compound as a white powder. $t_R$: 0.97 min (LC-MS 2); ESI-MS: 501.4 [M+H]/499.3 [M–H] (LC-MS 2). $^1$H NMR (400 MHz, MeOH-d4) δ ppm 8.40 (s, 1H), 7.49 (d, J=7.8 Hz, 2H), 7.40-7.29 (m, 2H), 7.22 (d, J=10.0 Hz, 1H), 7.11 (d, J=7.7 Hz, 1H), 7.05-6.90 (m, 2H), 6.63 (s, 1H), 3.85 (s, 3H), 2.69 (s, 3H), 2.52 (s, 3H), 2.15 (s, 3H).

Example 178

4-(4-chloro-2-fluorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one

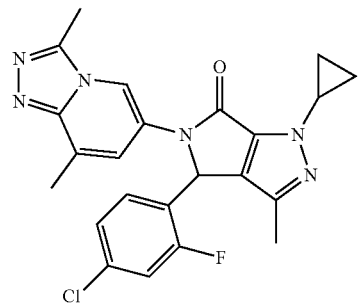 [SMILES: Cc1nn(C2CC2)c2c1C(c1ccc(Cl)cc1F)N(c1cc(C)c3nnc(C)n3c1)C2=O]

The title compound was prepared in analogy to the procedure described in Example 57 using 4-acetyl-5-(4-chloro-2-fluorophenyl)-1-(3,8-dimethyl-[1,2,4]triazolo[4,3-a]pyridin-6-yl)-3-hydroxy-1H-pyrrol-2(5H)-one (Step 168.1) as and cyclopropyl hydrazine as starting materials. Purification of the crude product afforded 208 mg of the title compound $t_R$: 0.99 min (LC-MS 2); ESI-MS: 451.3 [M+H]/449.3 [M–H]; (LC-MS 2). $^1$H NMR (400 MHz, DMSO-d6) δ ppm 8.45 (s, 1H), 7.47-7.35 (m, 2H), 7.31 (s, 1H), 7.25-7.13 (m, 1H), 6.59 (s, 1H), 3.93-3.72 (m, 1H), 2.60 (s, 3H), 2.44 (s, 3H), 1.96 (s, 3H), 1.21 (d, J=11.7 Hz, 2H), 1.04 (d, J=8.8 Hz, 2H).

Example 179

4-(4-chloro-2-fluorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one

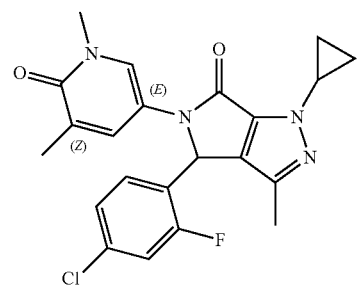 [SMILES: Cc1nn(C2CC2)c2c1C(c1ccc(Cl)cc1F)N(c1cc(C)c(=O)n(C)c1)C2=O]

The title compound was prepared in analogy to the procedure described in Example 57 using 5-(3-acetyl-2-(4-chloro-2-fluorophenyl)-4-hydroxy-5-oxo-2,5-dihydro-1H-pyrrol-1-yl)-1,3-dimethylpyridin-2(1H)-one (Step 170.1) and cyclopropyl hydrazine as starting materials. Purification of the crude product afforded 87 mg of the title compound $t_R$: 1.00 min (LC-MS 2); ESI-MS: 427.2 [M+H]$^+$/425.2 [M–H]$^-$ (LC-MS 2).

Example 180

4-(4-chloro-2-fluorophenyl)-5-(1,5-dimethyl-6-oxo-1,6-dihydropyridin-3-yl)-1-isopropyl-3-methyl-4,5-dihydropyrrolo[3,4-c]pyrazol-6(1H)-one

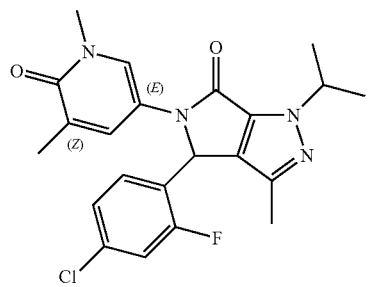 [SMILES: Cc1nn(C(C)C)c2c1C(c1ccc(Cl)cc1F)N(c1cc(C)c(=O)n(C)c1)C2=O]

The title compound was prepared in analogy to the procedure described in Example 57 using 5-(3-acetyl-2-(4-chloro-2-fluorophenyl)-4-hydroxy-5-oxo-2,5-dihydro-1H-pyrrol-1-yl)-1,3-dimethylpyridin-2(1H)-one (Step 170.1) and isopropyl hydrazine as starting materials. Purification of the crude product afforded 82 mg of the title compound $t_R$:1.05 min (LC-MS 2); ESI-MS: 429.2 [M+H]⁺/427.3 [M−H]⁻ (LC-MS 2).

Example 181

4-(2,4-difluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one

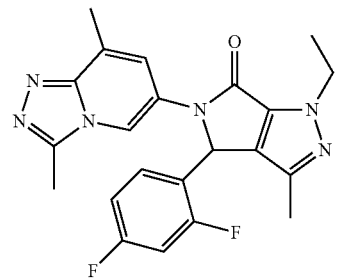 [SMILES: CCn1nc(C)c2c1C(=O)N(c1cc(C)c3nnc(C)n3c1)C2c1ccc(F)cc1F]

The title compound was prepared in analogy to the procedure described in Example 57 using 4-acetyl-5-(2,4-difluorophenyl)-1-(3,8-dimethyl-[1,2,4]triazolo[4,3-a]pyridin-6-yl)-3-hydroxy-1H-pyrrol-2(5H)-one (step 172.1) and ethyl hydrazine as starting materials. Purification of the crude product afforded 34 mg of 4-(2,4-difluorophenyl)-5-(3,8-dimethyl-[1,2,4]triazolo[4,3-a]pyridin-6-yl)-2-ethyl-3-methyl-4,5-dihydropyrrolo[3,4-c]pyrazol-6(2H)-one (Example 182) and 34 mg of the title compound $t_R$: 0.89 min (LC-MS 2); ESI-MS: 423.3 [M+H]⁺, ESI-MS: 421.2 [M−H]⁻ (LC-MS 2).
¹H NMR (400 MHz, MeOH-d4) δ 8.41 (s, 1H), 7.36 (s, 1H), 7.29 (q, J=8.4 Hz, 1H), 6.96 (dd, J=23.8, 8.9 Hz, 2H), 6.55 (s, 1H), 4.38 (q, J=7.2 Hz, 2H), 2.70 (s, 3H), 2.53 (s, 3H), 2.07 (s, 3H), 1.53 (t, J=7.2 Hz, 3H).

Example 182

4-(2,4-difluorophenyl)-5-(3,8-dimethyl-[1,2,4]triazolo[4,3-a]pyridin-6-yl)-2-ethyl-3-methyl-4,5-dihydropyrrolo[3,4-c]pyrazol-6(2H)-one

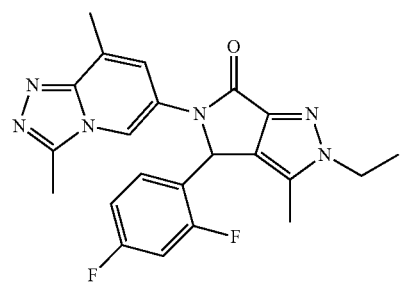 [SMILES: CCn1nc2c(c1C)C(c1ccc(F)cc1F)N(c1cc(C)c3nnc(C)n3c1)C2=O]

The preparation of the title compound is described in Example 181. $t_R$: 0.84 min (LC-MS 2); ESI-MS: 423.3 [M+H]⁺ (LC-MS 2).

Example 183

4-(4-chloro-2-fluorophenyl)-5-(3,8-dimethyl-[1,2,4]triazolo[4,3-a]pyridin-6-yl)-3-methyl-4,5-dihydropyrrolo[3,4-c]pyrazol-6(2H)-one

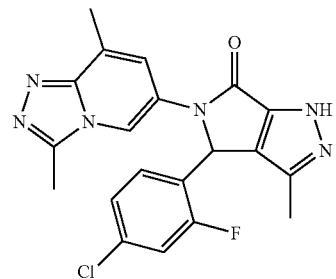 [SMILES: Cc1n[nH]c2c1C(c1ccc(Cl)cc1F)N(c1cc(C)c3nnc(C)n3c1)C2=O]

The title compound was prepared in analogy to the procedure described for Step 172.2 except for using 4-acetyl-5-(4-chloro-2-fluorophenyl)-1-(3,8-dimethyl-[1,2,4]triazolo[4,3-a]pyridin-6-yl)-3-hydroxy-1H-pyrrol-2(5H)-one (Step 168.1) as a starting material. Purification of the crude material afforded the title compound as a yellow solid. $t_R$: 0.76 min (LC-MS 2); ESI-MS: 411.3 [M+H]⁺/ESI-MS: 409.2 [M−H]⁻ (LC-MS 2).

Example 184

4-(4-chloro-2-fluorophenyl)-5-(3,8-dimethyl-[1,2,4]triazolo[4,3-a]pyridin-6-yl)-1-(2-methoxypyridin-3-yl)-3-methyl-4,5-dihydropyrrolo[3,4-c]pyrazol-6(1H)-one

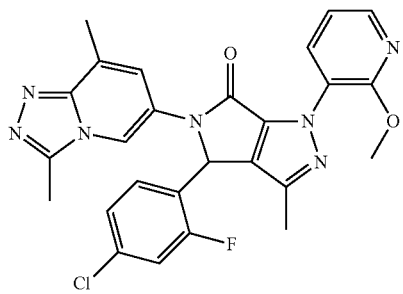 [SMILES: COc1ncccc1-n1nc(C)c2c1C(=O)N(c1cc(C)c3nnc(C)n3c1)C2c1ccc(Cl)cc1F]

The title compound was prepared in analogy to the procedure described for Step 172.3 except for using 4-(4-chloro-2-fluorophenyl)-5-(3,8-dimethyl-[1,2,4]triazolo[4,3-a]pyridin-6-yl)-3-methyl-4,5-dihydropyrrolo[3,4-c]pyrazol-6(2H)-one (Example 183) as a starting material. Purification of the crude product afforded 7 mg of 4-(2,4-difluorophenyl)-5-(3,8-dimethyl-[1,2,4]triazolo[4,3-a]pyridin-6-yl)-2-ethyl-3-methyl-4,5-dihydropyrrolo[3,4-c]pyrazol-6(2H)-one (Example 194) and 9 mg of the title compound $t_R$: 1.01 min (LC-MS 2); ESI-MS: 518.2 [M+H]$^+$, ESI-MS: 516.2 [M–H]$^-$ (LC-MS 2).

Example 185

4-(4-chloro-2-fluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one

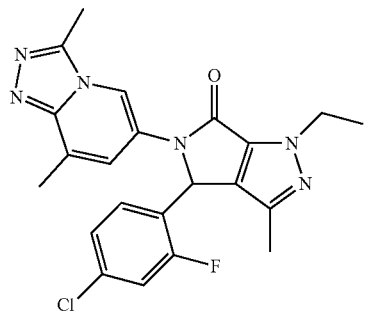 [SMILES: CCn1nc(C)c2c1C(=O)N(c1cc(C)c3nnc(C)n3c1)C2c1ccc(Cl)cc1F]

The title compound was prepared in analogy to the procedure described for Example 57 except for using 4-acetyl-5-(4-chloro-2-fluorophenyl)-1-(3,8-dimethyl-[1,2,4]triazolo[4,3-a]pyridin-6-yl)-3-hydroxy-1H-pyrrol-2(5H)-one (Step 168.1) and ethyl hydrazine as starting materials. Purification of the crude product afforded 34 mg of 4-(4-chloro-2-fluorophenyl)-5-(3,8-dimethyl-[1,2,4]triazolo[4,3-a]pyridin-6-yl)-2-ethyl-3-methyl-4,5-dihydropyrrolo[3,4-c]pyrazol-6(2H)-one (Example 186) and 119 mg of the title compound $t_R$: 0.96 min (LC-MS 2); ESI-MS: 439.3 [M+H]$^+$/437.2 [M–H]$^-$ (LC-MS 2). $^1$H NMR (400 MHz, MeOH-d4) δ ppm 7.91-7.38 (m, 1H), 6.56 (s, 1H), 6.44 (d, J=8.1 Hz, 2H), 6.35 (d, J=8.5 Hz, 1H), 5.75 (s, 1H), 3.57 (q, J=7.3 Hz, 2H), 1.90 (s, 3H), 1.73 (s, 3H), 1.27 (s, 3H), 0.79-0.65 (m, 3H).

Example 186

4-(4-chloro-2-fluorophenyl)-5-(3,8-dimethyl-[1,2,4]triazolo[4,3-a]pyridin-6-yl)-2-ethyl-3-methyl-4,5-dihydropyrrolo[3,4-c]pyrazol-6(2H)-one

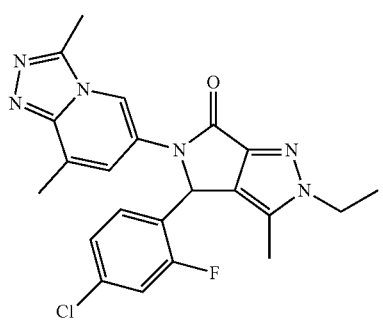 [SMILES: CCn1nc2c(c1C)C(c1ccc(Cl)cc1F)N(c1cc(C)c3nnc(C)n3c1)C2=O]

The preparation of the title compound is described in Example 185. $t_R$: 0.90 min (LC-MS 2); ESI-MS: 439.3 [M+H]$^+$ (LC-MS 2).

Example 187

4-(4-chloro-2-fluorophenyl)-5-(3,8-dimethyl-[1,2,4]triazolo[4,3-a]pyridin-6-yl)-1-(2-methoxyphenyl)-3-methyl-4,5-dihydropyrrolo[3,4-c]pyrazol-6(1H)-one

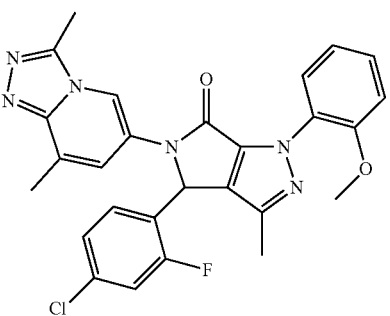 [SMILES: COc1ccccc1-n1nc(C)c2c1C(=O)N(c1cc(C)c3nnc(C)n3c1)C2c1ccc(Cl)cc1F]

The title compound was prepared in analogy to the procedure described for Example 57 except for using 4-acetyl-5-(4-chloro-2-fluorophenyl)-1-(3,8-dimethyl-[1,2,4]triazolo[4,3-a]pyridin-6-yl)-3-hydroxy-1H-pyrrol-2(5H)-one (Step 168.1) and 2-methoxy phenylhydrazine as starting materials. Purification of the crude material afforded the title compound as a yellow solid. $t_R$: 1.06 min (LC-MS 2); ESI-MS: 517.2 [M+H]$^+$/515.2 [M–H]$^-$ (LC-MS 2). $^1$H NMR (400 MHz, CDCl$_3$) δ ppm 8.18 (s, 1H), 7.50 (d, J=9.4 Hz, 1H), 7.46-7.35 (m, 1H), 7.17 (d, J=10.1 Hz, 1H), 7.09 (d, J=9.1 Hz, 3H), 7.04-6.90 (m, 2H), 6.36 (s, 1H), 3.86 (s, 3H), 2.66 (s, 3H), 2.59 (s, 3H), 2.19 (s, 3H).

Example 188

(S)-1-cyclopropyl-4-(2,4-difluorophenyl)-5-(3,8-dimethyl-[1,2,4]triazolo[4,3-a]pyridin-6-yl)-3-methyl-4,5-dihydropyrrolo[3,4-c]pyrazol-6(1H)-one

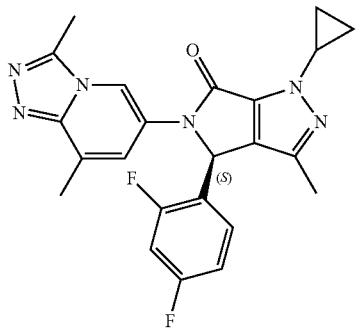

The title compound (54 mg, 44% yield) was obtained enantiomerically pure (>99% ee) after chiral preparative chromatography (system: Gilson PLC 2020; column: Chiralpak AD-H, 20×250 mm; mobile phase: heptane/EtOH/MeOH 80:10:10; flow: 10 mL/min; temperature: 38° C.; detection UV: 220 nm) of the racemic mixture of 1-cyclopropyl-4-(2,4-difluorophenyl)-5-(3,8-dimethyl-[1,2,4]triazolo[4,3-a]pyridin-6-yl)-3-methyl-4,5-dihydropyrrolo[3,4-c]pyrazol-6(1H)-one (Example 176).

(S)-1-cyclopropyl-4-(2,4-difluorophenyl)-5-(3,8-dimethyl-[1,2,4]triazolo[4,3-a]pyridin-6-yl)-3-methyl-4,5-dihydropyrrolo[3,4-c]pyrazol-6(1H)-one. $t_R$: 10.47 min (system: Agilent HPLC; column: Chiralpak AD-H, 4.6×250 mm; mobile phase: n-heptane/EtOH/MeOH 80:10:10; flow: 1 mL/min; temperature: 35° C.; detection UV: 220 nm).

(R)-1-cyclopropyl-4-(2,4-difluorophenyl)-5-(3,8-dimethyl-[1,2,4]triazolo[4,3-a]pyridin-6-yl)-3-methyl-4,5-dihydropyrrolo[3,4-c]pyrazol-6(1H)-one. $t_R$: 8.24 min (system: Agilent HPLC; column: Chiralpak AD-H, 4.6×250 mm; mobile phase: n-heptane/EtOH/MeOH 80:10:10; flow: 1 mL/min; temperature: 35° C.; detection UV: 220 nm).

Example 189

(S)-4-(4-chloro-2-fluorophenyl)-5-(3,8-dimethyl-[1,2,4]triazolo[4,3-a]pyridin-6-yl)-1-isopropyl-3-methyl-4,5-dihydropyrrolo[3,4-c]pyrazol-6(1H)-one

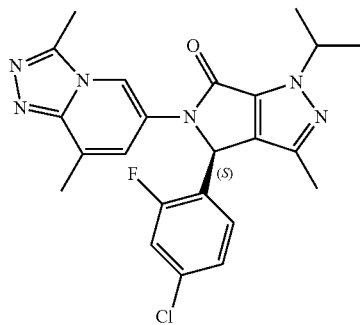

The title compound (65 mg, 43% yield) was obtained enantiomerically pure (>99% ee) after chiral preparative chromatography (system: MGII preparative SFC; column: Chiralpak AD-H, 30×250 mm; mobile phase: $scCO_2$/iPrOH 75:25; flow: 50 mL/min; temperature: 38° C.; detection UV: 220 nm) of the racemic mixture of 4-(4-chloro-2-fluorophenyl)-5-(3,8-dimethyl-[1,2,4]triazolo[4,3-a]pyridin-6-yl)-1-isopropyl-3-methyl-4,5-dihydropyrrolo[3,4-c]pyrazol-6(1H)-one (Example 168).

(S)-4-(4-chloro-2-fluorophenyl)-5-(3,8-dimethyl-[1,2,4]triazolo[4,3-a]pyridin-6-yl)-1-isopropyl-3-methyl-4,5-dihydropyrrolo[3,4-c]pyrazol-6(1H)-one. $t_R$: 3.68 min (system: Thar analytical SFC system; column: Pheno Lux Cellulose-2, 4.6×250 mm; mobile phase: $scCO_2$/iPrOH 60:40; flow: 2.4 mL/min; temperature: 35° C.; detection UV: 220 nm).

(R)-4-(4-chloro-2-fluorophenyl)-5-(3,8-dimethyl-[1,2,4]triazolo[4,3-a]pyridin-6-yl)-1-isopropyl-3-methyl-4,5-dihydropyrrolo[3,4-c]pyrazol-6(1H)-one. $t_R$: 6.01 min (system: Thar analytical SFC system; column: Pheno Lux Cellulose-2, 4.6×250 mm; mobile phase: $scCO_2$/iPrOH 60:40; flow: 2.4 mL/min; temperature: 35° C.; detection UV: 220 nm).

Example 190

(S)-4-(4-chloro-2-fluorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one

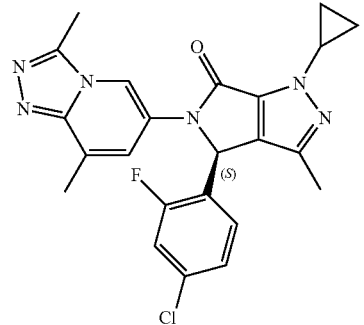

The title compound (82 mg, 43% yield) was obtained enantiomerically pure (>99% ee) after chiral preparative chromatography (system: MGII preparative SFC; column: Chiralpak AD-H, 30×250 mm; mobile phase: $scCO_2$/iPrOH 65:35; flow: 50 mL/min; temperature: 38° C.; detection UV: 220 nm) of the racemic mixture of 4-(4-chloro-2-fluorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one (Example 178).

(S)-4-(4-chloro-2-fluorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one. $t_R$: 7.6 min (system: Agilent HPLC; column: Chiralpak AD-H, 4.6×250 mm; mobile phase: n-heptane/EtOH/MeOH 60:20:20; flow: 1 mL/min; temperature: 35° C.; detection UV: 220 nm).

(R)-4-(4-chloro-2-fluorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one. $t_R$: 5.01 min (system: Agilent HPLC; column: Chiralpak AD-H, 4.6×250 mm; mobile phase: n-heptane/EtOH/MeOH 80:10:10; flow: 1 mL/min; temperature: 35° C.; detection UV: 220 nm).

Example 191

(S)-4-(2,4-difluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one

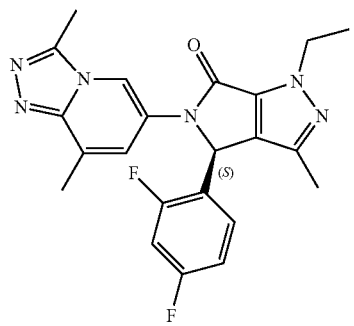

The title compound (34 mg, 48% yield) was obtained enantiomerically pure (>99% ee) after chiral preparative chromatography (system: Gilson PLC 2020; column: Chiralpak AD-H, 20×250 mm; mobile phase: heptane/EtOH/MeOH 80:10:10; flow: 12 mL/min; temperature: 38° C.; detection UV: 220 nm) of the racemic mixture of 4-(2,4-difluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one (Example 181).

(S)-4-(2,4-difluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one. $t_R$: 8.95 min (system: Agilent HPLC; column: Chiralpak AD-H, 4.6×250 mm; mobile phase: n-heptane/EtOH/MeOH 80:10:10; flow: 1 mL/min; temperature: 35° C.; detection UV: 220 nm).

(R)-4-(2,4-difluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one. $t_R$: 6.40 min (system: Agilent HPLC; column: Chiralpak AD-H, 4.6×250 mm; mobile phase: n-heptane/EtOH/MeOH 80:10:10; flow: 1 mL/min; temperature: 35° C.; detection UV: 220 nm).

Example 192

(S)-4-(4-chloro-2-fluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one

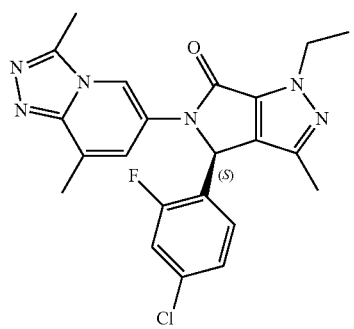

The title compound (52 mg, 47% yield) was obtained enantiomerically pure (>99% ee) after chiral preparative chromatography (system: MGII preparative SFC; column: Chiralpak AD-H, 30×250 mm; mobile phase: scCO$_2$/iPrOH 60:40; flow: 50 mL/min; temperature: 38° C.; detection UV: 220 nm) of the racemic mixture of 4-(4-chloro-2-fluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one (Example 185).

(S)-4-(4-chloro-2-fluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one. $t_R$: 3.07 min (system: Thar analytical SFC system; column: Chiral Pak AD-3, 4.6×250 mm; mobile phase: scCO$_2$/iPrOH 70:30; flow: 2.4 mL/min; temperature: 35° C.; detection UV: 220 nm).

(R)-4-(4-chloro-2-fluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one. $t_R$: 2.24 min (system: Thar analytical SFC system; column: Chiral Pak AD-3, 4.6×250 mm; mobile phase: scCO$_2$/iPrOH 70:30; flow: 2.4 mL/min; temperature: 35° C.; detection UV: 220 nm).

Example 193

4-(2,4-difluorophenyl)-5-(3,8-dimethyl-[1,2,4]triazolo[4,3-a]pyridin-6-yl)-2-(2-methoxypyridin-3-yl)-3-methyl-4,5-dihydropyrrolo[3,4-c]pyrazol-6(2H)-one

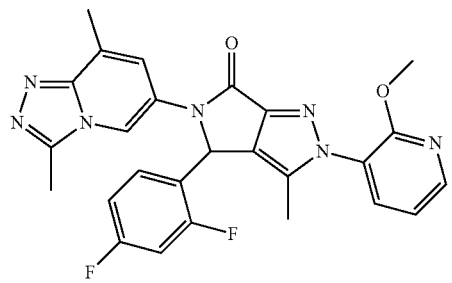 [SMILES: COc1ncccc1-n1nc2c(c1C)C(c1ccc(F)cc1F)N(c1cc(C)c3nnc(C)n3c1)C2=O]

The preparation of the title compound is described in Example 173. $t_R$: 0.92 min (LC-MS 2); ESI-MS: 503.2 [M+H]$^+$ (LC-MS 2).

Example 194

4-(4-chloro-2-fluorophenyl)-5-(3,8-dimethyl-[1,2,4]triazolo[4,3-a]pyridin-6-yl)-2-(2-methoxypyridin-3-yl)-3-methyl-4,5-dihydropyrrolo[3,4-c]pyrazol-6(2H)-one

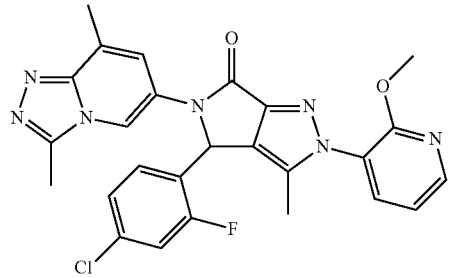 [SMILES: COc1ncccc1-n1nc2c(c1C)C(c1ccc(Cl)cc1F)N(c1cc(C)c3nnc(C)n3c1)C2=O]

The preparation of the title compound is described in Example 183. $t_R$: 0.98 min (LC-MS 2); ESI-MS: 518.2 [M+H]$^+$ (LC-MS 2).

Example 195

4-(4-chlorophenyl)-1-cyclopropyl-5-(3-(difluoromethyl)-8-methyl-[1,2,4]triazolo[4,3-b]pyridazin-6-yl)-3-methyl-4,5-dihydropyrrolo[3,4-c]pyrazol-6(1H)-one

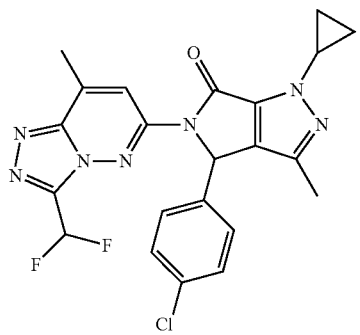 [SMILES: Cc1nn(C2CC2)c2c1C(c1ccc(Cl)cc1)N(c1cc(C)c3nnc(C(F)F)n3n1)C2=O]

Step 195.1:
6-chloro-3-hydrazinyl-4-methylpyridazine 3,6-Dichloro-4-methylpyridazine (Combi-Blocks) (60 g, 361 mmol) was dissolved in hydrazine monohydrate (Aldrich) (335 mL, 5411 mmol) and the solution was stirred at 80° C. for 1 h, forming a white precipitate. The reaction mixture is dilutes with water and the precipitated products isolated by filtration. The solid crude product is suspended in EtOH and left in an ultra sound bath for 1 h. The desired product (22.4 g) was obtained after filtration and drying under vacuum as a beige solid. $t_R$: 0.31 min (LC-MS 2); ESI-MS: 160.0 [M+H]$^+$ (LC-MS 2). $^1$H NMR (400 MHz; DMSO-d6) δ ppm 7.83 (br.s, 1H) 7.32 (s, 1H) 4.49 (br.s, 2H) 2.05 (s, 3H).

Step 195.2: 6-chloro-3-(difluoromethyl)-8-methyl-[1,2,4]triazolo[4,3-b]pyridazine To a beige suspension of 6-chloro-3-hydrazinyl-4-methylpyridazine (step 195.1) (22.44 g, 127 mmol) in dioxane (250 mL) was added difluoroacetic acid (Aldrich) (9.40 mL, 146 mmol) and the reaction mixture was stirred at rt for 5 min, then heated-up to 120° C. for 2.5 hr. With heating the suspension turned into a red-orange solution. The reaction mixture was cooled to rt. Et$_2$O (80 mL) was added and the suspension was stirred for 2 hours at 0° C. Precipitated solids were isolated by filtration, suspended in hexanes and filtered again. After repeated washings with hexanes the tittle compound was obtained as an orange solid.

$t_R$: 0.72 min (LC-MS 2); ESI-MS: 219.2 [M+H]$^+$ (LC-MS 2). $^1$H NMR (400 MHz; DMSO-d6) δ ppm 7.66 (t, 1H) 7.60 (s, 1H) 2.71 (s, 3H) 2.51 (s, 3H).

Step 195.3: 4-(4-chlorophenyl)-1-cyclopropyl-5-(3-(difluoromethyl)-8-methyl-[1,2,4]triazolo[4,3-b]pyridazin-6-yl)-3-methyl-4,5-dihydropyrrolo[3,4-c]pyrazol-6(1H)-one 4-(4-chlorophenyl)-1-cyclopropyl-3-methyl-4,5-dihydropyrrolo[3,4-c]pyrazol-6(1H)-one (Step 23.9) (200 mg, 0.695 mmol), 6-chloro-3-(difluoromethyl)-8-methyl-[1,2,4]triazolo[4,3-b]pyridazine (Step 195.2) (190 mg, 0.869 mmol), Pd$_2$(dba)$_3$ (Aldrich) (63.6 mg, 0.070 mmol), Xanthpos (Aldrich) (97 mg, 0.167 mmol) and cesium carbonate (Fluka) (453 mg, 1.390 mmol) were dissolved in dioxane (3.5 mL) under argon. The black solution was stirred at 100° C. for 5.5 h. The reaction mixture is quenched with 10 mL of NaHCO$_3$. EtOAc was added and the organic layer separated. The aqueous phase was extracted twice with EtOAc. Combined extracts were dried and concentrated. The crude material was purified by flash chromatography (ISCO flashmaster system; column 40 g. Solvent A: hexane; solvent B: EtOAc. Gradient (% B): 0% for 2 min, 0-25% for 13 min, 25% for 5 min, 25-50% for 15 min, 50% for 10 min; Flow 40 mL/min. Detection: 254 nm, 280 nm). Fractions containing product were collected, concentrated and dried under vacuum. The resulting product was then submitted to preparative HPLC (column: Waters Sunfire C18, 5 um, 30×100 mm; solvent A: Water+0.1% TFA; solvent B: acetonitrile+0.1% TFA. Gradient (% B): 50-70% in 16 minutes; Flow 50 mL per min. Fractions containing product are collected, evaporated and dried under vacuum to afford the title compound as a white solid. $t_R$: 1.18 min (LC-MS 2); ESI-MS: 470.3 [M+H]$^+$ (LC-MS 2). $^1$H NMR (400 MHz; DMSO-d6) δ ppm 1.10-1.21 (m, 2H) 1.28-1.40 (m, 2H) 1.99 (s, 3H) 2.72 (s, 3H) 3.86 (tt, J=7.24, 3.70 Hz, 1H) 6.41 (s, 1H) 7.24-7.46 (m, 5H) 8.47 (s, 1H).

Example 196

4-(4-chloro-2-fluorophenyl)-5-(1,5-dimethyl-6-oxo-1,6-dihydropyridin-3-yl)-3-methyl-4,5-dihydropyrrolo[3,4-c]pyrazol-6(2H)-one

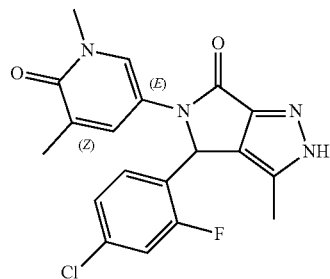 [SMILES: Cc1[nH]nc2c1C(c1ccc(Cl)cc1F)N(c1cc(C)c(=O)n(C)c1)C2=O]

The title compound was prepared in analogy to the procedure described in Step 147.2 using 4-acetyl-5-(2,4-difluorophenyl)-1-(3,8-dimethyl-[1,2,4]triazolo[4,3-a]pyridin-6-yl)-3-hydroxy-1H-pyrrol-2(5H)-one (step 170.1) and hydrazine monohydrate as starting materials. The resulting residue was purified by SFC (Thar 100; column: PFP, 25 cm, Ø 3 cm, 5 μm, 60 Å; gradient: 15% B for 1 min, 15-20% B in 6 min, 20-50% B in 1 min, 50% B for 1.5 min, 50%-15% B in 1 min, 15% B for 0.5 min; A: scCO$_2$, B: MeOH; flow: 100 mL/min) to afford 147 mg of the title compound $t_R$: 0.70 min (LC-MS 2); ESI-MS: 395.3 [M+H]/393.2 [M−H] (LC-MS 2).

The invention claimed is:

1. A compound of formula (I), or a pharmaceutically acceptable salt thereof,

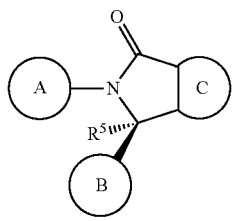
(I)

wherein
ring C is selected from i.
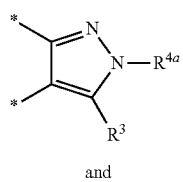
and
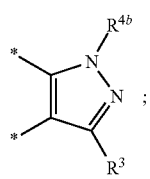
;

A is selected from

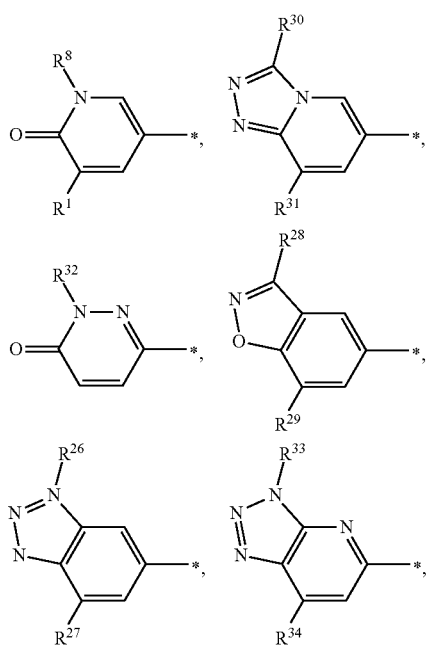

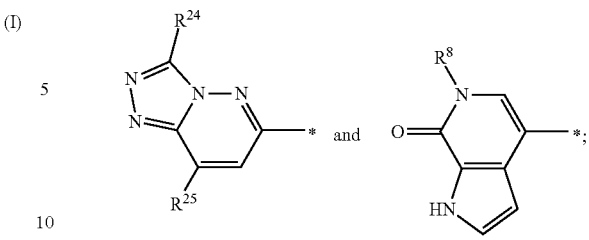

B is selected from

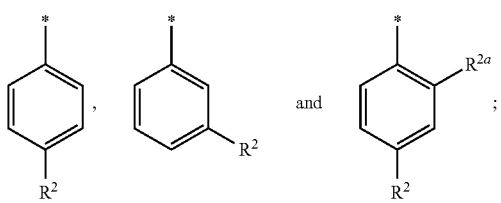

R³ is selected from H, methyl, ethyl, —CH₂F, —CF3, isopropyl, —OH, ethoxy, methoxy, cyclopropyl, —CH₂OCH₃ and —CH₂OH;

ii. $R^{4a}$ is selected from H, (C₁-C₄)alkyl, (C₃-C₆)cycloalkyl, —(CH₂)₂—OH, —(CH₂)₂—O—CH₃, —C(O)—NH(CH₃), —C(O)—N(CH₃)₂,

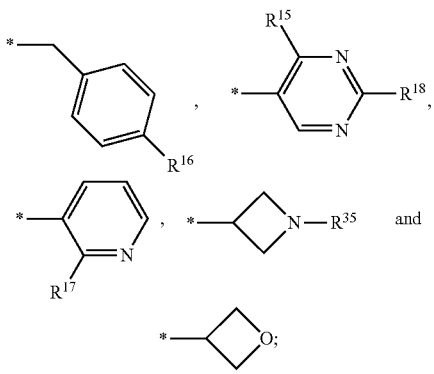

$R^{4b}$ is selected from H, (C₁-C₄)alkyl, (C₃-C₆)cycloalkyl, —(CH₂)₂—OH, —(CH₂)₂—O—CH₃, —(CH₂)₂—O—CH₂—CF₃, —(CH₂)—CH(OH)—CF₃, —C(O)—NH(CH₃), —C(O)—N(CH₃)₂,

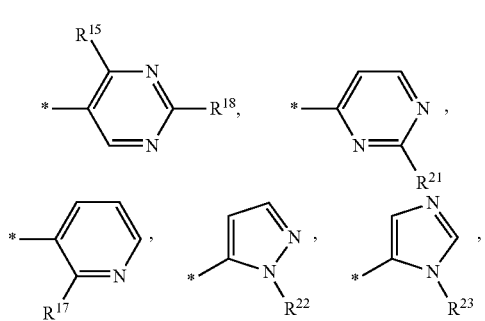

-continued

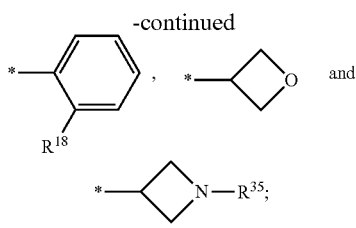

$R^5$ is H;
$R^1$ is selected from H, methyl, chloro and fluoro;
$R^2$ is selected from bromo, chloro, fluoro, —O—$CF_3$ and —$CF_3$;
$R^{2a}$ is fluoro;
$R^8$ is methyl;
$R^{15}$, $R^{16}$, $R^{18}$ and $R^{21}$ are all methoxy;
$R^{17}$ is methyl or methoxy;
$R^{22}$, $R^{23}$, $R^{26}$, $R^{27}$, $R^{28}$, $R^{30}$, $R^{32}$ and $R^{33}$ are all methyl;
$R^{24}$ is methyl or —$CHF_2$;
$R^{25}$ is methyl or —$NR^9R^{10}$;
$R^{29}$ is H or methyl;
$R^{31}$ is H, methyl or methoxy;
$R^{34}$ is H or methyl;
$R^9$ is H or methyl;
$R^{10}$ is H, methyl or —C(O)—($C_1$-$C_3$)alkyl;
$R^{35}$ is H, methyl, —C(O)$CH_3$ or —C(O)O$CH_2CH_3$;
and
* indicates the point of attachment to the remainder of the molecule;
with the proviso that
when ring C is i:

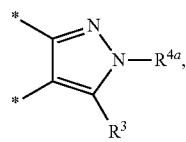

A is:

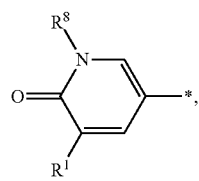

$R^1$ is selected from methyl, chloro and fluoro,
B is:

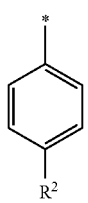

$R^2$ is chloro, fluoro or —$CF_3$,
and the remaining substituents are as defined herein,
then $R^3$ is selected from H, methyl, ethyl, —$CH_2F$, —$CF_3$, —OH, ethoxy, methoxy, —$CH_2OCH_3$ and —$CH_2OH$.

2. The compound of formula (I) or a pharmaceutically acceptable salt thereof, according to claim 1, wherein A is selected from

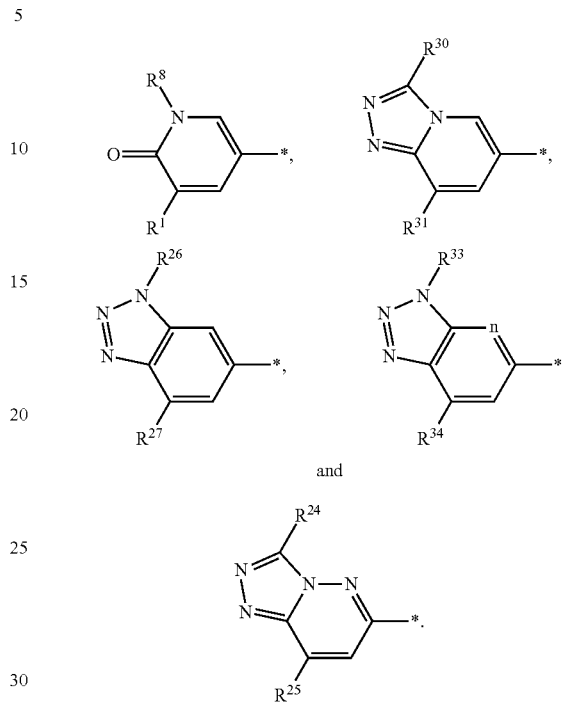

3. The compound of formula (I) or a pharmaceutically acceptable salt thereof, according to claim 1, wherein B is

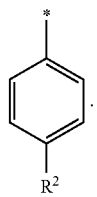

4. The compound of formula (I) or a pharmaceutically acceptable salt thereof, according to claim 1, wherein $R^3$ is selected from methyl, ethyl, isopropyl and methoxy, or is selected from H, methyl, ethyl, —$CF_3$, —OH, ethoxy and methoxy.

5. The compound of formula (I) or a pharmaceutically acceptable salt thereof, according to claim 1, wherein $R^{4a}$ is selected from methyl, isopropyl, cyclopropyl and

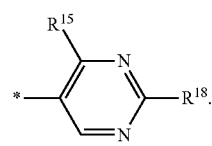

6. The compound of formula (I) or a pharmaceutically acceptable salt thereof, according to claim 1, wherein $R^{4b}$ is selected from ethyl, isopropyl, cyclopropyl, —$(CH_2)_2$—OH, —$(CH_2)_2$—O—$CH_3$,

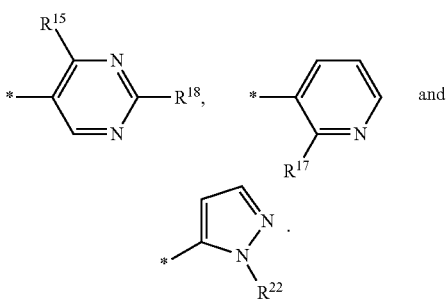

7. The compound of formula (I) or a pharmaceutically acceptable salt thereof, according to claim 1, wherein R¹ is methyl or chloro.

8. The compound of formula (I) or a pharmaceutically acceptable salt thereof, according to claim 1, wherein R² is chloro.

9. The compound of formula (I) or a pharmaceutically acceptable salt thereof, according to claim 1, wherein ring C is i:

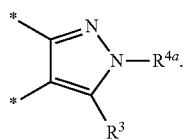

10. The compound of formula (I) or a pharmaceutically acceptable salt thereof, according to claim 1, wherein ring C is ii:

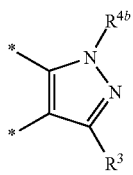

11. The compound of formula (I) or a pharmaceutically acceptable salt thereof, according to claim 1, wherein the stereochemistry is as shown in formula (Ia):

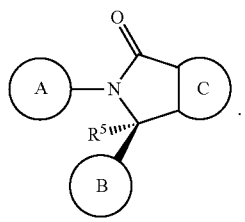

12. A compound of formula (I) or a pharmaceutically acceptable salt thereof, according to claim 1, selected from:
  Example 1: 4-(4-chlorophenyl)-2-(4-methoxybenzyl)-3-methyl-5-(1-methyl-6-oxo-1,6-dihydropyridin-3-yl)-4,5-dihydropyrrolo[3,4-c]pyrazol-6(2H)-one
  Example 2: 4-(4-chlorophenyl)-3-methyl-5-(1-methyl-6-oxo-1,6-dihydropyridin-3-yl)-4,5-dihydropyrrolo[3,4-c]pyrazol-6(2H)-one
  Example 3: 4-(4-chlorophenyl)-2,3-dimethyl-5-(1-methyl-6-oxo-1,6-dihydropyridin-3-yl)-4,5-dihydropyrrolo[3,4-c]pyrazol-6(2H)-one
  Example 4: 4-(4-chlorophenyl)-1,3-dimethyl-5-(1-methyl-6-oxo-1,6-dihydropyridin-3-yl)-4,5-dihydropyrrolo[3,4-c]pyrazol-6(1H)-one
  Example 5: 5-(5-chloro-1-methyl-6-oxo-1,6-dihydropyridin-3-yl)-4-(4-chlorophenyl)-3-methyl-4,5-dihydropyrrolo[3,4-c]pyrazol-6(2H)-one
  Example 6: 5-(5-chloro-1-methyl-6-oxo-1,6-dihydropyridin-3-yl)-4-(4-chlorophenyl)-2,3-dimethyl-4,5-dihydropyrrolo[3,4-c]pyrazol-6(2H)-one
  Example 7: (R)-5-(5-chloro-1-methyl-6-oxo-1,6-dihydropyridin-3-yl)-4-(4-chlorophenyl)-2,3-dimethyl-4,5-dihydropyrrolo[3,4-c]pyrazol-6(2H)-one
  Example 9: 5-(5-chloro-1-methyl-6-oxo-1,6-dihydropyridin-3-yl)-4-(4-chlorophenyl)-4,5-dihydropyrrolo[3,4-c]pyrazol-6(2H)-one
  Example 10: 5-(5-chloro-1-methyl-6-oxo-1,6-dihydropyridin-3-yl)-4-(4-chlorophenyl)-2-methyl-4,5-dihydropyrrolo[3,4-c]pyrazol-6(2H)-one
  Example 11: (R)-5-(5-chloro-1-methyl-6-oxo-1,6-dihydropyridin-3-yl)-4-(4-chlorophenyl)-2-methyl-4,5-dihydropyrrolo[3,4-c]pyrazol-6(2H)-one
  Example 13: 4-(4-chlorophenyl)-5-(1,5-dimethyl-6-oxo-1,6-dihydropyridin-3-yl)-2-methyl-4,5-dihydropyrrolo[3,4-c]pyrazol-6(2H)-one
  Example 14: 4-(4-chlorophenyl)-5-(5-fluoro-1-methyl-6-oxo-1,6-dihydropyridin-3-yl)-2-methyl-4,5-dihydropyrrolo[3,4-c]pyrazol-6(2H)-one
  Example 16: (R)-4-(4-chlorophenyl)-5-(1,5-dimethyl-6-oxo-1,6-dihydropyridin-3-yl)-2-methyl-4,5-dihydropyrrolo[3,4-c]pyrazol-6(2H)-one
  Example 17: 5-(5-chloro-1-methyl-6-oxo-1,6-dihydropyridin-3-yl)-4-(4-chlorophenyl)-2-cyclopropyl-3-methyl-4,5-dihydropyrrolo[3,4-c]pyrazol-6(2H)-one
  Example 19: (R)-5-(5-chloro-1-methyl-6-oxo-1,6-dihydropyridin-3-yl)-4-(4-chlorophenyl)-2-cyclopropyl-3-methyl-4,5-dihydropyrrolo[3,4-c]pyrazol-6(2H)-one
  Example 20: 4-(4-chlorophenyl)-2-cyclopropyl-5-(1,5-dimethyl-6-oxo-1,6-dihydropyridin-3-yl)-3-methyl-4,5-dihydropyrrolo[3,4-c]pyrazol-6(2H)-one
  Example 21: (R)-4-(4-chlorophenyl)-2-cyclopropyl-5-(1,5-dimethyl-6-oxo-1,6-dihydropyridin-3-yl)-3-methyl-4,5-dihydropyrrolo[3,4-c]pyrazol-6(2H)-one
  Example 23: 4-(4-chlorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one
  Example 24: 5-(5-chloro-1-methyl-6-oxo-1,6-dihydropyridin-3-yl)-4-(4-chlorophenyl)-1-cyclopropyl-3-methyl-4,5-dihydropyrrolo[3,4-c]pyrazol-6(1H)-one
  Example 25: 4-(4-chlorophenyl)-2,3-dimethyl-5-(3-methyl-[1,2,4]triazolo[4,3-a]pyridin-6-yl)-4,5-dihydropyrrolo[3,4-c]pyrazol-6(2H)-one
  Example 26: 4-(4-chlorophenyl)-5-(1,5-dimethyl-6-oxo-1,6-dihydropyridin-3-yl)-4,5-dihydropyrrolo[3,4-c]pyrazol-6(2H)-one
  Example 27: 4-(4-chlorophenyl)-5-(1,5-dimethyl-6-oxo-1,6-dihydropyridin-3-yl)-3-methyl-4,5-dihydropyrrolo[3,4-c]pyrazol-6(2H)-one
  Example 28: 4-(4-chlorophenyl)-5-(1,5-dimethyl-6-oxo-1,6-dihydropyridin-3-yl)-2,3-dimethyl-4,5-dihydropyrrolo[3,4-c]pyrazol-6(2H)-one
  Example 30: (R)-4-(4-chlorophenyl)-5-(1,5-dimethyl-6-oxo-1,6-dihydropyridin-3-yl)-2,3-dimethyl-4,5-dihydropyrrolo[3,4-c]pyrazol-6(2H)-one Example 31: 4-(4-chlorophenyl)-5-(5-fluoro-1-methyl-6-oxo-1,6-dihydropyridin-3-yl)-2,3-dimethyl-4,5-dihydropyrrolo[3,4-c]pyrazol-6(2H)-one Example 32: 4-(4-chlorophenyl)-2,3-dimethyl-5-(1-methyl-6-oxo-1,6-dihydropyridazin-3-yl)-4,5-dihydropyrrolo[3,4-c]pyrazol-6(2H)-one Example 33: 4-(4-chlorophenyl)-2,3-dimethyl-5-(3-methylbenzo[d]isoxazol-5-yl)-4,5-dihydropyrrolo[3,4-c]pyrazol-6(2H)-one Example 34: 4-(4-chlorophenyl)-1-cyclopropyl-5-(1,5-dimethyl-6-oxo-1,6-dihydropyridin-3-yl)-4,5-dihydropyrrolo[3,4-c]pyrazol-6(1H)-one Example 35: 5-(5-chloro-1-methyl-6-oxo-1,6-dihydropyridin-3-yl)-4-(4-chlorophenyl)-1-cyclopropyl-4,5-dihydropyrrolo[3,4-c]pyrazol-6(1H)-one Example 36: 4-(4-chlorophenyl)-5-(1,5-dimethyl-6-oxo-1,6-dihydropyridin-3-yl)-1-isopropyl-4,5-dihydropyrrolo[3,4-c]pyrazol-6(1H)-one Example 37: 5-(5-chloro-1-methyl-6-oxo-1,6-dihydropyridin-3-yl)-4-(4-chlorophenyl)-2-cyclopropyl-4,5-dihydropyrrolo[3,4-c]pyrazol-6(2H)-one Example 38: 5-(5-chloro-1-methyl-6-oxo-1,6-dihydropyridin-3-yl)-4-(4-chlorophenyl)-1-isopropyl-4,5-dihydropyrrolo[3,4-c]pyrazol-6(1H)-one Example 39: 4-(4-chlorophenyl)-2-cyclopropyl-5-(1,5-dimethyl-6-oxo-1,6-dihydropyridin-3-yl)-4,5-dihydropyrrolo[3,4-c]pyrazol-6(2H)-one Example 40: 5-(5-chloro-1-methyl-6-oxo-1,6-dihydropyridin-3-yl)-4-(4-chlorophenyl)-2-cyclopropyl-3-(trifluoromethyl)-4,5-dihydropyrrolo[3,4-c]pyrazol-6(2H)-one Example 41: 4-(4-chlorophenyl)-5-(1,5-dimethyl-6-oxo-1,6-dihydropyridin-3-yl)-2-isopropyl-4,5-dihydropyrrolo[3,4-c]pyrazol-6(2H)-one Example 42: 5-(5-chloro-1-methyl-6-oxo-1,6-dihydropyridin-3-yl)-4-(4-chlorophenyl)-2-isopropyl-4,5-dihydropyrrolo[3,4-c]pyrazol-6(2H)-one Example 43: 4-(4-chlorophenyl)-2-cyclopropyl-5-(1,5-dimethyl-6-oxo-1,6-dihydropyridin-3-yl)-3-(trifluoromethyl)-4,5-dihydropyrrolo[3,4-c]pyrazol-6(2H)-one Example 44: 5-(5-chloro-1-methyl-6-oxo-1,6-dihydropyridin-3-yl)-4-(4-chlorophenyl)-1-cyclopropyl-3-(trifluoromethyl)-4,5-dihydropyrrolo[3,4-c]pyrazol-6(1H)-one Example 45: 4-(4-chlorophenyl)-1-cyclopropyl-5-(1,5-dimethyl-6-oxo-1,6-dihydropyridin-3-yl)-3-(trifluoromethyl)-4,5-dihydropyrrolo[3,4-c]pyrazol-6(1H)-one Example 46: 4-(4-chlorophenyl)-2-(2,4-dimethoxypyrimidin-5-yl)-5-(3,7-dimethylbenzo[d]-isoxazol-5-yl)-3-isopropyl-4,5-dihydropyrrolo[3,4-c]pyrazol-6(2H)-one Example 47: 5-(5-chloro-1-methyl-6-oxo-1,6-dihydropyridin-3-yl)-4-(4-chlorophenyl)-2-(2,4-dimethoxypyrimidin-5-yl)-3-(trifluoromethyl)-4,5-dihydropyrrolo[3,4-c]pyrazol-6(2H)-one Example 49: (R)-4-(4-chlorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one Example 51: (R)-5-(5-chloro-1-methyl-6-oxo-1,6-dihydropyridin-3-yl)-4-(4-chlorophenyl)-1-cyclopropyl-3-methyl-4,5-dihydropyrrolo[3,4-c]pyrazol-6(1H)-one Example 52: 4-(4-chlorophenyl)-1-(2,4-dimethoxypyrimidin-5-yl)-5-(1,5-dimethyl-6-oxo-1,6-dihydropyridin-3-yl)-3-methyl-4,5-dihydropyrrolo[3,4-c]pyrazol-6(1H)-one Example 53: 5-(5-chloro-1-methyl-6-oxo-1,6-dihydropyridin-3-yl)-4-(4-chlorophenyl)-1-(2,4-dimethoxypyrimidin-5-yl)-3-methyl-4,5-dihydropyrrolo[3,4-c]pyrazol-6(1H)-one Example 54: 4-(4-chlorophenyl)-2-(2,4-dimethoxypyrimidin-5-yl)-3-isopropyl-5-(3-methylbenzo[d]isoxazol-5-yl)-4,5-dihydropyrrolo[3,4-c]pyrazol-6(2H)-one Example 55: 5-(5-chloro-1-methyl-6-oxo-1,6-dihydropyridin-3-yl)-4-(4-chlorophenyl)-2-(2,4-dimethoxypyrimidin-5-yl)-3-methyl-4,5-dihydropyrrolo[3,4-c]pyrazol-6(2H)-one Example 56: 4-(4-chlorophenyl)-2-(2,4-dimethoxypyrimidin-5-yl)-5-(1,5-dimethyl-6-oxo-1,6-dihydropyridin-3-yl)-3-methyl-4,5-dihydropyrrolo[3,4-c]pyrazol-6(2H)-one Example 57: 4-(4-chlorophenyl)-5-(1,5-dimethyl-6-oxo-1,6-dihydropyridin-3-yl)-1,3-dimethyl-4,5-dihydropyrrolo[3,4-c]pyrazol-6(1H)-one Example 58: 5-(5-chloro-1-methyl-6-oxo-1,6-dihydropyridin-3-yl)-4-(4-chlorophenyl)-1,3-dimethyl-4,5-dihydropyrrolo[3,4-c]pyrazol-6(1H)-one Example 59: 4-(4-chlorophenyl)-5-(1,5-dimethyl-6-oxo-1,6-dihydropyridin-3-yl)-1-(2-methoxypyrimidin-4-yl)-3-methyl-4,5-dihydropyrrolo[3,4-c]pyrazol-6(1H)-one Example 60: 4-(4-chlorophenyl)-1-(2,4-dimethoxypyrimidin-5-yl)-5-(1,5-dimethyl-6-oxo-1,6-dihydropyridin-3-yl)-3-ethyl-4,5-dihydropyrrolo[3,4-c]pyrazol-6(1H)-one Example 62: (R)-4-(4-chlorophenyl)-2-(2,4-dimethoxypyrimidin-5-yl)-5-(3,7-dimethylbenzo[d]isoxazol-5-yl)-3-isopropyl-4,5-dihydropyrrolo[3,4-c]pyrazol-6(2H)-one Example 63: 4-(4-chlorophenyl)-5-(1,5-dimethyl-6-oxo-1,6-dihydropyridin-3-yl)-1-isopropyl-3-methyl-4,5-dihydropyrrolo[3,4-c]pyrazol-6(1H)-one Example 64: 4-(4-chlorophenyl)-5-(1,5-dimethyl-6-oxo-1,6-dihydropyridin-3-yl)-2-isopropyl-3-methyl-4,5-dihydropyrrolo[3,4-c]pyrazol-6(2H)-one Example 65: 5-(5-chloro-1-methyl-6-oxo-1,6-dihydropyridin-3-yl)-4-(4-chlorophenyl)-2-isopropyl-3-methyl-4,5-dihydropyrrolo[3,4-c]pyrazol-6(2H)-one Example 66: 5-(5-chloro-1-methyl-6-oxo-1,6-dihydropyridin-3-yl)-4-(4-chlorophenyl)-1-isopropyl-3-methyl-4,5-dihydropyrrolo[3,4-c]pyrazol-6(1H)-one Example 67: 4-(4-chlorophenyl)-2-(2,4-dimethoxypyrimidin-5-yl)-5-(3,8-dimethyl-[1,2,4]triazolo[4,3-a]pyridin-6-yl)-3-isopropyl-4,5-dihydropyrrolo[3,4-c]pyrazol-6(2H)-one Example 68: 4-(4-chlorophenyl)-2-cyclopropyl-5-(1,5-dimethyl-6-oxo-1,6-dihydropyridin-3-yl)-3-ethyl-4,5-dihydropyrrolo[3,4-c]pyrazol-6(2H)-one Example 69: 4-(4-chlorophenyl)-1-cyclopropyl-5-(1,5-dimethyl-6-oxo-1,6-dihydropyridin-3-yl)-3-ethyl-4,5-dihydropyrrolo[3,4-c]pyrazol-6(1H)-one Example 70: 4-(4-chlorophenyl)-1-cyclopropyl-5-(3,8-dimethyl-[1,2,4]triazolo[4,3-a]pyridin-6-yl)-3-ethyl-4,5-dihydropyrrolo[3,4-c]pyrazol-6(1H)-one Example 71: 4-(4-chlorophenyl)-5-(1,5-dimethyl-6-oxo-1,6-dihydropyridin-3-yl)-1-(2-methoxypyridin-3-yl)-3-methyl-4,5-dihydropyrrolo[3,4-c]pyrazol-6(1H)-one Example 72: 5-(5-chloro-1-methyl-6-oxo-1,6-dihydropyridin-3-yl)-4-(4-chlorophenyl)-1-(2-methoxypyridin-3-yl)-3-methyl-4,5-dihydropyrrolo[3,4-c]pyrazol-6(1H)-one Example 73: 4-(4-chlorophenyl)-5-(1,5-dimethyl-6-oxo-1,6-dihydropyridin-3-yl)-3-hydroxy-2-methyl-4,5-dihydropyrrolo[3,4-c]pyrazol-6(2H)-one Example 74: 4-(4-chlorophenyl)-5-(1,5-dimethyl-6-oxo-1,6-dihydropyridin-3-yl)-3-methyl-1-(1-methyl-1H-pyrazol-5-yl)-4,5-dihydropyrrolo[3,4-c]pyrazol-6(1H)-one Example 76: 4-(4-chlorophenyl)-5-(1,5-dimethyl-6-oxo-1,6-dihydropyridin-3-yl)-3-ethoxy-2-methyl-4,5-dihydropyrrolo[3,4-c]pyrazol-6(2H)-one Example 77: 4-(4-chlorophenyl)-5-(1,5-dimethyl-6-oxo-1,6-dihydropyridin-3-yl)-3-methoxy-2-methyl-4,5-dihydropyrrolo[3,4-c]pyrazol-6(2H)-one Example 78: 4-(4-chlorophenyl)-5-(1,5-dimethyl-6-oxo-1,6-dihydropyridin-3-yl)-3-ethyl-1-(2-hydroxyethyl)-4,5-dihydropyrrolo[3,4-c]pyrazol-6(1H)-one Example 79: 4-(4-chlorophenyl)-5-(3,7-dimethylbenzo[d]isoxazol-5-yl)-3-ethyl-1-(2-hydroxyethyl)-4,5-dihydropyrrolo[3,4-c]pyrazol-6(1H)-one Example 80: 4-(4-chlorophenyl)-5-(3,7-dimethylbenzo[d]isoxazol-5-yl)-3-ethyl-2-(2-hydroxyethyl)-4,5-dihydropyrrolo[3,4-c]pyrazol-6(2H)-one Example 81: 4-(4-chlorophenyl)-5-(1,5-dimethyl-6-oxo-1,6-dihydropyridin-3-yl)-3-methyl-2-(2-methylpyridin-3-yl)-4,5-dihydropyrrolo[3,4-c]pyrazol-6(2H)-one Example 82: 4-(4-chlorophenyl)-5-(1,5-dimethyl-6-oxo-1,6-dihydropyridin-3-yl)-3-methyl-1-(2-methylpyridin-3-yl)-4,5-dihydropyrrolo[3,4-c]pyrazol-6(1H)-one Example 83: 4-(4-chlorophenyl)-5-(1,5-dimethyl-6-oxo-1,6-dihydropyridin-3-yl)-3-methyl-1-(1-methyl-1H-imidazol-5-yl)-4,5-dihydropyrrolo[3,4-c]pyrazol-6(1H)-one Example 84: 4-(4-chlorophenyl)-1-cyclopropyl-3-ethyl-5-(8-methoxy-3-methyl-[1,2,4]triazolo[4,3-a]pyridin-6-yl)-4,5-dihydropyrrolo[3,4-c]pyrazol-6(1H)-one Example 85: 4-(4-chlorophenyl)-1-cyclopropyl-5-(1,4-dimethyl-1H-benzo[d][1,2,3]triazol-6-yl)-3-methyl-4,5-dihydropyrrolo[3,4-c]pyrazol-6(1H)-one Example 86: 4-(4-chlorophenyl)-5-(1,5-dimethyl-6-oxo-1,6-dihydropyridin-3-yl)-3-ethyl-1-(2-methoxyethyl)-4,5-dihydropyrrolo[3,4-c]pyrazol-6(1H)-one Example 87: 4-(4-chlorophenyl)-5-(3,8-dimethyl-[1,2,4]triazolo[4,3-a]pyridin-6-yl)-3-ethyl-1-(2-methoxyethyl)-4,5-dihydropyrrolo[3,4-c]pyrazol-6(1H)-one Example 88: 4-(4-chlorophenyl)-5-(3,8-dimethyl-[1,2,4]triazolo[4,3-a]pyridin-6-yl)-3-ethyl-2-(2-methoxyethyl)-4,5-dihydropyrrolo[3,4-c]pyrazol-6(2H)-one Example 89: 4-(4-chlorophenyl)-5-(1,5-dimethyl-6-oxo-1,6-dihydropyridin-3-yl)-3-ethyl-1-(1-methyl-1H-pyrazol-5-yl)-4,5-dihydropyrrolo[3,4-c]pyrazol-6(1H)-one Example 90: 4-(4-chlorophenyl)-5-(3,8-dimethyl-[1,2,4]triazolo[4,3-a]pyridin-6-yl)-3-methyl-1-(1-methyl-1H-pyrazol-5-yl)-4,5-dihydropyrrolo[3,4-c]pyrazol-6(1H)-one Example 91: 1-cyclopropyl-5-(1,5-dimethyl-6-oxo-1,6-dihydropyridin-3-yl)-3-methyl-4-(3-(trifluoromethoxy)phenyl)-4,5-dihydropyrrolo[3,4-c]pyrazol-6(1H)-one Example 92: 4-(4-chlorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one Example 93: 4-(4-chlorophenyl)-2-cyclopropyl-5-(3,8-dimethyl-[1,2,4]triazolo[4,3-a]pyridin-6-yl)-3-methyl-4,5-dihydropyrrolo[3,4-c]pyrazol-6(2H)-one Example 94: 4-(4-chlorophenyl)-1-cyclobutyl-5-(1,5-dimethyl-6-oxo-1,6-dihydropyridin-3-yl)-3-methyl-4,5-dihydropyrrolo[3,4-c]pyrazol-6(1H)-one Example 95: 1-cyclopropyl-5-(1,5-dimethyl-6-oxo-1,6-dihydropyridin-3-yl)-3-methyl-4-(4-(trifluoromethoxy)phenyl)-4,5-dihydropyrrolo[3,4-c]pyrazol-6(1H)-one Example 96: 1-cyclopropyl-5-(1,5-dimethyl-6-oxo-1,6-dihydropyridin-3-yl)-3-methyl-4-(3-(trifluoromethyl)phenyl)-4,5-dihydropyrrolo[3,4-c]pyrazol-6(1H)-one Example 97: 1-cyclopropyl-5-(1,5-dimethyl-6-oxo-1,6-dihydropyridin-3-yl)-3-methyl-4-(4-(trifluoromethyl)phenyl)-4,5-dihydropyrrolo[3,4-c]pyrazol-6(1H)-one Example 98: 4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one Example 100: (R)-4-(4-chlorophenyl)-1-(2,4-dimethoxypyrimidin-5-yl)-5-(1,5-dimethyl-6-oxo-1,6-dihydropyridin-3-yl)-3-methyl-4,5-dihydropyrrolo[3,4-c]pyrazol-6(1H)-one Example 101: 4-(4-chlorophenyl)-5-(3,8-dimethyl-[1,2,4]triazolo[4,3-a]pyridin-6-yl)-1-(2-methoxypyridin-3-yl)-3-methyl-4,5-dihydropyrrolo[3,4-c]pyrazol-6(1H)-one Example 102: 4-(4-chlorophenyl)-1-cyclopropyl-3-methyl-5-(3-methyl-3H-[1,2,3]triazolo[4,5-b]pyridin-5-yl)-4,5-dihydropyrrolo[3,4-c]pyrazol-6(1H)-one Example 104: (R)-4-(4-chlorophenyl)-5-(1,5-dimethyl-6-oxo-1,6-dihydropyridin-3-yl)-1-isopropyl-3-methyl-4,5-dihydropyrrolo[3,4-c]pyrazol-6(1H)-one Example 105: 4-(4-chlorophenyl)-3-ethyl-5-(8-methoxy-3-methyl-[1,2,4]triazolo[4,3-a]pyridin-6-yl)-1-methyl-4,5-dihydropyrrolo[3,4-c]pyrazol-6(1H)-one Example 107: (R)-4-(4-chlorophenyl)-1-cyclopropyl-5-(3,8-dimethyl-[1,2,4]triazolo[4,3-a]pyridin-6-yl)-3-ethyl-4,5-dihydropyrrolo[3,4-c]pyrazol-6(1H)-one Example 108: 4-(4-chlorophenyl)-3-ethyl-5-(8-methoxy-3-methyl-[1,2,4]triazolo[4,3-a]pyridin-6-yl)-1-(2-(2,2,2-trifluoroethoxy)ethyl)-4,5-dihydropyrrolo[3,4-c]pyrazol-6(1H)-one Example 109: 4-(4-chlorophenyl)-5-(3,7-dimethyl-3H-[1,2,3]triazolo[4,5-b]pyridin-5-yl)-1-(2-methoxypyridin-3-yl)-3-methyl-4,5-dihydropyrrolo[3,4-c]pyrazol-6(1H)-one Example 110: 4-(4-chlorophenyl)-1-cyclopropyl-5-(3,7-dimethyl-3H-[1,2,3]triazolo[4,5-b]pyridin-5-yl)-3-methyl-4,5-dihydropyrrolo[3,4-c]pyrazol-6(1H)-one Example 111: 4-(4-chlorophenyl)-5-(3,8-dimethyl-[1,2,4]triazolo[4,3-b]pyridazin-6-yl)-1-(2-methoxypyridin-3-yl)-3-methyl-4,5-dihydropyrrolo[3,4-c]pyrazol-6(1H)-one Example 112: tert-butyl (6-(4-(4-chlorophenyl)-1-cyclopropyl-3-methyl-6-oxopyrrolo[3,4-c]-pyrazol-5(1H,4H,6H)-yl)-3-methyl-[1,2,4]triazolo[4,3-b]pyridazin-8-yl)(methyl)carbamate Example 113: 4-(4-chlorophenyl)-1-cyclopropyl-3-methyl-5-(3-methyl-8-(methylamino)-[1,2,4]triazolo[4,3-b]pyridazin-6-yl)-4,5-dihydropyrrolo[3,4-c]pyrazol-6(1H)-one Example 114: 4-(4-chlorophenyl)-5-(3,8-dimethyl-[1,2,4]triazolo[4,3-b]pyridazin-6-yl)-3-methyl-1-(1-methyl-1H-pyrazol-5-yl)-4,5-dihydropyrrolo[3,4-c]pyrazol-6(1H)-one Example 115: 4-(4-chlorophenyl)-5-(3,8-dimethyl-[1,2,4]triazolo[4,3-a]pyridin-6-yl)-2-ethyl-3-methyl-4,5-dihydropyrrolo[3,4-c]pyrazol-6(2H)-one Example 116: 4-(4-chlorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one Example 117: 4-(4-chlorophenyl)-3-cyclopropyl-5-(3,8-dimethyl-[1,2,4]triazolo[4,3-a]pyridin-6-yl)-1-(1-methyl-1H-pyrazol-5-yl)-4,5-dihydropyrrolo[3,4-c]pyrazol-6(1H)-one Example 119: (R)-4-(4-chlorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one Example 120: (R)-4-(4-chlorophenyl)-5-(1,5-dimethyl-6-oxo-1,6-dihydropyridin-3-yl)-3-methyl-1-(1-methyl-1H-pyrazol-5-yl)-4,5-dihydropyrrolo[3,4-c]pyrazol-6(1H)-one Example 122: (R)-4-(4-chlorophenyl)-1-cyclopropyl-5-(3,8-dimethyl-[1,2,4]triazolo[4,3-b]-pyridazin-6-yl)-3-methyl-4,5-dihydropyrrolo[3,4-c]pyrazol-6(1H)-one Example 125: (R)-4-(4-chlorophenyl)-5-(3,8-dimethyl-[1,2,4]triazolo[4,3-a]pyridin-6-yl)-3-methyl-1-(1-methyl-1H-pyrazol-5-yl)-4,5-dihydropyrrolo[3,4-c]pyrazol-6(1H)-one Example 126: N-(6-(4-(4-chlorophenyl)-1-cyclopropyl-3-methyl-6-oxopyrrolo[3,4-c]pyrazol-5(1H,4H,6H)-yl)-3-methyl-[1,2,4]triazolo[4,3-b]pyridazin-8-yl)acetamide Example 128: (R)-4-(4-chlorophenyl)-5-(1,5-dimethyl-6-oxo-1,6-dihydropyridin-3-yl)-1-(2-methoxypyridin-3-yl)-3-methyl-4,5-dihydropyrrolo[3,4-c]pyrazol-6(1H)-one Example 129: 4-(4-chlorophenyl)-3-cyclopropyl-5-(3,8-dimethyl-[1,2,4]triazolo[4,3-a]pyridin-6-yl)-1-methyl-4,5-dihydropyrrolo[3,4-c]pyrazol-6(1H)-one Example 130: 4-(4-chlorophenyl)-1-cyclopropyl-5-(3,8-dimethyl-[1,2,4]triazolo[4,3-a]pyridin-6-yl)-3-(methoxymethyl)-4,5-dihydropyrrolo[3,4-c]pyrazol-6(1H)-one Example 131: 4-(4-chlorophenyl)-1-cyclopropyl-5-(3,8-dimethyl-[1,2,4]triazolo[4,3-a]pyridin-6-yl)-3-(hydroxymethyl)-4,5-dihydropyrrolo[3,4-c]pyrazol-6(1H)-one Example 132: 4-(4-chlorophenyl)-1-cyclopropyl-5-(1,5-dimethyl-6-oxo-1,6-dihydropyridin-3-yl)-3-(methoxymethyl)-4,5-dihydropyrrolo[3,4-c]pyrazol-6(1H)-one Example 133: 4-(4-chlorophenyl)-1-cyclopropyl-5-(1,5-dimethyl-6-oxo-1,6-dihydropyridin-3-yl)-3-(hydroxymethyl)-4,5-dihydropyrrolo[3,4-c]pyrazol-6(1H)-one Example 134: 4-(4-chlorophenyl)-5-(1,5-dimethyl-6-oxo-1,6-dihydropyridin-3-yl)-3-methyl-2-(oxetan-3-yl)-4,5-dihydropyrrolo[3,4-c]pyrazol-6(2H)-one Example 135: 4-(4-chlorophenyl)-5-(1,5-dimethyl-6-oxo-1,6-dihydropyridin-3-yl)-3-methyl-1-(oxetan-3-yl)-4,5-dihydropyrrolo[3,4-c]pyrazol-6(1H)-one Example 136: 4-(4-chlorophenyl)-5-(3,8-dimethyl-[1,2,4]triazolo[4,3-a]pyridin-6-yl)-3-methyl-2-(oxetan-3-yl)-4,5-dihydropyrrolo[3,4-c]pyrazol-6(2H)-one Example 137: 4-(4-chlorophenyl)-5-(3,8-dimethyl-[1,2,4]triazolo[4,3-a]pyridin-6-yl)-3-methyl-1-(oxetan-3-yl)-4,5-dihydropyrrolo[3,4-c]pyrazol-6(1H)-one Example 138: 1-(azetidin-3-yl)-4-(4-chlorophenyl)-5-(1,5-dimethyl-6-oxo-1,6-dihydropyridin-3-yl)-3-methyl-4,5-dihydropyrrolo[3,4-c]pyrazol-6(1H)-one Example 139: 4-(4-chlorophenyl)-5-(1,5-dimethyl-6-oxo-1,6-dihydropyridin-3-yl)-3-methyl-2-(1-methylazetidin-3-yl)-4,5-dihydropyrrolo[3,4-c]pyrazol-6(2H)-one Example 140: 4-(4-chlorophenyl)-5-(1,5-dimethyl-6-oxo-1,6-dihydropyridin-3-yl)-3-methyl-1-(1-methylazetidin-3-yl)-4,5-dihydropyrrolo[3,4-c]pyrazol-6(1H)-one Example 141: 4-(4-chlorophenyl)-5-(1,5-dimethyl-6-oxo-1,6-dihydropyridin-3-yl)-N,N,3-trimethyl-6-oxo-5,6-dihydropyrrolo[3,4-c]pyrazole-2(4H)-carboxamide Example 142: 4-(4-chlorophenyl)-5-(1,5-dimethyl-6-oxo-1,6-dihydropyridin-3-yl)-N,N,3-trimethyl-6-oxo-5,6-dihydropyrrolo[3,4-c]pyrazole-1(4H)-carboxamide Example 143: 4-(4-chlorophenyl)-5-(1,5-dimethyl-6-oxo-1,6-dihydropyridin-3-yl)-N,3-dimethyl-6-oxo-5,6-dihydropyrrolo[3,4-c]pyrazole-1(4H)-carboxamide Example 144: 4-(4-chlorophenyl)-5-(1,5-dimethyl-6-oxo-1,6-dihydropyridin-3-yl)-N,3-dimethyl-6-oxo-5,6-dihydropyrrolo[3,4-c]pyrazole-2(4H)-carboxamide Example 145: 4-(4-chlorophenyl)-5-(3,8-dimethyl-[1,2,4]triazolo[4,3-a]pyridin-6-yl)-N,3-dimethyl-6-oxo-5,6-dihydropyrrolo[3,4-c]pyrazole-1(4H)-carboxamide Example 146: 4-(4-chlorophenyl)-5-(3,8-dimethyl-[1,2,4]triazolo[4,3-a]pyridin-6-yl)-N,3-dimethyl-6-oxo-5,6-dihydropyrrolo[3,4-c]pyrazole-2(4H)-carboxamide Example 147: 4-(4-chlorophenyl)-5-(1,5-dimethyl-6-oxo-1,6-dihydropyridin-3-yl)-3-ethyl-N,N-dimethyl-6-oxo-5,6-dihydropyrrolo[3,4-c]pyrazole-1(4H)-carboxamide Example 148: 4-(4-chlorophenyl)-5-(1,5-dimethyl-6-oxo-1,6-dihydropyridin-3-yl)-3-ethyl-N,N-dimethyl-6-oxo-5,6-dihydropyrrolo[3,4-c]pyrazole-2(4H)-carboxamide Example 149: (R)-4-(4-chlorophenyl)-5-(3,8-dimethyl-[1,2,4]triazolo[4,3-a]pyridin-6-yl)-N,N,3-trimethyl-6-oxo-5,6-dihydropyrrolo[3,4-c]pyrazole-1(4H)-carboxamide Example 150: (R)-4-(4-chlorophenyl)-5-(3,8-dimethyl-[1,2,4]triazolo[4,3-a]pyridin-6-yl)-N,N,3-trimethyl-6-oxo-5,6-dihydropyrrolo[3,4-c]pyrazole-2(4H)-carboxamide Example 151: 1-(azetidin-3-yl)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one Example 152: 2-(azetidin-3-yl)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(2H)-one Example 153: 1-(1-acetylazetidin-3-yl)-4-(4-chlorophenyl)-5-(1,5-dimethyl-6-oxo-1,6-dihydropyridin-3-yl)-3-methyl-4,5-dihydropyrrolo[3,4-c]pyrazol-6(1H)-one Example 154: 1-(1-acetylazetidin-3-yl)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one Example 155: Ethyl 3-(4-(4-chlorophenyl)-5-(1,5-dimethyl-6-oxo-1,6-dihydropyridin-3-yl)-3-methyl-6-oxo-5,6-dihydropyrrolo[3,4-c]pyrazol-1(4H)-yl)azetidine-1-carboxylate Example 156: Ethyl 3-(4-(4-chlorophenyl)-5-(3,8-dimethyl-[1,2,4]triazolo[4,3-a]pyridin-6-yl)-3-methyl-6-oxo-5,6-dihydropyrrolo[3,4-c]pyrazol-1(4H)-yl)azetidine-1-carboxylate Example 157: 4-(4-chlorophenyl)-5-(3,8-dimethyl-[1,2,4]triazolo[4,3-a]pyridin-6-yl)-3-methyl-1-(1-methylazetidin-3-yl)-4,5-dihydropyrrolo[3,4-c]pyrazol-6(1H)-one Example 158: 4-(4-chlorophenyl)-5-(3,8-dimethyl-[1,2,4]triazolo[4,3-a]pyridin-6-yl)-3-methyl-2-(1-methylazetidin-3-yl)-4,5-dihydropyrrolo[3,4-c]pyrazol-6(2H)-one Example 159: 4-(4-chlorophenyl)-1-cyclopropyl-5-(3,8-dimethyl-[1,2,4]triazolo[4,3-a]pyridin-6-yl)-3-(fluoromethyl)-4,5-dihydropyrrolo[3,4-c]pyrazol-6(1H)-one Example 160: 4-(4-(4-chlorophenyl)-1-cyclopropyl-3-methyl-6-oxopyrrolo[3,4-c]pyrazol-5(1H,4H,6H)-yl)-6-methyl-1H-pyrrolo[2,3-c]pyridin-7(6H)-one Example 161: (R)-4-(4-chlorophenyl)-1-cyclopropyl-3-methyl-5-(3-methyl-8-(methylamino)-[1,2,4]triazolo[4,3-b]pyridazin-6-yl)-4,5-dihydropyrrolo[3,4-c]pyrazol-6(1H)-one Example 162: (R)-4-(4-chlorophenyl)-1-cyclopropyl-5-(1,5-dimethyl-6-oxo-1,6-dihydropyridin-3-yl)-3-(methoxymethyl)-4,5-dihydropyrrolo[3,4-c]pyrazol-6(1H)-one Example 163: (R)-4-(4-chlorophenyl)-1-cyclopropyl-5-(3,8-dimethyl-[1,2,4]triazolo[4,3-a]pyridin-6-yl)-3-(methoxymethyl)-4,5-dihydropyrrolo[3,4-c]pyrazol-6(1H)-one Example 164: (R)-4-(4-chlorophenyl)-3-cyclopropyl-5-(3,8-dimethyl-[1,2,4]triazolo[4,3-a]pyridin-6-yl)-1-methyl-4,5-dihydropyrrolo[3,4-c]pyrazol-6(1H)-one Example 165: (R)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one Example 166: (R)-4-(4-chlorophenyl)-1-cyclopropyl-5-(3,8-dimethyl-[1,2,4]triazolo[4,3-a]pyridin-6-yl)-3-(hydroxymethyl)-4,5-dihydropyrrolo[3,4-c]pyrazol-6(1H)-one Example 167: (R)-4-(4-chlorophenyl)-5-(3,8-dimethyl-[1,2,4]triazolo[4,3-a]pyridin-6-yl)-3-methyl-1-((S)-3,3,3-trifluoro-2-hydroxypropyl)-4,5-dihydropyrrolo[3,4-c]pyrazol-6(1H)-one Example 168: 4-(4-chloro-2-fluorophenyl)-5-(3,8-dimethyl-[1,2,4]triazolo[4,3-a]pyridin-6-yl)-1-isopropyl-3-methyl-4,5-dihydropyrrolo[3,4-c]pyrazol-6(1H)-one Example 169: 4-(4-chloro-2-fluorophenyl)-5-(3,8-dimethyl-[1,2,4]triazolo[4,3-a]pyridin-6-yl)-2-isopropyl-3-methyl-4,5-dihydropyrrolo[3,4-c]pyrazol-6(2H)-one Example 170: 4-(4-chloro-2-fluorophenyl)-5-(1,5-dimethyl-6-oxo-1,6-dihydropyridin-3-yl)-1-ethyl-3-methyl-4,5-dihydropyrrolo[3,4-c]pyrazol-6(1H)-one Example 171: 4-(4-chloro-2-fluorophenyl)-5-(1,5-dimethyl-6-oxo-1,6-dihydropyridin-3-yl)-2-ethyl-3-methyl-4,5-dihydropyrrolo[3,4-c]pyrazol-6(2H)-one Example 172: 4-(2,4-difluorophenyl)-5-(3,8-dimethyl-[1,2,4]triazolo[4,3-a]pyridin-6-yl)-3-methyl-4,5-dihydropyrrolo[3,4-c]pyrazol-6(2H)-one Example 173: 4-(2,4-difluorophenyl)-5-(3,8-dimethyl-[1,2,4]triazolo[4,3-a]pyridin-6-yl)-1-(2-methoxypyridin-3-yl)-3-methyl-4,5-dihydropyrrolo[3,4-c]pyrazol-6(1H)-one Example 174: 4-(2,4-difluorophenyl)-5-(3,8-dimethyl-[1,2,4]triazolo[4,3-a]pyridin-6-yl)-1-isopropyl-3-methyl-4,5-dihydropyrrolo[3,4-c]pyrazol-6(1H)-one Example 175: 4-(2,4-difluorophenyl)-5-(3,8-dimethyl-[1,2,4]triazolo[4,3-a]pyridin-6-yl)-2-isopropyl-3-methyl-4,5-dihydropyrrolo[3,4-c]pyrazol-6(2H)-one Example 176: 1-cyclopropyl-4-(2,4-difluorophenyl)-5-(3,8-dimethyl-[1,2,4]triazolo[4,3-a]pyridin-6-yl)-3-methyl-4,5-dihydropyrrolo[3,4-c]pyrazol-6(1H)-one Example 177: 4-(2,4-difluorophenyl)-5-(3,8-dimethyl-[1,2,4]triazolo[4,3-a]pyridin-6-yl)-1-(2-methoxyphenyl)-3-methyl-4,5-dihydropyrrolo[3,4-c]pyrazol-6(1H)-one Example 178: 4-(4-chloro-2-fluorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one Example 179: 4-(4-chloro-2-fluorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one Example 180: 4-(4-chloro-2-fluorophenyl)-5-(1,5-dimethyl-6-oxo-1,6-dihydropyridin-3-yl)-1-isopropyl-3-methyl-4,5-dihydropyrrolo[3,4-c]pyrazol-6(1H)-one Example 181: 4-(2,4-difluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one Example 182: 4-(2,4-difluorophenyl)-5-(3,8-dimethyl-[1,2,4]triazolo[4,3-a]pyridin-6-yl)-2-ethyl-3-methyl-4,5-dihydropyrrolo[3,4-c]pyrazol-6(2H)-one Example 183: 4-(4-chloro-2-fluorophenyl)-5-(3,8-dimethyl-[1,2,4]triazolo[4,3-a]pyridin-6-yl)-3-methyl-4,5-dihydropyrrolo[3,4-c]pyrazol-6(2H)-one Example 184: 4-(4-chloro-2-fluorophenyl)-5-(3,8-dimethyl-[1,2,4]triazolo[4,3-a]pyridin-6-yl)-1-(2-methoxypyridin-3-yl)-3-methyl-4,5-dihydropyrrolo[3,4-c]pyrazol-6(1H)-one Example 185: 4-(4-chloro-2-fluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one Example 186: 4-(4-chloro-2-fluorophenyl)-5-(3,8-dimethyl-[1,2,4]triazolo[4,3-a]pyridin-6-yl)-2-ethyl-3-methyl-4,5-dihydropyrrolo[3,4-c]pyrazol-6(2H)-one Example 187: 4-(4-chloro-2-fluorophenyl)-5-(3,8-dimethyl-[1,2,4]triazolo[4,3-a]pyridin-6-yl)-1-(2-methoxyphenyl)-3-methyl-4,5-dihydropyrrolo[3,4-c]pyrazol-6(1H)-one Example 188: (S)-1-cyclopropyl-4-(2,4-difluorophenyl)-5-(3,8-dimethyl-[1,2,4]triazolo[4,3-a]pyridin-6-yl)-3-methyl-4,5-dihydropyrrolo[3,4-c]pyrazol-6(1H)-one Example 189: (S)-4-(4-chloro-2-fluorophenyl)-5-(3,8-dimethyl-[1,2,4]triazolo[4,3-a]pyridin-6-yl)-1-isopropyl-3-methyl-4,5-dihydropyrrolo[3,4-c]pyrazol-6(1H)-one Example 190: (S)-4-(4-chloro-2-fluorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one Example 191: (S)-4-(2,4-difluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one Example 192: (S)-4-(4-chloro-2-fluorophenyl)-5-(3,8-dimethyl-[1,2,4]triazolo[4,3-a]pyridin-6-yl)-1-ethyl-3-methyl-4,5-dihydropyrrolo[3,4-c]pyrazol-6(1H)-one Example 193: 4-(2,4-difluorophenyl)-5-(3,8-dimethyl-[1,2,4]triazolo[4,3-a]pyridin-6-yl)-2-(2-methoxypyridin-3-yl)-3-methyl-4,5-dihydropyrrolo[3,4-c]pyrazol-6(2H)-one Example 194: 4-(4-chloro-2-fluorophenyl)-5-(3,8-dimethyl-[1,2,4]triazolo[4,3-a]pyridin-6-yl)-2-(2-methoxypyridin-3-yl)-3-methyl-4,5-dihydropyrrolo[3,4-c]pyrazol-6(2H)-one Example 195: 4-(4-chlorophenyl)-1-cyclopropyl-5-(3-(difluoromethyl)-8-methyl-[1,2,4]triazolo[4,3-b]pyridazin-6-yl)-3-methyl-4,5-dihydropyrrolo[3,4-c]pyrazol-6(1H)-one and Example 196: 4-(4-chloro-2-fluorophenyl)-5-(1,5-dimethyl-6-oxo-1,6-dihydropyridin-3-yl)-3-methyl-4,5-dihydropyrrolo[3,4-c]pyrazol-6(2H)-one.

13. A pharmaceutical composition comprising a therapeutically effective amount of a compound according to claim 1 or a pharmaceutically acceptable salt thereof and one or more pharmaceutically acceptable carriers.

14. A combination comprising a therapeutically effective amount of a compound according to claim 1 or a pharmaceutically acceptable salt thereof and one or more therapeutically active agents, in particular anticancer agents.

15. A compound selected from (R)-4-(4-chlorophenyl)-1-cyclopropyl-5-(1,5-dimethyl-6-oxo-1,6-dihydropyridin-3-yl)-3-methyl-4,5-dihydropyrrolo[3,4-c]pyrazol-6(1H)-one or a pharmaceutically acceptable salt thereof.

16. A compound selected from 4-(4-chlorophenyl)-2-(2,4-dimethoxypyrimidin-5-yl)-5-(3,8-dimethyl-[1,2,4]triazolo[4,3-a]pyridin-6-yl)-3-isopropyl-4,5-dihydropyrrolo[3,4-c]pyrazol-6(2H)-one or a pharmaceutically acceptable salt thereof.

17. A compound selected from 4-(4-chlorophenyl)-2-cyclopropyl-5-(3,8-dimethyl-[1,2,4]triazolo[4,3-a]pyridin-6-yl)-3-methyl-4,5-dihydropyrrolo[3,4-c]pyrazol-6(2H)-one or a pharmaceutically acceptable salt thereof.

18. A compound selected from (R)-4-(4-chlorophenyl)-1-cyclopropyl-5-(3,8-dimethyl-[1,2,4]triazolo[4,3-a]pyridin-6-yl)-3-ethyl-4,5-dihydropyrrolo[3,4-c]pyrazol-6(1H)-one or a pharmaceutically acceptable salt thereof.

19. A compound selected from (R)-4-(4-chlorophenyl)-1-cyclopropyl-5-(3,8-dimethyl-[1,2,4]triazolo[4,3-a]pyridin-6-yl)-3-methyl-4,5-dihydropyrrolo[3,4-c]pyrazol-6(1H)-one or a pharmaceutically acceptable salt thereof.

20. A compound selected from (R)-4-(4-chlorophenyl)-1-cyclopropyl-5-(3,8-dimethyl-[1,2,4]triazolo[4,3-b]pyridazin-6-yl)-3-methyl-4,5-dihydropyrrolo[3,4-c]pyrazol-6(1H)-one or a pharmaceutically acceptable salt thereof.

21. A compound selected from 4-(4-chlorophenyl)-1-cyclopropyl-5-(1,5-dimethyl-6-oxo-1,6-dihydropyridin-3-yl)-3-(hydroxymethyl)-4,5-dihydropyrrolo[3,4-c]pyrazol-6(1H)-one or a pharmaceutically acceptable salt thereof.

22. A compound selected from (R)-4-(4-chlorophenyl)-1-cyclopropyl-5-(3,8-dimethyl-[1,2,4]triazolo[4,3-a]pyridin-6-yl)-3-(methoxymethyl)-4,5-dihydropyrrolo[3,4-c]pyrazol-6(1H)-one or a pharmaceutically acceptable salt thereof.

23. A compound selected from (R)-4-(4-chlorophenyl)-5-(3,8-dimethyl-[1,2,4]triazolo[4,3-a]pyridin-6-yl)-3-methyl-4,5-dihydropyrrolo[3,4-c]pyrazol-6(1H)-one or a pharmaceutically acceptable salt thereof.

24. A compound selected from (R)-4-(4-chlorophenyl)-1-cyclopropyl-5-(3,8-dimethyl-[1,2,4]triazolo[4,3-a]pyridin-6-yl)-3-(hydroxymethyl)-4,5-dihydropyrrolo[3,4-c]pyrazol-6(1H)-one or a pharmaceutically acceptable salt thereof.

* * * * *

UNITED STATES PATENT AND TRADEMARK OFFICE
CERTIFICATE OF CORRECTION

PATENT NO.        : 8,975,417 B2
APPLICATION NO.   : 14/282515
DATED             : March 10, 2015
INVENTOR(S)       : Vincent Bordas et al.

It is certified that error appears in the above-identified patent and that said Letters Patent is hereby corrected as shown below:

In the claims

In column 265, the formula spanning from lines 1-10, that appears as:

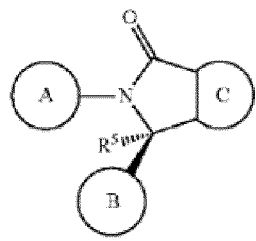

should appear as follows:

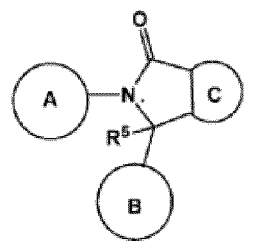

Signed and Sealed this
Third Day of May, 2016

Michelle K. Lee
*Director of the United States Patent and Trademark Office*